US011931405B2

(12) United States Patent
Geurtsen et al.

(10) Patent No.: US 11,931,405 B2
(45) Date of Patent: Mar. 19, 2024

(54) **BIOCONJUGATES OF *E. COLI* O-ANTIGEN POLYSACCHARIDES, METHODS OF PRODUCTION THEREOF, AND METHODS OF USE THEREOF**

(71) Applicants: Janssen Pharmaceuticals, Inc., Titusville, NJ (US); GlaxoSmithKline Biologicals S.A., Rixensart (BE)

(72) Inventors: Jeroen Geurtsen, Vleuten (NL); Jan Theunis Poolman, Vogelenzang (NL); Kellen Cristhina Fae, Mainz (DE); Pieter Jan Burghout, Pijnacker (NL); Eveline Marleen Weerdenburg, Uithoorn (NL); Patricia Ibarra Yon, Solothum (CH); Darren Robert Abbanat, Cornwal, NY (US); Stefan Jochen Kemmler, Zurich (CH); Michael Thomas Kowarik, Zurich (CH); Manuela Mally, Watt (CH); Veronica Gambillara Fonck, Meilen (CH); Martin Edward Braun, Cham (CH); Maria Paula Carranza Sandmeier, Rudolfstetten (CH)

(73) Assignees: Janssen Pharmaceuticals, Inc.; GlaxoSmithKline Biologicals S.A., Rixensart (BE)

( * ) Notice: Subject to any disclaimer, the term of this patent is extended or adjusted under 35 U.S.C. 154(b) by 29 days.

(21) Appl. No.: 17/815,705

(22) Filed: Jul. 28, 2022

(65) Prior Publication Data

US 2023/0118878 A1 Apr. 20, 2023

Related U.S. Application Data

(62) Division of application No. 16/822,340, filed on Mar. 18, 2020, now Pat. No. 11,446,370.

(60) Provisional application No. 62/819,746, filed on Mar. 18, 2019.

(51) Int. Cl.

| | |
|---|---|
| ***A61K 39/108*** | (2006.01) |
| ***A61K 39/00*** | (2006.01) |
| ***A61P 31/04*** | (2006.01) |
| ***A61P 37/04*** | (2006.01) |
| ***C07K 14/21*** | (2006.01) |
| ***C07K 19/00*** | (2006.01) |
| ***C12N 9/10*** | (2006.01) |

(52) U.S. Cl.

CPC .......... *A61K 39/0258* (2013.01); *A61P 31/04* (2018.01); *A61P 37/04* (2018.01); *C07K 14/21* (2013.01); *C07K 19/00* (2013.01); *C12N 9/1051* (2013.01); *C12Y 204/01* (2013.01); *A61K 2039/575* (2013.01); *A61K 2039/6037* (2013.01)

(58) Field of Classification Search

None

See application file for complete search history.

(56) References Cited

U.S. PATENT DOCUMENTS

| | | | |
|---|---|---|---|
| 3,700,612 | A | 10/1972 | Fath |
| 5,057,540 | A | 10/1991 | Kensil |
| 5,370,872 | A | 12/1994 | Cryz |
| 6,331,415 | B1 | 12/2001 | Cabilly |
| 6,858,211 | B1 | 2/2005 | Szu |
| 9,700,612 | B2 | 7/2017 | Kowarik |
| 9,849,169 | B2 | 12/2017 | Nagy |
| 10,150,952 | B2 | 12/2018 | Haas |
| 10,159,751 | B2 | 12/2018 | Labovitiadi |
| 10,206,992 | B2 | 2/2019 | Nagy |
| 10,441,647 | B2 | 10/2019 | Kowarik |
| 10,525,145 | B2 | 1/2020 | Labovitiadi |
| 10,577,592 | B2 | 3/2020 | Haas |
| 10,583,185 | B2 | 3/2020 | Poolman |
| 10,940,191 | B2 | 3/2021 | Nagy |
| 10,940,192 | B2 | 3/2021 | Kowarik |
| 11,015,177 | B2 | 5/2021 | Haas |
| 11,033,633 | B2 | 6/2021 | Labovitiadi |
| 11,446,370 | B2 | 9/2022 | Geurtsen |

(Continued)

FOREIGN PATENT DOCUMENTS

| | | |
|---|---|---|
| CN | 101983070 | 3/2011 |
| EP | 2289911 | 3/2011 |

(Continued)

OTHER PUBLICATIONS

DebRoy C, Fratamico PM, Yan X, Baranzoni G, Liu Y, et al. (2016) Correction: Comparison of O-Antigen Gene Clusters of All O-Serogroups of *Escherichia coli* and Proposal for Adopting a New Nomenclature for O-Typing. PLOS One 11(4): e0154551, Published: Apr. 27, 2016, 5 pages.

(Continued)

*Primary Examiner* — Brian Gangle

(74) *Attorney, Agent, or Firm* — Ice Miller LLP

(57) ABSTRACT

A bioconjugate of an *E. coli* glucosylated O4 antigen polysaccharide covalently linked to a carrier protein and compositions thereof are provided. Also provided are recombinant host cells for producing the bioconjugate, and methods of producing the bioconjugate using the recombinant host cells. The recombinant host cells contain a nucleic acid encoding a glucosyl transferase capable of modifying the *E. coli* O4 antigen with glucose branching to produce the glucosylated O4 antigen polysaccharide. Bioconjugates of an *E. coli* glucosylated O4 antigen polysaccharide described herein can be used alone or in combination with one or more additional *E. coli* O-antigen polysaccharides to induce antibodies against an *E. coli* glucosylated antigen, and to vaccinate a subject against extra-intestinal pathogenic *E. coli* (ExPEC).

22 Claims, 12 Drawing Sheets

Specification includes a Sequence Listing.

(56) References Cited

U.S. PATENT DOCUMENTS

| | | | |
|---|---|---|---|
| 2002/0177170 A1 | 11/2002 | Luo | |
| 2014/0038296 A1 | 2/2014 | Palsson | |
| 2015/0238588 A1 | 8/2015 | Kowarik | |
| 2018/0002679 A1 | 1/2018 | Haas | |
| 2019/0078064 A1 | 3/2019 | Haas | |
| 2020/0181586 A1 | 6/2020 | Haas | |
| 2020/0316184 A1 | 10/2020 | Geurtsen | |
| 2020/0353073 A1 | 11/2020 | Geurtsen | |
| 2021/0004617 A1 | 1/2021 | Gouraud | |
| 2021/0154286 A1 | 5/2021 | Kowarik | |

FOREIGN PATENT DOCUMENTS

| | | | |
|---|---|---|---|
| GB | 2220211 | A | 1/1990 |
| JP | S62500173 | | 1/1987 |
| JP | H10500102 | A | 1/1998 |
| JP | 2004515450 | A | 5/2004 |
| JP | 2007256214 | | 10/2007 |
| JP | 2008539743 | A | 11/2008 |
| JP | 2011514155 | | 5/2011 |
| JP | 4791866 | B2 | 10/2011 |
| JP | 2012525376 | A | 10/2012 |
| JP | 2017507178 | | 3/2017 |
| JP | 2018525423 | A | 9/2018 |
| RU | 2189253 | C1 | 9/2002 |
| WO | 8601806 | A1 | 3/1986 |
| WO | 86001806 | | 3/1986 |
| WO | 9303765 | A1 | 3/1993 |
| WO | 9522563 | | 8/1995 |
| WO | 9522563 | A1 | 8/1995 |
| WO | 2001078787 | A2 | 10/2001 |
| WO | 2003074679 | | 9/2003 |
| WO | 2003074687 | A1 | 9/2003 |
| WO | 2004078209 | A1 | 9/2004 |
| WO | 2006119987 | A2 | 11/2006 |
| WO | 2007109812 | A2 | 9/2007 |
| WO | 2007109813 | A1 | 9/2007 |
| WO | 2009036379 | | 3/2009 |
| WO | 2009089396 | A2 | 7/2009 |
| WO | 2009104074 | A2 | 8/2009 |
| WO | 2010105256 | | 9/2010 |
| WO | 2010125565 | A2 | 11/2010 |
| WO | 2011062615 | | 5/2011 |
| WO | 2012009568 | | 1/2012 |
| WO | 2012078482 | A1 | 6/2012 |
| WO | 2013034664 | A1 | 3/2013 |
| WO | 2014037585 | A1 | 3/2014 |
| WO | 2014057109 | A1 | 4/2014 |
| WO | 2014102265 | A1 | 7/2014 |
| WO | 2014111516 | A1 | 7/2014 |
| WO | 2015052344 | | 4/2015 |
| WO | 2015117711 | A1 | 8/2015 |
| WO | 2015124769 | A1 | 8/2015 |
| WO | 2016107818 | A1 | 7/2016 |
| WO | 2016107819 | A1 | 7/2016 |
| WO | 2017035181 | A1 | 3/2017 |
| WO | 2018077853 | A1 | 5/2018 |
| WO | 2019016187 | A1 | 1/2019 |
| WO | 2020191082 | | 9/2020 |
| WO | 2020191088 | | 9/2020 |

OTHER PUBLICATIONS

DebRoy et al., "Comparison of O-Antigen Gene Clusters of All O-Serogroups of *Escherichia coli* and Proposal for Adopting a New Nomenclature for O-Typing," PLoS One 11(1): e0147434, Jan. 29, 2016, 13 pages.

Int'l Search Report dated Jan. 24, 2018 in Int'l Application No. PCT/EP2017/077123, 6 pages.

International Search Report and Written Opinion for App. No. PCT/US2020/023415, dated Jun. 12, 2020, 21 pages.

International Search Report and Written Opinion issued in International Application No. PCT/EP2014/078709 dated May 12, 2015.

International Search Report issued in International Application No. PCT/EP2014/050895 dated Mar. 14, 2014.

J. Wibbenmeyer et al., "Cloning, expression, and characterization of the Fab fragment of the anti-lysozyme antibody HyHEL-5", Biochimica et Biophysica Acta, 1999, vol. 1430, No. 2, pp. 191-202.

Jann et al., "Structural Comparison of the O6 Specific Polysaccharides From *Escherichia coli* O6:K2:H1, *Escherichia coli* P6:K13:H1, and *Escherichia coli* O6:K54:H10," Carbohydrate Research, vol. 263, No. 2, pp. 217-225 (1994).

Jansson et al., "Structural studies of the *Escherichia coli* O-antigen 6," Carbohydrate Research, vol. 131, No. 2, pp. 277-283 (1984).

Jansson et al., "Structural studies of the O-specific side-chains of the *Escherichia coli* O2 lipopolysaccharide," Carbohydrate Res., vol. 161, pp. 273-279 (1987).

Jeffrey Skolnick, et al., "From genes to protein structure and function: novel applications of computational approaches in the genomic era", in TIBTECH, vol. 18, Jan. 2000, pp. 34-39 (6 pgs.).

Jiang et al., "Tungsten-Induced Protein Aggregation: Solution Behavior," Wiley InterScience, vol. 98, No. 12, pp. 4695-4710 (2009).

Johnson et al., "*Escherichia coli* sequence type ST131 as an emerging fluoroquinolone-resistant uropathogen among renal transplant recipients," Antimicrob Agents Chemother. vol. 54, No. 1, pp. 546-550 (2010).

Johnson et al., Extraintestinal Pathogenic *Escherichi coli*: "The other bad *E coli*", J Lab Clin Med., 139(3), pp. 155-162, 2002.

Josef Prassler, et al., "In vitro affinity maturation of HuCAL antibodies: complementarity determining region exchange and RapMat technology", in Immunotherapy, vol. 1, No. 4, 2009, pp. 571-583 (13 pgs.).

Kenne et al., "Structural studies of the *Escherichia coli* O-antigen 25," Carbohydrate Research, vol. 122, No. 2, pp. 249-256 (1983).

Kim et al., "Efficiency of a pneumococal Opsonophagocytic Killing Assay Improved by Multiplexing and by Colloring Colonies", Clinical and Dianostic laboratory Immunology, pp. 616-621, Jul. 2003.

Kohler et al., "What defines extraintestinal pathogenic *Escherichia coli*", Elsevier, International journal of Medical Microbiology 301, pp. 642-647, 2011.

Laurentin et al., "A Microtiter Modification of the anthrone-sulfuric acid colorimetric assay for glucose-based carbohydrates", Analytical Biochemistry, 315, pp. 143-145, 2003.

Lazar et al. (Mol. Cell. Biol., 8:1247-1252, 1988).

Lipsitch, "Bacterial vaccines and Serotype Replacement: Lessons from Haemophilus Influenzae and Prospects for *Streptococcus pneumoniae*", Emerging Infectious Diseases, vol. 5, No. 3, May/Jun. 1999, 10 pages.

Lukac et al., "Toxoid of Pseudomonas aeruginosa exotoxin A generated by deletion of an active-site residue," Infect Immun, vol. 56, No. 12, pp. 3095-3098 (1988).

Marie-Paule Lefranc, et al., "IMGT, the international ImMunoGeneTics database", in Nucleic Acids Research, vol. 27, No. 1, 1999, pp. 209-212 (4 pgs.).

Mario F Feldman et al, "Engineering N-linked protein glycosylation with diverse O antigen lipopolysaccharide structures in *Escherichia coli*", Proceedings of the National Academy of Sciences, vol. 102, No. 8, pp. 3016-3021, (Feb. 9, 2005).

Molina-Lopez et al., "Drug resistance, serotypes, and phylogenetic groups among uropathogenic *Escherichia coli* including O25-ST131 in Mexico City," J Infect Dev Ctries, vol. 5, No. 12, pp. 840-849 (2011).

Mora A et al, "Emergence of clonal groups O1:HNM-D-ST59, O15:H1-D-ST393, O20:H34/HNM-D-ST354, O25b: H4-B2-ST131 and ONT:H21,42-B1-ST101 among CTX-M-14-producing *Escherichia coli* clinical isolates in Galicia, northwest Spain", International Journal of Antimicrobial Agents, Elsevier Science, Amsterdam, NL, vol. 37, No. 1, ISSN 0924-8579, (Jan. 1, 2011), pp. 16-21, (Dec. 13, 2010), XP027557799.

Myung-Hoon Lee, et al., "Expression and functional reconstitution of a recombinant antibody (Fab') specific for human apolipoprotein B-100", Journal of Biotechnology, 2003, vol. 101, pp. 189-198.

N. Woodford et al., "Multiresistant Gram-negative bacteria: the role of high-risk clones in the dissemination of antibiotic resistance", FEMS Microbiol Rev, 2011, vol. 35, No. 5, pp. 736-755.

(56) References Cited

OTHER PUBLICATIONS

Nadine C. Chien, et al., "Significant structural and functional change of an antigen-binding site by a distant amino acid substitution: Proposal of a structural mechanism", in Proc. Natl. Acad. Sci., vol. 86, Jul. 1989, pp. 5532-5536 (5 pgs.).
Neil S. Greenspan, et al., "Defining epitopes: It's not as easy as it seems", in Nature Biotechnology, vol. 17, Oct. 1999, pp. 936-937 (2 pgs.).
Notification Concerning Transmittal of International Preliminary Report on Patentability dated Aug. 18, 2016, in connection with corresponding international Application No. PCT/EP2014/078709 (7 pgs.).
O. Clermont et al, "Rapid detection of the O25b-ST131 clone of *Escherichia coli* encompassing the CTX-M-15-producing strains", Journal of Antimicrobial Chemotherapy, (Aug. 1, 2009), vol. 64, No. 2, doi:10.1093/jac/dkp194, ISSN 0305-7453, pp. 274-277, XP055056568.
Office Action dated Mar. 29, 2018 in Russian Patent Application No. 2015134413, with English translation.
Office Action dated Oct. 17, 2018 in corresponding Russian Application No. 2015134413/10(052839), 17 pages including English-language translation.
Office Action dated Apr. 22, 2021 in corresponding Russian Patent Application No. 2019144146/10(085375), 9 pages, with English Translation.
Office Action dated Aug. 23, 2018 in corresponding Russian Application No. 2016135962, 17 pages including English-language translation.
Office Action dated Aug. 28, 2018 in corresponding Japanese Application No. 2015-553093; 12 pages including English-language translation.
Office Action dated Oct. 4, 2018 in corresponding Japanese Application No. 2016-550556; 9 pages including English-language translation.
Pablo Umana, et al., "Engineeredglycoforms of an antineuroblastoma IgG1 with optimized antibody-dependent cellular cyto9toxic activity", in Nature Biotechnology, vol. 17, Feb. 1999, pp. 176-180 (5 pgs.).
Phan et al., "The serum resistome of a globally disseminated multidrug resistant uropathogenic *Escherichia coil* clone," PLOS Genetics, vol. 9, No. 10, pp. 1-18 (2013).
Pinayev et al., "The Cell Cultures", Information Gazette, 2010, Issue 26, St. Petersburg, 61 pages.
Pitout et al., "Extraintestinal Pathogenic *Escherichia coli*: An Update on Antimicrobial Resistance, Laboratory Diagnosis and Treatment," Expert Rev. Anti. Infect. Then, vol. 10, No. 10, pp. 1165-1176 (2012).
Poolman et al., "Extraintestinal Pathogenic *Escherichia coli*, a Common Human Pathogen: Challenges for Vaccine Development and Progress in the Field," Journal of Infectious Diseases, vol. 213, pp. 6-13 (2016).
Poolman, J.T., et al, "The history of pneumococcal conjugate vaccines development: dose selection," Expert Reviews Vaccines, vol. 12 (12), pp. 1379-1394 (2013).
Reschedko, G.K. et al, "*Escherichia coli* as a Nosocomial Pathogen in ICUs", Clinical microbiology and antimicrobial chemotherapy, 2011, vol. 13, No. 4, pp. 314-321.
Response to Austrian Office Action dated Mar. 12, 2019 in Austrian Patent Application No. 2018204437.
Royt A et al., "Hypervariable sequences of antigen-recognition centers enable binding of various antigens by antibodies", Immunology, Moscow, "Mir" Publishers 2000, 4 pages including English-language translation, abstract only.
Russian Office Action dated Apr. 24, 2018, in connection with corresponding RU Application No. 2016135962/10 (056446) (5 pgs.).
Russian Office Action dated Dec. 27, 2017, in connection with corresponding RU Application No. 2015134413/10 (052839) (18 pgs., including English translation).
Russo et al., "A killed, genetically engineered derivative of a wild-type extraintestinal pathogenic *E coli* strain is a caccine candidate", Elsevier, Vaccine 25, pp. 3859-3870, 2007.
Russo et al., "Medical and Exonomic impact of extraintestinal infections due to *Escherichia coli*: focus on an Increasingly important endemic problem", Elsevier, Microbes and Infection 5, pp. 449-456, 2003.
S. Muller-Loennies, et al., "Structural Analysis of Oligosaccharides from Lipopolysaccharide (LPS) of *Escherichia coli* K12 Strain W3100 Reveals a Link between Inner and Outer Core LPS Biosynthesis", The Journal of Biological Chemistry, Sep. 5, 2003, vol. 278, No. 36, pp. 34090-34101.
Van Den Dobbelsteen Germie P J M et al, "Immunogenicity and safety of a tetravalent*E. coli*O-antigen bioconjugate vaccine in animal models", Vaccine, Elsevier, Amsterdam, NL, (Jul. 6, 2016), vol. 34, No. 35, doi:10.1016/J.VACCINE.2016.06.067, ISSN 0264-410X, pp. 4152-4160, XP029644969.
Ihssen Julian et al, "Production of glycoprotein vaccines in *Escherichia coli*", Microbial Cell Factories,, (Aug. 11, 2010), vol. 9, No. 1, doi:10.1186/1475-2859-9-61, ISSN 1475-2859, p. 61, XP021077209.
Roland Stenutz et al, "The structures of*Escherichia coli* O-polysaccharide antigens", FEMS Microbiology Reviews, Elsevier, Amsterdam; NL, vol. 30, doi:10.1111/J.1574-6976.2006.00016.X, ISSN 0168-6445, (Jan. 1, 2006), pp. 382-403, (Feb. 9, 2006), XP007921666.
ClinicalTrials.gov archive, "History of Changes for Study: NCT03819049, A Study of Three Different Doses of VAC52416 (ExPEC10V) in Adults Aged 60 to 85 Years in Stable Health", htt;s://clinicaltrials.gov/ct2/history/NCT03819049, Aug. 6, 2019 (v6), 6 pages.
Jansson et al., "Sturctural Studies of the O-Antigen Polysaccharide of *Escherichia coli* O4", Carbohydrate Research, 134 (1984) 283-291.
Saade, Elie, et al., "Charactertization of *Escherichia coli* isolates potentially covered by ExPEC4V and ExPEC10V, that were collected from post-transrectal ultrasound-guided prostate needle biopsy," Vasccine, Elsevier, Amsterdam, NL, vol. 38, No. 33, Jun. 16, 2020 pp. 5100-5104.
Savita Jadhav et al, "Virulence Characteristics and Genetic Affinities of Multiple Drug Resistant Uropathogenic *Escherichia coli* from a Semi Urban Locality in India", PLOS One, (Jan. 1, 2011), vol. 6, No. 3, doi:10.1371/journal.pone.0018063, ISSN 1932-6203, p. e18063, XP055056608.
Schito et al., "The ARESC study: an international survey on the antimicrobial resistance of pathogens involved in uncomplicated urinary tract infections", Elsevier, International Journal of Antimicrobial Agents 34, pp. 407-413, 2009.
Seidl et al., "Tungsten-Induced Denaturation and Aggregation of Epoetin Alfa During Primary Packaging as a Cause of Immunogenicity," Pharm. Res., vol. 29, pp. 1454-1467 (2012).
Simone Cagnacci, et al., "European Emergence of Ciprofloxacin-Resistant *Escherichia coli* Clonal Groups O25:H4-ST131 and O15:K52:H1 Causing Community-Acquired Uncomplicated Cystitis", in the Journal of Clinical Microbiology, Aug. 2008, vol. 46, No. 8, pp. 2605-2612 (8 pgs.).
Stenutz Roland et al, "The structures of *Escherichia coli* O-polysaccharide antigens", FEMS Microbiology Reviews, (May 2006), vol. 30, No. 3, ISSN 0168-6445, pp. 382-403, XP007921666.
Stevenson et al., "Structure of the O antigen of *Escherichia coli* K-12 and the sequence of its rfb gene cluster," J. Bacteriol., vol. 176, No. 13, pp. 4144-4156 (1994).
Stoute et al., "A Preliminary Evaluation of a Recombinant Circumsporozoite Protein Vaccine Against Plasmodium Falciparum Malaria," New England Journal of Medicine, vol. 336, pp. 86-91 (1997).
Szijarto et al., "Bactericidal Monoclonal Antibodies Specific to the Lipopolysaccharide 0 Antigen from Multidrug-Resistant *Escherichia coli* Clone ST131-025b:H4 Elicit Protection in Mice," Antimicrobial Agents and Chemotherapy, Jun. 2015, vol. 59, No. 6, pp. 3109-3116, XP009187151.
Szijarto et al., "Diagnostic Potential of Monoclonal Antibodies Specific to the Unique O-Antigen of Multidrug-Resistant Epidemic *Escherichia coli* Clone ST131-025b:H4," Clinical and Vaccine Immunology, Jul. 2014, vol. 21, No. 7, p. 930-939.

(56) References Cited

OTHER PUBLICATIONS

Terai et al., "*Escherichia coli* Virulence Factors and Serotypes in Acute Bacterial Prostatitis," Int. Journal of Urology, vol. 4, No. 3, pp. 289-294 (1997).
Vajdos et al., "Comprehensive Functional Maps of the Antigen-binding Site of an Anti-ErbB2 Antibody Obtained with Shotgun Scanning Mutagenesis," J Mol. Biol. 2002, vol. 320(2), pp. 415-428.
Valéria Szijártó et al, "The rapidly emerging ESBL-producing *Escherichia coli*O25-ST131 clone carries LPS core synthesis genes of the K-12 type", FEMS Microbiology Letters, (Jul. 1, 2012), vol. 332, No. 2, doi: 10.1111/j.1574-6968.2012.02585.x, ISSN 0378-1097, pp. 131-136, XP055056565.
Van Den Dobbelsteen et al., "Immunogenicity and safety of tetravalent *Escherichia coli* O-antigen bioconjugate vaccine in animal models," Vaccine, vol. 34, No. 35, pp. 4152-4160 (2016).
Wacker et al., "N-linked glycosylation in Campylobacter jejuni and its functional transfer into *Escherichia coli*," Science, vol. 298, No. 5599, pp. 1790-1793 (2002).
Wacker, M., et al., "Substrate specificity of bacterial oliogsaccharyltransferase suggests a common transfer mechanism for the bacterial and eukaryotic systems," PNAS, vol. 103, No. 18, pp. 7088-7093, May 2, 2006.
Written Opinion dated Dec. 21, 2018 in Int'l Application No. PCT/EP2017/077123, 8 pages.
Written opinion of the Int'l Searching Authority dated Jan. 24, 2018 in Int'l Application No. PCT/EP2017/077123, 6 pages.
Written Opinion of the International Preliminary Examining Authority dated Sep. 11, 2018 in PCT/EP2017/077123, 8 pages.
Written Opinion of the International Searching Authority dated Mar. 14, 2014, in connection with corresponding International Application No. PCT/EP2014/050895.
Yakubke et al., "Amino acids, peptides, proteins", MTR Publishers, 1985, 456 pages.
"Typhoid Vi Polysaccharide Vaccine Typhim VI," Sanofi Pasteur Inc., vol. 3., pp. 1-26 (Mar. 2014).
A. Cross et al, "Safety And Immunogenicity Of A Polyvalent *Escherichia coli* Vaccine In Human Volunteers", Journal of Infectious Diseases. JID, Chicago, IL., (Oct. 1, 1994), vol. 170, No. 4, doi:10.1093/infdis/170.4.834, ISSN 0022-1899, pp. 834-840, XP055311603.
Abbanat et al., Poster presented at ASM's Interscience Conference of Antimicrobial Agents and Chemotherapy (ICAAC), Jun. 16-20, 2016, Boston, 1 page.
Amor et al., "Distribution of Core Oligosaccharide Types in Lipopolysaccharides from *Escherichia coli*," Infection and Immunity, Mar. 2000, p. 1116-1124.
Angela M. Giusti, et al., "Somatic diversification of S107 from an antiphosphocholine to an anti-DNA autoantibody is due to a single base change in its heavy chain variable region", in Proc. Natl. Acad. Sci., vol. 84, May 1987, pp. 2926-2930 (5 pgs.).
Angela Novais, et al., "Contribution of IncFII and Broad-Host IncA/C and IncN Plasmids to the Local Expansion and Diversification of Phylogroup B2 *Escherichia coli* ST131 Clones Carrying blaCTX-M-15 and qnrS1 Genes", in Antimicrobial Agents and Chemotherapy, vol. 56, No. 5, May 2012, pp. 2763-2766 (4 pgs.).
Arturo Casadevall, et al., "Immunoglobulin isotype influences affinity and specificity", in PNAS, vol. 109, No. 31, Jul. 31, 2012, pp. 12272-12273 (2 pgs.).
B. A. Rogers et al, "*Escherichia coli* O25b-ST131: a pandemic, multiresistant, community-associated strain", Journal of Antimicrobial Chemotherapy, (Jan. 1, 2011), vol. 66, No. 1, doi:10.1093/jac/dkq415, ISSN 0305-7453, pp. 1-14, XP055056619.
B.R. Brodeur et al., "Mouse-Human Myelome Partners for the Production of Heterohybridomas", Monoclonal Antibody Production Techniques and Applications, Marcel Dekker, Inc., 1987, pp. 51-63.
Banerjee et al., "A new clone sweeps clean: the enigmatic emergence of *Escherichia coli* sequence type 131," Antimicrob Agents Chemother. vol. 58, No. 9, pp. 4997-5004 (2014).
Blanco et al., "Virulence factors and 0 groups of *Escherichia coli* isolates from patients with acute pyelonephritis, cystitis and asymptomatic bacteriuria," Eur. J. Epidemiol., vol. 12, No. 2, pp. 191-198 (1996).
Blanco et al., "Molecular epidemiology of *Escherichia coli* producing extended-spectrum {beta}-lactamases in Lugo (Spain): dissemination of clone O25b:H4-ST131 producing CTX-M-15," J. Antimicrob. Chemother., vol. 63, pp. 1135-1141 (2009).
Bowie etal. (Science, 1990, 247:1306-1310).
Brown et al., "Tolerance to Single, but Not Multiple, Amino Acid Replacements in Antibody Vh CDR2," The Journal of Immunology, 1996, 156: 3285-3291.
Burgess et al. (J. Cell Biol. 111:2129-2138, 1990).
Chris Galanos, et al., "Galactosamine-induced sensitization to the lethal effects of endotoxin", in Proc. Natl. Acad. Sci., vol. 76, No. 11, Nov. 1979, pp. 599-5943 (5 pgs.).
Claudia Sheedy, et al., "Isolation and affinity maturation of hapten-specific antibodies", in Biotechnolgy Advances 25, 2007, pp. 333-352 (20 pgs.).
Clermont et al, "The CTX-M-15-producing *Escherichia coli* diffusing clone belongs to a highly virulent B2 phylogenetic subgroup," J. Antimicrob. Chemother., vol. 61, No. 5, pp. 1024-1028 (2008).
Cristina Caldas, et al., "Humanization of the anti-CD18 antibody 6.7: an unexpected effect of a framework residue in binding to antigen", in Molecular Immunology, vol. 39, 2003, pp. 941-952 (12 pgs.).
Cryz et al., "Synthesis and Characterization of *Escherichia coli* 018 O-Polysaccharide Conjugate Vaccines," Infection and Immunity, Feb. 1990, p. 373-377.
Cryz S J et al, "Synthesis and characterization of a polyvalent *Escherichia coli* O-polysaccharide-toxin A conjugate vaccine", Vaccine, Elsevier Ltd, GB, (Jan. 1, 1995), vol. 13, No. 5, doi:10.1016/0264-410X(94)00009-C, ISSN 0264-410X, pp. 449-453, XP004057719.
D. Kozbor et al., "A Human Hybrid Myeloma for Production of Human Monoclonal Antibodies", The Journal of Immunology, Dec. 1984, vol. 133, No. 6, pp. 3001-3005.
Datsenko et al., "One-step inactivation of chromosomal genes in *Escherichia coli* K-12 using PCR products," PNAS, vol. 97, No. 12, pp. 6640-6645 (2000).
Debroy et al., "Detection of O antigens in *Escherichia coli*," Animal Health Research Reviews, vol. 12, No. 2, pp. 169-185 (2011).
Denka Seiken Co. Ltd.(Catalogue), Bacterial Antisera "Seiken", [Denka Seiken Co., Ltd, MSDS No. 200000-01, Feb. 16, 2010.
Duda et al., "The lipopolysaccharide of the mastitis isolate *Escherichia coli* strain 1303 comprises a novel O-antigen and the rare K-12 core type," Microbiology (2011), 157, 1750-1760, doi: 10.1099/mic.0.046912-0.
European Office Action dated Mar. 7, 2017, in connection with corresponding EP Application No. 14703783.2 (7 pgs.).
European Search Report issued in International Application No. 13151627.0 dated Mar. 28, 2013.
Extended European Search Report dated Jul. 16, 2014, in connection with corresponding EP Application No. 14154158.1 (5 pgs.).
Extended European Search Report dated Mar. 14, 2017, including the European Search Report and the European Search Opinion, in connection with corresponding EP Application No. 16201732.1 (10 pgs.).
Extended Search Report dated Sep. 10, 2021 in EP Application No. 21154782.3.
Extended Search Report dated Apr. 12, 2017 in EP Application No. 16195256.9, 8 pages.
Foxman, "Epidemiology of Urinary Tract Infections: Incidence, morbidity, and Economic Costs", The American Journal of Medicine, vol. 113(1A), 5S-13S, Jul. 2002.
Fratamico et al., "*Escherichia coli* serogroup O2 and O28ac O-antigen gene cluster sequences and detection of pathogenic *Escherichia coil* O2 and O28ac by PCR," Canadian Journal of Microbiology, vol. 56, No. 4, pp. 308-316 (2010).
Frenck, et al., "Safety and Immunogenicity of a vaccine for extra-intestinal pathogenic *Escherichia coli* (ESTELLA): a phase 2 randomised controlled trial," Lancet Infect. Dis. vol. 1, No. 6, pp. 631-640 (2019).

(56) References Cited

OTHER PUBLICATIONS

Fundin et al., "NMR analysis of the O-antigen polysaccharide from *Escherichia coli* strain F171," Magnetic Resonance in Chemistry, vol. 41, No. 3, pp. 202-205 (2003).
G. Kohler et al., "Continuous cultures of fused cells secreting antibody of predefined specificity", Nature, Aug. 7, 1975, vol. 256, pp. 495-497.
G. Peirano, et al., "Molecular characteristics of extended-spectrum β-lactamase-producing *Escherichia coli* from the Chicago area: high prevalence of ST131 producing CTX-M-15 in community hospitals", International Journal of Antimicrobial Agents, 2010, vol. 36, pp. 19-23.
G. Peirano, et al., "Molecular epidemiology of *Escherichia coli* producing CTX-M beta-lactamases: the worldwide emergence of clone ST131 O25:H4", in International Journal of Antimicrobial Agents, vol. 35, 2010, pp. 316-321 (7 pgs.).
Gabor Nagy et al., "Lipopolysaccharide: a tool and target in enterobacterial vaccine development", in Biological Chemistry, vol. 389, No. 5, Jan. 2008, 8 pgs. (XP055349068).
Gisele Peirano, et al., "Characteristics of *Escherichia coli* Sequence Type 131 Isolates That Produce Extended-Spectrum B-Lactamases: Global Distribution of the H30-Rx Sublineage", in Antimicrobial Agents and Chemotherapy, vol. 58, No. 7, Jul. 2014, pp. 3762-3767 (6 pgs.).
Glover et al., "Chemoenzymatic synthesis of Glycopeptides with PgIB, a bacterial oligosaccharyl transferase from Campylobacter jejuni," Chemistry and Biology, Current Biology, vol. 12, No. 12, pp. 1311-1316 (2005).
Helen Miajlovic, et al., "Response of Extraintestinal Pathogenic *Escherichia coli* to Human Serum Reveals a Protective Role for Rcs-Regulated Exopolysaccharide", in Infection and Immunity, vol. 82, No. 1, Jan. 2014, pp. 298-305 (8 pgs.).
Ho et al., Preclinical Laboratory Evaluation of a Bivalent *Staphylococcus aureus* Saccharide-Exotoxin A Protein Conjugate Vaccine, Human vaccines, 2:3, pp. 89-98, May/Jun. 2006.
Huttner et al., "Safety, immunogenicity, and preliminary clinical efficacy of a vaccine against extraintestinal pathogenic *Escherichia coli* in women with a history of recurrent urinary tract infection: a randomised, single-blind, placebo-controlled phase 1b trial", Lancet Infect Dis., 2017, vol. 17, No. 5, pp. 528-537.
Ihssen et al., "Production of glycoprotein vaccines in *Escherichia coli*," Microbial Cell Factories, vol. 9, No. 61, pp. 1-13 (2010).
Int'l Preminary Report on Patentability dated Feb. 14, 2019 in Int'l Application No. PCT/EP2017/077123, 16 pages.
Int'l Search Report and Written Opinion dated Jul. 20, 2017 in Int'l Application No. PCT/US2016/048278, 9 pages.
Int'l Search Report and Written Opinion dated Jun. 15, 2015 in Int'l Application No. PCT/EP2015/053739, 10 pages.
Int'l Search Report and Written Opinion dated Oct. 27, 2016 in Int'l Application No. PCT/US2016/048278, 16 pages.
International Search Report dated Jun. 12, 2020 in PCT/US2020/023404, 5 pages.
Written Opinion dated Jun. 12, 2020 in PCT/US2020/023404, 6 pages.

Gel 1:

| Lane | Sample Name | *gtrS* | Amount loaded (µl) |
|---|---|---|---|
| 1 | Marker | NA | 5.0 |
| 2 | A2525 | Negative | 4.0 |
| 3 | Y1382 | Positive | 3.6 |
| 4 | stGVXN4986 | Negative | 4.2 |
| 5 | E551 | Positive | 3.9 |
| 6 | OC24784 | Negative | 4.5 |
| 7 | OC24334 | Positive | 4.1 |
| 8 | OC24787 | Negative | 4.2 |
| 9 | stGVXN4983 | Positive | 3.9 |
| 10 | OC9487 neg. control | NA | 4.1 |
| 11 | Marker | NA | 5.0 |
| 12 | EMPTY | - | - |

Gel 2:

| Lane | Sample Name | *gtrS* | Amount loaded (µl) |
|---|---|---|---|
| 1 | Marker | NA | 5.0 |
| 2 | stGVXN4994 | Positive | 4.0 |
| 3 | OC24788 | Negative | 4.2 |
| 4 | OC24794 | Positive | 3.9 |
| 5 | OC9487 neg. control | Reduced | 4.1 |
| 6 | Marker | NA | 5.0 |

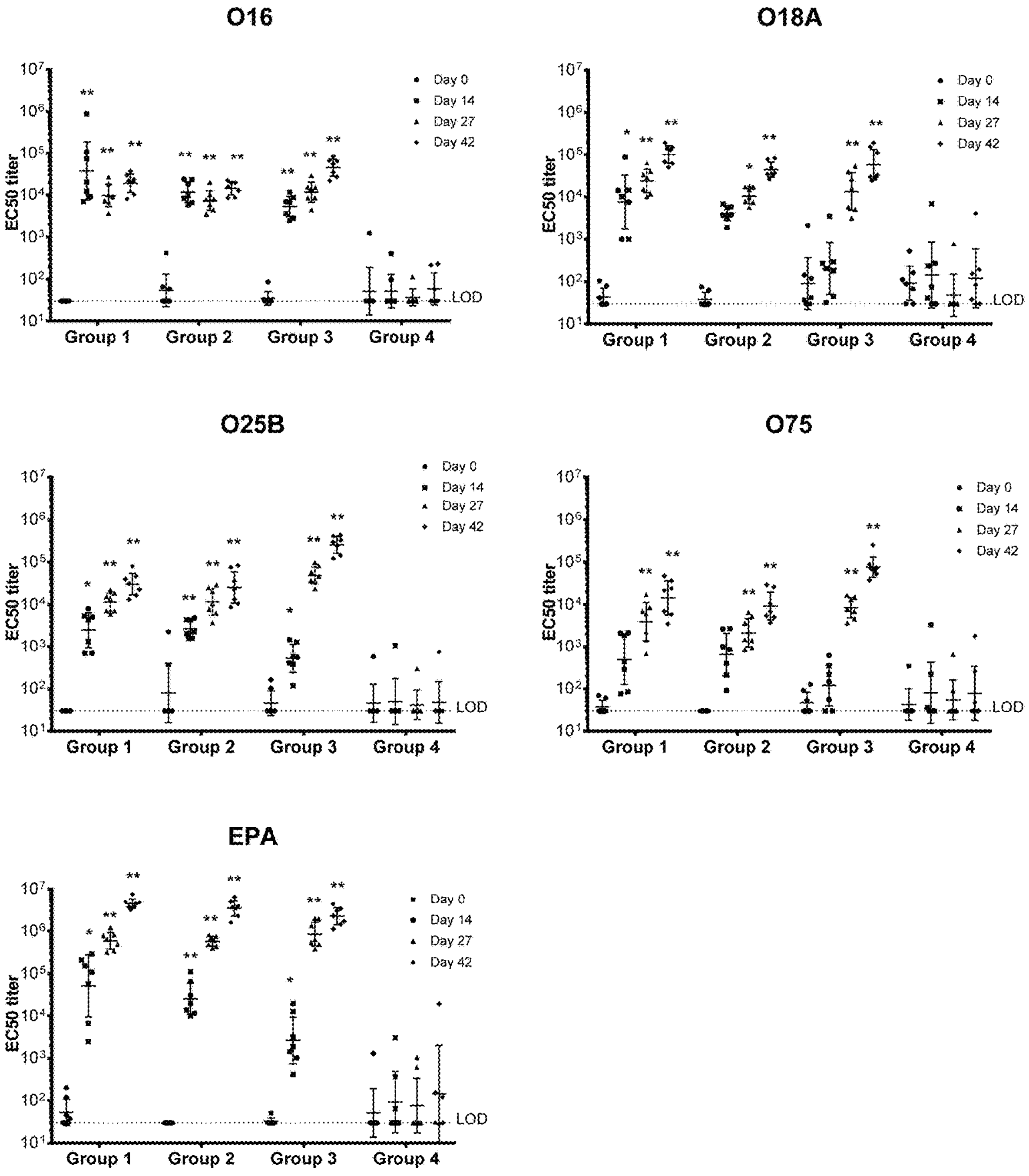
Fig. 8 - continued

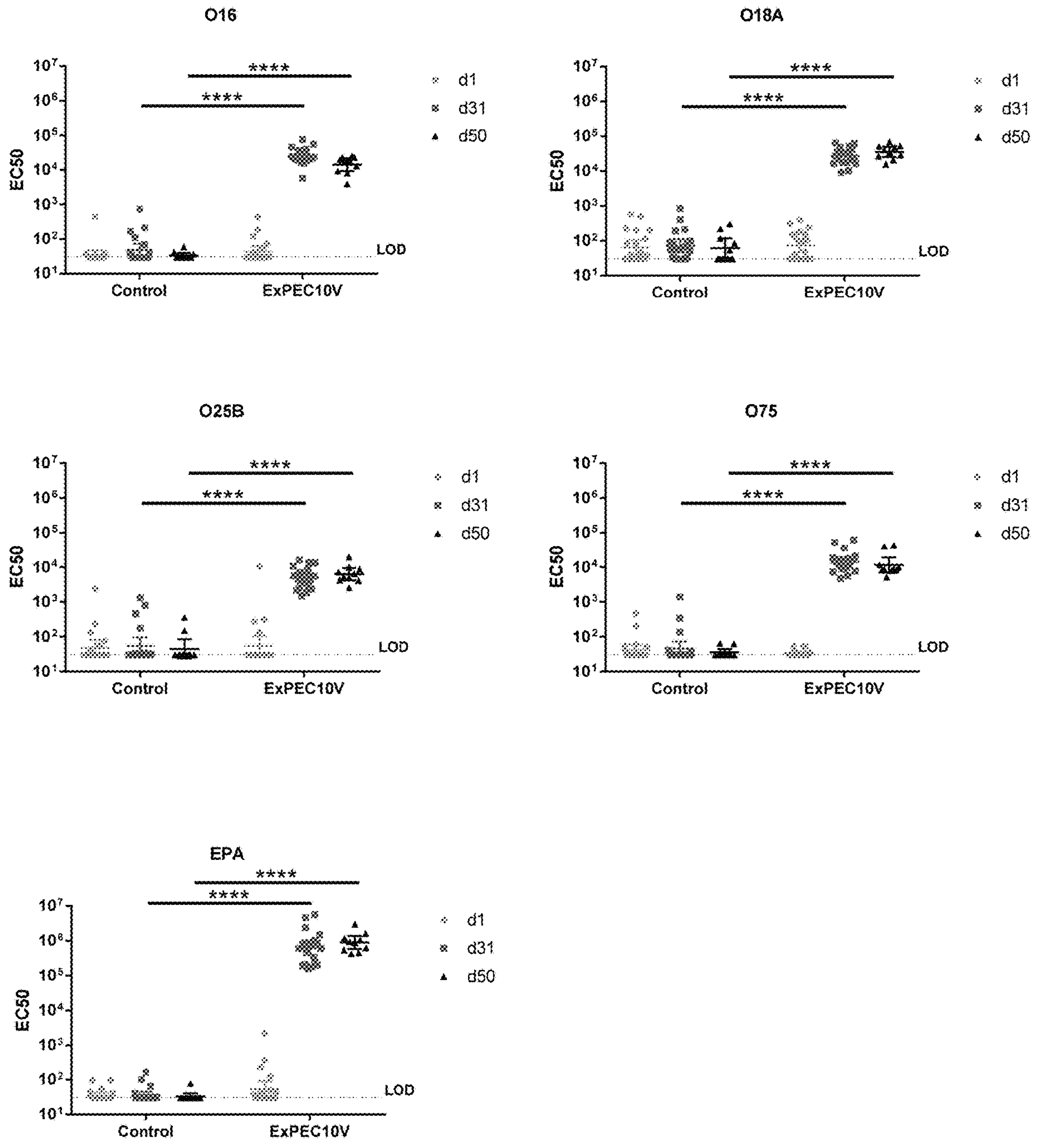
Fig. 9 - continued

BIOCONJUGATES OF *E. COLI* O-ANTIGEN POLYSACCHARIDES, METHODS OF PRODUCTION THEREOF, AND METHODS OF USE THEREOF

CROSS REFERENCE TO RELATED APPLICATION

This application is a divisional of U.S. patent application Ser. No. 16/822,340 filed Mar. 18, 2020, which claims priority to U.S. Provisional Application No. 62/819,746 filed on Mar. 18, 2019, the disclosures of which are incorporated herein by reference in their entirety.

REFERENCE TO SEQUENCE LISTING SUBMITTED ELECTRONICALLY

The contents of the sequence listing (SequenceListing_90US3.xml; Size: 156,438 bytes; and Date of Creation: Sep. 6, 2022) is part of the specification and is herein incorporated by reference in its entirety

BACKGROUND OF THE INVENTION

Extraintestinal pathogenic *Escherichia coli* (ExPEC) strains are normally harmless inhabitants of the human gastrointestinal tract, alongside commensal *E. coli* strains. ExPEC isolates cannot readily be distinguished from commensal isolates by serotype, although many clonal lineages are dominated by ExPEC, as defined by O-antigen, capsule and flagellar antigen serotypes (abbreviated as O:K:H, for example O25:K1:H4). In contrast to commensal *E. coli*, ExPEC strains express a broad array of virulence factors enabling them to colonize the gastrointestinal tract, as well as to cause a wide range of extraintestinal infections, which are associated with a significant healthcare cost burden due to hospitalization and death. Neonates, the elderly, and immunocompromised patients are particularly susceptible to ExPEC infection, including invasive ExPEC disease (IED).

ExPEC strains are the most common cause of urinary tract infections (UTI) and important contributors to surgical site infections and neonatal meningitis. The strains are also associated with abdominal and pelvic infections and nosocomial pneumonia, and are occasionally involved in other extraintestinal infections, such as osteomyelitis, cellulitis, and wound infections. All these primary sites of infection can result in ExPEC bacteremia. ExPEC is the most common cause of community-onset bacteremia and a major causative pathogen in nosocomial bacteremia and is found in about 17% to 37% of clinically significant blood isolates. Patients with an ExPEC-positive blood culture typically suffer sepsis syndrome, severe sepsis, or septic shock. Increasing resistance of ExPEC against first-line antibiotics including the cephalosporins, fluoroquinolones, and trimethoprim/sulfamethoxazole has been observed. The emergence and rapid global dissemination of ExPEC sequence type 131 (ST131) is considered a main driver of increased drug resistance, including multi-drug resistance. This clone is found in 12.5% to 30% of all ExPEC clinical isolates, exhibits mostly serotype O25b:H4, and shows high levels of resistance to fluoroquinolones, which is often accompanied by trimethoprim/sulfamethoxazole resistance and extended-spectrum beta-lactamases conferring resistance to cephalosporins.

The O-antigen comprises the immunodominant component of the cell wall lipopolysaccharide (LPS) in Gram-negative bacteria, including *E. coli*. There are currently >180 serologically unique *E. coli* O-antigens identified, with the vast majority of ExPEC isolates classified within less than 20 O-antigen serotypes. Full-length *E. coli* O-antigens are typically comprised of about 10 to 25 repeating sugar units attached to the highly conserved LPS core structure, with each component synthesized separately by enzymes encoded predominantly in the rfb and rfa gene clusters, respectively. Following polymerization of the O-antigen, the O-antigen polysaccharide backbone may be modified, typically through the addition of acetyl or glucose residues. These modifications effectively increase serotype diversity by creating antigenically distinct serotypes that share a common polysaccharide backbone, but differ in side branches. Genes encoding O-antigen modifying enzymes typically reside outside of the rfb cluster on the chromosome, and in some cases, these genes are found within lysogenic bacteriophages.

ExPEC isolates belonging to the O4 serogroup have been commonly identified in contemporary surveillance studies of U.S. and EU blood isolates. The structure of the O4 polysaccharide was determined as→2) α-L-Rha (1→6) α-D-Glc (1→3) α-L-FucNAc (1→3) β-D-GlcNAc (1→ from an *E. coli* O4:K52 strain (Jann et al., *Carbohydr. Res.* (1993) v. 248, pp. 241-250). A distinct form of the O4 polysaccharide structure was determined for O4:K3, O4:K6 and O4:K12 strains, in which the structure above was modified by the addition of an α-D-Glc (1→3) linked to the rhamnose residue of the polysaccharide (Jann et al., 1993, supra), this form of the polysaccharide referred to herein below as 'glucosylated O4'. The enzymes responsible for the O-antigen modification within *E. coli* O4 strains were not identified.

Efforts toward the development of a vaccine to prevent ExPEC infections have focused on O-antigen polysaccharide conjugates. A 12-valent O-antigen conjugate vaccine was synthesized through extraction and purification of O-antigen polysaccharide and chemical conjugation to detoxified *Pseudomonas aeruginosa* exotoxin A and tested for safety and immunogenicity in a Phase 1 clinical study (Cross et al., *J. Infect. Dis.* (1994) v. 170, pp. 834-40). This candidate vaccine was never licensed for clinical use. A bioconjugation system in *E. coli* has been developed recently, in which the polysaccharide antigen and the carrier protein are both synthesized in vivo and subsequently conjugated in vivo through the activities of the oligosaccharyl transferase PglB, a *Campylobacter jejuni* enzyme, expressed in *E. coli* (Wacker et al., *Proc. Nat. Acad. Sci.* (2006) v. 103, pp. 7088-93). This N-linked protein glycosylation system is capable of the transfer of diverse polysaccharides to a carrier protein, allowing for straightforward methods to purify the conjugate.

Bioconjugation has been used successfully to produce conjugate polysaccharide for an *E. coli* four-valent O-antigen candidate vaccine (Poolman and Wacker, *J. Infect. Dis.* (2016) v. 213(1), pp. 6-13). However, the development of a successful ExPEC vaccine requires coverage of predominant serotypes, and the presence of further O-antigen modifications in subsets of ExPEC isolates presents a further challenge in covering isolates displaying unmodified and modified LPS.

BRIEF SUMMARY OF THE INVENTION

In view of increasing antibiotic resistance among ExPEC isolates and the presence of further O-antigen modifications among predominant O-serotypes, there is a need for improved prophylactic and therapeutic treatments for these infections. The invention satisfies this need by defining the genetic composition of contemporary clinical isolates, including identifying the genes encoding O-antigen modifying enzymes, thus allowing for the engineering of recombinant host cells capable of synthesizing bioconjugates of the O-antigens including bioconjugates comprising selected O-antigen modifications.

In one aspect, provided herein is a bioconjugate of an *E. coli* glucosylated O4 antigen polysaccharide covalently linked to a carrier protein, wherein the *E. coli* glucosylated O4 antigen polysaccharide comprises the structure of Formula (O4-Glc+) as shown in Table 1, wherein n is an integer of 1 to 100, preferably 1 to 50, e.g. 3 to 50, e.g. 5 to 40, e.g. 7 to 25, e.g. 10 to 20.

In a particular embodiment, the *E. coli* glucosylated O4 antigen polysaccharide is covalently linked to an Asn residue in a glycosylation site comprising a glycosylation consensus sequence having SEQ ID NO: 1, preferably having SEQ ID NO: 2, in the carrier protein.

In some embodiments, the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

In a particular embodiment, the carrier protein is a detoxified exotoxin A of *Pseudomonas aeruginosa* (EPA). In such embodiments, the EPA preferably comprises 1 to 20, preferably 1 to 10, preferably 2 to 4, glycosylation consensus sequences having SEQ ID NO: 1, the consensus sequences preferably having SEQ ID NO: 2.

In a particular embodiment, the carrier protein comprises four glycosylation consensus sequences (EPA-4). In a preferred embodiment, the carrier protein comprises SEQ ID NO: 3.

In another aspect, provided herein is a composition or immunogenic composition comprising a bioconjugate of an *E. coli* glucosylated O4 antigen polysaccharide covalently linked to a carrier protein as described herein.

In some embodiments, a composition or immunogenic composition comprises at least one additional antigen polysaccharide covalently linked to a carrier protein.

In some embodiments, a composition or immunogenic composition comprises at least one additional antigen polysaccharide covalently linked to a carrier protein, wherein the at least one additional antigen polysaccharide is selected from the group consisting of *E. coli* O1A antigen polysaccharide, *E. coli* O2 antigen polysaccharide, *E. coli* O6A antigen polysaccharide, *E. coli* O8 antigen polysaccharide, *E. coli* O15 antigen polysaccharide, *E. coli* O16 antigen polysaccharide, *E. coli* O18A antigen polysaccharide, *E. coli* O25B antigen polysaccharide, and *E. coli* O75 antigen polysaccharide. In specific embodiments, the *E. coli* O1A antigen polysaccharide comprises the structure of Formula (O1A) as shown in Table 1, wherein n is an integer of 1 to 100, preferably 3 to 50, for example 5 to 40, e.g. 7 to 25, e.g. 10 to 20. In specific embodiments, the *E. coli* O2 antigen polysaccharide comprises the structure of Formula (O2) as shown in Table 1, wherein n is an integer of 1 to 100, preferably 3 to 50, for example 5 to 40, e.g. 7 to 25, e.g. 10 to 20. In specific embodiments, the *E. coli* O6A antigen polysaccharide comprises the structure of Formula (O6A) as shown in Table 1, wherein n is an integer of 1 to 100, preferably 3 to 50, for example 5 to 40, e.g. 7 to 25, e.g. 10 to 20. In specific embodiments, the *E. coli* O8 antigen polysaccharide comprises the structure of Formula (O8) as shown in Table 1, wherein n is an integer of 1 to 100, preferably 3 to 50, for example 5 to 40, e.g. 7 to 25, e.g. 10 to 20. In specific embodiments, the *E. coli* O15 antigen polysaccharide comprises the structure of Formula (O15) as shown in Table 1, wherein n is an integer of 1 to 100, preferably 3 to 50, for example 5 to 40, e.g. 7 to 25, e.g. 10 to 20. In specific embodiments, the *E. coli* O16 antigen polysaccharide comprises the structure of Formula (O16) as shown in Table 1, wherein n is an integer of 1 to 100, preferably 3 to 50, for example 5 to 40, e.g. 7 to 25, e.g. 10 to 20. In specific embodiments, the *E. coli* O18A antigen polysaccharide comprises the structure of Formula (O18A) as shown in Table 1, wherein n is an integer of 1 to 100, preferably 3 to 50, for example 5 to 40, e.g. 7 to 25, e.g. 10 to 20. In specific embodiments, the *E. coli* O25B antigen polysaccharide comprises the structure of Formula (O25B) as shown in Table 1, wherein n is an integer of 1 to 100, preferably 3 to 50, for example 5 to 40, e.g. 7 to 25, e.g. 10 to 20. In specific embodiments, the *E. coli* O75 antigen polysaccharide comprises the structure of Formula (O75) as shown in Table 1, wherein n is an integer of 1 to 100, preferably 3 to 50, for example 5 to 40, e.g. 7 to 25, e.g. 10 to 20.

In certain embodiments, each of the additional *E. coli* O1A, O2, O6A, O8, O15, O16, O18A, O25B, and/or O75 antigen polysaccharides is covalently bound to an Asn reside in a glycosylation site comprising a glycosylation consensus sequence having SEQ ID NO: 1, preferably having SEQ ID NO: 2, in each of the carrier protein. In particular embodiments, each of the carrier protein is a detoxified exotoxin A of *Pseudomonas aeruginosa* (EPA). Preferably, each EPA comprises 1-10, preferably 2-4, preferably 4 glycosylation sites each comprising a glycosylation consensus sequence having SEQ ID NO: 2. In particular embodiments, each EPA comprises SEQ ID NO: 3.

In particular embodiments, the composition or immunogenic composition comprises at least the *E. coli* O1A, O2, glucosylated O4, O6A and O25B antigen polysaccharides each covalently linked to a carrier protein. In particular embodiments, the composition or immunogenic composition comprises at least the *E. coli* O1A, O2, glucosylated O4, O6A, O8, O15, O16, O25B, and O75 antigen polysaccharides each covalently linked to a carrier protein. In particular embodiments, the composition or immunogenic composition comprises at least the *E. coli* O1A, O2, glucosylated O4, O6A, O8, O15, O16, O18A, O25B, and O75 antigen polysaccharides each covalently linked to a carrier protein.

In a particular aspect, provided is a composition or immunogenic composition that comprises:

(i) a bioconjugate of an *E. coli* glucosylated O4 antigen polysaccharide covalently linked to a detoxified Exotoxin A of *P. aeruginosa* (EPA-4) carrier protein comprising SEQ ID NO: 3, wherein the *E. coli* glucosylated O4 antigen polysaccharide comprises the structure of Formula (O4-Glc+);

(ii) a bioconjugate of an *E. coli* O1A antigen polysaccharide covalently linked to an EPA-4 carrier protein, wherein the *E. coli* O1A antigen polysaccharide comprises the structure of Formula (O1A);

(iii) a bioconjugate of an *E. coli* O2 antigen polysaccharide covalently linked to an EPA-4 carrier protein, wherein the *E. coli* O2 antigen polysaccharide comprises the structure of Formula (O2);

(iv) a bioconjugate of an *E. coli* O6A antigen polysaccharide covalently linked to an EPA-4 carrier protein, wherein the *E. coli* O6A antigen polysaccharide comprises the structure of Formula (O6A);

(v) a bioconjugate of an *E. coli* O8 antigen polysaccharide covalently linked to an EPA-4 carrier protein, wherein the *E. coli* O8 antigen polysaccharide comprises the structure of Formula (O8);

(vi) a bioconjugate of an *E. coli* O15 antigen polysaccharide covalently linked to an EPA-4 carrier protein, wherein the *E. coli* O15 antigen polysaccharide comprises the structure of Formula (O15);

(vii) a bioconjugate of an *E. coli* O16 antigen polysaccharide covalently linked to an EPA-4 carrier protein, wherein the *E. coli* O16 antigen polysaccharide comprises the structure of Formula (O16);

(viii) a bioconjugate of an *E. coli* O25B antigen polysaccharide covalently linked to an EPA-4 carrier protein, wherein the *E. coli* O25B antigen polysaccharide comprises the structure of Formula (O25B); and (ix) a bioconjugate of an *E. coli* O75 antigen polysaccharide covalently linked to an EPA-4 carrier protein, wherein the *E. coli* O75 antigen polysaccharide comprises the structure of Formula (O75), wherein the structure of each of Formulas (O4-Glc+), (O1A), (O2), (O6A), (O8), (O15), (O16), (O18A), (O25B), and (O75) is shown in Table 1, and each n is independently an integer of 1 to 100, preferably 1 to 50, e.g. 3 to 50, e.g. 5 to 40, e.g. 7 to 25, e.g. 10 to 20.

In certain embodiments, such composition or immunogenic composition further comprises:

(x) a bioconjugate of an *E. coli* O18A antigen polysaccharide covalently linked to an EPA-4 carrier protein, wherein the *E. coli* O18A antigen polysaccharide comprises the structure of Formula (O18A), wherein the structure of Formula (O18A) is shown in Table 1, and n in this structure is an integer of 1 to 100, preferably 1 to 50, e.g. 3 to 50, e.g. 5 to 40, e.g. 7 to 25, e.g. 10 to 20.

In certain embodiments, a bioconjugate of an *E. coli* O25B antigen polysaccharide is present in a composition described herein at a concentration that is about 1.5-6 times, e.g. about 2 to 4 times, higher than a concentration of any other bioconjugate in the composition.

In certain embodiments, a composition described herein comprises bioconjugates of *E. coli* O1A, O2, glucosylated O4, O6A, O8, O15, O16, O25B, and O75 antigen polysaccharides, wherein the bioconjugates of O1A:O2:glucosylated O4:O6A:O8:O15:O16:O25B:O75 are present in a ratio by weight of polysaccharide of 1:1:1:1:1:1:1:2:1, or 2:1:1:2:1:1:1:4:1.

In certain embodiments, a composition described herein comprises bioconjugates of *E. coli* O1A, O2, glucosylated O4, O6A, O8, O15, O16, O18A, O25B, and O75 antigen polysaccharides, wherein the bioconjugates of O1A:O2:glucosylated O4:O6A:O8:O15:O16:O18A:O25B:O75 are present in a ratio by weight of polysaccharide of 1:1:1:1:1:1:1:1:2:1, or 2:1:1:2:1:1:1:1:4:1.

In certain embodiments, a concentration of a bioconjugate of an *E. coli* O25B antigen polysaccharide in a composition described herein is 2 to 50 μg/mL, preferably 8 to 40 μg/mL, e.g. 16-32 μg/mL.

In another aspect, provided herein is a method of inducing antibodies against an *E. coli* glucosylated O4 antigen in a subject, comprising administering to the subject a bioconjugate of an *E. coli* glucosylated O4 antigen as described herein, or a composition or immunogenic composition as described herein.

In a particular embodiment, the antibodies have opsonophagocytic activity.

In another aspect, provided herein is a method of vaccinating a subject against extra-intestinal pathogenic *E. coli* (ExPEC), comprising administering to the subject a bioconjugate of an *E. coli* glucosylated O4 antigen polysaccharide as described herein, or a composition or immunogenic composition as described herein. In certain aspects, provided herein is a bioconjugate of an *E. coli* glucosylated O4 antigen polysaccharide as described herein, or a composition or immunogenic composition as described herein, for use in inducing antibodies against an *E. coli* glucosylated O4 antigen. In certain aspects, provided herein is a bioconjugate of an *E. coli* glucosylated O4 antigen polysaccharide as described herein, or a composition or immunogenic composition as described herein, for use in vaccination against extra-intestinal pathogenic *E. coli* (ExPEC). In certain aspects, provided herein is the use of a bioconjugate of an *E. coli* glucosylated O4 antigen polysaccharide as described herein, or a composition or immunogenic composition as described herein, for the manufacture of a medicament for inducing antibodies against an *E. coli* glucosylated O4 antigen in a subject. In certain aspects, provided herein is the use of a bioconjugate of an *E. coli* glucosylated O4 antigen polysaccharide as described herein, or a composition or immunogenic composition as described herein, for the manufacture of a medicament for vaccinating a subject against extra-intestinal pathogenic *E. coli* (ExPEC).

In another aspect, provided herein is a recombinant host cell for producing a bioconjugate of an *E. coli* glucosylated O4 antigen polysaccharide covalently linked to a carrier protein, wherein the glucosylated O4 antigen polysaccharide comprises the structure of Formula (O4-Glc+) as shown in Table 1, wherein n is integer of 1 to 100, preferably 1 to 50, e.g. 3 to 50, e.g. 5 to 40, e.g. 7 to 25, e.g. 10 to 20, the host cell comprising:

(i) a nucleotide sequence of an rfb gene cluster for the *E. coli* O4 antigen polysaccharide;

(ii) a nucleotide sequence encoding a glucosyl transferase having at least 80% sequence identity to SEQ ID NO: 4, wherein the glucosyl transferase is capable of modifying the *E. coli* O4 antigen polysaccharide to produce the *E. coli* glucosylated O4 antigen polysaccharide;

(iii) nucleotide sequences encoding a translocase and a glycosyltransferase having at least 80% sequence identity to SEQ ID NOs: 7 and 8 respectively, wherein the translocase is capable of translocating bactoprenol-linked glucose and the glycosyltransferase is capable of glucosylating bactoprenol;

(iv) a nucleotide sequence encoding the carrier protein; and (iv) a nucleotide sequence encoding an oligosaccharyl transferase capable of covalently linking the *E. coli* glucosylated O4 antigen polysaccharide to the carrier protein to produce the bioconjugate.

In a particular embodiment, a recombinant host cell comprises a nucleotide sequence encoding a glucosyl transferase that is capable of modifying the *E. coli* O4 antigen polysaccharide to produce the *E. coli* glucosylated O4 antigen polysaccharide and having an amino acid sequence that has at least 90%, preferably at least 95%, preferably at least 98% sequence identity to SEQ ID NO: 4. In certain embodiments, the glucosyl transferase comprises SEQ ID NO: 4.

In certain embodiments, the recombinant host cell comprises a nucleotide sequence encoding a translocase that is capable of translocating bactoprenol-linked glucose and having at least 90%, preferably at least 95%, preferably at least 98% sequence identity to SEQ ID NO: 7. In certain embodiments, the translocase comprises SEQ ID NO: 7.

In certain embodiments, the recombinant host cell comprises a nucleotide sequence encoding a glycosyltransferase that is capable of glucosylating bactoprenol and having at least 90%, preferably at least 95%, preferably at least 98% sequence identity to SEQ ID NO: 8. In certain embodiments, the glycosyltransferase comprises SEQ ID NO: 8. In certain embodiments, the recombinant host cell comprises a nucleotide sequence that encodes an oligosaccharyl transferase comprising the amino acid sequence of SEQ ID NO: 6. In preferred embodiments, the oligosaccharyl transferase comprises the amino acid sequence of SEQ ID NO: 6 having mutation N311V, more preferably SEQ ID NO: 6 having both mutations Y77H and N311V.

In certain embodiments, the recombinant host cell comprises a nucleotide sequence encoding a carrier protein comprising at least one glycosylation site comprising a glycosylation consensus sequence having SEQ ID NO: 1, preferably having SEQ ID NO: 2.

In certain embodiments, the rfb gene cluster for the *E. coli* O4 antigen polysaccharide comprises a sequence that encodes the enzymes that create the *E. coli* O4 antigen polysaccharide (Formula (O4-Glc−) in Table 1) and is at least 80%, e.g. at least 90%, e.g. at least 95%, e.g. at least 98% identical to SEQ ID NO: 9. In certain embodiments the rfb gene cluster comprises SEQ ID NO: 9.

In certain embodiments, the recombinant host cell comprises a nucleotide sequence encoding a carrier protein, wherein the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

In a particular embodiment, a recombinant host cell encodes a detoxified exotoxin A of *Pseudomonas aeruginosa* (EPA) carrier protein, preferably EPA comprising 1-10, preferably 2-4, preferably 4 glycosylation sites each comprising a glycosylation consensus sequence having SEQ ID NO: 2. In a preferred embodiment, EPA comprises the amino acid sequence of SEQ ID NO: 3.

Preferably, a recombinant host cell is *E. coli*, e.g. an *E. coli* K-12 strain, such as strain W3110.

In another aspect, provided is a method of producing a bioconjugate of an *E. coli* glucosylated O4 antigen polysaccharide covalently linked to a carrier protein, wherein the *E. coli* glucosylated O4 antigen polysaccharide comprises the structure of Formula (O4-Glc+) as shown in Table 1, wherein n is an integer of 1 to 100, preferably 1 to 50, e.g. 3 to 50, e.g. 5 to 40, e.g. 7 to 25, e.g. 10 to 20, the method comprising culturing the recombinant host cell of the invention under conditions for production of the bioconjugate. In some embodiments, the method further comprises isolating the bioconjugate from the recombinant host cell.

In another aspect, provided is a bioconjugate produced by a method as described herein. In another aspect, provided is a composition comprising a bioconjugate produced by a method as described herein.

In another aspect, provided is a method for making a recombinant host cell for producing a bioconjugate of an *E. coli* glucosylated O4 antigen polysaccharide covalently linked to a carrier protein, wherein the glucosylated O4 antigen polysaccharide comprises the structure of Formula (O4-Glc+) as shown in Table 1, wherein n is an integer of 1 to 100, preferably 1 to 50, e.g. 3 to 50, e.g. 5 to 40, e.g. 7 to 25, e.g. 10 to 20, the method comprising introducing one or more recombinant nucleic acid molecules into a cell to produce the recombinant host cell, wherein the recombinant host cell comprises:

(i) a nucleotide sequence of an rfb gene cluster for the *E. coli* O4 antigen polysaccharide;

(ii) a nucleotide sequence encoding a glucosyl transferase having at least 80% sequence identity to SEQ ID NO: 4, wherein the glucosyl transferase is capable of modifying the *E. coli* O4 antigen polysaccharide to produce the *E. coli* glucosylated O4 antigen polysaccharide;

(iii) nucleotide sequences encoding a translocase and a glycosyltransferase having at least 80% sequence identity to SEQ ID NOs: 7 and 8 respectively, wherein the translocase is capable of translocating bactoprenol-linked glucose and the glycosyltransferase is capable of glucosylating bactoprenol;

(iv) a nucleotide sequence encoding the carrier protein; and (v) a nucleotide sequence encoding an oligosaccharyl transferase capable of covalently linking the *E. coli* glucosylated O4 antigen polysaccharide to the carrier protein to produce the bioconjugate.

In a particular embodiment thereof, the glucosyl transferase that is capable of modifying the *E. coli* O4 antigen polysaccharide to produce the *E. coli* glucosylated O4 antigen polysaccharide has an amino acid sequence that has at least 90%, preferably at least 95%, preferably at least 98% sequence identity to SEQ ID NO: 4. In certain embodiments, the glucosyl transferase comprises SEQ ID NO: 4.

In certain embodiments, the oligosaccharyl transferase comprises the amino acid sequence of SEQ ID NO: 6, preferably of SEQ ID NO: 6 comprising the amino acid mutation N311V. In certain embodiments, the oligosaccharyl transferase comprises SEQ ID NO: 6 having the amino acid mutations Y77H and N311V.

In certain embodiments, the rfb gene cluster for the *E. coli* O4 antigen polysaccharide comprises a sequence that encodes the enzymes that create the *E. coli* O4 antigen polysaccharide (Formula (O4-Glc−) in Table 1) and is at least 80%, e.g. at least 90%, e.g. at least 95%, e.g. at least 98% identical to SEQ ID NO: 9. In certain embodiments the rfb gene cluster comprises SEQ ID NO: 9.

In certain embodiments, the translocase is capable of translocating bactoprenol-linked glucose and has at least 90%, preferably at least 95%, preferably at least 98% sequence identity to SEQ ID NO: 7. In certain embodiments, the translocase comprises SEQ ID NO: 7.

In certain embodiments, the glycosyltransferase is capable of glucosylating bactoprenol and has at least 90%, preferably at least 95%, preferably at least 98% sequence identity to SEQ ID NO: 8. In certain embodiments, the glycosyltransferase comprises SEQ ID NO: 8.

In certain embodiments, the carrier protein comprises at least one glycosylation site comprising a glycosylation consensus sequence having SEQ ID NO: 1, preferably having SEQ ID NO: 2. In certain embodiments, the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

In a particular embodiment, the carrier protein is a detoxified exotoxin A of *Pseudomonas aeruginosa* (EPA), preferably wherein the EPA comprises 1-10, preferably 2-4, preferably 4, glycosylation sites each comprising a glycosylation consensus sequence having SEQ ID NO: 2. In particular embodiments, the carrier protein is EPA with four glycosylation consensus sequences (EPA-4), preferably wherein the carrier protein comprises SEQ ID NO: 3.

In some embodiments, the recombinant host cell is an *E. coli* cell, e.g. from an *E. coli* K12 strain, such as from a W3110 strain.

In another aspect, provided is a method of preparing a bioconjugate of an $O_x$ antigen polysaccharide covalently linked to a carrier protein, the method comprising:

(i) providing a recombinant host cell comprising:
  a. a nucleotide sequence of an rfb gene cluster for the $O_x$-antigen polysaccharide;
  b. a nucleotide sequence encoding the carrier protein comprising at least one glycosylation site comprising a glycosylation consensus sequence having SEQ ID NO: 1, preferably having SEQ ID NO: 2; and
  c. a nucleotide sequence encoding an oligosaccharyl transferase $PglB_y$; and
(ii) culturing the recombinant host cell under conditions for production of the bioconjugate, wherein:

when the $O_x$-antigen is O1A antigen polysaccharide, the $PglB_y$ comprises the amino acid mutations of N311V, K482R, D483H, and A669V;

when the $O_x$-antigen is glucosylated O4 antigen polysaccharide, the $PglB_y$ comprises the amino acid mutation N311V or the amino acid mutations Y77H and N311V, and the recombinant host cell further comprises a sequence encoding a GtrS having at least 80% identity to SEQ ID NO: 4, and nucleotide sequences encoding a GtrA and a GtrB having at least 80% sequence identity to SEQ ID NOs: 7 and 8 respectively;

when the $O_x$-antigen is O6A antigen polysaccharide, the $PglB_y$ comprises the amino acid mutations of N311V, K482R, D483H, and A669V;

when the $O_x$-antigen is O8 antigen polysaccharide, the $PglB_y$ comprises no amino acid mutations at positions 77, 80, 287, 289, 311, 482, 483 and 669;

when the $O_x$-antigen is O15 antigen polysaccharide, the $PglB_y$ comprises the amino acid mutations of N311V, K482R, D483H, and A669V;

when the $O_x$-antigen is O16 antigen polysaccharide, the $PglB_y$ comprises the amino acid mutations of Y77H, S80R, Q287P, K289R, and N311V;

when the $O_x$-antigen is O18A antigen polysaccharide, the $PglB_y$ comprises no amino acid mutations at positions 77, 80, 287, 289, 311, 482, 483 and 669; and when the $O_x$-antigen is O75 antigen polysaccharide, the $PglB_y$ comprises the amino acid mutation of N311V, wherein in each case the amino acid mutations are relative to the wild-type $PglB_y$ having the amino acid sequence of SEQ ID NO: 6.

In certain embodiments, the carrier protein is detoxified exotoxin A of *Pseudomonas aeruginosa* (EPA). Preferably, the EPA carrier protein comprises 1-10, preferably 2-4, preferably 4, glycosylation sites each comprising a glycosylation consensus sequences having SEQ ID NO: 2. In a particular embodiment, the EPA carrier protein comprises SEQ ID NO: 3.

In another aspect, provided is a bioconjugate produced by a method of preparing a bioconjugate of an $O_x$ antigen polysaccharide covalently linked to a carrier protein as described herein. In another aspect, provided is a composition comprising such a bioconjugate. In such embodiments, a composition comprises at least 2, preferably at least 3, more preferably at least 5, still more preferably at least 7 of such bioconjugates.

BRIEF DESCRIPTION OF THE FIGURES

The foregoing summary, as well as the following detailed description of the invention, will be better understood when read in conjunction with the appended drawings. It should be understood that the invention is not limited to the precise embodiments shown in the drawings.

In the drawings:

FIG. 4A shows serum antibody levels measured by ELISA at day 0, 14 and 42 post-immunization; individual titers (log 10 EC50 titer) and GMT±95% CI are shown; the grey dotted line indicates the threshold above which the dilution curves of the samples have a 4PL fitting; FIG. 4B shows the results of the opsonophagocytic (OPK) assay to determine the functionality of the antibodies in serum samples obtained at day 42 post-immunization with glucosylated O4 (O4-Glc+)-EPA bioconjugate (4.0 μg); Wilcoxon rank sum test and Bonferroni correction; *P≤0.05, ***P≤0.0001;

FIG. 10A shows the overall study design for Cohort 1, and FIG. 10B shows the overall study design for Cohort 2. See Example 11 for details.

DETAILED DESCRIPTION OF THE INVENTION

Figure 1:
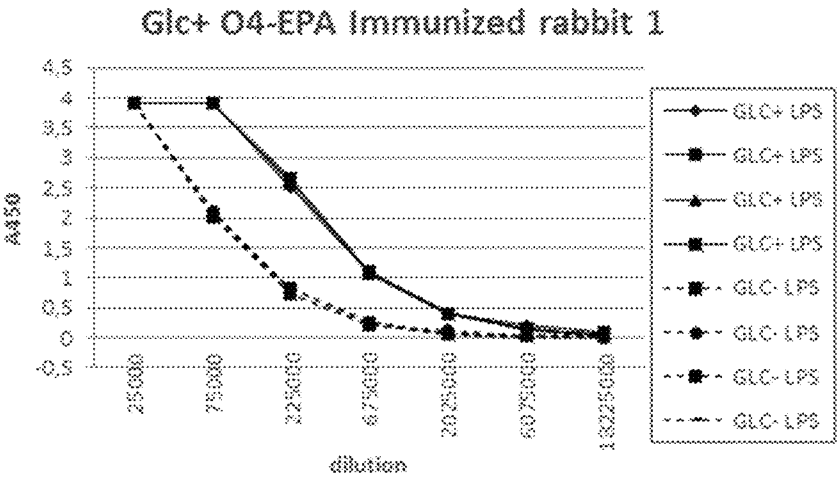
FIG. 1 shows ELISA IgG titers against unmodified (GLC−) or glucose-modified (GLC+) O4 LPS in sera from two rabbits immunized with Glc-modified O4 polysaccharide bioconjugate as described in Example 4; ELISA titers were determined in quadruplicate.
Figure 1:
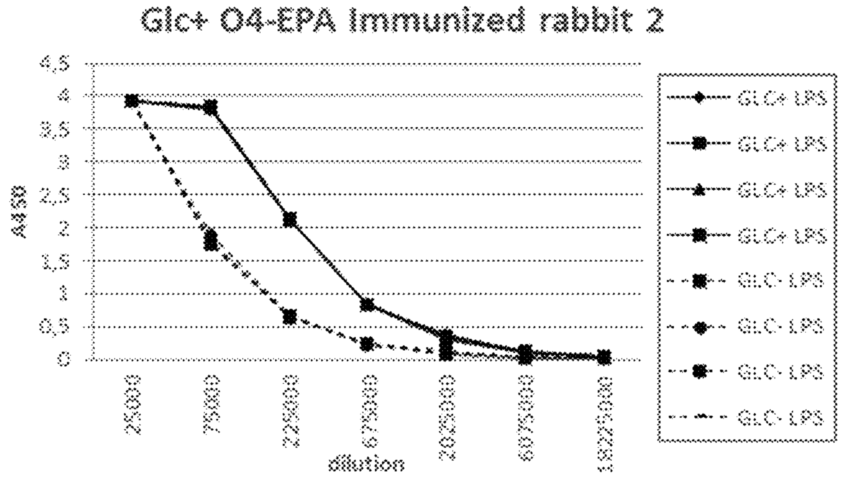

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series.

Those skilled in the art will recognize or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising," "containing," "including," and "having," whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

The identification of an O-antigen structural modification, namely glucose branching, within the *E. coli* O4 serotype (Jann et al., 1993) presents a challenge to the discovery and development of a glycoconjugate vaccine targeting bacterial isolates within this serotype. The proportion of clinical contemporary O4 isolates expressing the unmodified (not having a glucose side-branch) and modified (having a glucose side-branch) forms of the O4 O-antigen is unknown. Obtaining information on this characteristic is critical for selecting the relevant antigenic structure. In addition, the extent to which vaccine induced antibodies elicited to one form of the O4 polysaccharide will cross-react with the other form has not been determined. Purification of O-antigen free from lipid A and subsequent chemical conjugation to a carrier protein is a lengthy and laborious process. Additionally, the purification, lipid A detoxification and chemical conjugation processes can result in loss of epitopes, antigen heterogeneity and reduced immunogenicity of the conjugated polysaccharide. Synthesis of glycoconjugates by bioconjugation can overcome these limitations of classical purification and chemical conjugation, but the in vivo synthesis of glucose-branched O4 O-antigen requires the activity of a polysaccharide branching enzyme, which lies outside of the rfb gene cluster. To date, the O-antigen modifying enzyme responsible for glucose-branching in O4 *E. coli* strains has not been identified. Cloning the O4 rfb gene cluster into the bioconjugation *E. coli* strain expressing PglB will not be sufficient to synthesize the glucose-branched O4 glycoconjugate, but rather would only produce non-glucose-branched O4 bioconjugates (the structure of the glycan thereof is shown in Formula (O4) in Table 1). As used herein, the terms "glucosylated O4", "glucose-branched O4", "O4 Glc+" and "Glc+O4" O-antigen refer to O4 O-antigen with a glucose side-branch, and the structure thereof is shown in formula (O4-Glc+) in Table 1.

Disclosed herein is the gene encoding the O-antigen modifying enzyme responsible for glucose branching of the *E. coli* O4 antigen polysaccharide. Also disclosed herein are host cells, e.g., recombinantly engineered host cells comprising nucleic acid encoding enzymes capable of producing bioconjugates comprising the glucosylated O4 antigen polysaccharide covalently bound to a carrier protein in vivo. Such host cells can be used to generate bioconjugates comprising the glucosylated O4 antigen linked to a carrier protein, which can be used in, e.g., the formulation of therapeutic and/or prophylactic compositions (e.g., vaccines). Further provided herein are compositions comprising bioconjugates of the glucosylated O4 antigen polysaccharide, alone or in combination with other *E. coli* antigens (e.g., O1, O2, O6, O8, O15, O16, O18, O25, and/or O75 antigen polysaccharides and subserotypes thereof). The compositions can be used in prophylactic and/or therapeutic methods, e.g., vaccination of hosts against infection with *E. coli*, and are useful in the generation of antibodies, which can be used, e.g., in therapeutic methods such as for immunization of subjects.

As used here, the terms "O-antigen," "O-antigen polysaccharide," "O-antigen saccharide," and "OPS" refer to the O-antigen of Gram-negative bacteria. Typically, an O-antigen is a polymer of immunogenic repeating polysaccharide units. In a particular embodiment, the terms "O-antigen," "O-antigen polysaccharide," and "OPS" refer to the O-antigen of *Escherichia coli*. Different serotypes of *E. coli* express different O-antigens. In *E. coli*, the gene products involved in O-antigen biogenesis are encoded by the rfb gene cluster.

As used herein, "rfb cluster" and "rfb gene cluster" refer to a gene cluster that encodes enzymatic machinery capable of synthesizing an O-antigen backbone structure. The term rfb cluster can apply to any O-antigen biosynthetic cluster, and preferably refers to a gene cluster from the genus *Escherichia*, particularly *E. coli.*

As used herein, the term "O1A" refers to the O1A antigen of *E. coli* (a subserotype of *E. coli* serotype O1). The term "O2" refers to the O2 antigen of *E. coli* (*E. coli* serotype O2). The term "O6A" refers to the O6A antigen of *E. coli* (a subserotype of *E. coli* serotype O6). The term "O8" refers to the O8 antigen of *E. coli* (*E. coli* serotype O8). The term "O15" refers to the O15 antigen of *E. coli* (*E. coli* serotype O15). The term "O16" refers to the O16 antigen of *E. coli* (*E. coli* serotype O16). The term "O18A" refers to the O18A antigen of *E. coli* (a subserotype of *E. coli* serotype O18). The term "O25B" refers to the O25B antigen from *E. coli* (a subserotype of *E. coli* serotype O25). The term "O75" refers to the O75 antigen of *E. coli* (*E. coli* serotype O75).

The structures of *E. coli* O-antigen polysaccharides referred to throughout this application are shown below in Table 1. A single repeating unit for each *E. coli* O-antigen polysaccharide is shown.

TABLE 1

Structures of *E. coli* O-antigen Polysaccharides

| *E. coli* O-antigen Polysaccharide | Structure of Repeating Unit[1] |
|---|---|
| Non-glucosylated O4 antigen polysaccharide (O4-Glc-) | [→2)-α-L-Rhap-(1→6)-α-D-Glcp-(1→3)-α-L-FucpNAc-(1→3)-β-D-GlcpNAc-(1→]$_n$ |
| Glucosylated O4 antigen polysaccharide (O4-Glc+) | α-D-Glcp<br>1<br>↓<br>3<br>[→2)-α-L-Rhap-(1→6)-α-D-Glcp-(1→3)-α-L-FucpNAc-(1→3)-β-D-GlcpNAc-(1→]$_n$ |
| O1A antigen polysaccharide (O1A) | [→3)-α-L-Rhap-(1→3)-α-L-Rhap-(1→3)-β-L-Rhap-(1→4)-β-D-GlcpNAc-(1→]$_n$<br>2<br>↑<br>1<br>β-D-ManpNAc |
| O2 antigen polysaccharide (O2) | [→3)-α-L-Rhap-(1→2)-α-L-Rhap-(1→3)-β-L-Rhap-(1→4)-β-D-GlcpNAc-(1→]$_n$<br>2<br>↑<br>1<br>α-D-Fucp3NAc |

TABLE 1-continued

Structures of *E. coli* O-antigen Polysaccharides

| *E. coli* O-antigen Polysaccharide | Structure of Repeating Unit[1] |
|---|---|
| O6A antigen polysaccharide (O6) | [→4)-α-D-GalpNAc-(1→3)-β-D-Manp-(1→4)-β-D-Manp-(1→3)-α-D-GlcpNAc-(1→]$_n$<br>2<br>↑<br>1<br>β-D-Glcp |
| O8 antigen polysaccharide (O8) | α-D-Manp3Me-(1→[3)-β-D-Manp-(1→2)-α-D-Manp-(1→2)-α-D-Manp-(1→]$_n$ |
| O15 antigen polysaccharide (O15) | [→2)-β-D-Galp-(1→3)-α-L-FucpNAc-(1→3)-β-D-GlcpNAc-(1→]$_n$ |
| O16 antigen polysaccharide (O16) | [→2)-β-D-Galf-(1→6)-α-D-Glcp-(1→3)-α-L-Rhap-(1→3)-α-D-GlcpNAc-(1→]$_n$<br>2<br>↑<br>Ac |
| O18A antigen polysaccharide (O18A) | [→2)-α-L-Rhap-(1→6)-α-D-Glcp-(1→4)-α-D-Galp-(1→3)-α-D-GlcpNAc-(1→]$_n$<br>3<br>↑<br>1<br>β-D-GlcpNAc |
| O25B antigen polysaccharide (O25B) | β-D-Glcp<br>1<br>↓<br>6<br>[→4)-α-D-Glcp-(1→3)-α-L-Rhap-(1→3)-β-D-GlcpNAc-(1→]$_n$<br>3 2<br>↑ ↑<br>1 Ac<br>α-L-Rhap |
| O75 antigen polysaccharide (O75) | β-D-Manp<br>1<br>↓<br>4<br>[→3)-α-D-Galp-(1→4)-α-L-Rhap-(1→3)-β-D-GlcpNAc-(1→]$_n$ |

[1]Each n is independently an integer of 1 to 100, such as 1-50, 1-40, 1-30, 1-20, and 1-10, 3-50, 3-40, e.g. at least 5, such as 5-40, e.g. 7-30, e.g. 7 to 25, e.g. 10 to 20, but in some instances can be 1-2.

All monosaccharides described herein have their common meaning known in the art. Monosaccharides can have the D or L configuration. If D or L is not specified, the sugar is understood to have the D configuration. Monosaccharides are typically referred to by abbreviations commonly known and used in the art. For example, Glc refers to glucose; D-Glc refers to D-glucose; and L-Glc refers to L-glucose. Other common abbreviations for monosaccharides include: Rha, rhamnose; GlcNAc, N-acetylglucosamine; GalNAc, N-acetylgalactosamine; Fuc, fucose; Man, mannose; Man3Me, 3-O-methyl-mannose; Gal, galactose; FucNAc, N-acetylfucosamine; and Rib, ribose. The suffix "f" refers to furanose and the suffix "p" refers to pyranose.

The terms "RU," "repeat unit," and "repeating unit" as used with respect to an O-antigen refer to the biological repeat unit (BRU) of an O-antigen as it is synthesized in vivo by cellular machinery (e.g., glycosyltransferases). The number of RUs of an O-antigen may vary per serotype, and in embodiments of the invention typically varies from about 1-100 RUs, preferably about 1 to 50 RUs, such as 1-50 RUs, 1-40 RUs, 1-30 RUs, 1-20 RUs, and 1-10 RUs, and more preferably at least 3 RUs, at least 4 RUs, at least 5 RUs, such as 3-50 RUs, preferably 5-40 RUs, e.g. 7-25 RUs, e.g. 10-20 RUs. However, in some instances, the number of RUs of an O-antigen can be 1-2. The structure of each O-antigen that is specifically described herein is shown containing one RU with the variable "n" designating the number of RUs. In each O-antigen polysaccharide in a bioconjugate of the invention, n is independently an integer of 1-100, such as 1-50, 1-40, 1-30, 1-20, 1-10, preferably at least 3, more preferably at least 5, such as 3-50, preferably 5-40 (e.g. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40), but in some instances can be 1-2. In some embodiments n is independently an integer of about 7-25, e.g. about 10-20. The values may vary between individual O-antigen polysaccharides in a composition, and are provided here as average values, i.e. if a bioconjugate is described herein as having an n that is independently an integer of 5-40, the composition contains a majority of O-antigen polysaccharides with 5-40 repeat units, but may also contain some O-antigen polysaccharides that have less than 5 repeat units or more than 40 repeat units.

The term "glycoconjugate" refers to a sugar or saccharide antigen (e.g., oligo- and polysaccharide)-protein conjugate linked to another chemical species, including but not limited to proteins, peptides, lipids, etc. Glycoconjugates can be prepared chemically, e.g., by chemical (synthetic) linkage of the protein and sugar or saccharide antigen. The term glycoconjugate also includes bioconjugates.

The term "bioconjugate" refers to a conjugate between a protein (e.g., a carrier protein) and a sugar or saccharide antigen (e.g., oligo- and polysaccharide) prepared in a host cell background, preferably a bacterial host cell, e.g. an *E. coli* host cell, wherein host cell machinery links the antigen to the protein (e.g., N-links). Preferably, the term "bioconjugate" refers to a conjugate between a protein (e.g., carrier protein) and an O-antigen, preferably an *E. coli* O-antigen (e.g., O1A, O2, glucosylated O4, O6A, O8, O15, O16, O18A, O25B, O75, etc.) prepared in a host cell background, wherein host cell machinery links the antigen to the protein (e.g., N-links). Because bioconjugates are prepared in host cells by host cell machinery, the antigen and protein are covalently linked via a glycosidic linkage or bond in a bioconjugate. Bioconjugates can be prepared in recombinant host cells engineered to express the cellular machinery needed to synthesize the O-antigen and/or link the O-antigen to the target protein. Bioconjugates, as described herein, have advantageous properties over chemically prepared glycoconjugates where the glycans are purified from bacterial cell walls and subsequently chemically coupled to a carrier protein, e.g., bioconjugates require fewer chemicals in manufacture and are more consistent in terms of the final product generated, and contain less or no free (i.e. unbound to carrier protein) glycan. Thus, in typical embodiments, bioconjugates are preferred over chemically produced glycoconjugates.

The term "about," when used in conjunction with a number, refers to any number within ±1, ±5 or ±10% of the referenced number.

The term "percent (%) sequence identity" or "% identity" describes the number of matches ("hits") of identical amino acids of two or more aligned amino acid sequences as compared to the number of amino acid residues making up the overall length of the amino acid sequences. In other terms, using an alignment, for two or more sequences the percentage of amino acid residues that are the same (e.g. 90%, 95%, 97% or 98% identity) may be determined, when the sequences are compared and aligned for maximum correspondence as measured using a sequence comparison algorithm as known in the art, or when manually aligned and visually inspected. The sequences which are compared to determine sequence identity may thus differ by substitution(s), addition(s) or deletion(s) of amino acids. Suitable programs for aligning protein sequences are known to the skilled person. The percentage sequence identity of protein sequences can, for example, be determined with programs such as CLUSTALW, Clustal Omega, FASTA or BLAST, e.g using the NCBI BLAST algorithm (Altschul S F, et al (1997), Nucleic Acids Res. 25:3389-3402).

For example, for amino acid sequences, sequence identity and/or similarity can be determined by using standard techniques known in the art, including, but not limited to, the local sequence identity algorithm of Smith and Waterman, 1981, Adv. Appl. Math. 2:482, the sequence identity alignment algorithm of Needleman and Wunsch, 1970, J. Mol. Biol. 48:443, the search for similarity method of Pearson and Lipman, 1988, Proc. Nat. Acad. Sci. U.S.A. 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al, 1984, Nucl. Acid Res. 12:387-395, preferably using the default settings, or by inspection. In certain embodiments, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

Another example of a useful algorithm is the BLAST algorithm, described in: Altschul et al, 1990, J. Mol. Biol. 215:403-410; Altschul et al, 1997, Nucleic Acids Res. 25:3389-3402; and Karin et al, 1993, Proc. Natl. Acad. Sci. U.S.A. 90:5873-5787. A particularly useful BLAST program is the WU-BLAST-2 program which was obtained from Altschul et al, 1996, Methods in Enzymology 266:460-480. WU-BLAST-2 uses several search parameters, most of which are set to the default values.

An additional useful algorithm is gapped BLAST as reported by Altschul et al, 1993, Nucl. Acids Res. 25:3389-3402.

The term "Invasive Extraintestinal pathogenic *Escherichia coli* (ExPEC) disease (IED)" is defined herein as an acute illness consistent with systemic bacterial infection, which is microbiologically confirmed either by the isolation and identification of *E. coli* from blood or other normally sterile body sites, or by the isolation and identification of *E. coli* from urine in a patient with presence of signs and symptoms of invasive disease (systemic inflammatory response syndrome (SIRS), sepsis or septic shock) and no other identifiable source of infection.

Bioconjugates of *E. coli* Glucosylated O4 Antigen Polysaccharides

In one aspect, provided herein is a bioconjugate of an *E. coli* glucosylated O4 antigen polysaccharide covalently linked to a carrier protein. As used herein, the term "O4" refers to the O4 antigen from *E. coli* (*E. coli* serotype O4). O-antigen structural modification is known to exist within the *E. coli* O4 serotype. In particular, some O4 serotypes express a modified O-antigen having a branched glucose unit. As used herein, "glucosylated O4 antigen," "glucosylated O4 antigen polysaccharide, "O4-Glc+ antigen polysaccharide," and "O4-Glc+ antigen" refer to an O4 antigen (e.g., *E. coli* O4 antigen) having a glucose branch, in which D-glucose is linked to L-rhamnose in the repeating unit L-Rha→D-Glc→L-FucNAc→D-GlcNAc. In a particular embodiment, an *E. coli* glucosylated O4 antigen polysaccharide comprises the structure of formula (O4-Glc+), as shown in Table 1, wherein n is an integer of 1 to 100. In preferred embodiments, n is an integer of 3 to 50, e.g. 5 to 40, e.g. 7 to 25, e.g. 10 to 20.

*E. coli* O4 strains, independent of glucose branching status, carry a substantially identical rfb gene cluster encoding the genes responsible for production of the O4 antigen polysaccharide. However, in vivo synthesis of the modified O4 antigen having glucose branching requires the activity of a polysaccharide branching enzyme, which lies outside of the rfb gene cluster. To the best of the knowledge of the inventors, the identity of the polysaccharide branching enzyme responsible for glucose modification of the O4 antigen has remained unknown to date. Here, the inventors discovered the sequence of the polysaccharide branching enzyme responsible for glucose modification of the O4 antigen. Identification of this enzyme enables production of bioconjugates of the modified O4 antigen polysaccharide having glucose branching. The glucose modified form of the O4 antigen polysaccharide is present in predominant serotypes and can thus be used to provide an improved immune response, e.g for prophylactic or therapeutic use.

In particular, provided herein is the sequence of a gtrS gene encoding a glucosyltransferase enzyme specific for *E. coli* serotype O4 that glucosylates the O4 antigen. In general, the gtrA, gtrB, and gtrS genes encodes the enzymes responsible for O-antigen glucosylation. While the gtrA and gtrB genes in different serotypes are highly homologous and interchangeable, the gtrS gene encodes a serotype specific O-antigen glucosyl transferase. The gtrS gene of *E. coli* serotype O4 encodes the GtrS enzyme that modifies the O4 antigen by introducing glucose branching. Characterization of contemporary clinical *E. coli* isolates of the O4 serotype revealed the presence of gtrS in 78% of tested isolates, indicating that *E. coli* O4 antigen polysaccharide modified with the addition of a glucose residue is predominant in current infecting isolates.

In one embodiment, provided herein is a nucleic acid of a gtrS gene from *E. coli* serotype O4 encoding a GtrS glucosyltransferase comprising the amino acid sequence of SEQ ID NO: 4. In another embodiment, a gtrS nucleic acid encodes a GtrS protein from *E. coli* serotype O4 that is about 80%, 85%, 90%, 95%, 96%, 97%, 98%, 99%, or 100% identical to the amino acid sequence of SEQ ID NO: 4, preferably 98%, 99%, or 100% identical to the amino acid sequence of SEQ ID NO: 4. A GtrS protein that is at least 80% identical to the amino acid sequence of SEQ ID NO: 4 is capable of specifically glucosylating the *E. coli* O4 antigen polysaccharide to obtain a glucosylated O4 antigen having the structure of Formula (O4-Glc+) as shown in Table 1. One of ordinary skill in the art will be able to make mutated forms of the GtrS protein of SEQ ID NO: 4 having at least 80% sequence identity to SEQ ID NO: 4, and test such sequences for glucosylation activity of the *E. coli* O4 antigen in view of the present disclosure. Recombinant host cells comprising nucleic acid sequence encoding the glucosyl transferase gtrS gene of *E. coli* serotype O4, and use of the recombinant host cells in production of the glucose modified O4 antigen polysaccharides and bioconjugates thereof are described in greater detail below.

Sequences for gtrA and gtrB encoded proteins, which function as bactoprenol-linked glucose translocase (GtrA, flips the bactoprenol-linked glucose over the inner membrane to the periplasm) and bactoprenol glucosyl transferase (GtrB, links glucose to bactoprenol), respectively, may comprise amino acid sequences that are at least about 80% identical to SEQ ID NOs: 7 and 8, respectively. In certain embodiments, nucleic acid sequences encoding GtrA and GtrB proteins that are at least about 80%, 85%, 90%, 95%, 96%, 97%, 98%, 99%, or 100% identical to SEQ ID NOs: 7 and 8, respectively, and having bactoprenol-linked glucose translocase and bactoprenol glucosyl transferase activity, respectively, are also present in the host cells of the invention, that further comprise an O4-specific rfb locus, the O4-specific GtrS encoding sequence described above, an oligosaccharyl transferase as described herein, and a sequence encoding a carrier protein having one or more glycosylation consensus sequences as described herein, to produce bioconjugates of *E. coli* glucosylated O4 serotype (comprising glycan structure of Formula (O4-Glc+) in Table 1).

Bioconjugates of an *E. coli* glucosylated O4 antigen polysaccharide provided herein are covalently linked to a carrier protein, preferably by a glycosidic linkage. Any carrier protein known to those skilled in the art in view of the present disclosure can be used. Suitable carrier proteins include, but are not limited to, detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*. Bioconjugation with various different carrier proteins containing the required consensus glycosylation sequence has been described, showing that a wide range of proteins can be glycosylated using this technology (see, e.g. WO 06/119987, WO 2015/124769, WO 2015/158403, WO 2015/82571, WO 2017/216286, and WO 2017/67964, together showing a wide variety of carrier proteins that were successfully used in bioconjugation).

In certain embodiments a carrier protein is modified, e.g., modified in such a way that the protein is less toxic and/or more susceptible to glycosylation. In a specific embodiment, the carrier proteins used herein are modified such that the number of glycosylation sites in the carrier proteins is maximized in a manner that allows for lower concentrations of the protein to be administered, e.g., in an immunogenic composition, particularly in its bioconjugate form.

Thus, in certain embodiments, the carrier proteins described herein are modified to include 1, 2, 3, 4, 5, 6, 7, 8, 9, 10 or more glycosylation sites than would normally be associated with the carrier protein (e.g., relative to the number of glycosylation sites associated with the carrier protein in its native/natural, i.e., "wild-type" state). Introduction of glycosylation sites into a carrier protein can be accomplished by insertion of a glycosylation consensus sequence anywhere in the primary structure of the protein by, e.g., adding new amino acids to the primary structure of the protein such that a glycosylation site is added in full or in part, or by mutating existing amino acids in the protein in order to generate a glycosylation site. One of ordinary skill in the art will recognize that the amino acid sequence of a protein can be readily modified using approaches known in the art, e.g., recombinant approaches that include modification of the nucleic acid sequence encoding the protein. In specific embodiments, glycosylation consensus sequences are introduced into specific regions of the carrier protein, e.g., surface structures of the protein, at the N or C termini of the protein, and/or in loops that are stabilized by disulfide bridges at the base of the protein. In some embodiments, a glycosylation consensus sequence can be extended by addition of lysine residues for more efficient glycosylation.

Exemplary examples of glycosylation consensus sequences that can be inserted into or generated in a carrier protein include Asn-X-Ser(Thr), wherein X can be any amino acid except Pro (SEQ ID NO: 1); and Asp(Glu)-X-Asn-Z-Ser(Thr), wherein X and Z are independently selected from any amino acid except Pro (SEQ ID NO: 2).

In some embodiments, the *E. coli* glucosylated O4 antigen polysaccharide is covalently linked to an asparagine (Asn) residue in the carrier protein (e.g., N-linked), wherein the Asn residue is present in a glycosylation site comprising a glycosylation consensus sequence having SEQ ID NO: 1, more preferably having SEQ ID NO: 2. Typically, a carrier protein comprises 1-10 glycosylation sites, preferably 2 to 4 glycosylation sites, most preferably 4 glycosylation sites, such as 1-10, preferably 2-4, and more preferably 4 glycosylation sites each comprising a glycosylation consensus sequences having the amino acid sequence of SEQ ID NO: 1, and more preferably the amino acid sequence of SEQ ID NO: 2.

In particular embodiments, a carrier protein is a detoxified Exotoxin A of *P. aeruginosa*. For EPA, various detoxified protein variants have been described in literature and could be used as carrier proteins. For example, detoxification can be achieved by mutating and deleting the catalytically essential residues L552V and ΔE553 according to Lukac et al., 1988, *Infect Immun,* 56: 3095-3098, and Ho et al., 2006, *Hum Vaccin,* 2:89-98. As used herein, "EPA" refers to a detoxified Exotoxin A of *P. aeruginosa*. In those embodiments, wherein the carrier protein is EPA, an *E. coli* glucosylated O4 antigen polysaccharide can be covalently linked to an Asn residue in a glycosylation site comprising a glycosylation consensus sequence having SEQ ID NO: 1, and preferably covalently linked to an Asn residue in a glycosylation site comprising a glycosylation consensus sequence having SEQ ID NO: 2. Preferably, the EPA carrier protein comprises 1-10 glycosylation sites, preferably 2 to 4 glycosylation sites, most preferably 4 glycosylation sites, such as 1-10, preferably 2-4, and more preferably 4 glycosylation sites each comprising a glycosylation consensus sequence having the amino acid sequence of SEQ ID NO: 1, and more preferably the amino acid sequence of SEQ ID NO: 2.

In some embodiments, the EPA carrier protein comprises four glycosylation sites each comprising a glycosylation consensus sequence, for instance a glycosylation site comprising a glycosylation consensus sequence having SEQ ID NO: 2. As used herein, "EPA-4 carrier protein" and "EPA-4" refer to a detoxified Exotoxin A of *P. aeruginosa* carrier protein comprising four glycosylation sites each comprising a glycosylation consensus sequences having SEQ ID NO: 2. An exemplary preferred example of an EPA-4 carrier protein is EPA carrier protein comprising the amino acid sequence of SEQ ID NO: 3.

Compositions

In another aspect, provided herein is a composition comprising a bioconjugate of an *E. coli* glucosylated O4 antigen polysaccharide covalently linked to a carrier protein. The compositions provided herein can include any bioconjugate of an *E. coli* glucosylated O4 antigen polysaccharide covalently linked to a carrier protein (e.g., EPA) described herein.

In some embodiments, a composition is an immunogenic composition. As used herein, an "immunogenic composition" refers to a composition that can elicit an immune response in a host or subject to whom the composition is administered. Immunogenic compositions can further comprise a pharmaceutically acceptable carrier. In some embodiments, a composition is a pharmaceutical composition further comprising a pharmaceutically acceptable carrier. As used herein, a "pharmaceutically acceptable carrier" refers to a diluent, adjuvant, excipient or vehicle with which a composition is administered, and that is non-toxic and should not interfere with the efficacy of the active ingredient. For example, saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Other examples of suitable pharmaceutically acceptable carriers are described in "Remington's Pharmaceutical Sciences" by E. W. Martin.

In one embodiment, a composition of the invention comprises the bioconjugates of the invention in a Tris-buffered saline (TBS) pH 7.4 (e.g. containing Tris, NaCl and KCl, e.g. at 25 mM, 137 mM and 2.7 mM, respectively). In other embodiments, the compositions of the invention comprise bioconjugates of the invention in about 10 mM $KH_2PO_4$/$Na_2HPO_4$ buffer at pH of about 7.0, about 5% (w/v) sorbitol, about 10 mM methionine, and about 0.02% (w/v) polysorbate 80. In other embodiments, the compositions of the invention comprise bioconjugates of the invention in about 10 mM $KH_2PO_4$/$Na_2HPO_4$ buffer at pH of about 7.0, about 8% (w/v) sucrose, about 1 mM EDTA, and about 0.02% (w/v) polysorbate 80 (see e.g. WO 2018/077853 for suitable buffers for bioconjugates of *E. coli* O-antigens covalently bound to EPA carrier protein).

In some embodiments, the compositions described herein are monovalent formulations, and contain one *E. coli* O-antigen polysaccharide, e.g., in isolated form or as part of a glycoconjugate or bioconjugate, such as the *E. coli* glucosylated O4 antigen polysaccharide. Also provided herein are compositions (e.g., pharmaceutical and/or immunogenic compositions) that are multivalent compositions, e.g., bivalent, trivalent, tetravalent, etc. compositions. For example, a multivalent composition comprises more than one antigen, such as an *E. coli* O-antigen, glycoconjugate, or bioconjugate thereof. In particular embodiments, multivalent compositions provided herein comprise a bioconjugate of an *E. coli* glucosylated O4 antigen polysaccharide, and at least one additional antigen.

In one embodiment, a composition (e.g., pharmaceutical and/or immunogenic composition) is a monovalent composition comprising a bioconjugate of an *E. coli* glucosylated O4 antigen polysaccharide covalently linked to a carrier protein as described herein.

In another embodiment, a composition (e.g., pharmaceutical and/or immunogenic composition) is a multivalent composition comprising an *E. coli* glucosylated O4 antigen polysaccharide covalently linked to a carrier protein as described herein, and at least one additional antigen.

In some embodiments, the additional antigen is antigen saccharide or polysaccharide, more preferably an *E. coli* O-antigen polysaccharide, such as *E. coli* O-antigens of one or more of the O1, O2, O6, O8, O15, O16, O18, O25, and O75 serotypes and subserotypes thereof. In some embodiments, each of the additional *E. coli* O-antigen polysaccharides is a glycoconjugate, meaning that the *E. coli* O-antigen polysaccharide is covalently linked to another chemical species, e.g., protein, peptide, lipid, etc., most preferably a carrier protein, such as by chemical or enzymatic methods. In preferred embodiments, each of the additional *E. coli* O-antigen polysaccharides is a bioconjugate in which the O-antigen polysaccharide is covalently linked to, e.g. a carrier protein, via a glycosidic bond enzymatically by host cell machinery. Compositions provided herein in certain embodiments can comprise 1-20 additional glycoconjugates, more preferably bioconjugates of *E. coli* O-antigen polysaccharides, such as 1, 2, 3, 4, 5, 6, 7, 8, 9, 10, 11, 12, 13, 14, 15, 16, 17, 18, 19 or 20 additional glycoconjugates or preferably bioconjugates of *E. coli* O-antigen polysaccharides. Other antigens can be included in the compositions provided herein, such as peptide, protein, or lipid antigens, etc.

In some embodiments, a composition (e.g., pharmaceutical and/or immunogenic composition) comprises a bioconjugate of an *E. coli* glucosylated O4 antigen polysaccharide, and at least one additional antigen polysaccharide selected from the group consisting of *E. coli* O1A antigen polysaccharide, *E. coli* O2 antigen polysaccharide, *E. coli* O6A antigen polysaccharide, *E. coli* O8 antigen polysaccharide, *E. coli* O15 antigen polysaccharide, *E. coli* O16 antigen polysaccharide, *E. coli* O18A antigen polysaccharide, *E. coli* O25B antigen polysaccharide, and *E. coli* O75 antigen polysaccharide. Preferably, each of the additional O-antigen polysaccharides is covalently linked to a carrier protein, and is more preferably a bioconjugate.

In one embodiment, an O1A antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O1A antigen polysaccharide comprises the structure of formula (O1A) as shown in Table 1, wherein n is an integer of 1-100, preferably 3-50, e.g. 5-40, e.g. 7 to 25, e.g. 10 to 20. Preferably, the O1A antigen polysaccharide is part of a bioconjugate and is covalently linked to a carrier protein, e.g., EPA.

In one embodiment, an O2 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O2 antigen polysaccharide comprises the structure of formula (O2) as shown in Table 1, wherein n is an integer of 1-100, preferably 3-50, e.g. 5-40, e.g. 7 to 25, e.g. 10 to 20. Preferably, the O2 antigen polysaccharide is part of a bioconjugate and is covalently linked to a carrier protein, e.g., EPA.

In one embodiment, an O6A antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O6A antigen polysaccharide comprises the structure of formula (O6A) as shown in Table 1, wherein n is an integer of 1-100, preferably 3-50, e.g. 5-40, e.g. 7 to 25, e.g. 10 to 20. Preferably, the O6A antigen polysaccharide is part of a bioconjugate and is covalently linked to a carrier protein, e.g., EPA.

In one embodiment, an O8 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O8 antigen polysaccharide comprises the structure of formula (O8) as shown in Table 1, wherein n is an integer of 1-100, preferably 3-50, e.g. 5-40, e.g. 7 to 25, e.g. 10 to 20. Preferably, the O8 antigen polysaccharide is part of a bioconjugate and is covalently linked to a carrier protein, e.g., EPA.

In one embodiment, an O15 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O15 antigen polysaccharide comprises the structure of formula (O15) as shown in Table 1, wherein n is an integer of 1-100, preferably 3-50, e.g. 5-40, e.g. 7 to 25, e.g. 10 to 20. Preferably, the O15 antigen polysaccharide is part of a bioconjugate and is covalently linked to a carrier protein, e.g., EPA.

In one embodiment, an O16 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O16 antigen polysaccharide comprises the structure of formula (O16) as shown in Table 1, wherein n is an integer of 1-100, preferably 3-50, e.g. 5-40, e.g. 7 to 25, e.g. 10 to 20. Preferably, the O16 antigen polysaccharide is part of a bioconjugate and is covalently linked to a carrier protein, e.g., EPA.

In one embodiment, an O18A antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O18A antigen polysaccharide comprises the structure of formula (O18A) as shown in Table 1, wherein n is an integer of 1-100, preferably 3-50, e.g. 5-40, e.g. 7 to 25, e.g. 10 to 20. Preferably, the O18A antigen polysaccharide is part of a bioconjugate and is covalently linked to a carrier protein, e.g., EPA.

In one embodiment, an O25B antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O25B antigen polysaccharide comprises the structure of formula (O25B) as shown in Table 1, wherein n is an integer of 1-100, preferably 3-50, e.g. 5-40, e.g. 7 to 25, e.g. 10 to 20. Preferably, the O25B antigen polysaccharide is part of a bioconjugate and is covalently linked to a carrier protein, e.g., EPA.

In one embodiment, an O75 antigen polysaccharide (e.g., in isolated form or as part of a glycoconjugate or bioconjugate) is used in a composition provided herein (e.g., in combination with a glucosylated O4 antigen polysaccharide or bioconjugate thereof). In a specific embodiment, the O75 antigen polysaccharide comprises the structure of formula (O75) as shown in Table 1, wherein n is an integer of 1-100, preferably 3-50, e.g. 5-40, e.g. 7 to 25, e.g. 10 to 20. Preferably, the O75 antigen polysaccharide is part of a bioconjugate and is covalently linked to a carrier protein, e.g., EPA.

In another embodiment, a composition (e.g., a pharmaceutical and/or immunogenic composition) comprises at least the *E. coli* O1A, O2, glucosylated O4, O6A and O25B antigen polysaccharides, preferably bioconjugates of the O1A, O2, glucosylated O4, O6A and O25B antigen polysaccharides covalently linked to a carrier protein, e.g., EPA (i.e., a pentavalent composition).

In a preferred embodiment, a composition (e.g., a pharmaceutical and/or immunogenic composition) comprises at least the *E. coli* O1A, O2, glucosylated O4, O6A, O8, O15, O16, O25B and O75 antigen polysaccharides, preferably bioconjugates of the O1A, O2, glucosylated O4, O6A, O8, O15, O16, O25B and O75 antigen polysaccharides covalently linked to a carrier protein, e.g., EPA (i.e., a 9-valent composition).

In another preferred embodiment, a composition (e.g., a pharmaceutical and/or immunogenic composition) comprises at least the *E. coli* O1A, O2, glucosylated O4, O6A, O8, O15, O16, O18A, O25B and O75 antigen polysaccharides, preferably bioconjugates of the O1A, O2, glucosylated O4, O6A, O8, O15, O16, O18A, O25B and O75 antigen polysaccharides covalently linked to a carrier protein, e.g., EPA (i.e., a 10-valent composition).

Also contemplated herein are compositions which optionally further comprise additional O-antigens (e.g., in isolated form, or as part of a glycoconjugate or bioconjugate) from other *E. coli* serotypes.

In some embodiments, each of the additional *E. coli* O1A, O2, O6A, O8, O15, O16, O18A, O25B, and/or O75 antigen polysaccharides is covalently linked to a carrier protein. The O-antigen polysaccharide can be linked to a carrier protein by chemical or other synthetic methods, or the O-antigen polysaccharide can be part of a bioconjugate, and is preferably part of a bioconjugate. Any carrier protein known to those skilled in the art in view of the present disclosure can be used. Suitable carrier proteins include, but are not limited to, detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*. Preferably, the carrier protein is EPA.

In some embodiments, each of the additional *E. coli* O1A, O2, O6A, O8, O15, O16, O18A, O25B, and/or O75 antigen polysaccharides, particularly when part of a bioconjugate, is covalently linked to an asparagine (Asn) residue in the carrier protein, wherein the Asn residue is present in a glycosylation site comprising a glycosylation consensus sequence Asn-X-Ser(Thr), wherein X can be any amino acid except Pro (SEQ ID NO: 1), preferably wherein the Asn residue is present in a glycosylation site comprising a glycosylation consensus sequence Asp(Glu)-X-Asn-Z-Ser (Thr), wherein X and Z are independently selected from any amino acid except Pro (SEQ ID NO: 2). The carrier protein can comprise 1-10 glycosylation sites, preferably 2 to 4 glycosylation sites, most preferably 4 glycosylation sites, each comprising a glycosylation consensus sequence. In a particular embodiment, the carrier protein is EPA-4 carrier protein, for instance EPA-4 carrier protein comprising the amino acid sequence of SEQ ID NO: 3.

In a particular embodiment, provided herein is a composition (e.g., pharmaceutical and/or immunogenic composition) comprising: (i) a bioconjugate of an *E. coli* glucosylated O4 antigen polysaccharide covalently linked to a detoxified Exotoxin A of *P. aeruginosa* carrier protein comprising SEQ ID NO: 3 (EPA-4 carrier protein), wherein the *E. coli* glucosylated O4 antigen polysaccharide comprises the structure of Formula (O4-Glc+); (ii) a bioconjugate of an *E. coli* O1A antigen polysaccharide covalently linked to an EPA-4 carrier protein, wherein the *E. coli* O1A antigen polysaccharide comprises the structure of Formula (O1A); (iii) a bioconjugate of an *E. coli* O2 antigen polysaccharide covalently linked to an EPA-4 carrier protein, wherein the *E. coli* O2 antigen polysaccharide comprises the structure of Formula (O2); (iv) a bioconjugate of an *E. coli* O6A antigen polysaccharide covalently linked to an EPA-4 carrier protein, wherein the *E. coli* O6A antigen polysaccharide comprises the structure of Formula (O6A); (v) a bioconjugate of an *E. coli* O8 antigen polysaccharide covalently linked to an EPA-4 carrier protein, wherein the *E. coli* O8 antigen polysaccharide comprises the structure of Formula (O8); (vi) a bioconjugate of an *E. coli* O15 antigen polysaccharide covalently linked to an EPA-4 carrier protein, wherein the *E. coli* O15 antigen polysaccharide comprises the structure of Formula (O15); (vii) a bioconjugate of an *E. coli* O16 antigen polysaccharide covalently linked to an EPA-4 carrier protein, wherein the *E. coli* O16 antigen polysaccharide comprises the structure of Formula (O16); (viii) a bioconjugate of an *E. coli* O25B antigen polysaccharide covalently linked to an EPA-4 carrier protein, wherein the *E. coli* O25B antigen polysaccharide comprises the structure of Formula (O25B); and (ix) a bioconjugate of an *E. coli* O75 antigen polysaccharide covalently linked to an EPA-4 carrier protein, wherein the *E. coli* O75 antigen polysaccharide comprises the structure of Formula (O75), wherein each of the Formulas is provided in Table 1, and for each of the Formulas independently n is an integer of 1 to 100, e.g. 1 to 50, preferably 3 to 50, e.g. 5 to 40.

In a particular embodiment, said composition (e.g. pharmaceutical and/or immunogenic composition) further comprises: (x) a bioconjugate of an *E. coli* O18A antigen polysaccharide covalently linked to an EPA-4 carrier protein, wherein the *E. coli* O18A antigen polysaccharide comprises the structure of Formula (O18A) as shown in Table 1, wherein n for this structure is an integer of 1 to 100, e.g. 1 to 50, preferably 3 to 50, e.g. 5 to 40.

In some embodiments, a composition provided herein comprises a bioconjugate of an *E. coli* glucosylated O4 antigen polysaccharide, and at least a bioconjugate of an *E. coli* O25B antigen polysaccharide, wherein the bioconjugate of the *E. coli* O25B antigen polysaccharide is present in the composition at a concentration that is about 1.5 to 6 times, e.g. about 2 to 4 times higher, such as 1.5, 2, 3, 4, 5 or 6 times higher than the concentration of any of the other bioconjugates present in the composition.

In particular embodiments, a composition comprises bioconjugates of *E. coli* O1A, O2, glucosylated O4, O6A, O8, O15, O16, O25B, and O75 antigen polysaccharides, wherein the bioconjugates of O1A:O2:glucosylated O4:O6A:O8:O15:O16:O25B:O75 are present in a ratio (by weight of O-antigen polysaccharide) of 1:1:1:1:1:1:1:2:1, or 2:1:1:2:1:1:1:4:1.

In particular embodiments, a composition comprises bioconjugates of *E. coli* O1A, O2, glucosylated O4, O6A, O8, O15, O16, O18A, O25B, and O75 antigen polysaccharides, wherein the bioconjugates of O1A:O2:glucosylated O4:O6A:O8:O15:O16:O18A:O25B:O75 are present in a ratio (by weight of O-antigen polysaccharide) of 1:1:1:1:1:1:1:1:2:1, or 2:1:1:2:1:1:1:1:4:1.

In some embodiments, a composition provided herein comprises a bioconjugate of an *E. coli* glucosylated O4 antigen polysaccharide, and at least a bioconjugate of an *E. coli* O25B antigen polysaccharide, wherein the bioconjugate of the *E. coli* O25B antigen polysaccharide is present in the composition at a concentration of 2 to 50 μg/mL, preferably 8 to 40 μg/mL, more preferably 16-32 μg/mL, such as 16, 18, 20, 22, 24, 26, 28, 30, or 32 μg/mL. In such embodiments, the concentration of the bioconjugate of the *E. coli* O25B antigen polysaccharide is preferably about 1.5 to 6 times, e.g., about 2 to 4 times higher, such as 1.5, 2, 3, 4, 5, or 6 times higher than the concentration of any of the other bioconjugates present in the composition.

In certain embodiments, the compositions described herein (e.g., pharmaceutical and/or immunogenic compositions) comprise, or are administered in combination with, an adjuvant. The adjuvant for administration in combination with a composition described herein may be administered before (e.g. within 72 hours, 48 hours, 24 hours, 12 hours, 6 hours, 2 hours, 1 hour, 10 minutes), concomitantly with, or after (e.g. within 72 hours, 48 hours, 24 hours, 12 hours, 6 hours, 2 hours, 1 hour, 10 minutes) administration of said composition. As used herein, the term "adjuvant" refers to a compound that when administered in conjunction with or as part of a composition described herein augments, enhances and/or boosts the immune response to an *E. coli* O-antigen polysaccharide in a bioconjugate, but when the adjuvant compound is administered alone does not generate an immune response to the *E. coli* O-antigen polysaccharide in the bioconjugate. In some embodiments, the adjuvant enhances an immune response to an *E. coli* O-antigen polysaccharide in a bioconjugate thereof and does not produce an allergy or other adverse reaction. Adjuvants can enhance an immune response by several mechanisms including, e.g., lymphocyte recruitment, stimulation of B and/or T cells, and stimulation of macrophages.

Examples of suitable adjuvants include, but are not limited to, aluminum salts (alum) (such as aluminum hydroxide, aluminum phosphate, aluminum sulfate and aluminum oxide, including nanoparticles comprising alum or nano-alum formulations), calcium phosphate, monophosphoryl lipid A (MPL) or 3-de-O-acylated monophosphoryl lipid A (3D-MPL) (see e.g., United Kingdom Patent GB2220211, EP0971739, EP1194166, U.S. Pat. No. 6,491,919), AS01, AS02, AS03 and AS04 (all GlaxoSmithKline; see e.g. EP1126876, U.S. Pat. No. 7,357,936 for AS04, EP0671948, EP0761231, U.S. Pat. No. 5,750,110 for AS02), MF59 (Novartis), imidazopyridine compounds (see WO2007/109812), imidazoquinoxaline compounds (see WO2007/109813), delta-inulin, STING-activating synthetic cyclic-dinucleotides (e.g. US20150056224), combinations of lecithin and carbomer homopolymers (e.g. U.S. Pat. No. 6,676,958), and saponins, such as QuilA and QS21 (see e.g. Zhu D and W Tuo, 2016, Nat Prod Chem Res 3: e113 (doi:10.4172/2329-6836.1000e113), Matrix M, Iscoms, Iscomatrix, etc, optionally in combination with QS7 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Further examples of adjuvants are liposomes containing immune stimulants such as MPL and QS21 such as in AS01E and AS01B (e.g. US 2011/0206758). Other examples of adjuvants are CpG (Bioworld Today, Nov. 15, 1998) and imidazoquinolines (such as imiquimod and R848). See, e.g., Reed G, et al., 2013*, Nature Med,* 19: 1597-1608. In certain embodiments, the adjuvant contains a toll-like receptor 4 (TLR4) agonist. TLR4 agonists are well known in the art, see e.g. Ireton G C and S G Reed, 2013, Expert Rev Vaccines 12: 793-807. In certain embodiments, the adjuvant comprises a TLR4 agonist comprising lipid A, or an analog or derivative thereof, such as MPL, 3D-MPL, RC529 (e.g. EP1385541), PET-lipid A, GLA (glycopyranosyl lipid adjuvant, a synthetic disaccharide glycolipid; e.g. US20100310602, U.S. Pat. No. 8,722,064), SLA (e.g. Carter D et al, 2016, Clin Transl Immunology 5: e108 (doi: 10.1038/cti.2016.63), which describes a structure-function approach to optimize TLR4 ligands for human vaccines), PHAD (phosphorylated hexaacyl disaccharide), 3D-PHAD (the structure of which is the same as that of GLA), 3D-(6-acyl)-PHAD (3D(6A)-PHAD) (PHAD, 3D-PHAD, and 3D(6A)PHAD are synthetic lipid A variants, see e.g. avantilipids.com/divisions/adjuvants, which also provide structures of these molecules), E6020 (CAS Number 287180-63-6), ONO4007, OM-174, and the like.

In certain embodiments, the compositions described herein do not comprise, and are not administered in combination with, an adjuvant.

In certain embodiments, the compositions described herein are formulated to be suitable for the intended route of administration to a subject. For example, the compositions (e.g., pharmaceutical and/or immunogenic) described herein can be formulated for subcutaneous, parenteral, oral, sublingual, buccal, intradermal, transdermal, colorectal, intraperitoneal, rectal administration, intravenous, intranasal, intratracheal, intramuscular, topical, transdermal, or intradermal administration. In a specific embodiment, a composition provided herein (e.g., pharmaceutical and/or immunogenic) is formulated for intramuscular injection.

Methods of Use

Bioconjugates and compositions provided herein can be used to induce antibodies against an *E. coli* glucosylated O4 antigen in a subject, and to vaccinate a subject against *E. coli*, in particular extra-intestinal pathogenic *E. coli* (ExPEC). As used herein, "subject" means any animal, preferably a mammal, to whom will be or has been administered a bioconjugate or composition provided herein. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc. In certain embodiments, a subject is a human. A human subject may be of any age. In certain embodiments, a subject is a human of about two months to about 18 years old, e.g. of 1 year to 18 years old. In certain embodiments, a subject is a human of at least 18 years old. In certain embodiments, a subject is a human of 15 to 50 years old, e.g. 18 to 45 years old, e.g. 20 to 40 years old. In certain embodiments, a subject is a human male. In certain embodiments, a subject is a human female. In certain embodiments, a subject is immunocompromised. In certain embodiments, a subject is a human of at least 50 years, at least 55 years, at least 60 years, at least 65 years old. In certain embodiments, a subject is a human that is not older than 100 years, not older than 95 years, not older than 90 years, not older than 85 years, not older than 80 years, or not older than 75 years. In certain embodiments, a subject is a human of at least 60 years old, and not older than 85 years old. In certain embodiments, a subject is a human in stable health. In certain embodiments, a subject is a human adult of at least 60 and not more than 85 years old in stable health. In certain embodiments, a subject is a human that has a history of a urinary tract infection (UTI, i.e. a bacterial infection in the urethra, bladder, ureters, and/or kidneys), i.e. having had at least one UTI episode in his or her life. In certain embodiments, a subject is a human that has a history of UTI in the past twenty, fifteen, twelve, ten, nine, eight, seven, six, five, four, three, two or one years. In certain embodiments, a subject is a human that has a history of UTI in the past two years. In certain embodiments, a subject is a human subject that has a history of recurrent UTI, i.e. having had at least two UTIs in six months or at least three UTIs in one year. In certain embodiments, a subject is a human subject that has a history of recurrent UTI in the past two years. In certain embodiments, a subject is a human of 60 years or older in stable health. In certain embodiments, a subject is a human of 60 years or older that has a history of UTI in the past two years. In certain embodiments, a subject is a human of at least 60 years and less than 75 years old that has a history of UTI in the past two years. In certain embodiments, a subject is a human subject of 75 years or older that has a history of UTI in the past two years. In certain embodiments, a subject is a patient scheduled for undergoing elective urogenital and/or abdominal procedures or surgeries, e.g. transrectal ultrasound-guided prostate needle biopsy (TRUS-PNB).

In one aspect, provided herein is a method of inducing antibodies against an *E. coli* glucosylated O4 antigen in a subject, comprising administering to the subject any of the bioconjugates of an *E. coli* glucosylated O4 antigen covalently linked to a carrier protein described herein, or a composition comprising a bioconjugate of an *E. coli* glucosylated O4 antigen covalently linked to a protein, alone or further in combination with other *E. coli* O-antigen polysaccharides or glycoconjugates or bioconjugates thereof.

In certain embodiments, the antibodies induced, elicited or identified against an *E. coli* glucosylated O4 antigen have opsonophagocytic activity. In particular embodiments, the antibodies induced, elicited or identified are cross-reactive antibodies capable of mediating opsonophagocytic killing of both *E. coli* glucosylated and non-glucosylated O4 strains.

In certain embodiments, the antibodies induced, elicited or identified against an *E. coli* glucosylated O4 antigen specifically recognize unmodified and glucose modified O4 antigen polysaccharide. In certain embodiments, the antibodies induced, elicited or identified against an *E. coli* glucosylated O4 antigen specifically recognize *E. coli* of the O4 serotype. In certain embodiments, the antibodies induced by a bioconjugate of an *E. coli* glucosylated O4 antigen bind preferentially to glucosylated O4 antigen as compared to non-glucosylated O4 antigen.

Antibodies induced by the bioconjugates and compositions described herein can include immunoglobulin molecules and immunologically active portions of immunoglobulin molecules, i.e., molecules that contain an antigen binding site that specifically binds to an *E. coli* O-antigen polysaccharide, e.g., glucosylated O4 antigen polysaccharide.

Antibodies induced, elicited or identified using the bioconjugates or compositions provided herein can be used to monitor the efficacy of a therapy and/or disease progression. Any immunoassay system known in the art can be used for this purpose including, but not limited to, competitive and noncompetitive assay systems using techniques such as radioimmunoassays, ELISA (enzyme linked immunosorbent assays), electrochemiluminescence (ECL)-based immunoassays, "sandwich" immunoassays, precipitin reactions, gel diffusion precipitin reactions, immunodiffusion assays, immunoradiometric assays, fluorescent immunoassays, protein A immunoassays and immunoelectrophoresis assays. Several of these assays, e.g. ECL-based immunoassays, can be done in multiplex format, and typically multiplex assay formats are preferred.

Antibodies induced, elicited or identified using a bioconjugate of an *E. coli* glucosylated O4 antigen polysaccharide can be used to detect *E. coli* O4 strains, particularly glucosylated O4 strains, for example, from a plurality of *E. coli* strains and/or to diagnose an infection by an *E. coli* O4 or glucosylated O4 strain.

In another aspect, provided herein is a method of vaccinating a subject against *E. coli* (e.g. extra-intestinal pathogenic *E. coli*, ExPEC), comprising administering to the subject any of the bioconjugates of an *E. coli* glucosylated O4 antigen covalently linked to a carrier protein described herein, or a composition comprising a bioconjugate of an *E. coli* glucosylated O4 antigen covalent linked to a carrier protein, alone or further in combination with other *E. coli* O-antigens or glycoconjugates or bioconjugates thereof. One skilled in the art will understand that the subject will be vaccinated against *E. coli* strains whose O antigens or glycoconjugates or bioconjugates thereof are present in the composition administered. For example, administration of a composition comprising O1A, O2, glucosylated O4, O6A, and O25B antigen polysaccharides can be used to a vaccinate a subject against *E. coli* serotypes O1A, O2, O4, O6A, and O25B.

In certain embodiments, vaccination is for preventing an invasive ExPEC disease (IED), e.g., urosepsis, bacteremia, sepsis, etc. In certain embodiments, vaccination is to prevent or reduce the occurrence or severity of urinary tract infections. In certain embodiments, an IED can be hospital-acquired, e.g. in patients undergoing urogenital and/or abdominal procedures or surgeries. In certain embodiments, an IED can be healthcare-associated, e.g. in patients receiving health care for another condition, for instance via central lines, catheters, etc, e.g. in a hospital, ambulatory surgical center, end-stage renal disease facility, long-term care facility, etc. In certain embodiments, the IED can be community-acquired, e.g. in a patient that was not recently exposed to healthcare risks.

In another aspect, provided herein is a method of inducing an immune response against *E. coli* (e.g., ExPEC) in a subject, comprising administering to the subject any of the bioconjugates of an *E. coli* glucosylated O4 antigen covalently linked to a carrier protein described herein, or a composition comprising a bioconjugate of an *E. coli* glucosylated O4 antigen covalently linked to a carrier protein, alone or further in combination with other *E. coli* O-antigens or glycoconjugates or bioconjugates thereof. In one embodiment, the subject has an *E. coli* (e.g., ExPEC) infection at the time of administration. In a preferred embodiment, the subject does not have an *E. coli* (e.g., ExPEC) infection at the time of administration.

In certain embodiments, the compositions and bioconjugates described herein can be administered to a subject to induce an immune response that includes the production of antibodies, preferably antibodies having opsonophagocytic activity. Such antibodies can be isolated using techniques known to one of skill in the art (e.g., immunoaffinity chromatography, centrifugation, precipitation, etc.).

The ability of the bioconjugates and compositions described herein to generate an immune response in a subject can be assessed using any approach known to those of skill in the art or described herein. In some embodiments, the ability of a bioconjugate to generate an immune response in a subject can be assessed by immunizing a subject (e.g., a mouse, rat, rabbit, or monkey) or set of subjects with a bioconjugate described herein and immunizing an additional subject (e.g., a mouse, rat, rabbit, or monkey) or set of subjects with a control (PBS). The subjects or set of subjects can subsequently be challenged with ExPEC and the ability of the ExPEC to cause disease (e.g., UTI, bacteremia, or other disease) in the subjects or set of subjects can be determined. Those skilled in the art will recognize that if the subject or set of subjects immunized with the control suffer(s) from disease subsequent to challenge with the ExPEC but the subject or set of subjects immunized with a bioconjugate(s) or composition thereof described herein suffer less from or do not suffer from disease, then the bioconjugate is able to generate an immune response in a subject. The ability of a bioconjugate(s) or composition thereof described herein to induce antiserum that cross-reacts with an O antigen from ExPEC can be tested by, e.g., an immunoassay, such as an ELISA (see e.g., Van den Dobbelsteen et al, 2016, Vaccine 34: 4152-4160), or an ECL-based immunoassay.

For example, the ability of the bioconjugates described herein to generate an immune response in a subject can be assessed using a serum bactericidal assay (SBA) or opsonophagocytic killing assay (OPK assay, or OPKA), which represents an established and accepted method that has been used to obtain approval of glycoconjugate-based vaccines. Such assays are well-known in the art and, briefly, comprise the steps of generating and isolating antibodies against a target of interest (e.g., an O antigen polysaccharide, e.g., *E. coli* glucosylated O4 antigen polysaccharide) by administering to a subject (e.g., a mouse, rat, rabbit, or monkey) a compound that elicits such antibodies. Subsequently, the bactericidal capacity of the antibodies can be assessed by, e.g., culturing the bacteria in question (e.g., *E. coli* of the relevant serotype) in the presence of the antibodies and complement and—depending on the assay—neutrophilic cells and assaying the ability of the antibodies to mediate killing and/or neutralization of the bacteria, e.g., using standard microbiological approaches. For an example of OPK assay for *E. coli* bioconjugate vaccines, see e.g. Abbanat et al, 2017, Clin. Vaccine Immunol. 24: e00123-17. An OPK assay can be performed in monoplex or multiplex format, of which multiplex format (e.g. testing multiple serotypes at the same time) is typically preferred. A multiplex OPK assay is sometimes referred to herein as "MOPA".

In some embodiments, the methods described herein comprise administering an effective amount of bioconjugates of an *E. coli* glucosylated O4 antigen covalently linked to a carrier protein described herein, or a composition comprising a bioconjugate of an *E. coli* glucosylated O4 antigen covalently linked to a carrier protein, alone or further in combination with other *E. coli* O-antigens or glycoconjugates or bioconjugates thereof. In one embodiment, an "effective amount" is an amount that vaccinates a subject against *E. coli* (e.g., ExPEC). In another embodiment, an "effective amount" is an amount that induces an immune response against *E. coli* (e.g., ExPEC) in a subject, such as an immune response including the production of antibodies, preferably antibodies having opsonophagocytic activity.

In particular embodiments, wherein a composition provided herein comprises a bioconjugate of an *E. coli* glucosylated O4 antigen polysaccharide and at least a bioconjugate of an *E. coli* O25B antigen polysaccharide, an effective amount of the *E. coli* O25B antigen polysaccharide is about 1.5 to 6 times, e.g. about 2 to 4 times higher, such as 1.5, 2, 3, 4, 5 or 6 times higher than the concentration of any of the other bioconjugates present in the composition. In such embodiments, an effective amount of the *E. coli* O25B antigen polysaccharide is for instance about 5 to 18 μg per administration, such as 5, 6, 7, 8, 9, 10, 11, 12, 13, 14, 15, 16, 17, 18 μg per administration.

In certain embodiments, a bioconjugate or composition according to the invention is administered to a subject once. In certain embodiments, a bioconjugate or composition according to the invention is administered to a subject more than once, e.g. in a prime-boost regimen. In certain embodiments, the time between two administrations is at least two weeks, at least one month, at least two months, at least three months, at least six months, at least one year, at least two years, at least five years, at least ten years, or at least fifteen years. In humans, a desired immune response can typically be generated by a single administration of a bioconjugate or composition according to the invention. In certain embodiments, a repeat administration after for instance ten years is provided.

Host Cells

Provided herein are host cells, e.g., prokaryotic host cells, capable of producing *E. coli* O antigens and bioconjugates comprising such *E. coli* O antigens. The host cells provided herein preferably are modified to comprise (e.g., through genetic engineering) one or more of the nucleic acids encoding host cell machinery (e.g., glycosyltransferases) used to produce *E. coli* O-antigen polysaccharides and/or bioconjugates thereof.

Any host cells known to those of skill in the art can be used to produce the *E. coli* O antigen polysaccharides described herein (e.g., *E. coli* glucosylated O4 antigen polysaccharide) and bioconjugates comprising the *E. coli* O antigen polysaccharides described herein (e.g., a bioconjugate of *E. coli* glucosylated O4 antigen polysaccharide) including archaea, prokaryotic host cells, and eukaryotic host cells. In a preferred embodiment, a host cell is a prokaryotic host cell. Exemplary prokaryotic host cells for use in production of the *E. coli* O antigen polysaccharides described herein and bioconjugates comprising the *E. coli* O antigen polysaccharides described herein include, but are not limited to, *Escherichia* species, *Shigella* species, *Klebsiella* species, *Xanthomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species.

In a specific embodiment, the host cell used to produce the *E. coli* O antigen polysaccharides described herein and bioconjugates comprising the *E. coli* O antigen polysaccharides described herein is a prokaryotic host cell, and is preferably *E. coli*.

In certain embodiments, the host cells used to produce the *E. coli* O antigen polysaccharides and bioconjugates described herein are engineered to comprise heterologous nucleic acids, e.g., heterologous nucleic acids comprising rfb gene clusters of a desired O antigen serotype, heterologous nucleic acids that encode one or more carrier proteins and/or glycosyltransferases. In a specific embodiment, heterologous rfb genes, and/or heterologous nucleic acids that encode proteins involved in glycosylation pathways (e.g., prokaryotic and/or eukaryotic glycosylation pathways) can be introduced into the host cells described herein. Such nucleic acids can encode proteins including, but not limited to, oligosaccharyl transferases and/or glycosyltransferases.

Sequences of various genes and gene clusters encoding glycosyltransferases useful in making recombinant host cells that can, e.g., be used to prepare *E. coli* O antigen polysaccharides and bioconjugates thereof are described herein. Those skilled in the art will appreciate that due to the degeneracy of the genetic code, a protein having a specific amino acid sequence can be encoded by multiple different nucleic acids. Thus, those skilled in the art will understand that a nucleic acid provided herein can be altered in such a way that its sequence differs from a sequence provided herein, without affecting the amino acid sequence of the protein encoded by the nucleic acid.

Provided herein are host cells (e.g., recombinant host cells) for producing a bioconjugate of an *E. coli* glucosylated O4 antigen polysaccharide, O1A antigen polysaccharide, O2 antigen polysaccharide, O6A antigen polysaccharide, O8 antigen polysaccharide, O15 antigen polysaccharide, O16 antigen polysaccharide, O18A antigen polysaccharide, O25B antigen polysaccharide, or O75 antigen polysaccharide. The host cells provided herein comprise nucleic acids encoding enzymes (e.g., glycosyltransferases) capable of producing the *E. coli* O antigen polysaccharide. The host cells provided herein can naturally express nucleic acids capable of producing an O antigen of interest, or the host cells can be made to express such nucleic acids. In certain embodiments the nucleic acids are heterologous to the host cells and introduced into the host cells using genetic approaches known in the art. For example, the nucleic acids can be introduced into the host cell by genetic manipulation (e.g., the gene cluster is expressed on a plasmid or plasmids or integrated into the host cell genome (see, e.g., International Patent Application Publications WO 2014/037585, WO 2014/057109, WO 2015/052344).

In one embodiment, provided herein is a host cell (e.g., recombinant host cell) capable of producing a bioconjugate of an *E. coli* glucosylated O4 antigen polysaccharide covalently linked to a carrier protein. Such a host cell comprises, preferably by engineering a precursor cell, a nucleic acid sequence encoding a gtrS gene, which, to the best of the knowledge of the inventors, was identified herein for the first time as encoding a polysaccharide branching enzyme capable of transferring glucose to the *E. coli* O4 antigen (i.e., a glucosyltransferase specific to the *E. coli* O4 antigen polysaccharide), and particularly to L-Rha via an α-1,3-glycosidic linkage. An example of an amino acid sequence of such branching enzyme is provided in SEQ ID NO: 4. Other examples comprise amino acid sequences that are at least 80% identical thereto. Exemplary examples of nucleic acid sequence encoding gtrS genes specific to the *E. coli* O4 antigen polysaccharide include, but are not limited to, SEQ ID NO: 5, or degenerate nucleic acid sequences thereto that encode SEQ ID NO: 4, or nucleic acid sequences that encode functional O4-specific GtrS enzymes that have at least 80% identity to SEQ ID NO: 4.

In a specific embodiment, a host cell (e.g., recombinant host cell) capable of producing a bioconjugate of an *E. coli* glucosylated O4 antigen polysaccharide covalently linked to a carrier protein, comprises a nucleotide sequence encoding a glucosyl transferase having at least 80% sequence identity to SEQ ID NO: 4, such as about 80%, 85%, 90%, 91%, 92%, 93%, 94%, 95%, 95%, 97%, 98%, 99%, or 100% sequence identity to SEQ ID NO: 4. In view of the redundancy in the genetic code, one of ordinary skill in the art can make variants of nucleic encoding the amino acid sequences of glucosyl transferases, e.g., using codon optimized sequences, if desired.

In certain embodiments, a host cell (e.g., recombinant host cell) capable of producing a bioconjugate of an *E. coli* glucosylated O4 antigen polysaccharide covalently linked to a carrier protein, comprising a nucleotide sequence encoding a glucosyl transferase (GtrS) having at least 80% sequence identity to SEQ ID NO: 4, further comprises a nucleotide sequence encoding a bactoprenol-linked glucose translocase (GtrA) having at least 80% sequence identity to SEQ ID NO: 7, and a nucleotide sequence encoding a bactoprenol glucosyl transferase (GtrB) having at least 80% sequence identity to SEQ ID NO: 8. In certain embodiments, said nucleic acid sequences encode GtrA and GtrB proteins that are at least about 80%, 85%, 90%, 95%, 96%, 97%, 98%, 99%, or 100% identical to SEQ ID NOs: 7 and 8, respectively, and have bactoprenol-linked glucose translocase (SEQ 11) NO: 7) and bactoprenol glucosyl transferase (SEQ ID NO: 8) activity, respectively. In view of the redundancy in the genetic code, one of ordinary skill in the art can make variants of nucleic encoding the amino acid sequences of bactoprenol-linked glucose translocases and of bactoprenol glucosyl transferases, e.g., using codon optimized sequences, if desired.

A host cell (e.g., recombinant host cell) capable of producing a bioconjugate of an *E. coli* glucosylated O4 antigen polysaccharide covalently linked to a carrier protein provided herein further comprises a nucleotide sequence of an rfb gene cluster for the *E. coli* O4 antigen polysaccharide. An example of an rfb gene cluster useful for production of the *E. coli* O4 antigen polysaccharide is provided herein as SEQ ID NO: 9. Another example can be found in GenBank, locus AY568960. Degenerate nucleic acid sequences encoding the same enzymes as encoded by this sequence, or sequences that encode enzymes that are at least 80% identical, preferably at least 85%, 90%, 91%, 92%, 93%, 94%, 95%, 96%, 97%, 98%, 99% identical, can also be used.

In a specific embodiment, provided herein is a host cell (e.g., a recombinant host cell, preferably a recombinant prokaryotic host cell, preferably a recombinant *E. coli* host cell) that produces glucosylated O4 antigen polysaccharide, wherein the host cell comprises gtrS, an rfb gene cluster for the *E. coli* O4 antigen polysaccharide, and nucleic acid encoding a carrier protein. Such host cells can be engineered using recombinant approaches to comprise one or more plasmids comprising the gtrS gene, the rfb gene cluster, and/or nucleic acid encoding a carrier protein, or to comprise some or all of the relevant genes such as gtrS, the rfb cluster and/or the nucleic acid encoding the carrier protein integrated into the host cell genome. In certain embodiments, the genes or gene clusters have been integrated into the genome of the host cell using homologous recombination. An advantage of integration of genes into the genome of the host cell is stability in the absence of antibiotic selection.

In another specific embodiment, provided herein is a host cell (e.g., a recombinant host cell, preferably a recombinant prokaryotic host cell) that produces glucosylated O4 antigen polysaccharide, wherein the host cell comprises GtrS (glucosyltransferase), as well as the enzymes encoded by the O4 rfb cluster. In certain embodiments, some or all of the aforementioned enzymes are heterologous to the host cell.

In other specific embodiments, provided herein is a host cell (e.g. a recombinant host cell, preferably a recombinant prokaryotic host cell) that produces *E. coli* glucosylated O4 antigen polysaccharide, preferably a bioconjugate of *E. coli* glucosylated O4 antigen polysaccharide, wherein the host cell further comprises a nucleotide sequence encoding an oligosaccharyl transferase and/or a nucleotide sequence encoding a carrier protein. In one specific embodiment, the oligosaccharyl transferase is heterologous to the host cell. In another specific embodiment, the carrier protein is heterologous to the host cell. Preferably, the host cell comprises a heterologous nucleotide sequence encoding a glucosyl transferase having at least 80% sequence identity to SEQ ID NO: 4. In preferred embodiments, the rfb genes of the O4 cluster are heterologous to the host cell. Preferably the sequence encoding the enzyme that is capable of introducing the branched glucose side chain to the O4 antigen, i.e. the gtrS gene (encoding a glucosyl transferase having at least 80% sequence identity to SEQ ID NO:4) is heterologous to the host cell. A nucleic acid is heterologous to the host cell if the same sequence is not naturally present in said host cell. Heterologous nucleic acid can for instance be introduced in a parent cell by genetic engineering, e.g by transformation (e.g. chemical transformation or electroporation) and/or recombination. In certain embodiments, heterologous nucleic acid such as a desired rfb locus, gtrS coding sequence, carrier protein encoding sequence, and/or glycosyltransferase encoding sequence are integrated into the genome of the host cell, preferably a bacterial host cell, preferably an *E. coli* host cell. In preferred embodiments, the endogenous rfb locus and if applicable gtrS coding sequence have been inactivated, preferably deleted from the genome of the recombinant host cell as compared to a predecessor thereof, and preferably these are replaced by the desired heterologous rfb locus, and if applicable desired gtrS coding sequence, respectively. In certain embodiments the host cell is a K-12 of *E. coli* (as a non-limiting example, *E. coli* strain W3110 is a K-12 strain), or a B strain of *E. coli* (as a non-limiting example, *E. coli* strain BL21 is a B strain), or any other well-defined strain of *E. coli*, e.g. laboratory strains or production strains, in contrast to primary wild-type isolates. In preferred embodiments, the host cell is derived from *E. coli* that does not express O4 antigen or glucosylated O4 antigen, by introduction into such *E. coli* of the O4 rfb locus and the gtrS gene encoding a glucosyl transferase having at least 80% sequence identity to SEQ ID NO:4. Advantages of using well-characterized strains, such as *E. coli* K-12 or *E. coli* B, as precursors for host cells is the possibility to use a similar production process for different O-antigen bioconjugates, since the characteristics of the production strain are well-defined. Even though bioconjugates of different O-antigens will behave differently and expression processes can be optimized per production strain, at least the basic process for production of O-antigen bioconjugates will be more predictable using such well-defined precursor strains than when unknown strains such as wild-type isolates are used as precursors for production of host strains. This way, experience with production of earlier described *E. coli* O-antigen bioconjugates such as O1A, O2, O6A and O25B bioconjugates as described in for instance WO 2015/124769 and WO 2017/035181 can be used as basis to design production of other *E. coli* O-antigen bioconjugates. Unlike gtrS, the gtrA and gtrB genes are not serotype-specific, and in certain embodiments these are homologous to the host cell (e.g. *E. coli* K12 strain W3110 includes gtrA and gtrB genes that are capable of functioning together with the O4-serotype specific recombinantly introduced gtrS gene encoding a glucosyl transferase of SEQ ID NO: 4 or a glucosyl transferase that is at least 80% identical thereto, replacing the endogenous gtrS gene). In other embodiments, one or both of gtrA and gtrB genes (encoding GtrA and GtrB proteins that are at least about 80% identical to SEQ ID NOs: 7 and 8, respectively, and having bactoprenol-linked glucose translocase and bactoprenol glucosyl transferase activity respectively, are also recombinantly introduced in the host cell, for instance in case the host cell does not have endogenous gtrA and/or gtrB genes.

Also provided herein are host cells (e.g., recombinant host cells) capable of producing a bioconjugate of an *E. coli* O1A, O2, O6A, O8, O15, O16, O18A, O25B, or O75 antigen polysaccharide covalently linked to a carrier protein. Such host cells (e.g., recombinant host cells) comprise nucleotide sequence of an rfb gene cluster specific to the O-antigen polysaccharide. The rfb gene clusters can be isolated from wild-type *E. coli* strains, and combined with nucleic acids encoding an oligosaccharyl transferase (e.g., PglB) and carrier protein (e.g., EPA) within one host cell to obtain a recombinant host cell that produces the *E. coli* O-antigen of interest or bioconjugate thereof. For example, such host cells can be engineered using recombinant approaches to comprise one or more plasmids comprising the rfb gene cluster, oligosaccharyl transferase (e.g., PglB) and carrier protein (e.g., EPA) using bioconjugation technology such as that described in WO 2014/037585, WO 2009/104074, and WO 2009/089396. Preferably the host cells comprise the rfb gene clusters integrated into their genome. The nucleic acids encoding oligosaccharyl transferase, carrier protein, and where applicable gtrS gene, are in certain embodiments also integrated into the genome of the host cell. Heterologous or homologous gtrA and gtrB genes are in certain embodiments also integrated into the genome of the host cell.

Preparation of bioconjugates for O1A, O2, O6A and O25B antigens has been described in detail in WO 2015/124769 and WO 2017/035181. Exemplary gene clusters for each *E. coli* O antigen (rfb loci) have been described in Iguchi A, et al, DNA Research, 2014, 1-7 (doi: 10.1093/dnares/dsu043), and in DebRoy C, et al, PLoS One. 2016, 11(1):e0147434 (doi: 10.1371/journal.pone.0147434; correction in: Plos One. 2016, 11(4):e0154551, doi: 10.1371/journal.pone.0154551). Nucleic acid sequences for the rfb clusters and amino acid sequences for proteins encoded therein can also be found in public databases, such as GenBank. Exemplary sequences for rfb clusters that can be used in production strains for bioconjugates with polysaccharide antigens of the serotypes disclosed herein, are also provided in SEQ ID NOs: 9 and 11-19. Thus, for each of the desired bioconjugates mentioned above, the respective rfb cluster can be introduced into a host cell, to obtain host cells with the specific rfb cluster for the desired O-antigen, as well as containing nucleic acid encoding oligosaccharyltransferase and carrier protein. For reasons indicated above, preferably the host cells are recombinant host cells, and preferably are derived from strains with relatively well-known characteristics, such as *E. coli* laboratory or production strains, e.g. *E. coli* K12 or *E. coli* BL21, etc. Preferably, the rfb clusters are heterologous to the host cell, e.g. introduced into a precursor cell of the host cell, and preferably integrated into the genome thereof. Preferably an original rfb gene cluster, if such was present in a precursor cell, has been replaced by the rfb gene cluster for the O-antigen of interest in the host cell, to enable production of bioconjugate of the O-antigen of interest. Preferably the oligosaccharyltransferase is heterologous to the host cell, and in certain embodiments nucleic acid encoding such oligosaccharyltransferase is integrated into the genome of the host cell.

Any of the host cells provided herein (e.g., recombinant host cells, preferably recombinant prokaryotic host cells) comprise nucleic acids encoding additional enzymes active in the N-glycosylation of proteins, e.g., the host cell provided herein can further comprise a nucleic acid encoding an oligosaccharyl transferase or nucleic acids encoding other glycosyltransferases.

The host cells provided herein comprise a nucleic acid that encodes an oligosaccharyl transferase. Oligosaccharyl transferases transfer lipid-linked oligosaccharides to asparagine residues of nascent polypeptide chains that comprise an N-glycosylation consensus motif. The nucleic acid that encodes an oligosaccharyl transferase can be native to the host cell, or can be introduced into the host cell using genetic approaches. In preferred embodiments, the oligosaccharyl transferase is heterologous to the host cell. *E. coli* does not naturally comprise an oligosaccharyl transferase, and hence if *E. coli* is used as a host cell for production of bioconjugates, a heterologous oligosaccharyl transferase is comprised in such host cell, e.g. upon introduction by genetic engineering. The oligosaccharyl transferase can be from any source known in the art in view of the present disclosure.

In certain embodiments, an alternative to an oligosaccharyl transferase with N-glycosyltransferase activity, such as an O-glycosyltransferase, e.g. as a non-limiting example PglL, can be used, in conjunction with its own, different, glycosylation consensus sequence in the carrier protein, as for instance described in WO 2016/82597. Other glycosyltransferases, such as O-glycosyltransferases, can thus also be used as an oligosaccharyltransferase according to the invention.

In certain preferred embodiments, the oligosaccharyl transferase is an oligosaccharyl transferase from *Campylobacter*. For example, in one embodiment, the oligosaccharyl transferase is an oligosaccharyl transferase from *Campylobacter jejuni* (i.e., pglB; see, e.g., Wacker et al., 2002, Science 298:1790-1793; see also, e.g., NCBI Gene ID: 3231775, UniProt Accession No. O86154). In another embodiment, the oligosaccharyl transferase is an oligosaccharyl transferase from *Campylobacter lari* (see, e.g., NCBI Gene ID: 7410986).

In specific embodiments, the oligosaccharyl transferase is PglB oligosaccharyl transferase from *Campylobacter jejuni*, including the natural (wild-type) protein or any variant thereof, such as those described in International Patent Application Publications WO 2016/107818 and WO 2016/107819. PglB can transfer lipid-linked oligosaccharides to asparagine residues in the consensus sequences SEQ ID NO: 1 and SEQ ID NO: 2. In particular embodiments, the PglB oligosaccharyl transferase comprises SEQ ID NO: 6, or a variant thereof. In certain embodiments one or more endogenous glycosylation consensus sequences in a wild-type PglB have been mutated to avoid PglB autoglycosylation, e.g. SEQ ID NO: 6 comprising the mutation N534Q. Examples of variant PglB oligosaccharyl transferases suitable for use in the recombinant host cells provided herein include the PglB oligosaccharyl transferase of SEQ ID NO: 6 comprising at least one mutation selected from the group consisting of N311V, K482R, D483H, A669V, Y77H, S80R, Q287P, and K289R. In one particular embodiment, a variant PglB oligosaccharyl transferase has SEQ ID NO: 6 comprising the mutation N311V. In another particular embodiment, a variant PglB oligosaccharyl transferase has SEQ ID NO: 6 comprising the mutations Y77H and N311V. In another particular embodiment, a variant PglB oligosaccharyl transferase has SEQ ID NO: 6 comprising the mutations N311V, K482R, D483H, and A669V. In another particular embodiment, a variant PglB oligosaccharyl transferase has SEQ ID NO: 6 comprising the mutations Y77H, S80R, Q287P, K289R, and N311V. It was found and described herein that certain PglB oligosaccharyl transferase variants give surprisingly improved yields in production of *E. coli* O-antigen bioconjugates of specific serotypes. The improved or optimal PglB variant for a given *E. coli* O-antigen was not predictable. The invention in certain aspects therefore also provides methods for producing bioconjugates of specific *E. coli* O-antigens, using specific PglB variants as the oligosaccharyl transferase. Further variants of PglB that are at least 80%, 85%, 90%, 91%, 92%, 93%, 94%, 95%, 96%, 97%, 98%, 99% identical to SEQ ID NO: 6 and still have oligosaccharyl transferase activity, preferably having one or more of the specific amino acids on the indicated positions disclosed in combination herein (e.g. 77Y, 80S, 287Q, 289K, 311N, 482K, 483D, 669A; or 311V; or 311V, 482R, 483H, 669V; or 77H, 80R, 287P, 289R, 311V; or 77H, 311V; etc) can also be used for production of bioconjugates.

In a specific embodiment, a host cell (e.g., recombinant host cell) capable of producing a bioconjugate of an *E. coli* glucosylated O4 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutation N311V, or more preferably SEQ ID NO: 6 comprising the mutations Y77H and N311V.

In other specific embodiments, a host cell (e.g., recombinant host cell) capable of producing a bioconjugate of an *E. coli* O1A, O6A, or O15 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutations N311V, K482R, D483H, and A669V.

In a specific embodiment, a host cell (e.g., recombinant host cell) capable of producing a bioconjugate of an *E. coli* O16 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutations Y77H, S80R, Q287P, K289R, and N311V.

In a specific embodiment, a host cell (e.g., recombinant host cell) capable of producing a bioconjugate of an *E. coli* O75 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutation N311V.

In a specific embodiment, a host cell (e.g., recombinant host cell) capable of producing a bioconjugate of an *E. coli* O8, O18A, O25B, or O2 antigen polysaccharide covalently linked to a carrier protein further comprises a nucleotide sequence encoding PglB oligosaccharyl transferase from *Campylobacter jejuni* having the amino acid sequence of SEQ ID NO: 6, preferably wherein SEQ ID NO: 6 comprises no amino acid mutations at positions 77, 80, 287, 289, 311, 482, 483, and 669.

In some embodiments, any of the host cells provided herein comprise a nucleic acid encoding a carrier protein, e.g., a protein to which the O-antigen polysaccharide(s) produced by the host cell glycosylation machinery can be attached to form a bioconjugate. The host cell can comprise a nucleic acid encoding any carrier protein known to those skilled in the art in view of the present disclosure including, but not limited to, detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

In preferred embodiments, a host cell further comprises a nucleic acid encoding detoxified Exotoxin A of *P. aeruginosa* (EPA). Preferably, the EPA carrier protein comprises 1-10 glycosylation sites, preferably 2 to 4 glycosylation sites, most preferably 4 glycosylation sites, such as 1-10, preferably 2-4, and more preferably 4 glycosylation sites each comprising a glycosylation consensus sequence having the amino acid sequence of SEQ ID NO: 1, and more preferably having the amino acid sequence of SEQ ID NO: 2. In a specific embodiment, a host cell further comprises a nucleic acid encoding EPA-4 carrier protein comprising SEQ ID NO: 3.

In certain embodiments, the carrier proteins used in the generation of the bioconjugates by the host cells described herein comprise a "tag," i.e., a sequence of amino acids that allows for the isolation and/or identification of the carrier protein. For example, adding a tag to a carrier protein can be useful in the purification of that protein and, hence, the purification of conjugate vaccines comprising the tagged carrier protein. Exemplary tags that can be used herein include, without limitation, histidine (HIS) tags (e.g., hexa-histidine-tag, or 6×His-Tag), FLAG-TAG, and HA tags. In certain embodiments, the tags used herein are removable, e.g., removal by chemical agents or by enzymatic means, once they are no longer needed, e.g., after the protein has been purified. In other embodiments, the carrier protein does not comprise a tag.

In certain embodiments, the carrier proteins described herein comprise a signal sequence that targets the carrier protein to the periplasmic space of the host cell that expresses the carrier protein. In a specific embodiment, the signal sequence is from *E. coli* DsbA, *E. coli* outer membrane porin A (OmpA), *E. coli* maltose binding protein (MalE), *Erwinia* carotovorans pectate lyase (PelB), FlgI, NikA, or *Bacillus* sp. endoxylanase (XynA), heat labile *E. coli* enterotoxin LTIIb, *Bacillus* endoxylanase XynA, or *E. coli* flagellin (FlgI). In one embodiment, the signal sequence comprises SEQ ID NO: 10. A signal sequence may be cleaved off after translocation of the protein to the periplasm and may thus no longer be present in the final carrier protein of a bioconjugate.

In certain embodiments, additional modifications can be introduced (e.g., using recombinant techniques) into the host cells described herein. For example, host cell nucleic acids (e.g., genes) that encode proteins that form part of a possibly competing or interfering glycosylation pathway (e.g., compete or interfere with one or more heterologous genes involved in glycosylation that are recombinantly introduced into the host cell) can be deleted or modified in the host cell background (genome) in a manner that makes them inactive/dysfunctional (i.e., the host cell nucleic acids that are deleted/modified do not encode a functional protein). In certain embodiments, when nucleic acids are deleted from the genome of the host cells provided herein, they are replaced by a desirable sequence, e.g., a sequence that is useful for production of an O antigen polysaccharide or bioconjugate thereof.

Exemplary genes or gene clusters that can be deleted in host cells (and, in some cases, replaced with other desired nucleic acid sequences) include genes or gene clusters of host cells involved in glycolipid biosynthesis, such as waaL (see, e.g., Feldman et al., 2005, *PNAS USA* 102:3016-3021), the lipid A core biosynthesis cluster (waa), galactose cluster (gal), arabinose cluster (ara), colonic acid cluster (wc), capsular polysaccharide cluster, undecaprenol-p biosynthesis genes (e.g. uppS, uppP), und-P recycling genes, metabolic enzymes involved in nucleotide activated sugar biosynthesis, enterobacterial common antigen cluster (eca), and prophage O antigen modification clusters like the gtrABS cluster or regions thereof. In a specific embodiment, the host cells described herein are modified such that they do not produce any 0 antigen polysaccharide other than a desired O antigen polysaccharide, e.g., glucosylated O4 antigen polysaccharide.

In a specific embodiment, the waaL gene is deleted or functionally inactivated from the genome of a host cell (e.g., recombinant host cell) provided herein. The terms "waaL" and "waaL gene" refer to the O-antigen ligase gene encoding a membrane bound enzyme with an active site located in the periplasm. The encoded enzyme transfers undecaprenylphosphate (UPP)-bound O antigen to the lipid A core, forming lipopolysaccharide. Deletion or disruption of the endogenous waaL gene (e.g., ΔwaaL strains) disrupts transfer of the O-antigen to lipid A, and can instead enhance transfer of the O-antigen to another biomolecule, such as a carrier protein.

In another specific embodiment, one or more of the waaL gene, gtrA gene, gtrB gene, gtrS gene, and the rfb gene cluster is deleted or functionally inactivated from the original genome of a prokaryotic host cell provided herein.

In one embodiment, a host cell used herein is *E. coli* that produces a bioconjugate of glucosylated O4 antigen polysaccharide, wherein the waaL gene is deleted or functionally inactivated from the genome of the host cell, and a gtrS gene specific to *E. coli* O4 antigen polysaccharide is inserted. In certain embodiments for production strains for bioconjugates of the glucosylated O4 O-antigen, a gtrS gene encoding a glucosyl transferase having at least 80% sequence identity to SEQ ID NO:4 is inserted in the place of a gtrS gene of the parent strain, so as to replace the gtrS gene in that parent strain with the one that is responsible for glucosylation of the O4 antigen. An example of such a parent strain is *E. coli* K-12 strain W3110. The gtrA and gtrB genes can be homologous to the parent strain, or alternatively one or both of these genes can be heterologous to the parent strain. Typically, and unlike the gtrS gene, these gtrA and gtrB genes are not specific for the O-antigen structure.

Also provided herein are methods of making recombinant host cells. Recombinant host cells produced by the methods described herein can be used to produce bioconjugates of *E. coli* O antigens. The methods comprise introducing one or more recombinant nucleic acid molecules into a cell to produce the recombinant host cell. Typically, the recombinant nucleic acid molecules are heterologous. Any method known in the art in view of the present disclosure can be used to introduce recombinant nucleic acid molecules into a host cell. Recombinant nucleic acids can be introduced into the host cells described herein using any methods known to those of ordinary skill in the art, e.g., electroporation, chemical transformation, by heat shock, natural transformation, phage transduction, and conjugation. In specific embodiments, recombinant nucleic acids are introduced into the host cells described herein using a plasmid. For example, the heterologous nucleic acids can be expressed in the host cells by a plasmid (e.g., an expression vector). In another specific embodiment, heterologous nucleic acids are introduced into the host cells described herein using the method of insertion into the genome as for instance described in International Patent Application Publication WO 2014/037585, WO 2014/057109, or WO 2015/052344.

In one embodiment, a method of making a recombinant host cell for producing a bioconjugate of an *E. coli* glucosylated O4 antigen polysaccharide covalently linked to a carrier protein comprises introducing one or more recombinant nucleic acid molecules into a cell, preferably an *E. coli* cell, to produce the recombinant host cell. In such embodiments, the recombinant nucleic acid molecules introduced into the cell include (i) a nucleotide sequence of an rfb gene cluster for the *E. coli* O4 antigen polysaccharide; (ii) a nucleotide sequence encoding a glucosyl transferase having at least 80% sequence identity to SEQ ID NO: 4, wherein the glucosyl transferase is capable of modifying the *E. coli* O4 antigen polysaccharide to produce the *E. coli* glucosylated O4 antigen polysaccharide; (iii) a nucleotide sequence encoding a carrier protein; and (iv) a nucleotide sequence encoding an oligosaccharyl transferase capable of covalently linking the *E. coli* glucosylated O4 antigen polysaccharide to the carrier protein to produce the bioconjugate. In preferred embodiments, the nucleotide sequence encoding a glucosyl transferase having at least 80% sequence identity to SEQ ID NO: 4 replaces the endogenous gtrS gene. Deleting the endogenous gtrS has the advantage that it will not interfere with generation of the glucosylated O4 antigen polysaccharide structure. In certain embodiments, the nucleotide sequence of the rfb gene cluster for the *E. coli* O4 antigen polysaccharide replaces the endogenous rfb gene cluster of the parent strain that is used to make the recombinant host cell. If the cell does not yet encode gtrA and/or gtrB genes, nucleotide sequences encoding a translocase (gtrA) and a glycosyltransferase (gtrB), having at least 80% identity to SEQ ID NOs: 7 and 8, respectively, can be introduced into the cell. If the cell already encodes gtrA and gtrB genes (such as for instance the case in *E. coli* K-12 strain W3110), there is no need to introduce or change these genes.

In a specific embodiment, the glucosyl transferase (gtrS specific for adding glucose branch to O4 antigen) has SEQ ID NO: 4.

In a specific embodiment, the oligosaccharyl transferase is PglB from *C. jejuni*. In one such embodiment, the oligosaccharyl transferase comprises the amino acid sequence of SEQ ID NO: 6. In another such embodiment, the oligosaccharyl transferase comprises the amino acid sequence of SEQ ID NO: 6 comprising the mutation N311V. In another such embodiment, the oligosaccharyl transferase comprises the amino acid sequence of SEQ ID NO: 6 comprising the mutations Y77H and N311V.

In another specific embodiment, the carrier protein comprises at least one glycosylation site comprising a glycosylation consensus sequence having SEQ ID NO: 1, preferably SEQ ID NO: 2. In another specific embodiment, the carrier protein is EPA, preferably EPA-4, such as EPA-4 comprising SEQ ID NO: 3.

*E. coli* strains that are used routinely in molecular biology as both a tool and a model organism can for instance be used as parents for host cells in certain embodiments according to the invention. Non-limiting examples include *E. coli* K12 strains (for example, such as W1485, W2637, W3110, MG1655, DH1, DH5a, DH10, etc.), B strains (e.g. BL-21, REL606, etc.), C strains, or W strains. In one particular embodiment, the host strain is derived from parent strain W3110. This strain can for instance be obtained from the *E. coli* Genetic Stock Center at Yale. For more information on *E. coli*, see e.g. Ecoliwiki.net.

Methods of Producing Conjugates and Bioconjugates

Also provided are methods of producing glycoconjugates of the *E. coli* O antigen polysaccharides described herein. Glycoconjugates, including bioconjugates, can be prepared in vitro or in vivo, e.g., using the recombinant host cells described herein for production.

In some embodiments, glycoconjugates can be prepared by chemical synthesis, i.e., prepared outside of host cells (in vitro). For example, an *E. coli* O antigen polysaccharide can be conjugated to carrier proteins using methods known to those of ordinary skill in the art, including by means of using activation reactive groups in the polysaccharide/oligosaccharide as well as the carrier protein. See, e.g., Pawlowski et al., 2000, *Vaccine* 18:1873-1885; and Robbins, et al., 2009, *Proc Natl Acad Sci USA* 106:7974-7978), the disclosures of which are herein incorporated by reference. Such approaches comprise extraction of antigenic polysaccharides/oligosaccharides from host cells, purifying the polysaccharides/oligosaccharides, chemically activating the polysaccharides/oligosaccharides, and conjugating the polysaccharides/oligosaccharides to a carrier protein.

In some embodiments, the host cells described herein can be used to produce bioconjugates comprising an *E. coli* O antigen polysaccharide covalently linked to a carrier protein. Methods of producing such bioconjugates using host cells are known in the art. See, e.g., WO 2003/074687 and WO 2006/119987. Such methods comprise culturing any of the recombinant host cells described herein under conditions for production of the bioconjugate. Bioconjugates can be isolated, separated, and/or purified from recombinant host cells using any method known in the art in view of the present disclosure. For example, bioconjugates can be purified by any method known in the art for purification of a protein, for instance, by chromatography (e.g., ion exchange, anionic exchange, affinity, and sizing column chromatography), centrifugation, differential solubility, or by any other standard technique for the purification of proteins. See, e.g., methods described in WO 2009/104074. Further, the bioconjugates can be fused to heterologous polypeptide sequences to facilitate purification. The actual conditions used to purify a particular bioconjugate will depend, in part, on factors such as net charge, hydrophobicity, and/or hydrophilicity of the bioconjugate, and will be apparent to those skilled in the art. Preparation of bioconjugates for O1A, O2, O6A, and O25B, as well as vaccine compositions comprising these, have for instance been described in WO 2015/124769 and in WO 2017/035181.

Also provided are bioconjugates produced by the methods described herein, i.e., using the recombinant host cells described herein.

In some embodiments, a method of preparing a bioconjugate of an *E. coli* O-antigen polysaccharide covalently linked to a carrier protein comprises: (i) providing a recombinant host cell comprising (a) nucleotide sequence of an rfb gene cluster for the O-antigen polysaccharide; (b) a nucleotide sequence encoding a carrier protein, preferably EPA, comprising at least one glycosylation site comprising a glycosylation consensus sequence having SEQ ID NO: 1, preferably SEQ ID NO: 2, and more preferably comprising four glycosylation sites each comprising a glycosylation consensus sequence having SEQ ID NO: 2; and (c) nucleotide sequence encoding an oligosaccharyl transferase, for instance PglB oligosaccharyl transferase or variant thereof.

In certain embodiments, *E. coli* O-antigen polysaccharides produced using the recombinant host cells described herein are covalently bound to the carrier protein at a particular polysaccharide to protein ratio by weight (w/w). This ratio of amount of O-antigen polysaccharide by weight covalently bound to the carrier protein by weight is referred to as the "glycan/protein ratio" or "polysaccharide/protein ratio" or "PS/protein ratio". In some embodiments, the O-antigen polysaccharide is covalently bound to the carrier protein at a polysaccharide to protein (w/w) ratio of about 1:20 to 20:1, preferably 1:10 to 10:1, more preferably 1:3 to 3:1. In certain non-limiting embodiments for bioconjugates described herein, glycan/protein ratio is about 0.1 to 0.5, such as 0.1, 0.15, 0.2, 0.25, 0.3, 0.35, 0.4, 0.45, or 0.5. In such embodiments, the weight ratio of the O-antigen polysaccharide:protein is about 1:10 to 1:2, such as 1:10:1:9:1:8, 1:7, 1:6, 1:5, 1:4, 1:3, or 1:2, depending on the particular O-antigen serotype. In certain embodiments the glycan/protein ratio is from about 0.15 to about 0.45. In general, a higher glycan/protein ratio of O-antigen polysaccharide to carrier protein is preferred, because a high amount of carrier protein can lead to immunological interference in some instances. Also, a higher glycan/protein ratio would help getting sufficient O-antigen polysaccharide dosed in the form of bioconjugate, while keeping the amount of carrier protein relatively low, which is especially beneficial for multivalent compositions where multiple serotypes are to be covered by the composition, e.g. compositions comprising bioconjugates from at least 4 different O-antigens, at least 5 different O-antigens, at least 6 different O-antigens, at least 7 different O-antigens, at least 8 different O-antigens, at least 9 different O-antigens, at least 10 different O-antigens, etc.

A glycan/protein ratio of a conjugate according to the invention can be determined by determining the protein amount and the glycan amount. Protein amount can be determined by measurement of UV absorbance at 280 nm (A280). Glycan amount can be determined based on ion chromatography with pulsed amperometric detection (IC-PAD) of a sugar in the repeat unit (e.g. of Man for O8 in Table 1, and of GlcNAc for the other glycans in Table 1), after which the structural information of the repeat unit can be used to calculate the total glycan amount (e.g. the repeat unit of O1A has a molar mass of 845 Da and one mole of such a repeat unit contains one mole of GlcNAc, enabling calculation of the total glycan amount when the amount of GlcNAc has been determined by IC-PAD).

In some embodiments, a bioconjugate of an *E. coli* O25B antigen polysaccharide covalently linked to a carrier protein produced using a recombinant host cell according to the cells and methods described herein has a certain degree of acetylation at position 2 of the L-Rh sugar. The degree of O-acetylation of O25B antigen polysaccharide in a bioconjugate is preferably at least 30%, preferably at least 50%, such as at least 50%, 55%, 60%, 65%, 70%, 75%, 80%, 85%, 90%, 95%, or 100%.

Similarly, the degree of O-acetylation of an *E. coli* O16 antigen polysaccharide in a bioconjugate is preferably at least 30%, preferably at least 50%, such as at least 50%, 55%, 60%, 65%, 70%, 75%, 80%, 85%, 90%, 95%, or 100%.

In specific embodiments, a method of preparing a bioconjugate of an O-antigen polysaccharide comprises providing a recombinant host cell comprising nucleic acid sequence encoding a particular oligosaccharyl transferase enzyme, particularly a PglB oligosaccharyl transferase or variant thereof, depending on the O-antigen polysaccharide bioconjugate to be produced. The particular oligosaccharyl transferase enzyme variant may impact the yield of bioconjugate produced by the host cell. Typically, a higher yield is preferred, since the yield will impact the costs for producing a specific bioconjugate, which is especially important for multivalent compositions comprising several different bioconjugates.

In one particular embodiment, when the O-antigen is O1A, O6A, or O15 antigen polysaccharide, the PglB oligosaccharyl transferase comprises the amino acid mutations of N311V, K482R, D483H, and A669V, wherein the amino acid mutations are relative to the wild-type PglB having the amino acid sequence of SEQ ID NO: 6.

In another particular embodiment, when the O-antigen is glucosylated O4 antigen polysaccharide, the PglB oligosaccharyl transferase comprises the amino acid mutation N311V, or the amino acid mutations of Y77H and N311V, wherein the amino acid mutations are relative to the wild-type PglB having the amino acid sequence of SEQ ID NO: 6.

In another particular, embodiment, when the O-antigen is O16 antigen polysaccharide, the PglB oligosaccharyl transferase comprises the amino acid mutations of Y77H, S80R, Q287P, K289R, and N311V, wherein the amino acid mutations are relative to the wild-type PglB having the amino acid sequence of SEQ ID NO: 6.

In another particular embodiment, when the O-antigen is O75 antigen polysaccharide, the PglB oligosaccharyl transferase comprises the amino acid mutation of N311V, wherein the amino acid mutations are relative to the wild-type PglB having the amino acid sequence of SEQ ID NO: 6.

In another particular embodiment, when the O-antigen is O8, O18A, O25B, or O2 antigen polysaccharide, the PglB oligosaccharyl transferase comprises the amino acid sequence of SEQ ID NO: 6, wherein SEQ ID NO: 6 comprises no amino acid mutations at positions 77, 80, 287, 289, 311, 482, 483, and 669. In certain embodiments thereof, the PglB oligosaccharyl transferase comprises the amino acid sequence of SEQ ID NO: 6.

In some embodiments, bioconjugates of O-antigen polysaccharides produced by recombinant host cells encoding the oligosaccharyl transferase enzymes per the O-antigen/PglB oligosaccharyl transferase pairings indicated above preferably have one or more of the preferred attributes described herein, e.g., glycan/protein ratio and/or percent of multi-glycosylated carrier protein.

EMBODIMENTS

Embodiment 1 is a bioconjugate of an *E. coli* glucosylated O4 antigen polysaccharide covalently linked to a carrier protein, wherein the *E. coli* glucosylated O4 antigen polysaccharide comprises the structure of Formula (O4-Glc+):

α-D-Glcp
1
↓
3
[→2)-α-L-Rhap-(1→6)-α-D-Glcp-(1→3)-α-L-FucpNAc-(1→3)-β-D-GlcpNAc-(1→]$_n$ wherein n is an integer of 1 to 100, preferably 3 to 50, for example 5 to 40, for example 7 to 25, for example 10 to 20.

Embodiment 2 is the bioconjugate of embodiment 1, wherein the *E. coli* glucosylated O4 antigen polysaccharide is covalently linked to an Asn residue in a glycosylation site comprising a glycosylation consensus sequence having SEQ ID NO: 1, preferably having SEQ ID NO: 2, in the carrier protein.

Embodiment 3 is the bioconjugate of embodiment 1 or embodiment 2, wherein the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae.*

Embodiment 4 is the bioconjugate of embodiment 3, wherein the carrier protein is detoxified exotoxin A of *Pseudomonas aeruginosa* (EPA), preferably comprising 1 to 20, preferably 1 to 10, preferably 2 to 4, glycosylation consensus sequences having SEQ ID NO: 1, the consensus sequences preferably having SEQ ID NO: 2.

Embodiment 5 is the bioconjugate of embodiment 4, wherein the carrier protein comprises four glycosylation consensus sequences (EPA-4), preferably wherein the carrier protein comprises SEQ ID NO: 3.

Embodiment 6 is a composition comprising the bioconjugate of any one of embodiments 1-5.

Embodiment 7 is an immunogenic composition comprising the bioconjugate of any one of embodiments 1-5.

Embodiment 8 is the composition of embodiment 6 or immunogenic composition of embodiment 7, comprising at least one additional antigen polysaccharide covalently linked to a carrier protein.

Embodiment 9 is the composition or immunogenic composition of embodiment 8, wherein the at least one additional antigen polysaccharide is selected from the group consisting of *E. coli* O1A antigen polysaccharide, *E. coli* O2 antigen polysaccharide, *E. coli* O6A antigen polysaccharide, *E. coli* O8 antigen polysaccharide, *E. coli* O15 antigen polysaccharide, *E. coli* O16 antigen polysaccharide, *E. coli* O18A antigen polysaccharide, *E. coli* O25B antigen polysaccharide, and *E. coli* O75 antigen polysaccharide.

Embodiment 10 is the composition or immunogenic composition of embodiment 9, wherein (i) the *E. coli* O1A antigen polysaccharide comprises the structure of Formula (O1A):

```
[→3)-α-L-Rhap-(1→3)-α-L-Rhap-(1→3)-β-L-Rhap-(1→4)-β-D-GlcpNAc-(1→]n;
          2
          ↑
          1
    β-D-ManpNAc
```

(ii) the *E. coli* O2 antigen polysaccharide comprises the structure of Formula (O2):

```
[→3)-α-L-Rhap-(1→2)-α-L-Rhap-(1→3)-β-L-Rhap-(1→4)-β-D-GlcpNAc-(1→]n;
          2
          ↑
          1
    α-D-Fucp3NAc
```

(iii) the *E. coli* O6A antigen polysaccharide comprises the structure of Formula (O6A):

```
[→4)-α-D-GalpNAc-(1→3)-β-D-Manp-(1→4)-β-D-Manp-(1→3)-α-D-GlcpNAc-(1→]n;
                             2
                             ↑
                             1
                          β-D-Glcp
```

(iv) the *E. coli* O8 antigen polysaccharide comprises the structure of Formula (O8):

α-D-Manp3Me-(1→[3)-β-D-Manp-(1→2)-α-D-Manp-(1→2)-α-D-Manp-(1→]$_n$;

(v) the *E. coli* O15 antigen polysaccharide comprises the structure of Formula (O15):

[→2)-β-D-Galp-(1→3)-α-L-FucpNAc-(1→3)-β-D-GlcpNAc-(1→]$_n$;

(vi) the *E. coli* O16 antigen polysaccharide comprises the structure of Formula (O16):

```
[→2)-β-D-Galf-(1→6)-α-D-Glcp-(1→3)-α-L-Rhap-(1→3)-α-D-GlcpNAc-(1→]n;
                                        2
                                        ↑
                                        Ac
```

(vii) the *E. coli* O18A antigen polysaccharide comprises the structure of Formula (O18A):

[→2)-α-L-Rhap-(1→6)-α-D-Glcp-(1→4)-α-D-Galp-(1→3)-α-D-GlcpNAc-(1→]$_n$;
3
↑
1
β-D-GlcpNAc (viii) the *E. coli* O25B antigen polysaccharide comprises the structure of Formula (O25B):

β-D-Glcp
1
↓
6
[→4)-α-D-Glcp-(1→3)-α-L-Rhap-(1→3)-β-D-GlcpNAc-(1→]$_n$;
3 2
↑ ↑
1 Ac
α-L-Rhap and (ix) the *E. coli* O75 antigen polysaccharide comprises the structure of Formula (O75):

β-D-Manp
1
↓
4
[→3)-α-D-Galp-(1→4)-α-L-Rhap-(1→3)-β-D-GlcpNAc-(1→]$_n$, wherein each n is independently an integer of 1 to 100, preferably of 3 to 50, e.g. 5 to 40, e.g. 7 to 25, e.g. 10 to 20.

Embodiment 11 is the composition or immunogenic composition of embodiment 10, wherein each of the additional *E. coli* O1A, O2, O6A, O8, O15, O16, O18A, O25B, and/or O75 antigen polysaccharides is covalently bound to an Asn residue in a glycosylation site comprising a glycosylation consensus sequence having SEQ ID NO: 1, preferably having SEQ ID NO: 2, in each of the carrier protein.

Embodiment 12 is the composition or immunogenic composition of embodiment 11, wherein each of the carrier protein is a detoxified exotoxin A of *Pseudomonas aeruginosa* (EPA).

Embodiment 13 is the composition or immunogenic composition of embodiment 12, wherein each EPA comprises 1-10, preferably 2-4, glycosylation sites each comprising a glycosylation consensus sequence having SEQ ID NO: 2.

Embodiment 14 is the composition or immunogenic composition of embodiment 12, wherein each EPA comprises four glycosylation sites each comprising a glycosylation consensus sequence having SEQ ID NO: 2.

Embodiment 15 is the composition or immunogenic composition of embodiment 12, wherein each EPA comprises SEQ ID NO: 3.

Embodiment 16 is the composition or immunogenic composition of any one of embodiments 9-15, comprising at least the *E. coli* O1A, O2, glucosylated O4, O6A, and O25B antigen polysaccharides each covalently linked to a carrier protein.

Embodiment 17 is the composition or immunogenic composition of any one of embodiments 9-15, comprising at least the *E. coli* O1A, O2, glucosylated O4, O6A, O8, O15, O16, O25B and O75 antigen polysaccharides each covalently linked to a carrier protein.

Embodiment 18 is the composition or immunogenic composition of any one of embodiments 9-15, comprising at least the *E. coli* O1A, O2, glucosylated O4, O6A, O8, O15, O16, O18A, O25B, and O75 antigen polysaccharides each covalently linked to a carrier protein.

Embodiment 19 is a composition comprising:

(i) a bioconjugate of an *E. coli* glucosylated O4 antigen polysaccharide covalently linked to a detoxified Exotoxin A of *P. aeruginosa* (EPA-4 carrier protein) comprising SEQ ID NO: 3, wherein the *E. coli* glucosylated O4 antigen polysaccharide comprises the structure of Formula (O4-Glc+);

(ii) a bioconjugate of an *E. coli* O1A antigen polysaccharide covalently linked to an EPA-4 carrier protein, wherein the *E. coli* O1A antigen polysaccharide comprises the structure of Formula (O1A);

(iii) a bioconjugate of an *E. coli* O2 antigen polysaccharide covalently linked to an EPA-4 carrier protein, wherein the *E. coli* O2 antigen polysaccharide comprises the structure of Formula (O2);

(iv) a bioconjugate of an *E. coli* O6A antigen polysaccharide covalently linked to an EPA-4 carrier protein, wherein the *E. coli* O6A antigen polysaccharide comprises the structure of Formula (O6A);

(v) a bioconjugate of an *E. coli* O8 antigen polysaccharide covalently linked to an EPA-4 carrier protein, wherein the *E. coli* O8 antigen polysaccharide comprises the structure of Formula (O8);

(vi) a bioconjugate of an *E. coli* O15 antigen polysaccharide covalently linked to an EPA-4 carrier protein, wherein the *E. coli* O15 antigen polysaccharide comprises the structure of Formula (O15);

(vii) a bioconjugate of an *E. coli* O16 antigen polysaccharide covalently linked to an EPA-4 carrier protein, wherein the *E. coli* O16 antigen polysaccharide comprises the structure of Formula (O16);

(viii) a bioconjugate of an *E. coli* O25B antigen polysaccharide covalently linked to an EPA-4 carrier protein, wherein the *E. coli* O25B antigen polysaccharide comprises the structure of Formula (O25B); and (ix) a bioconjugate of an *E. coli* O75 antigen polysaccharide covalently linked to an EPA-4 carrier protein, wherein the *E. coli* O75 antigen polysaccharide comprises the structure of Formula (O75), wherein each of the structures of Formulas (O4-Glc+), (O1A), (O2), (O6A), (O8), (O15), (O16), (O25B), and (O75) is shown in Table 1, and each n is independently an integer of 1 to 100, preferably 3 to 50, e.g. 5 to 40, e.g. 7 to 25, e.g. 10 to 20.

Embodiment 20 is the composition of embodiment 19, further comprising:

(x) a bioconjugate of an *E. coli* O18A antigen polysaccharide covalently linked to an EPA-4 carrier protein, wherein the *E. coli* O18A antigen polysaccharide comprises the structure of Formula (O18A) shown in Table 1, and n is an integer of 1 to 100, preferably 3 to 50, e.g. 5 to 40, e.g. 7 to 25, e.g. 10 to 20.

Embodiment 21 is a method of inducing antibodies against an *E. coli* glucosylated O4 antigen in a subject, comprising administering to the subject the bioconjugate of any one of embodiments 1-5, or the composition or immunogenic composition of any one of embodiments 6-20.

Embodiment 22 is the method of embodiment 21, wherein the antibodies have opsonophagocytic activity.

Embodiment 23 is a method of vaccinating a subject against *E. coli*, in particular extra-intestinal pathogenic *E. coli* (ExPEC), comprising administering to the subject the bioconjugate of any one of embodiments 1-5, or the composition or immunogenic composition of any one of embodiments 6-20.

Embodiment 24 is the bioconjugate of any one of embodiments 1-5, or the composition or immunogenic composition of any one of embodiments 6-20 for use in inducing antibodies against an *E. coli* glucosylated O4 antigen.

Embodiment 25 is the bioconjugate of any one of embodiments 1-5, or the composition or immunogenic composition of any one of embodiments 6-20 for use in vaccination against extra-intestinal pathogenic *E. coli* (ExPEC).

Embodiment 26 is a recombinant host cell for producing a bioconjugate of an *E. coli* glucosylated O4 antigen polysaccharide covalently linked to a carrier protein, wherein the glucosylated O4 antigen polysaccharide comprises the structure of Formula (O4-Glc+) as shown in Table 1, wherein n is an integer of 1 to 100, preferably of 3 to 50, e.g. of 5 to 40, the host cell comprising:

(i) a nucleotide sequence of an rfb gene cluster for the *E. coli* O4 antigen polysaccharide;

(ii) a nucleotide sequence encoding a glucosyl transferase having at least 80% sequence identity to SEQ ID NO: 4, wherein the glucosyl transferase is capable of modifying the *E. coli* O4 antigen polysaccharide to produce the *E. coli* glucosylated O4 antigen polysaccharide;

(iii) nucleotide sequences encoding a translocase and a glycosyltransferase having at least 80% sequence identity to SEQ ID NOs: 7 and 8 respectively, wherein the translocase is capable of translocating bactoprenol-linked glucose and the glycosyltransferase is capable of glucosylating bactoprenol;

(iv) a nucleotide sequence encoding the carrier protein; and (v) a nucleotide sequence encoding an oligosaccharyl transferase capable of covalently linking the *E. coli* glucosylated O4 antigen polysaccharide to the carrier protein to produce the bioconjugate.

Embodiment 27 is the recombinant host cell of embodiment 26, wherein:

the glucosyl transferase has the amino acid sequence of SEQ ID NO: 4;

the oligosaccharyl transferase comprises the amino acid sequence of SEQ ID NO: 6, preferably SEQ ID NO: 6 comprising the amino acid mutation N311V, more preferably SEQ ID NO:6 comprising the amino acid mutations Y77H and N311V; and the carrier protein comprises at least one glycosylation site comprising a glycosylation consensus sequence having SEQ ID NO: 1, preferably having SEQ ID NO: 2.

Embodiment 28 is the recombinant host cell of embodiment 26 or embodiment 27, wherein the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

Embodiment 29 is the recombinant host cell of any one of embodiments 26-28, wherein the carrier protein is a detoxified exotoxin A of *Pseudomonas aeruginosa* (EPA).

Embodiment 30 is the recombinant host cell of embodiment 29, wherein the EPA comprises 1-10, preferably 2-4, glycosylation sites each comprising a glycosylation consensus sequence having SEQ ID NO: 2.

Embodiment 31 is the recombinant host cell of embodiment 30, wherein the carrier protein is EPA with four glycosylation consensus sequences (EPA-4), preferably wherein the carrier protein comprises SEQ ID NO: 3.

Embodiment 32 is the recombinant host cell of any one of embodiments 26-31, which is an *E. coli* cell, e.g. an *E. coli* K-12 strain, such as strain W3110.

Embodiment 33 is a method of producing a bioconjugate of an *E. coli* glucosylated O4 antigen polysaccharide covalently linked to a carrier protein, wherein the *E. coli* glucosylated O4 antigen polysaccharide comprises the structure of Formula (O4-Glc+) as shown in Table 1, wherein n is an integer of 1 to 100, preferably of 3 to 50, e.g. of 5 to 40, the method comprising culturing the recombinant host cell of any one of embodiments 26-32 under conditions for production of the bioconjugate.

Embodiment 34 is the method of embodiment 33, further comprising isolating the bioconjugate from the recombinant host cell.

Embodiment 35 is a bioconjugate produced by the method of embodiment 33 or 34.

Embodiment 36 is a composition comprising the bioconjugate of embodiment 35.

Embodiment 37 is a method for making a recombinant host cell for producing a bioconjugate of an *E. coli* glucosylated O4 antigen polysaccharide covalently linked to a carrier protein, wherein the glucosylated O4 antigen polysaccharide comprises the structure of Formula (O4-Glc+) as shown in Table 1, wherein n is an integer of 1 to 100, preferably of 3 to 50, e.g. of 5 to 40, the method comprising introducing one or more recombinant nucleic acid molecules into a cell to produce the recombinant host cell, wherein the recombinant host cell comprises:

(i) a nucleotide sequence of an rfb gene cluster for the *E. coli* O4 antigen polysaccharide;

(ii) a nucleotide sequence encoding a glucosyl transferase having at least 80% sequence identity to SEQ ID NO: 4, wherein the glucosyl transferase is capable of modifying the *E. coli* O4 antigen polysaccharide to produce the *E. coli* glucosylated O4 antigen polysaccharide;

(iii) nucleotide sequences encoding a translocase and a glycosyltransferase having at least 80% sequence identity to SEQ ID NOs: 7 and 8 respectively, wherein the translocase is capable of translocating bactoprenol-linked glucose and the glycosyltransferase is capable of glucosylating bactoprenol;

(iv) a nucleotide sequence encoding the carrier protein; and (v) a nucleotide sequence encoding an oligosaccharyl transferase capable of covalently linking the *E. coli* glucosylated O4 antigen polysaccharide to the carrier protein to produce the bioconjugate.

Embodiment 38 is the method of embodiment 37, wherein:

the glucosyl transferase has SEQ ID NO: 4;

the oligosaccharyl transferase comprises the amino acid sequence of SEQ ID NO: 6, preferably SEQ ID NO: 6 comprising the amino acid mutation N311V; and the carrier protein comprises at least one glycosylation site comprising a glycosylation consensus sequence having SEQ ID NO: 1, preferably having SEQ ID NO: 2.

Embodiment 39 is the method of embodiment 37 or embodiment 38, wherein the carrier protein is selected from the group consisting of detoxified Exotoxin A of *P. aeruginosa* (EPA), *E. coli* flagellin (FliC), CRM197, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

Embodiment 40 is the method of any one of embodiments 37-39, wherein the carrier protein is a detoxified exotoxin A of *Pseudomonas aeruginosa* (EPA).

Embodiment 41 is the method of embodiment 40, wherein the EPA comprises 1-10, preferably 2-4, glycosylation sites each comprising a glycosylation consensus sequence having SEQ ID NO: 2.

Embodiment 42 is the method of embodiment 41, wherein the carrier protein is EPA with four glycosylation consensus sequences (EPA-4), preferably wherein the carrier protein comprises SEQ ID NO: 3.

Embodiment 43 is the method of any one of embodiments 37-42, wherein the cell is an *E. coli* cell, e.g. from an *E. coli* K12 strain, such as from a W3110 strain.

Embodiment 44 is a composition according to embodiment 19 or embodiment 20, wherein the bioconjugate of the O25B antigen polysaccharide is present in the composition at a concentration that is about 1.5-6 times, e.g. about 2 to 4 times, higher than the concentration of any of the other bioconjugates.

Embodiment 45 is a composition according to embodiment 44, wherein the bioconjugates of O1A:O2:glucosylated O4:O6A:O8:O15:O16:O25B:O75 are present in a ratio by weight of polysaccharide of 1:1:1:1:1:1:1:2:1, or 2:1:1:2:1:1:1:4:1.

Embodiment 46 is a composition according to embodiment 44, wherein the bioconjugates of O1A:O2:glucosylated O4:O6A:O8:O15:O16:O18A:O25B:O75 are present in a ratio by weight of polysaccharide of 1:1:1:1:1:1:1:1:2:1, or 2:1:1:2:1:1:1:1:4:1.

Embodiment 47 is a composition according to any one of embodiments 44 to 46, wherein a concentration of the bioconjugate of the O25B antigen polysaccharide is 2 to 50 μg/mL, preferably 8 to 40 μg/mL, e.g. 16-32 μg/mL.

EXAMPLES

The following examples of the invention are to further illustrate the nature of the invention. It should be understood that the following examples do not limit the invention and the scope of the invention is to be determined by the appended claims.

Example 1: Epidemiological Data of *E. coli* Infections

To determine the O-serotype distribution of bacteremia-causing *E. coli*, global surveillance studies were performed. Between 2011 and 2017, more than 3200 *E. coli* bloodstream isolates were collected from patients ≥60 years of age hospitalized in countries within North America, Europe, the Asia-Pacific region, and South America. Each strain was analyzed for O antigen serotype using classical agglutination techniques and sequence-based O-genotyping. See Table 2.

Isolated human blood samples were analyzed to determine the identity of pathogens therein and their antibiotic resistance patterns. *E. coli* isolates were obtained from the samples following the analysis. *E. coli* identity was verified by MALDI-TOF MS. Further analysis on the *E. coli* isolates was performed using an antisera-based agglutination assay to determine their O-antigen serotype (DebRoy et al. (2011) Animal health research reviews/Conference of Research Workers in Animal Diseases 12, 169-185). Isolates un-typeable by the agglutination method, were further analyzed by whole-genome sequencing followed by O-genotyping based on O-serotype specific wzy and wzx gene sequences.

TABLE 2 distribution of the most common bacteremia-associated *E. coli* O-serotypes from a collection of 3217 blood isolates collected globally between 2011 and 2017, based on O-serotyping by agglutination plus O-genotyping of isolates un-typeable by agglutination. Subjects were hospitalized in the following countries: USA, Canada, Argentin, Brazil, UK, Germany, Spain, Italy, The Netherlands, France, Japan, Thailand, South Korea and Australia.

| O-serotype | Prevalence n (%) |
|---|---|
| O25 | 737 (22.9%) |
| O2 | 268 (8.3%) |
| O6 | 261 (8.1%) |
| O1 | 255 (7.9%) |
| O75 | 145 (4.5%) |
| O15 | 110 (3.4%) |
| O8 | 104 (3.2%) |
| O16 | 103 (3.2%) |
| O4 | 96 (3.0%) |
| O18 | 91 (2.8%) |

Stratification of on geographical location in the global set of bacteremia-associated *E. coli* showed a prevalence of the top 10 O-serotypes independent of location, suggesting these to be the predominant O-serotypes globally associated with bacteremia-causing *E. coli*.

In the global set of bacteremia-associated multi-drug resistant *E. coli* isolates (n=345), i.e. those strains that are resistant to at least three classes of clinically relevant antimicrobial drugs, the prevalence of the top 10 O-serotypes is 75.4%.

All information from epidemiology analysis taken together, the 10 predominant O-serotypes could cover an estimated 60-80% of *E. coli*-associated bacteremia infections, assuming coverage of subportions of the un-typeable strains.

A multivalent vaccine covering a significant proportion of bacteremia-causing *E. coli* serotypes would be very useful.

The O-serotypes of Table 2 would thus be good candidates for an O-antigen based multivalent vaccine. Such a vaccine could beneficially be prepared using bioconjugation technology.

One of the serotypes in the top-10 (Table 2) is O4. It would thus be beneficial to prepare a bioconjugate vaccine that includes O-antigen polysaccharide of *E. coli* serotype O4 coupled to a carrier protein.

Example 2: Characterization of Contemporary O4 Clinical Isolates for Genes Encoding O-Antigen Modifying Enzymes Two variants of *E. coli* O4 antigen polysaccharide have been described (see, e.g. Jann B, et al., 1993, Carbohydr. Res. 248: 241-250), one having an unbranched structure (structure shown as (O4-Glc−) in Table 1) and another variant substituted with an additional glucose side-branch (structure shown as (O4-Glc+) in Table 1). The proportion in which these two variants are found in contemporary clinical isolates was not known. Although both variants react with O4 antisera, it was also not known whether immunological differences between these variants exist. Moreover, an enzyme responsible for attaching the glucose side-branch to generate the (O4-Glc+) antigen polysaccharide was hitherto not identified, and a putative coding sequence thereof is likely residing outside the O4 rfb gene cluster.

A set of 32 agglutination-confirmed *E. coli* O4 clinical isolates originally isolated during the period of 2011-2012 from subjects in the United States and the European Union were subjected to whole genome sequence analysis. Extracted rfb gene cluster sequences from the 32 sequenced O4 isolates were aligned with those of the reference strain and compared at the nucleotide level. Except for some naturally occurring single nucleotide polymorphisms, the characterized isolates all displayed an rfb cluster that was identical to the O4 reference strain, indicating that *E. coli* O4 strains, independent of their Glc-branching status, carry an identical rfb gene cluster. Thus, to generate the *E. coli* O4-Glc+ antigen polysaccharide, a gene with unknown sequence that encodes an *E. coli* O4-specific branching enzyme and that must reside somewhere outside of the *E. coli* O4 rfb gene cluster is likely needed. The sequence of this unknown gene needs to be identified and employed if one wants to produce bioconjugates with the *E. coli* O4-Glc+ antigen polysaccharides in a strain that would otherwise only produce bioconjugates with *E. coli* O4-Glc- antigen polysaccharides.

The whole-genome sequence data were then analyzed for the presence of genes outside of the rfb gene cluster that may encode O-antigen modifying enzymes. Homologs of gtrAB in *Shigella flexneri* were first identified in *E. coli* O4. An open reading frame downstream of gtrAB in *E. coli* was then putatively identified as the *E. coli* O4-specific gene gtrS, that could encode the putative *E. coli* O4 specific branching enzyme GtrS responsible for adding a glucose branch to the *E. coli* O4 antigen.

The amino acid sequence of the *E. coli* O4 specific GtrS enzyme is provided as SEQ ID NO: 4. An exemplary nucleic acid sequence encoding this protein is provided as SEQ ID NO: 5.

Of the characterized *E. coli* O4 isolates, approximately 80% were found to carry the here identified gtrS gene (26 out of 32). Prevalence of the *E. coli* O4-specific gtrS sequence was also determined by PCR using sequence specific primers in an independent set of 20 agglutination-confirmed *E. coli* O4 clinical isolates isolated during the period of 2014-2016 from subjects in the United States and the European Union. This analysis demonstrated that 17 out of 20 isolates carried the O4 gtrS sequence, which corresponds to a prevalence of 85%.

Example 3: Cloning of O4 gtrS into *E. coli* W3110, Production and Structural Confirmation of Glc-Modified O4 Bioconjugates To test whether bioconjugates comprising O4-antigen polysaccharide modified with a branching glucose could be prepared, *E. coli* O4-antigen EPA bioconjugate production strains with the putative branching enzyme were constructed. For this, the endogenous O16-gtrS gene was substituted by the putative O4-gtrS gene (SEQ ID NO: 5, see Example 2) and the O16 rfb cluster was replaced with the O4 rfb cluster in *E. coli* strain W3110 ΔwzzE-wecG ΔwaaL Δwbbl-J-K by homologous recombination. Alternatively, in some strains, the O4 rfb cluster was encoded on a plasmid.

Subsequently, plasmids encoding a detoxified exotoxin A of *Pseudomonas aeruginosa* (EPA) carrier protein (a variant either having 2 or 4 consensus glycosylation sites, referred to as 'EPA-2' and 'EPA-4', respectively), and oligosaccharyl transferase PglB were introduced into the strains. O4-EPA bioconjugates modified with Glc were produced by growing the *E. coli* production strains in bioreactor cultures, and induction of PglB and EPA expression by IPTG and arabinose, respectively. The O4-EPA bioconjugates were extracted from the biomass periplasmic extract.

To confirm the detailed polysaccharide composition and linkage of the O4-EPA bioconjugates, multiple NMR experiments were performed on the bioconjugates having EPA-4 carrier protein (data not shown). The assignments obtained agreed with literature published (Jansson, P. E., et al., 1984, Carbohydr. Res. 134(2): 283-291; Jann B, et al., 1993, Carbohydr. Res. 248: 241-250). The 1D spectrum recorded at 313K showed a large HOD signal and small sharp signals from the O4 pentasaccharide RU with five anomeric, two NAc and two H6 signals (Rha and FucNAc).

The 1D proton assignments were confirmed by use of 2D proton-proton and proton-carbon correlation NMR experiments. First, 2D TOCSY (120 ms) experiments demonstrated the expected cross peaks from H1 and H6 (for Rha and FucNAc) for the O4 pentasaccharide RU and small peaks from the terminal RU and EPA. In the methyl region, TOCSY showed cross peaks from H6 to H1 for α-Rha and H6 to H5 for α-FucNAc for the O4 RU. Other peaks observed were from EPA amino acids and terminal Rha (tRha). Second, a carbon NMR spectrum contained well-dispersed and diagnostic single peaks for the O4 RU. The carbons were profiled indirectly through the attached protons by use of the HSQC experiment. The HSQC-DEPT experiment gave inverted peaks for $CH_2$ groups. The HSQC gave cross peaks for the O4 pentasaccharide RU [5 anomeric, ring, two N-acetyl and two methyl (Rha & FucNAc)] groups as well as EPA amino acids in characteristic regions. Each of the proton/carbon pairs for the O4 could be assigned based on the proton assignments and literature.

The structural characterization experiments thus confirmed that Glc-branched O4 bioconjugates (comprising polysaccharide antigen structures as indicated by Formula (O4-Glc+) in Table 1) could be produced, using the putative *E. coli* O4-gtrS gene identified in Example 2.

Example 4: Immunogenicity of a Glc-Branched O4 Bioconjugate in Rabbits

Glc-modified O4 bioconjugates (i.e. having glycans with the structure of Formula (O4-Glc+) as shown in Table 1)

were used for rabbit immunization by applying a speedy-rabbit protocol (Eurogentec). Sera from immunized rabbits were analyzed by ELISA for anti-O4 IgG titers against purified O4 lipopolysaccharide (LPS) with (Glc+; i.e. containing glucosylated O4 polysaccharide) or without Glc-branching (Glc−; i.e. containing non-glucosylated O4 polysaccharide). Immunization with the bioconjugate resulted in high IgG titers in both rabbits (FIG. 1). In both cases, antibody titers induced by the O4 bioconjugate were higher against Glc+ LPS as compared to Glc-LPS.

Figure 2:
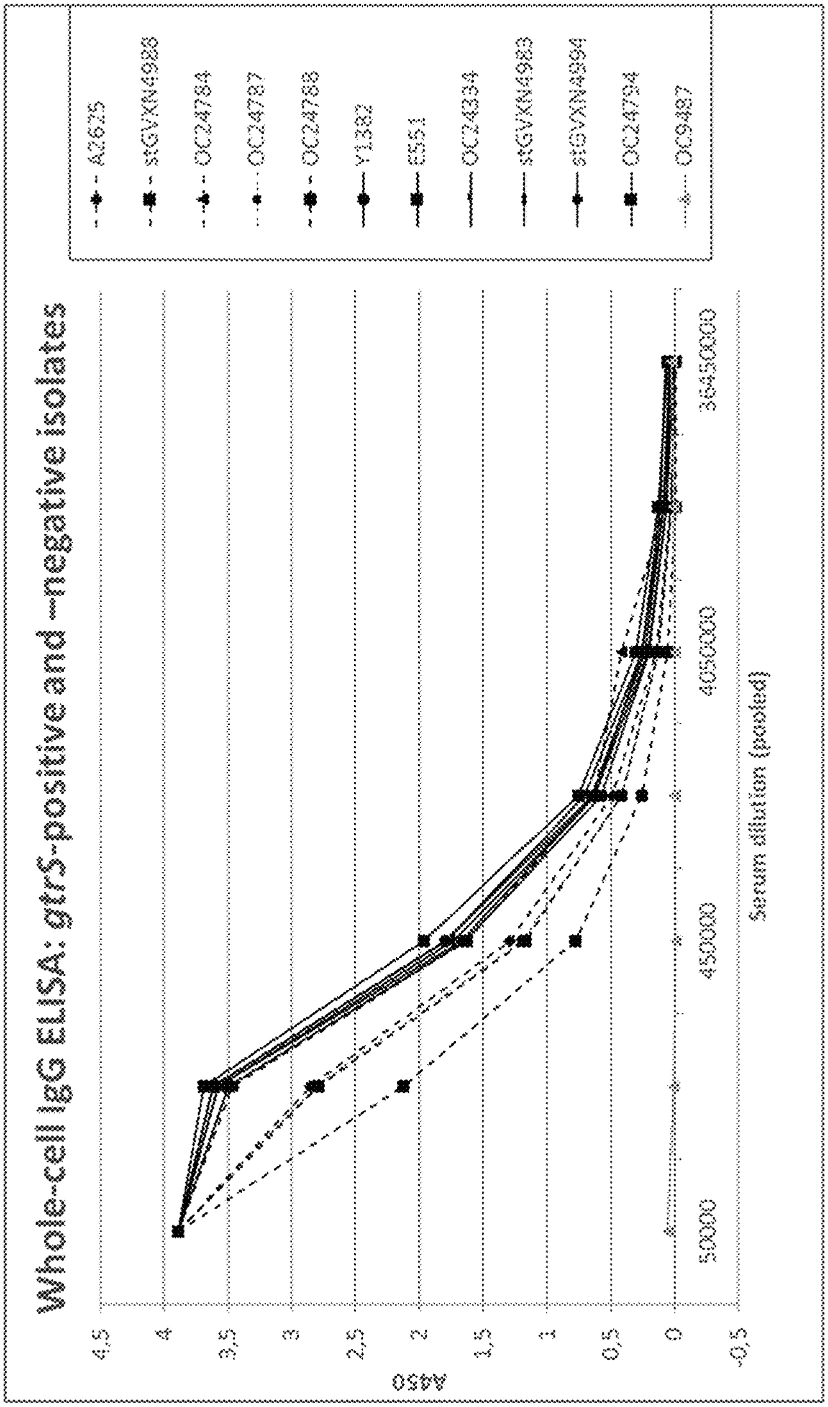
FIG. 2 shows IgG titers in whole cell ELISAs with pooled sera from rabbits immunized with a Glc-modified O4 bioconjugate against *E. coli* O4 isolates with characterized gtrS status as described in Example 4; the following isolates were gtrS-negative: A2625, stGVXN4988, OC24784, OC24787 and OC24788; the following isolates were gtrS-positive: Y1382, E551, OC24334, stGVXN4983, stGVXN4994 and OC24794; the negative control strain OC9487 (ATCC 35383; serotype O75) was also included.

Sera were also pooled and used in whole cell ELISA studies with test sets of *E. coli O*4 isolates with characterized gtrS status. Five gtrS-negative (no Glc-branching) and six gtrS-positive (Glc-branching) *E. coli* O4 isolates and a negative control strain were tested. Pooled sera from rabbits immunized with a Glc-modified O4 bioconjugate contained high titers of IgG specifically recognizing the tested O4 isolates (FIG. 2). In concordance with the LPS ELISA, all tested O4 isolates were recognized by the immune sera. The gtrS-positive isolates displayed an overall higher binding than the gtrS-negative isolates (FIG. 2). In particular, the following isolates were gtrS-positive: Y1382, E551, OC24334, stGVXN4983, stGVXN4994 and OC24794, and the following isolates were gtrS-negative: A2625, stGVXN4988, OC24784, OC24787, and OC24788. Immune sera did not bind the negative control strain of a non-related O-serotype, *E. coli* O C9487 (ATCC 35383).

The profiles of LPS extracted from the test set of gtrS-positive and -negative isolates in silver-stained polyacrylamide gels did not reveal marked differences between isolates expressing unmodified and modified forms of the O4 antigen confirming that the observed differences are not explained by quantitative differences in LPS expression levels (data not shown).

Figure 3:
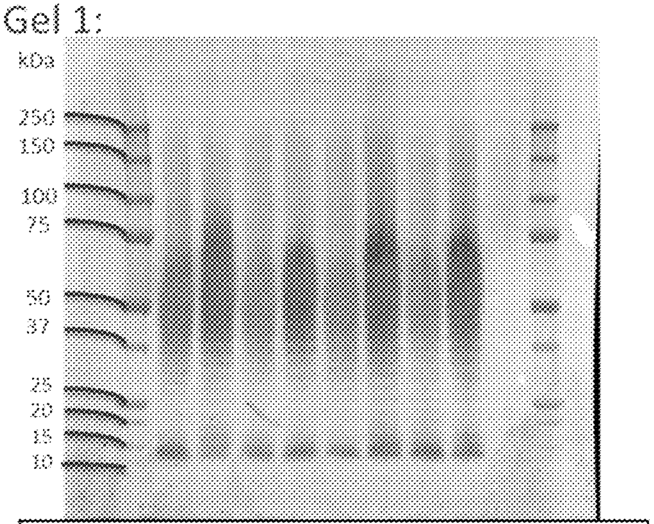
FIG. 3 shows Western blots of LPS extracted from gtrS-positive and -negative O4 isolates probed with pooled sera from rabbits immunized with modified O4 polysaccharide.
Figure 3:
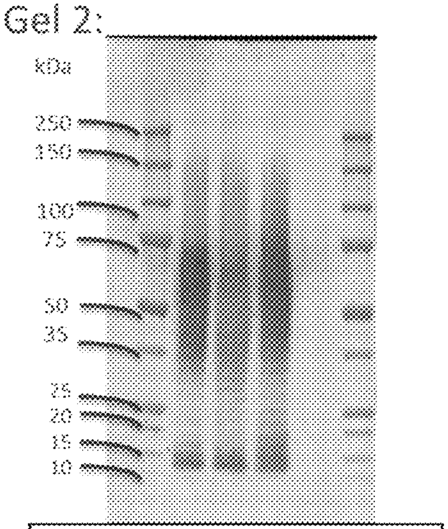

Western blots of extracted LPS using pooled immune sera were performed to assess recognition of O4 O-antigen by IgGs elicited in response to immunization with a Glc-modified O4 bioconjugate. Binding of both modified and unmodified O4 LPS by IgGs from modified O4 immunized rabbits was observed and included specific recognition of LPS bands spanning a wide range of sizes, including high molecular weight LPS bands (FIG. 3).

In the further experiments below, when reference is made to ‘O4’ bioconjugate or production strains or ‘EcoO4’, the bioconjugate or production strain of Glc-branched O4 (having glycan structure (O4-Glc+) in Table 1) is meant, unless specifically indicated otherwise (the terms ‘O4’ and ‘O4-Glc+’ are thus used interchangeably for bioconjugates or production strains in those experiments).

Example 5: Immunogenicity of a Glc-Branched O4 Bioconjugate in Rats

Sprague Dawley rats were immunized intramuscularly 3 times with formulation buffer or (O4-Glc+)-EPA bioconjugate (i.e. bioconjugate of glucosylated O4 antigen polysaccharide covalently coupled to EPA carrier protein; carrier protein was EPA-2 as described in Example 3 above) at 3 different doses (0.04 μg, 0.40 μg or 4.0 μg). Serum antibody levels were measured by ELISA at day 0, 14 and 42 post-immunization.

Figure 4A:
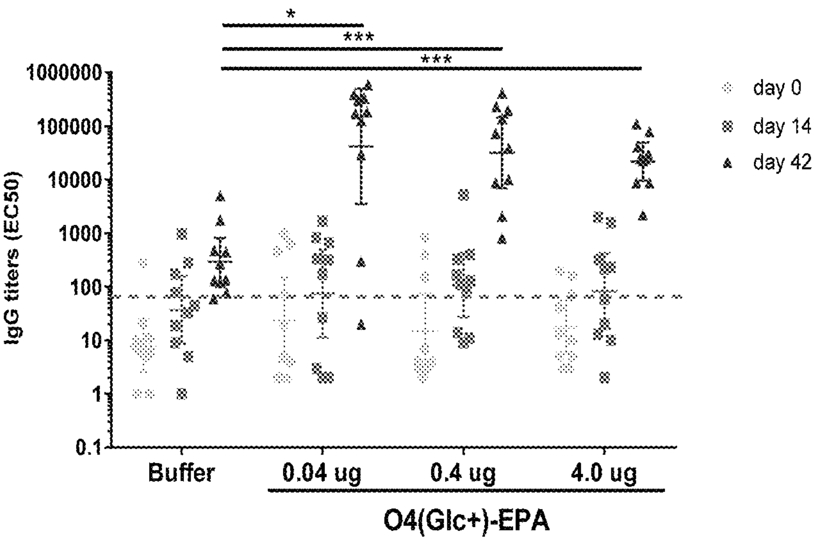
FIGS. 4A and 4B show antibody responses induced by glucosylated O4 (O4-Glc+)-EPA bioconjugates.
Figure 4B:
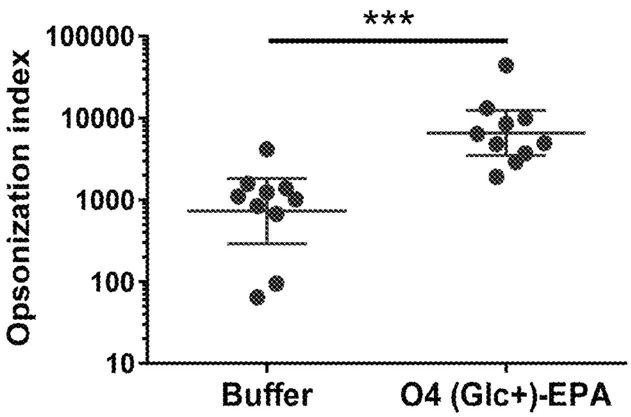

Immunization with 0.04 μg, 0.40 μg and 4.00 μg of (O4-Glc+)-EPA bioconjugate induced significant increase in the levels of IgG antibodies at day 42 post-immunization when compared to formulation buffer (FIG. 4A). The antibodies induced by (O4-Glc+)-conjugate were functional, i.e., capable of mediating killing of (O4-Glc+) *E. coli* strain (FIG. 4B).

Figure 5:
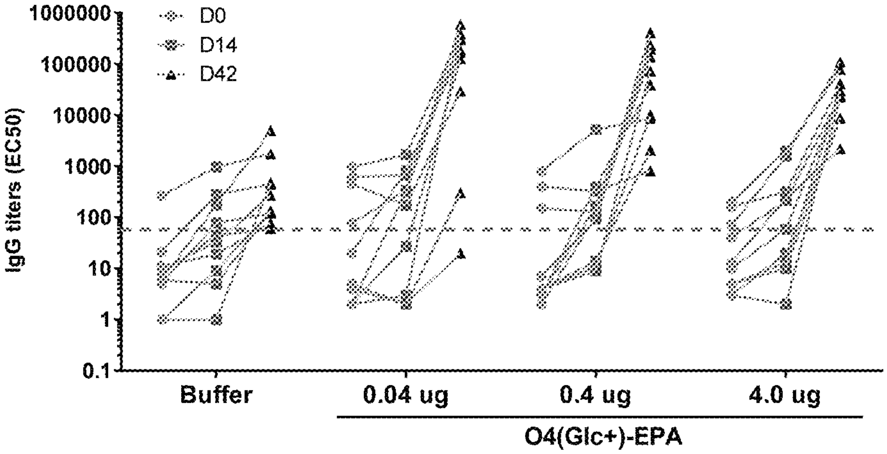
FIG. 5 shows the boost effect of glucosylated O4 (O4 Glc+)-EPA bioconjugate in Sprague Dawley rats immunized at 3 different doses as described in Example 4; serum antibody levels were measured by ELISA at day 0, 14 and 42 post-immunization; individual titers (log 10 EC50 titer) are shown for each animal; the lines between the data points connect IgG titers for each animal in time; the grey dotted line indicates the threshold above which the dilution curves of the samples have a 4PL fitting; statistical analysis was performed with Wilcoxon signed-rank test and Bonferroni correction for multiple comparisons (day 14 vs day 0, P=0.012 for 4.0 μg/dose; day 42 vs day 0, P=0.006 for all doses; day 42 vs day 14, P=0.006 for all doses)

Antibody levels induced by 0.04 μg, 0.40 μg and 4.0 μg of (O4-Glc+)-EPA bioconjugate were significantly increased at day 42 as compared to those detected at baseline (day 42 vs day 0, P=0.006 for all doses) and at day 14 post-immunization (day 42 vs day 14, P=0.006 for all doses) (FIG. 5). In the group that received 4.0 μg of bioconjugate, titers were also significantly increased at day 14 compared to day 0, indicating that a single dose of 4.0 μg of (O4-Glc+)-EPA bioconjugate induces significant increase in IgG titers (day 14 vs day 0, P=0.012). The significant increase in IgG titers observed between day 14 and 42, for all three concentrations of bioconjugate tested showed that a third dose of (O4-Glc+)-EPA bioconjugate is able to boost antibody responses (FIG. 5).

Figure 6:
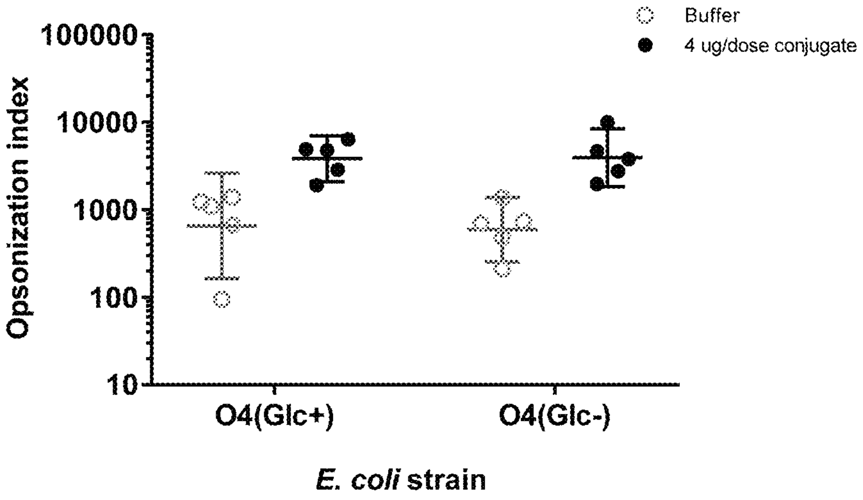
FIG. 6 shows the functionality of antibodies induced by O4-Glc+-EPA bioconjugate; Sprague Dawley rats were immunized intramuscularly 3 times with formulation buffer or O4(Glc+)-EPA bioconjugate at 4.00 μg/dose; functionality of the antibodies was determined by opsonophagocytic killing assay (OPKA) using O4(Glc+) and O4(Glc−) *E. coli* strains; individual opsonic titers (OI) and GMT±95% CI are shown.

Functionality of antibodies induced by O4-Glc+-EPA conjugate in the rats immunized intramuscularly 3 times with formulation buffer or the bioconjugate at 4.00 μg/dose was determined by opsonophagocytic killing assay (OPKA) using O4(Glu+) and O4(Glu−) *E. coli* strains. The antibodies induced by (O4-Glc+)-EPA bioconjugate were functional, i.e., capable of mediating killing of an (O4-Glc+) *E. coli* strain (FIG. 4B, FIG. 6). Notably, antibodies induced by (O4-Glc+)-EPA bioconjugate were capable of mediating killing of both (O4-Glc+) and (O4-Glc−, i.e. having glycans with structure of Formula (O4-Glc−) in Table 1, i.e. O4 polysaccharide without Glc-branching) *E. coli* strains (FIG. 6).

In conclusion, antibodies induced by O4-Glc+-EPA bioconjugate are cross-reactive and capable of mediating killing of *E. coli* O4 strains with and without glucose branching.

Example 6: Production Strains for *E. coli* O-Antigen Bioconjugates and Resulting Bioconjugate Products In addition to (O4-Glc+)-EPA bioconjugates prepared as described above, nine (9) other bioconjugates were produced. In particular, the additionally produced bioconjugates included *E. coli* O1A-EPA bioconjugate, O2-EPA bioconjugate, O6A-EPA bioconjugate, O8-EPA bioconjugate, O15-EPA bioconjugate, O16-EPA bioconjugate, O18A-EPA bioconjugate, O25B-EPA bioconjugate, and O75-EPA bioconjugate. The chemical structures of the glycans of these conjugates can be seen in the respective Formulas in Table 1. A composition comprising the 10 bioconjugates is referred to herein as ‘ExPEC10V’. A composition comprising the O1A-EPA, O2-EPA, O6A-EPA and O25B-EPA bioconjugates is referred to as ‘ExPEC4V’ (and was previously described in for instance WO 2015/124769 and WO 2017/035181).

*Escherichia coli* W3110 Parental Strain

The non-pathogenic *E. coli* K12 strain W3110 was used as the parental strain for the construction of all ten production strains. The *E. coli* K12 strain W3110 was obtained from the *Coli* Genetic Stock Center (Yale University, New Haven (Conn.), USA, product number CGSC #4474). Its relevant genotype was previously described (*E. coli* W3110, F-, lambda-, IN(rrnD-rrnE)1, rph-1) and its genomic sequence was previously published (Hayashi K, et al., 2006, Mol. Syst. Biol. 2006.0007 (doi:10.1038/msb4100049). The *E. coli* W3110 strain was genetically modified to enable production of each of the *E. coli* O-antigen bioconjugates (Table 3).

Bioconjugate Production Strains

The "ExPEC4V" and "ExPEC10V" compositions both comprise the O2-EPA and O25B-EPA bioconjugates from the same production strains. The "ExPEC4V" composition comprises the O1A-EPA bioconjugate from the stGVXN4411 or stLMTB10217 production strains, while the "ExPEC10V" composition comprises the O1A-EPA bioconjugate from the stLMTB10217 production strain. The "ExPEC4V" composition comprises the O6A-EPA bioconjugate from the stGVXN4112 production strain, while the "ExPEC10V" composition comprises the O6A-EPA bioconjugate from the stLMTB10923 production strain. Furthermore, the "ExPEC10V" composition comprises the O4-EPA (i.e. (O4-Glc+)-EPA), O8-EPA, O15-EPA, O16-EPA, O18A-EPA, and O75-EPA bioconjugates from production strains that are not used for "ExPEC4V". Different production strains could vary in the plasmids for expression of the EPA carrier protein and/or the oligosaccharyl transferase PglB, as indicated below. An overview of several production strains is given in Table 3 below.

which instead directs transfer of the O-antigen to the carrier protein to increase product yield.

O-Antigen Glucosylation (gtrABS) Genes

In the *E. coli* O8, O15, O16, O18A, O25B, and O75 production strains the *E. coli* W3110 genomic gtrABS genes, which are responsible for O16 O-antigen glucosylation, have been deleted. While the gtrA and gtrB genes in different serotypes are highly homologous and interchangeable, the gtrS gene encodes a serotype-specific O-antigen glycosyl transferase. In *E. coli* W3110 GtrS can transfer a glucose (Glc) residue to the GlcNAc sugar in the α-L-Rha-(1→3)-D-GlcNAc motif of the *E. coli* O16 O-antigen. In the *E. coli* O1A, O2 and O6A production strains no deletion or replacement of the gtrABS gene has occurred. These O-antigens miss the α-L-Rha-(1→3)-D-GlcNAc motif that is the natural substrate for *E. coli* O16 gtrS. In the *E. coli* O4 production strain, the W3110 gtrS gene has been replaced with the *E. coli* O4 gtrS gene to accommodate proper glucosylation of the *E. coli* O4 O-antigen.

TABLE 3

Overview of genetic engineering of *E. coli* production strains for O-antigen bioconjugates for ExPEC4V and ExPEC10V vaccine compositions

| | | Genomic mutations | | | Plasmids | |
|---|---|---|---|---|---|---|
| Serotype | Strain name | rfb gene cluster | waaL | gtrABS | pglB | epa |
| O1A (ExPEC4V) | stGVXN4411 | Δrfb::O1A rfb upecGVXN_032 | ΔwaaL | — | pGVXN970 | pGVXN1076 |
| O1A (ExPEC4V; ExPEC10V) | stLMTB10217 | Δrfb::O1A rfb upecGVXN_032 | ΔwaaL | — | pGVXN1221 | pGVXN1076 |
| O2 | stGVXN4906 | Δrfb::O2 rfb upecGVXN_116 | ΔwaaL | — | pGVXN971 | pGVXN1076 |
| O4 | BVEC-L-00684 | Δrfb::O4 rfb CCUG11450 | ΔwaaL | ΔgtrS::gtrS O4 | pGVXN1217 | pGVXN1076 |
| O6A (ExPEC4V) | stGVXN4112 | Δrfb::O6A rfb CCUG11309 | ΔwaaL | — | pGVXN114 | pGVXN659 |
| O6A (ExPEC10V) | stLMTB10923 | Δrfb::O6A rfb CCUG11309 | ΔwaaL | — | pGVXN1221 | pGVXN1076 |
| O8 | stLMTB11734 | Δrfb::O8 rfb E2420 | ΔwaaL | ΔgtrABS | pGVXN970 | pGVXN1076 |
| O15 | stLMTB11738 | Δrfb::O15 rfb OC24891 | ΔwaaL | ΔgtrABS | pGVXN1221 | pGVXN1076 |
| O16 | stLMTB11739 | Δrfb::O16 rfb OC24208 | ΔwaaL | ΔgtrABS | pGVXN2381 | pGVXN1076 |
| O18A | BVEC-L-00559 | Δrfb::O18A rfb OC24255 | ΔwaaL | ΔgtrABS | pGVXN970 | pGVXN1076 |
| O25B | stGVXN4459 | Δrfb::O25B rfb upecGVXN_138 | ΔwaaL | ΔgtrABS | pGVXN970 | pGVXN1076 |
| O75 | stLMTB11737 | Δrfb::O75 rfb CCUG31 | ΔwaaL | ΔgtrABS | pGVXN1217 | pGVXN1076 |

O-antigen Biosynthesis (rfb) Gene Cluster

In all *E. coli* O-antigen production strains, the naturally occurring *E. coli* W3110 genomic O16::IS5-antigen biosynthesis (rfb) gene cluster was replaced by the selected O-antigen-specific biosynthesis clusters from *E. coli* strains of the selected serotype, encoding for the serotype-specific O-antigen structures (see Table 1 for these O-antigen structures). The ten donor rfb clusters were selected or confirmed after whole-genome analysis of *E. coli* blood isolates. Replacement of the W3110 O16::IS5 rfb gene cluster, which is defective in O-antigen biosynthesis, has been achieved in a single homologous recombination event. In case of the O16 and O18A rfb gene clusters, the donor DNA recombined via the flanking gnd and rmlCA genes, while the rfb gene cluster for the other strains recombined via the flanking gnd and galF genes. Sequences of the rfb clusters in the production strains are provided in SEQ ID NOs: 9 and 11-19.

O-Antigen Ligase (waaL) Gene

All *E. coli* O-antigen production strains carry an artificially introduced deletion of the *E. coli* W3110 genomic O-antigen ligase encoded by the waaL gene. In the ΔwaaL strains the transfer of the O-antigen to lipid A is disrupted, Oligosaccharyl Transferase PglB All *E. coli* O-antigen production strains expressed a variant of the *C. jejuni* glycosyl transferase PglB, which can transfer the O-antigen onto an amino acid consensus sequence on a carrier protein by N-glycosylation. PglB has broad substrate recognition, but due to low product yields several production strains were prepared expressing a PglB variant having modified substrate specificities, which resulted in improved product yield (see e.g. WO 2016/107818, WO 2016/107819). The pglB gene was placed behind an Isopropyl β-D-1-thiogalactopyranoside (IPTG) inducible promoter on a plasmid. Table 4 below lists the PglB variants encoded by the plasmids used for production of the *E. coli* O-antigen production strains for the bioconjugates for the ExPEC4V and ExPEC10V compositions described above. Further plasmids with variation in vector backbone, antibiotic resistance marker, and/or alternative PglB variants have also been tested successfully for bioconjugate production.

TABLE 4

| PglB and EPA plasmids used in *E. coli* O-antigen Production Strains | | |
|---|---|---|
| Plasmid name | Gene | Description[1] |
| pGVXN114 | pglB | *C. jejuni* codon usage; SpR |
| pGVXN970 | pglB | *E. coli* codon usage optimized; SpR |
| pGVXN971 | $pglB^{N534Q}$ | *E. coli* codon usage optimized; The natural glycosylation site of PglB was inactivated; SpR |
| pGVXN1217 | $pglB^{N311V}$ | *E. coli* codon usage optimized; Substrate optimized PglB; SpR |
| pGVXN1221 | $pglB^{N311V, K482R, D483H, A669V}$ | *E. coli* codon usage optimized; Substrate optimized PglB; SpR |
| pGVXN2381 | $pglB^{Y77H, S80R, Q287P, K289R, N311V}$ | *E. coli* codon usage optimized; Substrate optimized PglB; SpR |
| pGVXN659 | EPA-4 | EPA with four bioconjugation sites; AmpR |
| pGVXN1076 | EPA-4 | EPA with four bioconjugation sites; KanR |

[1]SpR, spectinomycin resistant;
AmpR, ampicillin resistant;
KanR, kanamycin resistant Carrier Protein (EPA)

All *E. coli* O-antigen production strains expressed a genetically detoxified *P. aeruginosa* ADP-ribosyltransferase toxoid (EPA) as a carrier protein for the O-antigen. The EPA toxoid differs from wild-type EPA toxin in two residues: Leu552 was changed to Val and Glu553 (in the catalytic domain) was deleted. Glu553 deletions were reported to significantly reduce toxicity. In addition to the detoxification mutation, four (EPA-4) consensus N-glycosylation site motifs were introduced. The epa gene was placed behind a L-Arabinose (Ara) inducible promoter on a plasmid (Table 4). Table 4 is limited to the plasmids used in production strains for bioconjugates used in the "ExPEC4V" and "ExPEC10V" compositions described above. Plasmids with variation in vector backbone, antibiotic resistance marker, and/or EPA variants, e.g. varying in the number of consensus N-glycosylation site motifs (e.g. having two such motifs, EPA-2), have also been tested successfully for bioconjugate production.

Example 7: Optimizing the Oligosaccharyltransferase for Generation of Bioconjugates with Glucosylated O4 (O4-Glc+) Antigen Yield optimization for bioconjugate production can be achieved by modification of the *C. jejuni* oligosaccharyl transferase PglB, which can lead to a more efficient or higher degree of N-glycosylation of the O-antigen of interest to the EPA carrier protein. In an *E. coli* strain for production of bioconjugate with glucosylated O4 (O4-Glc+) O-antigen polysaccharide, such optimization strategy was applied and resulted in an (O4-Glc+)-specific optimized PglB variant improving bioconjugate product yield.

In this approach, an O4-Glc+O-antigen polysaccharide producing strain containing an EPA-expression plasmid was transformed with a variety of different PglB expression plasmids, each of which contained different amino acid substitutions in the PglB protein, altering substrate specificity. Bioconjugate production level and profile of each strain was assessed at shake-flask level in osmotic shock experiments, and readout was performed by capillary electrophoresis immunoassays on the periplasmic extract using O4-Glc+-specific monoclonal antibodies.

Figure 7:
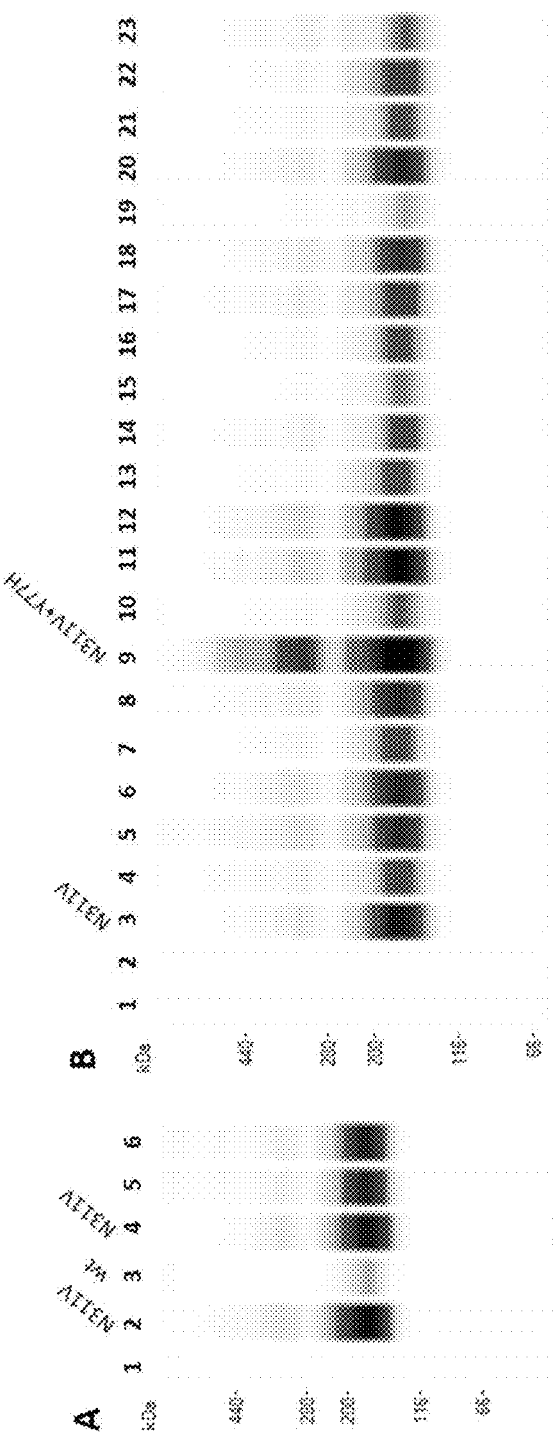
FIG. 7 shows capillary electrophoresis readout of PglB screen visualizing O4-Glc+ bioconjugate production for each tested strain in a blot-like image, using monoclonal antibodies to detect O4-Glc+ bioconjugate in the periplasmic fraction. Mono-glycosylated product approximately 180 kDa, di-glycosylated product approximately 320 kDa and tri-glycosylated product approximately 450 kDa. A) First screening round. Wt PglB in lane 3, N311V-PglB in lanes 2 and 4, empty control strain in lane 1 and other PglB variants in lanes 5 and 6. B) Second screening round. N311V PglB in lane 3, N311V+Y77H PglB in lane 9, empty control strain in lanes 1 and 2, other PglB variants in remaining lanes.

One of the tested PglB variants containing an N311V amino acid substitution was found to improve product yield of glucosylated O4 bioconjugates significantly (FIG. 7A).

In a further improvement where the N311V PglB-variant was further modified, an Y77H amino acid substitution further enhanced O4-Glc+-specific product yield and showed an increased degree of di- and tri-glycosylated product compared to the N311V PglB-variant, where other modifications were found to be neutral or had a negative effect on product yield (FIG. 7B). Plasmid pLMTB4008 (SpR) encodes *E. coli* codon usage optimized, (O4-Glc+)-substrate optimized, PglB variant with mutations Y77H and N311V.

The PglB variant with optimized substrate specificity for O4-Glc+O-antigen polysaccharide, containing N311V and Y77H amino acid substitutions relative to wild-type (wt) *C. jejuni* glycosyl transferase PglB, was found to double bioconjugate yield compared to the first round optimized PglB-N311V variant.

Similarly using screens, the most optimal yielding PglB variants were also determined for *E. coli* O-antigen bioconjugate production of the of the other nine serotypes in the ExPEC10V composition.

For bioconjugates having the O1A, O6A, or O15 antigen polysaccharide, PglB with amino acid mutations N311V, K482R, D483H, and A669V was found to give the highest yields.

For bioconjugates having the O2, O8, O18A, or O25B antigen polysaccharide, wild-type PglB (i.e. not having amino acid mutations at positions 77, 80, 287, 289, 311, 482, 483 and 669) was found to give the highest yields.

For bioconjugates having the O16 antigen polysaccharide, PglB with amino acid mutations Y77H, S80R, Q287P, K289R, and N311V was found to give the highest yields.

For bioconjugates having the O75 antigen polysaccharide, PglB with amino acid mutation N311V was found to give the highest yields.

It can be seen from these results that the optimal PglB variant is different for different O-antigens, and that the optimal PglB variant for producing a bioconjugate with a given O-antigen polysaccharide is unpredictable.

Example 8: Bioconjugates of O-Antigens from 10 *E. coli* Serotypes and their Quality Attributes O-glycan residues of the target O-antigens are structurally diverse and have variable repeating units. The specificity and affinity of the glycosyl transferase PglB is linked to the glycan structure. Thus, making a bioconjugate that has the desired quality attributes, e.g., purity, glycan/protein ratio, etc., is a challenging, non-straightforward, task. The right combination of PglB and EPA carrier protein determines the yield and may influence glycosylation efficiency. By optimizing the PglB and carrier proteins, bioconjugates having the desired quality attributes were produced. It may be also important to maintain a lower threshold value of total carrier protein, particularly when one or more O-antigen bioconjugates are combined together and administered in a single composition or vaccine, because very high amounts of carrier protein may lead to immunological interference. In order to avoid such a phenomenon, conjugates having a higher glycan/protein ratio are preferred. Hence, for ExPEC10V vaccine, bioconjugates with at least comparable (to the previously described ExPEC4V vaccine that has been subject to clinical trials) glycosylation ratio were developed.

The bioconjugates were each produced by culturing the respective host cells (Example 6, Table 3) in bioreactors (10 L and/or 200 L volumes) and expression of the bioconjugates, following methods previously described. Each drug substance was manufactured batch-wise by bacterial fed-batch fermentation to generate biomass containing the expressed bioconjugates of the corresponding polysaccharide serotype. Cells were cultured and induced with IPTG and arabinose. The bioconjugates were isolated from the periplasm of the cells in the bioreactor cultures by osmotic shock followed by chromatographic purification. This process was performed for each of the 10 bioconjugates.

The *E. coli* O-antigen bioconjugates thus prepared that are drug substances (DSs) for ExPEC10V and ExPEC4V showed comparable critical quality attributes: (1) process-related purity (measured by RP-HPLC) was higher than 95%, (2) polysaccharide/protein ratio ranged between about 0.1-0.5, mostly between 0.15 and 0.45, (3) bacterial endotoxin (Ph. Eur. 2.2.3) was less than 0.5 EU/μg polysaccharide. The average length of the individual polysaccharide chains was typically between about 10-20 repeating units (measured using high resolution SDS-PAGE).

The structures of the polysaccharide repeat units were confirmed (by NMR and MS/MS of the conjugates, intact or trypsin-digested) to be the ones shown in the Formulas for the corresponding serotypes in Table 1, for all ten bioconjugates that are DSs for the ExPEC10V composition described above.

The O18 serotype had the lowest yields of bioconjugate production amongst the ten serotypes of which bioconjugates were made for the ExPEC10V composition.

ExPEC10V drug product (DP) comprises a mixture of the ten monovalent DSs described above.

Example 9: Toxicology of ExPEC10V Vaccine

A single-dose pilot toxicity and local tolerance study (non-GLP) with ExPEC10V was conducted in female NZW rabbits. One group (n=2) received an intramuscular (IM) injection (on Day 0) of the control (saline), and a second group (n=4) received an IM injection of ExPEC10V at 105.6 μg total polysaccharide (PS)/dose (9.6:9.6:9.6:9.6:9.6:9.6:9.6:9.6:19.2:9.6 μg PS per dose, for respectively O-serotypes O1A, O2, O4, O6A, O8, O15, O16, O18A, O25B and O75) using a dosing volume of 0.6 mL (176 μg PS/mL). Necropsy was performed on Day 2.

There were no mortalities observed. In addition, there were no vaccine-related effects noted for clinical observations (including injection site effects using Draize scoring), body weight, food consumption, and body temperature. Histopathologically, there were no vaccine-related changes observed at the administration site or draining (iliac) lymph node. A minimal increase in germinal center formation in the spleen was observed in one out of four treated animals (Day 2), and was considered a normal, immunological response to the injected vaccine. Overall, the administration of a single IM dose of ExPEC10V to female rabbits was well-tolerated.

Example 10: Immunogenicity of ExPEC10V Blended Formulation in Rabbits

An ExPEC4V vaccine (comprising bioconjugates of *E. coli* O1A, O2, O6A, and O25B serotypes) has previously been shown to be immunogenic for these four serotypes in rats, rabbits, and humans (see e.g. WO 2015/124769; WO 2017/035181; Huttner et al, 2017, Lancet Infect Dis, http://dx.doi.org/10.1016/S1473-3099(17)30108-1; R W Frenck Jr, et al, abstract 5587, ASM Microbe 2018). The novel bioconjugates of the invention having the *E. coli* glucosylated O4 serotype were shown to be immunogenic in Examples 4 and 5 above. Immunogenicity of the bioconjugates of *E. coli* serotypes O8, O15, O16, O18A, and O75 (all having EPA-2 as carrier protein in this experiment) when separately administered (monovalent) to rats confirmed that also each of these bioconjugates was immunogenic, since ELISA data indicated that each of these bioconjugates could elicit high levels of *E. coli* O-antigen specific antibodies (not shown).

Immunogenicity of the 10-valent vaccine that contained a mixture of the 10 bioconjugates as described above was also tested. New Zealand White (NZW) rabbits (female, 12-16 weeks old) received 3 intramuscular immunizations with ExPEC10V or saline administered 2 weeks apart (Table 5; administration at days 0, 14, and 27). The 10 polysaccharides that are part of the ExPEC10V vaccine used in these experiments were conjugated to the carrier protein EPA containing 4 sites of glycosylation (EPA-4). The vaccine was formulated in 3 different doses: Group 1 ('high dose'): 8 ug/dose of O1A, O2, O6A, O4, O8, O15, O16, O18 and O75 and 16 ug/dose of O25B; Group 2 ('medium dose'): 4 ug/dose of O2, O4, O8, O15, O16, O18 and O75, 8 ug/dose of O1A and O6A and 16 ug/dose of O25B; Group 3 ('low dose'): 0.4 ug/dose of O2, O4, O8, O15, O16, O18 and O75, 0.8 ug/dose of O1A and O6A and 1.6 ug/dose of O25B. Animals from the control group (Group 4) received only saline (0.9% (w/v) sodium chloride solution) (Table 5).

Antibody responses were evaluated at day 0 (pre-immunization) and days 14, 27 and 42 post-immunization. Serum antibody levels induced by each of the bioconjugates included in the vaccine and the carrier protein EPA were measured by ELISA (total IgG), using type-specific LPS as coating material. The antibody titers were reported as EC50 values that correspond to the half maximal effective concentration based on duplicates of 12-step titration curves plotted in a 4-parameter logistic nonlinear regression model. Functional activity was determined by OPK.

TABLE 5

Description of experimental groups.

| Experimental groups | Dosing (μg/PS) O1A:O2:O6A:O25B:O4:O8:O15:O16:O18A:O75 | Sample size |
|---|---|---|
| Group 1 (high dose) | 8:8:8:16:8:8:8:8:8:8 | 7 |

TABLE 5-continued

| Description of experimental groups. | | |
|---|---|---|
| Experimental groups | Dosing (μg/PS) O1A:O2:O6A:O25B:O4:O8:O15:O16:O18A:O75 | Sample size |
| Group 2 (medium dose) | 8:4:8:16:4:4:4:4:4:4 | 7 |
| Group 3 (low dose) | 0.8:0.4:0.8:1.6:0.4:0.4:0.4:0.4:0.4:0.4 | 7 |
| Group 4 (control) | 0.9% (w/v) sodium chloride solution | 7 |

Figure 8:
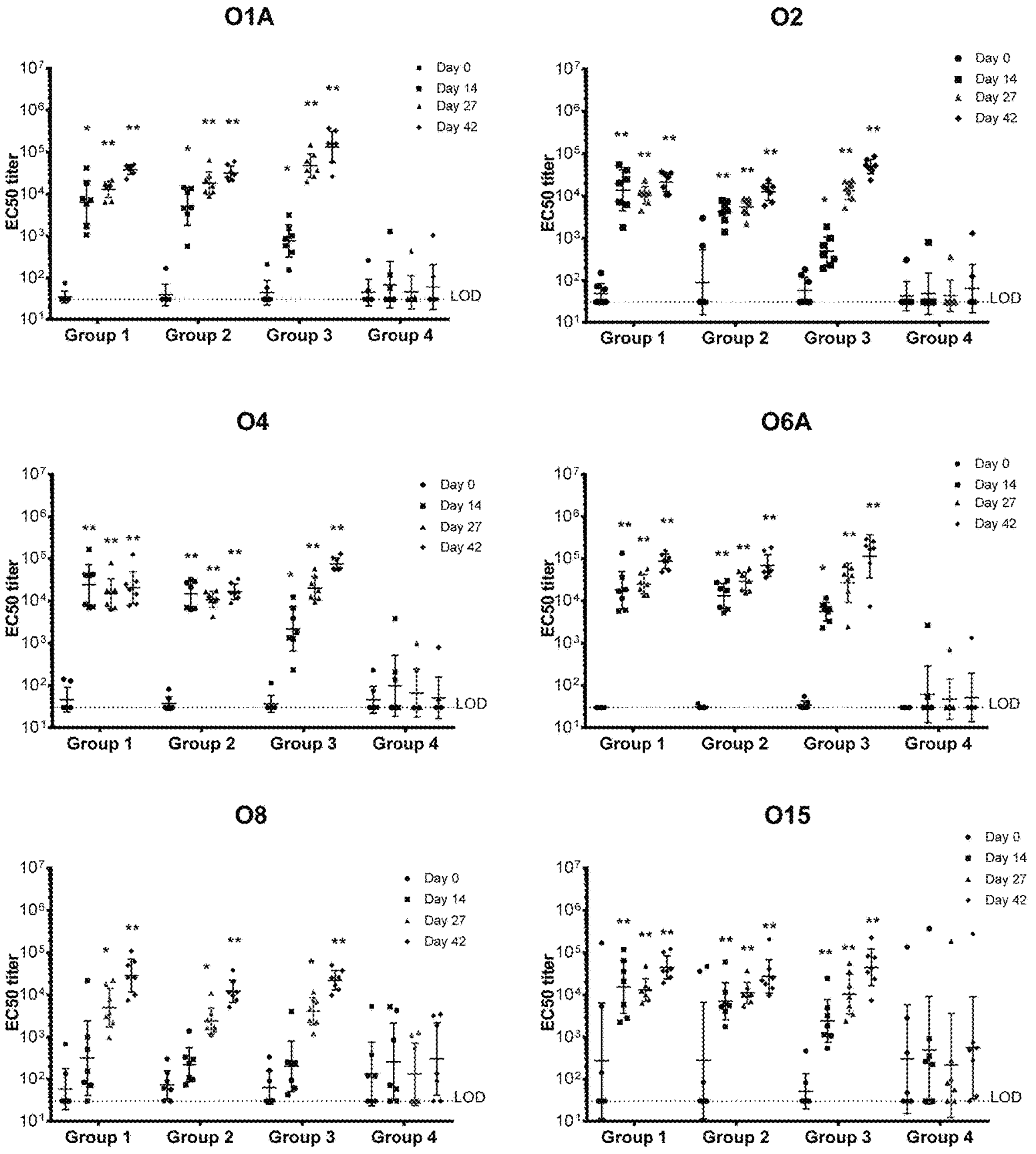
FIG. 8 shows antibody responses induced by ExPEC10V vaccine in New Zealand White rabbits. Animals received 3 intramuscular immunizations with ExPEC10V or saline administered 2 weeks apart. ExPEC10V vaccine was administered at 3 different concentrations (group 1: high dose, group 2: medium dose and group 3: low dose, Table 11) and a control group received only saline (group 4, 0.9% (w/v) sodium chloride solution). Antibody levels were measured by ELISA at day 0 (pre-vaccination) and days 14, 27 and 42 (post-vaccination). Individual titers (EC50 titer) and geometric mean titers (GMT)±95% CI are shown. Wilcoxon Rank Sum test with Bonferroni correction for multiple comparisons. Comparisons ExPEC10V vaccinated animals (group 1, 2 and 3) versus saline control (group 4). *p≤0.05, p≤0.01; *p≤0.001; ****p≤0.0001. LOD: limit of detection.

Results are shown in FIG. 8 and summarized in Table 6.

TABLE 6

| Summary of *E. coli* O-antigen specific antibody responses induced by ExPEC10V in NZW rabbits. | | | | | | | | | | |
|---|---|---|---|---|---|---|---|---|---|---|
| ExPEC10V dose | O1A | O2 | O6A | O25B | O4 | O8 | O15# | O16 | O18A | O75 |
| | Antibody responses day 14 post-vaccination | | | | | | | | | |
| High | * | ** | ** | * | ** | ns | ** | ** | * | ns |
| Mid | * | ** | ** | ** | ** | ns | ** | ** | ns | ns |
| Low | * | * | * | * | * | ns | ** | ** | ns | ns |
| | Antibody responses day 27 post-vaccination | | | | | | | | | |
| High | ** | ** | ** | ** | ** | * | ** | ** | ** | ** |
| Mid | ** | ** | ** | ** | ** | * | ** | ** | * | ** |
| Low | ** | ** | ** | ** | ** | * | ** | ** | ** | ** |
| | Antibody responses day 14 post-vaccination | | | | | | | | | |
| High | ** | ** | ** | ** | ** | ** | ** | ** | ** | ** |
| Mid | ** | ** | ** | ** | ** | ** | ** | ** | ** | ** |
| Low | ** | ** | ** | ** | ** | ** | ** | ** | ** | ** |

Serotype-specific antibody responses in which p values were statistically significant are shown by asterisks.

Serotype-specific antibody responses in which p values were not statistically significant are designated as ns.

Wilcoxon Rank Sum test with Bonferroni correction for multiple comparisons. Comparisons ExPEC10V vaccinated animals (Group 1, 2 and 3) versus saline control (Group 4).

* $p \le 0.05$,

** $p \le 0.01$.

#P values were statistically significant after excluding an outlier animal from the control group (sensitivity analysis).

The high dose of ExPEC10V (Group 1) induced significantly higher IgG antibody levels at all time-points investigated (Days 14, 27 and 42 post-immunization) when compared to saline control for O1A, O2, O4, O6A, O16, O18A and O25B (FIG. 8, Table 6). Significantly higher antibody titers induced by O8 and O75 conjugates when compared to saline control were observed at Days 27 and 42 post-immunization (FIG. 8, Table 6).

The medium dose of ExPEC10V (Group 2) and the low dose (Group 3) induced significantly higher antibody levels at all time-points investigated (Days 14, 27 and 42 post-immunization) when compared to saline control for O1A, O2, O4, O6A, O16 and O25B (FIG. 8, Table 6). Significantly higher antibody titers induced by O8, O18A and O75 conjugates when compared to saline control were observed at Days 27 and 42 post-immunization suggesting that the boost dose in rabbits increases the response to these O-serotypes (FIG. 8, Table 6).

For O15 conjugates, sensitivity analysis omitting an outlier animal from the control group showed that all three doses of ExPEC10V vaccine induced a significant increase in antibody responses when compared to saline control at Days 14, 27 and 42 post-immunization (FIG. 8, Table 6).

Antibodies induced by the carrier protein EPA were significantly higher than EPA antibody titers in the saline-treated (control) group for the three doses of ExPEC10V tested (high, medium and low) at all time points investigated (Days 14, 27 and 42) (FIG. 8).

Between dose comparisons (not shown) showed that at Day 14 post-vaccination, the high dose of ExPEC10V induced significantly higher antibody responses when compared to the low dose for most of the conjugates tested (O1A, O2, O4, O6A, O15, O16, O18A and O25B). The medium dose of ExPEC10V also induced significantly higher antibody responses compared to the low dose for O1A, O2, O4, O18A, O25B and O75. For O8 conjugate, all three formulations of ExPEC10V induced similar levels of antibodies at Day 14 post-vaccination.

The low dose of ExPEC10V induced a significant increase in antibody responses at Day 42 post vaccination (after a prime and two boost doses) when compared to the high and medium doses of ExPEC10V for O1A, O2, O4, O16, O25B and O75 conjugates. These findings are in line with other experiences with conjugate vaccines, where for instance no clear relationship between dose and the magnitude of the antibody response to primary vaccination was observed in infants vaccinated with pneumococcal conjugate vaccine (Poolman J T, et al. Expert Rev Vaccines. 2013, 12(12):1379-94).

There were no significant differences between the three doses of ExPEC10V tested at Day 42 post-vaccination for O6A, O8 and O15 conjugates. For the O18A conjugate, the high dose of ExPEC10V induced a significantly higher antibody response when compared to the medium dose at Day 42 post-vaccination.

For the carrier protein (EPA), the high and medium dose of ExPEC10V induced significantly higher antibody responses when compared to the low dose at day 14 post-vaccination. The high dose of the vaccine also induced significantly higher antibody responses when compared to the low dose at day 42 post-vaccination.

In conclusion, the three formulations of ExPEC10V (high, medium and low), administered via intramuscular injection on Days 0, 14, 27 are immunogenic in rabbits.

So far, functional antibodies capable of killing *E. coli* strains induced by this vaccine in rabbits were shown for serotypes O1A, O2, O4, O6A, O15, O16 and O25B.

In a further experiment, a GMP batch of the ExPEC10V vaccine (see Example 8 above for production) was prepared and injected into NZW rabbits as part of a toxicology study (Table 7). In this study, NZW rabbits (males and females) received 3 intramuscular injections (0.6 mL) of the ExPEC10V vaccine (day 1, 15 and 29) and a control group received 0.9% (w/v) sodium chloride solution (saline). Each dose of the vaccine contained 9.6 μg polysaccharide (PS) for serotypes O1A, O2, O4, O6A, O8, O15, O16, O18A and O75 and 19.2 μg PS for serotypes O25B, corresponding to 105.6 μg total PS (176 μg total PS/mL) and 382.8 μg of total EPA (638 μg EPA/mL). IgG titers against O-antigens and carrier protein (EPA) were determined from samples collected during the pre-treatment period (day 1) and days 31 and 50 post-immunization.

Figure 9:
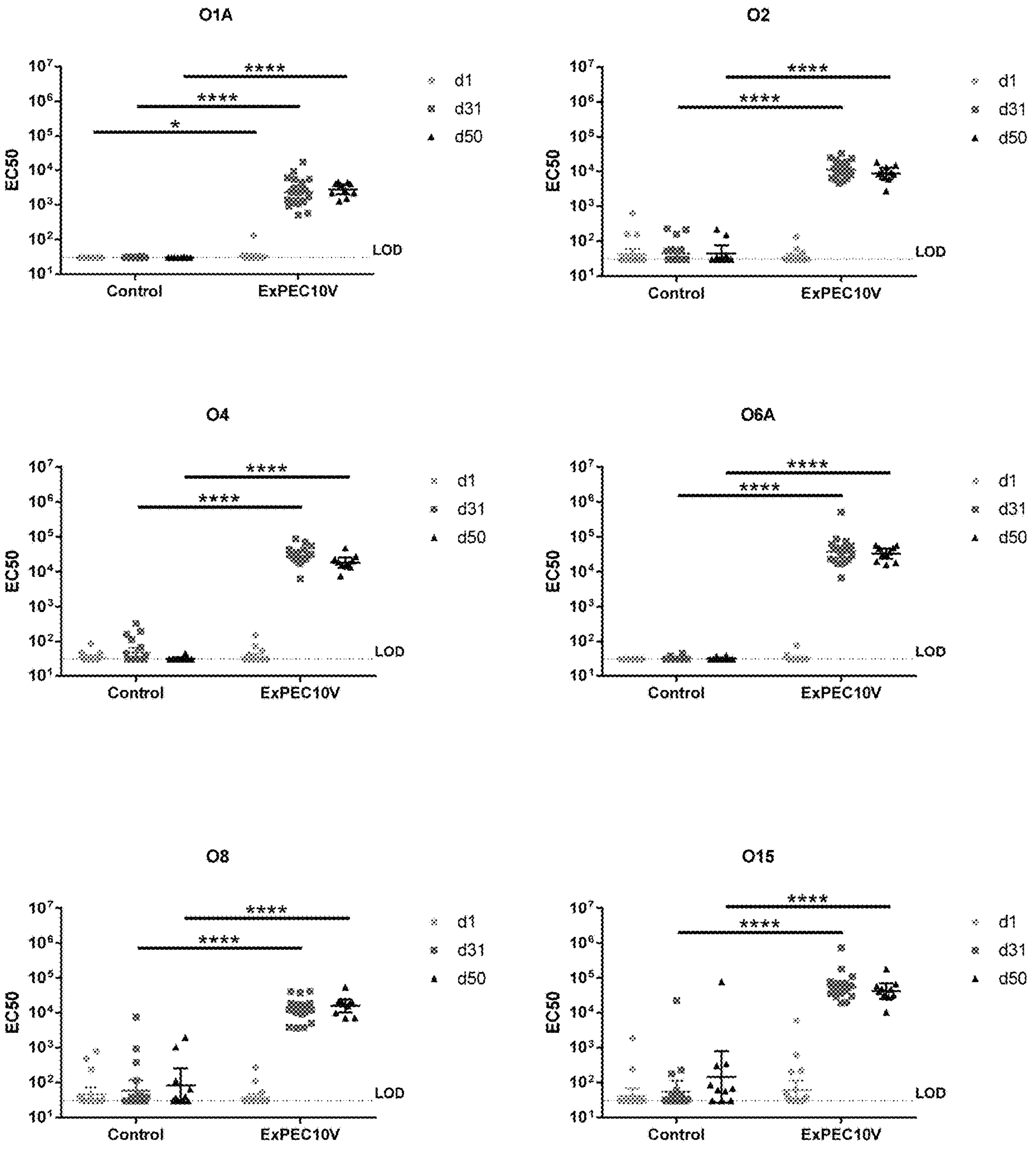
FIG. 9 shows antibody responses induced by ExPEC10V. New Zealand White rabbits received 3 intramuscular immunizations with ExPEC10V (105.6 μg total polysaccharide) or 0.9% w/v sodium chloride solution (control). IgG titers were determined by ELISA at day 1 (pre-immunization, n=20/group), day 31 (post-immunization, n=20/group) and day 50 (post-immunization, n=10/group). Plots show individual titers and geometric mean±95% confidence interval for each group. Differences in IgG titers between the ExPEC10V and control group were analyzed using a Tobit model with a likelihood ratio test. P-values≤0.05 were considered significant. *P≤0.05, ****P≤0.0001.

A significant increase in antibody responses against all O-antigens and the carrier protein EPA were observed at day 31 and 50 post-vaccination in the group that received ExPEC10V when compared to the control group that received only saline (FIG. 9, Table 8). For O1A serotype, a significantly higher antibody response was also observed at day 1 (baseline) when vaccinated animals were compared with the controls. These results suggest that some animals were pre-exposed to *E. coli* or have antibodies that cross-react with O1A-LPS.

Since the mechanism of action of conjugate vaccines in the prevention of invasive disease is not expected to be affected by antibiotic resistance mechanisms, it is believed that ExPEC10V vaccine provides protection against IED caused by drug-resistant- and drug-susceptible O1A, O2, O4, O6A, O8, O15, O16, O18A, O25B and O75 serotypes.

There is preceding clinical experience with ExPEC4V, an earlier vaccine candidate which comprised a subset of four of the *E. coli* O-antigen conjugates (O1A, O2, O6A and O25B) also found in ExPEC10V. Based on the results from four clinical studies (two completed phase 1 studies, one completed phase 2 study and an ongoing phase 2 study), ExPEC4V was well-tolerated by the study participants and no vaccine-related safety signals were observed at doses up to 16 μg polysaccharide (PS) per serotype (O1A, O2, O6A and O25B). Most adverse events (AEs) were Grade 1 and 2, very few Grade 3 AEs were reported. Late-onset solicited local AEs (AEs which start after Day 5 post-vaccination) were observed mainly with the higher doses of ExPEC4V. In each study, the ExPEC4V vaccine was shown to be immunogenic, demonstrating a dose-dependent vaccine immune response, and O-antigen specific Immunoglobulin G (IgG) titer increases, as measured by enzyme-linked immunosorbent assay (ELISA). Functional activity of the antibodies was demonstrated with an ExPEC4V-optimized opsonophagocytic killing assay (OPKA). Co-analysis of ELISA and OPKA test results showed correlation between the assay responses (Pearson correlation coefficients ≥0.61 and ≥0.48 for Day 30 and Day 360, respectively in a Phase 2 clinical trial [study 4V-BAC2001]), substantiating the use of ELISA as a primary measure of ExPEC4V antibody titers and to predict functional antibody activity. Analysis of the immunogenicity data has demonstrated the durability of the immune response through three years after vaccination with ExPEC4V. It has now also been observed that sera from humans vaccinated with ExPEC4V and that had high titers of serotype-specific opsonophagocytic antibodies, when passively transferred into mice that were subsequently intraperitoneally challenged with *E. coli* strains of O25B or O2 serotype, were able to mediate protection in vivo (not shown). Hence, ExPEC4V-specific opsonophagocytic human antibodies mediate bacterial killing in vivo, which is in line with other conjugate vaccines in which the proposed

TABLE 7

Experimental groups and ExPEC10V dose used in NZW rabbits.

| Groups | Treatment | Dose | Dosing days | Main (day 31) (males/females) | Recovery (day 50) (males/females) |
|---|---|---|---|---|---|
| 1 | control | 0 | 1, 15, 29 | 10 | 10 |
| 2 | ExPEC10V | 105.6 μg PS* | 1, 15, 29 | 10 | 10 |

*Each dose (0.6 mL dosing volume) contains 9.6:9.6:9.6:9.6:9.6:9.6:9.6:9.6:19.2:9.6 μg polysaccharide (PS) for serotypes O1A, O2, O4, O6A, O8, O15, O16, O18A, O25B, O75, respectively (176 μg total PS/mL). Each dose contains 382.8 μg EPA protein (638 μg EPA/mL).

TABLE 8

Immunogencity of ExPEC10V in NZW rabbits as part to a toxicology study.

| Treatment | Antibody responses day 14 post-vaccination | | | | | | | | | |
|---|---|---|---|---|---|---|---|---|---|---|
| ExPEC10V | O1A | O2 | O6A | O25B | O4 | O8 | O15 | O16 | O18A | O75 |
| Day 31 | **** | **** | **** | **** | **** | **** | **** | **** | **** | **** |
| Day 50 | **** | **** | **** | **** | **** | **** | **** | **** | **** | **** |

Antibody responses induced by ExPEC10V. Serotypes in which a significant increase in antibody responses was observed in the vaccine group compared to control are shown by asterisks. Tobit model with a likelihood ratio test.
**** P ≤ 0.0001.

Example 11: Phase 112a Trial with the ExPEC10V Vaccine in Humans

At present, there is no vaccine available to prevent IED The serotypes comprising the ExPEC10V vaccine (O1A, O2, O4, O6A, O8, O15, O16, O18A, O25B and O75) were selected to address invasive disease caused by the majority of clinically relevant ExPEC strains that also represent the majority of ExPEC isolates causing antimicrobial resistant IED, including ST131. The selected serotypes are representative for the ten prevalent ExPEC O-serotypes causing bloodstream infections in the older population and responsible for approximately 70% of bloodstream infections caused by ExPEC.

mechanism of protection is by induction of opsonophagocytic antibodies that mediate bacterial killing.

ExPEC10V includes a total of ten serotypes and increases coverage from about 50% (ExPEC4V) to approximately 70% of bloodstream infections caused by ExPEC in adults aged 60 years and older. Based on the clinical experience with ExPEC4V, and on the pre-clinical data for ExPEC10V as discussed in the examples above, it is expected that administration of ExPEC10V will induce immune responses to *E. coli* serotypes O1A, O2, O4, O6A, O8, O15, O16, O18A, O25B and O75 also in humans.

A randomized, observer-blind, first-in-human phase 1/2a study to evaluate the safety, reactogenicity, and immunogenicity of three different doses of the ExPEC10V vaccine is conducted in humans aged 60 to 85 years in stable health (study 10V-BAC1001). The study design includes 2 cohorts: A total of 1,004 participants are enrolled in the study with 404 participants (100 participants/ExPEC10V dose) aged ≥60 to ≤85 years in stable health in Cohort 1 and an additional of 600 participants aged ≥60 years in stable health with a history of UTI in the past 5 years in Cohort 2.

ExPEC10V is a 10-valent vaccine candidate in development for the prevention of invasive extraintestinal pathogenic *Escherichia coli* (ExPEC) disease (IED) in adults 60 years of age and older. ExPEC10V consists of the O-antigen polysaccharides (PSs) of the ExPEC serotypes O1A, O2, O4, O6A, O8, O15, O16, O18A, O25B and O75 separately bioconjugated to the carrier protein, a genetically detoxified form of exotoxin A (EPA) derived from *Pseudomonas aeruginosa*, and its production has been described above. The O4 PS is the glucosylated form, having the structure of Formula (O4-Glc+) in Table 1.

Objectives and Endpoints

Cohort 1—Phase 1/2a Observer-Blind Period with Open-Label Long-Term Follow-Up Period (N=404):

| Objectives | Endpoints |
|---|---|
| Primary | |
| To evaluate the safety and reactogenicity of different doses of ExPEC10V in participants ≥60 to ≤85 years of age | Solicited local and systemic adverse events (AEs) collected for 14 days post-vaccination (from Day 1 to Day 15)<br>Unsolicited AEs collected from the administration of the study vaccine until 29 days post-vaccination (from Day 1 to Day 30)<br>Serious adverse events (SAEs) collected from the administration of the study vaccine until Day 181 |
| To evaluate the dose-dependent immunogenicity of ExPEC10V on Day 15 in participants ≥60 to ≤85 years of age | Antibody titers for ExPEC10V, as determined by multiplex electrochemiluminescent (ECL)-based immunoassay and multiplex opsonophagocytic assay (MOPA) on Day 15 |
| Secondary | |
| To evaluate the correlation between multiplex ECL-based immunoassay (total antibody) and MOPA (functional antibody) serum titers on Day 15 | Antibody titers for ExPEC10V, as determined by multiplex ECL-based immunoassay and MOPA on Day 15 |
| To evaluate the dose-dependent immunogenicity of ExPEC10V on Days 30 and 181 in participants ≥60 to ≤85 years of age | Antibody titers for ExPEC10V, as determined by multiplex ECL-based immunoassay and MOPA on Days 30 and 181 |
| To evaluate, in the long-term follow-up (LTFU) period, the safety of the ExPEC10V dose selected for further clinical development based on the Day 30 primary analysis in participants ≥60 to ≤85 years of age | SAEs related to the study vaccine or study procedures collected from Day 182 until the end of the study |
| To evaluate, in the LTFU period, the immunogenicity of the ExPEC10V dose selected for further clinical development based on the Day 30 primary analysis | Antibody titers for ExPEC10V, as determined by multiplex ECL-based immunoassay and MOPA at Year 1 (Day 366), Year 2 (Day 731) and Year 3 (Day 1096) |

Cohort 2—Double-Blind Period with Double-Blind Long-Term Follow-Up Period (N=600):

| Objectives | Endpoints |
|---|---|
| Primary | |
| To evaluate the safety and reactogenicity of the selected dose of ExPEC10V in participants ≥60 years of age with a history of UTI in the past 5 years | Solicited local and systemic AEs collected for 14 days post-vaccination (from Day 1 to Day 15)<br>Unsolicited AEs collected from the administration of the study vaccine until 29 days post-vaccination (From Day 1 to Day 30)<br>SAEs collected from the administration of the study vaccine until Day 181 |

-continued

| Objectives | Endpoints |
| --- | --- |
| To evaluate the immunogenicity of the selected does of ExPEC10V on Day 30 in participants ≥60 years of age with a history of UTI in the past 5 years | Antibody titers for ExPEC10V, as determined by multiplex ECL-based immunoassay and MOPA on Day 30 |
| Secondary | |
| To evaluate the correlation between multiplex ECL-based immunoassay (total antibody) and MOPA (functional antibody) serum titers on Day 30 in participants ≥60 years of age with a history of UTI in the past 5 years | Antibody titers for ExPEC10V, as determined by multiplex ECL-based immunassay and MOPA on Day 30 |
| To evaluate the immunogenicity of the selected dose of ExPEC 10V on Days 15 and 181 in participants ≥60 years of age with a history of UTI in the past 5 years | Antibody titers for ExPEC10V, as determined by multiplex ECL-based immunoassay and MOPA on Days 15 and 181 |
| To evaluate, in the LTFU period, the safety of the selected dose of ExPEC10V in participants ≥60 years of age with a history of UTI in the past 5 years | SAEs related to the study vaccine or study procedures collected from Day 182 until the end of the study |
| To evaluate in the LTFU period, the immunogenicity of the selected dose of ExPEC10V in participants ≥60 years of age with a history of UTI in the past 5 years | Antibody titers for ExPEC10V, as determined by multiplex ECL-based immunoassay and MOPA at Year 1 (Day 366), Year 2 (Day 731), and Year 3 (Day 1096) |
| Exploratory | |
| To evaluate the effect of ExPEC10V on the intestinal (stool) microbiome by metagenomic analyses | Metagenomics of stool samples from a selected subset of participants to evaluate the effect of ExPEC 10V on:<br>Prevalence of pathogens (eg, Clostridium difficile) in the intestinal flora<br>Prevalence of ExPEC10V serotypes in the intestinal flora |

Overall Design

This is a randomized, multicenter, interventional study including two cohorts.

Figure 10A:
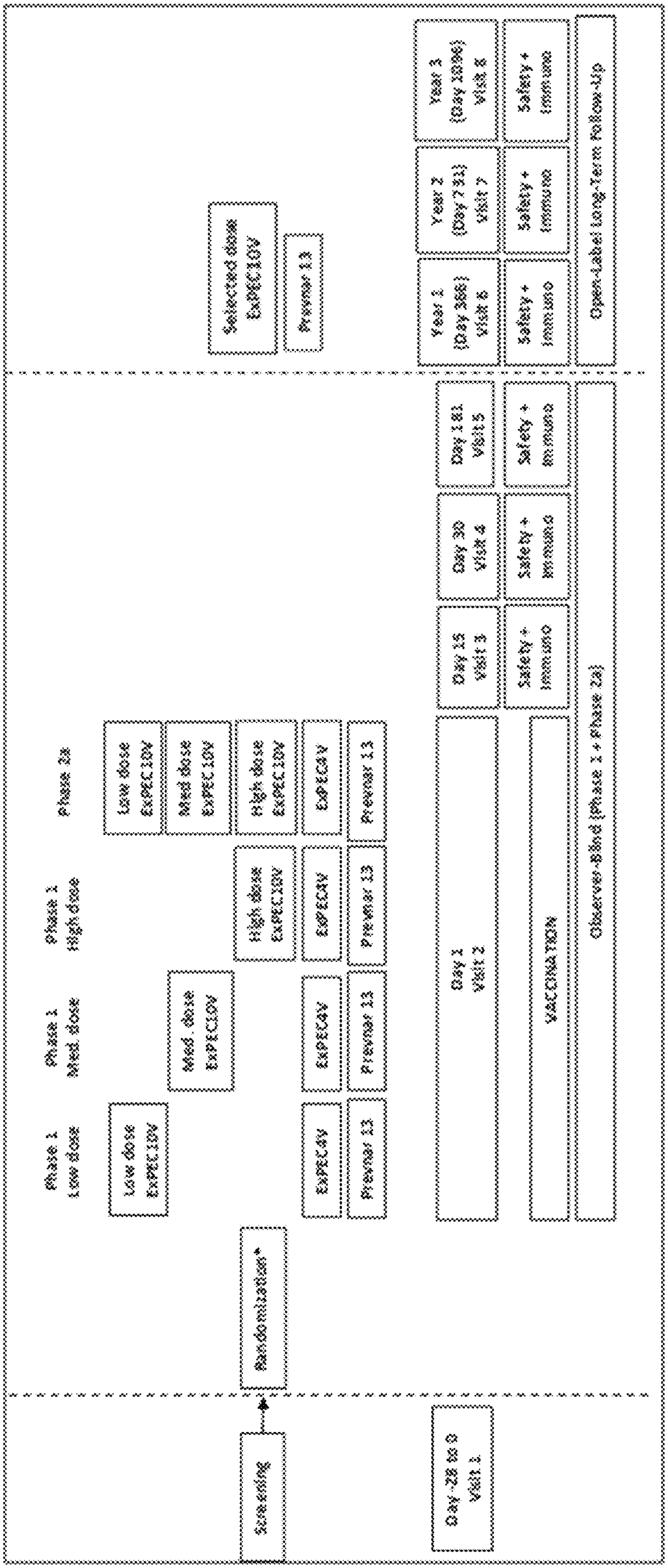
FIG. 10A and FIG. 10B shows the overall study design for a phase 1/2a clinical trial with ExPEC10V vaccine in humans.

For Cohort 1, the study has an observer-blind, active-controlled design, and a total of 404 adult participants aged ≥60 to ≤85 years in stable health with or without a history of UTI are included. The study design for Cohort 1 is comprised of three periods: a maximum of 28-day screening period, an observer-blinded 181-day follow-up period with vaccination on Day 1 and an open-label LTFU period which lasts from Day 182 until 3 years (Day 1096) post-vaccination (FIG. 10A). Only participants from the ExPEC10V selected dose group (approximately 100 participants) and participants from the Prevnar 13 group progress to the LTFU period. The end of Cohort 1 is the last participant's Year 3 visit (Day 1096).

Figure 10B:
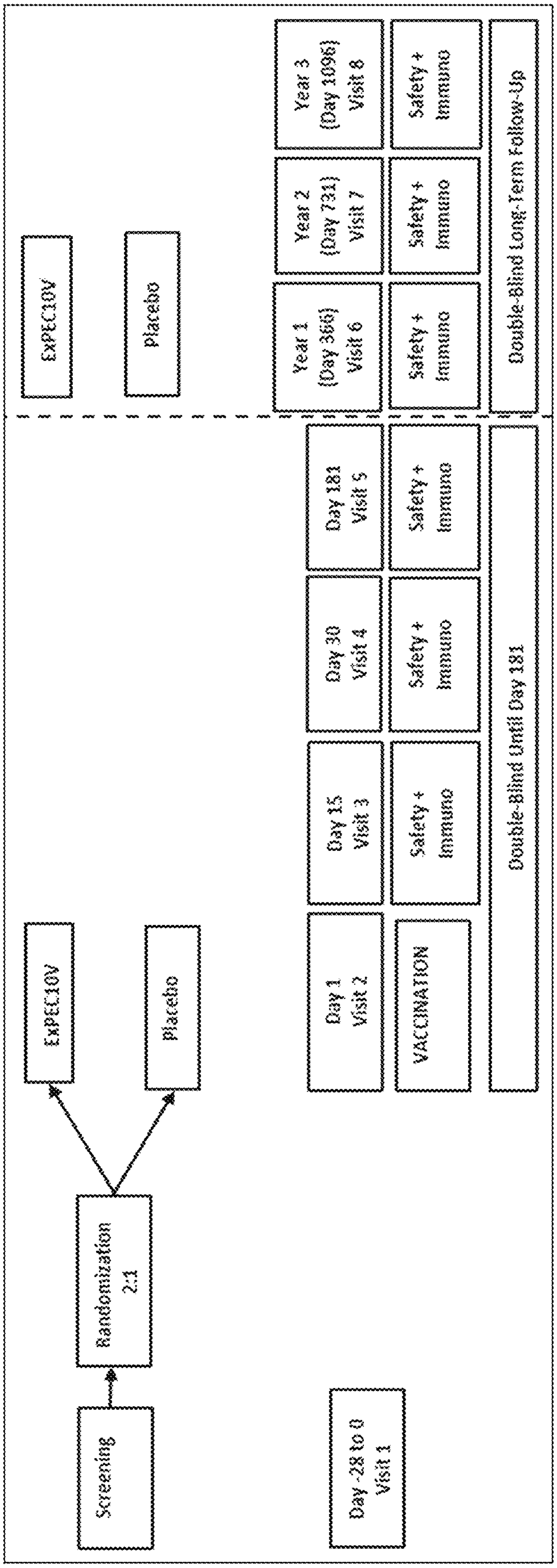

For Cohort 2, the study has a double-blind, placebo-controlled design, and a total of 600 adult participants aged ≥60 years in stable health with a history of UTI in the past 5 years is included. Enrollment commences after completion of the Phase 1/2a primary analysis and ExPEC10V dose selection from Cohort 1. The study design for Cohort 2 is comprised of three periods: a maximum 28-day screening period, a double-blind 181-day follow-up period with vaccination on Day 1, and a double-blind LTFU period which lasts from Day 182 until 3 years (Day 1096) post-vaccination (FIG. 10B). All participants in Cohort 2 progress to the LTFU period. The end of study is the last participant's Year 3 visit (Day 1096) in Cohort 2.

Cohort 1: Phase 1

In Phase 1 of Cohort 1, a total of 84 participants are enrolled in a staggered approach following stepwise dose-escalating procedures with safety evaluations in place before progressing from one step to the next. An internal Data Review Committee (DRC) is commissioned for this study to review the physical examination data (baseline as well as targeted), baseline demographic data and the 14-day post-vaccination safety data (including solicited local and systemic AEs, unsolicited AEs, SAES, clinical laboratory data and vital signs) of these 84 Phase 1 participants. In this phase of the study, participants were enrolled and randomized in six steps:

Step 1: Four sentinel participants were enrolled and randomized; two participants in the ExPEC10V low dose group (Table 11), and one participant each in the ExPEC4V and Prevnar 13 groups.

Step 2: Twenty-four participants were enrolled and randomized; 18 participants in the ExPEC10V low dose group (Table 11), and three participants each in the ExPEC4V and Prevnar 13 groups.

Step 3: Four sentinel participants were enrolled and randomized; two participants in the ExPEC10V medium dose group (Table 11), and one participant each in the ExPEC4V and Prevnar 13 groups.

Step 4: Twenty-four participants were enrolled and randomized; 18 participants in the ExPEC10V medium dose group (Table 11), and three participants each in the ExPEC4V and Prevnar 13 groups.

Step 5: Four sentinel participants were enrolled and randomized; two participants in the ExPEC10V high dose group (Table 11), and one participant each in the ExPEC4V and Prevnar 13 groups.

Step 6: Twenty-four participants were enrolled and randomized; 18 participants in the ExPEC10V high dose group (Table 11), and three participants each in the ExPEC4V and Prevnar 13 groups.

All participants received a single intramuscular (IM) injection of either ExPEC10V (1 of 3 doses), ExPEC4V or Prevnar 13 on Day 1 per the assigned study vaccination groups. The four sentinel participants at each of Steps 1, 3 and 5 were contacted by telephone 24 hours post-vaccination to collect safety information. The blinded 24-hour post-vaccination safety data in each group of four sentinel participants were reviewed by the principal investigator (PI), study responsible physician (SRP) and sponsor medical lead (SML). Randomization of additional participants for the next step was halted until this Day 2 sentinel safety evaluation was completed.

In the absence of any clinically significant findings, an additional 24 participants (for Steps 2, 4, and 6) were enrolled and randomized to one of three study vaccination groups (Table 11) to receive a single IM injection of either ExPEC10V (1 of 3 doses), ExPEC4V or Prevnar 13 on Day 1.

After vaccination of an additional 24 participants at each dose level (low dose in Step 2, medium dose in Step 4, and high dose in Step 6), 14-day post-vaccination safety data of all 28 (4+24) participants at each dose level was reviewed by the DRC before progressing to the next dose level or Phase 2a.

Cohort 1: Phase 2a

Based on acceptable safety and reactogenicity (in the absence of any safety concerns or any events meeting a specific study pausing rule) as determined by DRC after the review of 14-day post-vaccination safety data for the initial 84 participants, the remaining 320 participants from Cohort 1 were randomized and dosed in Phase 2a of the study. These additional 320 participants were enrolled and randomized in parallel in a ratio of 2:2:2:1:1 to one of the five study vaccination groups to receive a single IM injection of either ExPEC10V (1 of 3 doses), ExPEC4V or Prevnar 13 on Day 1 (Table 11).

In addition to performing the 14-day safety review for the initial 84 participants, the DRC also evaluates safety data of Cohort 1 over the course of the study and review any events that meet a specific study vaccination pausing rule or any other safety issue that may arise.

For Cohort 1, the primary analysis occurs when all participants have completed the Day 30 visit (Visit 4) or have discontinued earlier. The final analysis occurs when all participants have completed the Day 181 visit or have discontinued earlier. For participants progressing to the open-label long-term follow-up (LTFU) period (ExPEC10V selected dose group and Prevnar 13 group), yearly follow-up analyses include safety and immunogenicity data (multiplex ECL-based immunoassay and MOPA) collected up to the time of the visit at Year 1 (Day 366), Year 2 (Day 731) and Year 3 (Day 1096) after vaccination.

Cohort 2

In Cohort 2, the safety, reactogenicity, and immunogenicity of the selected dose of ExPEC10V (based on the primary analysis results of Cohort 1) is evaluated in participants aged ≥60 years in stable health with a history of UTI in the past 5 years. For Cohort 2, the study has a double-blind, placebo-controlled design, and a total of 600 participants are enrolled and randomized in parallel in a 2:1 ratio (400 participants in the ExPEC10V group and 200 in the placebo group).

All participants receive a single IM injection of either the selected dose of ExPEC10V or placebo on Day 1 per the assigned study vaccination groups (Table 12).

For Cohort 2, the primary analysis includes safety and immunogenicity data and occurs when all participants have completed the Day 30 visit (Visit 4) or have discontinued earlier. The final analysis occurs when all participants have completed the Day 181 visit or have discontinued earlier. For all participants, yearly follow-up analyses include safety and immunogenicity data (multiplex ECL-based immunoassay and MOPA) collected up to the time of the visit at Year 1 (Day 366), Year 2 (Day 731), and Year 3 (Day 1096) after vaccination.

A stool sample analysis is performed in a selected subset of participants to evaluate the effect of ExPEC10V on the prevalence of pathogens (eg, *Clostridium difficile*) and ExPEC10V serotypes in the intestinal flora using metagenomics.

Number of Participants

A total of 1004 participants is enrolled in the study; 404 participants in Cohort 1 and 600 participants in Cohort 2.

Intervention Groups

Description of Interventions

ExPEC10V: *E. coli* bioconjugate vaccine in phosphate buffered solution containing O-antigen PS of ExPEC serotypes O1A, O2, O4, O6A, O8, O15, O16, O18A, O25B and O75 separately bioconjugated to the EPA carrier protein. Single 0.5 mL IM (deltoid) injection of one of the three doses of ExPEC10V on Day 1.

ExPEC4V: *E. coli* bioconjugate vaccine in saline buffer solution containing O-antigen PS of ExPEC serotypes O1A, O2, O6A, O25B (4:4:4:8 μg PS/ExPEC serotypes) separately bioconjugated to the EPA carrier protein. Single 0.5 mL IM (deltoid) injection of ExPEC4V on Day 1.

Prevnar 13: Sterile suspension of saccharides of the capsular antigens of *Streptococcus pneumoniae* serotypes 1, 3, 4, 5, 6A, 6B, 7F, 9V, 14, 18C, 19A, 19F, and 23F, individually linked to non-toxic Diphtheria CRM197 protein. Single 0.5 mL IM (deltoid) injection on Day 1, supplied in a single-dose prefilled syringe.

Placebo: normal saline. Single 0.5 mL IM (deltoid) injection of placebo on Day 1.

The ExPEC study intervention materials are described in Table 9.

TABLE 9

BAC1001MV ExPEC Study Vaccines.

| Study Arm | O1A (μg) | O2 (μg) | O4 (μg) | O6A (μg) | O8 (μg) | O15 (μg) | O16 (μg) | O18A (μg) | O25B (μg) | O75 (μg) | EPA (μg) | PS (Total) (μg) |
|---|---|---|---|---|---|---|---|---|---|---|---|---|
| Low dose ExPEC10V | 4 | 4 | 4 | 4 | 4 | 4 | 4 | 4 | 8 | 4 | 160 | 44 |
| Medium dose ExPEC10V | 8 | 4 | 4 | 8 | 4 | 4 | 4 | 4 | 16 | 4 | 221 | 60 |

TABLE 9-continued

| BAC1001MV ExPEC Study Vaccines. | | | | | | | | | | | | |
|---|---|---|---|---|---|---|---|---|---|---|---|---|
| Study Arm | O1A (μg) | O2 (μg) | O4 (μg) | O6A (μg) | O8 (μg) | O15 (μg) | O16 (μg) | O18A (μg) | O25B (μg) | O75 (μg) | EPA (μg) | PS (Total) (μg) |
| High dose ExPEC10V | 8 | 8 | 8 | 8 | 8 | 8 | 8 | 8 | 16 | 8 | 320 | 88 |
| ExPEC4V | 4 | 4 | — | 4 | — | — | — | — | 8 | — | 72 | 20 |

EPA = a genetically detoxified form of exotoxin A derived from *Pseudomonas aeruginosa*;
PS = polysaccharide
ExPEC4V consists of the O-antigen polysaccharides (PSs) of the ExPEC serotypes O1A, O2, O6A, and O25B separately bioconjugated to the EPA carrier protein.
ExPEC10V consists of the O-antigen polysaccharides (PSs) of the ExPEC serotypes O1A, O2, O4, O6A, O8, O15 O16, O18A, O25B and O75 separately bioconjugated to the EPA carrier protein.
Dose is based on PS only.
The EPA (μg) are measured values.

ExPEC10V is composed of 10 monovalent drug substances (DSs). For this clinical study, 2 different concentrations (medium and high) of drug product (DP) are produced (Table 10). A third (low) concentration is obtained in the clinic by diluting the high concentration 1:1 with dilution buffer, which is the same as the formulation buffer. Each DP is formulated in Sodium/Potassium phosphate buffer at pH 7.0 (0.02% [w/w] Polysorbate 80, 5% [w/w] sorbitol, 10 mM methionine).

TABLE 10

| Composition of ExPEC10V vaccine for phase ½a clinical study | | | |
|---|---|---|---|
| | Amount (μg/mL)[a] | | |
| Ingredient Active[a] | Low Concentration[b] | Medium Concentration | High Concentration |
| O-antigen polysaccharide | | | |
| EcoO1A | 8 | 16 | 16 |
| EcoO2 | 8 | 8 | 16 |
| EcoO4 | 8 | 8 | 16 |
| EcoO6A | 8 | 16 | 16 |
| EcoO8 | 8 | 8 | 16 |
| EcoO15 | 8 | 8 | 16 |
| EcoO16 | 8 | 8 | 16 |
| EcoO18A | 8 | 8 | 16 |
| EcoO25B | 16 | 32 | 32 |
| EcoO75 | 8 | 8 | 16 |
| Carrier protein | | | |
| EPA | 320 | 441 | 640 |
| Excipients | | | |
| $KH_2PO_4$ | | 6.19 mM | |
| $Na_2HPO_4$ | | 3.81 mM | |
| Sorbitol | | 5% (w/w) | |
| Methionine | | 10 mM | |
| Polysorbate 80 | | 0.02% (w/w) | |

EPA = genetically detoxified *P. aeruginosa* exotoxin A used as carrier protein
[a]The active ingredient is a biologically synthesized conjugate composed of the PS antigen and a carrier protein (EPA); the dose is calculated on the PS moiety only.
[b]The "low concentration" is obtained in the clinic by diluting the "high concentration" 1:1 with dilution buffer Safety Evaluations Key safety assessments include solicited local and systemic AEs, unsolicited AEs, SAEs, physical examinations, vital sign measurements, and clinical laboratory tests.

Immunogenicity Evaluations

Key immunogenicity assessments of collected sera include the assessment of ExPEC10V and ExPEC4V serotype-specific total IgG antibody levels elicited by the vaccine as measured by a multiplex ECL-based immunoassay, and ExPEC10V and ExPEC4V serotype-specific functional antibodies as measured by an opsonophagocytic killing assay (OPKA) in multiplex format (MOPA). Immunogenicity assessments of pneumococcal antibody titers elicited by Prevnar 13 are not performed.

The levels of serum antibodies induced by ExPEC10V are measured by a multiplex electrochemiluminescent (ECL)-based immunoassay. This assay combines high binding carbon electrodes in a multi-spot 96-well format microplate that is coated with different *E. coli* O-LPS antigens or the carrier protein EPA. The levels of antigen-specific antibodies present in serum samples are detected using a secondary antibody (anti-human IgG) labeled with SULFO-TAG. The SULFO-TAG emits light in the presence of electrical stimulation at an intensity that increases proportionally to the amount of bound IgG antibodies. This assay was qualified according to International Conference on Harmonisation (ICH) recommendations.

The levels of functional antibodies induced by ExPEC10V are measured by a multiplex opsonophagocytic assay (MOPA). Briefly, heat-inactivated serum samples are serially diluted and incubated with different *E. coli* strains that are specifically resistant to different types of antibiotics. After that, human complement and phagocytic cells (HL60) are added to the reaction and, after a second incubation period, an aliquot of the reaction mix is transferred to different PVDF hydrophilic membrane filter plates containing media supplemented with specific antibiotic that selectively allow growth of a strain that is resistant to that particular antibiotic. After overnight grown, the colony forming units (CFUs) are counted to determine the number of surviving bacteria. This assay was qualified according to ICH recommendations.

For ExPEC10V serotype antibodies as measured by multiplex ECL-based immunoassay and MOPA, and EPA as measured by multiplex ECL-based immunoassay only, the following measures of immunogenicity are evaluated and tabulated by the study vaccination groups, for all immunogenicity time points:

- proportion of participants with a ≥2-fold and ≥4-fold increase in serum antibody titers from Day 1 (pre-vaccination)
- geometric mean titer (GMT)
- GMR: fold change from baseline, calculated from the post-baseline/baseline value.

For the LTFU period, descriptive summaries of immunogenicity are provided for each serotype.

Dose selection for later phases considers the totality of the evidence available at the time of the primary analysis of Cohort 1 (Day 30 results).

TABLE 11

| Cohort 1: Vaccination Schedule | | | | | | | | | |
|---|---|---|---|---|---|---|---|---|---|
| Study Vaccination Group | Vaccination on Day 1 | Phase 1 Step 1 Sentinel participants (Low dose) | Step 2 Additional participants (Low dose) | Step 3 Sentinel participants (Medium dose) | Step 4 Additional participants (Medium dose) | Step 5 Sentinel participants (High dose) | Step 6 Additional participants (High dose) | Phase 2a Step 7 Additional Phase 2a Participants | Total |
| G1 | Low dose ExPEC10V* | 2 | 18 | | | | | 80 | 100 |
| G2 | Medium dose ExPEC10V* | | | 2 | 18 | | | 80 | 100 |
| G3 | High dose ExPEC10V* | | | | | 2 | 18 | 80 | 100 |
| G4 | ExPEC4V** | 1 | 3 | 1 | 3 | 1 | 3 | 40 | 52 |
| G5 | Prevnar 13*** | 1 | 3 | 1 | 3 | 1 | 3 | 40 | 52 |
| Total | | 4 | 24 | 4 | 24 | 4 | 24 | 320 | 404 |

*ExPEC10V consists of the O-antigen polysaccharides (PSs) of the ExPEC serotypes O1A, O2, O4, O6A, O8, O15, O16, O18A, O25B and O75 separately bioconjugated to the carrier protein, a genetically detoxified form of exotoxin A (EPA) derived from *Pseudomonas aeruginosa*.
**ExPEC4V consists of the O-antigen polysaccharides (PSs) of the ExPEC serotypes O1A, O2, O6A, and O25B separately bioconjugated to the carrier protein, a genetically detoxified form of exotoxin A (EPA) derived from *Pseudomonas aeruginosa*.
*** Prevnar 13, Pneumococcal 13-valent conjugate vaccine (Diphtheria CRM197 protein) is a sterile suspension of saccharides of the capsular antigens of *Streptococcus pneumoniae* serotypes 1, 3, 4, 5, 6A, 6B, 7F, 9V, 14, 18C, 19A, 19F, and 23F, individually linked to non-toxic Diphtheria CRM197 protein.

TABLE 12

| Cohort 2: Vaccination Schedule | | |
|---|---|---|
| Study Vaccination Group | Vaccination on Day 1 | Total |
| G6 | ExPEC10V[a] | 400 |
| G7 | Placebo | 200 |
| Total | | 600 |

[a]ExPEC10V consists of the O-antigen polysaccharides (PSs) of the ExPEC serotypes O1A, O2, O4, O6A, O8, O15, O16, O18A, O25B, and O75 separately bioconjugated to the carrier protein, a genetically detoxified form of exotoxin A (EPA) derived from *Pseudomonas aeruginosa*.

The randomization ratio for the participants enrolled in Cohort 2 of the study is 2:1 (ExPEC10V:Placebo). The ExPEC10V dose used in Cohort 2 is based on the primary analysis (Day 30) results of Cohort 1.

Status

Enrollment and vaccination of Cohort 1 of the study described above was completed. The study is ongoing in a blinded manner. Based on ongoing review of the safety data, no major safety issues were identified, and the ExPEC10V vaccine has an acceptable safety profile.

The analysis of the immunogenicity of the Cohort 1 clinical samples is ongoing in a blinded fashion. The ECL data were 100% Acceptance Quality Limits (AQL) checked and uploaded for data management. Analysis of the MOPA samples is ongoing. Data unblinding and statistical analysis is performed by using a clinical research organization (CRO).

The Cohort 2 vaccinations are started once the ExPEC10V dose for that Cohort has been identified based on the finalized primary analysis of the Day 30 results from Cohort 1.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

SEQUENCES

```
SEQ ID NO: 1 (Glycosylation consensus sequence)
Asn-X-Ser(Thr), wherein X can be any amino acid except Pro

SEQ ID NO: 2 (Optimized glycosylation consensus sequence)
Asp(Glu)-X-Asn-Z-Ser(Thr), wherein X and Z are independently selected from any
amino acid except Pro

SEQ ID NO: 3 (EPA carrier protein comprising 4 glycosylation consensus
sequences (EPA-4))
G SGGGDQNATG SGGGKLAEEA FDLWNECAKA CVLDLKDGVR SSRMSVDPAI ADTNGQGVLH YSMVLEGGND
ALKLAIDNAL SITSDGLTIR LEGGVEPNKP VRYSYTRQAR GSWSLNWLVP IGHEKPSNIK VFIHELNAGN
QLSHMSPIYT IEMGDELLAK LARDATFFVR AHESNEMQPT LAISHAGVSV VMAQAQPRRE KRWSEWASGK
VLCLLDPLDG VYNYLAQQRC NLDDTWEGKI YRVLAGNPAK HDLDIKDNNN STPTVISHRL HFPEGGSLAA
LTAHQACHLP LEAFTRHRQP RGWEQLEQCG YPVQRLVALY LAARLSWNQV DQVIRNALAS PGSGGDLGEA
IREQPEQARL ALTLAAAESE RFVRQGTGND EAGAASADVV SLTCPVAKDQ NRTKGECAGP ADSGDALLER
NYPTGAEFLG DGGDVSFSTR GTQNWTVERL LQAHRQLEER GYVFVGYHGT FLEAAQSIVF GGVRARSQDL
DAIWRGFYIA GDPALAYGYA QDQEPDARGR IRNGALLRVY VPRWSLPGFY RTGLTLAAPE AAGEVERLIG
HPLPLRLDAI TGPEEEGGRV TILGWPLAER TVVIPSAIPT DPRNVGGDLD PSSIPDKEQA ISALPDYASQ
PGKPPREDLK LGSGGGDQNA T

SEQ ID NO: 4 (O4 GtrS amino acid sequence)
MNNLIMNNWCKLSIFIIAFILLWLRRPDILTNAQFWAEDSVFWYKDAYENGFLSSLTTPRNGYFQTVSTFIVGLTALL
NPDYAPFVSNFFGIMIRSVIIWFLFTERFNFLTLTTRIFLSIYFLCMPGLDEVHANITNAHWYLSLYVSMILIARNPS
SKSWRFHDIFFILLSGLSGPFIIFILAASCFKFINNCKDHISVRSFINFYLRQPYALMIVCALIQGTSIILTFNGTRS
SAPLGFSFDVISSIISSNIFLFTFVPWDIAKAGWDNLLLSYFLSVSILSCAAFVFVKGTWRMKVFATLPLLIIIFSMA
```

-continued

| SEQUENCES |
|---|

KPQLTDSAPQLPTLINGQGSRYFVNIHIAIFSLLCVYLLECVRGKVATLFSKIYLTILLFVMGCLNFVITPLPNMNWR
EGATLINNAKTGDVISIQVLPPGLTLELRKK

SEQ ID NO: 5 (Example O4 gtrS nucleic acid sequence)
ATGAATAATTTAATTATGAATAACTGGTGTAAATTATCTATATTTATTATTGCATTTATTTTGCTATGGCTTAGAAGG
CCGGATATACTCACAAACGCACAATTTTGGGCAGAAGATTCCGTTTTCTGGTATAAGGACGCCTATGAGAACGGATTC
TTAAGTTCACTAACAACGCCTAGGAATGGGTATTTCCAGACTGTTTCTACATTTATAGTTGGTCTGACTGCTTTATTA
AATCCAGATTATGCACCTTTTGTTTCTAATTTTTTTGGCATAATGATTCGCTCAGTAATTATATGGTTTTTATTTACA
GAAAGATTCAACTTCCTCACATTGACTACTAGGATTTTCTTATCTATTTATTTTCTATGCATGCCTGGATTGGATGAA
GTTCATGCAAATATAACAAATGCACATTGGTATTTGTCATTATATGTATCAATGATCCTGATAGCTCGCAATCCAAGT
TCAAAATCATGGAGGTTTCATGATATATTCTTTATCTTGCTATCCGGGCTCAGTGGCCCATTTATAATTTTCATTTTA
GCAGCTTCATGCTTTAAATTTATAAATAATTGTAAAGATCATATTAGTGTAAGATCTTTCATAAATTTCTACTTGCGT
CAGCCATACGCATTAATGATTGTTTGCGCTTTAATTCAAGGAACTTCTATAATTCTAACTTTCAATGGCACACGTTCC
TCAGCACCGCTAGGATTCAGTTTTGATGTGATTTCGTCTATTATATCATCGAATATTTTTTTATTTACATTTGTCCCA
TGGGATATTGCAAAGGCTGGGTGGGATAATTTACTGTTATCTTATTTTTTGTCTGTTTCGATTTTGTCGTGTGCGGCC
TTTGTTTTTGTTAAAGGTACGTGGCGAATGAAAGTATTTGCAACTTTACCATTGCTAATTATAATATTTTCAATGGCA
AAACCACAATTGACAGACTCGGCACCTCAATTGCCAACACTTATTAATGGGCAAGGTTCAAGATACTTCGTAAATATA
CATATTGCGATATTCTCTTTGCTATGTGTTTACTTACTTGAGTGCGTCAGGGGGAAAGTGGCAACTTTATTTTCCAAA
ATATACTTAACAATTTTGCTATTCGTGATGGGATGTTTGAATTTTGTTATCACCCCACTCCCAAACATGAACTGGAGG
GAAGGTGCTACTTTGATTAATAATGCAAAAACTGGTGATGTCATTTCGATTCAAGTGCTACCACCTGGCCTAACACTT
GAACTAAGGAAAAAATAA SEQ ID NO: 6 (Example Pg1B sequence (‘wild-type’))
MLKKEYLKNPYLVLFAMIILAYVFSVFCRFYWVWWASEFNEYFFNNQLMIISNDGYAFAEGARDMIAGFHQPNDLSYY
GSSLSALTYWLYKITPFSFESIILYMSTFLSSLVVIPTILLANEYKRPLMGFVAALLASIANSYYNRTMSGYYDTDML
VIVLPMFILFFMVRMILKKDFFSLIALPLFIGIYLWWYPSSYTLNVALIGLFLIYTLIFHRKEKIFYIAVILSSLTLS
NIAWFYQSAIIVILFALFALEQKRLNFMIIGILGSATLIFLILSGGVDPILYQLKFYIFRSDESANLTQGFMYFNVNQ
TIQEVENVDLSEFMRRISGSEIVFLFSLFGFVWLLRKHKSMIMALPILVLGFLALKGGLRFTIYSVPVMALGFGFLLS
EFKAIMVKKYSQLTSNVCIVFATILTLAPVFIHIYNYKAPTVFSQNEASLLNQLKNIANREDYVVTWWDYGYPVRYYS
DVKTLVDGGKHLGKDNFFPSFALSKDEQAAANMARLSVEYTEKSFYAPQNDILKTDILQAMMKDYNQSNVDLFLASLS
KPDFKIDTPKTRDIYLYMPARMSLIFSTVASFSFINLDTGVLDKPFTFSTAYPLDVKNGEIYLSNGVVLSDDFRSFKI
GDNVVSVNSIVEINSIKQGEYKITPIDDKAQFYIFYLKDSAIPYAQFILMDKTMFNSAYVQMFFLGNYDKNLFDLVIN
SRDAKVFKLKI SEQ ID NO: 7 (example gtrA amino acid sequence; *E. coli* W3110 yfdG, GenBank: BAA16209.1)
MLKLFAKYTSIGVLNTLIHWVVFGVCIYVAHTNQALANFAGFVVAVSFSFFANAKFTFKASTTTMRYMLYVGFMGTLS
ATVGWAADRCALPPMITLVTFSAISLVCGFVYSKFIVFRDAK SEQ ID NO: 8 (example gtrB amino acid sequence-*E. coli* W3110 yfdH, GenBank: BAA16210.1)
MKISLVVPVFNEEEAIPIFYKTVREFEELKSYEVEIVFINDGSKDATESIINALAVSDPLVVPLSFTRNFGKEPALFA
GLDHATGDAIIPIDVDLQDPIEVIPHLIEKWQAGADMVLAKRSDRSTDGRLKRKTAEWFYKLHNKISNPKIEENVGDF
RLMSRDVVENIKLMPERNLFMKGILSWVGGKTDIVEYVRAERIAGDTKFNGWKLWNLALEGITSFSTFPLRIWTYIGL
VVASVAFIYGAWMILDTIIFGNAVRGYPSLLVSILFLGGIQMIGIGVLGEYIGRTYIETKKRPKYIIKRVKK SEQ ID NO: 9 (example O4 rfb locus nucleotide sequence-O4-EPA production strain BVEC-L-00684f)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATCTGTCCGCCGGGCGTGACCATTATGAACGTGCGTCAG
GGCGAACCTTTAGGTTTAGGCCACTCCATTTTGTGTGCGCGACCTGCCATTGGTGACAACCCATTTGTCGTGGTACTG
CCAGACGTTGTGATCGACGATGCCAGCGCCGACCCGCTACGTTACAACCTTGCTGCCATGATTGCACGTTTCAACGAA
ACGGGCCGCAGCCAGGTGCTGGCAAAACGTATGCCGGGTGACCTCTCTGAATACTCCGTCATCCAGACTAAAGAGCCG
CTGGACCGTGAGGGTAAAGTCAGCCGCATTGTTGAATTTATCGAAAAACCGGATCAGCCGCAGACGCTGGACTCAGAC
ATCATGGCCGTAGGTCGCTATGTGCTTTCTGCCGATATTTGGCCGGAACTGGAACGTACTCAGCCTGGTGCATGGGGA
CGTATTCAGCTGACTGATGCTATTGCCGAGCTGGCGAAAAAACAATCCGTTGATGCAATGCTGATGACCGGCGACAGT
TACGACTGCGGCAAAAAAATGGGCTATATGCAGGCGTTTGTGAAGTATGGCCTACGCAACCTGAAAGAAGGGGCGAAG
TTCCGTAAAGGTATTGAGAAGCTGTTAAGCGAATAATGAAAATCTGACCGGATGTAACGGTTGATAAGAAAATTATAA
CGGCAGTGAAAATTCGCAGCAAAAGTAATTTGTTGCGAATCTTCCTGCCGTTGTTTTATATAAACCATCAGAATAACA
ACGAGTTAGCAGTAGGGTTTTATTCAAAGTTTTCCAGGATTTTCCTTGTTTCCAGAGCGGATTGGTAAGACAATTAGC
GTTTGAATTTTTCGGGTTTAGCGCGAGTGGGTAACGCTCGTCACATCATAGGCATGCATGCAGTGCTCTGGTAGCTGT
AAAGCCAGGGGCGGTAGCGTGCATTAATACCTCTATTAATCAAACTGAGAGCCGCTTATTTCACAGCATGCTCTGAAG
TAATATGGAATAAATTAAGTGAAAATACTTGTTACTGGTGGCGCAGGATTTATTGGTTCAGCTGTAGTTCGTCACATT
ATAAATAATACGCAGGATAGTGTTGTTAATGTCGATAAATTAACGTACGCCGGAAACCGGGAATCACTTGCTGATGTT
TCTGATTCTGAACGCTATGTTTTTGAACATGCGGATATTTGCGATGCACCTGCAATGGCACGGATTTTTGCTCAGCAT
CAGCCGGATGCAGTGATGCACCTGGCTGCTGAAAGCCATGTTGACCGTTCAATTACAGGCCCTGCGGCATTTATTGAA
ACCAATATTGTTGGTACTTATGTCCTTTTGGAAGCCGCTCGCAATTACTGGTCTGCTCTTGATAGCGACAAGAAAAAT
AGCTTCCGTTTTCATCATATTTCTACTGACGAAGTATATGGTGATTTGCCTCATCCTGACGAGGTAAATAATACAGAA
GAATTACCCTTATTTACTGAGACAACAGCTTACGCGCCAAGCAGCCCTTATTCCGCATCCAAAGCATCCAGCGATCAT
TTAGTCCGCGCGTGGAAACGTACCTATGGTTTACCGACCATTGTGACTAATTGCTCTAACAATTATGGTCCTTATCAT
TTCCCGGAAAAATTGATTCCATTGGTTATTCTCAATGCTCTGGAAGGTAAAGCATTACCTATTTATGGTAAAGGGGAT
CAAATTCGCGACTGGCTGTATGTTGAAGATCATGCGCGTGCGTTATATACCGTCGTAACCGAAGGTAAAGCGGGTGAA
ACTTATAACATTGGTGGGCACAACGAAAAGAAAAACATAGATGTAGTGCTCACTATTTGTGATTTGCTGGATGAGATT
GTACCGAAAGAGAAATCTTATCGTGAGCAAATCACTTATGTTGCCGATCGTCCGGGACACGATCGCCGTTATGCGATT
GATGCTGAGAATATTGGTCGCGAATTGGGATGGAAACCACAGGAAACGTTTGAGAGCGGGATTCGGAAGACAGTGGAA -continued

| SEQUENCES |
| --- |
| TGGTATCTGTCCAATACAAAATGGGTTGATAATGTGAAAAGTGGTGCCTATCAATCGTGGATTGAAGAGAACTATGAG<br>GGCCGCCAGTAATGAATATCCTCCTTTTTGGCAAAACAGGGCAGGTAGGTTGGGAACTACAGCGTGCTCTGGCACCTC<br>TGGGTAACTTGATTGCTCTTGATGTTCATTCCACTGATTATTGTGGCGATTTCAGTAACCCCGAAGGTGTGGCTGAAA<br>CCGTCAAAAAAATTCGCCCAGATGTTATTGTTAATGCTGCTGCTCATACCGCGGTAGATAAGGCTGAGTCAGAACCAG<br>AATTTGCACAATTACTCAATGCGACCAGCGTTGAAGCAATTGCAAAAGCGGCTAATGAAGTTGGGGCTTGGGTAATTC<br>ATTACTCAACTGACTACGTCTTCCCTGGAAATGGCGACATGCCATGGCTCGAGACTGATGTAACCGCTCCGCTCAATG<br>TTTATGGCAAAACCAAATTGGCTGGAGAAAGAGCATTACAAGAACATTGCGCAAAGCATCTTATTTTCCGTACCAGCT<br>GGGTATATGCAGGTAAAGGAAATAACTTTGCCAAAACAATGTTACGTCTGGCAAAAGAGCGCGAAGAACTGGCTGTGA<br>TAAACGATCAGTTTGGCGCACCAACAGGTGCTGAATTGCTGGCTGATTGCACCGCTCATGCCATTCGCGTGGCATTAA<br>AAAAACCAGAAGTTGCTGGCTTGTACCATCTGGTAGCAAATGGCACAACAACCTGGCACGATTACGCCGCGCTAGTAT<br>TCGAAGAAGCCCGTAAAGCAGGGATTGACCTTGCACTTAACAAACTCAACGCCGTACCAACAACGGCTTATCCTACTC<br>CAGCCCGCCGTCCTCATAATTCTCGCCTCAATACCGAAAAGTTTCAGCAGAACTTTGCGCTTGTCTTGCCTGACTGGC<br>AGGTGGGCGTGAAACGTATGCTCAACGAATTATTTACGACTACGGCAATTTAACAAATTTTTGCATCTCGCTCATGAT<br>GCCAGAGCGGGATGAATTAAAAGGAATGGTGAAATGAAAACGCGTAAAGGTATTATTCTGGCTGGTGGTTCCGGCACT<br>CGTCTTTATCCTGTGACGATGGCAGTGAGTAAACAACTGCTGCCGATTTATGATAAGCCGATGATTTATTATCCGCTT<br>TCAACGCTTATGTTAGCGGGTATTCGCGATATTCTTATTATCAGTACGCCACAGGATACACCGCGTTTCCAACAATTG<br>TTGGGGGACGGGAGTCAGTGGGGGCTTAATCTACAGTATAAAGTACAACCGAGTCCGGATGGCCTGGCGCAAGCGTTT<br>ATTATTGGTGAAGACTTTATTGGTGGTGATGATTGTGCACTCGTACTTGGCGATAATATCTTCTATGGACACGACTTG<br>CCGAAATTAATGGAAGCTGCTGTTAACAAAGAAATCGGTGCAACGGTATTTGCTTATCACGTCAATGATCCTGAACGT<br>TATGGTGTCGTGGAGTTTGATAATAACGGTACTGCAATTAGCCTGGAAGAAAAACCGCTGGAACCAAAAAGTAACTAT<br>GCGGTTACTGGGCTTTATTTCTATGACAATGATGTTGTAGAAATGGCGAAAAACCTTAAGCCTTCTGCCCGTGGCGAA<br>CTGGAAATTACCGATATTAACCGTATTTATATGGAGCAGGGACGTTTGTCTGTCGCTATGATGGGGCGTGGTTATGCC<br>TGGTTGGATACTGGTACACATCAAAGTCTTATTGAAGCAAGTAACTTCATTGCCACCATTGAAGAGCGTCAGGGATTA<br>AAGGTATCTTGCCCGGAAGAGATTGCTTACCGTAAAGGGTTTATTGATGCTGAGCAGGTGAAAGTATTAGCCGAACCG<br>CTGAAGAAAAATGATTATGGTCAGTATCTGCTAAAAATGATTAAAGGTTATTAATAAAATGAACGTAATTAAAACTGA<br>AATTCCTGATGTGCTGATTTTTGAACCAAAAGTTTTTGGTGATGAACGTGGCTTCTTTTTTGAGAGTTTTAACCAGAA<br>AGTATTTGAAGAAGCTGTAGGACGGAAGGTTGAATTTGTTCAGGATAACCATTCTAAGTCTAAAATAAATGTATTGCG<br>TGGGATGCATTATCAAACACAAAATACTCAAGGAAAACTGGTTCGGGTAATTTCTGGTTCAGTATATGATGTTGCCGT<br>AGATTTAAGAGAAAAATCAAAGACATTTGGCAAATGGGTGGGTGTAGAATTATCTGGGAATAATAAAAGACAATTGTG<br>GATCCCCGAAGGTTTTGCCCATGGTTTTTATGTGTTGGAGGAGAATACCGAATTTGTTTATAAATGTACCGATACTTA<br>TAACCCTGCTCATGAACACACATTGCTATGGAATGATCCAACTATCAATATAAGTTGGCCAATCATACAAAACTGCAA<br>GCCAATTATTTCTGAAAAAGATGCTAATGGACATCTTTTTTCACATAAAACCTATTTCTGAAATGCAATATTATGAGT<br>TTAATTAGAAACAGTTTCTATAATATTGCTGGTTTTGCTGTGCCGACATTAGTTGCAGTCCCTGCTTTGGGGATTCTT<br>GCCAGGCTGCTTGGACCGGAGAATTTTGGACTTTTCACACTAGCATTCGCTTTGATAGGATATGCAAGTATTTTCGAC<br>GCCGGGATTAGTCGAGCTGTAATCAGAGAAATCGCTCTTTATCGAGAAAGTGAAAAAGAGCAAATACAAATTATTTCG<br>ACAGCAAGTGTAATCGTACTATTCTTAGGGGTGGTTGCAGCTTTGTTACTTTATTTTAGTAGTAATAAAGTTGTTGAG<br>TTATTGAATGTTAGTTCCGTTTATATTGAAACAGCAGTGCGTGCATTCTCTGTTATTTCATTTATAATACCTGTGTAT<br>CTGATTAACCAGATTTGGCTTGGTTATCTGGAAGGGCTAGAAAAATTTGCAAATATAAATGTTCAGAGAATGATTTCT<br>AGCACAAGCTTGGCTATATTACCAGTGATATTTTGTTATTACAATCCCTCGTTGCTTTATGCTATGTATGGGTTGGTG<br>GTTGGGCGTGTGATTTCATTTTTGATTAGCGCAATAATTTGTCGAGATATTATTCTTAAAAGTAAACTTTACTTTAAT<br>GTGGCAACTTGCAATCGTCTTATCTCTTTTGGTGGATGGATAACAGTTAGTAATATCATAAGCCCAATCATGGCATAT<br>TTCGACCGCTTTATCATCTCTCATATTATGGGGGCTTCGAGAATTGCATTTTATACAGCGCCCTCAGAGGGTGTATCA<br>AGGTTAATTAATATCCCATATGCTTTGGCAAGAGCTCTATTTCCTAAATTGGCATATAGCAATAATGATGATGAACGA<br>AAAAAATTACAACTACAGAGCTACGCAATTATAAGCATTGTATGTCTACCCATAGTTGTTATTGGTGTCATTTTTGCC<br>TCATTCATAATGACAACATGGATGGGACCTGATTATGCCTTAGAAGCAGCAACTATCATGAAAATACTTCTTGCTGGT<br>TTTTTCTTTAACTCTTTAGCGCAAATACCTTATGCATACTTGCAATCTATCGGAAAGTCAAAAATTACCGCATTTGTG<br>CATCTCATAGAACTTGCGCCATACTTATTATTATTGTATTACTTCACAATGCATTTCGGCATAATTGGCACGGCAATC<br>GCTTGGTCACTTAGAACATTTTGTGATTTTGTTATACTACTTTCGATATCGAGAAGAAAATGATTGCGGTTGATATTG<br>CGCTTGCAACCTACAATGGTGCTAATTTTATTCGGCAACAGATTGAATCTATCCAGAAACAAACTTATAGAAATTGGC<br>GTCTTATAATAAGTGATGATAACTCGAGTGATGATACTGTTGATATTATTAAGGATATGATGTCTAACGACAGTCGTA<br>TCTATTTGGTAGGAAATAAAAGACAAGGAGGGGTTATTCAGAACTTTAATTATGCTCTTTCACAAACTACATCTGAAA<br>TTGTGTTACTATGTGACCAGGATGACATTTGGCCGGAGGAGCGTCTGGAAATTCTTATAGATAAATTTAAGGCCTTGC<br>AGCGTAATGATTTTGTTCCGGCAATGATGTTTACTGATTTGAAATTAGTAGACGAAAATAATTGTTTGATTGCAGAAA<br>GTTTTTATCGAACGAATAATATTAATCCACAAGATAATCTGAAAAATAATAATCTTCTCTGGCGTTCAACGGTATATG<br>GCTGTACTTGCATCATGAATAAGAAACTTGTTGATATTGCATTGCCTATACCTACATATGCACATATGCATGATCAAT<br>GGTTGGCATTATTAGCGAAGCAATATGGTAACATTTTTTATTTCGACTATGCGTCTGTTCGTTATAGGCAACATTCTA<br>CAAATGTTGTTGGTGGTAGAAATAAAACGCCATTTCAAAAATTTAATTCCATACAAAAAAACCTAAAAAGGATTAATT<br>TGCTAGTGGATAGAACTGTTGCTTTAATTAAATCAAATAACGATTTCTATCCAGGGAATAAAATGGAAAATAAAATTG<br>ATTACTTAAAATTTGGAGTGAATGAAGTATTACCTTATCTTTTTAAAGGAAACAAGAAAGTTTTTTCACTTTGTGTAT<br>TAATTAGTTTGGCATTACAAAAATGATATATTTATTATTTTTTTTTGCACTGTTTATGATCTGTACGTTTTTAACACA<br>CAGGCGACAGGCATTATATGTTGTATCTGCGTTAGTATTTCTTTTTTTGGCTTTAACCTATCCATCAGGAGGGGACTG<br>GATAGGTTATTTTCTCCATTATGACTGCATGGTTAATGAGCAGTGTAATAATGGTTTTATAATGTTTGAACCTGGATA<br>TGAATTAATTGTTTCCTTATTTGGATATTTGGGATTTCAGACAATTATTATTTTTATAGCCGCTGTAAATGTAATTCT<br>AATATTAAATTTTGCAAAGCATTTTGAAAACGGAAGTTTTGTTATTGTTGCGATAATGTGCATGTTCCTTTGGAGTGT<br>TTATGTTGAGGCGATTAGACAGGCTCTGGCCTTATCTATAGTTATATTTGGGATTCATTCTCTTTTTTTGGGTAGAAA<br>AAGGAAATTTATAACATTAGTATTATTTGCGTCAACTTTCCATATAACTGCTTTGATTTGTTTTCTTCTAATGACTCC<br>TCTATTTTCAAAGAAATTAAGCAAGATAATAAGTTATAGCCTATTAATTTTCAGTAGCTTCTTTTTCGCTTTTTCTGA<br>AACCATATTAAGTGCACTCCTTGCAATTTTGCCAGAAGGATCCATTGCCAGTGAAAAATTAAGTTTTTACTTAGCAAC<br>CGAGCAATACAGGCCACAGTTATCTATTGGGAGTGGCACTATTCTTGACATTATACTTATTTTTCTGATATGTGTAAG<br>TTTTAAACGAATAAAGAAATATATGCTCGCTAATTATAATGCTGCAAATGAGATATTGCTTATTGGTTGCTGTCTTTA<br>TATTTCTTTCGGTATTTTTATCGGGAAAATGATGCCAGTTATGACTCGCATTGGTTGGTATGGTTTTCCATTTGTTAT<br>AGTACTTCTTTATATTAACTTGGGTTATTCAGAATATTTTAAGAGGTATATAAATAAAAGAGGGTGTGGGTATAGCAA<br>ATTATTAATTGCTTTTTATTTTTTGCTACAAATTTTGCGACCATTAACATATGATTATAGCTATTATAATATAATGCA<br>CCAGGATACTTTGCTGAATAGGTTTGATGCATTAGATGATGCATCATTAAGACAATCAGCGAAGAGAAAATGTTTCGA<br>TTTGGGAAAGATAGGATATGGTTTCTTATGTAGTATATAATATCCTGCATTCATTCGGATAATTTCCTATGGAAGTGT<br>CCTTTGCTCTGTCTGTCCTCATTTGTTGAAATTTTATGTTAATAAGAAGCTTTAGATAACCACTTAGGAACTGTATGT<br>TTGATCTGTCCAAAAATTATATTATTGTAAGTGCGACGGCGCTGGCTTCCGGAGGTGCATTAACTATATTAAAGCAAT |

-continued

| SEQUENCES |
|---|
| TTATAAAACATGCATCACAAAATTCAAATGACTATATTATGTTTGTATCTGCGGGATTGGAGTTGCCGGTCTGTGATA |
| ACATCATTTACATAGAAAACACACCAAAAGGATGGTTGAAAAGAATATATTGGGATTGGTTCGGTTGTCGGAAGTTTA |
| TCTCGGAACATAAGATTAACGTTAAGAAAGTAATTTCTCTACAAAATTCCAGTTTGAATGTTCCTTACGAACAGATTA |
| TTTACTTGCACCAGCCAATTCCTTTTAGTAAAGTTGATTCTTTTTTAAAAAATATCACATCCGATAACGTAAAGCTTT |
| TTTTATATAAAAAGTTTTATTCCTATTTTATATTTAAATATGTGAATGCCAATACAACCATCGTAGTGCAAACGAATT |
| GGATGAAAAAAGGAGTGCTGGAGCAATGTGATAAAATTAGTACCGAAAGGGTCCTTGTTATAAAACCTGATATCAAAG |
| CATTTAATAATACTAATTTTGATGTAGATATGGATGTATCTGCAAAAACACTCTTATATCCAGCGACACCACTTACCT |
| ATAAAAATCATTTGGTCATTCTGAAGGCGTTGGTTATTTTAAAGAAAAAGTATTTTATAGATGATCTGAAATTCCAAG |
| TGACTTTTGAAAAGAATAGGTACAAAAATTTTGATAAGTTTGTGCAATTAAATAACTTAAGCAAAAACGTTGATTATC |
| TCGGCGTTCTTTCATACTCGAACTTGCAAAAAAAATATATGGCGGCATCTTTAATCGTTTTTCCTAGCTATATCGAAT |
| CATATGGGTTACCACTCATCGAAGCTGCTAGTTTAGGAAAAAAAAATCATTAGTAGTGATCTTCCTTATGCCCGGGATG |
| TTTTAAAGGATTATAGCGGCGTAGATTTTGTAATTTACAATAATGAAGATGGCTGGGCTAAGGCGTTGTTTAATGTTT |
| TAAATGGCAATTCGAAGCTCAATTTTAGGCCTTATGAAAAAGATAGTCGTTCATCTTGGCCACAGTTCTTCTCTATTT |
| TGAAATAAGGTGTATTATGTTTAATGGTAAAATATTGTTAATTACTGGTGGTACGGGGTCTTTCGGTAATGCTGTTCT |
| AAGACGTTTTCTTGACACTGATATCAAAGAAATACGTATTTTTTCCCGGGATGAAAAAAAACAAGATGACATGAGGAA |
| AAAATATAATAATCCGAAACTTAAGTTCTATATAGGTGATGTTCGCGACTATTCGAGTATCCTCAATGCTTCTCGAGG |
| TGTTGATTTTATTTATCATGCTGCAGCTCTGAAGCAAGTACCTTCCTGCGAATTCCACCCAATGGAAGCTGTAAAAAC |
| GAATGTTTTAGGTACGGAAAACGTACTGGAAGCGGCAATAGCTAATGGAGTTAGGCGAATTGTATGTTTGAGTACAGA |
| TAAAGCTGTATATCCTATCAATGCAATGGGTATTTCCAAAGCGATGATGGAAAAAGTAATGGTAGCAAAATCGCGCAA |
| TGTTGACTGCTCTAAAACGGTTATTTGCGGTACACGTTATGGCAATGTAATGGCATCTCGTGGTTCAGTTATCCCATT |
| ATTTGTCGATCTGATTAAATCAGGTAGACCAATGACGATAACAGACCCTAATATGACTCGTTTCATGATGACTCTCGA |
| AGACGCTGTTGATTTGGTTCTTTACGCATTTGAACATGGCAATAATGGTGATATTTTTGTCCAAAAGGCACCTGCGGC |
| TACCATCGAAACGTTGGCTATTGCACTCAAAGAATTACTTAATGTAAACCAACACCCTGTAAATATAATCGGCACCCG |
| ACACGGGGAAAAACTGTACGAAGCGTTATTGAGCCGAGAGGAAATGATTGCAGCGGAGGATATGGGTGATTATTATCG |
| TGTTCCACCAGATCTCCGCGATTTGAACTATGGAAAATATGTGGAACATGGTGACCGTCGTATCTCGGAAGTGGAAGA |
| TTATAACTCTCATAATACTGATAGGTTAGATGTTGAGGGAATGAAAAAATTACTGCTAAAACTTCCTTTTATCCGGGC |
| ACTTCGGTCTGGTGAAGATTATGAGTTGGATTCATAATATGAAAATTTTAGTTACTGGCGCTGCAGGGTTTATCGGTC |
| GAAATTTGGTATTCCGGCTTAAGGAAGCTGGATATAACGAACTCATTACGATAGATCGTAACTCTTCTTTGGCGGATT |
| TAGAGCAGGGACTTAAGCAGGCAGATTTTATTTTTCACCTTGCTGGGGTAAATCGTCCCGTGAAGGAGTGTGAATTTG |
| AAGAGGGAAATAGTAATCTAACTCAACAGATTGTTGATATCCTGAAAAAAAACAATAAAAATACTCCTATCATGCTGA |
| GTTCTTCCATCCAGGCTGAATGTGATAACGCTTATGGAAAGAGTAAAGCAGCTGCGGAAAAAATCATTCAGCAGTATG |
| GGGAAACGACAAACGCTAAATATTATATTTATCGCTTGCCGAATGTATTCGGTAAGTGGTGTCGACCAAATTATAACT |
| CCTTTATAGCAACTTTCTGCCATCGCATTGCAAATGATGAAGCTATTACAATTAATGATCCTTCAGCAGTTGTAAATC |
| TGGTGTATATAGATGACTTTTGTTCTGACATATTAAAGCTATTAGAAGGAGCGAACGAAACTGGTTACAGGACATTTG |
| GTCCAATTTATTCTGTTACTGTTGGTGAAGTGGCACAATTAATTTACCGGTTTAAAGAAAGTCGCCAAACATTAATCA |
| CCGAAGATGTAGGTAATGGATTTACACGTGCATTGTACTCAACATGGTTAAGTTACCTGTCTCCTGAACAGTTTGCGT |
| ATACGGTTCCTTCTTATAGTGATGACAGAGGGGTATTCTGTGAAGTATTGAAAACGAAAAACGCGGGCCAGTTTTCGT |
| TCTTTACTGCGCATCCAGGAATTACTCGGGGTGGTCATTATCATCATTCCAAAAATGAGAAATTTATTGTCATCCGAG |
| GAAGTGCTTGTTTCAAATTTGAAAATATTGTCACGAGTGAACGATATGAACTTAATGTTTCCTCTGATGATTTAAAA |
| TTGTTGAAACAGTTCCGGGATGGACGCATAACATTACTAATAATGGCTCGGATGAGCTAGTTGTTATGCTTTGGGCAA |
| ATGAAATATTTAATCGTTCTGAACCAGATACTATAGCGAGAGTTTTATCGTGAAAAAATTGAAAGTCATGTCGGTTGT |
| TGGGACTCGTCCAGAAATTATTCGACTCTCGCGTGTCCTTGCAAAATTAGATGAATATTGTGACCACCTTATTGTTCA |
| TACCGGGCAAAACTACGATTATGAACTGAATGAAGTTTTTTTCAAAGATTTGGGTGTTCGCAAACCTGATTATTTTCT |
| TAATGCCGCAGGTAAAAATGCAGCAGAGACTATTGGACAAGTTATCATTAAAGTTGATGAGGTCCTTGAACAGGAAAA |
| ACCAGAAGCCATGTTAGTACTTGGCGATACTAACTCCTGTATTTCAGCAATACCAGCAAAGCGTCGAAGAATTCCGAT |
| CTTCCATATGGAGGCTGGGAATCGTTGTTTTGACCAACGCGTACCGGAAGAAACTAACAGAAAAATAGTTGATCATAC |
| CGCTGATATCAATATGACATATAGTGATATCGCGCGTGAATATCTTCTGGCTGAAGGTGTACCAGCCGATAGAATTAT |
| TAAAACCGGTAGCCCAATGTTTGAAGTACTCACTCATTATATGCCGCAGATTGATGGTTCCGATGTACTTTCTCGCCT |
| GAATTTAACACCTGGGAATTTCTTTGTGGTAAGTGCCCACAGAGAAGAAAATGTTGATACCCCTAAACAACTTGTGAA |
| ACTGGCGAATATACTTAATACCGTGGCTGAAAAATATGATGTCCCGGTAGTTGTTTCTACTCATCCTCGCACTCGTAA |
| CCGCATCAACGAAAACGGTATTCAATTCCATAAAAATATCTTGCTTCTTAAGCCATTAGGATTTCACGATTACAACCA |
| TCTGCAAAAAAATGCACGTGCTGTTTTATCGGATAGTGGGACTATTACAGAAGAGTCCTCCATTATGAACTTCCCTGC |
| ACTCAATATACGAGAAGCGCACGAACGCCCGGAAGGCTTCGAAGAAGGGGCAGTAATGATGGTCGGTCTTGAATCTGA |
| TCGCGTTTTACAGGCATTAGAAATTATTGCAACACAGCCTCGTGGAGAAGTACGCTTACTTCGTCAGGTTAGTGACTA |
| TAGCATGCCAAATGTTTCAGATAAAGTTCTGCGTATTATCCATTCATATACTGACTACGTTAAACGGGTTGTCTGGAA |
| GCAATACTAATGAAACTTGCATTAATCATTGATGATTATTTGCCCCATAGCACACGCGTTGGGGCTAAAATGTTTCAT |
| GAGTTAGGCCTTGAATTACTGAGCAGAGGCCATGATGTAACTGTAATTACGCCTGACATCTCATTACAAGCAATTTAT |
| TCTATTAGTATGATTGATGGTATAAAGGTTTGGCGTTTCAAAAGTGGACCTTTAAAGGATGTAGGTAAGGCTAAACGT |
| GCCATAAATGAAACTCTTTTATCTTTTCGCGCATGGCGCGCATTTAAGCACCTCATTCAACATGATACATTTGATGGT |
| ATCGTTTATTATTCCCCCTCTATTTTTTGGGGCGACTTGGTTAAAAAAATAAAACAACGATGCCAGTGCCCAAGCTAT |
| CTGATCCTAAGGGATATGTTTCCACAGTGGGTCATTGATGCAGGTATGTTGAAAGCCGGTTCACCAATTGAAAAATAT |
| TTTAGGTATTTTGAAAAAAAGTCATATCAGCAGGCTGGCCGGATAGGGGTAATGTCTGATAAGAATCTTGAGATATTT |
| CGCCAGACCAATAAAGGTTATCCGTGTGAAGTTTTACGTAATTGGGCCTCAATGACTCCTGTGTCTGCCAGCGATGAT |
| TATCATTCACTTCGTCAAAAATACGATCTAAAAGATAAAGTCATTTTTTTCTATGGCGGTAATATTGGGCATGCTCAG |
| GATATGGCAAACTTAATGCGCCTTGCGCGTAATATGATGCGTTATCATGATGCTCATTTCCTGTTTATAGGGCAGGGT |
| GATGAAGTTGAGCTGATAAAATCTCTTGCTGCAGAATGGAATTTAACTAATTTCACTCATCTACCTTCAGTGAACCAG |
| GAAGAGTTTAAATTAATTTTATCTGAAGTTGATGTCGGCCTGTTCTCCCTTTCATCTCGCCATTCTTCACATAATTTC |
| CCCGGAAAATTACTAGGGTATATGGTTCAATCAATCCCGATCCTTGGGAGTGTGAATGGCGGCAATGATTTAATGGAT |
| GTAATTAATAAGCACAGAGCCGGTTTCATTCATGTTAATGGTGAAGATGATAAACTGTTTGAATCTGCACAATTGCTT |
| CTTAGTGATTCAGTTTTAAGAAAACAGCTAGGTCAGAACGCTAATGTGTTGTTAAAGTCTCAATTTTCGGTTGAATCG |
| GCGGCACATACTATCGAAGTCCGACTGGAGGCTGGAGAATGCGTTTAGTTGATGACAATATTCTGGATGAACTTTTTC |
| GCACTGCAGCAAATTCTGAACGTTTGCGCGCTCATTATTTATTGCACGCATCTCATCAGGAGAAGGTTCAACGTTTAC |
| TTATTGCATTTGTACGCGACAGCTATGTTGAACCCCATTGGCATGAGTTACCGCATCAGTGGGAAATGTTTGTCGTCA |
| TGCAAGGGCAATTAGAAGTTTGTTTGTATGAGCAAAATGGTGAGATCCAAAAACAGTTTGTTGTTGGAGACGGTACGG |
| GAATAAGCGTCGTGGAATTTTCCCCAGGAGATATACATAGTGTCAAATGCCTGTCACCAAAAGCCCTTATGTTGGAGA |
| TAAAGGAGGGGCCATTTGACCCACTCAAAGCTAAGGCTTTTTCTAAGTGGTATAGGGCGATACACCACCGTTTATTC |
| TTCTATCTTATTCTATACATGCTGGGTTACCATCTTAGCTTCTTCAAGCCGCGCAACCCCGCGGTGACCACCCCTGAC |

-continued

| SEQUENCES |
| --- |

AGGAGTAGCTAGCATTTGACCACCCCTGACAGGATTAGCTAGCATATGAGCTCGAGGATATCTACTGTGGGTACCCGG
GATCCGTGTAGGCTGGAGCTGCTTCGAAGTTCCTATACTTTCTAGAGAATAGGAACTTCGGAATAGGAACTAAGGAGG
ATATTCATAT

SEQ ID NO: 10 (example signal sequence for EPA carrier protein)
MKKIWLALAG LVLAFSASA SEQ ID NO: 11 (example O1A rfb locus nucleotide sequence-O1A-EPA production strain stGVXN4411 and stLMTB10217)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATCTGTCCGCCGGGCGTGACCATTATGAACGTGCGTCAG
GGCGAACCTTTAGGTTTAGGCCACTCCATTTTGTGTGCGCGACCTGCCATTGGTGACAACCCATTTGTCGTGGTACTG
CCAGACGTTGTGATCGACGATGCCAGCGCCGACCCGCTACGTTACAACCTTGCTGCCATGATTGCACGTTTCAACGAA
ACGGGCCGCAGCCAGGTGCTGGCAAAACGTATGCCGGGTGACCTCTCTGAATACTCCGTCATCCAGACTAAAGAGCCG
CTGGACCGTGAGGGTAAAGTCAGCCGCATTGTTGAATTTATCGAAAAACCGGATCAGCCGCAGACGCTGGACTCAGAC
ATCATGGCCGTAGGTCGCTATGTGCTTTCTGCCGATATTTGGCCGGAACTGGAACGTACTCAGCCTGGTGCATGGGGA
CGTATTCAGCTGACTGATGCTATTGCCGAGCTGGCGAAAAAACAATCCGTTGATGCAATGCTGATGACCGGCGACAGT
TACGACTGCGGCAAAAAAATGGGCTATATGCAGGCGTTTGTGAAGTATGGCCTACGCAACCTGAAAGAAGGGGCGAAG
TTCCGTAAAGGTATTGAGAAGCTGTTAAGCGAATAATGAAAATCTGACCGGATGTAACGGTTGATAAGAAAATTATAA
CGGCAGTGAAAATTCGCAGCAAAAGTAATTTGTTGCGAATCTTCCTGCCGTTGTTTTATATAAACCATCAGAATAACA
ACGAGTTAGCAGTAGGGTTTTATTCAAAGTTTTCCAGGATTTTCCTTGTTTCCAGAGCGGATTGGTAAGACAATTAGC
GTTTGAATTTTTCGGGTTTAGCGCGAGTGGGTAACGCTCGTCACATCATAGGCATGCATGCAGTGCTCTGGTAGCTGT
AAAGCCAGGGGCGGTAGCGTGCATTAATACCTCTATTAATCAAACTGAGAGCCGCTTATTTCACAGCATGCTCTGAAG
TAATATGGAATAAATTAAGCTAGCGTGAAGATACTTGTTACTAGGGGCGCAGGATTTATTGGTTCTGCTGTAGTTCGT
CACATTATAAATAATACGCAGGATAGTGTTGTTAATGTCGATAAATTAACGTACGCCGGAAACCTGGAATCACTTGCT
GATGTTTCTGACTCTGAACGCTATGTTTTTGAACATGCGGATATTTGCGATGCTGCTGCAATGGCGCGGATTTTTGCT
CAGCATCAGCCGGATGCAGTGATGCACCTGGCTGCTGAAAGCCATGTGGATCGTTCAATTACAGGCCCTGCGGCATTT
ATTGAAACCAATATTGTTGGTACTTATGTCCTTTTGGAAGCGGCTCGCAATTACTGGTCTGCTCTTGATGGCGACAAG
AAAAATAGCTTCCGTTTTCATCATATTTCTACTGACGAAGTCTATGGTGATTTGCCTCATCCTGACGAAGTAAATAAT
AAAGAACAATTACCCCTCTTTACTGAGACGACAGCTTACGCGCCTAGTAGTCCTTATTCCGCATCAAAAGCATCCAGC
GATCATTTAGTCCGCGCGTGGAAACGTACCTATGGTTTACCGACTATTGTGACTAACTGTTCGAATAACTACGGTCCT
TATCACTTTCCGGAAAAATTGATTCCACTAGTAATTCTTAATGCTCTGGAAGGTAAGGCATTACCTATTTATGGCAAA
GGGGATCAAATTCGTGACTGGCTGTATGTTGAAGATCATGCGCGTGCGTTATATACCGTAGTTACTGAAGGTCAAGCG
GGTGAAACCTATAACATTGGCGGACACAACGAAAAGAAAAACATCGATGTTGTGCTGACTATTTGTGATTTGTTGGAC
GAGATAGTCCCGAAAGAGAAATCTTATCGTGAGCAAATTACTTATGTTGCTGATCGCCCAGGGCATGATCGCCGTTAT
GCGATTGATGCTGAGAAGATTGGTCGCGAATTGGGATGGAAACCACAGGAAACGTTTGAGAGTGGGATTCGTAAAACG
GTGGAATGGTATTTGGCTAATGCAAAATGGGTTGATAATGTGAAAAGTGGTGCCTATCAATCGTGGATTGAACAGAAC
TATGAGGGCCGCCAGTAATGAATATCCTCCTTTTTGGCAAAACAGGGCAGGTAGGTTGGGAACTACAGCGTGCTCTGG
CACCTCTGGGTAATTTGATTGCTCTTGATGTTCACTCCACTGATTACTGTGGTGATTTTAGTAACCCTGAAGGTGTGG
CTGAAACAGTCAAAAGAATTCGACCTGATGTTATTGTTAATGCTGCGGCTCACACCGCAGTAGATAAGGCTGAGTCAG
AACCCGAATTTGCACAATTACTCAATGCGACTAGCGTTGAATCAATTGCAAAAGCGGCAAATGAAGTTGGGGCTTGGG
TAATTCATTACTCAACTGACTACGTATTCCCTGGAAATGGCGACACGCCATGGCTGGAGATGGATGCAACCGCACCGC
TAAATGTTTACGGTGAAACCAAGTTAGCTGGAGAAAAAGCATTACAAGAGCATTGTGCGAAGCACCTAATTTTCCGTA
CCAGCTGGGTCTATGCAGGTAAAGGAAATAATTTCGCCAAAACGATGTTGCGTCTGGCAAAAGAGCGTGAAGAACTAG
CCGTTATTAATGATCAGTTTGGTGCGCCAACAGGTGCTGAACTGCTGGCTGATTGTACGGCACATGCCATTCGTGTCG
CACTGAATAAACCGGATGTCGCAGGCTTGTACCATTTGGTAGCCAGTGGTACCACAACCTGGTACGATTATGCTGCGC
TGGTTTTTGAAGAGGCGCGCAATGCAGGCATTCCTCTTGCACTCAACAAGCTCAACGCAGTACCAACAACTGCCTATC
CTACACCAGCTCGTCGTCCACATAACTCTCGCCTTAATACAGAAAAATTTCAGCAGAATTTTGCGCTTGTATTGCCTG
ACTGGCAGGTTGGTGTGAAACGCATGCTCAACGAATTATTTACGACTACAGCAATTTAATAGTTTTTGCATCTTGTTC
GTGATGGTGGAGCAAGATGAATTAAAAGGAATGATGAAATGAAAACGCGTAAAGGTATTATTTTAGCGGGTGGTTCTG
GTACTCGTCTTTATCCTGTGACTATGGTCGTCAGTAAACAGCTATTACCTATATATGATAAACCGATGATCTATTATC
CGCTTTCTACACTGATGTTAGCGGGTATTCGCGATATTCTGATTATTAGTACGCCACAGGATACTCCTCGTTTTCAAC
AACTGCTGGGTGACGGTAGCCAGTGGGGCCTGAATCTTCAGTACAAAGTGCAACCGAGTCCGGATGGTCTTGCGCAGG
CATTTATTATCGGTGAAGAGTTTATTGGTGGTGATGATTGTGCTTTGGTACTTGGTGATAATATCTTCTACGGTCACG
ACCTGCCTAAGTTAATGGATGCCGCTGTTAACAAAGAAAGTGGTGCAACGGTATTTGCCTATCACGTTAATGATCCTG
AACGCTATGGTGTCGTTGAGTTTGATAAAAACGGTACGGCGATCAGCCTGGAAGAAAAACCGCTACAACCAAAAAGTA
ATTATGCGGTAACCGGGCTTTATTTTTATGATAACGACGTTGTCGAAATGGCGAAAAATCTTAAGCCTTCTGCCCGCG
GTGAACTGGAAATTACCGATATTAACCGTATCTATATGGAACAAGGGCGTTTATCTGTTGCCATGATGGGGCGTGGTT
ATGCGTGGTTAGACACGGGGACACATCAGAGCCTGATTGAGGCAAGCAACTTTATTGCAACAATTGAAGAGCGTCAGG
GGCTGAAAGTTTCCTGCCCGGAAGAAATTGCTTACCGTAAAGGGTTTGTTGATGCTGAGCAGGTGAAAGTATTAGCTG
AACCTCTGAAAAAAAATGCTTATGGTCAGTATCTGCTGAAAATGATTAAAGGTTATTAATAAAATGAACGTAATTAAA
ACAGAAATTCCTGATGTACTGATTTTTGAACCGAAAGTTTTTGGTGATGAGCGTGGTTTCTTTTTTGAGAGCTTTAAC
CAGAAGGTTTTTGAGGAAGCTGTAGGCCGCAAAGTTGAATTTGTTCAGGATAACCATTCGAAGTCTAGTAAAGGTGTT
TTACGCGGGCTGCATTATCAGTTGGAACCTTATGCACAAGGAAAATTGGTGCGTTGCGTTGTCGGTGAAGTTTTTGAC
GTAGCTGTTGATATTCGTAAATCGTCATCGACTTTTGGCAAATGGGTTGGGGTGAATTTATCTGCTGAGAATAAGCGG
CAATTGTGGATTCCTGAGGGATTTGCACATGGTTTTTTAGTGCTGAGTGAGACGGCGGAGTTTTTGTATAAGACGACA
AATTATTATCATCCTCAGAGTGATAGAGGAATAAAATGGGATGATCCAAGCATCAATATTTCATGGCCAGTCGATTCA
CAAGTGCTGCTATCAGCTAAAGATAATAAGCATCCTCCATTAACAAAGATTGAAATGTATAGTTAAGATCACGATAAA
TCTTGGAAGGGTTGCAAAATTGAATAAAATAGTGAGCAAAAGTGAAATAAGGAACGTAATCCACAATGCTGGCTATAT
GATGATTACTCAGATAGCTTTATATGTTGCACCATTATTTATACTGAGTTATCTGTTAAAAACACTGGGGGTTGCACA
GTTTGGTAATTATGCCTTAATACTATCAATCGTTGCATATTTACAGATTATAACGGATTATGGTTTTTCTTTTAGTGC
AAGTCGTGCGATCTCACAGAATAGAGAGGACAAAGAATATATATCAAAAATTTATCTGTCAACTATGACTATCAAGTT
GGCGATATGCGCTTTCTTATTCTTATTGCTCATGCTATTTTTAAATCTTTTGCCTGTGCAAGCTGAATTAAAACAAGG
AATATTATATGGATATCTTCTTGTAATAGGAAATACTTTCCAACCACAATGGTTTTTCCAAGGTATCGAAAAATTAAA
AATCATAGCCCTTTCTAATGTTATATCAAGATGCGCCGCGTGTTTACTTGTATTTATCTATGTGAGGAATAGCGAGGA -continued

| SEQUENCES |
| --- |
| TTTACAAAAAGCACTTTTAGTACAGTCACTTCCATTAGTAATTTCTGCGATTGGATTAAATATATTTATATTGAAATA |
| TATCAATATTATTTTTCCGGAAAAAAAATTATTTAAGGTAATTTTAAAAGAAGGTAAGGATTTTTTTCTTGCATCACT |
| TTATTCTGTTATTCTCAATAATAGTGGCATTTTTCTATTAGGGATTTTTACTAATCCTGTTATTGTTGGTGTATATGC |
| CGCCGCTGAAAAGATAGTCAAGGCCGTATTGTCGCTATTTACACCACTGACGCAAGCTATATATCCTTATAATTGTCG |
| TAAGTTTTCACTATCCGTATTTGACGGCATTGAGGCAGCAAAAAAAACTGGTATACCAATTATAATTTTAGCATTTAT |
| AGCTGCTGTTATCGTTGCAATTACCTTACCTGTTGCAATCGACTATCTTAATTTTCCAAAAGAAACAATTTTTGTAGG |
| TCAAATATTAAGTGCATGGATCTTTTTTGGTGTTCTTAATAATGTATTCGGCATTCAGATATTGAGTGCATCAGGAAG |
| AAGTAAAATATATAGTAGGATGGTATTCGTATCAGCGCTTATAACATTACTTTTGATTACTCTATTATTGCAGTTTTG |
| TAACGCCACTGGAGTGGCATGTGCAATATTATTGGGTGAAATGTTCTTATCAATATTGTTACTTAAGCGATATAAAAA |
| AATAATTTAAGGAATAGTTATGAAGAAGTTATTATTAGTGTTCGGTACTAGGCCTGAAGCAATAAAGATGGCCTCTAT |
| CATTGAATTATTAAAAAAAGATTGTAGATTCGAATATAAAATATGTGTGACAGGCCAACATAAAGAGATGCTTGATCA |
| AGTTATGCAAGTATTTGATGTTAAACCTGATTATAATTTACGGATTATGCAGCCTGGGCAAACATTAGTATCTATAGC |
| AACAAATATACTCTCACGGTTAAGTGAAGTTTTAATTATAGAAAAGCCAGATATTATACTTGTGCATGGGGATACAAC |
| GACTACCCTTGCTGCTACTTTAGCTGGGTATTACCACCAAATAAAAGTTTGTCATGTGGAAGCAGGATTAAGAACAGG |
| GGATATTTACTCTCCTTGGCCTGAAGAGGGCAATCGTAAAGTTACAGGGGCATTAGCATGTATTCATTTCGCCCCAAC |
| AGAGAGATCAAAAGATAATCTCCTGAGGGAGGGGGTCAAAGTAAATAATATATTTGTAACGGGTAATACCGTCATCGA |
| CTCTTTATTTATTGCAAAAGATATCATAGATAATGACCCTAATATAAAGAACGCTTTACATAATAAATTTAATTTTCT |
| TGATAAAAGCCGACGAGTAGTACTTATAACAGGTCATCGAAGAGAAAATTTCGGGAAAGGTTTTGAAGATATATGCTT |
| TGCAATAAAGGAATTAGCTTTCATTTATCCTAATGTAGATTTTATTTATCCGGTGCATCTTAATCCCAATGTAATGGA |
| ACCAGTACATCGTATATTAGATAATATATGTAATATTTACCTTATTGAGCCCTTGGATTATTTGCCTTTTGTTTATTT |
| AATGAATGAGTCATATTTAATATTGACTGATTCAGGGGGGATACAAGAAGAAGCGCCTTCGTTAGGTAAACCGGTTTT |
| GGTTATGCGTGATACTACTGAACGCCCTGAGGCGGTTGAGGCTGGTACTGTTGTATTAGTGGGGACTTCTAAGATAAA |
| AATAGTAAATAAAGTAACGGAGCTATTAAACAATGCTGATATCTACAATGCTATGTCTCTGTTACATAATCCATATGG |
| CGATGGAACAGCTGCTCAAAAAATTCTTAATGTGCTCGCCCAAGAGCTAATTTAATTTAAGCTAAAAATATGTTATTA |
| ATTATTGCTGATTATCCAAACGAAATGAATATGCGCGAGGGAGCTATGCAACGAATAGATGCGATAGACTCTCTCATT |
| CGAGATCGCAAGCGAGTGTATTTGAATATTTCATTCAAAAAGCATCTAGTTCGCTCAAATAGTTCCTTTAATAATGTT |
| ATAGTTGAAAATCTAAATGCAATTATTCACAGAAACATCATAAAACAGTACATGCAAAAATCAACAACTATATATGTT |
| CATTCTGTTTATAATTTATTAAAGGTTATAACGCTCATTGATCTAAAAAAAACAATTCTTGATATACATGGTGTTGTA |
| CCGGAAGAACTTTTGGCAGATAATAAAAAATTACTTAGTAAAGTATATAACATGGTGGAAAAAAAAGGTGTCCTTGGA |
| TGCAAAAAATTAATACACGTCAGTACAGAAATGCAAAAACACTATGAAGCAAAATATGGAGTAAACTTGGCTGAAAGG |
| TCAATAGTGCTCCCGATTTTTGAATATAAAAATATAACCCAATCGCAAAACAAATGGACAGAAAATAAAATACGAAGT |
| ATCTATCTTGGAGGATTACAAACATGGCAAAATATTGATAAAATGATTCAAGTTTGTGATGACACAGTGATAAACAAT |
| GAAGCAGGTAAGTATGAATTCAACTTTTTCATCCCACAGAGTAACTTGGAAGGGTTTATAGATAAATATTCGTTAAAA |
| TTACATAATATCAATGCTAATGCATCTACGCTATCACGTGATGAAGTAATTCCCTTTCTAAAAGAATGTCATATTGGT |
| TTTGTATTGCGCGATGATATAATAGTAAACAGAGTTGCGTGCCCTACAAAATTGGTTGAATATTTAGAGTGTGGTGTC |
| GTTCCAGTTGTGCTCTCCCCACTTATAGGTGATTTTTATTCGATGGGATATCAATACATTACTACAGAGGAAATGGCT |
| AACAGAAGTATAAGTTTGTTGGATCTTGAAAAAATGGCTGCACATAATTTACAAATTTTGACTTCTTATCAGAAGAGA |
| ACCTACAAGGCACAGAAAGAACTTATTGCTCAACTGTGCTGAATTTTTTACATATATAAAATTATGTAAGCATATCGC |
| GGGTCAGGTAATTGTATGCGTATCAAATATAAAGATAACGGTTATATATTATGTTTTCTATTATGTTTCATTTTGAGC |
| TACTTAGTTTTACTCAAATCTGACTACTTTCCTGCTGATTTTCTGCCATATACAGAAATATACGATGGGACATACGGA |
| GAAATCAATAATATTGAGCCTGCCTTTTTATATTTAACACGGTTGTTTCATTATTTAAATTTCCCCTATATATTTTTT |
| GCAATGTTAGTTTGTGCCTTATGTTTAAGTTGGAAAATAAAATATGCAAGAAAAATAATTAAAGATAGTTATATATAT |
| TTGTTCTTGTATGTATATGTATCATTTTATGTGTTTTTGCATGAAATGACTCAATTGCGCATAGCAATTGCAGTCACT |
| ATGTGCTATGTGTCGGTTTATTATTACTTTTATAAAAATTGTATTAAACATGCACTGCCATGGATGGTGTTGGCTATT |
| TTGTTTCATTACAGCGCCTTGCTTTTATTTATGTCATTATTTATATACAGTTATAGGAGGTTATTAATAGTAATTATA |
| GGGTTTGTAATATGTATGAGCTTTTTAAACGTGTATGCAGATACAATTGCACTATATTTGCCAAATGAAAAAATAGTA |
| AATTATTTATATAGTATTTCATCATCATTAGACAATAGAAATGATTTGGCAATATTCAACCTGAATAATATAATATTT |
| TTATCAATATTTATTTTGATCTTTTATCTTAGCCGATATATAAAATTAAATGATAATGAGGCGAAGTTTATTAAGTAT |
| GTGCAATGTTCAGGAATATTAGCCTTTTGTATTTTCTTTCTGGCTAGTGGAGTCCCGGTCATTGCTTATCGAACTGCA |
| GAGTTGCTGCGAATATTTTATCCGATGGCTTTAGTATTAATCCTTTCGCATATAAAAAATAATAATATGCGTTATTTT |
| ATTGCAGTCATTATAGTTATCCTTTCAGGCTTAATGTTGTTTATAACACTAAGGGCTGTATCAATAGTTGGTCAAGGA |
| TTATAAAATGAATGTTGCTATTTTGTTGTCTACGTATAATGGCGAAAAATATTTAGAGGAACAACTGGATTCATTGCT |
| GCTTCAAAGTTATCAGGATTTTGTAGTGTATATCCGTGATGACGGATCATCTGATAGAACTGTAAATATAATAAACCA |
| ATACGTAATGAAAGATAACAGATTTATTAACGTGGGTAATTCAGAAAATCTTGGTTGTGCTGCTTCGTTTATTAATTT |
| ATTAAGAAATGCTTCAGCCGATATTTATATGTTTTGTGACCAAGATGATTATTGGCTTCCGAATAAATTACAGCGTGC |
| TGTGGATTATTTTTCGGCTATTGATCCTTTACAACCTACCTTGTATCATTGCGATCTAAGCGTTGTTGATGAAAAACT |
| TAATATTATACAAAATTCATTTTTGCAGCATCAGAAAATGTCAGCGTATGATTCAATGAGAAAAAATAATCTTTTCAT |
| ACAAAATTTTGTTGTTGGTTGTTCATGTGCTGTTAATGCTTCACTTGCGGAATTTGTTCTTTCGCGAATTGGAGAGCA |
| GCATGTAAAAATGATAGCTATGCATGACTGGTGGTTAGCCGTGACTGCAAAACTTTTTGGTCGAATCCATTTTGATAA |
| TACTCAAACGATTCTTTATCGACAACATCAGGGCAATGTATTAGGTGCAAAATCATCAGGTATGATGCGTTTTATTCG |
| ATTAGGATTAAATGGGCAAGGGATTTCGCGAGTAGTATCTTTTAGAAAAAAAGTTTGTGCGCAAAATAAGCTTCTTTT |
| AGATGTCTATGATAAAGATTTAAATCTTGAGCAAAAAAAATCTATCAGGCTTGTAATTGAGGGCCTTAAAGAGAACTC |
| TTCAATTGCTGACCTTTTAAAATGTTTCTATCATGGTAGCTATATGCAAGGTTTTAAACGTAATCTTGCCTTAATATA |
| TTCAGTTCTTTACACAAAAAAAAGAAGATAGTGTATCCTTATGAAAAAAATTGCTATTATCGGTACTGTTGGCATACC |
| AGCATCATATGGCGGATTTGAAACATTAGTTGAAAATTTAACAAGATACAATTCCTCGGGAGTTGAATATAATGTTTT |
| TTGTTCATCGTTTCACTACAAATCCCACCAAAAAAAACATAATGGGGCCCGTTTAATTTATATTCCGCTTAAAGCCAA |
| TGGATGGCAGAGCATTGCGTATGACATAATTTCGTTAGCATATTCTATTTTTTTGAAGCCTGATGTGATTCTGATTTT |
| AGGGGTTTCTGGTTGTTCATTTTTGCCTTTCTTCAAACTCTTAACACGCGCTAAGTTTATTACTAATATTGATGGCCT |
| GGAATGGCGAAGAGATAAATGGAATTCAAAAGTGAAACGTTTCTTAAAATTTTCAGAAAAAATCGCAGTTCAATATTC |
| GGATGTCGTTATTACGGATAATGAGGCAATTTCTGAGTACGTTTTTAACGAGTATAATAAAGATAGCCGAGTTATTGC |
| CTATGGAGGGGATCATGCATGGTTAAATACTGAGGATGTATTTACAACAAGAAATTATAAAAGCGATTACTACCTTTC |
| TGTATGTCGTATCGAACCCGAAAACAATGTAGAATTAATTTTAAAAACATTTTCAAAGCTAAAATATAAAATAAAATT |
| TATTGGAAATTGGAATGGCAGCGAGTTTGGAAAGAAACTTAGGCTGCATTATTCTAACTATCCAAATATTGAAATGAT |
| TGATCCGATTTATGATCTTCAACAATTATTTCACTTACGAAATAATTGCATAGGATATATACATGGTCATTCGGCTGG |
| AGGAACAAACCCTTCTTTAGTCGAGGCAATGCATTTTAGTAAACCTATATTTGCATATGATTGTAAGTTTAATAGGTA |
| CACTACTGAAAATGAAGCATGTTATTTTTCTAATGAATCTGACCTCGCAGAGAAAATCATAATGCATTGTGAGCTATC |
| ATTAGGTGTCTCTGGCACGAAAATGAAAGAAATTGCTAACCAGAAATACACTTGGAGACGAATAGCAGAAATGTATGA |

-continued

| SEQUENCES |
| --- |
| GGATTGCTATTAACTCTGTTAAACTTCAAATCTTTTACAATATATGGCATGACTATAAGCGCATTAATTGTTTTTCAA<br>GCCGCTCTCGCGGTGACCACCCCCTGACAGGGGATCCGTGTAGGCTGGAGCTGCTTCGAAGTTCCTATACTTTCTAGA<br>GAATAGGAACTTCGGAATAGGAACTAAGGAGGATATTCATATGGATAAAGCCGTAAGCATATAAGCATGGATAAGCTA<br>TTTATACTTTAATAAGTACTTTGTATACTTATTTGCGAACATTCCAGGCCGCGAGCATTCAGCGCGGTGATCACACCT<br>GACAGGAGTATGTAATGTCCAAGCAACAGATCGGCGTAGTCGGTATGGCAGTGATGGGACGCAACCTTGCGCTCAACA<br>TCGAAAGCCGTGGTTATACCGTCTCTATTTTCAACCGTTCCCGTGAGAAGACGGAAGAAGTGATTGCCGAAAATCCAG<br>GCAAGAAACTGGTTCCTTACTATACGGTGAAAGAGTTTGTCGAATCTCTGGAAACGCCTCGTCGCATCCTGTTAATGG<br>TGAAAGCAGGTGCAGGCACGGATGCTGCTATTGATTCCCTCAAACCATATCTCGATAAAGGAGACATCATCATTGATG<br>GTGGTAACACCTTCTTCCAGGACACTATTCGTCGTAATCGTGAGCTTTCAGCAGAGGGCTTTAACTTCATCGGTACCG<br>GTGTTTCTGGCGGTGAAGAGGGGGCGCTGAAAGGTCCTTCTATTATGCCTGGTGGCCAGAAAGAAGCCTATGAATTGG<br>TAGCACCGATCCTGACCAAAATCGCCGCCGTAGCTGAAGACGGTGAACCATGCGTTACCTATATTGGTGCCGATGGCG<br>CAGGTCACTATGTGAAGATGGTTCACAACGGTATTGAATACGGCGATATGCAGCTGATTGCTGAAGCCTATTCTCTGC<br>TTAAAGGTGGCCTGAACCTCACCAACGAAGAACTGGCGCAGACCTTTACCGAGTGGAATAACGGTGAACTGAGCAGTT<br>ACCTGATCGACATCACCAAAGATATCTTCACCAAAAAAGATGAAGACGGTAACTACCTGGTTGATGTGATCCTGGATG<br>AAGCGGCTAACAAAGGTACCGGTAAATGGACCAGCCAGAGCGCGCTGGATCTCGGCGAACCGCTGTCGCTGATTACCG<br>AGTCTGTGTTTGCACGTTATATCTCTTCTCTGAAAGATCAGCGTGTTGCCGCATCTAAAGTTCTCTCTGGTCCGCAAG<br>CACAGCCAGCAGGCGACAAGGCTGAGTTCATCGAAAAAGTTCGTCGTGCGCTGTATCTGGGCAAAATCGTTTCTTACG<br>CCCAGGGCTTCTCTCAGCTGCGTGCTGCGTCTGAAGAGTACAACTGGGATCTGAACTACGGCGAAATCGCGAAGATTT<br>TCCGTGCTGGCTGCATCATCCGTGCGCAGTTCCTGCAGAAAATCACCGATGCTTATGCCGAAAATCCACAGATCGCTA<br>ACCTGTTGCTGGCTCCGTACTTCAAGCAAATTGCCGATGACTACCAGCAGGCGCTGCGTGATGTCGTTGCTTATGCAG<br>TACAGAACGGTATTCCGGTTCCGACCTTCTCCGCAGCGGTTGCCTATTACGACAGCTACCGTGCTGCTGTTCTGCCTG<br>CGAACCTGATCCAGGCACAGCGTGACTATTTTGGTGCGCATACTTATAAGCGTATCGATAAAGAAGGTGTGTTCCATA<br>CCGAATGGCTGGATTAA |
| SEQ ID NO: 12 (example O2 rfb locus nucleotide sequence-O2-EPA<br>production strain stGVXN4906)<br>ATGACGAATTTAAAAGCAGTTATTCCTGTAGCGGGTCTCGGGATGCATATGTTGCCTGCCACTAAGGCGATACCCAAA<br>GAGATGCTACCAATCGTCGACAAGCCAATGATTCAGTACATTGTTGACGAGATTGTGGCTGCAGGGATCAAAGAAATC<br>CTCCTGGTAACTCACGCGTCCAAGAACGCGGTCGAAAACCACTTCGACACCTCTTATGAGTTAGAATCACTCCTTGAG<br>CAGCGCGTGAAGCGTCAACTGCTGGCGGAAGTACAGTCCATCTGTCCGCCGGGCGTGACCATTATGAACGTGCGTCAG<br>GGCGAACCTTTAGGTTTAGGCCACTCCATTTTGTGTGCGCGACCTGCCATTGGTGACAACCCATTTGTCGTGGTACTG<br>CCAGACGTTGTGATCGACGATGCCAGCGCCGACCCGCTACGTTACAACCTTGCTGCCATGATTGCACGTTTCAACGAA<br>ACGGGCCGCAGCCAGGTGCTGGCAAAACGTATGCCGGGTGACCTCTCTGAATACTCCGTCATCCAGACTAAAGAGCCG<br>CTGGACCGTGAGGGTAAAGTCAGCCGCATTGTTGAATTTATCGAAAAACCGGATCAGCCGCAGACGCTGGACTCAGAC<br>ATCATGGCCGTAGGTCGCTATGTGCTTTCTGCCGATATTTGGCCGGAACTGGAACGTACTCAGCCTGGTGCATGGGGA<br>CGTATTCAGCTGACTGATGCTATTGCCGAGCTGGCGAAAAAACAATCCGTTGATGCAATGCTGATGACCGGCGACAGT<br>TACGACTGCGGCAAAAAAATGGGCTATATGCAGGCGTTTGTGAAGTATGGCCTACGCAACCTGAAAGAAGGGGCGAAG<br>TTCCGTAAAGGTATTGAGAAGCTGTTAAGCGAATAATGAAAATCTGACCGGATGTAACGGTTGATAAGAAAATTATAA<br>CGGCAGTGAAAATTCGCAGCAAAAGTAATTTGTTGCGAATCTTCCTGCCGTTGTTTTATATAAACCATCAGAATAACA<br>ACGAGTTAGCAGTAGGGTTTTATTCAAAGTTTTCCAGGATTTTCCTTGTTTCCAGAGCGGATTGGTAAGACAATTAGC<br>GTTTGAATTTTTCGGGTTTAGCGCGAGTGGGTAACGCTCGTCACATCATAGGCATGCATGCAGTGCTCTGGTAGCTGT<br>AAAGCCAGGGGCGGTAGCGTGCATTAATACCTCTATTAATCAAACTGAGAGCCGCTTATTTCACAGCATGCTCTGAAG<br>TAATATGGAATAAATTAAGTGAAAATACTTGTTACTGGTGGCGCAGGATTTATTGGTTCAGCTGTAGTTCGTCACATT<br>ATAAATAATACGCAGGATAGTGTTGTTAATGTCGATAAATTAACGTACGCCGGAAACCGGGAATCACTTGCTGATGTT<br>TCTGATTCTGAACGCTATGTTTTTGAACATGCGGATATTTGCGATGCACCTGCAATGGCACGGATTTTTGCTCAGCAT<br>CAGCCGGATGCAGTGATGCACCTGGCTGCTGAAAGCCATGTTGACCGTTCAATTACAGGCCCTGCGGCATTTATTGAA<br>ACCAATATTGTTGGTACTTATGTCCTTTTGGAAGCCGCTCGCAATTACTGGTCTGCTCTTGATAGCGACAAGAAAAAT<br>AGCTTCCGTTTTCATCATATTTCTACTGACGAAGTCTATGGTGATTTGCCTCATCCAGATGAAGTAAATAATACAGAA<br>GAATTACCCTTATTTACTGAGACGACAGCTTACGCGCCAAGCAGCCCTTATTCCGCATCCAAAGCATCCAGCGATCAT<br>TTAGTCCGCGCATGGAAACGTACGTATGGTTTACCGACCATTGTGACTAATTGCTCGAACAACTATGGTCCGTATCAC<br>TTCCCGGAAAAGCTTATTCCATTGGTTATTCTTAATGCACTGGAAGGTAAGGCATTACCTATTTATGGCAAAGGGGAT<br>CAAATTCGCGACTGGTTGTATGTAGAGGATCATGCTCGTGCGTTATATACCGTCGTAACCGAAGGTAAAGCGGGTGAA<br>ACTTATAACATTGGCGGACACAACGAAAAGAAAAACATCGATGTTGTGCTGACTATTTGTGATTTGTTGGATGAGATT<br>GTACCGAAAGAGAAATCTTATCGTGAGCAAATTACTTATGTTGCTGATCGCCCAGGGCATGATCGCCGTTATGCAATT<br>GATGCCGATAAAATTAGCCGCGAATTGGGCTGGAAACCACAGGAAACGTTTGAGAGCGGGATTCGCAAAACGGTGGAA<br>TGGTATCTGGCTAATACAAATTGGGTTGAGAATGTGAAAAGCGGTGCTTATCAGTCATGGATCGAACAAAACTATGAG<br>GGCCGTCAGTAATGAATATCCTGCTTTTCGGCAAAACAGGGCAGGTGGGTTGGGAACTGCAGCGTGCTCTGGCGCCGC<br>TGGGTAATCTGATCGCTCTTGATGTTCACTCCACTAATTATTGTGGAGATTTCAGCAACCCCGAAGGTGTGGCAGAAA<br>CCGTCAAAAAAATTCGTCCTGACGTTATTGTTAATGCTGCTGCTCACACTGCAGTAGATAAAGCAGAATCAGAACCGG<br>ATTTCGCACAATTACTTAACGCGACAAGCGTCGAAGCGATTGCAAAAGCTGCTAATGAAGTCGGGGCCTGGGTTATAC<br>ACTACTCTACTGATTATGTTTTCCCAGGCAGTGGTGACGCGCCATGGCTGGAAACGGATGCAACAGCACCGCTAAATG<br>TTTACGGTGAAACAAAATTAGCTGGGGAAAAGGCATTACAAGAACATTGCGCAAAGCATCTTATTTTCCGTACCAGCT<br>GGGTATACGCTGGTAAAGGAAATAACTTTGCTAAAACGATGTTGCGTTTGGCAAAAGAACGCGAAGAACTGGCTGTGA<br>TAAACGATCAGTTTGGCGCACCAACAGGTGCTGAATTGCTGGCTGATTGCACCGCTCATGCCATTCGCGTGGCATTAA<br>AAAAACCAGAAGTCGCTGGCTTGTACCATCTGGTAGCAAGTGGCACAACAACCTGGCACGATTATGCTGCGCTGGTTT<br>TTGAAGAGGCGCGCAAAGCAGGGATTAATCTTGCACTTAACAAACTTAACGCCGTGCCAACAACGGCCTATCCCACAC<br>CAGCCCGTCGACCCCATAACTCTCGCCTCAATACAGAAAAGTTTCAGCAGAACTTTGCGCTTGTCTTGCCTGACTGGC<br>AGGTGGGCGTGAAACGTATGCTCAACGAATTATTTACGACTACGGCAATTTAACAAATTTTTGCATCTCGCTCATGAT<br>GCCAGAGCGGGATGAATTAAAAGGAATGGTGAAATGAAAACGCGTAAAGGTATTATTCTGGCTGGTGGTTCCGGCACT<br>CGTCTTTATCCTGTGACGATGGCAGTGAGTAAACAATTGCTGCCGATTTATGATAAGCCGATGATTTATTATCCGCTT<br>TCAACGCTTATGTTAGCGGGTATTCGCGATATTCTTATTATTAGTACGCCACAGGATACACCGCGTTTCCAACAATTA<br>TTGGGGGACGGGAGCCAGTGGGGTCTTAATCTACAGTATAAAGTACAACCGAGTCCGGATGGCCTGGCGCAAGCGTTT<br>ATTATTGGCGAAGACTTTATTGGTGGTGATGATTGTGCACTCGTACTTGGCGATAATATCTTCTATGGACACGACTTG<br>CCGAAATTGATGGAAGCTGCTGTTAACAAAGAAAGCGGTGCAACGGTATTTGCTTATCACGTTAATGATCCTGAACGC<br>TATGGTGTCGTGGAGTTTGATAATAACGGTACGGCAATTAGCCTGGAAGAAAAACCGCTGGAGCCAAAAAGCAACTAT<br>GCGGTTACTGGGCTTTATTTCTATGACAATGACGTTGTGGAAATGGCTAAAAACCTTAAGCCTTCTGCCCGTGGCGAA<br>CTGGAAATTACCGATATTAACCGTATTTATATGGAACAAGGACGTTTGTCTGTAGCCATGATGGGGCGTGGCTATGCA |

-continued

| SEQUENCES |
| --- |
| TGGTTGGATACAGGGACGCATCAAAGCCTTATTGAAGCAAGTAACTTCATTGCAACAATTGAAGAGCGTCAGGGATTA<br>AAGGTATCTTGCCCGGAAGAGATTGCTTACCGTAAAGGGTTTATTGATGCCGAGCAGGTGAAAGTATTAGCCGAACCG<br>CTTATCAAGAATCAATATGGTCAATATTTGCTGAAAATGATCAGCGAATAGTATATGGGAACTCAATGATGGATATTA<br>AATTAATCTCTTTGCAAAAACATGGGGATGAGCGCGGTGCATTAATTGCTCTTGAAGAGCAACGAAATATACCTTTCG<br>AAGTCAAAAGAATATATTACATACTTGAGACTCTTAATGGAGTAAGACGCGGATTTCATGCGCACAAGGTTACTCGTC<br>AGTTAGCTATTGTAGTCAAGGGAGCTTGTAAATTTCATCTGGATAATGGTAAAGAAACAAAGCAGGTGGAACTTAATG<br>ATCCAACAATTGCGTTGCTGATAGAACCCTATATATGGCATGAAATGTATGATTTTAGTGATGATTGTGTGCTGCTTG<br>TAATTGCGGATGATTTCTATAAAGAGTCTGATTATATCCGCAATTATGATGATTTTATTAGAAGAGTAAATTCAATTG<br>AGAATTCATAAGCTAAGTGACGTCCAGACAACATCAATTGGTGATGGAACAACTATCTGGCAGTTTGTTGTGATACTA<br>AAAGGTGCTGTAATTGGTAATAATTGCAACATCTGTGCAAATACCTTAATTGAAAATAACGTTGTAATTGGTAACAAT<br>GTCACAGTCAAAAGCGGTGTGTATATTTGGGATGGCGTTAAAATAGAGGATAATGTTTTTATTGGTCCTTGTGTAGCA<br>TTTACAAATGATAAGTATCCTCGCTCTAAAGTCTATCCTGATGAATTTTTGCAAACAATAATACGCAAAGGAGCATCA<br>ATAGGTGCTAACGCAACCATCCTGCCAGGAATTGAAATTGGTGAAAAAGCAATCGTTGGTGCGGGGAGTGTTGTAACC<br>AAAAATGTACCGCCATGCGCAATAGTAGTAGGTAATCCAGCTCGATTTATTAAATGGGTAGAGGATAATGAATAAAAT<br>TGATTTTTTAGATCTTTTTGCAATTAACCAGCGACAGCACAAAGAATTAGTCTCTGCGTTTAGTAGGGTGCTAGATTC<br>TGGTTGGTATATCATGGGCGAAGAACTTGAGCAGTTCGAGAAAGAGTTCGCAGAATACTGTGGAGTTAAGTATTGCAT<br>TGGTGTAGCAAATGGCCTTGATGCGTTGATACTAGTATTGAGGGCATGGAAAGAACTTGGCTATCTTGAAGACGGTGA<br>CGAGGTATTAGTACCGGCAAATACATATATTGCTTCTATTCTTGCTATAACAGAGAACAAACTTGTTCCTGTTCTTGT<br>TGAACCAGATATAGAAACTTATAATATTAATCCTGCTTTAATTGAAAATTACATTACGGAAAAAACTAAAGCAATATT<br>ACCGGTTCACTTATATGGTCTATTGTGCAATATGCCAGAAATTAGTGCAATCGCCAGAAAATATAATCTGTTGATTCT<br>TGAAGATTGTGCACAAGCACATGGTGCAATACGTGATGGTCGCAAAGCTGGAGCTTGGGGGGATGCTGCAGGATTTAG<br>TTTTTATCCAGGAAAAAACCTTGGAGCTTTGGGGGATGCGGGAGCTGTTACTACAAATAATGCAGAATTATCCTCAAC<br>TATAAAAGCTTTGCGAAATTATGGGTCACATAAGAAATATGAAAATATTTATCAGGGATTGAATAGTCGATTGGATGA<br>ACTGCAAGCAGCCTTATTGCGTGTAAAAATCCATACATTACCGGAAGATACTGCGATTCGGCAAAGGATTGCTGAAAA<br>ATATATTCGTGAAATAAAAAACCCTGCGATTACGTTACCAGTGTACGAAGGCCAAGGTGCGCATGTTTGGCATTTATT<br>TGTAGTAAGAATCGCTAATCGTGAAAAATTCCAGTCATACTTATTAGAGAAGGGTATCAAAACCTTAATTCACTATCC<br>ATTACCACCCCATAAGCAGCAAGCATATCAAAATATGTCTAGCCTTAGCCTTCCAATTACTGAGCAAATTCATGATGA<br>AGTCATTTCTTTACCTATAAGTCCGGTAATGAGTGAAGATGATGTCAATTATGTAATCAAAATGGTCAATGATTACAA<br>GTAATGAAAAAATTTCTTCAGGTAACTATATTATCCGCTATCTATACATTCATTAAAATGATTGCGGGTTTTATCATC<br>GGTAAGGTAGTAGCAATTTATACAGGGCCATCAGGGGTAGCAATGCTTGGCCAAGTGCAAAGTTTAATCACAATAGTT<br>GCAGGTACTACCTCTGCACCTGTAAGCACAGGCCTTGTTCGATATACTGCGGAAAATTGGCAAGAAGGACAAGAAGCA<br>TGCGCGCCATGGTGGCGCGCATGCTTAAGGGTTACTCTGTTTTTATTCTTGCTTATTATTCCCGTTGTTATTATATTG<br>TCGAAAAATATTAGTGAGTTACTTTTTAGCGATGGACAATACACATGGTTAATCATTTTCGCATGTTGTATATTGCCA<br>TTCTCCATTATAAATACATTGATCGCTTCAGTTTTAAATGGTCAACAATTTTATAAGCAATATATATTGGTTGGGATG<br>TTTTCTGTATTCATTTCTACTATGTTTATGATTTTGTTGATTGTAGCTTATAATCTTAAAGGTGCATTGATTGCCACA<br>GCTATAAATAGTGCTATTGCTGGTCTTGTATTGGTTTTATTTTGTCTCAATAAATCTTGGTTTAGATTTAAATATTGG<br>TGGGGTAAAACGGATAAAGACAAAATTATAAAAATTATTCATTATACTCTGATGGCTCTGGTTTCTGTTATCTCCATG<br>CCTACAGCATTGATGTGTATTAGAAAAATATTGATTGCTAAAACTGGTTGGGAGGATGCAGGGCAATGGCAGGCCGTA<br>TGGAAGATATCTGAGGTTTATCTTGGTGTTGTGACAATTGCTTTGTCAACATATTTCTTACCAAGATTGACAATTATA<br>AAAACAAGTTTCCTTATAAAAAAAGAAGTAAATAGTACTATATTATACATAATATCTATTACTTCATTCATGGCGTTG<br>AGTATCTATTTATTCCGCGATTTGGTAATAACAGTTTTATTTACTGAACAGTTTCGCTCAGCTCGTGAATTATTTTTA<br>TTACAACTTATAGGGGATGTAATAAAAATTGCTGGGTTTCTTTATGCATACCCTCTTCAAAGTCAGGGGCATACTAAA<br>CTATTCATCAGTTCAGAAGTGATTTTTTCTATGCTCTTTATCATTACCACCTATATTTTTGTTGTAAATTATGGAGTA<br>CATGGTGCTAACATAAGTTATGTCATTACATATAGTTTATATTTTGTGTTTGCATTTGTGTTTACTAATTTTATTAAT<br>GTTAGAAGAAATAATTAAAAACAGAGGTTGAATTTTGAAAATAATTATACCTGTCTTAGGATTTGGCAGGGCTGGTGG<br>TGAAAGAGTTCTTTCTAAGCTGGCAACTGAATTGATGAATTATGGACATGATGTAAGTTTTGTTGTTCCAGATAATAG<br>AACTAATCCATATTATGCTACCACAGCAAAAATTGTCACGAGTAAATCTAGTCAAAACCGTGTAAAAATATTGAGAAT<br>CATTAAAAATTACTATAATCTGTGGCGTAAATGCATAGAGTTAAATCCTGATGCTGTAGTTGCTAGTTTTCATTTGAC<br>TGCCTATCTTGTCGCATTATTACCAATCACCCGTCGTAAGAAATATTATTATATTCAGGCGTATGAAGTTAATTTTTT<br>TGATAATATAATATGGAAATTAATAGCGGGTTTAACATATTATTTACCGCTTAAAAAAATACTAAATAGTCCTAATTT<br>GCTTCCTCATAAACATGATGATTTTATAGGAGTAGTTCCTGCAGGAGTAGATTTAAACGTTTTCTATCCGAAACCATC<br>AAATAGGTTATTAAATGGTCACACATCAATAGGGATTATTGGTAGAAAAGAGAAGCACAAAGGAACTAGCGAAATTAT<br>TTCAGTATTGTGTTCACTGGAAAATAAAGCTGGAATTATAATCAATATTGCGATCTATCTTGAAGAAGTTGATAAGCA<br>GCGTTTAATCGCTGCCGGGTTTCAGGTTAATTTTTTTCCGATTACTTCTGATTTAGAATTGGCATCCTTTTATCGAAG<br>CAATGACATCATGATTGCTGTTGGGTTAATTGAAGATGGCGCTTTCCATTATCCTTGTGCTGAATCAATGGCTTGTGG<br>TTGTCTTGTTATTTCAAATTATGCGCCACTTACTGAAACTAACAGTGTACTTAAATTAGTCAAGTTTGATGCTTGCAA<br>ACTTGGTGAAGCAATTAATCTTTGTCTCAATCTTGACCTAGAAGAAAAAAGCAAAGAAATCCAATCTAATATTTCTGT<br>GTTGAATAAATATGACTGGAAAATTGTTGGTGAAACTTTCAATAGTTTATTGTTAGATGCAAATAAATAGTATACGTT<br>GATGGGGAAAATATGAATATTGTTAAAACTGATATTCCAGATCTGATCGTTCTTGAACCAAAAGTGTTTAGTGATGAA<br>CGCGGCTTTTTTATGGAGAGTTATAATCAGATTGAATTTGAGAAGGCAATAGGAAGGCACGTAAATTTTGTTCAGGAT<br>AATCATTCAAAATCTAGTAAAGGCGTACTACGTGGGTTGCATTATCAATTAGCACCGTATGCACAGGCTAAATTAGTT<br>CGATGTGTTGTAGGTCAGGTATTTGATGTTGCTGTTGATCTTAGAAAAAATTCACCAACGTTCAAAAAATGGTTTGGA<br>ATAACCCTTTCCGCAGAAAATAAACGACAATTATGGATACCCGAAGGATTTGCTCATGGTTTCTTGGTGACCAGTGAT<br>GAAGCTGAGTTCATTTATAAGACAACTAACTACTATGCTCCTGGTCATCAGCAAGCAATTATTTACAATGATCCTATT<br>TTAAACATCGATTGGCCTTTCTGCAGTAGTGCTCTGTCATTATCACAAAAAGATCAAGAAGCAAAATTATTTTCAGAA<br>TTATTGGACAGTGAACTGTTCTAATAAAGTGTGCCACCTTATCCGTCTGAAGGATAGGTGGTTGCTTATATTTTTTTG<br>AGTATGTTTGTATAATGACAGAAAATAGTCCGAAATATAAACACGATAAAAGCTTAATAAGTTTTATCTACTTATTTT<br>TTATATTTACACTTATTGTAGGCTTTATTATCGCAAATACCCAGTTTTTGGGGCGAAGTAGAGACTATGATAATTATA<br>TACAGATCTTTTCTGGTAAAGAAGGGGAGGGGGTTCTTGAATTATTTTATCGCGGATTGATGTTAATAACGACCAGCT<br>ATGAAACTATCATTTTTATAATTTTAACATGTTCTTTTTTTATAAAGGCAAGGTTTCTCGCTAACTATTCGCGTAATT<br>TTTCAGGCTTGACCTTATTCTTTATTTATTATGCAAGCGTTGCACTTTGGGTTTTAGATTATACTCAATTCAGAAATG<br>GTCTATGTATTTCCATTTTAATGTTTTCCGTATACTATTTATTTATAAATAAACCGACTTATTTTTATTTCTCGGTAT<br>TATGTGCAATTGCAACTCATTGGTCTGCTTTGCCTTTTTTGCTTTTATATCCTTTTGTCTATTCAACAAAAATAAGAC<br>GCCTTGGTTATTTTTGTTTCAGTATTCTTGTTTTGATTGCGATCTCAGGAGAAGGAAAAGAGATCATATCTTTTATAA<br>GAAATTTTGGAGTGGGACAAAAAATAGGAAATGAAGCTGGTGTAAATTTAATAAATTCATTATCCCTTACCGCTATTT<br>CCTGGTTTATTATTAGTTACATATCAAGCATTGGAAATGAAAGGAGAAATTTAAGGCTTTTCTTTTGTTATGGTGTCA<br>TGCAATACGTGACTTTTAGCCTTTTCTCTCTACCTGTTATGGCTTTCCGTATTTTGGAAATGTATTTTTTCCTTATGC |

-continued

SEQUENCES

TAACCATTGGGGTGTTTATTAAGCAAAAAAAGAATTATTATTTTATTTTTTGCAAAGTGTTAATTTTATTGTATCTAA
CATACTATTATCATATGGTCTTTGGAGTGATTAATGTGTAAGGCTAAGGTGTTGGCTATAATTGTTACTTACAACCCG
GAAATTATTCGATTGACGGAATGTATTAACTCTTTAGCCCCACAAGTTGAGAGAATAATTCTTGTAGATAATGGCTCA
AATAATAGTGATTTGATAAAAAATATCAGTATTAATAACCTTGAAATTATTTTACTTTCGGAAAACAAAGGCATTGCA
TTTGCTCAGAACCATGGTGTTAAGAAGGGCCTGGAAGCAAAAGAGTTTGACTATTTATTTTTCTCAGATCAGGATACT
TGCTTTCCTAGCGATGTTATTGAAAAACTTAAGAGTACATTTACGAAAAATAATAAAAAAGGTAAAAATGTTGCTTGT
GCTTCTCCTTTTTTTAAAGACCATCGTTCAAATTATATGCATCCGTCAGTCAGCCTAAATATTTTTACGAGTACAAAA
GTTATATGTAGTGAAGTAGACGATGATCTTTATCCCTCGCATGTTATTGCTTCTGGGATGTTAATGTCTCGTGAAGCA
TGGCGCGTCGTCGGACCATTTTGTGAAAAACTCTTTATAGACTGGGTTGATACAGAATGGTGTTGGCGTGCATTAGCT
AATAATATGATTATTGTTCAGACACCATCAGTCATCATTTCTCATGAACTTGGGTATGGGCAGAAAATTTTTGCTGGT
CGATCTGTTACAATACATAATTCTTTCAGAAATTTTTATAAAATACGCAATGCAATATACTTAATGCTGCATTCAAAT
TATAGCTTCAAGTATCGTTATCATGCTTTTTTTCATGCGACAAAGAATGTTGTATTTGAAATTTTATATTCGAAAGAA
AAATTAAATTCACTGAAGGTTTGTTTTAAAGCTGTACGTGATGGTATGTTCAATAATTTTTAATACGAAAATAGTTAG
GCTCAAGGTGTTTAAATGGAAGAAAATAATATGAAGACGGTCGCTGTAGTTGGCACAGTGGGTGTTCCTGCTTGTTAT
GGTGGGTTCGAATCACTTGTTCAGAATCTAATTGATTATCAATCTGATGGTATACAATATCAGATATTTTGCTCTTCA
AAAAAATATGATAAAAAATTTAAAAATTATAAAAATGCAGAATTAATCTATTTGCCGATAAATGCCAATGGCGTCTCT
AGCATAATTTATGATATTATGTGTTTAATTATTTGTTTATTCAAAAGGCCAGATGTTGTTTTAATATTGGGGGTGTCT
GGTTGTTTATTTCTACCAATTTATAAACTATTTTCAAAATCAAAGATTATTGTCAATATTGATGGGCTTGAATGGCGT
AGAAATAAATGGGGAACGTTTGCTAAGAAATTTCTTAAAATATCTGAGGCGATATCTATTAGAATAGCTGATATTATC
ATTTCAGATAATCAAGCAATAGCTGATTATGTGGAAAATAAGTACAAGAAAAAAAGTGTAGTTATAGCTTATGGCGGA
GATCATGCCACTAATCTTAGTACACCGATAGACAATGATCAAAAAAAAGAAGGTTATTATTTGGGGCTTTGTAGGATA
GAGCCTGAGAATAATATAGAAATGATTCTGAATGCCTTCATTAATACAGATAAAAAAATTAAATTTATGGGTAATTGG
GATAACAGCGAGTATGGACGCCAGCTAAAAAAATATTATTCAAACTATCCAAATATCACCCTACTAGAACCTAACTAT
AATATTGAAGAGCTTTATAAACTAAGAAAAAATTGTCTTGCATACATTCATGGACACTCGGCTGGTGGAACAAACCCT
TCTTTAGTTGAAGCGATGCATTTTAATATTCCTATTTTTGCTTTCGATTGTGACTTTAATCGTTACACAACTAACAAT
TTAGCTCATTACTTTAATGATTCTGAACAACTTAGCTTATTAGCAGAAAGTTTGTCTTTTGGAAATCTTAAATGTCGA
GTATTAGATTTAAAAAATTATGCTGAAGATATGTATAACTGGAGGCATATAGCTGCTATGTATGAATCTATTTATTAA
ACGCATTAACAATAATATAATTGACCTTATATAGCAGGGAAAGATCACGTAACGCTGCGGCGCGCCGATCCCCATATG
AATATCCTCCTTAGTTCCTATTCCGAAGTTCCTATTCTTTCTAGAGAATAGGAACTTCGGAATAGGAACTAAGGAGGA
TATTCATATGGATAAAGCCGTAAGCATATAAGCATGGATAAGCTATTTATACTTTAATAAGTACTTTGTATACTTATT
TGCGAACATTCCAGGCCGCGAGCATTCAGCGCGGTGATCACACCTGACAGGAGTATGTAATGTCCAAGCAACAGATCG
GCGTAGTCGGTATGGCAGTGATGGGACGCAACCTTGCGCTCAACATCGAAAGCCGTGGTTATACCGTCTCTATTTTCA
ACCGTTCCCGTGAGAAGACGGAAGAAGTGATTGCCGAAAATCCAGGCAAGAAACTGGTTCCTTACTATACGGTGAAAG
AGTTTGTCGAATCTCTGGAAACGCCTCGTCGCATCCTGTTAATGGTGAAAGCAGGTGCAGGCACGGATGCTGCTATTG
ATTCCCTCAAACCATATCTCGATAAAGGAGACATCATCATTGATGGTGGTAACACCTTCTTCCAGGACACTATTCGTC
GTAATCGTGAGCTTTCAGCAGAGGGCTTTAACTTCATCGGTACCGGTGTTTCTGGCGGTGAAGAGGGGGCGCTGAAAG
GTCCTTCTATTATGCCTGGTGGCCAGAAAGAAGCCTATGAATTGGTAGCACCGATCCTGACCAAAATCGCCGCCGTAG
CTGAAGACGGTGAACCATGCGTTACCTATATTGGTGCCGATGGCGCAGGTCACTATGTGAAGATGGTTCACAACGGTA
TTGAATACGGCGATATGCAGCTGATTGCTGAAGCCTATTCTCTGCTTAAAGGTGGCCTGAACCTCACCAACGAAGAAC
TGGCGCAGACCTTTACCGAGTGGAATAACGGTGAACTGAGCAGTTACCTGATCGACATCACCAAAGATATCTTCACCA
AAAAAGATGAAGACGGTAACTACCTGGTTGATGTGATCCTGGATGAAGCGGCTAACAAAGGTACCGGTAAATGGACCA
GCCAGAGCGCGCTGGATCTCGGCGAACCGCTGTCGCTGATTACCGAGTCTGTGTTTGCACGTTATATCTCTTCTCTGA
AAGATCAGCGTGTTGCCGCATCTAAAGTTCTCTCTGGTCCGCAAGCACAGCCAGCAGGCGACAAGGCTGAGTTCATCG
AAAAAGTTCGTCGTGCGCTGTATCTGGGCAAAATCGTTTCTTACGCCCAGGGCTTCTCTCAGCTGCGTGCTGCGTCTG
AAGAGTACAACTGGGATCTGAACTACGGCGAAATCGCGAAGATTTTCCGTGCTGGCTGCATCATCCGTGCGCAGTTCC
TGCAGAAAATCACCGATGCTTATGCCGAAAATCCACAGATCGCTAACCTGTTGCTGGCTCCGTACTTCAAGCAAATTG
CCGATGACTACCAGCAGGCGCTGCGTGATGTCGTTGCTTATGCAGTACAGAACGGTATTCCGGTTCCGACCTTCTCCG
CAGCGGTTGCCTATTACGACAGCTACCGTGCTGCTGTTCTGCCTGCGAACCTGATCCAGGCACAGCGTGACTATTTTG
GTGCGCATACTTATAAGCGTATCGATAAAGAAGGTGTGTTCCATACCGAATGGCTGGATTAA

SEQ ID NO: 13 (example O6A rfb locus nucleotide sequence-O6A-EPA production strain stGVXN4112 and stLMTB10923)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATTTGCCCGCCGGGCGTGACAATTATGAACGTGCGTCAG
GGCGAACCTTTAGGTTTGGGCCACTCCATTTTATGTGCACGACCTGCCATTGGTGACAATCCATTTGTCGTGGTGCTG
CCAGACGTTGTGATCGACGACGCCAGCGCCGACCCGCTGCGCTACAACCTTGCTGCCATGATTGCGCGCTTCAACGAA
ACGGGCCGCAGCCAGGTGCTGGCAAAACGTATGCCGGGTGACCTCTCTGAATACTCTGTCATCCAGACCAAAGAGCCG
CTGGACCGCGAAGGTAAAGTCAGCCGCATTGTTGAATTCATCGAAAAACCGGATCAGCCGCAGACGCTGGACTCAGAC
ATCATGGCCGTTGGTCGCTATGTGCTTTCTGCCGATATTTGGCCGGAACTTGAACGCACTCAGCCTGGTGCATGGGGG
CGTATTCAGCTGACTGATGCCATTGCCGAACTGGCGAAAAAACAGTCCGTTGATGCCATGCTGATGACCGGCGACAGC
TACGACTGCGGTAAAAAAATGGGTTATATGCAAGCGTTCGTGAAGTATGGACTACGCAACCTCAAAGAAGGGGCGAAG
TTCCGTAAAGGGATTGAGAAGCTGTTAAGCGAATAATGAAAATCTGACCGGATGTAACGGTTGATAAGAAAATTATAA
CGGCAGTGAAGATTAGCGGCGAAAGTAATTTGTTGCGAATTTTCCTGCCGTTGTTTTATATAAACAATCAGAATAACA
ACGACTTAGCAATAGGATTTTCGTCAAAGTTTTCCAGGATTTTCCTTGTTTCCAGAGCGGATTGGTAAGACAATTAGC
ATTTGAATTTTACGGGTTTAGCGCGAGTGGGTAACGCTCGTCACATCGTAGACATGCATGCAGTGCTCTGGTAGCTGT
AAAGCCAGGGGCGGTAGCGTGCTGAAATTATAAAGTCATTCTTATAGAACATCGCATTTCAATAATATAATTACACCT
AAATGAATAGGATACAACGTGTGCACAATTATTTAAGGCTTAAAGATAAAATAAAAAACGTATTTTTAGGGTTGTATA
TATTGCAGTTATTTAATTATATCGCGCCATTGGTAATTATCCCTATCCTGATAAAATATATTGGGTTGGGGGAATATG
GGGAATTGGTCTATATTACATCTATTTATCAAATAGTGGCTTTGATTATTGATTTTGGCTTTACTTACACAGGACCTG
TGGTTGCTGCGAGACATAGATGTGAGACCCAAAATTTACAGCGCTATTACTCAATAGTTGTTCTTTTAAAATCATTGC
TTTTTATAATTGCATTAACATGTGTATTTTTATTGTGCAGATTAAATATAGTCCACTTGTCATTTTTTGGGTTTTTGT
CAATTTTTCTATGCACTATTGGTAATATATTATCGCCCAATTGGTTTTTGCAGGGGATTGGTGATTTTAAAAAACTTT
CATACTCACAAGTAATAGTGAGAATAACATTGTTTATCATACTTCTTGTTTATGTCTGTAGTGGCGGAGATAATGTTT
TTATCCTAAGTTTTTTGCAAAATGCAACATTACTCATATGCTGTATATACTTATGGCCAAATATTCATATTAGCCATG
TTGTTCATCTTAAACCTAATGAATGCATTGTGGAATTTAAGAAGGCAGGAAATGTTTTTATTGGCGTAATAGGTACGA -continued

| SEQUENCES |
| --- |
| TTGGTTACAATGGTCTAATTCCTGTGTTAATTGGAAACCTTTGCGGTAATACGAGTCTTGGTGTTTTTTCAATCGTTC<br>AAAAAATGACAACAGCATGTCAAAGTCTAATTAATCCAATATCACAGTATATGTTATCTCAAGTTTCAGAAATTAAAC<br>CTCAAGATAAACTGTTTTATTATAGAATTAAAAAAGTTTTTTGTGCATTTAACAATTAGCATAATTGCATGTTTAT<br>GTTATATGGGGTTAGGGCAATATGTGGCGACTTTTATAGGTAAAGTTGACGTTTCATTTGTTATTATTTTATTTGCGT<br>CAATAATTACCATTTTTTCATCTTTAAATAATGTCCTTGGTATACAGTTTCTTATACCGACAGATAATGTAAAAATAC<br>TACGAAGTATAAATGTTATGGCGGGAATTATTGTTGTTAGTTTGTCCTGGCTGTTAATATCACGCTTTGACATTCTGG<br>GGGGGGTTTTATTAAACCTAATTGGTGAGTTTCTTGTATTCAGTATGCTAGCTTTTATTGCCCATCGAAAGTGGGGAG<br>CGAGAGTATAATGAAAGTGAAGGCGGTTCCTGCTATTACATTCTATTTAAGTTTAATGCTGACAATTTTAGTGTTACT<br>GTTTGGTAATGAACCAAATAAATCACAATATATCCTTGTTATAGCAACGATAACAGTTTTTTATATCGCATATATCAC<br>TAATAAAATAACTTCTCCGGCCAGCCTTCTCGTTATATCATCTTTTGTGTTTTTAGGTTGTCGCCCCTTTATTATCTTT<br>GTTTGCAAACTATGATTATAGGATTGCCGATTGGTTTATTGAAGGATATATGGATGACGATGTGATTTTGGCTAACTA<br>TGCTATAACACTAATGTATTATGGTTATACATTGGGACTAATTCTATGCAAAAATACTGAAAAATTTTATCCGCATGG<br>TCCTTATCCTGAAAAACAATTGCTAAAAATAAAGTTTCTTTTGACTTTATTTTTTCTGGGTTCGATAGGTATGGTTGT<br>AAAAGGGATATTCTTTTTTAACTTTATAGAATCTAATAGTTATGTTGATATTTATCAATCAAATATAACAACGCCAAT<br>AGGTTATGATTTTCTATCTTATTTATTTTATTGTTCTTTTTTCCTTATATGTGCGTTTCATATACAGTTCAGAACAAA<br>TAAAAAATTTCTTTTTATTGCGATATGCATTGCTGCATTTAGCACCTTGAAGGGTAGTCGTAGTGAAGCTATAACGTT<br>TCTTTTAACGGTTACATGTATATATTTTAATGAAGTAAAGACAAGAAACTTACGTCTGCTGATTACAATGATTTTTGT<br>TTTTAGCGTCATTTTTGTGATTAGTGAATTTATCTCAATGTGGCGCACTGGAGGGAGTTTTTTTCAATTAATGCAGGG<br>TAATAATCCTGTTATAAACTTTGTATACGGCATGGGAGTATCATATCTTTCCATTTATCAATCAGTAAAACTACAACT<br>ATTGTCAGGGGGATATAATGTTACCTATCTATTCAGCCAGTTAATAATAACTTGCTCGTCAATATTTAATGTCAAATT<br>GAGCTTGCCGGAAATAAGCTATAGCCATTTGGCCTCATACACAGCAAACCCAGAACTATATAATCTTGGGTTCGGACT<br>TGGGGGGAGTTATTTAGCAGAATCGTTTTTAGCATTTGGTCTGATTGGATGTTTCATTATACCCTTTTTACTTTTACT<br>TAATTTAAATGTATTGGAAAAATATACAAAAAACAAACCAATTATATATTTTGTTTATTATAGTGTGTTGCCACCTAT<br>ATTATTCACACCAAGAGAGACTTTGTTCTATTTCTTCCCCTATCTTGTCAAAAGTATATTTGTTGCTTTTTTAGTTAC<br>ATTATACATCCAGTATAAAAAGGATTGACCAAAATGTCAGAAAAAAAATGTCAGCATAATAATCCCAAGTTATAACAGG<br>GCTCATATTCTTAAGGAGGTCATACCAAGTTATTTTCAGGATGAGACTTTAGAGGTTATAGTTATCAATGATGGATCA<br>ACAGATAATACAAATAGTGTATTAGCTGAACTGAAGGAAAAATATTCTCAGTTAGTTATTTTAGAAAATGAAACGAAT<br>AAAAAACAGATGTATTCTAAAAACCGAGGGATTGAAATAGCCAAAGGGAAATATATTTTTTTTGGTGATGATGACTCT<br>TACCTCTTACCCGGTGTTATATCTCGGTTATTGGCTACAAAATATGAGACAGGCGCTGATGTAATCGGCGCAAGAATA<br>CTTTATATGAATAATAACGAGAAAACAATTGAAGATTGCATAAATCGACATAAAAAAGAGGGGCGTTTTGTTAGTGAT<br>CTAAATAGATTGGATTTTAGTTATACATGTGATTTGGACCATCCGATTGAATGTTTTTATGCACAGCCTTTTGTTCTA<br>GCTGAAAGGGAACTAATATCGAAATATCGATTTGATATATCTTATACGGGAAACTGCTATCGTGAGGAAACTGATTTC<br>ATGCTATCTCTATTTATTAAAAATAAAAAATTTATATATGATTCAAAGGCTTTGTTAATAAATTTACCTCCAAGAAAA<br>GCGACGGGAGGGGCAAGAACAGCTAATCGATTAAAATATCATTACGAAAGTTGCATAAATAATTATAGATTTTTAAAA<br>AAATATAATGATAATTTGAATCTTCTTTCAGGACAAAAGCATGCTATATTTTACCGACAGTGTCAATTCGTTCTGCTA<br>AAAATGAAGTCGTTTATCGGGAAGTTTTTAAAATGATTATATATATCGCCGCGTATAATGGTTCAGGAGGGCAAGGTG<br>GGGTGGAAAGGGTTGTTGCCCAACAATGTAACATTCTTAAAAATTTGGGGGTTAAAGTCATTATACTTGATAAAACAT<br>ACTTCAAAATTTCTAACAAAATTCGTAACAAAAAAATACAAGTAGCACTTTATCCAATATTAGTTTCTCTTTATTTAA<br>CCTTACAAAAATTACGTGGCGTGACGTTTAAAGTTATTGCACATGGCTATTGTTCTCCTTTTTATAGGAATGACATCT<br>TAATAGCTCATGGCAATATGAAATGTTATTTTCAAACAGTCATGAATAAAAAACCTAATCGGTTGTCTGGCAGTGGTC<br>TTTTATCTTTCTATGAGCGTTGGGCTGGAGCATTTTCAAAAAATATCTGGGCTGTTTCAAATAAGGTTAAAAGTGAAT<br>GGAATGAGCTTTACAATATTAATTCACATAAAATCAAAGTTGTTCGAAATTTTATAAATCTTGCACAATTTGATTACA<br>CTGATGTTAATGAAGCAGAATATGTGACATTTGTCGGGCGATTGGAAAAAGGAAAAGGAATAGATGATCTGTATTACA<br>TATGTAAAAATCTGCCAGATACTTCCTTCCATTTAGTTTCAAGTATTCCCGCCCCACAAAATTTTGCTTCGCTAAATA<br>ATGTTCTGACCAGCATTGCTGTCCCCTATGCGAAAATGCCAGAAATATTTAAGAAATCCAGAGTACTTATTTTACCGT<br>CCTATTATGAAGGATATGAGCTGGTTACTATTGAAGCGCTATGCTGTGGTTGCCCTGTGATAGGCTATAATGTTGGTG<br>CAATTAGAGAGTTGTATGCAGAAAGTTTTCCTGGCGTATTTATTGCCAATAATAAAGAAGATTTAGCACAAGTAGCCT<br>ACAAATTAATTAGTCTTGATAATGAAAAATATTATCATTTGAGACAAACTATTTATAGCAAGCGTGAGCTTTTTTCTG<br>AAGAGAGATATGCGGAAATTTTAACGGCGGCATTTAATGAAAAAAAATAAGAAACTCTGTCTCATTTCAATTAACTCA<br>TATAATGAACTTACCGGAGGAGGAGTATATTTACGTACGCTTGTTAGTTTTCTACAAAAACAGAATGTTAATTTAACA<br>CTTATTGATAAAAAATCCTCAGGTAAACTATTCGAAGACAATACTTTTCAACATATATCATTTATTAAAGGTAAACGT<br>CAGGATATAATATCCAGGCTTTTTTTTATACCATCATTTTATGTCCCTTATATTTTCTCAATAATTAAAATTTTACGG<br>AAGCAAGATATTCTTGCTTTTCACAACTCTCGGCTTGGATTGTTATGTCTGCTTTTTAGAATACTCATGCCCCACAAA<br>AAGATCATATTGTTTACGGATAACTTCGAATATGACTTAATAAGACAAAAAGATAAAAACATAACTACTTTTATTGAA<br>AAATTAATTGTTTATCTCAATGAATTTATCGGGCTTAAGAATTCAGATTTAGTTAGCTATATTACCCGGCAAGATAAA<br>AATGCAATGGATAAATTTTATGGGATTAAAAAAAGCAGAAATTTAATTCTCCCTGTGATATTTAGTAGAGAAAAACCA<br>ACTGATGTATTGTCAGCTCACTTTATTAATGAGTATAATCGATTGAATAATGATAATAGGAAAAAAGTAGTATTTACT<br>GCATCTTTTGATTTTTTTCCAAATATAGATGCTGCCAACTATGTTTTAAATGCAGCAAAGTCTAATAATGATTATTGC<br>TATATTTTGGCAGGTAGGAAAAGTACTACTTTGAATCTTCCTGATTTGGATAATTTATTTTTTTTCGATAATCTATCT<br>AATAGTGAAATGTCATATTTATTATCTGCTTGTGATGTTTTTTATTCTCCTATAGTTTTAGGAAGTGGAATGAAAACA<br>AAAATTGCAGAAGCACTATCATATGGATTATATATTTATGCGACAGAGCATTCCTTAATCGGCTATGATGAAATTATA<br>CACAATAAGGAGTGTGTTAAAAAAATCTCACATTTGGATGAGGAATTTCCTAAAGATTTCAAGATGAAAAGTATCAAT<br>AAACAGCTAATAATGTCTTATCAGCAAAAATATTATTCACATTATCGGTTTAATGGCCATGAACTTGATATAATAAAT<br>TTTGACGATTAGTTAGTGGAGATATAATATGAACATATTAGTAACTGGTGGTGCTGGATATATCGGATCTCATACGGC<br>TATTGAATTACTGAATGCAGGTCATGAGATTATCGTTCTGGACAATTTCAGTAATGCTTCATACAAGTGTATCGAAAA<br>AATAAAAGAAATTACTCGACGTGATTTTATAACAATTACTGGAGATGCTGGGTGTAGGAAGACACTCTCCGCTATTTT<br>CGAGAAACACGCCATAGATATAGTTATTCATTTTGCTGGCTTTAAATCTGTTTCAGAGTCTAAAAGTGAACCCTTAAA<br>GTATTACCAGAATAATGTTGGAGTGACCATTACTTTATTACAGGTAATGGAAGAGTACAGAATTAAAAAATTTATCTT<br>TAGTTCATCTGCGACAGTCTATGGTGAACCAGAGATAATTCCAATTCCAGAAACAGCTAAAATTGGAGGAACTACGAA<br>TCCATATGGCACATCGAAGTATTTTGTTGAAAAAATTCTAGAGGATGTTAGTTCCACGGGAAAACTGGATATAATTTG<br>CTTGAGATATTTTAATCCTGTCGGTGCTCATTCTAGTGGTAAAATAGGTGAGGCTCCATCTGGTATCCCTAATAATCT<br>TGTTCCTTATTTATTGGATGTTGCGAGTGGTAAACGTGATAAATTATTTATTTATGGCAATGATTACCCTACTAATGA<br>TGGAACAGGTGTAAGGGATTTTATTCATGTTGTTGACTTAGCGAAAGGTCATTTGGCTGCAATGAATTATTTAAGTAT<br>CAATTCGGGATATAATATCTTTAATCTTGGTACAGGAAAAGGTTATTCGGTACTTGAATTAATCACTACATTTGAAAA<br>ATTAACAAACATTAAGGTCAATAAATCTTTTATAGAGAGAAGGGCAGGGGATGTTGCGTCTTGTTGGGCTGATGCAGA<br>TAAAGCTAATTCTTTATTGGACTGGCAAGCCGAACAAACTCTAGAACAGATGTTATTGGACTCGTGGCGTTGGAAAAA<br>AAATTATCCAGACGGATTCTGAATATAAAAGGTTTCAGTTTTATGAATCAATCAGAGCAGAGAAAAAAAATACTGGTT |

-continued

| SEQUENCES |
|---|
| CTTACACCTCGCTTTCCCTACCCTGTCATTGGAGGGGATAGATTAAGAGTCTATATGTTATGTAAAGAACTTTCCAAA<br>AAATATGATCTTATTCTTCTGAGCTTATGTGATCAACCACTAGAACTTGAAATAAATATAAATGACTCGGTCTTCAAA<br>GAAATTCATCGTGTCTATCTACCAAAATATAAATCATATTATAATGTATTAAAAGCTTTGGTTACGCAAAAACCGTTG<br>CAAATTGCTTATTATCAATCGGACACATTTAAGAATAAATACAATAAATTAATTAAACAATGCGATGCAGTATTTTGT<br>CATCTGATAAGAGTTGCTGATTATGTTAAGGATACAGACAAGTTCAAAATTCTTGATATGACAGATGCAATATCTTTG<br>AATTACAGTCGCGTTAAAAAATTAGCAAGTAAAAAAAGTTTGCGTGCAATTATTTATTCTCTGGAACAAAAAAGATTA<br>GAATCATATGAACGTTCTGTGGCGAATCTTTTTGATTTGACCACTTTTATTTCATCCGTAGACCGTGACTATCTCTAC<br>CCTAATCTGGGCAGTAATATCCATATAGTCAATAATGGGGTTGATACATCAGCCTTGAGATATATAAAAAGAGAAATA<br>AAAATCGATAAGCCTGTGGAACTTATATTTATCGGAAATATGTATTCTTTACAAAATATGGATGCTGCAAAACATTTT<br>GCTAAGAATATTTTACCTTGCTTGTATGATGAGTTTAATATTATTTTTAAAGTGATTGGTAAGATCTCAGAAACTAAT<br>AAAAATATATTAAATTCATTTAAAAATACAATTGCTTTAGGTACTGTTGATGATATCAATTCTTCCGCTTCTACAGGG<br>CATATAGGTATATGTCCTGTTCGTCTTGGAGCAGGCGTACAAAATAAAATTCTTGAATACATGGCTTTAGGTTTACCA<br>TGTATTACATCTAGCATTGGTTATGAAGGTATTAATGCAAAATCAGGTAGCGAAATTTTTGTTGCAGATACAGTAGAG<br>CAATATAAAAACGTACTAAGAGAAATAATTTACGATTATAATCGTTATACTGAAGTGGCTGAAAATGCCCGTAGTTTT<br>GTAGAAAATAATTTTTCTTGGGAATCAAAAGTTGCCAATTTAATGAATACATTAGATGAGAAATTATATGAACAATAA<br>TAAAATTATTACACCTATCATTATGGCTGGTGGTTCAGGCAGTCGGTTGTGGCCACTATCAAGAATTCTCTATCCGAA<br>ACAATTTCTTAGCCTAATCGGTAGTCATACCATGCTTCAAACAACGGCTAATCGTCTGGATGGTTTGGATTGTACCAA<br>CCCTTATGTCATTTGTAATGAACAATACCGCTTTATAGTTGCTGAACAGCTTAGAAAAATCGATAGATTGACTTCAAA<br>GAATATCATCCTTGAGCCTGTTGGGCGTAACACTGCCCCTGCAATTGCATTAGCGGCGTTGCTGATGTCTAAGTCTGA<br>TAAAAGTGCAGATGATCTTATGCTCGTACTGGCTGCAGATCACGTTATACACGATGAAGAAAAATTTTGTAACGCTGT<br>TAGATCGGCAATTCCATACGCTGCTGATGGGAAATTGGTAACATTTGGTATAATTCCAGACAAAGCAGAAACTGGTTA<br>TGGTTATATACATCGAGGACAATATATTAATCAGGAAGATTCGGATGCATTTATAGTGTCATCATTTGTTGAAAAGCC<br>AAATCATGAGACAGCCACTAAATATCTTGCTTCCGGTGAGTATTATTGGAATAGCGGTATGTTTTTGTTTAGTGCAAA<br>TCGTTATATAGAGGAACTTAAACAATTTCGGCCTGATATTTTATCCGCTTGTGAAAAAGCAATTGCTTCAGCGAACTT<br>TGACCTTGATTTTGTGCGTTTAGATGAAAGTTCTTTCTCTAAGTGCCCTGAAGAATCAATTGATTACGCTGTAATGGA<br>AAAAACAAAAGACGCAATTGTTATTCCAATGGATGCTGGCTGGAGTGATGTCGGTTCATGGTCTTCTCTTTGGGAAAT<br>TAATGATAAAGACTCAGACGGCAACGTAATAGTTGGGGATATTTTCTCTCATGAAACAAAGAATTCTTTCATATATGC<br>CGAATCGGGAATTGTTGCTACAGTTGGAGTGGAAAATTTAGTTGTTGTCCAAACAAAGGATGCTGTTCTTGTCTCAGA<br>GAGAAATAAAGTTCAGGATGTAAAGAAAATAGTAGAACAAATTAAAAATTCAGGTCGTAGCGAGCATTATGTTCATCG<br>CGAAGTATATCGTCCTTGGGGTAAATATGATTCCATTGACACAGGGGAGCGTTATCAGGTCAAACGTATAACAGTAAA<br>TCCTGGTGAAGGACTTTCTTTACAAATGCACCATCATAGGGCAGAACATTGGATCATAGTTTCTGGAACTGCAAGGGT<br>GACTATAGGTTCTGAAACTAAGATTCTTAGCGAAAATGAATCTGTTTACATACCTCTTGGTGTAATACACTGCTTGGA<br>AAATCCAGGGAAAATTCCTCTTGATTTAATTGAAGTTCGTTCTGGATCTTATTTAGAAGAAGACGATGTTATCCGTTT<br>TCAGGACCGATATGGTCGTAGCTAAATTTTTGATAATGTAACGTTAGTAGAAGAGCGCTAATATTTTTAGTTAATCTG<br>TAATAAGTATTATTTGTTTAAGGTATATCATGTCGAGTTTACCCTGCTTTAAAGCCTATGATATTCGCGGGAAATTAG<br>GCGAAGAACTGAATGAAGATATTGCCTGGCGCATTGGTCGCGCTTATGGCGAATTTCTCAAACCGAAAACCATTGTGT<br>TAGGCGGTGACGTCCGACTCACCAGCGAAACCTTAAAACTGGCGCTGGCGAAGGGGTTACAGGATGCGGGCGTCGATG<br>TGCTGGATATTGGCATGTCCGGCACCGAAGAGATCTATTTCGCCACGTTCCATCTCGGCGTGGATGGCGGCATCGAAG<br>TTACCGCCAGCCATAACCCGATGGATTACAACGGCATGAAACTGGTGCGCGAAGGGGCTCGCCCGATCAGCGGTGATA<br>CCGGACTGCGCGACATCCAGCGTCTGGCAGAAGCCAACGACTTTCCTCCCGTTGATGAAACCAAACGCGGTCGCTATC<br>AGCAAATCAATCTGCGTGACGCTTACGTTGATCACCTGTTCGGTTATATCAACGTCAAAAACCTCACGCCGCTCAAGC<br>TGGTGATTAACTCCGGGAACGGCGCGGCGGGTCCGGTGGTGGACGCCATTGAAGCCCGCTTTAAAGCCCTCGGCGCAC<br>CCGTGGAATTAATCAAAGTGCACAACACGCCGGACGGCAATTTCCCCAACGGTATTCCTAACCCGCTACTGCCGGAAT<br>GTCGCGACGACACCCGCAATGCGGTCATCAAACACGGCGCGGATATGGGCATTGCCTTTGATGGCGATTTTGACCGCT<br>GTTTCCTGTTTGACGAAAAAGGGCAGTTTATTGAGGGCTACTACATTGTCGGCCTGCTGGCAGAAGCGTTCCTCGAAA<br>AAAATCCCGGCGCGAAGATCATCCACGATCCACGTCTCTCCTGGAACACCGTTGATGTGGTGACTGCCGCAGGCGGCA<br>CCCCGGTAATGTCGAAAACCGGACACGCCTTTATTAAAGAACGTATGCGCAAGGAAGACGCTATCTACGGTGGCGAAA<br>TGAGCGCCCACCATTACTTCCGTGATTTCGCTTACTGCGACAGCGGCATGATCCCGTGGCTGCTGGTCGCCGAACTGG<br>TGTGCCTGAAAGGAAAAACGCTGGGCGAACTGGTGCGCGACCGGATGGCAGCGTTTCCGGCAAGCGGTGAGATCAACA<br>GCAAACTGGCACACCCCGTTGAGGCGATTAACCGCGTGGAACAGCACTTTAGCCGCGAGGCGCTGGCGGTGGATCGCA<br>CCGATGGCATCAGCATGACCTTTGCCGACTGGCGCTTTAACCTGCGCTCCTCTAACACCGAACCGGTGGTGCGGTTGA<br>ATGTGGAATCGCGCGGCGATGTACCGCTGATGGAAGAAAAGACAAAACTTATCCTTGAGTTACTGAACAAGTAATTCA<br>GTAATTTCATATAAATGGGTTTTAAAAAACGGAAAAGATGAGATATCCGGTGTGGTATATCCAAGGTAATGCTATTCA<br>GTATCTCTATGAGTGAGTTAACATCTATACCACATTTAAGCCGCACACTTCGGGATCCCCATATGAATATCCTCCTTA<br>GTTCCTATTCCGAAGTTCCTATTCTTTCTAGAGAATAGGAACTTCGGAATAGGAACTAAGGAGGATATTCATATGGAT<br>AAAGCCGTAAGCATATAAGCATGGATAAGCTATTTATACTTTAATAAGTACTTTGTATACTTATTTGCGAACATTCCA<br>GGCCGCGAGCATTCAGCGCGGTGATCACACCTGACAGGAGTATGTAATGTCCAAGCAACAGATCGGCGTAGTCGGTAT<br>GGCAGTGATGGGACGCAACCTTGCGCTCAACATCGAAAGCCGTGGTTATACCGTCTCTATTTTCAACCGTTCCCGTGA<br>GAAGACGGAAGAAGTGATTGCCGAAAATCCAGGCAAGAAACTGGTTCCTTACTATACGGTGAAAGAGTTTGTCGAATC<br>TCTGGAAACGCCTCGTCGCATCCTGTTAATGGTGAAAGCAGGTGCAGGCACGGATGCTGCTATTGATTCCCTCAAACC<br>ATATCTCGATAAAGGAGACATCATCATTGATGGTGGTAACACCTTCTTCCAGGACACTATTCGTCGTAATCGTGAGCT<br>TTCAGCAGAGGGCTTTAACTTCATCGGTACCGGTGTTTCTGGCGGTGAAGAGGGGGCGCTGAAAGGTCCTTCTATTAT<br>GCCTGGTGGCCAGAAAGAAGCCTATGAATTGGTAGCACCGATCCTGACCAAAATCGCCGCCGTAGCTGAAGACGGTGA<br>ACCATGCGTTACCTATATTGGTGCCGATGGCGCAGGTCACTATGTGAAGATGGTTCACAACGGTATTGAATACGGCGA<br>TATGCAGCTGATTGCTGAAGCCTATTCTCTGCTTAAAGGTGGCCTGAACCTCACCAACGAAGAACTGGCGCAGACCTT<br>TACCGAGTGGAATAACGGTGAACTGAGCAGTTACCTGATCGACATCACCAAAGATATCTTCACCAAAAAAGATGAAGA<br>CGGTAACTACCTGGTTGATGTGATCCTGGATGAAGCGGCTAACAAAGGTACCGGTAAATGGACCAGCCAGAGCGCGCT<br>GGATCTCGGCGAACCGCTGTCGCTGATTACCGAGTCTGTGTTTGCACGTTATATCTCTTCTCTGAAAGATCAGCGTGT<br>TGCCGCATCTAAAGTTCTCTCTGGTCCGCAAGCACAGCCAGCAGGCGACAAGGCTGAGTTCATCGAAAAAGTTCGTCG<br>TGCGCTGTATCTGGGCAAAATCGTTTCTTACGCCCAGGGCTTCTCTCAGCTGCGTGCTGCGTCTGAAGAGTACAACTG<br>GGATCTGAACTACGGCGAAATCGCGAAGATTTTCCGTGCTGGCTGCATCATCCGTGCGCAGTTCCTGCAGAAAATCAC<br>CGATGCTTATGCCGAAAATCCACAGATCGCTAACCTGTTGCTGGCTCCGTACTTCAAGCAAATTGCCGATGACTACCA<br>GCAGGCGCTGCGTGATGTCGTTGCTTATGCAGTACAGAACGGTATTCCGGTTCCGACCTTCTCCGCAGCGGTTGCCTA<br>TTACGACAGCTACCGTGCTGCTGTTCTGCCTGCGAACCTGATCCAGGCACAGCGTGACTATTTTGGTGCGCATACTTA<br>TAAGCGTATCGATAAAGAAGGTGTGTTCCATACCGAATGGCTGGATTAA |

-continued

| SEQUENCES |
|---|

SEQ ID NO: 14 (example O8 rfb locus nucleotide sequence-O8-EPA production strain stLMTB11734)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATCTGTCCGCCGGGCGTGACCATTATGAACGTGCGTCAG
GGCGAACCTTTAGGTTTAGGCCACTCCATTTTGTGTGCGCGACCTGCCATTGGTGACAACCCATTTGTCGTGGTACTG
CCAGACGTTGTGATCGACGATGCCAGCGCCGACCCGCTACGTTACAACCTTGCTGCCATGATTGCACGTTTCAACGAA
ACGGGCCGCAGCCAGGTGCTGGCAAAACGTATGCCGGGTGACCTCTCTGAATACTCCGTCATCCAGACTAAAGAGCCG
CTGGACCGTGAGGGTAAAGTCAGCCGCATTGTTGAATTTATCGAAAAACCGGATCAGCCGCAGACGCTGGACTCAGAC
ATCATGGCCGTAGGTCGCTATGTGCTTTCTGCCGATATTTGGCCGGAACTGGAACGTACTCAGCCTGGTGCATGGGGA
CGTATTCAGCTGACTGATGCTATTGCCGAGCTGGCGAAAAAACAATCCGTTGATGCAATGCTGATGACCGGCGACAGT
TACGACTGCGGCAAAAAAATGGGCTATATGCAGGCGTTTGTGAAGTATGGCCTACGCAACCTGAAAGAAGGGGCGAAG
TTCCGTAAAGGTATTGAGAAGCTGTTAAGCGAATAATGAAAATCTGACCGGATGTAACGGTTGATAAGAAAATTATAA
CGGCAGTGAAAATTCGCAGCAAAAGTAATTTGTTGCGAATCTTCCTGCCGTTGTTTTATATAAACCATCAGAATAACA
ACGAGTTAGCAGTAGGGTTTTATTCAAAGTTTTCCAGGATTTTCCTTGTTTCCAGAGCGGATTGGTAAGACAATTAGC
GTTTGAATTTTTCGGGTTTAGCGCGAGTGGGTAACGCTCGTCACATCATAGGCATGCATGCAGTGCTCTGGTAGCTGT
AAAGCCAGGGGCGGTAGCGTGCATTAATACCTCTATTAATCAAACTGAGAGCCGCTTATTTCACAGCATGCTCTGAAG
TAATATGGAATAAATTAAGCTAGCGATCGCTTAAGATCTAGGATTTCATTATGTTACTTCCTGTAATTATGGCTGGTG
GTACCGGCAGTCGTCTCTGGCCGATGTCACGCGAGCTTTATCCGAAACAGTTCCTCCGCCTGTTCGGGCAGAACTCCA
TGCTGCAGGAAACCATCACCCGACTCTCGGGCCTTGAAATCCATGAACCGATGGTCATCTGTAACGAAGAGCACCGCT
TCCTGGTGGCTGAACAGCTACGCCAGCTCAATAAGCTGTCGAATAATATTATTCTTGAGCCGGTCGGGCGCAACACCG
CCCCGGCCATCGCCCTGGCAGCCCTTCAGGCCACCCGCGACGGCGACGACCCGCTGATGCTGGTTCTCGCCGCTGACC
ATATCATCAATAACCAGTCGGCCTTCCACGACGCCATCCGGGTCGCCGAGCAGTATGCTGATGAAGGTCATCTGGTCA
CCTTCGGTATCGTGCCGAATGCCCCGGAAACTGGCTACGGTTACATTCAGCGCGGCGTGGCGCTCACCGATAGTGCCC
ATTCCGCGTACCAGGTGGCCCGCTTTGTGGAGAAGCCGGATCGCGAGCGCGCCGAGGCTTACCTCGCCTCCGGGGAGT
ACTACTGGAACAGCGGCATGTTTATGTTCCGCGCCAAGAAATACCTCATCGAGCTGGCCAAATACCGTCCGGATATCC
TGGAAGCCTGCCAGGCTGCGGTGAATGCCGCCGATAATGGCAGCGATTTCATCAATATCCCGCATGATATTTTCTGCG
AGTGCCCGGATGAGTCCGTGGACTATGCCGTTATGGAGAAAACCGCCGATGCGGTGGTGGTCGGTCTCGATGCTGACT
GGAGCGACGTCGGCTCCTGGTCCGCACTATGGGAGGTCAGCCCGAAAGACGAGCAGGGCAATGTCCTCAGCGGTGACG
CGTGGGTACACAACAGCGAAAACTGCTACATCAACAGCGACGAGAAGCTAGTGGCGGCCATTGGCGTAGAGAATCTGG
TGATTGTCAGCACTAAGGACGCCGTGCTGGTGATGAATCGCGAGCGTTCCCAGGACGTGAAGAAGGCGGTCGAGTTCC
TCAAGCAGAACCAGCGCAGCGAGTACAAGCGCCACCGTGAGATTTACCGCCCCTGGGGCCGTTGCGACGTAGTGGTCC
AGACCCCGCGCTTCAACGTCAACCGCATCACGGTGAAACCAGGCGGTGCCTTCTCGATGCAGATGCACCACCATCGCG
CCGAGCATTGGGTTATTCTCGCCGGCACCGGTCAGGTGACTGTCAACGGTAAGCAGTTCCTGTTGTCCGAGAACCAGT
CCACCTTTATTCCGATTGGCGCCGAGCACTGCCTGGAAAACCCTGGCTGTATTCCGCTGGAAGTGCTGGAGATCCAGT
CGGGGGCGTACCTTGGCGAGGACGACATTATTCGTATTAAAGACCAGTATGGTCGTTGCTAATTATTTTCGGGACAAG
ACGCAGAATGACACAGTTAACTTGTTTTAAAGCTTATGACATCCGTGGTGAACTGGGTGAGGAACTGAACGAGGACAT
CGCCTACCGTATCGGTCGCGCCTACGGCGAATTTCTGAAACCCGGGAAGATAGTGGTGGGGGGCGATGTGCGCCTCAC
AAGCGAGTCGCTGAAGCTGGCGCTGGCCCGCGGGTTAATGGACGCCGGTACCGACGTGCTGGACATCGGCCTGAGCGG
TACCGAAGAGATTTACTTTGCCACCTTCCACCTTGGGGTAGATGGTGGCATCGAGGTGACCGCGAGCCACAATCCTAT
GAACTACAACGGCATGAAGCTGGTGCGCGAGAATGCGAAGCCCATCAGCGGCGACACCGGCCTGCGGGATATCCAGCG
CCTGGCGGAGGAAAACCAGTTCCCGCCAGTGGACCCGGCGCGTCGCGGGACCCTGAGCAAGATATCGGTACTGAAGGA
GTATGTTGACCATCTGATGAGCTACGTGGACTTCTCGAACTTCACCCGTCCACTGAAGTTGGTGGTGAACTCCGGAAA
CGGGGCTGCGGGGCACGTGATTGATGAGGTGGAGAAACGCTTCGCGGCGGCTGGGGTGCCGGTAACCTTTATCAAGGT
GCATCACCAGCCGGATGGCCATTTCCCTAACGGTATCCCGAATCCGCTGCTGCCGGAGTGCCGCCAGGATACCGCCGA
CGCGGTGCGCGAGCATCAGGCCGACATGGGGATTGCCTTTGACGGCGACTTCGATCGCTGCTTCCTGTTCGATGACGA
AGCTTCGTTTATCGAGGGGTATTACATTGTCGGCCTGCTGGCTGAGGCGTTCCTGCAGAAGCAGCCGGGAGCGAAAAT
CATTCACGACCCGCGCTTGACGTGGAACACGGTAGACATCGTGACCCGCAACGGCGGCCAGCCGGTGATGTCGAAGAC
GGGGCATGCGTTCATCAAGGAGCGGATGCGTCAGGAAGACGCTATCTACGGCGGGGAGATGAGTGCGCACCATTACTT
CCGCGATTTCGCCTACTGCGATAGCGGGATGATCCCGTGGCTGCTGGTGGCGGAGCTGCTGTGTCTGAAGAACAGCTC
GCTGAAATCGCTGGTGGCGGACCGCCAGAAGGCGTTCCCTGCGTCGGGAGAGATCAACCGCAAGCTAAGTAATGCTGC
TGAGGCGATCGCCCGCATCCGGGCGCAGTATGAGCCGGCGGCTGCACACATCGACACAACGGACGGGATCAGTATTGA
ATACCCTGAATGGCGCTTTAACCTGCGCACGTCTAACACCGAGCCGGTGGTGCGTCTGAACGTTGAGTCCAGAGCTGA
TGTGGCGCTTATGAATGAAAAAACGACCGAGCTGTTACACCTGTTAAGCGGGGAATAAGGTGAGAGATTTACTAACGA
CGATTTATCGTTATCGGGGATTTATCTGGAGCAGTGTTAAACGTGATTTTCAGGCACGCTATCAAACTAGTATGCTGG
GCGCACTATGGCTCGTTTTACAACCGCTCTCTATGATTCTGGTCTATACCCTGGTTTTTTCCGAGGTGATGAAGGCAA
GAATGCCCGATAATACCGGGTCGTTTGCCTATAGTATTTATCTCTGTTCCGGGGTACTGACCTGGGGATTATTTACTG
AGATGCTGGATAAAGGTCAGAGCGTATTTATTAACAATGCTAATCTGATCAAGAAACTCAGTTTTCCGAAAATCTGTC
TGCCGATCATCGTGACGTTATCGGCGGTGCTAAATTTCGCGATTATTTTCAGTCTGTTTCTAATTTTTATCATTGTCA
CCGGTAACTTCCCCGGCTGGCTCTTTCTCTCGGTGATACCGGTCCTGCTTTTGCAGATCCTGTTTGCCGGTGGGCTGG
GGATGATCCTTGGTGTCATGAACGTCTTTTTCAGGGATGTGGGGCAACTGGTTGGCGTTGCGCTGCAATTCTGGTTTT
GGTTCACACCCATTGTTTATGTACTGAATTCATTACCTGCATGGGCAAAAAATCTGATGATGTATAACCCGATGACTC
GGATCATGCAATCTTATCAGTCCATCTTCGCCTATCATCTGGCCCCCAACTGGTATTCGCTATGGCCAGTATTGGCTC
TCGCCATTATTTTCTGCGTCATCGGTTTCAGGATGTTCCGCAAGCATGCGGCGGATATGGTGGATGAATTATAATGAG
TTATATCAGAGTAAATAATGTCGGTAAGGCGTATCGCCAGTATCACTCAAAGACCGGGAGACTGATCGAATGGTTATC
CCCTCTGAATACCAAACGCCATAATTTGAAATGGATCCTCCGCGATATTAATTTCGAAGTCGCTCCGGGCGAGGCTGT
CGGTATTATCGGTATCAACGGTGCAGGCAAGAGTACCCTGCTTAAACTCATAACCGGGACGTCCAGGCCGACGACTGG
AGAAATTGAAATCTCCGGACGTGTCGCTGCATTACTCGAATTGGGGATGGGTTTCATTCTGATTTCACTGGTCGGCA
GAATGTTTATATGTCTGGGCAACTGTTGGGGTTATCGTCAGAGAAAATAACTGAACTGATGCCGCAAATTGAAGAGTT
TGCTGAGATTGGGGACTATATCGATCAACCTGTGCGCGTCTACTCCAGTGGGATGCAAGTTCGATTAGCTTTTAGTGT
AGCGACGGCTATCCGTCCTGATGTGCTAATTATCGATGAGGCATTATCTGTTGGGGATGCATATTTCCAGCATAAAAG
CTTTGAGCGTATTCGAAAATTTCGTCAGGAAGGGACCACGCTGTTGCTGGTATCCCATGATAAACAAGCGATCCAAAG
CATTTGCGACCGGGCCATTTTATTGAATAAAGGCCAAATTGAAATGGAAGGTGAACCTGAAGCAGTGATGGATTATTA
CAATGCTCTTCTGGCCGATAAACAAAATCAGTCCATTAAACAAGTTGAGCATAATGGTAAAACGCAAACTGTTTCAGG
CACTGGTGAGGTGACTATCTCTGAGGTTCATCTTCTCGATGAACAGGGCAATGTGACTGAATTTGTTTCGGTAGGGCA -continued

| SEQUENCES |
| --- |
| TCGTGTCAGCTTGCAGGTCAACGTTGAGGTCAAGGACGATATTCCTGAGCTTGTTGTCGGATATATGATTAAGGATCG<br>ACTTGGGCAGCCGATTTTCGGGACCAATACGTACCATCTCAATCAGACACTCACCTCCCTGAAAAAAGGAGAAAAGCG<br>TTCGTTCTTATTTTCTTTCGATGCGAGATTGGGGGTTGGCTCCTATTCTGTCGCTGTCGCGTTGCATACTTCCAGTAC<br>GCACCTCGGCAAAAACTATGAATGGCGCGATCTGGCCGTGGTATTCAACGTCGTTAACACGGAACAACAAGAGTTTGT<br>CGGCGTGTCCTGGTTGCCGCCTGAACTGGAGATTTCTTAATGGGTTCGTCGTTTTATCGTTCATTTGAAGAACGACAC<br>AGAGGTTCGGTTGAAGAAATCAAGCGCCGCTTGAGTTTTTATTTACCTTTTCTTGCAGGTCTGAAGGACATTTATCCT<br>GATGGCGTGATTGCGGATATTGGTTGCGGACGTGGCGAATGGTTGGAGATCCTGACTGAAAATGGCATTGCGAACATC<br>GGCGTCGATCTCGATGATGGCATGCTGGCGCGCGCCAGGGAGGCCGGACTGAATGTGCAGAAAATGGATTGTCTGCAG<br>TTTTTGCAAAGTCAGGCGGATCAGAGCCTGATAGCGTTGACCGGTTTTCATATTGCTGAGCATTTGCCGTTTGAGGTC<br>CTGCAGCAACTCGCCATGCATACCCTACGGGTGCTGAAACCAGGTGGTTTGCTGATCCTCGAAACGCCGAACCCGGAG<br>AATGTAAGCGTCGGCACCTGTTCATTTTATATGGATCCAACGCATAATCATCCTCTGCCACCGCCACTGCTTGAGTTT<br>TTACCTATTCATTATGGTTTTACCCGAGCAATTACCGTTCGTCTGCAGGAAAAAGAGGTTCTTCAATCTCCGGATGCA<br>GCCGTTAATTTGGTCGATGTACTCAAAGGGGTGAGCCCCGACTACAGCATCATTGCTCAGAAAGCAGCGCCAACAGAT<br>ATTCTTGAACGCTTTGACACCCTGTTTACCCAGCAGTACGGTCTGACGCTGGATGCTCTGAGCAACCGTTACGATGCG<br>ATTTTGCGCCAACAGTTTTCGTCCGTTGTCTCACGGCTGGAGACGTTGAACCAAACCTATATGCAACAGATAAGCCAA<br>ATGTCAGAGACTATTCAGACGTTGCAAGGTGAGGTTGACGATCTGAGTCATGTCATCGATCAGAACCATCAGCTTCAT<br>CAGCAAATGGCGGATTTACATAACAGTCGTTCATGGCGTATTACTCAACCACTACGCTGGTTGTCTTTGCAACGTCAA<br>TTATTACGTCAGGAAGGGGCTAAAGTGCGAGCCCGTAGGGCTGGGAAAAAAATATTGCGCAAAGGGATGGCGCTCTCG<br>CTGGTCTTTTTCCATCGTTACCCTAAGTCTAAGGTTTATCTGTTTAAGGTTCTGAGAAAAACTGGCTGCTATACATTG<br>CTACAACGTTTGTTCCAACGCGTAATGCTGGTGCAATCTGACACGATGATGATGCAGTCCAGAAGATATGATGTGGGT<br>ACTGAAGAAATGACAAGTCGCGCGATGAGTATTTATAACGAATTAAAAAATAAAAATACGGAGAAATAACGATGCGTA<br>TTGTCATAGATTTACAAGGCGCACAGACGGAAAGCCGCTTTCGTGGCATCGGTCGTTATAGTATCGCAATCGCCAGAG<br>GCATAATCAGAAATAACAGCCGGCATGAGATTTTCATCGCGCTATCCGCCATGCTGGATGAGTCGATTGCAAATATTA<br>AGGCGCAATTTGCCGATCTCCTGCCGGCAGAAAATATAGTCGTATGGCATGCCGTAGGCCCTGTTCGTGCGATGGACC<br>AAGGTAATGAATGGCGTCGGGAGAGCGCAGAACTGATTCGGGAAGCGTTTCTTGAATCATTGTGTCCAGATGTCGTTT<br>TCATTACGAGTTTGTTTGAAGGTCATGTCGACGATGCGGCTACATCGGTACACAAATTTAGTCGTCAGTATAAAGTAG<br>CCGTACTGCACCACGATCTTATCCCCCTCGTGCAGGCGGAAACCTATCTGCAGGACGATGTATACAAACCCTACTATT<br>TACAGAAAGTTGAGTGGTTAAAAAACGCTGACCTTTTGTTGACTAACTCTGCTTATACCGCACAGGAAGCGATCGAGC<br>ATCTGCATTTACAGGGCGATCATGTGCAGAATATTGCAGCCGCAGTCGATTCTCAGTTTTGTATGGCGGAGGTGGCAG<br>CGAGCGAAAAAGAGACCGTCCTTGGCCATTACGGTATTCAGCGCGAGTTCATGTTGTATGCGCCCGGAGGATTTGACT<br>CAAGGAAAAACTTTAAACGGTTGATTGAGGCCTATGCCGGGCTCAGTGATGCCTTACGTCGCAGTCATCAACTGGTCA<br>TCGTCAGTAAGCTTTCCATCGGTGATCGTCAGTATCTGGAATCCCTTGCGTCAGGTAATGGTTTACAGCAGGGCGAAC<br>TGGTACTCACTGGTTATGTGCCGGAAGATGAGCTGATCCAGCTCTATCGCCTATGTAAGCTGTTCATCTTTGCTTCAC<br>TACATGAAGGTTTTGGGTTGCCGGTTCTGGAAGCAATGTCGTGCGGTGCGCCGGTGATTGGCTCAAATGTCACCAGTA<br>TTCCTGAAGTCATCGGTAATCCTGAGGCATTATTCGACCCGTATTCTGTCTCTTCCATGAGGGATAAGATCGCGCAAT<br>GTTTGACTGATGATACCTTCCTCGCGCGTCTGAAAGAAATGGCGCAGCAGCAAGCGCGTAATTTCTCTTGGGATAAAG<br>CTGCGGTGACTGCTCTGGAAGCTTTCGAAAAGATCGCGGTAGAAGACACCGGTACTGCGCAGGTTTTGCCTGAAGCTT<br>TGATTCAGAAGATCCTTGCTATCTCACAAGGGCAGCCAGATGACCGCGATCTGCGCTTGTGCGCAACGGCCATTGATT<br>ACAATCTGAAAACGGCAGAACTTTATCAAATCGACGATAAATCGCTGAACTGGCGTGTGGAAGGCCCATTCGATAGCT<br>CATATAGTCTGGCGTTGGTCAACCGCGAATTTGCCCGGGCACTCTCAGCCGATGGTGTAGAGGTTTTATTGCATTCCA<br>CTGAAGGACCAGGTGATTTTGCCCCAGATGCCTCGTTTATGGCACAGTCGGAAAATAGTGATCTTCTGGCATTTTATA<br>ATCAATGTCAGACCCGCAAGAGTAACGAAAAGATAGATATTATTAGCAGAAATATCTATCCACCGCGGGTTACCAAAA<br>TGGATGCCAAAGTAAAATTCCTTCATTGTTATGCTTGGGAAGAAACGGGCTTTCCGCAACCGTGGATCAATGAATTTA<br>ATCGGGAACTTGACGGAGTGCTGTGTACTTCGGAACATGTTCGTAAAATACTGATTGATAACGGACTGAATGTGCCCG<br>CATTTGTTGTTGGCAATGGCTGTGACCATTGGCTCAATATCCCAGCCGAGACGACAAAAGATGTGGATCACGGAACAT<br>TCCGTTTCCTGCACGTCTCTTCTTGTTTCCCACGCAAAGGGATACAGGCAATGCTTCAGGCTTGGGGGAAGGCGTTCA<br>CTCGTCGTGACAATGTTATCTTAATCATTAAGACTTTTAACAATCCGCACAATGAAATTGACGCATGGCTGGCTCAGG<br>CCCAGGCTCAATTCATAGACTATCCCAAAGTTGAAGTGATCAAAGAGGATATGTCAGCCACCGAGCTTAAAGGGCTTT<br>ATGAAAGCTGTGATGTTTTGGTTGCTCCAGGTTGCGCTGAAGGCTTTGGTTTACCTATTGCTGAAGCAATGCTGAGTG<br>GGCTACCGGCTATCGTCACCAATTGGAGCGGGCAACTTGATTTTGTTAATTCACAAAATTCATGGCTGGTTGACTATC<br>AGTTCACTCGGGTAAAAACGCACTTTGGTCTGTTTTCCTCAGCCTGGGCCAGTGTGGATATTGACAACTTAACAGATG<br>CATTAAAAGCGGCAGCCTCAACCGATAAATCAGTGCTGCGTGACATGGCCAATGCTGGTCGCGAGCTTCTTCTGCAGC<br>AGTTTACCTGGAAAGCGGTGGCTGATCGTTCTTGCCAGGCGGTCAAGACTCTGCGTGCGCATATTGATATTGCACAGC<br>ATCGGGCGCGCATTGGCTGGGTGACGACCTGGAACACGAAATGTGGATCGCAACCTATTCCCAGCATCTGGTGGAAA<br>GCGCACCTCATGGCGCGGATGTTGTTTTTGCTCCCCAGGTCAGCGCTGGCGATCTTGTGTGTGCAGACGAAGAGTTTG<br>TACTTCGCAACTGGATTGTAGGTAAAGAGAGCAACTATCTGGAAAACCTCCAGCCACACATTGATGCTCTGAGACTCG<br>ATGTCATTGTGATCCAATTCAACTATGGATTCTTTAATCATCGAGAACTGTCGGCGTTTATTCGTCGCCAGCATGACG<br>CCGGTCGTTCAGTTGTTATGACGATGCACTCAACTGTGGATCCGCTGGAAAAAGAGCCGAGCTGGAATTTCCGTCTTG<br>CTGAAATGAAAGAGGCGCTGGCACTTTGCGACCGGTTGTTGGTGCATTCGATTGCCGATATGAACCGCCTTAAAGATT<br>TAGGCTTAACTGCGAATGTTGCTTTATTCCCGCACGGTGTTATCAACTACTCCGCAGCGAGCGTCACACGTCAACAGC<br>AGTCTTTACCGCTAATTGCGAGCTATGGCTTCTGCTTACCGCATAAGGGCCTGATGGAACTAGTAGAATCCGTCCATA<br>GACTCAAGCAAGCCGGTAAACCGGTTCGTTTACGACTGGTGAACGCAGAGTATCCTGTTGGGGAGTCACGCGATCTGG<br>TGGCAGAGCTTAAAGCTGCTGCTCAGCGGTTAGGTGTTACCGATCTGATTGAGATGCATAATGATTTCCTACCTGATG<br>CGGAGAGTCTGCGGTTGCTTTCAGAAGCCGATCTTCTGATTTTTGCTTATCAGAATACTGGGGAGTCTGCTAGCGGGG<br>CGGTACGTTATGGTATGGCGACTCAAAAACCTGTTGCGGTAACGCCCCTGGCGATATTTGATGATTTGGACGATGCCG<br>TCTTTAAATTTGATGGATGCAGCGTCGATGATATCAGTCAGGGGATTGACCGGATCCTGAATTCCATCCGTGAACAGA<br>ACTCTTGGGCAACCAGGACTCAACAACGTGCCGATGCATGGCGGGAACAACATGATTATCAAGCTGTTTCACGCCGTC<br>TGGTTAATATGTGTCAAGGCTTAGCTAAAGCTAAATATTTTAAATAAAAATATCTCTCTTGTATTTTTTGCCTTTGAA<br>TACAAGAGGGGTTAGATAATGTGTCATTTATTATGAAAATTATTTTTGCTACTGAGCCAATTAAATACCCATTAACGG<br>GCATCGGTCGGTATTCCCTGGAGCTGGTTAAGCGGCTGGCGGTCGCCCGCGAAATTGAAGAATTAAAGCTATTTCACG<br>GTGCGTCGTTTATAGAACAGATCCCTTTGGTGGAGAATAAAAGCGATACCAAAGCCAGCAATCATGGTCGTCTGTCGG<br>CGTTTCTACGCCGACAGACGCTGTTGATTGAGGCTTATCGCTTGCTGCATCCGCGGCGCCAGGCGTGGGCATTGCGCG<br>ACTATAAGGATTATATCTACCATGGCCCCAATTTTTATCTGCCGCATAAACTGGAACGCGCCGTGACCACGTTTCATG<br>ACATATCCATTTTTACCTGCCCGGAATATCATCCAAAAGATCGGGTTCGCTATATGGAGAAGTCCCTGCATGAGAGTC<br>TGGATTCGGCAAAGCTGATCCTGACCGTTTCTGATTTCTCGCGCAGTGAAATTATCCGCTTGTTCAACTATCCGGCGG<br>AGCGGATCGTAACCACCAAGCTAGCCTGCAGCAGTGACTATATCCCACGCAGCCCGGCAGAGTGTCTGCCGGTACTGC<br>AGAAATATCAGCTGGCGTGGCAGGCCTACGCGCTATATATCGGCACTATGGAGCCACGTAAAAATATCCGAGGCCTGC |

-continued

SEQUENCES

TGCATGCCTATCAGCTGCTACCGATGGAGATCCGCATGCGCTATCCGCTAATCCTTAGCGGCTATCGCGGCTGGGAAG
ACGATGTGCTGTGGCAGTTAGTCGAGCGCGGTACTCGGGAAGGCTGGATCCGTTACCTCGGATATGTTCCGGATGAAG
ACCTGCCGTATCTGTACGCAGCGGCCAGAGTCTTTGTTTATCCCTCCTTCTACGAGGGATTCGGTTTACCTATTCTTG
AAGCGATGTCTTGCGGTGTGCCGGTAGTATGCTCCAATGTCACCTCTTTGCCTGAGGTTGTTGGCGATGCCGGCCTCG
TTGCCGATCCTAATGATATAGACGCGATTAGCGCGCAAATTTTGCAGAGCCTGCAAGATGATAGCTGGCGGGAAATCG
CCACCGCGCGCGGTCTTGCTCAGGCGAAACAGTTTTCGTGGGAGAACTGTGCGACACAGACCATTAACGCCTATAAAT
TACTCTAAGGGTGTCAGTTGAGAGTTCTACACGTCTATAAGACTTACTATCCCGATACCTACGGCGGTATTGAGCAGG
TCATTTATCAGCTAAGTCAGGGCTGCGCCCGCCGGGGAATCGCAGCCGATGTTTTCACTTTTAGCCCGGACAAAGATA
CAGGTCCTGTCGCTTACGAAGATCATCGGGTCATTTATAATAAACAGCTTTTTGAAATTGCCTCCACGCCGTTTTCGC
TGAAAGCGTTAAAGCGTTTTAAGCTGATTAAAGATGACTACGATATCATCAACTACCATTTTCCGTTTCCCTTTATGG
ATATGCTGCATCTTTCGGCGCGGCCTGACGCCAGGACTGTGGTGACCTATCACTCTGATATAGTGAAACAAAAACGGT
TAATGAAGCTGTACCAGCCGCTGCAGGAGCGATTTCTCAGCGGCGTAGATTGCATCGTTGCCTCGTCGCCCAATTACG
TGGCTTCCAGCCAGACCCTGAAAAAATATCTGGATAAAACGGTGGTGATCCCGTTTGGTCTGGAGCAGCAGGACGTGC
AGCACGATCCGCAGAGGGTCGCGCACTGGCGGGAAACTGTCGGCGATAAGTTCTTTCTCTTCGTCGGCACTTTCCGCT
ACTACAAAGGGCTGCATATTCTGATGGATGCCGCTGAGCGTAGCCGACTGCCAGTGGTGGTTGTAGGGGGCGGGCCGC
TGGAATCGGAAGTGCGGCGTGAAGCGCAGCAGCGCGGGCTGAGCAATGTGATGTTTACCGGCATGCTCAACGACGAAG
ATAAGTACATTCTCTTCCAGCTCTGCCGGGGCGTGGTATTCCCCTCGCATCTGCGCTCTGAGGCGTTTGGCATTACGT
TATTGGAAGGCGCACGCTTTGCAAGGCCGCTGATCTCTTGCGAGATCGGTACAGGTACCTCTTTCATTAACCAGGACA
AAGTGAGTGGTTGCGTGATTCCGCCGAATGATAGCCAGGCGCTGGTGGAGGCGATGAATGAGCTCTGGAATAACGAGG
AAACCTCCAACCGCTATGGCGAAAACTCGCGTCGTCGTTTTGAAGAGATGTTTACTGCCGACCATATGATTGACGCCT
ATGTCAATCTCTACACTACATTGCTGGAAAGCAAATCCTGAGCGGCCGCGAGCTCGTCGACTCGAGGATCCGTGTAGG
CTGGAGCTGCTTCGAAGTTCCTATACTTTCTAGAGAATAGGAACTTCGGAATAGGAACTAAGGAGGATATTCATATGG
ATAAAGCCGTAAGCATATAAGCATGGATAAGCTATTTATACTTTAATAAGTACTTTGTATACTTATTTGCGAACATTC
CAGGCCGCGAGCATTCAGCGCGGTGATCACACCTGACAGGAGTATGTAATGTCCAAGCAACAGATCGGCGTAGTCGGT
ATGGCAGTGATGGGACGCAACCTTGCGCTCAACATCGAAAGCCGTGGTTATACCGTCTCTATTTTCAACCGTTCCCGT
GAGAAGACGGAAGAAGTGATTGCCGAAAATCCAGGCAAGAAACTGGTTCCTTACTATACGGTGAAAGAGTTTGTCGAA
TCTCTGGAAACGCCTCGTCGCATCCTGTTAATGGTGAAAGCAGGTGCAGGCACGGATGCTGCTATTGATTCCCTCAAA
CCATATCTCGATAAAGGAGACATCATCATTGATGGTGGTAACACCTTCTTCCAGGACACTATTCGTCGTAATCGTGAG
CTTTCAGCAGAGGGCTTTAACTTCATCGGTACCGGTGTTTCTGGCGGTGAAGAGGGGGCGCTGAAAGGTCCTTCTATT
ATGCCTGGTGGCCAGAAAGAAGCCTATGAATTGGTAGCACCGATCCTGACCAAAATCGCCGCCGTAGCTGAAGACGGT
GAACCATGCGTTACCTATATTGGTGCCGATGGCGCAGGTCACTATGTGAAGATGGTTCACAACGGTATTGAATACGGC
GATATGCAGCTGATTGCTGAAGCCTATTCTCTGCTTAAAGGTGGCCTGAACCTCACCAACGAAGAACTGGCGCAGACC
TTTACCGAGTGGAATAACGGTGAACTGAGCAGTTACCTGATCGACATCACCAAAGATATCTTCACCAAAAAAGATGAA
GACGGTAACTACCTGGTTGATGTGATCCTGGATGAAGCGGCTAACAAAGGTACCGGTAAATGGACCAGCCAGAGCGCG
CTGGATCTCGGCGAACCGCTGTCGCTGATTACCGAGTCTGTGTTTGCACGTTATATCTCTTCTCTGAAAGATCAGCGT
GTTGCCGCATCTAAAGTTCTCTCTGGTCCGCAAGCACAGCCAGCAGGCGACAAGGCTGAGTTCATCGAAAAAGTTCGT
CGTGCGCTGTATCTGGGCAAAATCGTTTCTTACGCCCAGGGCTTCTCTCAGCTGCGTGCTGCGTCTGAAGAGTACAAC
TGGGATCTGAACTACGGCGAAATCGCGAAGATTTTCCGTGCTGGCTGCATCATCCGTGCGCAGTTCCTGCAGAAAATC
ACCGATGCTTATGCCGAAAATCCACAGATCGCTAACCTGTTGCTGGCTCCGTACTTCAAGCAAATTGCCGATGACTAC
CAGCAGGCGCTGCGTGATGTCGTTGCTTATGCAGTACAGAACGGTATTCCGGTTCCGACCTTCTCCGCAGCGGTTGCC
TATTACGACAGCTACCGTGCTGCTGTTCTGCCTGCGAACCTGATCCAGGCACAGCGTGACTATTTTGGTGCGCATACT
TATAAGCGTATTGATAAAGAAGGTGTGTTCCATACCGAATGGCTGGATTAA

SEQ ID NO: 15 (example O15 rfb locus nucleotide sequence-O15-EPA production strain stLMTB11738)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATCTGTCCGCCGGGCGTGACCATTATGAACGTGCGTCAG
GGCGAACCTTTAGGTTTAGGCCACTCCATTTTGTGTGCGCGACCTGCCATTGGTGACAACCCATTTGTCGTGGTACTG
CCAGACGTTGTGATCGACGATGCCAGCGCCGACCCGCTACGTTACAACCTTGCTGCCATGATTGCACGTTTCAACGAA
ACGGGCCGCAGCCAGGTGCTGGCAAAACGTATGCCGGGTGACCTCTCTGAATACTCCGTCATCCAGACTAAAGAGCCG
CTGGACCGTGAGGGTAAAGTCAGCCGCATTGTTGAATTTATCGAAAAACCGGATCAGCCGCAGACGCTGGACTCAGAC
ATCATGGCCGTAGGTCGCTATGTGCTTTCTGCCGATATTTGGCCGGAACTGGAACGTACTCAGCCTGGTGCATGGGGA
CGTATTCAGCTGACTGATGCTATTGCCGAGCTGGCGAAAAAACAATCCGTTGATGCAATGCTGATGACCGGCGACAGT
TACGACTGCGGCAAAAAAATGGGCTATATGCAGGCGTTTGTGAAGTATGGCCTACGCAACCTGAAAGAAGGGGCGAAG
TTCCGTAAAGGTATTGAGAAGCTGTTAAGCGAATAATGAAAATCTGACCGGATGTAACGGTTGATAAGAAAATTATAA
CGGCAGTGAAAATTCGCAGCAAAAGTAATTTGTTGCGAATCTTCCTGCCGTTGTTTTATATAAACCATCAGAATAACA
ACGAGTTAGCAGTAGGGTTTTATTCAAAGTTTTCCAGGATTTTCCTTGTTTCCAGAGCGGATTGGTAAGACAATTAGC
GTTTGAATTTTTCGGGTTTAGCGCGAGTGGGTAACGCTCGTCACATCATAGGCATGCATGCAGTGCTCTGGTAGCTGT
AAAGCCAGGGGCGGTAGCGTGCATTAATACCTCTATTAATCAAACTGAGAGCCGCTTATTTCACAGCATGCTCTGAAG
TAATATGGAATAAATTAAGCTAGCATGAGCAAAACTAAACTAAATGTTCTTTACCTTGCAATAAGTCAGGGTGCCAAT
TACCTACTGCCATTATTAATTTTTCCTTATCTTGTTAGAGTCATTGGTGTATCGAATTTTGGTGATCTGAGTTTTTCA
TTGATAACTATACAAGTGTTGTTAATGGTTGTTGAATATGGTTTTGGATATAGTGGGACAAGAGAAATAGCACTAAAT
AACGATAAAAAATACCATTCTGAATTTTTTTGCGGTGTGGTGCTTGCTCGTTTTATATTAATGCTAATTGCAGCTATA
ATACTCATAATACTCTGTTTTTTTTATGTTTTTAACGACGTTAAGTCTTTGTTATGTGTTGGTTTTCTGTCCGTAATT
GCAGGTGTTTTCAATCCAAATTGGTTTTTGCAAGGTAAGGAAATGATGAGTGTGATGGCTGTGCTGTCACTATTTTCA
CGAGGCATAGCAGTCGTTGCAGTTTATCTAATTATAAAACCCGCAACGCCGATGTACATCAGTGCCTTATTATTGAGC
ATGCCATATATTTTGTATTCATTCTGTGGCGTTGCCTACTTACTTATTATCAAGGAGATTTTTTTATGTAGGCCACCG
ATAAAGAAAATTCAAGTAATTTTAAAAAATGGATTTCATTTTTTTTGTTCAACACTTGCGACTAGTGCATACACAATG
TTGACCCCTCTTGTATTGGGTGGCGTATCTGGAAAGTTTGATGTAGGCATCTTTAACTCAGCTAACATGATCAAACAA
GGTTTGGCTGGACTTGCATCACCATTAGTCCAAGCTTTTTATCCAAGAATTAACATTTTGCAAAGAGAGAATCCATAT
ATTGCAAACTTAAAATCTAGAATGATTCTTAAATACTTGCTTGTTTTTTACATGGCTTTAGCAATACCATTTTTACTT
TTTGCCAACCAATTATCATTATTAATATTCGGCATGAAAGGTGAAGTAATTGCAGGTGCAATGCAATTAATGACATTG
CTTCCTATATTCATAGGTTTTAATACAGTTGTCGGGTTACTTGTATTAGTACCTAATGGGATGCAAAAACAGTATTTC
AAATCTATTTTCCTAGGAACTATTACTTGTTTAAGCATAGTTTATCCAGCATGTAAATATTATGGAGCAACGGGTGCG
ATTGTGAGTCTTATTGTAGCTGAAATTTTCGTTGGCATGGGAATGCTTAAACAATTCATTAAAGTAAATAAAACCGTA -continued

| SEQUENCES |
| --- |
| TGTAGGCCTCATAAATTATGAATATCTCGGTAATAATATCTGTTTGGAAACGCCCAGTTCAATTAGAATTGATTCTCT<br>CTGAGCTCGATTCTCAGGCTAAAGACAATAGTCTACACCTAGAAGTAATTGTTTCCGATAGTCATAGTGGTAAAGAAA<br>TTGATGATGTAGTTGCTGATAATATTCATAAAAAGAAAAATATTAATATTATCCATCAACATACTAAAAATATACTCT<br>CCGCTAAGCGCAATTTCGGAGCATCCCTAGCCCATGGGGATTATTTAATATTTCTTGATGATGATTGTATACCCGCAA<br>GTGGATATATATCATCGTTGCTGAACTATTTAAAAAAAATGAATAGTAAAAGCGTTTTATGTGGGGAAGTTAGATTCG<br>AAAATGAACTCATTGAGACCAGCAATTACTATCGCTACAGGAACTCTTTACACCCTAAGTTTAGTGATAGTCCTGATA<br>TCTCTATGAATGCCTGGACTTTTGTCGCAATGAATTGTGTTCTTGATAGAAAGGCATTTTCATCAGGTATAGTTTCAT<br>ATAATGAAAATTTTATTGGTTATGGTTGTGAAGATCATGAGTTTGGGTGGCAACTTGAAAAAAATGACTTCAAAATTA<br>TTTTTGCTGATTTTAAAATATTACATCACGAATACAGTGGCGATATAGAAGGATATACAAAAAAAAATTCGTGCTACAG<br>CACGTGATGGTATGAATGTATTAAGCAAAGTAAGGCCTGAAATGTTTTCTACTAATAAAAAATTATTCCTAGTTGAGA<br>AAATATTTAGTAAACACAAAACGTTTAGTAAAATATGCCAATCAATATTTTTCAATAAATTTATTTTTAAAAAAATAA<br>TACAATTTTTAAAAAAAACAGATGCAAATAAAAAACTCTATTTCCCAATTCTTTACAGATATGTGTTGATTTCGGCAT<br>ATATACATGGTATTGGAGAGCGTGGCACCTCAAAAACAGATGATTTGCTTAAGAACTGGTATATATAGATGATGCTAT<br>CTTCATTTATTAAGACATTTGTATGGAAGGTAAAAAACAATGAAGTATAATGCATTGATGGCTTTTTTATTATTTTTT<br>GTTGTTTTTTTTAGATTGTCGCTGATAATACCTTTCTTATATTTGGCATTTATTCCTGCATTTTTTGGTATTATGTAT<br>TTAGTGCGTAATTTTATGATTACTATGGGCAATGGATTGGTATCTATAGATCGTAAAAATTTGTTGCTGTTATCTATA<br>TTCATAATTATTTTTTTATTTTGTTTGGTTTTCGATTTGTTTCAAAAAAGCCATTCTTTTCAAAGTTATTTTACCGTT<br>AGATTATTTATGTTGTTTTTATTTTCATTTGTTCCTGCGTATTATTTAGTAAATAGATTCATAAAGGGTGACTTGAAA<br>TTAATGGAGCGAATATTAGTGTATTCTCTCTGGGTTCAAATAGTTATTTTTTTTGGTATGTATATAAGTCCAGAGTTA<br>AAAAGATTGTTATATACTTTCTTTGGTATGTCTGACTCTGTTAATCTTTGGGAACAAAATGCTAAAGTAAGAGGATTT<br>GGGTTGTCGGGTGAAATAAATTTCATGACACCATTTTTGATGATCTATATGTCATTTTTTTATGATGAAAAGGCGTTAT<br>GCTTTAATTACTTTAATTTGTCTGACTCAAATCGTAAATTCTAACATGGCTGTGATTGCAGCCATTATTGGTATCGGT<br>TGCTCTAGACTTAATATTAATATAAAAATTGCAACAGTATTGATTTTGGGAGTTTTAGTTTATAGCTTAGGAGCGGTG<br>TTCTTTCCTCGATTTTATGATGAGTTCGTTTCTGGAGATGGCACAAGAACTCTGGATATCTTATTACAGCAACATGTG<br>TTTGTTGTAGGTAATTTAGATTTTTTTAATATTATATTTGGATTACAGCAAAACATATCTTCATCAATCCCCGATATT<br>AAACAAAGTTCGGATATGGGCTGGGTTATACTGTTTAATTACGGTGGGTTAACATTTATTACACTCTTTTTATTTTTA<br>ATCTTTACTATTTCTATTGCGACATTTGGAATGACATATCAAGCAATTATATGGATGTTAATTGGGATAATTTTCAAT<br>ACCAAAGGTTTAGTTTTAGGATCTAACGGCTATTTCTTTCTATCTTTTATATATATGTTTTTGAATAGAGTAACACTT<br>AGTGGACAGAGTTCAATTACTAATAAGTTAGGTCAAGTAAGTAAATAGCTTCCAGAGTATATTTGTCAATGATTTGAG<br>GTTCGGTTATTATGTTTTCATCTAAAACACTGTTAATTACTGGTGGTACTGGCTCTTTCGGGAATGCTGTATTAAATA<br>GATTTCTTGATACAGATATTGCAGAAATCCGTATATTTAGTCGTGATGAAAAAAAACAAGATGATATGCGGAAAAAAT<br>ACAATAATCAAAAATTAAAGTTCTATATTGGTGATGTCAGAGATTACCGTAGTATTTTGAATGCGACTCGCGGTGTTG<br>ATTTTATATATCATGCAGCGGCACTTAAGCAAGTTCCATCATGTGAATTTCATCCTATGGAAGCCGTTAAAACTAATA<br>TCCTTGGTACGGAAAATGTTCTTGAAGCAGCTATAGCGAATGAAGTGAAGAGGGTTGTATGCCTAAGTACTGATAAAG<br>CTGTATACCCGATTAACGCAATGGGTATTTCAAAAGCTATGATGGAAAAGGTCATGGTCGCGAAATCCCGTAATGTTG<br>ATCGCAATAAAACAGTAATATGTGGTACCCGTTATGGGAATGTTATGGCATCTCGCGGTTCAGTTATTCCATTATTTG<br>TTGATCTTATTAGAGCGGGCAAGCCACTCACAATAACTGATCCTAATATGACCCGCTTTATGATGACTCTTGAGGATG<br>CGGTAGATTTAGTTCTTTATGCGTTTGAACATGGTAATAATGGTGATATCTTTGTGCAAAAAGCACCTGCAGCAACTA<br>TTGACACATTAGCTATTGCTTTAAAGGAATTACTAAATGTTCCTGACCATCCGGTAAATGTCATTGGAACGCGTCATG<br>GCGAGAAATTATATGAAGCTCTACTTAGTCGTGAGGAAATGATCGCTGCTATAGATATGGGCGATTATTACCGTGTCC<br>CGCCAGATCTTCGTGACCTTAATTATGGCAAATATGTTGAGCAAGGTGATAGCCGAATATCTGAAATAGAAGATTATA<br>ACTCTCATAATACTCAACGGTTAGATGTTGAAGGCATGAAAGAGCTCTTGCTAAAATTAGCCTTTATTCGAGCAATTC<br>GTGCTGGTGAAAAATATAATCTGGATTCATGATATGAAAATATTAGTTACTGGTGCAAATGGTTTTATTGGTCGTAAT<br>TTATGTTTGAGGCTTGAGGAACTTGGTTATAAAGATCTTATTAGAATTGATCGAGAATCAACGAAGCAAGATCTTGAA<br>CAAGGCTTACAGGATGCCGATTTTATTTATCACTTAGCTGGTATCAATAGACCTAAGACTGATGATGAGTTTATTTCT<br>GGAAACAGTGATTTAACAAAGCATATAGTTGAGTATCTCCTTTCTATTGGTAAGAATACACCAATTATGCTAAGTTCT<br>TCGATACAAGCTGAACTTAATAATGCTTATGGGGTTAGCAAAGCTGTAGCTGAAAGCTATGTCGAAAAATATGCTGCT<br>GCTAGTGGTTCTTCGTATTATATTTTCAGATATCCAAACGTTTTTGGTAAATGGTGTAAGCCAAACTATAATTCTTTT<br>ATAGCAACTTTTTGCTACAATATTTCCAATGATATTGAGATTACTATCAATGATGCAGCAGCGCCAGTCAATCTGGTC<br>TATATTGATGATGTTTGTACTGATGCTATAGCTCTTCTCTCTGGGACGGTTGAAAGTGGATATAAAGTTGTTGCACCA<br>ATTTATTCAACAACAGTTGGTGAAGTTGCAGAATTAATTTATAGCTTCAAAAATAGCCGTTCCACCCTGATCACAGAG<br>GCTGTCGGGGCGGGATTTACCCGTGCATTGTATTCTACATGGCTGAGTTATTTACCAGCAGAGAAGTTTGCGTACAAG<br>GTACCTTTTTATGGGGATGCCCGCGGAGTCTTTTGTGAGATGTTGAAAACGCCTTCAGCGGGGCAGTTTTCATTTTTT<br>ACTGCTCACCCTGGTATTACGCGTGGCGGACATTACCATCACAGTAAAAATGAGAAGTTTTTGGTCATTCGAGGTCAG<br>GCATGCTTTAAATTTGAACATGTGATTACCGGTGAGCGATATGAACTGAAAGTTTCATCGGGTGAGTTTAAGATTGTT<br>GAAACAGTTCCTGGTTGGACACATGACATTACAAATATTGGAACTGATGAATTAATAGTCATGCTCTGGGCAAATGAA<br>ATTTTCAACCGTGATGAGCCCGATACTATTGCGAGACCTCTATAATGAAAAAATTAAAAGTTATGTCTGTTGTTGGAA<br>CCCGTCCTGAGATTATCCGTTTGTCGAGGGTTCTTGCTAAGTTTGATGAATACTGCGAGCATATTATTGTCCATACTG<br>GTCAAAATTATGATTACGAATTAAATGAAGTGTTCTTCAATGACTTGGGTGTTCGAAAACCTGATTATTTTTTAAATG<br>CAGCGGGTAAAAATGCGGCGGAAACCATTGGTCAGGTTATTATTAAGGTAGATGAAGTATTAGAAATCGAAAAACCTG<br>AAGCAATACTGGTATTGGGCGATACGAATTCATGTATTTCTGCCATTCCGGCCAAACGCCGTAAAGTGCCTATATTTC<br>ATATGGAAGCAGGTAACCGTTGTTTCGATCAACGCGTGCCTGAAGAAACCAACAGACGTATTGTTGACCATACGGCTG<br>ATATCAATATGACCTACAGTGATATTGCTCGTGAATATCTCTTGGCTGAAGGTATCCCAGCTGATCGGATCATAAAAA<br>CTGGTAGCCCTATGTTTGAGGTTCTTTCATATTATATGCCCCAAATTGATGGTTCAGATGTGCTATCGCGTTTGAATC<br>TACAGTCTGGTGAGTTTTTTGTAGTAAGTGCGCATCGTGAAGAGAATGTTGATTCTCCAAAACAGCTCGTAAAGCTTG<br>CGAACATTCTAAATACTGTTGCTGAAAAATATAATCTTCCAGTTATTGTCTCCACACACCCAAGGACACGTAACCGAA<br>TCCGTGAGCAAGGAATTGAATTTCATTCAAATATAAATCTACTGAAACCATTGGGTTTCCATGATTATAACCACTTGC<br>AGAAGAACTCACGAGCTGTGCTTTCAGATAGCGGTACTATCACTGAAGAGTCATCCATCATGAATTTCCCAGCGGTAA<br>ACATCCGGGAAGCGCATGAGCGTCCGGAAGGCTTTGAGGAAGCATCCGTCATGATGGTGGGGTTAGAGTGTGAACGCG<br>TATTACAAGCGCTGGATATTCTGGCAACACAACCGCGAGGTGAAGTCCGTCTTTTACGTCAGGTTAGTGATTACAGCA<br>TGCCAAATGTGTCGGATAAAGTTGTCAGAATTGTTCACTCTTACACAGATTATGTTAAGAGAGTCGTCTGGAAAGAAT<br>ATTGATGAAACTTGCTTTAATCATAGATGATTACCTGCCCAACAGTACTCGTGTTGGTGCAAAAATGTTTCATGAACT<br>TGCTCAAGAATTTATCCAGCGTGGGCACGATGTTACGGTAATTACTCCTGGTACGGGCATGCAAGAAGAGATTTCTTT<br>TGATACCTTTCAGGGGGTAAAAACATGGCGTTTTAAAAGCGGGCCGCTCAAGGATGTAAGTAAAATTCAGCGAGCGGT<br>CAATGAAACGCTTTTGTCCTATCGGGCGTGGAAAGCCATCAAAAAATGGGTAAAAAAAGAGACCTTTGAGGGGGTGAT<br>TTATTATTCACCTTCCATATTCTGGGGGCCTTTAGTTAAAAAAATTAAAGCTCGTTGCCAATGTCCTGCTTATCTTAT<br>TTTAAGAGATATGTTTCCACAATGGGTAATTGATGCAGGAATGCTTAATGCTGGTTCCCCAATAGAACGCTACTTTCG |

-continued

| SEQUENCES |
| --- |
| TCTTTTTGAAAAAATATCTTATCGTCAGGCAAATCGTATTGGACTTATGTCTGATAAGAATCTTGATGTTTTTCGGAA<br>AGATAATAAAGGCTATCCGTGCGAAGTTTTGCGTAATTGGGCATCCCTAACACCAACGATCATACCCAAGGATTATAT<br>ACCACTACGTAAGCGACTTGGCCTAGAGGATAAAACCATTTTCTTCTATGGTGGAAACATAGGTCATGCACAGGACAT<br>GACAAACTTGATGCGACTTGTGAGAAACATGGCAGCATATCCTCAAGCTCATTTCCTATTTATTGGCCAGGGGGATGA<br>AGTTGAATTAATTAATTCATTAGCATCTGAGTGGGCATTGACGAATTTCACCTATTTGCCCTCGGTTAACCAAGATGA<br>ATTTAAGTTCATTTTGTCGGAAATGGATATCGGCTTGTTTTCTCTTTCCGCTAGACACTCTTCCCATAATTTTCCTGG<br>TAAGTTATTAGGCTATATGGTTCAGTCGCTACCTATTTTAGGTAGCGTAAATGCCGGAAATGATTTGCTCGACATTGT<br>CAATCAAAATAATGCGGGATTAATCCATGTCAATGGTGAGGACGATAAATTATGTCAATCTGCGCTATTAATGTTGCA<br>TGATATTGATGTGCGCCGGCAACTTGGTTCGGGGGCGAATATATTGTTGAAAGAACAATTCTCCGTTGAGTCTGCGGC<br>ACAGACGATAGAAATGAGGTTGGAGGCATGCAATGCGATTAATTGATAATGACCAACTCGACGAATTATATGATCAAG<br>CCGGGCAATCGGAACGTTTACGTTCCCACCTTATGATGCACGGCTCGCATCAAGAAAAGGTACAGCGTTTACTTATTG<br>CATTAGTAAAGGGCAGCTATGTTGAACCGCATTATCACGAACTTCCTCATCAGTGGGAAATGTTCATTGTTATGGAGG<br>GGCAACTTCAGGTTTGTTTGTATGGTAGAAATGGTGAGGTTATAAAGCAATTTATAGCAGGAGATAATACTGGAATGA<br>GCATTGTGGAGTTTTCTCCGGGCGATATACACAGTGTCGAATGCCTATCTCCGCGTGCTCTTATGGTGGAAGTTAAGG<br>AGGGGCCATTTGACCCTTCTTTTGCAAAATCGTTCGTGTGAGCGGCCGCGAGCTCGTCGACTCGAGGATCCGTGTAGG<br>CTGGAGCTGCTTCGAAGTTCCTATACTTTCTAGAGAATAGGAACTTCGGAATAGGAACTAAGGAGGATATTCATATGG<br>ATAAAGCCGTAAGCATATAAGCATGGATAAGCTATTTATACTTTAATAAGTACTTTGTATACTTATTTGCGAACATTC<br>CAGGCCGCGAGCATTCAGCGCGGTGATCACACCTGACAGGAGTATGTAATGTCCAAGCAACAGATCGGCGTAGTCGGT<br>ATGGCAGTGATGGGACGCAACCTTGCGCTCAACATCGAAAGCCGTGGTTATACCGTCTCTATTTTCAACCGTTCCCGT<br>GAGAAGACGGAAGAAGTGATTGCCGAAAATCCAGGCAAGAAACTGGTTCCTTACTATACGGTGAAAGAGTTTGTCGAA<br>TCTCTGGAAACGCCTCGTCGCATCCTGTTAATGGTGAAAGCAGGTGCAGGCACGGATGCTGCTATTGATTCCCTCAAA<br>CCATATCTCGATAAAGGAGACATCATCATTGATGGTGGTAACACCTTCTTCCAGGACACTATTCGTCGTAATCGTGAG<br>CTTTCAGCAGAGGGCTTTAACTTCATCGGTACCGGTGTTTCTGGCGGTGAAGAGGGGGCGCTGAAAGGTCCTTCTATT<br>ATGCCTGGTGGCCAGAAAGAAGCCTATGAATTGGTAGCACCGATCCTGACCAAAATCGCCGCCGTAGCTGAAGACGGT<br>GAACCATGCGTTACCTATATTGGTGCCGATGGCGCAGGTCACTATGTGAAGATGGTTCACAACGGTATTGAATACGGC<br>GATATGCAGCTGATTGCTGAAGCCTATTCTCTGCTTAAAGGTGGCCTGAACCTCACCAACGAAGAACTGGCGCAGACC<br>TTTACCGAGTGGAATAACGGTGAACTGAGCAGTTACCTGATCGACATCACCAAAGATATCTTCACCAAAAAAGATGAA<br>GACGGTAACTACCTGGTTGATGTGATCCTGGATGAAGCGGCTAACAAAGGTACCGGTAAATGGACCAGCCAGAGCGCG<br>CTGGATCTCGGCGAACCGCTGTCGCTGATTACCGAGTCTGTGTTTGCACGTTATATCTCTTCTCTGAAAGATCAGCGT<br>GTTGCCGCATCTAAAGTTCTCTCTGGTCCGCAAGCACAGCCAGCAGGCGACAAGGCTGAGTTCATCGAAAAAGTTCGT<br>CGTGCGCTGTATCTGGGCAAAATCGTTTCTTACGCCCAGGGCTTCTCTCAGCTGCGTGCTGCGTCTGAAGAGTACAAC<br>TGGGATCTGAACTACGGCGAAATCGCGAAGATTTTCCGTGCTGGCTGCATCATCCGTGCGCAGTTCCTGCAGAAAATC<br>ACCGATGCTTATGCCGAAAATCCACAGATCGCTAACCTGTTGCTGGCTCCGTACTTCAAGCAAATTGCCGATGACTAC<br>CAGCAGGCGCTGCGTGATGTCGTTGCTTATGCAGTACAGAACGGTATTCCGGTTCCGACCTTCTCCGCAGCGGTTGCC<br>TATTACGACAGCTACCGTGCTGCTGTTCTGCCTGCGAACCTGATCCAGGCACAGCGTGACTATTTTGGTGCGCATACT<br>TATAAGCGTATTGATAAAGAAGGTGTGTTCCATACCGAATGGCTGGATTAA |
| SEQ ID NO: 16 (example O16 rfb locus nucleotide sequence-O16-EPA<br>production strain stLMTB11739)<br>ATGACGAATTTAAAAGCAGTTATTCCTGTAGCGGGTCTCGGGATGCATATGTTGCCTGCCACTAAGGCGATACCCAAA<br>GAGATGCTACCAATCGTCGACAAGCCAATGATTCAGTACATTGTTGACGAGATTGTGGCTGCAGGGATCAAAGAAATC<br>CTCCTGGTAACTCACGCGTCCAAGAACGCGGTCGAAAACCACTTCGACACCTCTTATGAGTTAGAATCACTCCTTGAG<br>CAGCGCGTGAAGCGTCAACTGCTGGCGGAAGTACAGTCCATCTGTCCGCCGGGCGTGACCATTATGAACGTGCGTCAG<br>GGCGAACCTTTAGGTTTAGGCCACTCCATTTTGTGTGCGCGACCTGCCATTGGTGACAACCCATTTGTCGTGGTACTG<br>CCAGACGTTGTGATCGACGATGCCAGCGCCGACCCGCTACGTTACAACCTTGCTGCCATGATTGCACGTTTCAACGAA<br>ACGGGCCGCAGCCAGGTGCTGGCAAAACGTATGCCGGGTGACCTCTCTGAATACTCCGTCATCCAGACTAAAGAGCCG<br>CTGGACCGTGAGGGTAAAGTCAGCCGCATTGTTGAATTTATCGAAAAACCGGATCAGCCGCAGACGCTGGACTCAGAC<br>ATCATGGCCGTAGGTCGCTATGTGCTTTCTGCCGATATTTGGCCGGAACTGGAACGTACTCAGCCTGGTGCATGGGGA<br>CGTATTCAGCTGACTGATGCTATTGCCGAGCTGGCGAAAAAACAATCCGTTGATGCAATGCTGATGACCGGCGACAGT<br>TACGACTGCGGCAAAAAAATGGGCTATATGCAGGCGTTTGTGAAGTATGGCCTACGCAACCTGAAAGAAGGGGCGAAG<br>TTCCGTAAAGGTATTGAGAAGCTGTTAAGCGAATAATGAAAATCTGACCGGATGTAACGGTTGATAAGAAAATTATAA<br>CGGCAGTGAAAATTCGCAGCAAAAGTAATTTGTTGCGAATCTTCCTGCCGTTGTTTTATATAAACCATCAGAATAACA<br>ACGAGTTAGCAGTAGGGTTTTATTCAAAGTTTTCCAGGATTTTCCTTGTTTCCAGAGCGGATTGGTAAGACAATTAGC<br>GTTTGAATTTTTCGGGTTTAGCGCGAGTGGGTAACGCTCGTCACATCATAGGCATGCATGCAGTGCTCTGGTAGCTGT<br>AAAGCCAGGGGCGGTAGCGTGCATTAATACCTCTATTAATCAAACTGAGAGCCGCTTATTTCACAGCATGCTCTGAAG<br>TAATATGGAATAAATTAAGTGAAAATACTTGTTACTGGTGGCGCAGGATTTATTGGTTCAGCTGTAGTTCGTCACATT<br>ATAAATAATACGCAGGATAGTGTTGTTAATGTCGATAAATTAACGTACGCCGGAAACCGGGAATCACTTGCTGATGTT<br>TCTGATTCTGAACGCTATGTTTTTGAACATGCGGATATTTGCGATGCACCTGCAATGGCACGGATTTTTGCTCAGCAT<br>CAGCCGGATGCAGTGATGCACCTGGCTGCTGAAAGCCATGTTGACCGTTCAATTACAGGCCCTGCGGCATTTATTGAA<br>ACCAATATTGTTGGTACTTATGTCCTTTTGGAAGCCGCTCGCAATTACTGGTCTGCTCTTGATAGCGACAAGAAAAAT<br>AGCTTCCGTTTTCATCATATTTCTACTGACGAAGTCTATGGTGATTTGCCTCATCCAGATGAAGTAAATAATACAGAA<br>GAATTACCCTTATTTACTGAGACGACAGCTTACGCGCCAAGCAGCCCTTATTCCGCATCCAAAGCATCCAGCGATCAT<br>TTAGTCCGCGCGTGGAAACGTACATATGGTTTACCGACAATTGTGACTAATTGCTCGAACAACTATGGTCCTTATCAT<br>TTCCCGGAAAAGCTTATTCCACTGGTTATTCTTAATGCACTGGAAGGTAAGGCATTACCTATTTATGGCAAAGGAGAT<br>CAGATCCGCGACTGGTTGTATGTTGAAGATCATGCGCGTGCGTTATATACCGTCGTAACCGAAGGTAAAGCGGGTGAA<br>ACTTATAACATTGGTGGGCACAACGAAAAGAAAAACATCGATGTAGTGCTCACTATTTGTGATTTGCTGGATGAGATT<br>GTACCGAAAGAGAAATCTTATCGTGAGCAAATCACTTATGTTGCTGATCGTCCGGGACACGATCGCCGCTATGCTATT<br>GATGCTGAGAAGATTGGTCGCGCATTGGGATGGAAACCACAGGAAACGTTTGAGAGCGGGATTCGTAAAACGGTGGAA<br>TGGTACCTGTCCAATACAAAATGGGTTGATAATGTGAAAAGTGGTGCCTATCAATCGTGGATTGAACAGAACTATGAG<br>GGCCGCCAGTAATGAATATCCTCCTTTTTGGCAAAACAGGGCAGGTAGGTTGGGAACTACAGCGTGCTCTGGCACCTT<br>TGGGTAATTTGATTGCTTTTGATGTTCACTCTACTGATTATTGCGGTGATTTTAGTAATCCTGAAGGTGTAGCTGAAA<br>CCGTAAGAAGCATTCGGCCGGATATTATTGTCAATGCAGCCGCTCACACCGCAGTAGACAAAGCAGAATCAGAACCGG<br>AGTTTGCACAATTAATTAACGCAACAAGTGTCGAAGCGATTGCGAAAGCAGCAAATGAAGTTGGAGCCTGGGTTATCC<br>ATTACTCGACTGATTACGTCTTCCCTGGAAATGGCGATATGCCATGGCTGGAGACGGATGCAACCGCACCACTAAATG<br>TTTACGGTGAAACCAAGTTAGCCGGAGAAAAAGCGTTACAGGAATATTGCGCGAAGCATCTTATTTTCCGGACCAGCT<br>GGGTCTATGCAGGAAAAGGAAATAACTTCGCCAAAACGATGTTACGTCTGGCAAAAGAGCGTGAAGAATTAGCGGTTA<br>TTAACGATCAGTTTGGTGCGCCAACAGGTGCTGAACTGCTGGCTGATTGTACAGCACATGCCATTCGTGTCGCACTGA |

-continued

| SEQUENCES |
| --- |
| ATAAACCGGATGTCGCAGGCTTGTACCATTTGGTAGCCAGTGGTACCACAACCTGGTACGATTATGCTGCGCTGGTTT<br>TTGAAGAGGCGCGCAAAGCAGGCATTCCCCTTGCACTCAACAAGCTCAACGCAGTACCAACAACAGCCTATCCTACAC<br>CAGCTCGTCGTCCACATAACTCTCGCCTTAATACAGAAAAATTTCAGCAGAACTTTGCGCTTGTCTTGCCTGACTGGC<br>AGGTTGGCGTGAAACGAATGCTCAATGAATTATTTACGACTACAGCAATTTAATAGTTTTTGCATCTTGTTCGTGATG<br>GTGGAGCAAGATGAATTAAAAGGAATGATGAAATGAAAATGCGTAAAGGTATTATTTTAGCGGGTGGTTCTGGTACAC<br>GTCTTTATCCTGTGACTATGGCTGTCAGTAAACAGCTATTACCTATTTATGATAAACCGATGATCTATTACCCGCTCT<br>CTACACTGATGTTGGCGGGTATTCGCGATATTTTGATTATCAGTACACCTCAGGATACTCCTCGTTTTCAACAATTGC<br>TGGGTGACGGTAGCCAGTGGGGCCTGAATCTTCAGTACAAAGTGCAACCTAGCCCAGATGGCCTCGCGCAGGCATTTA<br>TCATCGGTGAAGAGTTTATTGGTGGTGATGATTGTGCTTTGGTTCTTGGTGATAATATCTTTTACGGTCACGATCTGC<br>CGAAGCTAATGGAGGCCGCTGTTAACAAAGAAAGTGGTGCAACGGTATTTGCCTATCACGTTAATGATCCAGAACGCT<br>ATGGTGTCGTTGAGTTTGATAAAAACGGTACGGCAATCAGTCTGGAAGAAAAACCGTTAGAACCAAAGAGTAATTACG<br>CCGTTACAGGTCTGTACTTTTATGATAACGACGTGGTTCAGATGGCGAAAAACTTGAAGCCGTCTGCACGTGGTGAGT<br>TAGAAATTACAGATATTAACCGTATTTATCTTGAGCAGGGACGTCTGTCTGTCGCGATGATGGGGCGTGGCTACGCGT<br>GGCTGGACACGGGGACTCATCAGAGTCTGATAGAAGCAAGTAATTTTATTGCGACAATTGAAGAGCGCCAGGGATTGA<br>AGGTTTCCTGTCCTGAAGAGATTGCATTTCGTAAAGGTTTTATTGATGTTGAGCAAGTAAGAAAATTAGCTGTACCAC<br>TAATAAAGAATAATTATGGGCAGTATCTTTATAAAATGACGAAGGATTCAAATTAATGAATGTGATTAGAACTGAAAT<br>TGAAGATGTGCTAATTCTGGAGCCAAGAGTATTTGGTGATGATAGAGGTTTCTTTTATGAGAGCTTTAATCAATCAGC<br>ATTTGAACATATTCTAGGCTATCCGGTCAGCTTTGTTCAAGACAATCACTCACGTTCATCAAAAAATGTACTCAGAGG<br>CCTTCACTTTCAACGCGGCGAGTACGCACAAGATAAACTTGTACGCTGCACTCATGGAGCAGTTTTTGATGTTGCTGT<br>TGATATTCGACCCAATTCGGTATCCTTTGGTAAATGGGTTGGTGTTCTGCTTTCAGCTGATAATAAGCAGCAGTTGTG<br>GATACCAAAAGGGTTTGCTCATGGCTTTTTGGTTCTGTCTGATATCGCTGAATTTCAATATAAAACTACAAACTATTA<br>TCATCCTGAAAGCGATTGTGGAATATGTTGGAATGATGAACGCATTGCAATTGATTGGCCCCAAACATCAGGGTTAAT<br>CCTTTCGCCAAAAGATGAAAGGCTCTTTACGTTAGATGAGCTTATCAGATTAAAATTAATTGCATGAATACGAATAAA<br>TTATCTTTAAGAAGAAACGTTATATATCTGGCTGTCGTTCAAGGTAGCAATTATCTTTTACCATTGCTTACATTTCCA<br>TATCTTGTAAGAACACTTGGTCCTGAAAATTTCGGTATATTCGGTTTTTGCCAAGCGACTATGCTATATATGATAATG<br>TTTGTTGAATATGGTTTCAATCTCACAGCAACTCAGAGTATTGCCAAAGCAGCAGATAGTAAAGATAAAGTAACGTCT<br>ATTTTTTGGGCGGTGATATTTTCAAAAATAGTTCTTATCGTCATTACATTGATTTTCTTAACGTCGATGACCTTGCTT<br>GTTCCTGAATATAACAAGCATGCCGTAATTATATGGTCGTTTGTTCCTGCATTAGTCGGGAATTTAATCTACCCTATC<br>TGGCTGTTTCAGGGAAAAGAAAAAATGAAATGGCTGACTTTAAGTAGTATTTTATCCCGCTTGGCTATTATCCCTCTA<br>ACATTTATTTTTGTGAACACAAAGTCAGATATAGCAATTGCCGGTTTTATTCAGTCAAGTGCAAATCTGGTTGCTGGA<br>ATTATTGCACTAGCTATCGTTGTTCATGAAGGTTGGATTGGTAAAGTTACGCTATCATTACATAATGTGCGTCGATCT<br>TTAGCAGACGGTTTTCATGTTTTTATTTCCACATCTGCTATTAGTTTATATTCTACGGGAATAGTTATTATCCTGGGA<br>TTTATATCTGGACCAACGTCCGTAGGGAATTTTAATGCGGCCAATACTATAAGAAACGCGCTTCAAGGGCTATTAAAT<br>CCTATCACCCAAGCAATATACCCAAGAATATCAAGTACGCTTGTTCTTAATCGTGTGAAGGGTGTGATTTTAATTAAA<br>AAATCATTGACCTGCTTGAGTTTGATTGGTGGTGCTTTTTCATTAATTCTGCTCTTGGGTGCATCTATACTAGTAAAA<br>ATAAGTATAGGGCCGGGATATGATAATGCAGTGATTGTGCTAATGATTATATCGCCTCTGCCTTTTCTTATTTCATTA<br>AGTAATGTCTATGGCATTCAAGTTATGCTGACCCATAATTATAAGAAAGAATTCAGTAAGATTTTAATCGCTGCGGGT<br>TTGTTGAGTTTGTTGTTGATTTTTCCGCTAACAACTCTTTTTAAAGAGATTGGTGCAGCAATAACATTGCTTGCAACA<br>GAGTGCTTAGTTACGTCACTCATGCTGATGTTCGTAAGAAATAATAAATTACTGGTTTGCTGAGGATTTTATGTACGA<br>TTATATCATTGTTGGTTCTGGTTTGTTTGGTGCCGTTTGTGCGAATGAGTTAAAAAAGCTAAACAAAAAAGTTTTAGT<br>GATTGAGAAAAGAAATCATATCGGTGGAAATGCGTACACAGAGGACTGTGAGGGTATCCAGATTCATAAATATGGTGC<br>ACATATTTTTCATACCAATGATAAATATATATGGGATTACGTTAATGATTTAGTAGAATTTAATCGTTTTACTAATTC<br>TCCACTGGCGATTTATAAAGACAAATTATTCAACCTTCCTTTTAATATGAATACTTTCCACCAAATGTGGGGAGTTAA<br>AGATCCTCAAGAAGCTCAAAATATCATTAATGCTCAGAAAAAAAAGTATGGTGACAAGGTACCTGAAAATTTGGAGGA<br>GCAGGCGATTTCATTAGTTGGGGAGGACTTATACCAAGCATTGATAAAGGGTTATACGGAGAAGCAGTGGGGAAGAAG<br>TGCAAAAGAATTGCCTGCATTTATTATTAAGCGAATCCCAGTGAGATTTACGTTTGATAACAATTATTTTTCCGATCG<br>CTATCAAGGTATTCCGGTGGGAGGCTACACTAAGCTTATTGAAAAAATGCTTGAAGGTGTGGACGTAAAATTAGGCAT<br>TGATTTTTTGAAAGACAAAGATTCTCTAGCGAGTAAAGCCCATAGAATCATCTACACTGGACCCATTGATCAGTACTT<br>CGACTATAGGTTTGGAGCGTTAGAATATCGCTCTTTAAAATTTGAGACGGAACGCCATGAATTTCCAAACTTCCAAGG<br>GAATGCAGTAATAAATTTCACTGATGCTAATGTACCATATACCAGAATAATTGAGCATAAACATTTTGACTATGTTGA<br>GACAAAGCATACGGTTGTTACAAAAGAATATCCATTAGAGTGGAAAGTTGGCGACGAACCCTACTATCCAGTTAATGA<br>TAATAAAAACATGGAGCTTTTTAAGAAATATAGAGAGTTAGCTAGCAGAGAAGACAAGGTTATATTTGGCGGGCGTTT<br>GGCCGAGTATAAATATTATGATATGCATCAAGTGATATCTGCCGCTCTTTATCAAGTGAAAAATATAATGAGTACGGA<br>TTAATGATCTATCTTGTAATTAGTGTCTTTCTCATTACAGCATTTATCTGTTTATATCTTAAGAAGGATATATTTTAT<br>CCAGCCGTATGCGTTAATATCATCTTCGCACTGGTCTTATTGGGATATGAAATAACGTCAGATATATATGCTTTTCAG<br>TTAAATGACGCTACGTTGATTTTTCTACTTTGCAATGTTTTGACATTTACCCTGTCATGTTTATTGACGGAAAGTGTA<br>TTAGATCTAAATATCAGAAAAGTCAATAATGCTATTTATAGCATACCATCGAAGAAAGTGCATAATGTAGGCTTGTTA<br>GTTATTTCTTTTTCGATGATATATATATGCATGAGGTTAAGTAACTACCAGTTCGGGACTAGCTTACTTAGCTATATG<br>AATTTGATAAGAGATGCTGATGTTGAAGACACATCAAGAAATTTCTCAGCATACATGCAGCCAATCATTCTAACTACT<br>TTTGCTTTATTTATTTGGTCTAAAAAATTTACTAATACAAAGGTAAGTAAAACATTTACTTTACTTGTTTTTATTGTA<br>TTCATCTTTGCAATTATACTGAATACTGGTAAGCAAATTGTCTTTATGGTTATCATCTCTTATGCATTCATCGTAGGT<br>GTTAATAGAGTAAAACATTATGTTTATCTTATTACAGCTGTAGGTGTTCTATTCTCCTTGTATATGCTCTTTTTACGT<br>GGACTGCCTGGGGGGATGGCATATTATCTATCCATGTATTTGGTCAGCCCTATAATCGCGTTTCAGGAGTTTTATTTT<br>CAGCAAGTATCTAACTCTGCCAGTTCTCATGTCTTTTGGTTTTTTGAAAGGCTGATGGGGCTATTAACAGGTGGAGTC<br>TCTATGTCGTTGCATAAAGAATTTGTGTGGGTGGGTTTGCCAACAAATGTTTATACTGCTTTTTCGGATTATGTTTAT<br>ATTTCCGCGGAGCTAAGCTATTTGATGATGGTTATTCATGGCTGTATTTCAGGTGTTTTATGGAGATTGTCTCGAAAT<br>TACATATCTGTGAAAATATTTTATTCATATTTTATTTATACCTTTTCTTTCATTTTTTATCATGAAAGCTTCATGACT<br>AATATTAGCAGTTGGATACAAATAACTCTTTGTATCATAGTATTCTCTCAATTTCTTAAGGCCCAGAAAATAAAGTGA<br>AAATGTATTTTTTGAATGATTTAAATTTCTCTAGACGCGATGCTGGATTTAAAGCAAGAAAAGATGCACTGGACATTG<br>CTTCAGATTATGAAAACATTTCTGTTGTTAACATTCCTCTATGGGGTGGAGTAGTCCAGAGAATTATTAGTTCTGTTA<br>AGCTTAGTACATTTCTCTGCGGTCTTGAAAATAAAGATGTTTTAATTTTCAATTTCCCGATGGCCAAACCATTTTGGC<br>ATATATTGTCATTCTTTCACCGCCTTCTAAAATTTAGAATAGTACCTCTGATTCATGATATTGATGAATTAAGAGGAG<br>GAGGGGGTAGTGATTCTGTGCGGCTTGCTACCTGTGATATGGTCATAAGTCACAATCCACAAATGACAAAGTACCTTA<br>GTAAATATATGTCTCAGGATAAAATCAAAGACATAAAAAATATTTGATTACCTCGTCTCATCTGATGTGGAGCATCGAG<br>ATGTTACGGATAAGCAACGAGGGGTCATATATGCTGGCAACCTTTCTAGGCATAAATGTTCTTTCATATATACTGAAG<br>GATGCGATTTTACTCTCTTTGGTGTCAACTATGAAAATAAAGATAATCCTAAATATCTTGGAAGTTTTGATGCTCAAT<br>CTCCGGAAAAGATTAACCTCCCAGGCATGCAATTTGGACTCATTTGGGATGGAGATTCTGTCGAAACCTGTAGTGGTG |

-continued

| SEQUENCES |
| --- |

CCTTTGGCGACTATTTAAAGTTTAATAACCCTCATAAGACATCTCTTTATCTTTCAATGGAACTTCCAGTATTTATAT
GGGATAAAGCCGCCCTTGCGGATTTCATTGTAGATAATAGAATAGGATATGCAGTGGGATCAATCAAAGAAATGCAAG
AGATTGTTGACTCCATGACAATAGAAACTTATAAGCAAATTAGTGAGAATACAAAAATTATTTCTCAGAAAATTCGAA
CAGGAAGTTACTTCAGGGATGTTCTTGAAGAGGTGATCGATGATCTTAAAACTCGCTAAACGATATGGTCTCTGTGGT
TTTATTCGGCTTGTTAGAGATGTCTTATTGACTCGTGTATTTTACCGGAACTGTAGAATTATTCGATTTCCCTGCTAT
ATTCGCAATGATGGTAGCATTAATTTTGGTGAAAATTTCACAAGTGGAGTCGGTCTCAGGCTGGATGCATTTGGACGT
GGCGTGATTTTTTTTTCCGATAATGTGCAAGTTAACGACTATGTTCATATCGCCTCAATTGAGAGCGTTACGATAGGT
CGGGATACGCTTATTGCAAGTAAAGTATTTATTACCGATCATAATCACGGTTCCTTTAAGCACTCTGATCCAATGAGT
TCGCCAAATATACCTCCAGACATGCGCACGTTGGAATCTTCAGCTGTTGTAATTGGCCAGAGGGTTTGGTTGGGTGAG
AATGTGACGGTTTTGCCTGGAACAATTATTGGTAATGGAGTCGTAGTCGGCGCCAATTCTGTTGTTAGAGGTTCTATT
CCCGAAAATACTGTCATTGCGGGAGTACCAGCAAAAATCATAAAGAAATACAATCATGAGACCAAATTATGGGAAAAA
GCATAGTCGTTGTTTCTGCGGTCAATTTTACCACTGGCGGTCCATTTACCATTTTGAAAAAATTTTTGGCAGCAACTA
ATAATAAAGAAAATGTCAGTTTTATCGCATTAGTCCATTCTGCTAAAGAGTTAAAAGAAAGTTATCCATGGGTTAAAT
TCATTGAGTTTCCTGAGGTTAAAGGGTCGTGGCTAAAACGTTTGCACTTTGAATATGTAGTTTGTAAAAAACTTTCAA
AAGAGCTGAATGCTACGCATTGGATTTGTCTGCATGATATTACGGCCAATGTCGTCACTAAAAAAAGATATGTGTATT
GTCATAACCCTGCCCCTTTTTATAAAGGAATTTTATTCCGTGAAATTCTTATGGAGCCTAGCTTTTTCTTATTTAAAA
TGCTATACGGGCTGATATATAAAATAAACATTAAAAAAAATACTGCAGTGTTTGTTCAACAATTCTGGATGAAAGAAA
AATTTATCAAGAAATATTCTATAAATAACATCATTGTCAGTCGGCCAGAAATTAAATTATCTGATAAAAGCCAACTTA
CTGATGATGATTCTCAATTTAAGAATAACCCTTCTGAGTTGACAATATTTTACCCTGCTGTTCCACGAGTATTTAAAA
ATTACGAGCTTATTATTAGTGCAGCAAGGAAATTGAAAGAACAATCCAATATTAAATTTCTGCTTACTATCAGTGGTA
CAGAAAATGCGTATGCAAAATATATTATCAGTCTTGCAGAAGGACTGGATAATGTTCATTTCCTCGGGTACTTGGATA
AAGAAAAAAATCGATCATTGTTATAATATTTCAGATATAGTTTGTTTTCCCTCTAGGTTAGAAACATGGGGATTGCCGT
TGTCTGAGGCTAAAGAGCGAGGTAAGTGGGTATTAGCATCAGATTTCCCATTTACTAGAGAAACTCTTGGTAGTTATG
AAAAGAAAGCTTTTTTTGATTCTAATAACGATGACATGTTAGTTAAACTTATTATTGACTTCAAAAAAGGTAACCTCA
AAAAAGATATCTCTGATGCAAATTTCATTTATCGTAATGAAAATGTATTAGTTGGGTTTGATGAACTAGTTAATTTTA
TTACTGAAGAACATTGAAATGGTATATATAATAATCGTTTCCCACGGACATGAAGACTACATCAAAAAATTACTCGAA
AATCTTAATGCTGACGATGAGCACTACAAGATTATCGTACGCGACAACAAAGACTCTCTATTATTGAAACAAATATGC
CAGCATTATGCAGGCCTGGACTATATTAGTGGAGGTGTATACGGCTTTGGTCATAATAATAATATTGCGGTGGCGTAT
GTAAAGGAAAAATATAGACCCGCAGATGATGATTACATTTTGTTTTTGAATCCCGATATCATCATGAAGCATGATGAT
TTGCTGACATATATTAAATATGTCGAAAGTAAGCGTTATGCTTTTAGTACATTATGCCTGTTCCGAGATGAAGCGAAA
TCTTTACATGATTATTCCGTAAGAAAATTTCCTGTGCTTTCTGATTTTATTGTGTCATTTATGTTAGGGATTAATAAA
ACAAAAATTCCTAAAGAAAGTATCTATTCTGATACGGTTGTTGATTGGTGCGCAGGATCATTTATGCTGGTACGTTTT
TCAGATTTTGTGCGTGTAAATGGCTTCGATCAAGGTTACTTTATGTACTGTGAAGATATTGACCTGTGCTTGAGGCTT
AGCCTGGCTGGTGTCAGACTTCATTATGTTCCCGCTTTTCATGCGATACATTATGCTCATCATGACAATCGAAGTTTT
TTTTCAAAAGCCTTCAGATGGCACTTAAAAAGTACTTTTAGATATTTAGCCAGAAAACGTATTTTATCAAATCGCAAC
TTTGATCGAATTTCATCAGTTTTTCACCCGTAAGAGCTCGGTACCCGGGCCTAGGGTGTAGGCTGGAGCTGCTTCGAA
GTTCCTATACTTTCTAGAGAATAGGAACTTCGGAATAGGAACTAAGGAGGATATTCATATCCGTCGACGGCGGCCGCC
CTGCAGGCATGCAAGCTTGATCCATATGGATCGCTAGCTTAATTAAATAAAGCCGTAAGCATATAAGCATGGATAAGC
TATTTATACTTTAATAAGTACTTTGTATACTTATTTGCGAACATTCCAGGCCGCGAGCATTCAGCGCGGTGATCACAC
CTGACAGGAGTATGTAATGTCCAAGCAACAGATCGGCGTAGTCGGTATGGCAGTGATGGGACGCAACCTTGCGCTCAA
CATCGAAAGCCGTGGTTATACCGTCTCTATTTTCAACCGTTCCCGTGAGAAGACGGAAGAAGTGATTGCCGAAAATCC
AGGCAAGAAACTGGTTCCTTACTATACGGTGAAAGAGTTTGTCGAATCTCTGGAAACGCCTCGTCGCATCCTGTTAAT
GGTGAAAGCAGGTGCAGGCACGGATGCTGCTATTGATTCCCTCAAACCATATCTCGATAAAGGAGACATCATCATTGA
TGGTGGTAACACCTTCTTCCAGGACACTATTCGTCGTAATCGTGAGCTTTCAGCAGAGGGCTTTAACTTCATCGGTAC
GGGTGTTTCTGGCGGTGAAGAGGGGGCGCTGAAAGGTCCTTCTATTATGCCTGGTGGCCAGAAAGAAGCCTATGAATT
GGTAGCACCGATCCTGACCAAAATCGCCGCCGTAGCTGAAGACGGTGAACCATGCGTTACCTATATTGGTGCCGATGG
CGCAGGTCACTATGTGAAGATGGTTCACAACGGTATTGAATACGGCGATATGCAGCTGATTGCTGAAGCCTATTCTCT
GCTTAAAGGTGGCCTGAACCTCACCAACGAAGAACTGGCGCAGACCTTTACCGAGTGGAATAACGGTGAACTGAGCAG
TTACCTGATCGACATCACCAAAGATATCTTCACCAAAAAAGATGAAGACGGTAACTACCTGGTTGATGTGATCCTGGA
TGAAGCGGCTAACAAAGGTACGGGTAAATGGACCAGCCAGAGCGCGCTGGATCTCGGCGAACCGCTGTCGCTGATTAC
CGAGTCTGTGTTTGCACGTTATATCTCTTCTCTGAAAGATCAGCGTGTTGCCCGCATCTAAAGTTCTCTCTGGTCCGCA
AGCACAGCCAGCAGGCGACAAGGCTGAGTTCATCGAAAAAGTTCGTCGTGCGCTGTATCTGGGCAAAATCGTTTCTTA
CGCCCAGGGCTTCTCTCAGCTGCGTGCTGCGTCTGAAGAGTACAACTGGGATCTGAACTACGGCGAAATCGCGAAGAT
TTTCCGTGCTGGCTGCATCATCCGTGCGCAGTTCCTGCAAAAAATCACCGATGCTTATGCCGAAAATCCACAGATCGC
TAACCTGTTGCTGGCTCCGTACTTCAAGCAAATTGCCGATGACTACCAGCAGGCGCTGCGTGATGTCGTTGCTTATGC
AGTACAGAACGGTATTCCGGTTCCGACCTTCTCCGCAGCGGTTGCCTATTACGACAGCTACCGTGCTGCTGTTCTGCC
TGCGAACCTGATCCAGGCACAGCGTGACTATTTTGGTGCGCATACTTATAAGCGTATTGATAAAGAAGGTGTGTTCCA
TACCGAATGGCTGGATTAA

SEQ ID NO: 17 (example O18A rfb locus nucleotide sequence-O18A-EPA production strain BVEC-L-00559)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATCTGTCCGCCGGGCGTGACCATTATGAACGTGCGTCAG
GGCGAACCTTTAGGTTTAGGCCACTCCATTTTGTGTGCGCGACCTGCCATTGGTGACAACCCATTTGTCGTGGTACTG
CCAGACGTTGTGATCGACGATGCCAGCGCCGACCCGCTACGTTACAACCTTGCTGCCATGATTGCACGTTTCAACGAA
ACGGGCCGCAGCCAGGTGCTGGCAAAACGTATGCCGGGTGACCTCTCTGAATACTCCGTCATCCAGACTAAAGAGCCG
CTGGACCGTGAGGGTAAAGTCAGCCGCATTGTTGAATTTATCGAAAAACCGGATCAGCCGCAGACGCTGGACTCAGAC
ATCATGGCCGTAGGTCGCTATGTGCTTTCTGCCGATATTTGGCCGGAACTGGAACGTACTCAGCCTGGTGCATGGGGA
CGTATTCAGCTGACTGATGCTATTGCCGAGCTGGCGAAAAAACAATCCGTTGATGCAATGCTGATGACCGGCGACAGT
TACGACTGCGGCAAAAAAATGGGCTATATGCAGGCGTTTGTGAAGTATGGCCTACGCAACCTGAAAGAAGGGGCGAAG
TTCCGTAAAGGTATTGAGAAGCTGTTAAGCGAATAATGAAAATCTGACCGGATGTAACGGTTGATAAGAAAATTATAA
CGGCAGTGAAAATTCGCAGCAAAAGTAATTTGTTGCGAATCTTCCTGCCGTTGTTTTATATAAACCATCAGAATAACA
ACGAGTTAGCAGTAGGGTTTTATTCAAAGTTTTCCAGGATTTTCCTTGTTTCCAGAGCGGATTGGTAAGACAATTAGC
GTTTGAATTTTTCGGGTTTAGCGCGAGTGGGTAACGCTCGTCACATCATAGGCATGCATGCAGTGCTCTGGTAGCTGT
AAAGCCAGGGGCGGTAGCGTGCATTAATACCTCTATTAATCAAACTGAGAGCCGCTTATTTCACAGCATGCTCTGAAG -continued

| SEQUENCES |
|---|
| TAATATGGAATAAATTAAGTGAAAATACTTGTTACTGGTGGCGCAGGATTTATTGGTTCAGCTGTAGTTCGTCACATT<br>ATAAATAATACGCAGGATAGTGTTGTTAATGTCGATAAATTAACGTACGCCGGAAACCGGGAATCACTTGCTGATGTT<br>TCTGATTCTGAACGCTATGTTTTTGAACATGCGGATATTTGCGATGCACCTGCAATGGCACGGATTTTTGCTCAGCAT<br>CAGCCGGATGCAGTGATGCACCTGGCTGCTGAAAGCCATGTTGACCGTTCAATTACAGGCCCTGCGGCATTTATTGAA<br>ACCAATATTGTTGGTACTTATGTCCTTTTGGAAGCCGCTCGCAATTACTGGTCTGCTCTTGATAGCGACAAGAAAAAT<br>AGCTTCCGTTTTCATCATATTTCTACTGACGAAGTCTATGGTGATTTGCCTCATCCAGATGAAGTAAATAATACAGAA<br>GAATTACCCTTATTTACTGAGACGACAGCTTACGCGCCAAGCAGCCCTTATTCCGCATCCAAAGCATCCAGCGATCAT<br>TTAGTCCGCGCGTGGAAACGTACATATGGTTTACCGACAATTGTGACTAATTGCTCGAACAACTATGGTCCTTATCAT<br>TTCCCGGAAAAGCTTATTCCACTGGTTATTCTTAATGCACTGGAAGGTAAGGCATTACCTATTTATGGCAAAGGAGAT<br>CAGATCCGCGACTGGTTGTATGTTGAAGATCATGCGCGTGCGTTATATACCGTCGTAACCGAAGGTAAAGCGGGTGAA<br>ACTTATAACATTGGTGGCACAACGAAAAGAAAAACATCGATGTAGTGCTCACTATTTGTGATTTGCTGGATGAGATT<br>GTACCGAAAGAGAAATCTTATCGTGAGCAAATCACTTATGTTGCTGATCGTCCGGGACACGATCGCCGCTATGCTATT<br>GATGCTGAGAAGATTGGTCGCGCATTGGGATGGAAACCACAGGAAACGTTTGAGAGCGGGATTCGTAAAACGGTGGAA<br>TGGTACCTGTCCAATACAAAATGGGTTGATAATGTGAAAAGTGGTGCCTATCAATCGTGGATTGAACAGAACTATGAG<br>GGCCGCCAGTAATGAATATCCTCCTTTTGGCAAAACAGGGCAGGTAGGTTGGGAACTACAGCGTGCTCTGGCACCTT<br>TGGGTAATTTGATTGCTTTTGATGTTCACTCTACTGATTATTGCGGTGATTTTAGTAATCCTGAAGGTGTAGCTGAAA<br>CCGTAAGAAGCATTCGGCCGGATATTATTGTCAATGCAGCCGCTCACACCGCAGTAGACAAAGCAGAATCAGAACCGG<br>AGTTTGCACAATTAATTAACGCAACAAGTGTCGAAGCGATTGCGAAAGCAGCAAATGAAGTTGGAGCCTGGGTTATCC<br>ATTACTCGACTGATTACGTCTTCCCTGGAAATGGCGATATGCCATGGCTGGAGACGGATGCAACCGCACCACTAAATG<br>TTTACGGTGAAACCAAGTTAGCCGGAGAAAAAGCGTTACAGGAATATTGCGCGAAGCATCTTATTTTCCGGACCAGCT<br>GGGTCTATGCAGGAAAAGGAAATAACTTCGCCAAAACGATGTTACGTCTGGCAAAAGAGCGTGAAGAATTAGCGGTTA<br>TTAACGATCAGTTTGGTGCGCCAACAGGTGCTGAACTGCTGGCTGATTGTACAGCACATGCCATTCGTGTCGCACTGA<br>ATAAACCGGATGTCGCAGGCTTGTACCATTTGGTAGCCAGTGGTACCACAACCTGGTACGATTATGCTGCGCTGGTTT<br>TTGAAGAGGCGCGCAAAGCAGGCATTCCCCTTGCACTCAACAAGCTCAACGCAGTACCAACAACAGCCTATCCTACAC<br>CAGCTCGTCGTCCACATAACTCTCGCCTTAATACAGAAAAATTTCAGCAGAACTTTGCGCTTGTCTTGCCTGACTGGC<br>AGGTTGGCGTGAAACGAATGCTCAATGAATTATTTACGACTACAGCAATTTAATAGTTTTTGCATCTTGTTCGTGATG<br>GTGGAGCAAGATGAATTAAAAGGAATGATGAAATGAAAATGCGTAAAGGTATTATTTTAGCGGGTGGTTCTGGTACAC<br>GTCTTTATCCTGTGACTATGGCTGTCAGTAAACAGCTATTACCTATTTATGATAAACCGATGATCTATTACCCGCTCT<br>CTACACTGATGTTGGCGGGTATTCGCGATATTTTGATTATCAGTACACCTCAGGATACTCCTCGTTTTCAACAATTGC<br>TGGGTGACGGTAGCCAGTGGGGCCTGAATCTTCAGTACAAAGTGCAACCTAGCCCAGATGGCCTCGCGCAGGCATTTA<br>TCATCGGTGAAGAGTTTATTGGTGGTGATGATTGTGCTTTGGTTCTTGGTGATAATATCTTTTACGGTCACGATCTGC<br>CGAAGCTAATGGAGGCCGCTGTTAACAAAGAAAGTGGTGCAACGGTATTTGCCTATCACGTTAATGATCCAGAACGCT<br>ATGGTGTCGTTGAGTTTGATAAAAACGGTACGGCAATCAGTCTGGAAGAAAAACCGTTAGAACCAAAGAGTAATTACG<br>CCGTTACAGGTCTGTACTTTTATGATAACGACGTGGTTCAGATGGCGAAAAACTTGAAGCCGTCTGCACGTGGTGAGT<br>TAGAAATTACAGATATTAACCGTATTTATCTTGAGCAGGGACGTCTGTCTGTCGCGATGATGGGGCGTGGCTACGCGT<br>GGCTGGACACGGGGACTCATCAGAGTCTGATAGAAGCAAGTAATTTTATTGCGACAATTGAAGAGCGCCAGGGATTGA<br>AGGTTTCCTGTCCTGAAGAGATTGCATTTCGTAAAGGTTTTATTGATGTTGAGCAAGTAAGAAAATTAGCTGTACCAC<br>TAATAAAGAATAATTATGGGCAGTATCTTTATAAAATGACGAAGGATTCAAATTAATGAATGTGATTAGAACTGAAAT<br>TGAAGATGTGCTAATTCTGGAGCCAAGAGTATTTGGTGATGATAGAGGTTTCTTTTATGAGAGCTTTAATCAATCAGC<br>ATTTGAACATATTCTAGGCTATCCGGTCAGCTTTGTTCAAGACAATCACTCACGTTCATCAAAAAATGTACTCAGAGG<br>CCTTCACTTTCAACGCGGCGAGTACGCACAAGATAAACTTGTACGCTGCACTCATGGAGCAGTTTTTGATGTTGCTGT<br>TGATATTCGACCCAATTCGGTATCCTTTGGTAAATGGGTTGGTGTTCTGCTTTCAGCTGATAATAAGCAGCAGTTGTG<br>GATACCAAAAGGGTTTGCTCATGGCTTTTTGGTTCTGTCTGATATCGCTGAATTTCAATATAAAACTACAAACTATTA<br>TCATCCTGAAAGCGATTGTGGAATATGTTGGAATGATGAACGCATTGCAATTGATTGGCCCCAAACATCAGGGTTAAT<br>CCTTTCGCCAAAAGATGAAAGGCTCTTTACGTTAGATGAGCTTATCAGATTAAAATTAATTGCATGAGGCCGGCCTTA<br>AGGAGGACTAGTCCCGGCGCGCCATGAGTTTAATCAAAAACAGTTTTTGGAACCTTTGCGGGTATGTACTTCCAGCTA<br>TTGTGACACTACCAGCTTTGGGTATTATGGGGCGAAAATTAGGCCCAGAATTATTTGGTGTATTCACTTTGGCATTAG<br>CTGTTGTGGGTTATGCAAGCATTTTTGATGCAGGCCTTACTCGCGCAGTGATACGAGAAGTCGCAATTGAAAAAGATA<br>ATGAAGAAAATAAGTTGAAAATTATTTCTTCAGCGACAGTTGTAATTATTTATTTGAGTTTGGCCGCCTCACTCTTAT<br>TATTTTTTTTTAGTGGTCATATCGCATTGCTACTGAACATTAGTGAGACTTTTTTTCATAATGTAAGTGTCTCGCTTA<br>AAATTCTCGCAGCATCCATACCATTATTTTTGATTACTCAAATATGGTTGTCAATTTTAGAAGGTGAAGAAAGATTTG<br>GTTTACTTAATATCTACAAATCAATTACGGGAGTGATATTAGCAATCTCACCGGCATTATTTATACTTATTAAACCCT<br>CTTTGATGTATGCGATAATAGGCTTAGTTCTAGCAAGGTTTTTATGTTTTATTTTGGCTTTTATAATTTGTCACGATA<br>AAGTGCTTAAAGCTAAACTAACAATCGATATACCAACAATTAAAAGATTGTTTATGTTCGGTGGTTGGATTACAGTAA<br>GTAATATCATCAGCCCTGTGCTATCATATTTGATAGGTTTATTGTTTCAAATCAACTTGGGGCTGCTAATGTTGCTT<br>TTTATACTGCACCATCAGAAATTATTTCTCGGCTTAGTATAATTCCAGGTGCGTTTTCAAGAGCCTTATTTCCAAGAT<br>TAGCTAATGCAAATAATTCCGCTGAAAGATATAAAACGAAAAGATTAATTACAATTTCACTTTTAATAATCATCACCC<br>CTATTTTTTGTATTGGCGTGTTATTTTCAGAGAAGATAATGGTTTTATGGATGGGGGCATCATTTTTTGGTGAGCCTG<br>GTTTGGTATTATCAATATTACTGATTGGCTTTATTTTTAATGGATTGGCACAAGTACCATTTGCCAGTATTCAATCCC<br>GAGGTCATGCTAAGATAACTGCATTTGTTCATCTCTTAGAGTTGTTTCCTTATTTATTACTTTTATTTTACCTCATAA<br>AAGCACATGGGGTTGTTGGCGCGGGTATTGCGTGGTCAGTGAGGATGATAGTAGATTATATAGCATTAAGTCTTTTGG<br>ACGGTAAGTATATTAATAAATAAAATTCAAAATGCAAGTTAATAACTCATGGCTTTATTTGGGTAGGTGACAATTTAT<br>AATGATATATATATTAACTTTAACTCTTCTTCTAGTTATAGCCATAATGTTTTCTCTTCTCGGCACAAAAAGTAGGAT<br>CACATCTCCATTACCTTTGCATTTTTTACCATGGTTACTAACTTTAATTGTCGGGATAAGTAATTACGATCAATTTTA<br>CGAGTTTAATGAAAGAAGCTTTTACTCTTTGTTGATTTGGTTTACAGTTATTTTTATATTTTATTTCATAGGGGAACT<br>GGTTAATTATAAACGTGAAAATATAAATGTTTATTATGGTCTTTCACATATTAAATATGAATGTAAAAAATATTGGAT<br>CATTGTCATCCCAATTTCATTATATACCATTTTCGAAATATATATGGTTGGTATGGGGGGAGCAGATGGATTCTTTCT<br>CAATTTACGTCTTGCAAATACATTGGAGGGCTATACGGGTAAAAAATTTATCTTAATGCCTGCTGTATATCCTCTAAT<br>GATGGCTATGTTCGCAATTGTTTGTCTAACAAAAACTTCCAAATTAAATAAATACTCCATTTATTTCTGGATGTTTTT<br>GTATTGTATTGGCACAATGGGAAAATTTTCAATATTAACGCCAATATTGACATATTTAATTATTTATGACTTCAAACA<br>TAGATTAAAAGTAAAAAAAACAATAAAGTTTACATTGTTGATAATTATATTAGCTTTAACTTTGCATTTTACACGTAT<br>GGCTGAGAATGACCACTCAACATTTTTATCTATTTTAGGGCTCTATATTTATTCACCAATAATTGCTTTAGGCCAGTT<br>GAATGAAGTAAATAGTAGTCATTTTGGTGAGTATACGTTTAGATTCATATATGCTATAACTAATAAAATTGGCCTTAT<br>TAAAGAATTGCCAGTAAATACTATTCTTGACTATTCATACGTTCCTGTACCAACAAATGTATATACTGCACTTCAACC<br>ATTTTACCAGGATTTTGGTTATACTGGCATCATATTTGGAGCAGTATTATACGGACTAATATATGTGAGTTTATACAC<br>GGCCGGTGTTCGTGGAAATAATACACAGGCATTACTGATTTACGCATTGTTTTCAGTTAGCAGTGCAACGGCTTTCTT<br>CGCTGAAACGCTAGTAACGAATTTAGCTGGAAATGTGATGTTAGTATTATGTACCATCTTACTATGGCGATTTACAGT |

-continued

| SEQUENCES |
| --- |
| AATATGCAAACCAGTACAGTAACCATTCTAATGGCCACCTACAATGGCGAGGCCTTCATCAAAAATCAGATTTTGTCA<br>CTACAACAACAAACATTTTCTAACTGGCGGTTATTTATTCAGGATGATGGGTCTACAGACAATACTATATCTATAATA<br>AAAAACTTCCAAAAATCTGACTCCAGAATTCGGCTAGTTGATGATAATTTGAAAGGTCAAGGTGCAGGAAAAAATTTT<br>TTATCGCTGATAAAGTACAGCGAGACAGATTATACAATTTATTGTGACCAAGATGATATTTGGTTAGAAAACAAAATA<br>TTTGAATTAGTAAAGTATGCAAATGAAATTAAATTGAATGTATCAGATGCGCCTTCGCTAGTTTATGCTGATGGCTAT<br>GCTTATATGGATGGTGAGGGTACAATCGATTTTTCTGGGATATCTAACAATCATGCTGATCAATTAAAGGATTTTCTT<br>TTTTTTAATGGTGGATACCAAGGATGTTCTATTATGTTCAATCGTGCAATGACCAAATTTCTTCTGAATTATCGAGGA<br>TTTGTATATCTACATGACGATATCACAACATTAGCTGCATACGCTCTTGGTAAAGTTTATTTTCTCCCGAAATACCTT<br>ATGTTATATAGACAGCACACGAATGCGGTAACTGGTATCAAAACATTCCGCAATGGATTGACTTCTAAATTTAAATCA<br>CCAGTAAACTATCTTTTATCACGAAAACATTATCAGGTAAAAAAATCTTTTTTTGAATGTAACAGCTCTATCTTATCA<br>GAGACGAATAAAAAAGTTTTTTTGGATTTTATTTCATTTTGTGAATCAAATAATAAATTTACAGATTTTTTTAAGTTA<br>TGGCGAGGTGGGTTTAGATTAAATAACAGTAGAACTAAATTATTATTAAAATTCTTAATACGGAGAAAATTTAGCGAA<br>TGATTTCAATACTTACACCTACTTTTAATCGGCAACATACTTTATCAAGGCTATTCAATTCTCTTATATTACAAACTG<br>ATAAAGATTTTGAGTGGATAATAATTGATGATGGTAGTATAGATGCAACAGCGGTACTTGTAGAAGATTTTAGAAAAA<br>AATGTGATTTTGACTTGATTTATTGCTATCAGGAAAATAATGGTAAGCCCATGGCTTTAAACGCTGGTGTTAAAGCTT<br>GTAGAGGCGATTATATCTTTATTGTTGACAGTGATGATGCACTAACTCCCGATGCCATAAAATTAATTAAAGAATCAA<br>TACATGATTGCTTATCTGAGAAGGAAAGTTTCAGCGGAGTCGGTTTTAGAAAAGCATATATAAAAGGGGGGATTATTG<br>GTAATGATTTAAATAATTCTTCAGAACATATATACTATTTAAATGCGACTGAGATTAGCAATTTAATAAATGGTGATG<br>TTGCATATTGTTTTAAAAAAGAAAGTTTGGTAAAAAATCCATTCCCCCGTATAGAAGATGAAAAATTTGTTCCAGAAT<br>TATATATTTGGAATAAAATAACTGACAAGGCGAAGATTCGATTTAACATAAGCAAAGTTATATATCTTTGTGAGTATC<br>TTGATGATGGTCTTTCTAAAAATTTCCATAACCAGCTTAAAAAATACCCAAAGGGGTTTAAGATTTATTACAAAGATC<br>AAAGAAAACGAGAGAAAACTTATATAAAAAAAACAAAGATGCTAATTAGATATTTGCAATGTTGTTATTATGAGAAAA<br>TAAAATGAAAATACTATTTGTCATTACAGGTTTAGGCCTTGGAGGTGCTGAGAAGCAGGTTTGTCTTTTAGCTGATAA<br>ATTAAGTTTAAGCGGGCACCATGTAAAGATTATTTCACTTGGACATATGTCTAATAATAAAGTCTTTCCTAGCGAAAA<br>TAATGTTAATGTCATTAATGTAAATATGTCAAAAAACATTTCTGGAGTTATAAAAGGTTGTGTCAGAATTAGAGATGT<br>TATAGCTAATTTCAAACCAGACATTGTACACAGTCATATGTTTCATGCAAACATTATCACTAGATTGTCTGTAATTGG<br>AATCAAAAACAGACCTGGTATTATATCAACTGCACATAATAAAAATGAAGGTGGGTATTTCAGAATGCTCACATATAG<br>AATAACCGATTGTTTAAGTGATTGTTGTACAAATGTTAGCAAAGAAGCAGTGGATGAGTTTTTACGGATAAAAGCCTT<br>TAATCCCGCTAAAGCAATTACTATGTATAATGGGATAGATACCAATAAATTTAAATTTGATTTATTGGCAAGGAGGGA<br>AATTCGAGACGGTATTAATATAAAAAATGATGATATATTATTACTTGCTGCAGGTCGTTTAACGTTAGCTAAAGATTA<br>TCCTAATTTATTGAATGCAATGACTCTGCTTCCTGAACACTTTAAACTTATTATTATTGGTGATGGTGAATTGCGTGA<br>CGAAATTAATATGCTTATAAAAAAATTGCAATTATCTAATAGGGTGTCCTTGTTGGGAGTTAAAAAAAATATTGCTCC<br>CTATTTTTCTGCATGTGATATTTTTGTTCTCTCTTCTCGTTGGGAAGGATTTGGATTAGTCGTGGCAGAAGCTATGTC<br>ATGTGAGCGAATTGTTGTTGGCACGGATTCAGGGGGAGTAAGAGAAGTTATTGGTGACGATGATTTTCTTGTACCCAT<br>ATCTGATTCAACACAACTTGCAAGCAAAATTGAAAAATTGTCTTTGAGCCAGATACGTGATCACATTGGTTTTCGGAA<br>TCGTGAGCGTATTTTAAAAAATTTCTCAATAGATACTATTATTATGCAGTGGCAAGAACTCTATGGAACTATAATTTG<br>CTCAAAACATGAAAGGTAGATTTATATTTGGAACGTGTCTTTTGTTTGAATTTAATTCAATCTCAATTGAGATTTTTG<br>TATTTCAAAAATACCATCATAGCTAACGATGATTGGTATTTATTTTAAGATGCTTTCTATAAATATATTGACGTTTTT<br>AATGCGCCGAAACGATTGGGCTGGGAACAGAGAAGTAAAACTGTTTTGAGAATGAAGAGTTTTTGAGATGTTTATGGA<br>TATTAAAAATTGATCCAGTGAATTAATTATTTATAATAAATCAAGATTTAATGTTAATAAATGATAATCTTTTCTGAC<br>ACTCATATTAATTATGAGTGGTACGTTTGGTAAACGGTAAACTATTATATGACAGCTAGAACAACTAAAGTTTTGCAC<br>TTACAATTACTCCCACTCTTAAGTGGCGTTCAAAGGGTAACATTAAACGAAATTAGTGCGTTATATACTGATTATGAT<br>TATACACTAGTTTGCTCAAAAAAAGGTCCACTAACAAAAGCATTGCTGGAATATGATGTCGATTGTCATTGTATCCCC<br>GAACTTACGAGAGAAATTACCGTAAAGAATGATTTTAAAGCATTGTTCAAGCTTTATAAGTTCATAAAAAAAGAAAAA<br>TTTGACATTGTGCATACACATTCTTCAAAAACAGGTATTTTGGGGCGAGTTGCTGCCAAATTAGCACGTGTTGGAAAG<br>GTGATCCACACTGTACATGGTTTTTCTTTTCCAGCCGCATCTAGTAAAAAAAGTTATTACCTTTATTTTTTCATGGAA<br>TGGATAGCAAAGTTCTTTACGGATAAGTTAATCGTCTTGAATGTAGATGATGAATATATAGCAATAAACAAATTAAAA<br>TTCAAGCGGGATAAAGTTTTTTTAATTCCTAATGGAGTAGACACTGATAAGTTTTCTCCTTTAGAAAATAAAATTTAT<br>AGTAGCACCTTGAATCTAGTAATGGTTGGTAGATTATCCAAGCAAAAAGATCCTGAGACATTATTGCTTGCTGTTGAA<br>AAACTGCTGAATGAAAATGTTAATGTTAAGCTGACACTTGTAGGAGATGGTGAACTAAAAGAACAGTTAGAAAGCAGG<br>TTCAAACGGCAAGATGGACGTATAATTTTTCATGGATGGTCAGATAACATTGTTAATATTTTAAAAGTTAATGATCTT<br>TTTATATTACCTTCTCTTTGGGAGGGTATGCCATTAGCAATTTTAGAAGCATTGAGCTGTGGACTTCCATGTATAGTC<br>ACTAATATTCCAGGTAATAATAGCTTAATAGAAGATGGCTATAATGGTTGTTTGTTTGAAATTAGAGATTGTCAGTTA<br>TTATCTCAAAAAATCATGTCATATGTTGGTAAGCCAGAACTGATTGCACAGCAATCTACCAATGCACGATCATTTATT<br>CTGAAAAATTATGGATTAGTTAAAAGAAATAATAAGGTCAGACAGCTATATGATAATTAAGAGCTCGGTACCCGGGCC<br>TAGGGTGTAGGCTGGAGCTGCTTCGAAGTTCCTATACTTTCTAGAGAATAGGAACTTCGGAATAGGAACTAAGGAGGA<br>TATTCATATCCGTCGACGGCGGCCGCCCTGCAGGCATGCAAGCTTGATCCATATGGATCGCTAGCTTAATTAAATAAA<br>GCCGTAAGCATATAAGCATGGATAAGCTATTTATACTTTAATAAGTACTTTGTATACTTATTTGCGAACATTCCAGGC<br>CGCGAGCATTCAGCGCGGTGATCACACCTGACAGGAGTATGTAATGTCCAAGCAACAGATCGGCGTAGTCGGTATGGC<br>AGTGATGGGACGCAACCTTGCGCTCAACATCGAAAGCCGTGGTTATACCGTCTCTATTTTCAACCGTTCCCGTGAGAA<br>GACGGAAGAAGTGATTGCCGAAAATCCAGGCAAGAAACTGGTTCCTTACTATACGGTGAAAGAGTTTGTCGAATCTCT<br>GGAAACGCCTCGTCGCATCCTGTTAATGGTGAAAGCAGGTGCAGGCACGGATGCTGCTATTGATTCCCTCAAACCATA<br>TCTCGATAAAGGAGACATCATCATTGATGGTGGTAACACCTTCTTCCAGGACACTATTCGTCGTAATCGTGAGCTTTC<br>AGCAGAGGGCTTTAACTTCATCGGTACCGGTGTTTCTGGCGGTGAAGAGGGGGCGCTGAAAGGTCCTTCTATTATGCC<br>TGGTGGCCAGAAAGAAGCCTATGAATTGGTAGCACCGATCCTGACCAAAATCGCCGCCGTAGCTGAAGACGGTGAACC<br>ATGCGTTACCTATATTGGTGCCGATGGCGCAGGTCACTATGTGAAGATGGTTCACAACGGTATTGAATACGGCGATAT<br>GCAGCTGATTGCTGAAGCCTATTCTCTGCTTAAAGGTGGCCTGAACCTCACCAACGAAGAACTGGCGCAGACCTTTAC<br>CGAGTGGAATAACGGTGAACTGAGCAGTTACCTGATCGACATCACCAAAGATATCTTCACCAAAAAAGATGAAGACGG<br>TAACTACCTGGTTGATGTGATCCTGGATGAAGCGGCTAACAAAGGTACGGGTAAATGGACCAGCCAGAGCGCGCTGGA<br>TCTCGGCGAACCGCTGTCGCTGATTACCGAGTCTGTGTTTGCACGTTATATCTCTTCTCTGAAAGATCAGCGTGTTGC<br>CGCATCTAAAGTTCTCTCTGGTCCGCAAGCACAGCCAGCAGGCGACAAGGCTGAGTTCATCGAAAAAGTTCGTCGTGC<br>GCTGTATCTGGGCAAAATCGTTTCTTACGCCCAGGGCTTCTCTCAGCTGCGTGCTGCGTCTGAAGAGTACAACTGGGA<br>TCTGAACTACGGCGAAATCGCGAAGATTTTCCGTGCTGGCTGCATCATCCGTGCGCAGTTCCTGCAAAAAATCACCGA<br>TGCTTATGCCGAAAATCCACAGATCGCTAACCTGTTGCTGGCTCCGTACTTCAAGCAAATTGCCGATGACTACCAGCA<br>GGCGCTGCGTGATGTCGTTGCTTATGCAGTACAGAACGGTATTCCGGTTCCGACCTTCTCCGCAGCGGTTGCCTATTA<br>CGACAGCTACCGTGCTGCTGTTCTGCCTGCGAACCTGATCCAGGCACAGCGTGACTATTTTGGTGCGCATACTTATAA<br>GCGTATTGATAAAGAAGGTGTGTTCCATACCGAATGGCTGGATTAA |

-continued

| SEQUENCES |
| --- |

SEQ ID NO: 18 (example O25B rfb locus nucleotide sequence-O25B-EPA production strain stGVXN4459)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATCTGTCCGCCGGGCGTGACCATTATGAACGTGCGTCAG
GGCGAACCTTTAGGTTTAGGCCACTCCATTTTGTGTGCGCGACCTGCCATTGGTGACAACCCATTTGTCGTGGTACTG
CCAGACGTTGTGATCGACGATGCCAGCGCCGACCCGCTACGTTACAACCTTGCTGCCATGATTGCACGTTTCAACGAA
ACGGGCCGCAGCCAGGTGCTGGCAAAACGTATGCCGGGTGACCTCTCTGAATACTCCGTCATCCAGACTAAAGAGCCG
CTGGACCGTGAGGGTAAAGTCAGCCGCATTGTTGAATTTATCGAAAAACCGGATCAGCCGCAGACGCTGGACTCAGAC
ATCATGGCCGTAGGTCGCTATGTGCTTTCTGCCGATATTTGGCCGGAACTGGAACGTACTCAGCCTGGTGCATGGGGA
CGTATTCAGCTGACTGATGCTATTGCCGAGCTGGCGAAAAAACAATCCGTTGATGCAATGCTGATGACCGGCGACAGT
TACGACTGCGGCAAAAAAATGGGCTATATGCAGGCGTTTGTGAAGTATGGCCTACGCAACCTGAAAGAAGGGGCGAAG
TTCCGTAAAGGTATTGAGAAGCTGTTAAGCGAATAATGAAAATCTGACCGGATGTAACGGTTGATAAGAAAATTATAA
CGGCAGTGAAAATTCGCAGCAAAAGTAATTTGTTGCGAATCTTCCTGCCGTTGTTTTATATAAACCATCAGAATAACA
ACGAGTTAGCAGTAGGGTTTTATTCAAAGTTTTCCAGGATTTTCCTTGTTTCCAGAGCGGATTGGTAAGACAATTAGC
GTTTGAATTTTTCGGGTTTAGCGCGAGTGGGTAACGCTCGTCACATCATAGGCATGCATGCAGTGCTCTGGTAGCTGT
AAAGCCAGGGGCGGTAGCGTGCATTAATACCTCTATTAATCAAACTGAGAGCCGCTTATTTCACAGCATGCTCTGAAG
TAATATGGAATAAATTAAGCTAGCAGTGAAGATACTTGTTACTGGTGGCGCAGGATTTATTGGTTCTGCTGTTGTTCG
TCACATAATAAATAATACGCAAGATAGTGTTGTTAATGTCGATAAATTAACATACGCCGGAAACCTGGAATCACTTGC
AGATGTTTCTGATTCTGAACGCTATTTCTTTGAACATGCGGATATTTGTGATGCAGCTGCAATGGCACGGATTTTTGC
TCAGCATCAGCCGGATGCAGTGATGCACCTGGCAGCTGAAAGCCATGTTGACCGTTCAATTACAGGCCCTGCGGCATT
TATTGAAACCAATATTGTGGGTACTTATGTCCTTTTAGAAGCGGCTCGGAATTATTGGTCTGGTCTGGATGATGAAAA
GAAAAAAAACTTCCGTTTTCATCATATTTCTACTGATGAGGTGTATGGTGACTTACCCCATCCGGATGAAGTAAATAG
CAATGAAACGTTGCCGCTATTTACGGAAACGACAGCATACGCGCCAAGTAGTCCATATTCTGCTTCTAAAGCTTCCAG
CGATCATTTGGTTCGCGCATGGAAACGTACTTATGGTTTACCGACCATTGTGACTAATTGCTCGAACAACTATGGTCC
TTATCATTTCCCGGAAAAGCTTATTCCACTGGTTATTCTTAATTCACTGGAAGGTAAGGCATTACCTATTTATGGCAA
AGGAGATCAGATCCGCGACTGGTTGTATGTAGAGGATCATGCTCGAGCGTTATATACCGTCGTAACCGAAGGTAAAGC
GGGCGAAACTTATAACATTGGTGGACACAACGAAAAGAAAAACATCGACGTAGTGTTCACTATTTGTGATTTGTTGGA
TGAGATAGTCCCGAAAGAGAAATCTTACCGCGAGCAAATTACTTATGTTACCGATCGTCCGGGACACGATCGCCGTTA
TGCGATTGATGCTGAGAAGATTGGTCGCGAATTGGGATGGAAACCACAGGAAACGTTTGAGAGTGGGATTCGTAAAAC
GGTGGAATGGTACCTGTCCAATACAAAATGGGTTGATAATGTGAAAAGTGGTGCCTATCAATCGTGGATTGAACAGAA
CTATGAGGGCCGCCAGTAATGAATATCCTCCTTTTTGGCAAAACAGGGCAGGTAGGTTGGGAACTACAGCGTGCTCTG
GCACCTCTGGGTAATTTGATTGCTCTTGATGTTCACTCCACTGATTACTGTGGTGATTTTAGTAATCCTGAAGGTGTA
GCTGAAACCGTAAGAAGCATTCGGCCTGATATTATTGTCAACGCAGCCGCTCACACCGCAGTAGACAAAGCAGAATCA
GAACCGAAGTTTGCACAATTACTGAACGCGACGAGTGTCGAAGCGATCGCGAAAGCAGCCAATGAAGTCGGCGCCTGG
GTTATTCACTACTCTACTGACTACGTATTTCCGGGGACCGGTGAAATACCATGGCAGGAGGAGGATGCAACCGCACCG
CTAAATGTTTACGGTGAAACCAAGTTAGCGGGAGAAAAAGCATTACAAGAGCATTGTGCGAAGCACCTTATTTTCCGG
ACCAGCTGGGTCTATGCAGGTAAAGGAAATAACTTCGCCAAAACAATGTTGCGTCTGGCAAAAGAGCGTGAAGAATTA
GCCGTTATTAATGATCAGTTTGGTGCGCCAACTGGCGCAGAGTTACTGGCTGATTGTACGGCACATGCTATTCGTGTG
GCACTGAATAAACCGGAAGTCGCAGGCTTGTACCATCTGGTAGCTAGTGGTACCACAACGTGGCACGATTATGCTGCG
CTGGTTTTTGAAGAGGCGCGCAAAGCAGGCATTCCCCTTGCACTCAACAAGCTCAACGCAGTACCAACAACAGCCTAT
CCTACACCAGCTCGTCGTCCACATAACTCTCGCCTTAATACAGAAAAATTTCAGCAGAACTTTGCGCTTGTCTTGCCT
GACTGGCAGGTTGGCGTGAAACGAATGCTTAACGAATTATTTACGACTACAGCAATTTAATAGTTTTTGCATCTTGTT
CGTAATGGTGGAGCAAGATGTATTAAAAGGAATGATGAAATGAAAACGCGTAAAGGTATTATTTTGGCGGGTGGTTCT
GGTACTCGTCTTTATCCTGTGACGATGGCCGTCAGTAAACAGCTGTTACCGATTTATGATAAACCGATGATCTATTAC
CCGCTCTCTACACTGATGTTAGCGGGTATTCGCGATATTCTGATTATCAGTACACCACAGGATACTCCTCGTTTTCAA
CAACTGCTGGGTGACGGGAGCCAGTGGGGCCTGAATCTTCAGTACAAAGTGCAACCGAGTCCGGATGGTCTTGCGCAG
GCGTTTATTATCGGTGAAGAGTTTATTGGTGGTGATGATTGTGCTTTGGTACTTGGTGATAATATCTTCTACGGCCAC
GACCTGCCGAAGTTAATGGACGTAGCTGTTAACAAAGAAAGTGGTGCAACGGTATTTGCCTATCACGTTAATGATCCT
GAACGTTATGGTGTCGTGGAGTTTGATAATAACGGTACTGCAATTAGCCTGGAAGAAAAACCGCTGGAACCAAAAAGT
AACTATGCGGTTACTGGGCTTTATTTCTATGACAATGACGTTGTGGAAATGGCGAAAAACCTTAAGCCTTCTGCCCGA
GGTGAACTGGAAATTACCGATATTAACCGTATTTATATGGAACAAGGACGTTTGTCTGTCGCTATGATGGGGCGTGGC
TATGCATGGCTGGATACAGGGACGCATCAAAGTCTTATTGAAGCAAGCAACTTCATTGCCACCATTGAAGAGCGCCAG
GGACTAAAGGTTTCCTGTCCGGAAGAAATTGCTTATCGTAAAGGGTTTATTGATGCTGAGCAGGTAAAAGTATTAGCC
GAACCGTTGAAGAAAAATGCTTATGGTCAGTATCTGCTCAAAATGATTAAAGGTTATTAATAAGATGAACGTAATTAA
AACTGAAATTCCTGATGTGCTGATTTTTGAACCAAAAGTTTTTGGGGATGAACGTGGCTTCTTTTTTGAGAGTTTTAA
TCAGAGGATTTTTGAAGAAGCAGTAGGTCGTAAGGTTGAGTTTGTTCAGGATAACCATTCTAAGTCCAGTAAAGGTGT
TTTACGTGGTCTTCATTATCAGTTAGAACCTTATGCTCAAGGAAAACTGGTGCGCTGTGTTGTTGGCGAGGTTTTTGA
TGTTGCGGTTGATATTCGTAAATCGTCACCTACATTTGGGAAATGGGTTGGGGTGAATTTGTCTGCTGAGAATAAGCG
TCAGTTGTGGATTCCTGAGGGATTTGCACATGGTTTTTTGGTGCTGAGTGATTTAGCAGAAGTTTTATATAAAACGAA
TCAATATTATGCTCCATCACATGAAAAAAATATTATATGGAATGACCTCTTGCTTAATATTAAATGGCCGAGCACAGC
ACTGATCACTCTGTCTGATAAGGATGCAAATGGGGAAAGATTTGAACTAAGTGAGTTTTGAAATGTCTCTCTTAAAAC
ATAGTATATGGAATGTTGCGGGCTACTTTATACCAACATTAATTGCAATTCCCGCCTTTGGATTAATTGCGAGGAAAA
TTGGTGTAGAACTATTTGGTTTGTATACGTTAGCAATGATTTTTATAGGGTATGCAAGTATATTTGATGCTGGGTTAA
CAAGAGCTGTTGTGCGTGAAATAGCATTACTAAAAAACAGAGTGGACGATTGTAATACGATAATAGTAACTTCTATTA
TCGCTGTGATATTTTTAGGGTTTATCGGAGGCGGGGGAGTGTTTCTGCTTAAAGGCGATATTATTGAACTGTTAAATA
TCTCACCAATATATTACGCCGATTCGATAAAGTCTCTAGTATTATTATCATCTCTGATACCTGTATTCTTAGTCACGC
AAATACTATTAGCAGAGCTTGAGGGTCGGGAATATTTTGGGATTCTAAATATACAAAAAAGTGTAGGGAATTCTTTAA
TTGCAGGGTTACCTGCATTATTTGTTTTAATTAATCAAACGCTTTTTTCTGCAATTATTGGTGTAGCGATTGCAAGAG
TTATATGCTTGTGGTTAAGCTACATTATGAGCAGGGAAAGAATAACTATCGATATCTCATTTTTTTCAATAACTGTTT
TAAAGCGGTTATTTAGATATGGCGGGTGGGTAACTATAAGTAACATAATATCTCCTATATTAGCGAGTATGGATAGAT
TTATTCTATCCCATATCCAGGGAGCATCAAAAATATCATTCTATACAGTCCCTAATGAGCTGGTAACTAGGCTTGGAA
TAGTTCCAGGCTCTCTTGGGAAAGCTGTTTTTCCAAAATTAAGTCATGCAAGGAATTTTACAGCGTCATATGCAGAGC
AAAAAAAAGCTTATATATTAATGACTGTCATTGTAATGCCTTTGGTTTTATTTGTATATTATTACGCAAAGTTTATTT
TAACATTGTGGATGGGGGCTGAGTATGCAGGGATTTCGGTCGAAATATTACGGATTATGCTTATAGGGTATATTTTTA -continued

| SEQUENCES |
|---|
| ACTGTTATTCACAAATCTCTTTTGCCAACATACAGGCCTTTGGAAAAGCAAAATACACTGCATACATCCATATGATGG |
| AATTTATTCCTTATTTGATAATGTTATATATAATTTCAAAGGAATATGGGGTTATTGGTGTTGCGTGGTTATGGACAA |
| TTCGAGTAATAATTGATTTTTTGATGCTTTTATATATGAGTTATCGTTGTAATAATCTTATGAAAAAAGGGTAGCCTG |
| ATGATATATATTGTGGTATTAAATTGGAATGGGGCTATAGATACCATTAATTGTGTTAAAAGTTTAATGGATTTAAAT |
| GTTAGCGATTATAAAATTATCATTGTTGATAACTGTTCTATGGATAACTCATATGATACTATAAAAGAAAATCTTAAT |
| TCATTATATATTGCTGATAAAAGTATCATTGAGGTGAAGTATGAGGATAGAAATAAATATAAAACCTTAGAAAACGAT |
| AAAATCATATTAATACAATCTCCGCAAAATAATGGGTACGCAAGTGGTAATAATATTGGCATAGAGTTCGCTCTTAAT |
| CAGGAGAATATGAAATACGTCTGGGTTCTGAATAATGATACTGAAGTGGATAAAGAGGCTTTAACTCATTTAATTAGT |
| AAATGTGATTCAGATAAAAGTATAGGGATTTGCGGTTCTCGTTTAGTCTATTTTGCCGACAGAGAGATGCAGCAAGGA |
| CTAGGTGGGGTGCATAACAAATGGTTATGCACTACAAAAAATTATGAAATGGGAAGATTAGTTTCCAAAAAATATGAT |
| GATGAAGTCATTAGTAATGATATAGATTATATAATTGGCGCATCGATGTTTTTCTCTAGAGAATGTTTGGAAACAGTT |
| GGATTGATGAATGAAGAATATTTTTTATACTATGAAGAGTTAGATATTTGCCTCAGAGCAAAAGCAAAGAACTTTAAA |
| TTAGGTATTTGCTCAGAAAGTTTGGTTTATCATAAAATAGGTGCAAGTACTGATGGGGGAAAGAGCATGATGGCTGAT |
| CTTTGCTCAATAAAAAATAGGCTGGTCATTACAGAAAGGTTTTATCCCCAATATTATTGGACGGTATGGTTGTCACTT |
| TTTGTTGTAGCATTTAACCGTGCTAGAAGAGGTGAGTTTAATAAGATGAAAAGATGTTTGAATGTTATGTTTAACTTC |
| AAACGAAACAAAGGTAGCAAATGCCATTAGAATATGCACTTAATCATGGTGTTAATAAATCTATAGTTTGATATGTTA |
| TTAAAGGGTATTTAATGAAAGTGGCTTTTTTATCTGCTTATGATCCACTATCTACATCCAGTTGGTCTGGCACACCTT |
| ATTATATGCTAAAGGCATTATCGAAGAGAAATATTTCCATTGAAATATTAGGACCGGTAAATAGCTATATGATATACA |
| TGTTAAAAGTATATAAATTAATATTAAGGTGTTTCGGAAAAGAATATGATTATAGTCATTCGAAGTTGCTTTCCAGGT |
| ATTACGGTAGAATATTCGGTAGGAAATTAAAAAAAATTGATGGTTTGGATTTTATTATCGCACCTGCAGGTTCCTCAC |
| AAATTGCTTTTTTAAAAACAACCATACCAATAATATATCTATCGGATACAACATATGATCAATTAAAAAGCTATTATC |
| CGAATTTAAATAAAAAAACAATTATAAATGATGAGGATGCAAGTTTAATCGAACGCAAGGCTATTGAAAAAGCAACAG |
| TAGTATCTTTCCCATCTAAATGGGCAATGGATTTTTGCAGGAATTATTACAGATTAGATTTTGATAAATTAGTTGAAA |
| TACCATGGGGGGCTAATTTATTTGATGATATTCACTTTGCTAATAAAAATATAATTCAAAAGAATAGTTATACTTGTC |
| TTTTCTTGGGAGTTGATTGGGAAAGAAAAGGTGGGAAAACAGCCTTGAAAGCAATTGAATATGTAAGGCAGTTATATG |
| GGATCGATGTTAGACTAAAAATTTGTGGATGTACTCCGAATCAAAAGATTTTACCTACTTGGGTTGAATTAATTGATA |
| AAGTAGATAAAAATAACGTTGACGAATATCAGAAATTCATCGATGTGTTATCTAACGCTGATATACTTCTTTTACCAA |
| CCATTGCTGAATGTTATGGAATGGTATTTTGTGAAGCTGCTGCTTTTGGATTGCCTGTTGTCGCTACAGATACAGGTG |
| GAGTCAGTTCTATAGTTATCAACGAAAGGACGGGGATATTAATTAAAGACCCGTTAGACTATAAGCACTTTGGAAATG |
| CAATTCATAAAATAATTAGTTCCGTAGAGACTTATCAAAACTACTCCCAAAACGCAAGAATTAGATATAATAATATAT |
| TGCATTGGGACAATTGGGCTAAAAGATAATTGAGATTATGTATGAGCATAAGAATAGAAGAATCAAATAGCACAAAA |
| AGAATTATATGTTTATTTATACTTTTTCTTGTTTTCCCTGATTTTTTGTTTTATACATTAGGGGTTGATAATTTTAGC |
| ATTTCAACGATAATCTCAATTACATTGCTTTTTGTTTTTTTAAGAGCTAAAAATATTTGCAAAGATAATTTTCTAATA |
| ATAGTAGCGTTATTCATATTGTTGTGTTTTAACTGTTTGTTAAGTATGCTATTTAATATTGAACAGGCTTTAACATTT |
| AAAGTTGTACTTTCAATATATAGCATCTTAATAATGGCATACGTCTCCTCTTGTTATGCACAGACGTTGTGGTTATGT |
| TCTGAAGAAATACTTAAGAGATCCGTCTTTTATTTGTTCGCATTTCTTTGCCTTATTGGCATTATAAGTATTCTTTTA |
| CAGAAGACTGAGATTATACATGATAAAAGTATGATTCTTTTTCCTGAACCATCAGCATTTGCATTGGTTTTTATACCT |
| ATCTTTTCATTTTGTTTATACTATACAAGAGGGGGGGGCTACTATTGCTCTATATATTATCTTTGGGTATTGCGTTA |
| GGTATCCAGAATTTAACAATGTTGGTAGGCATTGTGATTAGTGTTTTTGTGATGAAAAAAATAACTATAAGGCAAACT |
| ATTGTTATACTTTTGGGGGCATGGATTTTTTCCATGATATTAAGTGATTTAGACATTTCTTACTATATACATCGCGGCTT |
| GATTTTAAAAATACTACGAACCTATCAGTGCTTGTATATCTTTCAGGAATTGAAAGAGCTTTCTTGAATTTTATTACA |
| AGTTATGGTCTTGGTATTGGTTTTCAACAAATGGGAGTGAATGGGGAGATAGGAATATATCAACAAATTTTAGCTGAA |
| CTTGATGCCCCTATGTTAAATATATACGATGGCTCATTTATTTCTTCTAAGTTAATATCTGAGTTTGGGGTTATTGGT |
| GCATTAATGTGTATTTTCTATTTTTTTATTTTTTCCCGATTTTATCTGCGTTTCAAAAAAAGTAAGAGATATTCACCG |
| CAGTATATTTTAGCATATAGCTTCTACATGTGTTTCTTCATCCCTCTTTTTATACGTGGTGCTGGTTATATAAACCCC |
| TATGTGTTTATGTTATTTTCATCAATATTTTTGTGCAAATATCACGCTAAAAATATCTTGATGAAATCTAATGTCCAG |
| ATAGCTATATAATAGTAGATTATATTATCATTATCACGTAAATTACATATTAATAGCATATATGATAACTAGGACATA |
| AATAATGTGCATTAAAAAAAAACTTAAGTTAATTAAACGATATGGCCTTTATGGTGGTCTTAGGCTTCTTAAAGATAT |
| ATTCTTAACAAAATTTTTATTTTGTTCAAATGTTAGGATTATTAGATTTCCATGTTATATTAGAAAAGATGGAAGTGT |
| TAGTTTTGGAAAAGGTTTTACATCAGGTGTAGGATTACGAGTTGATGCATTTATGGATGCCGTAGTTTCCATTGGAGA |
| AAATGTTCAAATTAATGACTATGTTCACATCGCGGCTATTAATAATGTCATTATTGGTAGAGATACATTAATAGCAAG |
| TAAAGTATTTATTAGTGATCATAATCATGGTATTTTTCTAAATCCGATATCCATAGTTCACCAACTATTATTCCTTC |
| GTCTAGGCCCCTTGAATCTGCACCTGTGTATATTGGAGAGCGTGTGTGGATTGGCGAAAATGTGACAATATTACCAGG |
| TGCGTGTATAGGTAATGGTGTAGTTATTGGCGCAAACAGTGTTGTTCGTGGTGAGATTCCTAATAATGTGATCATTGC |
| TGGTGTTCCAGCTAAAATTGTTAAAAAATATAACTATGAGCGTATGCAATGGGAAAGAATATAGTTGTAATATCGGCT |
| GTTAATTTTACAACCGGAGGCCCCTTTACCGTACTAAAAAATGTGCTTACAGCAACTAAAGATAGAGCCGAATGTAAA |
| TTTATTGCACTGGTCATAGCTCTGCTGAACTAATGGAATTATTTCCGTGGGTTGAATTTATAGAGTATCCAGAAGTC |
| AAGTCTTCGTGGGTTAAAAGATTATATTTCGAATATATAACTTGCAATAGATTATCTAAGGTGATTAAGGCAACTCAT |
| TGGGTATGCTTACATGATATTACAGCAAATGTTAGTGTACCCTATAGATTTGTTTATTGCCACAATCCTGCACCGTTC |
| TATAAATATTTAAGCTATCGAGATATTATAGGAGAACCTAAATTTTATCTTTTTTATCTTTTTTATGGGCTTTTATAC |
| AATATCAATATAAAAAGAACACAGCAGTTTTTGTTCAGCAGCAGTGGCTAAAAAAAGAATTCGAAAAAAAATATAAG |
| TTAAAGAATGTTGTTGTTAGTCGCCCTGAAGATATTTGCCCTTTTGAAAGTGATGGTTTGGTAAGAAATAATAATAAA |
| AAGGATGTGAGGATATTTTACCCAGCAGTGCCCCGTATATTTAAAAACTTTGAAGTTATCATACGTGCTGCACAAATA |
| TTACAAGATAAAAATATTCATTTTTATCTTACTTTTGATGGTACTGAAAATAAGTATGCAAAAGAATATATAAATTA |
| GCTTCCGAACTGAAAAATGTACATTTCCTCGGTTACCTTAATGCAACCGAGATGGTTAACTTTTATCAAGATTCAGAT |
| ATTATTTGTTTCCCATCGAAACTAGAAACGTGGGGATTACCATTATCAGAAGCTAAAACATACAAAAAATGGATATTT |
| GCGGCAGACTTACCTTATGCTCATGAAGTTTTATATAACTATTCAAAACTAGATATTTTCCATTTGACGATGAGAAA |
| ATACTTGTTCGCTACATATTAGAGTACACAAGTAAAAATATGCATGAAGATATAAAAAATAGTAGGGTGAATTTTAAT |
| AATGATGCATTGACTGGTTTTGAACAGTTTATTGAATATATCCTCAAGGGGAACTGACGTGGTTTATATTATAATCGT |
| TTCACATGGCCATGATGACTATATAGAAAATCTTTTATTAAATTTAAAGTTGCCCTCTGGAAGATTTAAAATAATAGT |
| TCGTGATAACAAAAGTTCAATGGTTTTAAAAAAAACATGCGAAAAAAATTGCGTAACCTATTTGCATGGAGGGCAATA |
| TGGATTTGGACATAATAATAACATAGCAGTGTCATATATAATTAATAACTTCATGATTATGAATAATGATTATTTTCT |
| CTTTCTTAACCCCGATGTATTCATAACCAGTGAAAGTTTGATTAATTATGTTGATTATATAATTAGTAATGATTATAA |
| GTTTAGCACATTATGTCTTTATCGAGATTTTACTAAAAGCAAACATGATTATTCAATACGGAGTTTTCCAACTTTATA |
| TGATTTTCTTTGTTCTTTTTTATTGGGGGTGAATAAAAGTAAAATTAAGAAGGAAAATATACTTTCTGATACTGTAGT |
| TGATTGGTGTGCTGGCTCATTTATGCTTATTCATGCTTTAAGTTTCTTAAATGTGAATGGTTTTGATCAAAAATATTT |
| TATGTATTGTGAAGATATTGACCTTTGTATGCGTTTAAAATTAAGTGGAGTAGATCTTTACTATACTCCCCATTTTGA |

-continued

| SEQUENCES |
| --- |

TGCTATTCATTATGCGCAGCATGAAAATAGAAGAATATTTACTAAAGCATTTCGATGGCATATAAGGAGTATTACGCG
CTACATATTACGGAAACCAATTCTTTCTTATAAAAACTATAGAAAAATTACATCCGAACTGGTAAAGTGATTAAGGAT
CCGTGTAGGCTGGAGCTGCTTCGAAGTTCCTATACTTTCTAGAGAATAGGAACTTCGGAATAGGAACTAAGGAGGATA
TTCATATGGATAAAGCCGTAAGCATATAAGCATGGATAAGCTATTTATACTTTAATAAGTACTTTGTATACTTATTTG
CGAACATTCCAGGCCGCGAGCATTCAGCGCGGTGATCACACCTGACAGGAGTATGTAATGTCCAAGCAACAGATCGGC
GTAGTCGGTATGGCAGTGATGGGACGCAACCTTGCGCTCAACATCGAAAGCCGTGGTTATACCGTCTCTATTTTCAAC
CGTTCCCGTGAGAAGACGGAAGAAGTGATTGCCGAAAATCCAGGCAAGAAACTGGTTCCTTACTATACGGTGAAAGAG
TTTGTCGAATCTCTGGAAACGCCTCGTCGCATCCTGTTAATGGTGAAAGCAGGTGCAGGCACGGATGCTGCTATTGAT
TCCCTCAAACCATATCTCGATAAAGGAGACATCATCATTGATGGTGGTAACACCTTCTTCCAGGACACTATTCGTCGT
AATCGTGAGCTTTCAGCAGAGGGCTTTAACTTCATCGGTACCGGTGTTTCTGGCGGTGAAGAGGGGGCGCTGAAAGGT
CCTTCTATTATGCCTGGTGGCCAGAAAGAAGCCTATGAATTGGTAGCACCGATCCTGACCAAAATCGCCGCCGTAGCT
GAAGACGGTGAACCATGCGTTACCTATATTGGTGCCGATGGCGCAGGTCACTATGTGAAGATGGTTCACAACGGTATT
GAATACGGCGATATGCAGCTGATTGCTGAAGCCTATTCTCTGCTTAAAGGTGGCCTGAACCTCACCAACGAAGAACTG
GCGCAGACCTTTACCGAGTGGAATAACGGTGAACTGAGCAGTTACCTGATCGACATCACCAAAGATATCTTCACCAAA
AAAGATGAAGACGGTAACTACCTGGTTGATGTGATCCTGGATGAAGCGGCTAACAAAGGTACCGGTAAATGGACCAGC
CAGAGCGCGCTGGATCTCGGCGAACCGCTGTCGCTGATTACCGAGTCTGTGTTTGCACGTTATATCTCTTCTCTGAAA
GATCAGCGTGTTGCCGCATCTAAAGTTCTCTCTGGTCCGCAAGCACAGCCAGCAGGCGACAAGGCTGAGTTCATCGAA
AAAGTTCGTCGTGCGCTGTATCTGGGCAAAATCGTTTCTTACGCCCAGGGCTTCTCTCAGCTGCGTGCTGCGTCTGAA
GAGTACAACTGGGATCTGAACTACGGCGAAATCGCGAAGATTTTCCGTGCTGGCTGCATCATCCGTGCGCAGTTCCTG
CAGAAAATCACCGATGCTTATGCCGAAAATCCACAGATCGCTAACCTGTTGCTGGCTCCGTACTTCAAGCAAATTGCC
GATGACTACCAGCAGGCGCTGCGTGATGTCGTTGCTTATGCAGTACAGAACGGTATTCCGGTTCCGACCTTCTCCGCA
GCGGTTGCCTATTACGACAGCTACCGTGCTGCTGTTCTGCCTGCGAACCTGATCCAGGCACAGCGTGACTATTTTGGT
GCGCATACTTATAAGCGTATTGATAAAGAAGGTGTGTTCCATACCGAATGGCTGGATTAA

SEQ ID NO: 19 (example O75 rfb locus nucleotide sequence-O75-EPA
production strain stLMTB11737)
ATGACGAATTTAAAAGCAGTTATTCCTGTAGCGGGTCTCGGGATGCATATGTTGCCTGCCACTAAGGCGATACCCAAA
GAGATGCTACCAATCGTCGACAAGCCAATGATTCAGTACATTGTTGACGAGATTGTGGCTGCAGGGATCAAAGAAATC
CTCCTGGTAACTCACGCGTCCAAGAACGCGGTCGAAAACCACTTCGACACCTCTTATGAGTTAGAATCACTCCTTGAG
CAGCGCGTGAAGCGTCAACTGCTGGCGGAAGTACAGTCCATCTGTCCGCCGGGCGTGACCATTATGAACGTGCGTCAG
GGCGAACCTTTAGGTTTAGGCCACTCCATTTTGTGTGCGCGACCTGCCATTGGTGACAACCCATTTGTCGTGGTACTG
CCAGACGTTGTGATCGACGATGCCAGCGCCGACCCGCTACGTTACAACCTTGCTGCCATGATTGCACGTTTCAACGAA
ACGGGCCGCAGCCAGGTGCTGGCAAAACGTATGCCGGGTGACCTCTCTGAATACTCCGTCATCCAGACTAAAGAGCCG
CTGGACCGTGAGGGTAAAGTCAGCCGCATTGTTGAATTTATCGAAAAACCGGATCAGCCGCAGACGCTGGACTCAGAC
ATCATGGCCGTAGGTCGCTATGTGCTTTCTGCCGATATTTGGCCGGAACTGGAACGTACTCAGCCTGGTGCATGGGGA
CGTATTCAGCTGACTGATGCTATTGCCGAGCTGGCGAAAAAACAATCCGTTGATGCAATGCTGATGACCGGCGACAGT
TACGACTGCGGCAAAAAAATGGGCTATATGCAGGCGTTTGTGAAGTATGGCCTACGCAACCTGAAAGAAGGGGCGAAG
TTCCGTAAAGGTATTGAGAAGCTGTTAAGCGAATAATGAAAATCTGACCGGATGTAACGGTTGATAAGAAAATTATAA
CGGCAGTGAAAATTCGCAGCAAAAGTAATTTGTTGCGAATCTTCCTGCCGTTGTTTTATATAAACCATCAGAATAACA
ACGAGTTAGCAGTAGGGTTTTATTCAAAGTTTTCCAGGATTTTCCTTGTTTCCAGAGCGGATTGGTAAGACAATTAGC
GTTTGAATTTTTCGGGTTTAGCGCGAGTGGGTAACGCTCGTCACATCATAGGCATGCATGCAGTGCTCTGGTAGCTGT
AAAGCCAGGGGCGGTAGCGTGCATTAATACCTCTATTAATCAAACTGAGAGCCGCTTATTTCACAGCATGCTCTGAAG
TAATATGGAATAAATTAAGCTAGCAGTGAAGATACTTGTTACTGGTGGCGCAGGATTTATTGGTTCTGCTGTTGTTCG
TCACATAATAAATAATACGCAAGATAGTGTTGTTAATGTCGATAAATTAACATACGCCGGAAACCTGGAATCGCTCGC
TGAAATTTCTGATTCTGAACGTTATTCATTTGAGCATGCAGATATCTGCGATGCCGAAGCGATGGCTCGTATTTTCGC
ACAGCACCAGCCAGACGCGGTGATGCACCTGGCAGCAGAGAGCCACGTTGACCGCTCAATAACTGGCCCTGCGGCATT
TATTGAAACCAATATTGTGGGTACTTATGTTCTTTTAGAAGCGGCGCGCAATTATTGGTCTGGTCTGGATGATGAAAA
GAAAAAAAACTTCCGCTTTCATCATATTTCTACTGATGAGGTGTATGGTGACTTACCCCATCCGGATGAAGTAAATAG
CAATGAAACGTTGCCGCTATTTACGGAAATGACAGCATACGCGCCAAGTAGTCCATATTCTGCTTCTAAAGCTTCCAG
CGATCATTTGGTTCGCGCATGGAAACGTACTTATGGTTTACCGACCATTGTGACTAATTGCTCGAACAACTATGGTCC
TTATCATTTCCCGGAAAAGCTTATTCCACTGGTTATTCTTAATGCACTGGAAGGTAAGGCATTACCTATTTATGGCAA
AGGAGATCAGATCCGCGACTGGTTGTATGTAGAGGATCATGCTCGAGCGTTATATACCGTCGTAACCGAAGGTAAAGC
GGGCGAAACTTATAACATTGGTGGACACAACGAAAAGAAAAACATCGACGTAGTGTTCACTATTTGTGATTTGTTGGA
TGAGATAGTCCCGAAAGAGAAATCTTATCGTGAGCAAATTACCTATGTTGCTGATCGCCCAGGGCATGATCGCCGTTA
TGCAATTGATGCCGATAAAATTAGCCGCGAATTGGGCTGGAAACCACAGGAAACGTTTGAGAGCGGGATTCGTAAAAC
TGTGGAATGGTATCTGTCCAATACAAAATGGGTTGATAATGTGAAAAGTGGTGCCTATCAATCGTGGATTGAACAGAA
CTATGGGGGCCGCCACTAATGAATATCCTCCTTTTTGGCAAAACAGGGCAGGTTGGTTGGGAACTACAGCGTGCTCTG
GCACCTCTGGGTAATTTGATTGCTCTTGATGTTCACTCCACTGATTACTGTGGTGATTTTAGTAACCCTGAAGGTGTG
GCTGAAACCGTTAGAAGCATTCGGCCTGATATTATTGTCAACGCAGCCGCTCACACCGCAGTAGACAAAGCAGAATCA
GAACCGGAGTTTGCACAATTACTGAACGCGACGAGTGTCGAAGCGATCGCGAAAGCAGCCAATGAAGTCGGCGCTTGG
GTTATTCACTACTCTACTGACTACGTATTTCCGGGGACCGGTGAAATACCATGGCAGGAGGAGGATGCAACCGCACCG
CTAAATGTTTACGGTGAAACCAAGTTAGCAGGAGAAAAAGCATTACAAGAGCATTGTGCGAAGCACCTTATTTTCCGG
ACCAGCTGGGTCTATGCAGGTAAAGGAAATAACTTCGCCAAAACGATGTTGCGTCTGGCAAAAGAGCGTGAAGAATTA
GCCGTTATTAATGATCAGTTTGGTGCGCCAACTGGCGCAGAGTTGCTGGCTGATTGTACGGCACATGCCATTCGTGTG
GCACTGAATAAACCGGAAGTCGCAGGTTTGTACCATCTGGTAGCCAGTGGTACCACAACCTGGCACGATTATGCTGCG
CTGGTTTTTGAAGAGGCGCGCAAAGCAGGCATTCCCCTTGCACTCAACAAGCTCAACGCAGTACCAACAACAGTCTAT
CCTACACCAGCTCGTCGTCCACATAACTCTCGCCTTAATACAGAAAAATTTCAGCAGAACTTTGCGCTTGTCTTGCCT
GACTGGCAGGTTGGTGTGAAACGCATGCTCAACGAATTATTTACGACTACAGCAATTTAATAGTTTTTGCATCTTGTT
CGTGATGGTGGAACAAGATGAATTAAAAGGAATGATGGAATGAATACGCGTAAAGGTATTATTTTAGCGGGTGGTTCT
GGTACACGTCTTTATCCTGTGACTATGGCTGTCAGTAAACAGCTGTTACCGATTTATGATAAACCGATGATCTATTAC
CCGCTCTCTACACTGATGTTGGCGGGTATTCGCGATATTTTGATTATCAGCACGCCACAGGATACTCCTCGTTTTCAA
CAACTGCTGGGTGATGGGAGCCAGTGGGGGCTAAATCTTCACTACAAAGTGCAACCGAGTCCGGATGGTCTTGCGCAG
GCATTTATCATCGGTGAAGAGTTTATCGGTGGTGATGATTGTGCTTTGGTACTTGGTGATAATATCTTCTACGGTCAC
GACCTGCCTAAGTTAATGGATGCCGCTGTTAACAAAGAAAGTGGTGCAACGGTATTTGCCTATCACGTTAATGATCCT
GAACGCTATGGTGTCGTTGAGTTTGATAAAAACGGTACTGCAATCAGCCTGGAAGAAAAACCGTTACAACCAAAAAGT
AATTATGCGGTAACCGGGCTTTATTTCTATGATAACTACGTTGTGGAAATGGCGAAAAATCTTAAGCCTTCTGCCCGC
GGTGAACTGGAAATTACCGATATTAACCGTATCTATATGGAACAGGGGCATTTATCTGTTGCCATGATGGGACGTGGA -continued

| SEQUENCES |
|---|
| TATGCCTGGCTGGACACGGGGACACATCAAAGTCTTATTGAAGCAAGCAACTTCATTGCCACCATTGAAGAGCGCCAG<br>GGCTTGAAAGTTTCCTGCCCGGAAGAAATTGCTTACCGTAAAGGGTTTATTGATGCTGAGCAGGTGAAAGTATTAGCT<br>AAACCGCTGAAAAAAAATGCTTATGGTCAGTATCTGCTAAAAATGATTAAAGGTTATTAATAAAATGAATGTTATTAA<br>AACAGAAATTCCAGATGTACTGATTTTTGAACCGAAAGTTTTTGGTGATGAGCGTGGTTTCTTTATGGAAAGCTTTAA<br>TCAGAAAGTTTTCGAAGAGGCTGTAGGGCGGAAGGTTGAATTTGTTCAGGATAATCATTCTAAATCGTGTAAAGGTGT<br>ACTTAGAGGTTTACACTTTCAGCTTCCTCCCTTTGAGCAGGCAAAATTAGTAAGGTGTATAGTTGGCGAGGTATTTGA<br>TGTTGCAGTAGACATTAGACCTAATTCTGAAACATTTGGTTCATGGGTTGGAGTAACTCTTTCGTCAGAAAATAAAAG<br>GCAGCTATGGATTCCAGAAGGATTCGCCCATGGTTTTTTAACTTTAAGTGATATTGCAGAGTTTGTTTATAAAACTAA<br>CAACTATTATTCTTTAAATCATGAAAGGGGAGTCATTTGGAACGATGAGGAAATTAACATTGCCTGGCCCTCTCAATC<br>AGAGAAGATTCTGTCACAGAAAGATATTAATTTACCATCATTTAGATTTGTTCAAATGTTTAGCAAGTAGTGTTATCT<br>TTACACTGCACATAGTCATCATTTTTTATGCTTTAAGTAAATTATATTGCACATCTATAACACAAAGCGCAATAATAT<br>TTCGACCTGATGAAGGTTTGTGGTTATTTATCTTTCTAGGCGTTTTTTATGACTAAAATAGTTGTGGTTTCTACAGCT<br>CCAATATTCCCGACAAATAATGGGTACAAAAGTTCTGTATTAGGAAGAATTGATGAGTTATTAAATGAGGATAATGAG<br>GTCGTTTTGATTGAAATAAACCTTGAAAATGTTACGGAAAAGAAAGATGAATTAATACCAACAAGATTTAATAATATT<br>CAAAGATATGAAGTAAAAAAAATATCTAGATCATTTATTGCCGAGTTACAAATATTATTTGATATCAGAACTCGGTAT<br>GAACAATTATTTTCTTCTGCTGACATTAGAGATAACATAAAAAAGATAATTGATTTAGAAAAACCTTCTATTATTATT<br>GCTGAGTCTATATGGGCGTTGCAAGCATTGCCTATTGAAATTAGTGCGAGAATACACTGTGTTATTCATGATGTGGCA<br>ACTGATTTCTTTAAAGAAATGTTTGTATCTCATAATGAGGTTGTACGAAAAATTTTGTTTTTTAATGATTACCTAAAG<br>TTGAAAATTACTGAAGAAAATATTATCAAACGTTTGAGAGTTGAGCAATTTATCTTTCTGACAGAAGAAGATAAATGT<br>TGGTATAAAACAAGATACAATATTGATGAGGGTTGTTGTTCCTTAGCGAGCAATCATCTTTATGTAGAAAAGATTAAG<br>AGAACTATCAATTTCCAAACCCCTTTCCTGCTTATTCCCGGTAGCATTGAATTTTCACAAAATTTTTACGGCTTAAAT<br>TGGTTTATAAAAAATATATATCCTGGATTAAATAGGAAAATAAGAATAGTTGTAACAGGAAAGGCATCAGATAAAAAA<br>ATAAAGATGTTAAACTGTGGAGAGGAAATTACCTTTACGGGAGAGCTTGACTTTTCCACATATAATAAACTTAGCTCA<br>ACATGCTTGTGTGTTATTGCACCGATTACAACGGGCACTGGAATTAAAATAAAAATATTAGAAGCTGTACAAAAAGGT<br>ATTCCTGTACTTACAACAAAATTTGCTTCAAAAGGAATATGTTCCGATTTATGTTTTTATTGCGAGGAGGATACTGAC<br>ACAAACTTTGTCAATTTAATTAACAGTTTTCTTGAAACGACATTAAGAGTCCAAGAATGAATTTATTGCTTTTTTCAG<br>TCCTTGCGTTTGGTTTAATATTGGCTTTGGCCCATAATAATAAAAGTGGAGATATTAACGCATACTTAATGTTTTTTC<br>TCGTGGTCCTAATGGTATTAATATCAGGGCTGCGTATGAATGATAGTGATTATATCGAATACAGGAAAATGTATAATG<br>AAGTGCCTATTTTATGTGACTTTAGTCTCGCATCTATAAGAGATATACATGGGGAGGTAGGCTATCTATTCTTATCAT<br>CAATCTTTAAAACTTTATGCTTGCCATTTCAATTATTTCTTTTTTTTATTGCTTTTTTATCACTCCTGCTTACATATT<br>TTTCATTCAGAAAAATAAGTTTAATACCGATACTATCGTTAGTTTTTTATTTAAGCCATGCTTTTATAGTTAGAGATT<br>TGATTCAAATTAGGGCAGGATTAGCTGTTAGCATATCATTATATTCAATAATTAAATTTAAAGGAAATAAAAGTATAA<br>TTACAGGAGTTTTATTTGCTTCTTTGATTCATTCTGGGGCGCTTATTATTGCTCTTTGTTATCCTTTTTTCAAAAAAA<br>AATACATAACATTAAAAATGATGTTGTTTTTATTTTTAGTGTCAATTATTTTTTCTTATTTGAATGGGCTTAATTTAT<br>CGATACAACTCTTATCTCAATATAGTTTGCTTCCAACTGCAATTTCGAATTATGTTGGTTGGGAAGAATATGATTATC<br>GGGTGAGTATATTTACTAATCCGGTTTTTATTAAAGGTGTTTTTTTAATTGTCTTAATGCACAAATATGTACTTTCAG<br>ATATTAAAAATGAGAAAATTATAGTGCTTTATAACTTATATGTTTTAGGTGTATTAGCTATGGTTGCATTGAGTGGGA<br>TGGCTATTCTTTCAGGCCGTCTTTCATCCTTTCTGACACTAGGTGAAAGCATTTTAATTGTATATGCTCTGTTCTACA<br>AAAGAAATACACCTCTGGCGTTTCTAATTTTTTCTTTTTTAACAATTGTGCAATTAGGATATGATCTATTTATTTCTA<br>ATGTGCATCCTGAGCTTACTCTGATTATATTTGGGTGAATCTAAGTGAAAAATAATAAAATAGGCATACTTATCTCTA<br>AAATACAAAATCTTGGACCTGTGAATGTAGTACGAGGATTGATAAAAGAAAATAAAAAATATGCTTTTACTGTTTTTT<br>GTTTAACAAATAGCGTAGATAAAAATATATATGATGAGTTATGCTGTTTAGGAGCCAAGGTTATATTAATACCAGATG<br>GTACTTGGTTCAGCAAAATTTTATTTGTGAGAAGTTTTTTAAAGGAACATCCACATAATATCTTACATTCACATGGGA<br>TCACGGCCGATATGTTTTCTTACTTTCTGAATGGCGTGAAAATATCTACTATTCACAATAGACTAGATGAGGATTATA<br>TCCCATTATTTGGCGCGGTTAAAGGGAATGCTATATATTATCTTCATCGTTTTATATTACGAAGATTTAATCATATCG<br>TTGCTTGCTCAGCAGCGGTCCAATCAAAACTGAAACAATCGAAAGTAAAAACTAAAATAACCACCATCCAGAATGGGA<br>TTGATATAACTAGGTTTAAGACACTTGAGTCTGATAAAAAAAAATTATTGAGGGAAAAACACGGATTTGATAGTGAAA<br>AAAGAATATTTATATATTGTGGCTCGTTATCATTAAGGAAAAATATTGCTTACCTCTTGGAACACTTAGCCATCGAAG<br>AAAATGATATATTTTTAATTCTAGGTGATGGTGAACTTTTTAGATATTGTAAGGATAAATATTCTAAAGATTTACGGT<br>ATATATTTATGGGGAAAGTTGAATGCCCTCTTGAATATTATCAATTATCAGATATTTTTGTTTCCGCTTCTTTATCGG<br>AAGGGCTCCCCTTGGCACTATTAGAAGCTGCCTCTACTGGGTGCTATTTATATGTTAGCGATATAGAGCCCCATAGAG<br>AAATTGCATCTCTATTAGGAGAGGAAAATATTTCTATGTTTAAAATTAAGGATGGATCATATAATTATTTGCAACCTA<br>AAATAAAAAAAGCTGACTATAACGCTCTTTCTGACGATAAACTTTACAATATATCCGATAAAAAAATGTCAAATCTTT<br>ATGACAAACTTTTTGTTTCTTTATTAGAGCAGAGGCACTAATATAATGATTTATGTTTCGGTAATTTCTCATGGTCAT<br>TTCAAAACTCTTAAGGAATTAGGAGCAGTATCAAAATTAAATAATCACAGCAGAATTAAAGTTATCATCAAAGATAAT<br>TTAGGAGAGAGCGAGCTTTTGGATTTTTGTCAGGAAAACAAAATAACTTATTTAAGGTCTAAAGAGAAAAAAGGATTT<br>GGAGAGAATAATAATGAAGTTTTTTCCTCTATATCCTCCTTAATTACTAAGGAAGATTTTTTTGTGGTTATGAATCCT<br>GATATATATATTGAGTGCTCTGATCTATTAGATGTCGTAGATGAGTGTGGTTCAGCGAATGTTAATCTAGCAACGATA<br>AATTTATACAGGGATTTTGATAAAAAAACATATGATAACTCAGTAAGGAAATTTCCCTCGGCAATTGATTTTTTTATG<br>TCATTTTTATTTAAGAAAAATGACTGTGTAGTAAATAAGAACAAAATAACGAAACCAACATATGTTGATTGGGCTGCA<br>GGTTCTTTTCTAATATTTAATGCCTTCTTTTATTCAAAACTCAACGGATTCAACGAAAAGTATTTTATGTATTGCGAA<br>GATATTGATATATGTTGGCGAGCTAAAAAACACTTCAATACTTCAGTTTTATACTATCCATGCTATGCAGCAATTCAT<br>TTGGCACAATTTAACAATCGTAGGATTTTTAGTAGACATTTCATTTGGCATATAAAAAGTATTATCCTTTTTTTATTA<br>TATAAAAATGGTATGCTGCGTTCTAGTAAGTTGCTTTAATGCTAATATTCTTTTAAGAGGTGAGAATGATACCTGTTA<br>TTTTGGCTGGTGGTTCGGGAAGTCGCTTGTGGCCACTTTCACGAGAAAAGTTCCCCAAGCAGTTTTTAAAGTTGACTG<br>GCAGTTTGACAATGTTGCAGTCAACATTGTCACGTCTTAATAATTTAAATGCTGATGATTCAATAGTTATATGCAACG<br>AAGAGCATAGATTTATTGTTGCAGAACAATTAAGAGAGTTAGGCAAACTTTCAAATAACATTATTCTTGAACCCAAAG<br>GTCGTAATACAGCCCCTGCTATAACACTCGCAGCATTAGCAGCAAAAAGAAAATTCGCTGATGAAGATCCATTGATTC<br>TTATTTTAGCTGCAGATCACAACATCCAAGACGAACATGTTTTCTGTGAGGCAATTAATAAGGCGTCATCTTTAGCTA<br>GTTATGGAAAACTAGTGACTTTTGGTATCGTTCCATTCAAACCTGAAACTGGGTATGGCTATATTCGTCGCGGTGATG<br>AAGTGCCTGTAGATGAGCAGCATGCGGTGGCCTTTGAAGTGGCGCAGTTTGTCGAAAAACCGAATCTGGAAACCGCGC<br>AGGCCTATGTGGCAAGCGGCGAATATTACTGGAACAGCGGTATGTTCCTGTTCCGTGCCGGACGCTATCTCGAAGAAC<br>TGAAAAAGTATCGTCCGGATATTCTCGATGCCTGTGAAAAAGCGATGAGCGCCGTCGATCCGGATCTCGATTTTATTC<br>GTGTGGATGAAGAGGCGTTTCTCGCTTGTCCGGAAGAGTCGGTGGATTACGCGGTCATGGAATGCACGGCAGATGCCG<br>TTGTGGTGCCGATGGATGCGGGCTGGAGCGATGTCGGTTCCTGGTCTTCATTATGGGAGATCAGCGCCCACACCGCCG<br>AGGGCAACGTTTGCCACGGCGATGTGATTAATCACAAAACTGAAAACAGCTATGTGTACGCCGAATCTGGCCTGGTCA<br>CCACCGTCGGGGTGAAAGATTTGGTGGTAGTGCAGACCAAAGATGCAGTGCTGATTGCCGACCGTAATGCGGTGCAGG |

-continued

SEQUENCES

ATGTGAAGAAAGTGGTCGAGCAGATCAAAGCTGATGGTCGCCATGAGCATCGGGTGCATCGCGAAGTGTATCGTCCGT
GGGGCAAATATGACTCTATCGACGCGGGCGACCGCTACCAGGTGAAACGCATCACCGTGAAACCGGGCGAAGGTTTGT
CGGTACAGATGCATTATCATCGCGCGGAACACTGGGTGGTTGTCGCGGGAACGGCAAAAGTCACTATCAACGGTGATA
TCAAACTGCTTGGTGAAAACGAGTCCATTTATATTCCGCTGGGGGCGATGCACTGCCTGGAAAACCCGGGGAAAATAG
ATTTAGAATTAATTGAAGTTCGCTCTGGTGCATATCTTGAAGAAGATGATGTTATTAGATGTTATGATCGCTATGGAC
GAAAGTAATATATAATAATTATTTCAGAATTAGAAATGATAATTATAAGTTTTCGTCTGGATAAACAATAGATAGTAT
GGGTTGGAAAATATGAGTTCTTTAACTTGTTTTAAAGCTTACGACATTCGCGGGAAATTAGGTGAAGAACTGAATGAA
GATATCGCCTGGCGCATTGGTCGCGCCTATGGCGAATTTCTCAAACCGAAAACCATTGTGTTAGGCGGTGATGTCCGT
CTCACCAGCGAAACCTTAAAACTGGCGCTGGCAAAAGGTTTACAGGATGCGGGCGTCGATGTGCTGGATATTGGCATG
TCCGGCACCGAAGAGATTTATTTCGCCACGTTCCATCTCGGCGTGGATGGCGGCATTGAAGTTACCGCCAGCCATAAT
CCGATGGATTACAACGGCATGAAGCTGGTGCGCGAAGGGGCTCGCCCGATCAGCGGTGATACCGGACTGCGCGACGTC
CAGCGTCTGGCAGAAGCTAACGACTTTCCTCCCGTCGATGAAACCAAACGCGGTCGCTATCAGCAAATCAATCTGCGT
GACGCTTACGTTGATCACCTGTTCGGTTATATCAATGTCAAAAACCTTACGCCGCTCAAGCTGGTGATCAACTCCGGG
AATGGCGCAGCGGGTCCGGTGGTGGACGCTATCGAAGCCCGCTTTAAAGCCCTCGGCGCACCGGTGGAGTTAATCAAA
GTGCATAACACGCCGGACGGCAATTTCCCCAACGGTATTCCTAACCCGTTGCTGCCGGAATGTCGCGACGACACCCGC
AATGCGGTCATCAAACACGGCGCGGATATGGGCATTGCCTTTGATGGCGATTTTGACCGCTGTTTCCTGTTTGACGAA
AAAGGGCAGTTTATTGAGGGCTACTACATTGTCGGCCTGCTGGCAGAAGCGTTCCTCGAAAAAAATCCCGGCGCGAAG
ATCATCCACGATCCACGTCTCTCCTGGAACACCATTGATGTGGTGACGGCCGCGGGCGGCACGCCGGTGATGTCGAAA
ACAGGACACGCCTTTATTAAAGAACGTATGCGCAAGGAAGACGCCATCTACGGTGGCGAAATGAGCGCTCACCATTAC
TTCCGCGATTTCGCTTACTGTGACAGCGGCATGATCCCGTGGCTGCTGGTCGCCGAACTGGTGTGCCTGAAAGGAAAA
ACGCTGGGCGAACTGGTGCGCGACCGGATGGCGGCGTTTCCGGCAAGCGGTGAGATCAACAGAAAACTGGCGCACCCT
GTTGAGGCGATTAACCGCGTGGAACAGCATTTTAGCCGTGAGGTGCTGGCGGTGGATCGCACCGATGGCATCAGCATG
ACCTTTGCCGACTGGCGCTTTAACCTGCGCTCTTCCAACACCGAACCGGTGGTGCGCCTGAATGTGGAATCTCGCGGT
GATGTTCAGGTTATGGTAATCCATACTCAAGAAATATTATCAATTTTGACGTCATAAAGAATAAGCCCTGACAAGTTA
GGGCTTAATTAATATATATTTTTTTTGAATTGGGGATTTGTGGTAAGATTTTTAATATGTTATTTAATGTGGTTGAAT
TAATGTTGACTGGAAAATAATAATGAGAACGAAAAAAGCATTACACAACTTTAAAGTTGATTTATTAATTACTTTTTT
ATTGGTTTTGCTAGGGTTTTATATTCGAACTGTTTTTGTTTCAAAAATGGGAAGTGATATTACTGGAGTGATGTTACT
ATTCACACAGTTGACAGCATATCTCAATTTGGCAGAATTAGGTATTGGAATTGCAGCTGCCAGCGTATTATATAAACC
GCTCAGCGAGAATGAATACAATAAAATAACTTACATAATATCTTTGCTCTCAGTCATATACAAATATATATTTGTGTT
TGTTTTGATTCTTGGCGTTGTTATAGGTATCTGTATTTATTACTTTATTGATTCTGTAAAGGTTGTAAATGGCGTTTT
TTTATATTGGGCTTTGTTCGTTTTTAATACATCGTTGACATATAGTTATGCTAAATACTCCACATTATTAACTGCTAA
TCAGCGGTACTCAGCAGTAAGAAAAATTCAAGGTGGCGGAAAAGTTATAATAATTGTATTTCAGATATTAATTTTGTG
CTTTACGCAAAGTTTCATACTTTATTTGTTAGTTGAGACTTTAGGTATTTTTTCTCAATATTTGATTTTTAAAAAAAT
AATTGGGAACGGAAATCAATATCTCAGTAATGAGGTTTTACTTATTGAAAGCGATAAACTTTTGATAAAAAAAGAATT
AAAAATAAGAATAAAAAATATGTTCTTCCATAAAATAGGTGCTGTGCTTGTCCTTAATACAGACTACCTGCTTGTATC
AAAGTTTCTGACATTAAGTTATGTGACAATTTTTGGCAGCTATATGATGGTATTTCAGATAGTAACTGTTTTGATGTC
AAGTTTTGTTAATGCTATTACTGCAGGAATGGGTAATTACTTAATTAATAAAAGTAATTTAGAAATTAAGGAAATTAC
ACGTCAATTTTATGTGATATTTATCGCCTTTGCAACATTCATATCACTAAATATGTTTTTTCTTGTTAATGATTTTAT
CGCAAAATGGATAGGTGTTAATTATACATTAAGTAACACCCTAGTTGCATTAATGATTGTTAACGTATTCATTAGTGT
TGTCAGGGTACCTTCTGATATATTAAAAAACGCAAGTGGACATTTTGGTGATATTTATTATCCATTATTAGAAGGTGT
GCTGAATATTACGATATCCATCATTTTGGCTATCATTATTGGATTACCTGGCATTATTATAGGGACAATAGTATCTAA
CTTAATAGTAATAATGCTTGCGAAACCATTATATCTTTACTCTAAGTTATTTAATCTTAGAAATCCGACGAGGGTTTA
TTTTGAATTTATTTCTCGGCCTATGTTATATTCATTATGTGTGATTGGGGTGAGCTATTTATTGCGCGATGAAATATA
TTCATTTAAAGTAAGTACATGGTTGGATTTTATTAACAAGCTACTCTTAGTCTCTACTCCTAGCATATTGGTAATATG
TGCTATTTTCTCTACGGATAGTGACTTTAGATTATTTTTCAGAAAAATTATATATGTGATTATGAAGAAATAAAAATT
TCGAAAATGTATTAATCGAAATTATGCAACGAGCTTTATTTTTATAAATGATATGTGATCTTTTCGCGAATAGGAGTA
AGGATCCGTGTAGGCTGGAGCTGCTTCGAAGTTCCTATACTTTCTAGAGAATAGGAACTTCGGAATAGGAACTAAGGA
GGATATTCATATGGATAAAGCCGTAAGCATATAAGCATGGATAAGCTATTTATACTTTAATAAGTACTTTGTATACTT
ATTTGCGAACATTCCAGGCCGCGAGCATTCAGCGCGGTGATCACACCTGACAGGAGTATGTAATGTCCAAGCAACAGA
TCGGCGTAGTCGGTATGGCAGTGATGGGACGCAACCTTGCGCTCAACATCGAAAGCCGTGGTTATACCGTCTCTATTT
TCAACCGTTCCCGTGAGAAGACGGAAGAAGTGATTGCCGAAAATCCAGGCAAGAAACTGGTTCCTTACTATACGGTGA
AAGAGTTTGTCGAATCTCTGGAAACGCCTCGTCGCATCCTGTTAATGGTGAAAGCAGGTGCAGGCACGGATGCTGCTA
TTGATTCCCTCAAACCATATCTCGATAAAGGAGACATCATCATTGATGGTGGTAACACCTTCTTCCAGGACACTATTC
GTCGTAATCGTGAGCTTTCAGCAGAGGGCTTTAACTTCATCGGTACCGGTGTTTCTGGCGGTGAAGAGGGGGCGCTGA
AAGGTCCTTCTATTATGCCTGGTGGCCAGAAAGAAGCCTATGAATTGGTAGCACCGATCCTGACCAAAATCGCCGCCG
TAGCTGAAGACGGTGAACCATGCGTTACCTATATTGGTGCCGATGGCGCAGGTCACTATGTGAAGATGGTTCACAACG
GTATTGAATACGGCGATATGCAGCTGATTGCTGAAGCCTATTCTCTGCTTAAAGGTGGCCTGAACCTCACCAACGAAG
AACTGGCGCAGACCTTTACCGAGTGGAATAACGGTGAACTGAGCAGTTACCTGATCGACATCACCAAAGATATCTTCA
CCAAAAAAGATGAAGACGGTAACTACCTGGTTGATGTGATCCTGGATGAAGCGGCTAACAAAGGTACCGGTAAATGGA
CCAGCCAGAGCGCGCTGGATCTCGGCGAACCGCTGTCGCTGATTACCGAGTCTGTGTTTGCACGTTATATCTCTTCTC
TGAAAGATCAGCGTGTTGCCGCATCTAAAGTTCTCTCTGGTCCGCAAGCACAGCCAGCAGGCGACAAGGCTGAGTTCA
TCGAAAAAGTTCGTCGTGCGCTGTATCTGGGCAAAATCGTTTCTTACGCCCAGGGCTTCTCTCAGCTGCGTGCTGCGT
CTGAAGAGTACAACTGGGATCTGAACTACGGCGAAATCGCGAAGATTTTCCGTGCTGGCTGCATCATCCGTGCGCAGT
TCCTGCAGAAAATCACCGATGCTTATGCCGAAAATCCACAGATCGCTAACCTGTTGCTGGCTCCGTACTTCAAGCAAA
TTGCCGATGACTACCAGCAGGCGCTGCGTGATGTCGTTGCTTATGCAGTACAGAACGGTATTCCGGTTCCGACCTTCT
CCGCAGCGGTTGCCTATTACGACAGCTACCGTGCTGCTGTTCTGCCTGCGAACCTGATCCAGGCACAGCGTGACTATT
TTGGTGCGCATACTTATAAGCGTATTGATAAAGAAGGTGTGTTCCATACCGAATGGCTGGATTAA

The invention claimed is:

1. A recombinant host cell for producing a bioconjugate of an *E. coli* glucosylated O4 antigen polysaccharide covalently linked to a carrier protein, wherein the glucosylated O4 antigen polysaccharide comprises the structure of Formula α-D-Glcp
1
↓
3
[→2)-α-L-Rhap-(1→6)-α-D-Glcp-(1→3)-α-L-FucpNAc-
-(1→3)-β-D-GlcpNAc-(1→]$_n$, wherein n is an integer of 5 to 40, the host cell comprising:

(i) a nucleotide sequence of an rfb gene cluster for the *E. coli O*4 antigen polysaccharide;

(ii) a nucleotide sequence encoding a glucosyl transferase, wherein the glucosyl transferase is capable of modifying the *E. coli O*4 antigen polysaccharide to produce the *E. coli* glucosylated O4 antigen polysaccharide;

(iii) a nucleotide sequence encoding a translocase that is capable of translocating bactoprenol-linked glucose;

(iv) a nucleotide sequence encoding a glycosyltransferase that is capable of glucosylating bactoprenol;

(v) a nucleotide sequence encoding the carrier protein; and (vi) a nucleotide sequence encoding an oligosaccharyl transferase capable of covalently linking the *E. coli* glucosylated O4 antigen polysaccharide to the carrier protein to produce the bioconjugate.

2. The host cell of claim 1, wherein the glucosyl transferase has at least 99% sequence identity to SEQ ID NO: 4.

3. The host cell of claim 1, wherein the translocase has at least 99% sequence identity to SEQ ID NO: 7, and the glycosyltransferase has at least 99% sequence identity to SEQ ID NO: 8.

4. The recombinant host cell of claim 1, wherein:

the glucosyl transferase comprises the amino acid sequence of SEQ ID NO: 4.

5. The recombinant host cell of claim 4, wherein:

the translocase comprises the amino acid sequence of SEQ ID NO: 7, and the glycosyltransferase comprises the amino acid sequence of SEQ ID NO: 8.

6. The recombinant host cell of claim 1, wherein:

the oligosaccharyl transferase comprises the amino acid sequence of SEQ ID NO: 6 having the amino acid mutation N311V, or the amino acid sequence of SEQ ID NO: 6 having amino acid mutations Y77H and N311V.

7. The recombinant host cell of claim 1, wherein the carrier protein comprises at least one glycosylation site comprising a glycosylation consensus sequence of Asn-X-Ser(Thr), wherein X can be any amino acid except Pro; or an optimized glycosylation consensus sequence of Asp (Glu)-X-Asn-Z-Ser(Thr), wherein X and Z are independently selected from any amino acid except Pro.

8. The recombinant host cell of claim 1, wherein the carrier protein is a detoxified exotoxin A of *Pseudomonas aeruginosa* (EPA).

9. The recombinant host cell of claim 8, wherein the carrier protein comprises SEQ ID NO: 3.

10. The recombinant host cell of claim 1, which is an *E. coli* cell.

11. The recombinant host cell of claim 10, which is from an *E. coli* K-12 strain.

12. The recombinant host cell of claim 11, which is from strain W3110.

13. The recombinant host cell of claim 1, wherein the glucosyl transferase comprises the sequence of SEQ ID NO: 4, the translocase comprises the sequence of SEQ ID NO: 7, the glycosyltransferase comprises the sequence of SEQ ID NO: 8, the oligosaccharyl transferase comprises the sequence of SEQ ID NO: 6, SEQ ID NO: 6 with the amino acid mutation N311V, or SEQ ID NO: 6 with the amino acid mutations Y77H and N311V, the carrier protein comprises SEQ ID NO: 3, and the *E. coli* cell is an *E. coli* K-12 strain.

14. A recombinant host cell for producing a bioconjugate of an *E. coli* glucosylated O4 antigen polysaccharide covalently linked to a carrier protein, wherein the glucosylated O4 antigen polysaccharide comprises the structure of Formula α-D-Glcp
1
↓
3
[→2)-α-L-Rhap-(1→6)-α-D-Glcp-(1→3)-α-L-FucpNAc-(1→3)-β-D-GlcpNAc-(1→]$_n$, wherein n is an integer of 5 to 40, the host cell comprising:

(i) a nucleotide sequence of an rfb gene cluster for the *E. coli O*4 antigen polysaccharide;

(ii) a gtrS gene encoding a glucosyl transferase enzyme specific for *E. coli* serotype O4 that glucosylates the O4 antigen polysaccharide;

(iii) a grtA gene encoding a bactoprenol-linked glucose translocase;

(iv) a gtrB gene encoding a bactoprenol glucosyl transferase;

(v) a nucleotide sequence encoding the carrier protein; and (vi) a nucleotide sequence encoding an oligosaccharyl transferase capable of covalently linking the *E. coli* glucosylated O4 antigen polysaccharide to the carrier protein to produce the bioconjugate.

15. The recombinant host cell of claim 14, wherein the glucosyl transferase enzyme encoded by the gtrS gene comprises SEQ ID NO: 4.

16. The recombinant host cell of claim 15, wherein the bactoprenol-linked glucose translocase encoded by the gtrA gene comprises SEQ ID NO: 7 and wherein the bactoprenol glucosyl transferase encoded by the gtrB gene comprises SEQ ID NO: 8.

17. The recombinant host cell of claim 14, wherein the oligosaccharyl transferase comprises the amino acid sequence of SEQ ID NO: 6 having the amino acid mutation N311V, or the amino acid sequence of SEQ ID NO: 6 having amino acid mutations Y77H and N311V.

18. The recombinant host cell of claim 14, wherein the carrier protein comprises at least one glycosylation site comprising a glycosylation consensus sequence of Asn-X-Ser(Thr), wherein X can be any amino acid except Pro; or an optimized glycosylation consensus sequence of Asp (Glu)-X-Asn-Z-Ser(Thr), wherein X and Z are independently selected from any amino acid except Pro.

19. The recombinant host cell of claim 14, wherein the carrier protein is a detoxified exotoxin A of *Pseudomonas aeruginosa* (EPA).

20. The recombinant host cell of claim 14, wherein the carrier protein comprises SEQ ID NO: 3.

21. A method of producing a bioconjugate of an *E. coli* glucosylated O4 antigen polysaccharide covalently linked to a carrier protein, comprising the step of culturing the recombinant cell of claim 1 under conditions wherein the bioconjugate is produced.

22. A method of producing a bioconjugate of an *E. coli* glucosylated O4 antigen polysaccharide covalently linked to a carrier protein, comprising the step of culturing the recombinant cell of claim 14 under conditions wherein the bioconjugate is produced.

* * * * *

SEQUENCE LISTING

Sequence total quantity: 19
SEQ ID NO: 1 moltype = length =
SEQUENCE: 1

```
000

SEQ ID NO: 2            moltype =   length =
SEQUENCE: 2
000

SEQ ID NO: 3            moltype = AA  length = 652
FEATURE                 Location/Qualifiers
source                  1..652
                        mol_type = protein
                        organism = synthetic construct
SEQUENCE: 3
GSGGGDQNAT GSGGGKLAEE AFDLWNECAK ACVLDLKDGV RSSRMSVDPA IADTNGQGVL  60
HYSMVLEGGN DALKLAIDNA LSITSDGLTI RLEGGVEPNK PVRYSYTRQA RGSWSLNWLV  120
PIGHEKPSNI KVFIHELNAG NQLSHMSPIY TIEMGDELLA KLARDATFFV RAHESNEMQP  180
TLAISHAGVS VVMAQAQPRR EKRWSEWASG KVLCLLDPLD GVYNYLAQQR CNLDDTWEGK  240
IYRVLAGNPA KHDLDIKDNN NSTPTVISHR LHFPEGGSLA ALTAHQACHL PLEAFTRHRQ  300
PRGWEQLEQC GYPVQRLVAL YLAARLSWNQ VDQVIRNALA SPGSGGDLGE AIREQPEQAR  360
LALTLAAAES ERFVRQGTGN DEAGAASADV VSLTCPVAKD QNRTKGECAG PADSGDALLE  420
RNYPTGAEFL GDGGDVSFST RGTQNWTVER LLQAHRQLEE RGYVFVGYHG TFLEAAQSIV  480
FGGVRARSQD LDAIWRGFYI AGDPALAYGY AQDQEPDARG RIRNGALLRV YVPRWSLPGF  540
YRTGLTLAAP EAAGEVERLI GHPLPLRLDA ITGPEEEGGR VTILGWPLAE RTVVIPSAIP  600
TDPRNVGGDL DPSSIPDKEQ AISALPDYAS QPGKPPREDL KLGSGGGDQN AT          652

SEQ ID NO: 4            moltype = AA  length = 421
FEATURE                 Location/Qualifiers
source                  1..421
                        mol_type = protein
                        organism = synthetic construct
SEQUENCE: 4
MNNLIMNNWC KLSIFIIAFI LLWLRRPDIL TNAQFWAEDS VFWYKDAYEN GFLSSLTTPR  60
NGYFQTVSTF IVGLTALLNP DYAPFVSNFF GIMIRSVIIW FLFTERFNFL TLTTRIFLSI  120
YFLCMPGLDE VHANITNAHW YLSLYVSMIL IARNPSSKSW RFHDIFFILL SGLSGPFIIF  180
ILAASCFKFI NNCKDHISVR SFINFYLRQP YALMIVCALI QGTSIILTFN GTRSSAPLGF  240
SFDVISSIIS SNIFLFTFVP WDIAKAGWDN LLLSYFLSVS ILSCAAFVFV KGTWRMKVFA  300
TLPLLIIIFS MAKPQLTDSA PQLPTLINGQ GSRYFVNIHI AIFSLLCVYL LECVRGKVAT  360
LFSKIYLTIL LFVMGCLNFV ITPLPNMNWR EGATLINNAK TGDVISIQVL PPGLTLELRK  420
K                                                                 421

SEQ ID NO: 5            moltype = DNA  length = 1266
FEATURE                 Location/Qualifiers
source                  1..1266
                        mol_type = other DNA
                        organism = synthetic construct
SEQUENCE: 5
atgaataatt taattatgaa taactggtgt aaattatcta tatttattat tgcatttatt  60
ttgctatggc ttagaaggcc ggatatactc acaaacgcac aattttgggc agaagattcc  120
gttttctggt ataaggacgc ctatgagaac ggattcttaa gttcactaac aacgcctagg  180
aatgggtatt tccagactgt ttctacattt atagttggtc tgactgcttt attaaatcca  240
gattatgcac cttttgtttc taattttttt ggcataatga ttcgctcagt aattatatgg  300
tttttattta cagaaagatt caacttcctc acattgacta ctaggatttt cttatctatt  360
tattttctat gcatgcctgg attggatgaa gttcatgcaa atataacaaa tgcacattgg  420
tatttgtcat tatatgtatc aatgatcctg atagctcgca atccaagttc aaaatcatgg  480
aggtttcatg atatattctt tatcttgcta tccgggctca gtggcccatt tataattttc  540
attttagcag cttcatgctt taaatttata aataattgta aagatcatat tagtgtaaga  600
tctttcataa atttctactt gcgtcagcca tacgcattaa tgattgtttg cgctttaatt  660
caaggaactt ctataattct aactttcaat ggcacacgtt cctcagcacc gctaggattc  720
agttttgatg tgatttcgtc tattatatca tcgaatattt ttttatttac atttgtccca  780
tgggatattg caaaggctgg gtgggataat ttactgttat cttatttttt gtctgtttcg  840
attttgtcgt gtgcggcctt tgtttttgtt aaaggtacgt ggcgaatgaa agtatttgca  900
actttaccat tgctaattat aatattttca atggcaaaac cacaattgac agactcggca  960
cctcaattgc caacacttat taatgggcaa ggttcaagat acttcgtaaa tatacatatt  1020
gcgatattct ctttgctatg tgtttactta cttgagtgcg tcaggggggaa agtggcaact  1080
ttattttcca aaatatactt aacaattttg ctattcgtga tgggatgttt gaattttgtt  1140
atcaccccac tcccaaacat gaactggagg gaaggtgcta ctttgattaa taatgcaaaa  1200
actggtgatg tcatttcgat tcaagtgcta ccacctggcc taacacttga actaaggaaa  1260
aaataa                                                            1266

SEQ ID NO: 6            moltype = AA  length = 713
FEATURE                 Location/Qualifiers
source                  1..713
                        mol_type = protein
                        organism = synthetic construct
SEQUENCE: 6
MLKKEYLKNP YLVLFAMIIL AYVFSVFCRF YWVWWASEFN EYFFNNQLMI ISNDGYAFAE  60
GARDMIAGFH QPNDLSYYGS SLSALTYWLY KITPFSFESI ILYMSTFLSS LVVIPTILLA  120
NEYKRPLMGF VAALLASIAN SYYNRTMSGY YDTDMLVIVL PMFILFFMVR MILKKDFFSL  180
IALPLFIGIY LWWYPSSYTL NVALIGLFLI YTLIFHRKEK IFYIAVILSS LTLSNIAWFY  240
QSAIIVILFA LFALEQKRLN FMIIGILGSA TLIFLILSGG VDPILYQLKF YIFRSDESAN  300
```

```
LTQGFMYFNV NQTIQEVENV DLSEFMRRIS GSEIVFLFSL FGFVWLLRKH KSMIMALPIL  360
VLGFLALKGG LRFTIYSVPV MALGFGFLLS EFKAIMVKKY SQLTSNVCIV FATILTLAPV  420
FIHIYNYKAP TVFSQNEASL LNQLKNIANR EDYVVTWWDY GYPVRYYSDV KTLVDGGKHL  480
GKDNFFPSFA LSKDEQAAAN MARLSVEYTE KSFYAPQNDI LKTDILQAMM KDYNQSNVDL  540
FLASLSKPDF KIDTPKTRDI YLYMPARMSL IFSTVASFSF INLDTGVLDK PFTFSTAYPL  600
DVKNGEIYLS NGVVLSDDFR SFKIGDNVVS VNSIVEINSI KQGEYKITPI DDKAQFYIFY  660
LKDSAIPYAQ FILMDKTMFN SAYVQMFFLG NYDKNLFDLV INSRDAKVFK LKI         713

SEQ ID NO: 7           moltype = AA  length = 120
FEATURE                Location/Qualifiers
source                 1..120
                       mol_type = protein
                       organism = Escherichia coli
SEQUENCE: 7
MLKLFAKYTS IGVLNTLIHW VVFGVCIYVA HTNQALANFA GFVVAVSFSF FANAKFTFKA  60
STTTMRYMLY VGFMGTLSAT VGWAADRCAL PPMITLVTFS AISLVCGFVY SKFIVFRDAK  120

SEQ ID NO: 8           moltype = AA  length = 306
FEATURE                Location/Qualifiers
source                 1..306
                       mol_type = protein
                       organism = Escherichia coli
SEQUENCE: 8
MKISLVVPVF NEEEAIPIFY KTVREFEELK SYEVEIVFIN DGSKDATESI INALAVSDPL  60
VVPLSFTRNF GKEPALFAGL DHATGDAIIP IDVDLQDPIE VIPHLIEKWQ AGADMVLAKR  120
SDRSTDGRLK RKTAEWFYKL HNKISNPKIE ENVGDFRLMS RDVVENIKLM PERNLFMKGI  180
LSWVGGKTDI VEYVRAERIA GDTKFNGWKL WNLALEGITS FSTFPLRIWT YIGLVVASVA  240
FIYGAWMILD TIIFGNAVRG YPSLLVSILF LGGIQMIGIG VLGEYIGRTY IETKKRPKYI  300
IKRVKK                                                            306

SEQ ID NO: 9           moltype = DNA  length = 14440
FEATURE                Location/Qualifiers
source                 1..14440
                       mol_type = other DNA
                       organism = synthetic construct
SEQUENCE: 9
atgacgaatt taaaagcagt tattcctgta gcgggtctcg ggatgcatat gttgcctgcc  60
actaaggcga tacccaaaga gatgctacca atcgtcgaca agccaatgat tcagtacatt  120
gttgacgaga ttgtggctgc agggatcaaa gaaatcctcc tggtaactca cgcgtccaag  180
aacgcggtcg aaaaccactt cgacacctct tatgagttag aatcactcct tgagcagcgc  240
gtgaagcgtc aactgctggc ggaagtacag tccatctgtc cgccgggcgt gaccattatg  300
aacgtgcgtc agggcgaacc tttaggttta ggccactcca ttttgtgtgc gcgacctgcc  360
attggtgaca acccatttgt cgtggtactg ccagacgttg tgatcgacga tgccagcgcc  420
gacccgctac gttacaacct tgctgccatg attgcacgtt tcaacgaaac gggccgcagc  480
caggtgctgg caaaacgtat gccgggtgac ctctctgaat actccgtcat ccagactaaa  540
gagccgctgg accgtgaggg taaagtcagc cgcattgttg aatttatcga aaaaccggat  600
cagccgcaga cgctggactc agacatcatg gccgtaggtc gctatgtgct ttctgccgat  660
atttggccgg aactggaacg tactcagcct ggtgcatggg gacgtattca gctgactgat  720
gctattgccg agctggcgaa aaaacaatcc gttgatgcaa tgctgatgac cggcgacagt  780
tacgactgcg gcaaaaaaat gggctatatg caggcgtttg tgaagtatgg cctacgcaac  840
ctgaaagaag gggcgaagtt ccgtaaaggt attgagaagc tgttaagcga ataatgaaaa  900
tctgaccgga tgtaacggtt gataagaaaa ttataacggc agtgaaaatt cgcagcaaaa  960
gtaatttgtt gcgaatcttc ctgccgttgt tttatataaa ccatcagaat aacaacgagt  1020
tagcagtagg gttttattca aagttttcca ggattttcct tgtttccaga gcggattggt  1080
aagacaatta gcgtttgaat ttttcgggtt tagcgcgagt gggtaacgct cgtcacatca  1140
taggcatgca tgcagtgctc tggtagctgt aaagccaggg gcggtagcgt gcattaatac  1200
ctctattaat caaactgaga gccgcttatt tcacagcatg ctctgaagta atatggaata  1260
aattaagtga aaatacttgt tactggtggc gcaggattta ttggttcagc tgtagttcgt  1320
cacattataa ataatacgca ggatagtgtt gttaatgtcg ataaattaac gtacgccgga  1380
aaccgggaat cacttgctga tgtttctgat tctgaacgct atgtttttga acatgcggat  1440
atttgcgatg cacctgcaat ggcacggatt tttgctcagc atcagccgga tgcagtgatg  1500
cacctggctg ctgaaagcca tgttgaccgt tcaattacag gccctgcggc atttattgaa  1560
accaatattg ttggtactta tgtccttttg gaagccgctc gcaattactg gtctgctctt  1620
gatagcgaca agaaaaatag cttccgtttt catcatattt ctactgacga agtatatggt  1680
gatttgcctc atcctgacga ggtaaataat acagaagaat taccccttatt tactgagaca  1740
acagcttacg cgccaagcag cccttattcc gcatccaaag catccagcga tcatttagtc  1800
cgcgcgtgga aacgtaccta tggtttaccg accattgtga ctaattgctc taacaattat  1860
ggtccttatc atttcccgga aaaattgatt ccattggtta ttctcaatgc tctggaaggt  1920
aaagcattac ctatttatgg taaaggggat caaattcgcg actggctgta tgttgaagat  1980
catgcgcgtg cgttatatac cgtcgtaacc gaaggtaaag cgggtgaaac ttataacatt  2040
ggtgggcaca acgaaaagaa aaacatagat gtagtgctca ctatttgtga tttgctggat  2100
gagattgtac cgaaagagaa atcttatcgt gagcaaatca cttatgttgc cgatcgtccg  2160
ggacacgatc gccgttatgc gattgatgct gagaatattg gtcgcgaatt gggatggaaa  2220
ccacaggaaa cgtttgagag cgggattcgg aagacagtgg aatggtatct gtccaataca  2280
aaatgggttg ataatgtgaa aagtggtgcc tatcaatcgt ggattgaaga gaactatgag  2340
ggccgccagt aatgaatatc ctccttttg gcaaaacagg gcaggtaggt tgggaactac  2400
agcgtgctct ggcacctctg ggtaacttga ttgctcttga tgttcattcc actgattatt  2460
gtggcgattt cagtaacccc gaaggtgtgg ctgaaaccgt caaaaaaatt cgcccagatg  2520
ttattgttaa tgctgctgct cataccgcgg tagataaggc tgagtcagaa ccagaatttg  2580
```

-continued

```
cacaattact caatgcgacc agcgttgaag caattgcaaa agcggctaat gaagttgggg  2640
cttgggtaat tcattactca actgactacg tcttccctgg aaatggcgac atgccatggc  2700
tcgagactga tgtaaccgct ccgctcaatg tttatggcaa aaccaaattg gctggagaaa  2760
gagcattaca agaacattgc gcaaagcatc ttattttccg taccagctgg gtatatgcag  2820
gtaaaggaaa taactttgcc aaaacaatgt tacgtctggc aaaagagcgc gaagaactgg  2880
ctgtgataaa cgatcagttt ggcgcaccaa caggtgctga attgctggct gattgcaccg  2940
ctcatgccat tcgcgtggca ttaaaaaaac cagaagttgc tggcttgtac catctggtag  3000
caaatggcac aacaacctgg cacgattacg ccgcgctagt attcgaagaa gcccgtaaag  3060
cagggattga ccttgcactt aacaaactca acgccgtacc aacaacggct tatcctactc  3120
cagcccgccg tcctcataat tctcgcctca ataccgaaaa gtttcagcag aactttgcgc  3180
ttgtcttgcc tgactggcag gtgggcgtga aacgtatgct caacgaatta tttacgacta  3240
cggcaattta acaaattttt gcatctcgct catgatgcca gagcgggatg aattaaaagg  3300
aatggtgaaa tgaaaacgcg taaaggtatt attctggctg gtggttccgg cactcgtctt  3360
tatcctgtga cgatggcagt gagtaaacaa ctgctgccga tttatgataa gccgatgatt  3420
tattatccgc tttcaacgct tatgttagcg ggtattcgcg atattcttat tatcagtacg  3480
ccacaggata caccgcgttt ccaacaattg ttgggggacg ggagtcagtg gggcttaat   3540
ctacagtata aagtacaacc gagtccggat ggcctggcgc aagcgtttat tattggtgaa  3600
gactttattg gtggtgatga ttgtgcactc gtacttggcg ataatatctt ctatggacac  3660
gacttgccga aattaatgga agctgctgtt aacaaagaaa tcggtgcaac ggtatttgct  3720
tatcacgtca atgatcctga acgttatggt gtcgtggagt ttgataataa cggtactgca  3780
attagcctgg aagaaaaacc gctggaacca aaaagtaact atgcggttac tgggctttat  3840
ttctatgaca atgatgttgt agaaatggcg aaaaacctta agccttctgc ccgtggcgaa  3900
ctggaaatta ccgatattaa ccgtatttat atggagcagg gacgtttgtc tgtcgctatg  3960
atggggcgtg gttatgcctg gttggatact ggtacacatc aaagtcttat tgaagcaagt  4020
aacttcattg ccaccattga agagcgtcag ggattaaagg tatcttgccc ggaagagatt  4080
gcttaccgta aagggtttat tgatgctgag caggtgaaag tattagccga accgctgaag  4140
aaaaatgatt atggtcagta tctgctaaaa atgattaaag gttattaata aaatgaacgt  4200
aattaaaact gaaattcctg atgtgctgat ttttgaacca aaagtttttg gtgatgaacg  4260
tggcttcttt tttgagagtt ttaaccagaa agtatttgaa gaagctgtag gacggaaggt  4320
tgaatttgtt caggataacc attctaagtc taaaataaat gtattgcgtg ggatgcatta  4380
tcaaacacaa aatactcaag gaaaactggt tcgggtaatt tctggttcag tatatgatgt  4440
tgccgtagat ttaagagaaa aatcaaagac atttggcaaa tgggtgggtg tagaattatc  4500
tgggaataat aaaagacaat tgtggatccc cgaaggtttt gcccatggtt tttatgtgtt  4560
ggaggagaat accgaatttg tttataaatg taccgatact tataaccctg ctcatgaaca  4620
cacattgcta tggaatgatc caactatcaa tataagttgg ccaatcatac aaaactgcaa  4680
gccaattatt tctgaaaaag atgctaatgg acatcttttt tcacataaaa cctatttctg  4740
aaatgcaata ttatgagttt aattagaaac agtttctata atattgctgg ttttgctgtg  4800
ccgacattag ttgcagtccc tgctttgggg attcttgcca ggctgcttgg accggagaat  4860
tttggacttt tcacactagc attcgctttg ataggatatg caagtatttt cgacgccggg  4920
attagtcgag ctgtaatcag agaaatcgct ctttatcgag aaagtgaaaa agagcaaata  4980
caaattattt cgacagcaag tgtaatcgta ctattcttag ggtggtggttgc agctttgtta  5040
ctttatttta gtagtaataa agttgttgag ttattgaatg ttagttccgt ttatattgaa  5100
acagcagtgc gtgcattctc tgttatttca tttataaatac ctgtgtatct gattaaccag  5160
atttggcttg gttatctgga agggctagaa aaatttgcaa atataaatgt tcagagaatg  5220
atttctagca caagcttggc tatattacca gtgatatttt gttattacaa tccctcgttg  5280
ctttatgcta tgtatgggtt ggtggttggg cgtgtgattt catttttgat tagcgcaata  5340
atttgtcgag atattattct taaaagtaaa ctttacttta atgtggcaac ttgcaatcgt  5400
cttatctctt ttggtggatg gataacagtt agtaatatca taagcccaat catggcatat  5460
ttcgaccgct ttatcatctc tcatattatg gggcttcgaa gaattgcatt ttatacagcg  5520
ccctcagagg gtgtatcaag gttaattaat atcccatatg ctttggcaag agctctattt  5580
cctaaattgg catatagcaa taatgatgat gaacgaaaaa aattacaact acagagctac  5640
gcaattataa gcattgtatg tctacccata gttgttattg gtgtcatttt tgcctcattc  5700
ataatgacaa catggatggg acctgattat gccttagaag cagcaactat catgaaaata  5760
cttcttgctg gtttttctt taactcttta gcgcaaatac cttatgcata cttgcaatct   5820
atcggaaagt caaaaattac cgcatttgtg catctcatag aacttgcgcc atacttatta  5880
ttattgtatt acttcacaat gcatttcggc ataattggca cggcaatcgc ttggtcactt  5940
agaacatttt gtgattttgt tatactactt tcgatatcga gaagaaaatg attgcggttg  6000
atattgcgct tgcaacctac aatggtgcta attttattcg gcaacagatt gaatctatcc  6060
agaaacaaac ttatagaaat tggcgtctta taataagtga tgataactcg agtgatgata  6120
ctgttgatat tattaaggat atgatgtcta acgacagtcg tatctatttg gtaggaaata  6180
aaagacaagg aggggtatt  cagaacttta attatgctct ttcacaaact acatctgaaa   6240
ttgtgttact atgtgaccag gatgacattt ggccggagga gcgtctggaa attcttatag  6300
ataaatttaa ggccttgcag cgtaatgatt ttgttccggc aatgatgttt actgatttga  6360
aattagtaga cgaaaataat tgtttgattg cagaaagttt ttatcgaacg aataatatta  6420
atccacaaga taatctgaaa aataataatc ttctctggcg ttcaacggta tatggctgta  6480
cttgcatcat gaataagaaa cttgttgata ttgcattgcc tatacctaca tatgcacata  6540
tgcatgatca atggttggca ttattagcga agcaatatgg taacattttt tatttcgact  6600
atgcgtctgt tcgttatagg caacattcta caaatgttgt tggtggtaga aataaaacgc  6660
catttcaaaa atttaattcc atacaaaaaa acctaaaaag gattaatttg ctagtggata  6720
gaactgttgc tttaattaaa tcaaataacg atttctatcc agggaataaa atggaaaata  6780
aaattgatta cttaaaattt ggagtgaatg aagtattacc ttatcttttt aaaggaaaca  6840
agaaagtttt ttcactttgt gtattaatta gtttggcatt acaaaaatga tatatttatt  6900
attttttttt gcactgttta tgatctgtac gtttttaaca cacaggcgac aggcattata  6960
tgttgtatct gcgttagtat ttctttttttt ggctttaacc tatccatcag gaggggactg  7020
gataggttat tttctccatt atgactgcat ggttaatgag cagtgtaata atggttttat  7080
aatgtttgaa cctggatatg aattaattgt ttccttattt ggatatttgg gatttcagac  7140
aattattatt tttatagccg ctgtaaatgt aattctaata ttaaattttg caaagcattt  7200
tgaaaacgga agttttgtta ttgttgcgat aatgtgcatg ttcctttgga gtgtttatgt  7260
tgaggcgatt agacaggctc tggccttatc tatagttata tttgggattc attctctttt  7320
```

-continued

```
tttgggtaga aaaaggaaat ttataacatt agtattattt gcgtcaactt tccatataac  7380
tgctttgatt tgttttcttc taatgactcc tctattttca aagaaattaa gcaagataat  7440
aagttatagc ctattaattt tcagtagctt ctttttcgct ttttctgaaa ccatattaag  7500
tgcactcctt gcaattttgc cagaaggatc cattgccagt gaaaaattaa gtttttactt  7560
agcaaccgag caatacaggc cacagttatc tattgggagt ggcactattc ttgacattat  7620
acttattttt ctgatatgtg taagttttaa acgaataaag aaatatatgc tcgctaatta  7680
taatgctgca aatgagatat tgcttattgg ttgctgtctt tatatttctt tcggtatttt  7740
tatcgggaaa atgatgccag ttatgactcg cattggttgg tatggtttc  catttgttat  7800
agtacttctt tatattaact tgggttattc agaatatttt aagaggtata taaataaaag  7860
agggtgtggg tatagcaaat tattaattgc tttttatttt ttgctacaaa ttttgcgacc  7920
attaacatat gattatagct attataatat aatgcaccag gatactttgc tgaataggtt  7980
tgatgcatta gatgatgcat cattaagaca atcagcgaag agaaaatgtt tcgatttggg  8040
aaagatagga tatggtttct tatgtagtat ataatatcct gcattcattc ggataatttc  8100
ctatggaagt gtcctttgct ctgtctgtcc tcatttgttg aaattttatg ttaataagaa  8160
gctttagata accacttagg aactgtatgt ttgatctgtc caaaaattat attattgtaa  8220
gtgcgacggc gctggcttcc ggaggtgcat taactatatt aaagcaattt ataaaacatg  8280
catcacaaaa ttcaaatgac tatattatgt ttgtatctgc gggattggag ttgccggtct  8340
gtgataacat catttacata gaaaacacac caaaaggatg gttgaaaaga atatattggg  8400
attggttcgg ttgtcggaag tttatctcgg aacataagat taacgttaag aaagtaattt  8460
ctctacaaaa ttccagtttg aatgttcctt acgaacagat tatttacttg caccagccaa  8520
ttccttttag taaagttgat tcttttttaa aaaatatcac atccgataac gtaaagcttt  8580
ttttatataa aaagttttat tcctatttta tatttaaata tgtgaatgcc aatacaacca  8640
tcgtagtgca aacgaattgg atgaaaaaag gagtgctgga gcaatgtgat aaaattagta  8700
ccgaaagggt ccttgttata aaacctgata tcaaagcatt taataatact aattttgatg  8760
tagatatgga tgtatctgca aaaacactct tatatccagc gacaccactt acctataaaa  8820
atcatttggt cattctgaag gcgttggtta ttttaaagaa aaagtatttt atagatgatc  8880
tgaaattcca agtgactttt gaaaagaata ggtacaaaaa ttttgataag tttgtgcaat  8940
taaataactt aagcaaaaac gttgattatc tcggcgttct ttcatactcg aacttgcaaa  9000
aaaaatatat ggcggcatct ttaatcgttt ttcctagcta tatcgaatca tatgggttac  9060
cactcatcga agctgctagt ttaggaaaaa aaatcattag tagtgatctt ccttatgccc  9120
gggatgtttt aaaggattat agcggcgtag attttgtaat ttacaataat gaagatggct  9180
gggctaaggc gttgtttaat gttttaaatg gcaattcgaa gctcaatttt aggccttatg  9240
aaaaagatag tcgttcatct tggccacagt tcttctctat tttgaaataa ggtgtattat  9300
gtttaatggt aaaatattgt taattactgg tggtacgggg tctttcggta atgctgttct  9360
aagacgtttt cttgacactg atatcaaaga aatacgtatt ttttcccggg atgaaaaaaa  9420
acaagatgac atgaggaaaa aatataataa tccgaaactt aagttctata taggtgatgt  9480
tcgcgactat tcgagtatcc tcaatgcttc tcgaggtgtt gattttattt atcatgctgc  9540
agctctgaag caagtacctt cctgcgaatt ccacccaatg gaagctgtaa aaacgaatgt  9600
tttaggtacg gaaaacgtac tggaagcggc aatagctaat ggagttaggc gaattgtatg  9660
tttgagtaca gataaagctg tatatcctat caatgcaatg ggtatttcca aagcgatgat  9720
ggaaaaagta atggtagcaa aatcgcgcaa tgttgactgc tctaaaacgg ttatttgcgg  9780
tacacgttat ggcaatgtaa tggcatctcg tggttcagtt atcccattat ttgtcgatct  9840
gattaaatca ggtagaccaa tgacgataac agaccctaat atgactcgtt tcatgatgac  9900
tctcgaagac gctgttgatt tggttcttta cgcatttgaa catggcaata atggtgatat  9960
ttttgtccaa aaggcacctg cggctaccat cgaaacgttg gctattgcac tcaaagaatt  10020
acttaatgta aaccaacacc ctgtaaatat aatcggcacc cgacacgggg aaaaactgta  10080
cgaagcgtta ttgagccgag aggaaatgat tgcagcggag gatatgggtg attattatcg  10140
tgttccacca gatctccgcg atttgaacta tggaaaatat gtggaacatg gtgaccgtcg  10200
tatctcggaa gtggaagatt ataactctca taatactgat aggttagatg ttgagggaat  10260
gaaaaaatta ctgctaaaac ttccttttat ccgggcactt cggtctggtg aagattatga  10320
gttggattca taatatgaaa attttagtta ctggcgctgc agggtttatc ggtcgaaatt  10380
tggtattccg gcttaaggaa gctggatata acgaactcat tacgatagat cgtaactctt  10440
ctttggcgga tttagagcag ggacttaagc aggcagattt tatttttcac cttgctgggg  10500
taaatcgtcc cgtgaaggag tgtgaatttg aagagggaaa tagtaatcta actcaacaga  10560
ttgttgatat cctgaaaaaa aacaataaaa atactcctat catgctgagt tcttccatcc  10620
aggctgaatg tgataacgct tatggaaaga gtaaagcagc tgcggaaaaa atcattcagc  10680
agtatgggga aacgacaaac gctaaatatt atatttatcg cttgccgaat gtattcggta  10740
agtggtgtcg accaaattat aactccttta tagcaacttt ctgccatcgc attgcaaatg  10800
atgaagctat tacaattaat gatccttcag cagttgtaaa tctggtgtat atagatgact  10860
tttgttctga catattaaag ctattagaag gagcgaacga aactggttac aggacatttg  10920
gtccaattta ttctgttact gttggtgaag tggcacaatt aatttaccgg tttaaagaaa  10980
gtcgccaaac attaatcacc gaagatgtag gtaatggatt tacacgtgca ttgtactcaa  11040
catggttaag ttacctgtct cctgaacagt ttgcgtatac ggttccttct tatagtgatg  11100
acagaggggt attctgtgaa gtattgaaaa cgaaaaacgc gggccagttt tcgttcttta  11160
ctgcgcatcc aggaattact cggggtggtc attatcatca ttccaaaaat gagaaattta  11220
ttgtcatccg aggaagtgct tgtttcaaat ttgaaaatat tgtcacgagt gaacgatatg  11280
aacttaatgt ttcctctgat gattttaaaa ttgttgaaac agttccggga tggacgcata  11340
acattactaa taatggctcg gatgagctag ttgttatgct ttgggcaaat gaaatattta  11400
atcgttctga accagatact atagcgagag ttttatcgtg aaaaaattga aagtcatgtc  11460
ggttgttggg actcgtccag aaattattcg actctcgcgt gtccttgcaa aattagatga  11520
atattgtgac caccttattg ttcataccgg gcaaaactac gattatgaac tgaatgaagt  11580
ttttttcaaa gatttgggtg ttcgcaaacc tgattatttt cttaatgccg caggtaaaaa  11640
tgcagcagag actattggac aagttatcat taaagttgat gaggtccttg aacaggaaaa  11700
accagaagcc atgttagtac ttggcgatac taactcctgt atttcagcaa taccagcaaa  11760
gcgtcgaaga attccgatct tccatatgga ggctgggaat cgttgttttg accaacgcgt  11820
accggaagaa actaacagaa aaatagttga tcataccgct gatatcaata tgacatatag  11880
tgatatcgcg cgtgaatatc ttctggctga aggtgtacca gccgatagaa ttattaaaac  11940
cggtagccca atgtttgaag tactcactca ttatatgccg cagattgatg gttccgatgt  12000
actttctcgc ctgaatttaa cacctgggaa tttctttgtg gtaagtgccc acagagaaga  12060
```

```
aaatgttgat acccctaaac aacttgtgaa actggcgaat atacttaata ccgtggctga  12120
aaaatatgat gtcccggtag ttgtttctac tcatcctcgc actcgtaacc gcatcaacga  12180
aaacggtatt caattccata aaaatatctt gcttcttaag ccattaggat ttcacgatta  12240
caaccatctg caaaaaaatg cacgtgctgt tttatcggat agtgggacta ttacagaaga  12300
gtcctccatt atgaacttcc ctgcactcaa tatacgagaa gcgcacgaac gcccggaagg  12360
cttcgaagaa ggggcagtaa tgatggtcgg tcttgaatct gatcgcgttt tacaggcatt  12420
agaaattatt gcaacacagc ctcgtggaga agtacgctta cttcgtcagg ttagtgacta  12480
tagcatgcca aatgtttcag ataaagttct gcgtattatc cattcatata ctgactacgt  12540
taaacgggtt gtctggaagc aatactaatg aaacttgcat taatcattga tgattatttg  12600
ccccatagca cacgcgttgg ggctaaaatg tttcatgagt taggccttga attactgagc  12660
agaggccatg atgtaactgt aattacgcct gacatctcat tacaagcaat ttattctatt  12720
agtatgattg atggtataaa ggtttggcgt ttcaaaagtg gacctttaaa ggatgtaggt  12780
aaggctaaac gtgccataaa tgaaactctt ttatcttttc gcgcatggcg cgcatttaag  12840
cacctcattc aacatgatac atttgatggt atcgtttatt attccccctc tattttttgg  12900
ggcgacttgg ttaaaaaaat aaaacaacga tgccagtgcc caagctatct gatcctaagg  12960
gatatgtttc cacagtgggt cattgatgca ggtatgttga aagccggttc accaattgaa  13020
aaatatttta ggtattttga aaaaaagtca tatcagcagg ctggccggat aggggtaatg  13080
tctgataaga atcttgagat atttcgccag accaataaag gttatccgtg tgaagtttta  13140
cgtaattggg cctcaatgac tcctgtgtct gccagcgatg attatcattc acttcgtcaa  13200
aaatacgatc taaaagataa agtcattttt ttctatggcg gtaatattgg gcatgctcag  13260
gatatggcaa acttaatgcg ccttgcgcgt aatatgatgc gttatcatga tgctcatttc  13320
ctgtttatag ggcagggtga tgaagttgag ctgataaaat ctcttgctgc agaatggaat  13380
ttaactaatt tcactcatct accttcagtg aaccaggaag agtttaaatt aattttatct  13440
gaagttgatg tcggcctgtt ctccctttca tctcgccatt cttcacataa tttccccgga  13500
aaattactag ggtatatggt tcaatcaatc ccgatccttg ggagtgtgaa tggcggcaat  13560
gatttaatgg atgtaattaa taagcacaga gccggtttca ttcatgttaa tggtgaagat  13620
gataaactgt ttgaatctgc acaattgctt cttagtgatt cagttttaag aaaacagcta  13680
ggtcagaacg ctaatgtgtt gttaaagtct caattttcgg ttgaatcggc ggcacatact  13740
atcgaagtcc gactggaggc tggagaatgc gtttagttga tgacaatatt ctggatgaac  13800
tttttcgcac tgcagcaaat tctgaacgtt tgcgcgctca ttatttattg cacgcatctc  13860
atcaggagaa ggttcaacgt ttacttattg catttgtacg cgacagctat gttgaacccc  13920
attggcatga gttaccgcat cagtgggaaa tgtttgtcgt catgcaaggg caattagaag  13980
tttgtttgta tgagcaaaat ggtgagatcc aaaaacagtt tgttgttgga gacggtacgg  14040
gaataagcgt cgtggaattt tccccaggag atatacatag tgtcaaatgc ctgtcaccaa  14100
aagcccttat gttggagata aaggaggggc catttgaccc actcaaagct aaggcttttt  14160
ctaagtggtt atagggcgat acaccaccgt ttattcttct atcttattct atacatgctg  14220
ggttaccatc ttagcttctt caagccgcgc aaccccgcgg tgaccacccc tgacaggagt  14280
agctagcatt tgaccacccc tgacaggatt agctagcata tgagctcgag gatatctact  14340
gtgggtaccc gggatccgtg taggctggag ctgcttcgaa gttcctatac tttctagaga  14400
ataggaactt cggaatagga actaaggagg atattcatat                        14440

SEQ ID NO: 10          moltype = AA  length = 19
FEATURE                Location/Qualifiers
source                 1..19
                       mol_type = protein
                       organism = synthetic construct
SEQUENCE: 10
MKKIWLALAG LVLAFSASA                                               19

SEQ ID NO: 11          moltype = DNA  length = 13043
FEATURE                Location/Qualifiers
source                 1..13043
                       mol_type = other DNA
                       organism = synthetic construct
SEQUENCE: 11
atgacgaatt taaaagcagt tattcctgta gcgggtctcg ggatgcatat gttgcctgcc  60
actaaggcga tacccaaaga gatgctacca atcgtcgaca agccaatgat tcagtacatt  120
gttgacgaga ttgtggctgc agggatcaaa gaaatcctcc tggtaactca cgcgtccaag  180
aacgcggtcg aaaaccactt cgacacctct tatgagttag aatcactcct tgagcagcgc  240
gtgaagcgtc aactgctggc ggaagtacag tccatctgtc cgccgggcgt gaccattatg  300
aacgtgcgtc agggcgaacc tttaggttta ggccactcca ttttgtgtgc gcgacctgcc  360
attggtgaca acccatttgt cgtggtactg ccagacgttg tgatcgacga tgccagcgcc  420
gacccgctac gttacaacct tgctgccatg attgcacgtt tcaacgaaac gggccgcagc  480
caggtgctgg caaaacgtat gccgggtgac ctctctgaat actccgtcat ccagactaaa  540
gagccgctgg accgtgaggg taaagtcagc cgcattgttg aatttatcga aaaaccggat  600
cagccgcaga cgctggactc agacatcatg gccgtaggtc gctatgtgct ttctgccgat  660
atttggccgg aactggaacg tactcagcct ggtgcatggg gacgtattca gctgactgat  720
gctattgccg agctggcgaa aaaacaatcc gttgatgcaa tgctgatgac cggcgacagt  780
tacgactgcg gcaaaaaaat gggctatatg caggcgtttg tgaagtatgg cctacgcaac  840
ctgaaagaag gggcgaagtt ccgtaaaggt attgagaagc tgttaagcga ataatgaaaa  900
tctgaccgga tgtaacggtt gataagaaaa ttataacggc agtgaaaatt cgcagcaaaa  960
gtaatttgtt gcgaatcttc ctgccgttgt tttatataaa ccatcagaat aacaacgagt  1020
tagcagtagg gttttattca aagttttcca ggattttcct tgtttccaga gcggattggt  1080
aagacaatta gcgtttgaat ttttcgggtt tagcgcgagt gggtaacgct cgtcacatca  1140
taggcatgca tgcagtgctc tggtagctgt aaagccaggg gcggtagcgt gcattaatac  1200
ctctattaat caaactgaga gccgcttatt tcacagcatg ctctgaagta atatggaata  1260
aattaagcta gcgtgaagat acttgttact aggggcgcag gatttattgg ttctgctgta  1320
gttcgtcaca ttataaataa tacgcaggat agtgttgtta atgtcgataa attaacgtac  1380
gccggaaacc tggaatcact tgctgatgtt tctgactctg aacgctatgt tttgaacat  1440
```

-continued gcggatattt gcgatgctgc tgcaatggcg cggatttttg ctcagcatca gccggatgca 1500
gtgatgcacc tggctgctga aagccatgtg gatcgttcaa ttacaggccc tgcggcattt 1560
attgaaacca atattgttgg tacttatgtc cttttggaag cggctcgcaa ttactggtct 1620
gctcttgatg gcgacaagaa aaatagcttc cgttttcatc atatttctac tgacgaagtc 1680
tatggtgatt tgcctcatcc tgacgaagta aataataaag aacaattacc cctctttact 1740
gagacgacag cttacgcgcc tagtagtcct tattccgcat caaaagcatc cagcgatcat 1800
ttagtccgcg cgtggaaacg tacctatggt ttaccgacta ttgtgactaa ctgttcgaat 1860
aactacggtc cttatcactt tccggaaaaa ttgattccac tagtaattct taatgctctg 1920
gaaggtaagg cattacctat ttatggcaaa ggggatcaaa ttcgtgactg gctgtatgtt 1980
gaagatcatg cgcgtgcgtt atataccgta gttactgaag gtcaagcggg tgaaacctat 2040
aacattggcg gacacaacga aaagaaaaac atcgatgttg tgctgactat ttgtgatttg 2100
ttggacgaga tagtcccgaa agagaaatct tatcgtgagc aaattactta tgttgctgat 2160
cgcccagggc atgatcgccg ttatgcgatt gatgctgaga agattggtcg cgaattggga 2220
tggaaaccac aggaaacgtt tgagagtggg attcgtaaaa cggtggaatg gtatttggct 2280
aatgcaaaat gggttgataa tgtgaaaagt ggtgcctatc aatcgtggat tgaacagaac 2340
tatgagggcc gccagtaatg aatatcctcc tttttggcaa aacagggcag gtaggttggg 2400
aactacagcg tgctctggca cctctgggta atttgattgc tcttgatgtt cactccactg 2460
attactgtgg tgattttagt aaccctgaag gtgtggctga aacagtcaaa agaattcgac 2520
ctgatgttat tgttaatgct gcggctcaca ccgcagtaga taaggctgag tcagaacccg 2580
aatttgcaca attactcaat gcgactagcg ttgaatcaat tgcaaaagcg gcaaatgaag 2640
ttggggcttg ggtaattcat tactcaactg actacgtatt ccctggaaat ggcgacacgc 2700
catggctgga gatggatgca accgcaccgc taaatgttta cggtgaaacc aagttagctg 2760
gagaaaaagc attacaagag cattgtgcga agcacctaat ttccgtacc agctgggtct 2820
atgcaggtaa aggaaataat ttcgccaaaa cgatgttgcg tctggcaaaa gagcgtgaag 2880
aactagccgt tattaatgat cagtttggtg cgccaacagg tgctgaactg ctggctgatt 2940
gtacggcaca tgccattcgt gtcgcactga ataaaccgga tgtcgcaggc ttgtaccatt 3000
tggtagccag tggtaccaca acctggtacg attatgctgc gctggttttt gaagaggcgc 3060
gcaatgcagg cattcctctt gcactcaaca agctcaacgc agtaccaaca actgcctatc 3120
ctacaccagc tcgtcgtcca cataactctc gccttaatac agaaaaattt cagcagaatt 3180
ttgcgcttgt attgcctgac tggcaggttg gtgtgaaacg catgctcaac gaattattta 3240
cgactacagc aatttaatag tttttgcatc ttgttcgtga tggtggagca agatgaatta 3300
aaaggaatga tgaaatgaaa acgcgtaaag gtattatttt agcgggtggt tctggtactc 3360
gtctttatcc tgtgactatg gtcgtcagta aacagctatt acctatatat gataaaccga 3420
tgatctatta tccgctttct acactgatgt tagcgggtat tcgcgatatt ctgattatta 3480
gtacgccaca ggatactcct cgttttcaac aactgctggg tgacggtagc cagtggggcc 3540
tgaatcttca gtacaaagtg caaccgagtc cggatggtct tgcgcaggca tttattatcg 3600
gtgaagagtt tattggtggt gatgattgtg ctttggtact tggtgataat atcttctacg 3660
gtcacgacct gcctaagtta atggatgccg ctgttaacaa agaaagtggt gcaacggtat 3720
ttgcctatca cgttaatgat cctgaacgct atggtgtcgt tgagtttgat aaaaacggta 3780
cggcgatcag cctggaagaa aaaccgctac aaccaaaaag taattatgcg gtaaccgggc 3840
tttatttttta tgataacgac gttgtcgaaa tggcgaaaaa tcttaagcct tctgcccgcg 3900
gtgaactgga aattaccgat attaaccgta tctatatgga acaagggcgt ttatctgttg 3960
ccatgatggg gcgtggttat gcgtggttag acacggggac acatcagagc ctgattgagg 4020
caagcaactt tattgcaaca attgaagagc gtcaggggct gaaagtttcc tgcccggaag 4080
aaattgctta ccgtaaaggg tttgttgatg ctgagcaggt gaaagtatta gctgaacctc 4140
tgaaaaaaaa tgcttatggt cagtatctgc tgaaaatgat taaaggttat taataaaatg 4200
aacgtaatta aaacagaaat tcctgatgta ctgatttttg aaccgaaagt ttttggtgat 4260
gagcgtggtt tctttttttga gagctttaac cagaaggttt ttgaggaagc tgtaggccgc 4320
aaagttgaat ttgttcagga taaccattcg aagtctagta aaggtgtttt acgcgggctg 4380
cattatcagt tggaacctta tgcacaagga aaattggtgc gttgcgttgt cggtgaagtt 4440
tttgacgtag ctgttgatat tcgtaaatcg tcatcgactt ttggcaaatg ggttggggtg 4500
aatttatctg ctgagaataa gcggcaattg tggattcctg agggatttgc acatggtttt 4560
ttagtgctga gtgagacggc ggagtttttg tataagacga caaattatta tcatcctcag 4620
agtgatagag gaataaaatg ggatgatcca agcatcaata tttcatggcc agtcgattca 4680
caagtgctgc tatcagctaa agataataag catcctccat taacaaagat tgaaatgtat 4740
agttaagatc acgataaatc ttggaagggt tgcaaaattg aataaaatag tgagcaaaag 4800
tgaaataagg aacgtaatcc acaatgctgg ctatatgatg attactcaga tagctttata 4860
tgttgcacca ttatttatac tgagttatct gttaaaaaca ctgggggttg cacagtttgg 4920
taattatgcc ttaatactat caatcgttgc atatttacag attataacgg attatggttt 4980
ttcttttagt gcaagtcgtg cgatctcaca gaatagagag gacaaagaat atatatcaaa 5040
aatttatctg tcaactatga ctatcaagtt ggcgatatgc gctttcttat tcttattgct 5100
catgctattt ttaaatcttt tgcctgtgca agctgaatta aaacaaggaa tattatatgg 5160
atatcttctt gtaataggaa atactttcca accacaatgg tttttccaag gtatcgaaaa 5220
attaaaaatc atagcccttt ctaatgttat atcaagatgc gccgcgtgtt tacttgtatt 5280
tatctatgtg aggaatagcg aggatttaca aaaagcactt ttagtacagt cacttccatt 5340
agtaatttct gcgattggat taaatatatt tatattgaaa tatatcaata ttattttttcc 5400
ggaaaaaaaa ttatttaagg taattttaaa agaaggtaag gatttttttc ttgcatcact 5460
ttattctgtt attctcaata atagtggcat ttttctatta gggattttta ctaatcctgt 5520
tattgttggt gtatatgccg ccgctgaaaa gatagtcaag gccgtattgt cgctatttac 5580
accactgacg caagctatat atccttataa ttgtcgtaag ttttcactat ccgtatttga 5640
cggcattgag gcagcaaaaa aaactggtat accaattata attttagcat ttatagctgc 5700
tgttatcgtt gcaattacct tacctgttgc aatcgactat cttaattttc caaaagaaac 5760
aatttttgta ggtcaaatat taagtgcatg gatctttttt ggtgttctta ataatgtatt 5820
cggcattcag atattgagtg catcaggaag aagtaaaata tatagtagga tggtattcgt 5880
atcagcgctt ataacattac ttttgattac tctattattg cagttttgta acgccactgg 5940
agtggcatgt gcaatattat tgggtgaaat gttcttatca atattgttac ttaagcgata 6000
taaaaaaata atttaaggaa tagttatgaa gaagttatta ttagtgttcg gtactaggcc 6060
tgaagcaata aagatggcct ctatcattga attattaaaa aaagattgta gattcgaata 6120
taaaatatgt gtgacaggcc aacataaaga gatgcttgat caagttatgc aagtatttga 6180

-continued

```
tgttaaacct gattataatt tacggattat gcagcctggg caaacattag tatctatagc  6240
aacaaatata ctctcacggt taagtgaagt tttaattata gaaaagccag atattatact  6300
tgtgcatggg gatacaacga ctacccttgc tgctacttta gctgggtatt accaccaaat  6360
aaaagtttgt catgtggaag caggattaag aacaggggat atttactctc cttggcctga  6420
agagggcaat cgtaaagtta caggggcatt agcatgtatt catttcgccc caacagagag  6480
atcaaaagat aatctcctga gggagggggt caaagtaaat aatatatttg taacgggtaa  6540
taccgtcatc gactctttat ttattgcaaa agatatcata gataatgacc ctaatataaa  6600
gaacgcttta cataataaat ttaattttct tgataaaagc cgacgagtag tacttataac  6660
aggtcatcga agagaaaatt tcgggaaagg ttttgaagat atatgctttg caataaagga  6720
attagctttc atttatccta atgtagattt tatttatccg gtgcatctta atcccaatgt  6780
aatggaacca gtacatcgta tattagataa tatatgtaat atttacctta ttgagccctt  6840
ggattatttg ccttttgttt atttaatgaa tgagtcatat ttaatattga ctgattcagg  6900
ggggatacaa gaagaagcgc cttcgttagg taaaccggtt ttggttatgc gtgatactac  6960
tgaacgccct gaggcggttg aggctggtac tgttgtatta gtggggactt ctaagataaa  7020
aatagtaaat aaagtaacgg agctattaaa caatgctgat atctacaatg ctatgtctct  7080
gttacataat ccatatggcg atggaacagc tgctcaaaaa attcttaatg tgctcgccca  7140
agagctaatt taatttaagc taaaaatatg ttattaatta ttgctgatta tccaaacgaa  7200
atgaatatgc gcgagggagc tatgcaacga atagatgcga tagactctct cattcgagat  7260
cgcaagcgag tgtatttgaa tatttcattc aaaaagcatc tagttcgctc aaatagttcc  7320
tttaataatg ttatagttga aaatctaaat gcaattattc acagaaacat cataaaacag  7380
tacatgcaaa aatcaacaac tatatatgtt cattctgttt ataatttatt aaaggttata  7440
acgctcattg atctaaaaaa aacaattctt gatatacatg gtgttgtacc ggaagaactt  7500
ttggcagata ataaaaaatt acttagtaaa gtatataaca tggtggaaaa aaaaggtgtc  7560
cttggatgca aaaaattaat acacgtcagt acagaaatgc aaaaacacta tgaagcaaaa  7620
tatggagtaa acttggctga aaggtcaata gtgctcccga tttttgaata taaaaatata  7680
acccaatcgc aaaacaaatg gacagaaaat aaaatacgaa gtatctatct tggaggatta  7740
caaacatggc aaaatattga taaaatgatt caagtttgtg atgacacagt gataaacaat  7800
gaagcaggta agtatgaatt caacttttttc atcccacaga gtaacttgga agggtttata  7860
gataaatatt cgttaaaatt acataaatatc aatgctaatg catctacgct atcacgtgat  7920
gaagtaattc cctttctaaa agaatgtcat attggtttg tattgcgcga tgatataata  7980
gtaaacagag ttgcgtgccc tacaaaattg gttgaatatt tagagtgtgg tgtcgttcca  8040
gttgtgctct ccccacttat aggtgatttt tattcgatgg gatatcaata cattactaca  8100
gaggaaatgg ctaacagaag tataagtttg ttggatcttg aaaaaatggc tgcacataat  8160
ttacaaattt tgacttctta tcagaagaga acctacaagg cacagaaaga acttattgct  8220
caactgtgct gaatttttta catatataaa attatgtaag catatcgcgg gtcaggtaat  8280
tgtatgcgta tcaaatataa agataacggt tatatattat gttttctatt atgtttcatt  8340
ttgagctact tagttttact caaatctgac tactttcctg ctgattttct gccatataca  8400
gaaatatacg atgggacata cggagaaatc aataatattg agcctgcctt tttatattta  8460
acacggttgt ttcattattt aaatttcccc tatatatttt ttgcaatgtt agtttgtgcc  8520
ttatgtttaa gttggaaaat aaaatatgca agaaaaataa ttaaagatag ttatatatat  8580
ttgttcttgt atgtatatgt atcattttat gtgtttttgc atgaaatgac tcaattgcgc  8640
atagcaattg cagtcactat gtgctatgtg tcggtttatt attactttta taaaaattgt  8700
attaaacatg cactgccatg gatggtgttg gctattttgt ttcattacag cgccttgctt  8760
ttatttatgt cattatttat atacagttat aggaggttat taatagtaat tatagggttt  8820
gtaatatgta tgagcttttt aaacgtgtat gcagatacaa ttgcactata tttgccaaat  8880
gaaaaaatag taaattattt atatagtatt tcatcatcat tagacaatag aaatgatttg  8940
gcaatattca acctgaataa tataatattt ttatcaatat ttattttgat cttttatctt  9000
agccgatata taaaattaaa tgataatgag gcgaagttta ttaagtatgt gcaatgttca  9060
ggaatattag cctttttgtat tttcttttctg gctagtggag tcccggtcat tgcttatcga  9120
actgcagagt tgctgcgaat attttatccg atggctttag tattaatcct ttcgcatata  9180
aaaaaataata atatgcgtta ttttattgca gtcattatag ttatcctttc aggcttaatg  9240
ttgtttataa cactaagggc tgtatcaata gttggtcaag gattataaaa tgaatgttgc  9300
tattttgttg tctacgtata atggcgaaaa atatttagag gaacaactgg attcattgct  9360
gcttcaaagt tatcaggatt ttgtagtgta tatccgtgat gacggatcat ctgatagaac  9420
tgtaaatata ataaaccaat acgtaatgaa agataacaga tttattaacg tgggtaattc  9480
agaaaatctt ggttgtgctg cttcgtttat taatttatta agaaatgctt cagccgatat  9540
ttatatgttt tgtgaccaag atgattattg gcttccgaat aaattacagc gtgctgtgga  9600
ttattttttcg gctattgatc ctttacaacc taccttgtat cattgcgatc taagcgttgt  9660
tgatgaaaaa cttaatatta tacaaaattc atttttgcag catcagaaaa tgtcagcgta  9720
tgattcaatg agaaaaaata atcttttcat acaaaatttt gttgttggtt gttcatgtgc  9780
tgttaatgct tcacttgcgg aatttgttct ttcgcgaatt ggagagcagc atgtaaaaat  9840
gatagctatg catgactggt ggttagccgt gactgcaaaa ctttttggtc gaatccattt  9900
tgataatact caaacgattc tttatcgaca acatcagggc aatgtattag gtgcaaaatc  9960
atcaggtatg atgcgtttta ttcgattagg attaaatggg caagggattt cgcgagtagt  10020
atcttttaga aaaaaagttt gtgcgcaaaa taagcttctt ttagatgtct atgataaaga  10080
tttaaatctt gagcaaaaaa aatctatcag gcttgtaatt gagggcctta aagagaactc  10140
ttcaattgct gaccttttaa aatgtttcta tcatggtagc tatatgcaag gttttaaacg  10200
taatcttgcc ttaatatatt cagttcttta cacaaaaaaa agaagatagt gtatccttat  10260
gaaaaaaatt gctattatcg gtactgttgg cataccagca tcatatggcg gatttgaaac  10320
attagttgaa aatttaacaa gatacaattc ctcgggagtt gaatataatg tttttttgttc  10380
atcgtttcac tacaaatccc accaaaaaaa acataatggg gcccgtttaa tttatattcc  10440
gcttaaagcc aatggatggc agagcattgc gtatgacata atttcgttag catattctat  10500
tttttgaag cctgatgtga ttctgatttt aggggtttct ggttgttcat ttttgccttt  10560
cttcaaactc ttaacacgcg ctaagtttat tactaatatt gatggcctgg aatggcgaag  10620
agataaatgg aattcaaaag tgaaacgttt cttaaaattt tcagaaaaaa tcgcagttca  10680
atattcggat gtcgttatta cggataatga ggcaatttct gagtacgttt ttaacgagta  10740
taataaagat agccgagtta ttgcctatgg aggggatcat gcatggttaa atactgagga  10800
tgtatttaca acaagaaatt ataaaagcga ttactacctt tctgtatgtc gtatcgaacc  10860
cgaaaacaat gtagaattaa ttttaaaaac attttcaaag ctaaaatata aaataaaatt  10920
```

```
tattggaaat tggaatggca gcgagtttgg aaagaaactt aggctgcatt attctaacta  10980
tccaaatatt gaaatgattg atccgattta tgatcttcaa caattatttc acttacgaaa  11040
taattgcata ggatatatac atggtcattc ggctggagga acaaaccctt ctttagtcga  11100
ggcaatgcat tttagtaaac ctatatttgc atatgattgt aagtttaata ggtacactac  11160
tgaaaatgaa gcatgttatt tttctaatga atctgacctc gcagagaaaa tcataatgca  11220
ttgtgagcta tcattaggtg tctctggcac gaaaatgaaa gaaattgcta accagaaata  11280
cacttggaga cgaatagcag aaatgtatga ggattgctat taactctgtt aaacttcaaa  11340
tcttttacaa tatatggcat gactataagc gcattaattg tttttcaagc cgctctcgcg  11400
gtgaccaccc cctgacaggg gatccgtgta ggctggagct gcttcgaagt tcctatactt  11460
tctagagaat aggaacttcg gaataggaac taaggaggat attcatatgg ataaagccgt  11520
aagcatataa gcatggataa gctatttata ctttaataag tactttgtat acttatttgc  11580
gaacattcca ggccgcgagc attcagcgcg gtgatcacac ctgacaggag tatgtaatgt  11640
ccaagcaaca gatcggcgta gtcggtatgg cagtgatggg acgcaacctt gcgctcaaca  11700
tcgaaagccg tggttatacc gtctctattt tcaaccgttc ccgtgagaag acggaagaag  11760
tgattgccga aaatccaggc aagaaactgg ttccttacta tacggtgaaa gagtttgtcg  11820
aatctctgga aacgcctcgt cgcatcctgt taatggtgaa agcaggtgca ggcacggatg  11880
ctgctattga ttccctcaaa ccatatctcg ataaaggaga catcatcatt gatggtggta  11940
acaccttctt ccaggacact attcgtcgta atcgtgagct ttcagcagag ggctttaact  12000
tcatcggtac cggtgtttct ggcggtgaag agggggcgct gaaaggtcct tctattatgc  12060
ctggtggcca gaaagaagcc tatgaattgg tagcaccgat cctgaccaaa atcgccgccg  12120
tagctgaaga cggtgaacca tgcgttacct atattggtgc cgatggcgca ggtcactatg  12180
tgaagatggt tcacaacggt attgaatacg gcgatatgca gctgattgct gaagcctatt  12240
ctctgcttaa aggtggcctg aacctcacca acgaagaact ggcgcagacc tttaccgagt  12300
ggaataacgg tgaactgagc agttacctga tcgacatcac caaagatatc ttcaccaaaa  12360
aagatgaaga cggtaactac ctggttgatg tgatcctgga tgaagcggct aacaaaggta  12420
ccggtaaatg gaccagccag agcgcgctgg atctcggcga accgctgtcg ctgattaccg  12480
agtctgtgtt tgcacgttat atctcttctc tgaaagatca gcgtgttgcc gcatctaaag  12540
ttctctctgg tccgcaagca cagccagcag gcgacaaggc tgagttcatc gaaaaagttc  12600
gtcgtgcgct gtatctgggc aaaatcgttt cttacgccca gggcttctct cagctgcgtg  12660
ctgcgtctga agagtacaac tgggatctga actacggcga aatcgcgaag attttccgtg  12720
ctggctgcat catccgtgcg cagttcctgc agaaaatcac cgatgcttat gccgaaaatc  12780
cacagatcgc taacctgttg ctggctccgt acttcaagca aattgccgat gactaccagc  12840
aggcgctgcg tgatgtcgtt gcttatgcag tacagaacgg tattccggtt ccgaccttct  12900
ccgcagcggt tgcctattac gacagctacc gtgctgctgt tctgcctgcg aacctgatcc  12960
aggcacagcg tgactatttt ggtgcgcata cttataagcg tatcgataaa gaaggtgtgt  13020
tccataccga atggctggat taa                                          13043
```

```
SEQ ID NO: 12          moltype = DNA  length = 13790
FEATURE                Location/Qualifiers
source                 1..13790
                       mol_type = other DNA
                       organism = synthetic construct
SEQUENCE: 12
atgacgaatt taaaagcagt tattcctgta gcgggtctcg ggatgcatat gttgcctgcc  60
actaaggcga tacccaaaga gatgctacca atcgtcgaca agccaatgat tcagtacatt  120
gttgacgaga ttgtggctgc agggatcaaa gaaatcctcc tggtaactca cgcgtccaag  180
aacgcggtcg aaaaccactt cgacacctct tatgagttag aatcactcct tgagcagcgc  240
gtgaagcgtc aactgctggc ggaagtacag tccatctgtc cgccgggcgt gaccattatg  300
aacgtgcgtc agggcgaacc tttaggttta ggccactcca ttttgtgtgc gcgacctgcc  360
attggtgaca acccatttgt cgtggtactg ccagacgttg tgatcgacga tgccagcgcc  420
gacccgctac gttacaacct tgctgccatg attgcacgtt tcaacgaaac gggccgcagc  480
caggtgctgg caaaacgtat gccgggtgac ctctctgaat actccgtcat ccagactaaa  540
gagccgctgg accgtgaggg taaagtcagc cgcattgttg aatttatcga aaaaccggat  600
cagccgcaga cgctggactc agacatcatg gccgtaggtc gctatgtgct ttctgccgat  660
atttggccgg aactggaacg tactcagcct ggtgcatggg gacgtattca gctgactgat  720
gctattgccg agctggcgaa aaaacaatcc gttgatgcaa tgctgatgac cggcgacagt  780
tacgactgcg gcaaaaaaat gggctatatg caggcgtttg tgaagtatgg cctacgcaac  840
ctgaaagaag gggcgaagtt ccgtaaaggt attgagaagc tgttaagcga ataatgaaaa  900
tctgaccgga tgtaacggtt gataagaaaa ttataacggc agtgaaaatt cgcagcaaaa  960
gtaatttgtt gcgaatcttc ctgccgttgt tttatataaa ccatcagaat aacaacgagt  1020
tagcagtagg gttttattca aagttttcca ggattttcct tgtttccaga gcggattggt  1080
aagacaatta gcgtttgaat ttttcgggtt tagcgcgagt gggtaacgct cgtcacatca  1140
taggcatgca tgcagtgctc tggtagctgt aaagccaggg gcggtagcgt gcattaatac  1200
ctctattaat caaactgaga gccgcttatt tcacagcatg ctctgaagta atatggaata  1260
aattaagtga aaatacttgt tactggtggc gcaggattta ttggttcagc tgtagttcgt  1320
cacattataa ataatacgca ggatagtgtt gttaatgtcg ataaattaac gtacgccgga  1380
aaccgggaat cacttgctga tgtttctgat tctgaacgct atgtttttga acatgcggat  1440
atttgcgatg cacctgcaat ggcacggatt tttgctcagc atcagccgga tgcagtgatg  1500
cacctggctg ctgaaagcca tgttgaccgt tcaattacag gccctgcggc atttattgaa  1560
accaatattg ttggtactta tgtccttttg gaagccgctc gcaattactg gtctgctctt  1620
gatagcgaca agaaaaatag cttccgtttt catcatattt ctactgacga agtctatggt  1680
gatttgcctc atccagatga agtaaataat acagaagaat taccccttatt tactgagacg  1740
acagcttacg cgccaagcag cccttattcc gcatccaaag catccagcga tcatttagtc  1800
cgcgcatgga aacgtacgta tggtttaccg accattgtga ctaattgctc gaacaactat  1860
ggtccgtatc acttcccgga aaagcttatt ccattggtta ttcttaatgc actggaaggt  1920
aaggcattac ctatttatgg caaaggggat caaattcgcg actggttgta tgtagaggat  1980
catgctcgtg cgttatatac cgtcgtaacc gaaggtaaag cgggtgaaac ttataacatt  2040
ggcggacaca acgaaaagaa aaacatcgat gttgtgctga ctatttgtga tttgttggat  2100
gagattgtac cgaaagagaa atcttatcgt gagcaaatta cttatgttgc tgatcgccca  2160
```

```
gggcatgatc gccgttatgc aattgatgcc gataaaatta gccgcgaatt gggctggaaa  2220
ccacaggaaa cgtttgagag cgggattcgc aaaacggtgg aatggtatct ggctaataca  2280
aattgggttg agaatgtgaa aagcggtgct tatcagtcat ggatcgaaca aaactatgag  2340
ggccgtcagt aatgaatatc ctgcttttcg gcaaaacagg gcaggtgggt tgggaactgc  2400
agcgtgctct ggcgccgctg ggtaatctga tcgctcttga tgttcactcc actaattatt  2460
gtggagattt cagcaacccc gaaggtgtgg cagaaaccgt caaaaaaatt cgtcctgacg  2520
ttattgttaa tgctgctgct cacactgcag tagataaagc agaatcagaa ccggatttcg  2580
cacaattact taacgcgaca agcgtcgaag cgattgcaaa agctgctaat gaagtcgggg  2640
cctgggttat acactactct actgattatg ttttcccagg cagtggtgac gcgccatggc  2700
tggaaacgga tgcaacagca ccgctaaatg tttacggtga aacaaaatta gctggggaaa  2760
aggcattaca agaacattgc gcaaagcatc ttattttccg taccagctgg gtatacgctg  2820
gtaaaggaaa taactttgct aaaacgatgt tgcgtttggc aaaagaacgc gaagaactgg  2880
ctgtgataaa cgatcagttt ggcgcaccaa caggtgctga attgctggct gattgcaccg  2940
ctcatgccat tcgcgtggca ttaaaaaaac cagaagtcgc tggcttgtac catctggtag  3000
caagtggcac aacaacctgg cacgattatg ctgcgctggt ttttgaagag gcgcgcaaag  3060
cagggattaa tcttgcactt aacaaactta acgccgtgcc aacaacggcc tatcccacac  3120
cagcccgtcg accccataac tctcgcctca atacagaaaa gtttcagcag aactttgcgc  3180
ttgtcttgcc tgactggcag gtgggcgtga aacgtatgct caacgaatta tttacgacta  3240
cggcaattta acaaattttt gcatctcgct catgatgcca gagcgggatg aattaaaagg  3300
aatggtgaaa tgaaaacgcg taaaggtatt attctggctg gtggttccgg cactcgtctt  3360
tatcctgtga cgatggcagt gagtaaacaa ttgctgccga tttatgataa gccgatgatt  3420
tattatccgc tttcaacgct tatgttagcg ggtattcgcg atattcttat tattagtacg  3480
ccacaggata caccgcgttt ccaacaatta ttgggggacg ggagccagtg gggtcttaat  3540
ctacagtata aagtacaacc gagtccggat ggcctggcgc aagcgtttat tattggcgaa  3600
gactttattg gtggtgatga ttgtgcactc gtacttggcg ataatatctt ctatggacac  3660
gacttgccga aattgatgga agctgctgtt aacaaagaaa gcggtgcaac ggtatttgct  3720
tatcacgtta atgatcctga acgctatggt gtcgtggagt ttgataataa cggtacggca  3780
attagcctgg aagaaaaacc gctggagcca aaaagcaact atgcggttac tgggctttat  3840
ttctatgaca atgacgttgt ggaaatggct aaaaacctta agccttctgc ccgtggcgaa  3900
ctggaaatta ccgatattaa ccgtatttat atggaacaag gacgtttgtc tgtagccatg  3960
atggggcgtg gctatgcatg gttggataca gggacgcatc aaagccttat tgaagcaagt  4020
aacttcattg caacaattga agagcgtcag ggattaaagg tatcttgccc ggaagagatt  4080
gcttaccgta aagggtttat tgatgccgag caggtgaaag tattagccga accgcttatc  4140
aagaatcaat atggtcaata tttgctgaaa atgatcagcg aatagtatat gggaactcaa  4200
tgatggatat taaattaatc tctttgcaaa aacatgggga tgagcgcggt gcattaattg  4260
ctcttgaaga gcaacgaaat atacctttcg aagtcaaaag aatatattac atacttgaga  4320
ctcttaatgg agtaagacgc ggatttcatg cgcacaaggt tactcgtcag ttagctattg  4380
tagtcaaggg agcttgtaaa tttcatctgg ataatggtaa agaaacaaag caggtggaac  4440
ttaatgatcc aacaattgcg ttgctgatag aaccctatat atggcatgaa atgtatgatt  4500
ttagtgatga ttgtgtgctg cttgtaattg cggatgattt ctataaagag tctgattata  4560
tccgcaatta tgatgatttt attagaagag taaattcaat tgagaattca taagctaagt  4620
gacgtccaga caacatcaat tggtgatgga acaactatct ggcagtttgt tgtgatacta  4680
aaaggtgctg taattggtaa taattgcaac atctgtgcaa ataccttaat tgaaaataac  4740
gttgtaattg gtaacaatgt cacagtcaaa agcggtgtgt atatttggga tggcgttaaa  4800
atagaggata atgtttttat tggtccttgt gtagcattta caaatgataa gtatcctcgc  4860
tctaaagtct atcctgatga atttttgcaa acaataatac gcaaaggagc atcaataggt  4920
gctaacgcaa ccatcctgcc aggaattgaa attggtgaaa aagcaatcgt tggtgcgggg  4980
agtgttgtaa ccaaaaatgt accgccatgc gcaatagtag taggtaatcc agctcgattt  5040
attaaatggg tagaggataa tgaataaaat tgatttttta gatctttttg caattaacca  5100
gcgacagcac aaagaattag tctctgcgtt tagtagggtg ctagattctg gttggtatat  5160
catgggcgaa gaacttgagc agttcgagaa agagttcgca gaatactgtg gagttaagta  5220
ttgcattggt gtagcaaatg gccttgatgc gttgatacta gtattgaggg catggaaaga  5280
acttggctat cttgaagacg gtgacgaggt attagtaccg gcaaatacat atattgcttc  5340
tattcttgct ataacagaga acaaacttgt tcctgttctt gttgaaccag atatagaaac  5400
ttataatatt aatcctgctt taattgaaaa ttacattacg gaaaaaaacta aagcaatatt  5460
accggttcac ttatatggtc tattgtgcaa tatgccagaa attagtgcaa tcgccagaaa  5520
atataatctg ttgattcttg aagattgtgc acaagcacat ggtgcaatac gtgatggtcg  5580
caaagctgga gcttgggggg atgctgcagg atttagtttt tatccaggaa aaaaccttgg  5640
agctttgggg gatgcgggag ctgttactac aaataatgca gaattatcct caactataaa  5700
agctttgcga aattatgggt cacataagaa atatgaaaat atttatcagg gattgaatag  5760
tcgattggat gaactgcaag cagccttatt gcgtgtaaaa atccatacat taccggaaga  5820
tactgcgatt cggcaaagga ttgctgaaaa atatattcgt gaaataaaaa accctgcgat  5880
tacgttacca gtgtacgaag gccaaggtgc gcatgtttgg catttatttg tagtaagaat  5940
cgctaatcgt gaaaaattcc agtcatactt attagagaag ggtatcaaaa ccttaattca  6000
ctatccatta ccaccccata agcagcaagc atatcaaaat atgtctagcc ttagccttcc  6060
aattactgag caaattcatg atgaagtcat ttctttacct ataagtccgg taatgagtga  6120
agatgatgtc aattatgtaa tcaaaatggt caatgattac aagtaatgaa aaaatttctt  6180
caggtaacta tattatccgc tatctataca ttcattaaaa tgattgcggg ttttatcatc  6240
ggtaaggtag tagcaattta tacagggcca tcaggggtag caatgcttgg ccaagtgcaa  6300
agtttaatca caatagttgc aggtactacc tctgcacctg taagcacagg ccttgttcga  6360
tatactgcgg aaaattggca agaaggacaa gaagcatgcg cgccatggtg gcgcgcatgc  6420
ttaagggtta ctctgttttt attcttgctt attattcccg ttgttattat attgtcgaaa  6480
aatattagtg agttactttt tagcgatgga caatacacat ggttaatcat tttcgcatgt  6540
tgtatattgc cattctccat tataaataca ttgatcgctt cagttttaaa tggtcaacaa  6600
ttttataagc aatatatatt ggttgggatg ttttctgtat tcatttctac tatgtttatg  6660
attttgttga ttgtagctta taatcttaaa ggtgcattga ttgccacagc tataaatagt  6720
gctattgctg gtcttgtatt ggttttattt tgtctcaata aatcttggtt tagatttaaa  6780
tattggtggg gtaaaacgga taaagacaaa attataaaaa ttattcatta tactctgatg  6840
gctctggttt ctgttatctc catgcctaca gcattgatgt gtattagaaa aatattgatt  6900
```

-continued

```
gctaaaactg gttgggagga tgcagggcaa tggcaggccg tatggaagat atctgaggtt  6960
tatcttggtg ttgtgacaat tgctttgtca acatatttct taccaagatt gacaattata  7020
aaaacaagtt tccttataaa aaaagaagta aatagtacta tattatacat aatatctatt  7080
acttcattca tggcgttgag tatctattta ttccgcgatt tggtaataac agttttattt  7140
actgaacagt ttcgctcagc tcgtgaatta tttttattac aacttatagg ggatgtaata  7200
aaaattgctg ggtttcttta tgcataccct cttcaaagtc aggggcatac taaactattc  7260
atcagttcag aagtgatttt ttctatgctc tttatcatta ccacctatat ttttgttgta  7320
aattatggag tacatggtgc taacataagt tatgtcatta catatagttt atattttgtg  7380
tttgcatttg tgtttactaa ttttattaat gttagaagaa ataattaaaa acagaggttg  7440
aattttgaaa ataattatac ctgtcttagg atttggcagg gctggtggtg aaagagttct  7500
ttctaagctg gcaactgaat tgatgaatta tggacatgat gtaagttttg ttgttccaga  7560
taatagaact aatccatatt atgctaccac agcaaaaatt gtcacgagta aatctagtca  7620
aaaccgtgta aaaatattga gaatcattaa aaattactat aatctgtggc gtaaatgcat  7680
agagttaaat cctgatgctg tagttgctag ttttcatttg actgcctatc ttgtcgcatt  7740
attaccaatc acccgtcgta agaaatatta ttatattcag gcgtatgaag ttaatttttt  7800
tgataatata atatggaaat taatagcggg tttaacatat tatttaccgc ttaaaaaaat  7860
actaaatagt cctaatttgc ttcctcataa acatgatgat tttataggag tagttcctgc  7920
aggagtagat ttaaacgttt tctatccgaa accatcaaat aggttattaa atggtcacac  7980
atcaataggg attattggta gaaaagagaa gcacaaagga actagcgaaa ttatttcagt  8040
attgtgttca ctggaaaata aagctggaat tataatcaat attgcgatct atcttgaaga  8100
agttgataag cagcgtttaa tcgctgccgg gtttcaggtt aattttttc cgattacttc  8160
tgatttagaa ttggcatcct tttatcgaag caatgacatc atgattgctg ttgggttaat  8220
tgaagatggc gctttccatt atccttgtgc tgaatcaatg gcttgtggtt gtcttgttat  8280
ttcaaattat gcgccactta ctgaaactaa cagtgtactt aaattagtca agtttgatgc  8340
ttgcaaactt ggtgaagcaa ttaatctttg tctcaatctt gacctagaag aaaaaagcaa  8400
agaaatccaa tctaatattt ctgtgttgaa taaatatgac tggaaaattg ttggtgaaac  8460
tttcaatagt ttattgttag atgcaaataa atagtatacg ttgatgggga aaatatgaat  8520
attgttaaaa ctgatattcc agatctgatc gttcttgaac caaaagtgtt tagtgatgaa  8580
cgcggctttt ttatggagag ttataatcag attgaatttg agaaggcaat aggaaggcac  8640
gtaaattttg ttcaggataa tcattcaaaa tctagtaaag gcgtactacg tgggttgcat  8700
tatcaattag caccgtatgc acaggctaaa ttagttcgat gtgttgtagg tcaggtattt  8760
gatgttgctg ttgatcttag aaaaaattca ccaacgttca aaaaatggtt tggaataacc  8820
ctttccgcag aaaataaacg acaattatgg atacccgaag gatttgctca tggtttcttg  8880
gtgaccagtg atgaagctga gttcatttat aagacaacta actactatgc tcctggtcat  8940
cagcaagcaa ttatttacaa tgatcctatt ttaaacatcg attggccttt ctgcagtagt  9000
gctctgtcat tatcacaaaa agatcaagaa gcaaaattat tttcagaatt attggacagt  9060
gaactgttct aataaagtgt gccaccttat ccgtctgaag gataggtggt tgcttatatt  9120
tttttgagta tgtttgtata atgacagaaa atagtccgaa atataaacac gataaaagct  9180
taataagttt tatctactta ttttttatat ttacacttat tgtaggcttt attatcgcaa  9240
atacccagtt tttggggcga agtagagact atgataatta tatacagatc ttttctggta  9300
aagaagggga gggggttctt gaattatttt atcgcggatt gatgttaata acgaccagct  9360
atgaaactat catttttata attttaacat gttctttttt tataaaggca aggtttctcg  9420
ctaactattc gcgtaatttt tcaggcttga ccttattctt tatttattat gcaagcgttg  9480
cactttgggt tttagattat actcaattca gaaatggtct atgtatttcc attttaatgt  9540
tttccgtata ctatttattt ataaataaac cgacttattt ttatttctcg gtattatgtg  9600
caattgcaac tcattggtct gctttgcctt ttttgctttt atatcctttt gtctattcaa  9660
caaaaataag acgccttggt tatttttgtt tcagtattct tgttttgatt gcgatctcag  9720
gagaaggaaa agagatcata tcttttataa gaaattttgg agtgggacaa aaaataggaa  9780
atgaagctgg tgtaaattta ataaattcat tatcccttac cgctatttcc tggtttatta  9840
ttagttacat atcaagcatt ggaaatgaaa ggagaaattt aaggcttttc ttttgttatg  9900
gtgtcatgca atacgtgact tttagccttt tctctctacc tgttatggct ttccgtattt  9960
tggaaatgta ttttttcctt atgctaacca ttggggtgtt tattaagcaa aaaaagaatt  10020
attattttat tttttgcaaa gtgttaattt tattgtatct aacatactat tatcatatgg  10080
tctttggagt gattaatgtg taaggctaag gtgttggcta taattgttac ttacaacccg  10140
gaaattattc gattgacgga atgtattaac tctttagccc cacaagttga gagaataatt  10200
cttgtagata atggctcaaa taatagtgat ttgataaaaa atatcagtat taataacctt  10260
gaaattattt tactttcgga aaacaaaggc attgcatttg ctcagaacca tggtgttaag  10320
aagggcctgg aagcaaaaga gtttgactat ttatttttct cagatcagga tacttgcttt  10380
cctagcgatg ttattgaaaa acttaagagt acatttacga aaaataataa aaaaggtaaa  10440
aatgttgctt gtgcttctcc ttttttttaaa gaccatcgtt caaattatat gcatccgtca  10500
gtcagcctaa atatttttac gagtacaaaa gttatatgta gtgaagtaga cgatgatctt  10560
tatccctcgc atgttattgc ttctgggatg ttaatgtctc gtgaagcatg gcgcgtcgtc  10620
ggaccatttt gtgaaaaact ctttatagac tgggttgata cagaatggtg ttggcgtgca  10680
ttagctaata atatgattat tgttcagaca ccatcagtca tcatttctca tgaacttggg  10740
tatgggcaga aaatttttgc tggtcgatct gttacaatac ataattcttt cagaaatttt  10800
tataaaatac gcaatgcaat atacttaatg ctgcattcaa attatagctt caagtatcgt  10860
tatcatgctt tttttcatgc gacaaagaat gttgtatttg aaattttata ttcgaaagaa  10920
aaattaaatt cactgaaggt ttgtttttaaa gctgtacgtg atggtatgtt caataatttt  10980
taatacgaaa atagttaggc tcaaggtgtt taaatggaag aaaataatat gaagacggtc  11040
gctgtagttg gcacagtggg tgttcctgct tgttatggtg ggttcgaatc acttgttcag  11100
aatctaattg attatcaatc tgatggtata caatatcaga tattttgctc ttcaaaaaaa  11160
tatgataaaa aatttaaaaa ttataaaaat gcagaattaa tctatttgcc gataaatgcc  11220
aatggcgtct ctagcataat ttatgatatt atgtgtttaa ttatttgttt attcaaaagg  11280
ccagatgttg ttttaatatt gggggtgtct ggttgtttat ttctaccaat ttataaacta  11340
ttttcaaaat caaagattat tgtcaatatt gatgggcttg aatggcgtag aaataaatgg  11400
ggaacgtttg ctaagaaatt tcttaaaata tctgaggcga tatctattag aatagctgat  11460
attatcattt cagataatca agcaatagct gattatgtgg aaaataagta caagaaaaaa  11520
agtgtagtta tagcttatgg cggagatcat gccactaatc ttagtacacc gatagacaat  11580
gatcaaaaaa aagaaggtta ttatttgggg ctttgtagga tagagcctga gaataatata  11640
```

```
gaaatgattc tgaatgcctt cattaataca gataaaaaaa ttaaatttat gggtaattgg  11700
gataacagcg agtatggacg ccagctaaaa aaatattatt caaactatcc aaatatcacc  11760
ctactagaac ctaactataa tattgaagag ctttataaac taagaaaaaa ttgtcttgca  11820
tacattcatg gacactcggc tggtggaaca aacccttctt tagttgaagc gatgcatttt  11880
aatattccta tttttgcttt cgattgtgac tttaatcgtt acacaactaa caatttagct  11940
cattacttta atgattctga acaacttagc ttattagcag aaagtttgtc ttttggaaat  12000
cttaaatgtc gagtattaga tttaaaaaat tatgctgaag atatgtataa ctggaggcat  12060
atagctgcta tgtatgaatc tatttattaa acgcattaac aataatataa ttgaccttat  12120
atagcaggga aagatcacgt aacgctgcgg cgcgccgatc cccatatgaa tatcctcctt  12180
agttcctatt ccgaagttcc tattctttct agagaatagg aacttcggaa taggaactaa  12240
ggaggatatt catatggata aagccgtaag catataagca tggataagct atttatactt  12300
taataagtac tttgtatact tatttgcgaa cattccaggc cgcgagcatt cagcgcggtg  12360
atcacacctg acaggagtat gtaatgtcca agcaacagat cggcgtagtc ggtatggcag  12420
tgatgggacg caaccttgcg ctcaacatcg aaagccgtgg ttataccgtc tctattttca  12480
accgttcccg tgagaagacg gaagaagtga ttgccgaaaa tccaggcaag aaactggttc  12540
cttactatac ggtgaaagag tttgtcgaat ctctggaaac gcctcgtcgc atcctgttaa  12600
tggtgaaagc aggtgcaggc acggatgctg ctattgattc cctcaaacca tatctcgata  12660
aaggagacat catcattgat ggtggtaaca ccttcttcca ggacactatt cgtcgtaatc  12720
gtgagctttc agcagagggc tttaacttca tcggtaccgg tgtttctggc ggtgaagagg  12780
gggcgctgaa aggtccttct attatgcctg gtggccagaa agaagcctat gaattggtag  12840
caccgatcct gaccaaaatc gccgccgtag ctgaagacgg tgaaccatgc gttacctata  12900
ttggtgccga tggcgcaggt cactatgtga agatggttca caacggtatt gaatacggcg  12960
atatgcagct gattgctgaa gcctattctc tgcttaaagg tggcctgaac ctcaccaacg  13020
aagaactggc gcagaccttt accgagtgga ataacggtga actgagcagt tacctgatcg  13080
acatcaccaa agatatcttc accaaaaaag atgaagacgg taactacctg gttgatgtga  13140
tcctggatga agcggctaac aaaggtaccg gtaaatggac cagccagagc gcgctggatc  13200
tcggcgaacc gctgtcgctg attaccgagt ctgtgtttgc acgttatatc tcttctctga  13260
aagatcagcg tgttgccgca tctaaagttc tctctggtcc gcaagcacag ccagcaggcg  13320
acaaggctga gttcatcgaa aaagttcgtc gtgcgctgta tctgggcaaa atcgtttctt  13380
acgcccaggg cttctctcag ctgcgtgctg cgtctgaaga gtacaactgg gatctgaact  13440
acggcgaaat cgcgaagatt ttccgtgctg gctgcatcat ccgtgcgcag ttcctgcaga  13500
aaatcaccga tgcttatgcc gaaaatccac agatcgctaa cctgttgctg gctccgtact  13560
tcaagcaaat tgccgatgac taccagcagg cgctgcgtga tgtcgttgct tatgcagtac  13620
agaacggtat tccggttccg accttctccg cagcggttgc ctattacgac agctaccgtg  13680
ctgctgttct gcctgcgaac ctgatccagg cacagcgtga ctattttggt gcgcatactt  13740
ataagcgtat cgataaagaa ggtgtgttcc ataccgaatg gctggattaa             13790

SEQ ID NO: 13          moltype = DNA  length = 13777
FEATURE                Location/Qualifiers
source                 1..13777
                       mol_type = other DNA
                       organism = synthetic construct
SEQUENCE: 13
atgacgaatt taaaagcagt tattcctgta gcgggtctcg ggatgcatat gttgcctgcc  60
actaaggcga tacccaaaga gatgctacca atcgtcgaca agccaatgat tcagtacatt  120
gttgacgaga ttgtggctgc agggatcaaa gaaatcctcc tggtaactca cgcgtccaag  180
aacgcggtcg aaaaccactt cgacacctct tatgagttag aatcactcct tgagcagcgc  240
gtgaagcgtc aactgctggc ggaagtacag tccatttgcc cgccgggcgt gacaattatg  300
aacgtgcgtc agggcgaacc tttaggtttg ggccactcca ttttatgtgc acgacctgcc  360
attggtgaca atccatttgt cgtggtgctg ccagacgttg tgatcgacga cgccagcgcc  420
gacccgctgc gctacaacct tgctgccatg attgcgcgct tcaacgaaac gggccgcagc  480
caggtgctgg caaaacgtat gccgggtgac ctctctgaat actctgtcat ccagaccaaa  540
gagccgctgg accgcgaagg taaagtcagc cgcattgttg aattcatcga aaaaccggat  600
cagccgcaga cgctggactc agacatcatg gccgttggtc gctatgtgct ttctgccgat  660
atttggccgg aacttgaacg cactcagcct ggtgcatggg ggcgtattca gctgactgat  720
gccattgccg aactggcgaa aaaacagtcc gttgatgcca tgctgatgac cggcgacagc  780
tacgactgcg gtaaaaaaat gggttatatg caagcgttcg tgaagtatgg actacgcaac  840
ctcaaagaag gggcgaagtt ccgtaaaggg attgagaagc tgttaagcga ataatgaaaa  900
tctgaccgga tgtaacggtt gataagaaaa ttataacggc agtgaagatt agcggcgaaa  960
gtaatttgtt gcgaattttc ctgccgttgt tttatataaa caatcagaat aacaacgact  1020
tagcaatagg attttcgtca aagttttcca ggattttcct tgtttccaga gcggattggt  1080
aagacaatta gcatttgaat tttacgggtt tagcgcgagt gggtaacgct cgtcacatcg  1140
tagacatgca tgcagtgctc tggtagctgt aaagccaggg gcggtagcgt gctgaaatta  1200
taaagtcatt cttatagaac atcgcatttc aataatataa ttacacctaa atgaatagga  1260
tacaacgtgt gcacaattat ttaaggctta aagataaaat aaaaaacgta tttttagggt  1320
tgtatatatt gcagttattt aattatatcg cgccattggt aattatccct atcctgataa  1380
aatatattgg gttgggggaa tatggggaat tggtctatat tacatctatt tatcaaatag  1440
tggctttgat tattgatttt ggctttactt acacaggacc tgtggttgct gcgagacata  1500
gatgtgagac ccaaaattta cagcgctatt actcaatagt tgttctttta aaatcattgc  1560
tttttataat tgcattaaca tgtgtatttt tattgtgcag attaaatata gtccacttgt  1620
catttttgg gtttttgtca atttttctat gcactattgg taatatatta tcgcccaatt  1680
ggtttttgca ggggattggt gattttaaaa aactttcata ctcacaagta atagtgagaa  1740
taacattgtt tatcatactt cttgtttatg tctgtagtgg cggagataat gtttttatcc  1800
taagtttttt gcaaaatgca acattactca tatgctgtat atacttatgg ccaaatattc  1860
atattagcca tgttgttcat cttaaaccta atgaatgcat tgtggaattt aagaaggcag  1920
gaaatgtttt tattggcgta ataggtacga ttggttacaa tggtctaatt cctgtgttaa  1980
ttggaaacct ttgcggtaat acgagtcttg gtgtttttc aatcgttcaa aaaatgacaa  2040
cagcatgtca aagtctaatt aatccaatat cacagtatat gttatctcaa gtttcagaaa  2100
ttaaacctca agataaactg ttttattata gaattaaaaa aagttttttt gtgcatttaa  2160
```

-continued

```
caattagcat aattgcatgt ttatgttata tggggttagg gcaatatgtg gcgactttta  2220
taggtaaagt tgacgtttca tttgttatta ttttatttgc gtcaataatt accatttttt  2280
catctttaaa taatgtcctt ggtatacagt ttcttatacc gacagataat gtaaaaatac  2340
tacgaagtat aaatgttatg gcgggaatta ttgttgttag tttgtcctgg ctgttaatat  2400
cacgctttga cattctgggg ggggttttat taaacctaat tggtgagttt cttgtattca  2460
gtatgctagc ttttattgcc catcgaaagt ggggagcgag agtataatga aagtgaaggc  2520
ggttcctgct attacattct atttaagttt aatgctgaca attttagtgt tactgtttgg  2580
taatgaacca aataaatcac aatatatcct tgttatagca acgataacag tttttttatat  2640
cgcatatatc actaataaaa taacttctcc ggccagcctt ctcgttatat catcttttgt  2700
gtttttaggt tgtcgccctt tattatcttt gtttgcaaac tatgattata ggattgccga  2760
ttggtttatt gaaggatata tggatgacga tgtgattttg gctaactatg ctataacact  2820
aatgtattat ggttatacat tgggactaat tctatgcaaa aatactgaaa aattttatcc  2880
gcatggtcct tatcctgaaa aacaattgct aaaaaataaag tttcttttga ctttattttt  2940
tctgggttcg ataggtatgg ttgtaaaagg gatattcttt tttaacttta tagaatctaa  3000
tagttatgtt gatatttatc aatcaaatat aacaacgcca ataggttatg attttctatc  3060
ttatttattt tattgttctt ttttccttat atgtgcgttt catatacagt tcagaacaaa  3120
taaaaaattt ctttttattg cgatatgcat tgctgcattt agcaccttga agggtagtcg  3180
tagtgaagct ataacgtttc ttttaacggt tacatgtata tattttaatg aagtaaagac  3240
aagaaactta cgtctgctga ttacaatgat ttttgttttt agcgtcattt ttgtgattag  3300
tgaatttatc tcaatgtggc gcactggagg gagttttttt caattaatgc agggtaataa  3360
tcctgttata aactttgtat acggcatggg agtatcatat ctttccattt atcaatcagt  3420
aaaactacaa ctattgtcag gggatataa tgttacctat ctattcagcc agttaataat  3480
aacttgctcg tcaatattta atgtcaaatt gagcttgccg gaaataagct atagccattt  3540
ggcctcatac acagcaaacc cagaactata taatcttggg ttcggacttg gggggagtta  3600
tttagcagaa tcgtttttag catttggtct gattggatgt ttcattatac ccttttttact  3660
tttacttaat ttaaatgtat tggaaaaata tacaaaaaac aaaccaatta tatattttgt  3720
ttattatagt gtgttgccac ctatattatt cacaccaaga gagactttgt tctatttctt  3780
cccctatctt gtcaaaagta tatttgttgc ttttttagtt acattataca tccagtataa  3840
aaaggattga ccaaaatgtc agaaaaaaat gtcagcataa taatcccaag ttataacagg  3900
gctcatattc ttaaggaggt cataccaagt tattttcagg atgagacttt agaggttata  3960
gttatcaatg atggatcaac agataataca aatagtgtat tagctgaact gaaggaaaaa  4020
tattctcagt tagttatttt agaaaatgaa acgaataaaa aacagatgta ttctaaaaac  4080
cgagggattg aaatagccaa agggaaatat attttttttg gtgatgatga ctcttacctc  4140
ttacccggtg ttatatctcg gttattggct acaaaatatg agacaggcgc tgatgtaatc  4200
ggcgcaagaa tactttatat gaataataac gagaaaacaa ttgaagattg cataaatcga  4260
cataaaaaag aggggcgttt tgttagtgat ctaaatagat tggattttag ttatacatgt  4320
gatttggacc atccgattga atgtttttat gcacagcctt ttgttctagc tgaaagggaa  4380
ctaatatcga aatatcgatt tgatatatct tatacgggaa actgctatcg tgaggaaact  4440
gatttcatgc tatctctatt tattaaaaat aaaaaattta tatatgattc aaaggctttg  4500
ttaataaatt tacctccaag aaaagcgacg ggaggggcaa gaacagctaa tcgattaaaa  4560
tatcattacg aaagttgcat aaataattat agatttttaa aaaaatataa tgataatttg  4620
aatcttcttt caggacaaaa gcatgctata ttttaccgac agtgtcaatt cgttctgcta  4680
aaaatgaagt cgtttatcgg gaagttttta aaatgattat atatatcgcc gcgtataatg  4740
gttcaggagg gcaaggtggg gtggaaaggg ttgttgccca acaatgtaac attcttaaaa  4800
atttgggggt taaagtcatt atacttgata aaacatactt caaaatttct aacaaaattc  4860
gtaacaaaaa aatacaagta gcactttatc caatattagt ttctctttat ttaaccttac  4920
aaaaattacg tggcgtgacg tttaaagtta ttgcacatgg ctattgttct ccttttttata  4980
ggaatgacat cttaatagct catggcaata tgaaatgtta ttttcaaaca gtcatgaata  5040
aaaaacctaa tcggttgtct ggcagtggtc ttttatcttt ctatgagcgt tgggctggag  5100
cattttcaaa aaatatctgg gctgtttcaa ataaggttaa aagtgaatgg aatgagcttt  5160
acaatattaa ttcacataaa atcaaagttg ttcgaaattt tataaatctt gcacaatttg  5220
attacactga tgttaatgaa gcagaatatg tgacatttgt cgggcgattg gaaaaaggaa  5280
aaggaataga tgatctgtat tacatatgta aaaatctgcc agatacttcc ttccatttag  5340
tttcaagtat tcccgcccca caaaattttg cttcgctaaa taatgttctg accagcattg  5400
ctgtccccta tgcgaaaatg ccagaaatat ttaagaaatc cagagtactt attttaccgt  5460
cctattatga aggatatgag ctggttacta ttgaagcgct atgctgtggt tgccctgtga  5520
taggctataa tgttggtgca attagagagt tgtatgcaga aagttttcct ggcgtattta  5580
ttgccaataa taaagaagat ttagcacaag tagcctacaa attaattagt cttgataatg  5640
aaaaatatta tcatttgaga caaactattt atagcaagcg tgagcttttt tctgaagaga  5700
gatatgcgga aattttaacg gcggcattta atgaaaaaaa ataagaaact ctgtctcatt  5760
tcaattaact catataatga acttaccgga ggaggagtat atttacgtac gcttgttagt  5820
tttctacaaa aacagaatgt taatttaaca cttattgata aaaaatcctc aggtaaacta  5880
ttcgaagaca atacttttca acatatatca tttattaaag gtaaacgtca ggatataata  5940
tccaggcttt tttttatacc atcattttat gtcccttata ttttctcaat aattaaaatt  6000
ttacggaagc aagatattct tgcttttcac aactctcggc ttggattgtt atgtctgctt  6060
tttagaatac tcatgcccca caaaaagatc atattgttta cggataactt cgaatatgac  6120
ttaataagac aaaaagataa aaacataact actttttattg aaaaattaat tgtttatctc  6180
aatgaattta tcgggcttaa gaattcagat ttagttagct atattacccg gcaagataaa  6240
aatgcaatgg ataaatttta tgggattaaa aaaagcagaa atttaattct ccctgtgata  6300
tttagtagag aaaaaccaac tgatgtattg tcagctcact ttattaatga gtataatcga  6360
ttgaataatg ataataggaa aaaagtagta tttactgcat cttttgattt ttttccaaat  6420
atagatgctg ccaactatgt tttaaatgca gcaaagtcta ataatgatta ttgctatatt  6480
ttggcaggta ggaaaagtac tactttgaat cttcctgatt tggataattt attttttttc  6540
gataatctat ctaatagtga aatgtcatat ttattatctg cttgtgatgt tttttattct  6600
cctatagttt taggaagtgg aatgaaaaca aaaattgcag aagcactatc atatggatta  6660
tatatttatg cgacagagca ttccttaatc ggctatgatg aaattataca caataaggag  6720
tgtgttaaaa aaatctcaca tttggatgag gaatttccta aagatttcaa gatgaaaagt  6780
atcaataaac agctaataat gtcttatcag caaaaatatt attcacatta tcggtttaat  6840
ggccatgaac ttgatataat aaattttgac gattagttag tggagatata atatgaacat  6900
```

-continued

```
attagtaact ggtggtgctg gatatatcgg atctcatacg gctattgaat tactgaatgc  6960
aggtcatgag attatcgttc tggacaattt cagtaatgct tcatacaagt gtatcgaaaa  7020
aataaaagaa attactcgac gtgattttat aacaattact ggagatgctg ggtgtaggaa  7080
gacactctcc gctattttcg agaaacacgc catagatata gttattcatt ttgctggctt  7140
taaatctgtt tcagagtcta aagtgaacc cttaaagtat taccagaata atgttggagt  7200
gaccattact ttattacagg taatggaaga gtacagaatt aaaaaattta tctttagttc  7260
atctgcgaca gtctatggtg aaccagagat aattccaatt ccagaaacag ctaaaattgg  7320
aggaactacg aatccatatg gcacatcgaa gtattttgtt gaaaaaattc tagaggatgt  7380
tagttccacg ggaaaactgg atataatttg cttgagatat tttaatcctg tcggtgctca  7440
ttctagtggt aaaataggtg aggctccatc tggtatccct aataatcttg ttccttattt  7500
attggatgtt gcgagtggta aacgtgataa attatttatt tatggcaatg attaccctac  7560
taatgatgga acaggtgtaa gggattttat tcatgttgtt gacttagcga aaggtcattt  7620
ggctgcaatg aattatttaa gtatcaattc gggatataat atctttaatc ttggtacagg  7680
aaaaggttat tcggtacttg aattaatcac tacatttgaa aaattaacaa acattaaggt  7740
caataaatct tttatagaga gaagggcagg ggatgttgcg tcttgttggg ctgatgcaga  7800
taaagctaat tctttattgg actggcaagc cgaacaaact ctagaacaga tgttattgga  7860
ctcgtggcgt tggaaaaaaa attatccaga cggattctga atataaaagg tttcagtttt  7920
atgaatcaat cagagcagag aaaaaaaata ctggttctta cacctcgctt tccctaccct  7980
gtcattggag gggatagatt aagagtctat atgttatgta aagaactttc caaaaaatat  8040
gatcttattc ttctgagctt atgtgatcaa ccactagaac ttgaaataaa tataaatgac  8100
tcggtcttca aagaaattca tcgtgtctat ctaccaaaat ataaatcata ttataatgta  8160
ttaaaagctt tggttacgca aaaaccgttg caaattgctt attatcaatc ggacacattt  8220
aagaataaat acaataaatt aattaaacaa tgcgatgcag tattttgtca tctgataaga  8280
gttgctgatt atgttaagga tacagacaag ttcaaaattc ttgatatgac agatgcaata  8340
tctttgaatt acagtcgcgt taaaaaatta gcaagtaaaa aaagtttgcg tgcaattatt  8400
tattctctgg aacaaaaaag attagaatca tatgaacgtt ctgtggcgaa tctttttgat  8460
ttgaccactt ttatttcatc cgtagaccgt gactatctct accctaatct gggcagtaat  8520
atccatatag tcaataatgg ggttgataca tcagccttga gatatataaa aagagaaata  8580
aaaatcgata agcctgtgga acttatattt atcggaaata tgtattcttt acaaaatatg  8640
gatgctgcaa aacattttgc taagaatatt ttaccttgct tgtatgatga gtttaatatt  8700
atttttaaag tgattggtaa gatctcagaa actaataaaa atatattaaa ttcatttaaa  8760
aatacaattg ctttaggtac tgttgatgat atcaattctt ccgcttctac agggcatata  8820
ggtatatgtc ctgttcgtct tggagcaggc gtacaaaata aaattcttga atacatggct  8880
ttaggtttac catgtattac atctagcatt ggttatgaag gtattaatgc aaaatcaggt  8940
agcgaaattt ttgttgcaga tacagtagag caatataaaa acgtactaag agaaataatt  9000
tacgattata atcgttatac tgaagtggct gaaaatgccc gtagttttgt agaaaataat  9060
ttttcttggg aatcaaaagt tgccaattta atgaatacat tagatgagaa attatatgaa  9120
caataataaa attattacac ctatcattat ggctggtggt tcaggcagtc ggttgtggcc  9180
actatcaaga attctctatc cgaaacaatt tcttagccta atcggtagtc ataccatgct  9240
tcaaacaacg gctaatcgtc tggatggttt ggattgtacc aacccttatg tcatttgtaa  9300
tgaacaatac cgctttatag ttgctgaaca gcttagaaaa atcgatagat tgacttcaaa  9360
gaatatcatc cttgagcctg ttgggcgtaa cactgcccct gcaattgcat tagcggcgtt  9420
gctgatgtct aagtctgata aaagtgcaga tgatcttatg ctcgtactgg ctgcagatca  9480
cgttatacac gatgaagaaa aattttgtaa cgctgttaga tcggcaattc catacgctgc  9540
tgatgggaaa ttggtaacat ttggtataat tccagacaaa gcagaaactg gttatggtta  9600
tatacatcga ggacaatata ttaatcagga agattcggat gcatttatag tgtcatcatt  9660
tgttgaaaag ccaaatcatg agacagccac taaatatctt gcttccggtg agtattattg  9720
gaatagcggt atgtttttgt ttagtgcaaa tcgttatata gaggaactta aacaatttcg  9780
gcctgatatt ttatccgctt gtgaaaaagc aattgcttca gcgaactttg accttgattt  9840
tgtgcgttta gatgaaagtt ctttctctaa gtgccctgaa gaatcaattg attacgctgt  9900
aatggaaaaa acaaaagacg caattgttat tccaatggat gctggctgga gtgatgtcgg  9960
ttcatggtct tctctttggg aaattaatga taaagactca gacggcaacg taatagttgg  10020
ggatattttc tctcatgaaa caaagaattc tttcatatat gccgaatcgg gaattgttgc  10080
tacagttgga gtggaaaatt tagttgttgt ccaaacaaag gatgctgttc ttgtctcaga  10140
gagaaataaa gttcaggatg taaagaaaat agtagaacaa attaaaaatt caggtcgtag  10200
cgagcattat gttcatcgcg aagtatatcg tccttggggt aaatatgatt ccattgacac  10260
aggggagcgt tatcaggtca aacgtataac agtaaatcct ggtgaaggac tttctttaca  10320
aatgcaccat catagggcag aacattggat catagtttct ggaactgcaa gggtgactat  10380
aggttctgaa actaagattc ttagcgaaaa tgaatctgtt tacatacctc ttggtgtaat  10440
acactgcttg gaaaatccag ggaaaattcc tcttgattta attgaagttc gttctggatc  10500
ttatttagaa gaagacgatg ttatccgttt tcaggaccga tatggtcgta gctaaatttt  10560
tgataatgta acgttagtag aagagcgcta atatttttag ttaatctgta ataagtatta  10620
tttgtttaag gtatatcatg tcgagtttac cctgctttaa agcctatgat attcgcggga  10680
aattaggcga agaactgaat gaagatattg cctggcgcat tggtcgcgct tatggcgaat  10740
ttctcaaacc gaaaaccatt gtgttaggcg gtgacgtccg actcaccagc gaaaccttaa  10800
aactggcgct ggcgaagggg ttacaggatg cgggcgtcga tgtgctggat attggcatgt  10860
ccggcaccga agagatctat ttcgccacgt tccatctcgg cgtggatggc ggcatcgaag  10920
ttaccgccag ccataacccg atggattaca acggcatgaa actggtgcgc gaaggggctc  10980
gcccgatcag cggtgatacc ggactgcgcg acatccagcg tctggcagaa gccaacgact  11040
ttcctcccgt tgatgaaacc aaacgcggtc gctatcagca aatcaatctg cgtgacgctt  11100
acgttgatca cctgttcggt tatatcaacg tcaaaaacct cacgccgctc aagctggtga  11160
ttaactccgg gaacggcgcg gcgggtccgg tggtggacgc cattgaagcc cgctttaaag  11220
ccctcggcgc acccgtggaa ttaatcaaag tgcacaacac gccggacggc aatttcccca  11280
acggtattcc taacccgcta ctgccggaat gtcgcgacga cacccgcaat gcggtcatca  11340
aacacggcgc ggatatgggc attgcctttg atggcgattt tgaccgctgt ttcctgtttg  11400
acgaaaaagg gcagtttatt gagggctact acattgtcgg cctgctggca gaagcgttcc  11460
tcgaaaaaaa tcccggcgcg aagatcatcc acgatccacg tctctcctgg aacaccgttg  11520
atgtggtgac tgccgcaggc ggcacccggg taatgtcgaa aaccggacac gcctttatta  11580
aagaacgtat gcgcaaggaa gacgctatct acggtggcga aatgagcgcc caccattact  11640
```

```
tccgtgattt cgcttactgc gacagcggca tgatcccgtg gctgctggtc gccgaactgg  11700
tgtgcctgaa aggaaaaacg ctgggcgaac tggtgcgcga ccggatggca gcgtttccgg  11760
caagcggtga gatcaacagc aaactggcac accccgttga ggcgattaac cgcgtggaac  11820
agcactttag ccgcgaggcg ctggcggtgg atcgcaccga tggcatcagc atgacctttg  11880
ccgactggcg ctttaacctg cgctcctcta acaccgaacc ggtggtgcgg ttgaatgtgg  11940
aatcgcgcgg cgatgtaccg ctgatggaag aaaagacaaa acttatcctt gagttactga  12000
acaagtaatt cagtaatttc atataaatgg gttttaaaaa acggaaaaga tgagatatcc  12060
ggtgtggtat atccaaggta atgctattca gtatctctat gagtgagtta acatctatac  12120
cacatttaag ccgcacactt cgggatcccc atatgaatat cctccttagt tcctattccg  12180
aagttcctat tctttctaga gaataggaac ttcggaatag gaactaagga ggatattcat  12240
atggataaag ccgtaagcat ataagcatgg ataagctatt tatactttaa taagtacttt  12300
gtatacttat ttgcgaacat tccaggccgc gagcattcag cgcggtgatc acacctgaca  12360
ggagtatgta atgtccaagc aacagatcgg cgtagtcggt atggcagtga tgggacgcaa  12420
ccttgcgctc aacatcgaaa gccgtggtta taccgtctct attttcaacc gttcccgtga  12480
gaagacggaa gaagtgattg ccgaaaatcc aggcaagaaa ctggttcctt actatacggt  12540
gaaagagttt gtcgaatctc tggaaacgcc tcgtcgcatc ctgttaatgg tgaaagcagg  12600
tgcaggcacg gatgctgcta ttgattccct caaaccatat ctcgataaag gagacatcat  12660
cattgatggt ggtaacacct tcttccagga cactattcgt cgtaatcgtg agctttcagc  12720
agagggcttt aacttcatcg gtaccggtgt ttctggcggt gaagaggggg cgctgaaagg  12780
tccttctatt atgcctggtg gccagaaaga agcctatgaa ttggtagcac cgatcctgac  12840
caaaatcgcc gccgtagctg aagacggtga accatgcgtt acctatattg gtgccgatgg  12900
cgcaggtcac tatgtgaaga tggttcacaa cggtattgaa tacggcgata tgcagctgat  12960
tgctgaagcc tattctctgc ttaaaggtgg cctgaacctc accaacgaag aactggcgca  13020
gacctttacc gagtggaata acggtgaact gagcagttac ctgatcgaca tcaccaaaga  13080
tatcttcacc aaaaaagatg aagacggtaa ctacctggtt gatgtgatcc tggatgaagc  13140
ggctaacaaa ggtaccggta aatggaccag ccagagcgcg ctggatctcg gcgaaccgct  13200
gtcgctgatt accgagtctg tgtttgcacg ttatatctct tctctgaaag atcagcgtgt  13260
tgccgcatct aaagttctct ctggtccgca agcacagcca gcaggcgaca aggctgagtt  13320
catcgaaaaa gttcgtcgtg cgctgtatct gggcaaaatc gtttcttacg cccagggctt  13380
ctctcagctg cgtgctgcgt ctgaagagta caactgggat ctgaactacg gcgaaatcgc  13440
gaagattttc cgtgctggct gcatcatccg tgcgcagttc ctgcagaaaa tcaccgatgc  13500
ttatgccgaa aatccacaga tcgctaacct gttgctggct ccgtacttca agcaaattgc  13560
cgatgactac cagcaggcgc tgcgtgatgt cgttgcttat gcagtacaga acggtattcc  13620
ggttccgacc ttctccgcag cggttgccta ttacgacagc taccgtgctg ctgttctgcc  13680
tgcgaacctg atccaggcac agcgtgacta ttttggtgcg catacttata agcgtatcga  13740
taaagaaggt gtgttccata ccgaatggct ggattaa                          13777
```

```
SEQ ID NO: 14          moltype = DNA  length = 15027
FEATURE                Location/Qualifiers
source                 1..15027
                       mol_type = other DNA
                       organism = synthetic construct
SEQUENCE: 14
atgacgaatt taaaagcagt tattcctgta gcgggtctcg ggatgcatat gttgcctgcc  60
actaaggcga tacccaaaga gatgctacca atcgtcgaca agccaatgat tcagtacatt  120
gttgacgaga ttgtggctgc agggatcaaa gaaatcctcc tggtaactca cgcgtccaag  180
aacgcggtcg aaaaccactt cgacacctct tatgagttag aatcactcct tgagcagcgc  240
gtgaagcgtc aactgctggc ggaagtacag tccatctgtc cgccgggcgt gaccattatg  300
aacgtgcgtc agggcgaacc tttaggttta ggccactcca ttttgtgtgc gcgacctgcc  360
attggtgaca acccatttgt cgtggtactg ccagacgttg tgatcgacga tgccagcgcc  420
gacccgctac gttacaacct tgctgccatg attgcacgtt tcaacgaaac gggccgcagc  480
caggtgctgg caaaacgtat gccgggtgac ctctctgaat actccgtcat ccagactaaa  540
gagccgctgg accgtgaggg taaagtcagc cgcattgttg aatttatcga aaaaccggat  600
cagccgcaga cgctggactc agacatcatg gccgtaggtc gctatgtgct ttctgccgat  660
atttggccgg aactggaacg tactcagcct ggtgcatggg gacgtattca gctgactgat  720
gctattgccg agctggcgaa aaaacaatcc gttgatgcaa tgctgatgac cggcgacagt  780
tacgactgcg gcaaaaaaat gggctatatg caggcgtttg tgaagtatgg cctacgcaac  840
ctgaaagaag gggcgaagtt ccgtaaaggt attgagaagc tgttaagcga ataatgaaaa  900
tctgaccgga tgtaacggtt gataagaaaa ttataacggc agtgaaaatt cgcagcaaaa  960
gtaatttgtt gcgaatcttc ctgccgttgt tttatataaa ccatcagaat aacaacgagt  1020
tagcagtagg gttttattca aagttttcca ggattttcct tgtttccaga gcggattggt  1080
aagacaatta gcgtttgaat ttttcgggtt tagcgcgagt gggtaacgct cgtcacatca  1140
taggcatgca tgcagtgctc tggtagctgt aaagccaggg gcggtagcgt gcattaatac  1200
ctctattaat caaactgaga gccgcttatt tcacagcatg ctctgaagta atatggaata  1260
aattaagcta gcgatcgctt aagatctagg atttcattat gttacttcct gtaattatgg  1320
ctggtggtac cggcagtcgt ctctggccga tgtcacgcga gctttatccg aaacagttcc  1380
tccgcctgtt cgggcagaac tccatgctgc aggaaaccat cacccgactc tcgggccttg  1440
aaatccatga accgatggtc atctgtaacg aagagcaccg cttcctggtg gctgaacagc  1500
tacgccagct caataagctg tcgaataata ttattcttga gccggtcggg cgcaacaccg  1560
ccccggccat cgccctggca gcccttcagg ccacccgcga cggcgacgac ccgctgatgc  1620
tggttctcgc cgctgaccat atcatcaata accagtcggc cttccacgac gccatccggg  1680
tcgccgagca gtatgctgat gaaggtcatc tggtcacctt cggtatcgtg ccgaatgccc  1740
cggaaactgg ctacggttac attcagcgcg gcgtggcgct caccgatagt gcccattccg  1800
cgtaccaggt ggcccgcttt gtggagaagc cggatcgcga gcgcgccgag gcttacctcg  1860
cctccgggga gtactactgg aacagcggca tgtttatgtt ccgcgccaag aaatacctca  1920
tcgagctggc caaataccgt ccggatatcc tggaagcctg ccaggctgcg gtgaatgccg  1980
ccgataatgg cagcgatttc atcaatatcc cgcatgatat tttctgcgag tgcccggatg  2040
agtccgtgga ctatgccgtt atggagaaaa ccgccgatgc ggtggtggtc ggtctcgatg  2100
ctgactggag cgacgtcggc tcctggtccg cactatggga ggtcagcccg aaagacgagc  2160
```

-continued

```
agggcaatgt cctcagcggt gacgcgtggg tacacaacag cgaaaactgc tacatcaaca  2220
gcgacgagaa gctagtggcg gccattggcg tagagaatct ggtgattgtc agcactaagg  2280
acgccgtgct ggtgatgaat cgcgagcgtt cccaggacgt gaagaaggcg gtcgagttcc  2340
tcaagcagaa ccagcgcagc gagtacaagc gccaccgtga gatttaccgc cctggggcc   2400
gttgcgacgt agtggtccag accccgcgct tcaacgtcaa ccgcatcacg gtgaaaccag  2460
gcggtgcctt ctcgatgcag atgcaccacc atcgcgccga gcattgggtt attctcgccg  2520
gcaccggtca ggtgactgtc aacggtaagc agttcctgtt gtccgagaac cagtccacct  2580
ttattccgat tggcgccgag cactgcctgg aaaaccctgg ctgtattccg ctggaagtgc  2640
tggagatcca gtcgggggcg taccttggcg aggacgacat tattcgtatt aaagaccagt  2700
atggtcgttg ctaattattt tcgggacaag acgcagaatg acacagttaa cttgttttaa  2760
agcttatgac atccgtggtg aactgggtga ggaactgaac gaggacatcg cctaccgtat  2820
cggtcgcgcc tacggcgaat ttctgaaacc cgggaagata gtggtggggg gcgatgtgcg  2880
cctcacaagc gagtcgctga agctggcgct ggcccgcggg ttaatggacg ccggtaccga  2940
cgtgctggac atcggcctga gcggtaccga agagatttac tttgccacct tccaccttgg  3000
ggtagatggt ggcatcgagg tgaccgcgag ccacaatcct atgaactaca acggcatgaa  3060
gctggtgcgc gagaatgcga agcccatcag cggcgacacc ggcctgcggg atatccagcg  3120
cctggcggag gaaaaccagt tcccgccagt ggacccggcg cgtcgcggga ccctgagcaa  3180
gatatcggta ctgaaggagt atgttgacca tctgatgagc tacgtggact tctcgaactt  3240
cacccgtcca ctgaagttgg tggtgaactc cggaaacggg gctgcggggc acgtgattga  3300
tgaggtggag aaacgcttcg cggcggctgg ggtgccggta acctttatca aggtgcatca  3360
ccagccggat ggccatttcc ctaacggtat cccgaatccg ctgctgccgg agtgccgcca  3420
ggataccgcc gacgcggtgc gcgagcatca ggccgacatg gggattgcct ttgacggcga  3480
cttcgatcgc tgcttcctgt tcgatgacga agcttcgttt atcgaggggt attacattgt  3540
cggcctgctg gctgaggcgt tcctgcagaa gcagccggga gcgaaaatca ttcacgaccc  3600
gcgcttgacg tggaacacgg tagacatcgt gacccgcaac ggcggccagc cggtgatgtc  3660
gaagacgggg catgcgttca tcaaggagcg gatgcgtcag gaagacgcta tctacggcgg  3720
ggagatgagt gcgcaccatt acttccgcga tttcgcctac tgcgatagcg ggatgatccc  3780
gtggctgctg gtggcggagc tgctgtgtct gaagaacagc tcgctgaaat cgctggtggc  3840
ggaccgccag aaggcgttcc ctgcgtcggg agagatcaac cgcaagctaa gtaatgctgc  3900
tgaggcgatc gcccgcatcc gggcgcagta tgagccggcg gctgcacaca tcgacacaac  3960
ggacgggatc agtattgaat accctgaatg gcgctttaac ctgcgcacgt ctaacaccga  4020
gccggtggtg cgtctgaacg ttgagtccag agctgatgtg gcgcttatga atgaaaaaac  4080
gaccgagctg ttacacctgt taagcgggga ataaggtgag agatttacta acgacgattt  4140
atcgttatcg gggatttatc tggagcagtg ttaaacgtga ttttcaggca cgctatcaaa  4200
ctagtatgct gggcgcacta tggctcgttt tacaaccgct ctctatgatt ctggtctata  4260
ccctggtttt ttccgaggtg atgaaggcaa gaatgcccga taataccggg tcgtttgcct  4320
atagtattta tctctgttcc ggggtactga cctggggatt atttactgag atgctggata  4380
aaggtcagag cgtatttatt aacaatgcta atctgatcaa gaaactcagt tttccgaaaa  4440
tctgtctgcc gatcatcgtg acgttatcgg cggtgctaaa tttcgcgatt attttcagtc  4500
tgtttctaat ttttatcatt gtcaccggta acttccccgg ctggctcttt ctctcggtga  4560
taccggtcct gcttttgcag atcctgtttg ccggtgggct ggggatgatc cttggtgtca  4620
tgaacgtctt tttcagggat gtggggcaac tggttggcgt tgcgctgcaa ttctggtttt  4680
ggttcacacc cattgtttat gtactgaatt cattacctgc atgggcaaaa aatctgatga  4740
tgtataaccc gatgactcgg atcatgcaat cttatcagtc catcttcgcc tatcatctgg  4800
cccccaactg gtattcgcta tggccagtat tggctctcgc cattattttc tgcgtcatcg  4860
gtttcaggat gttccgcaag catgcggcgg atatggtgga tgaattataa tgagttatat  4920
cagagtaaat aatgtcggta aggcgtatcg ccagtatcac tcaaagaccg ggagactgat  4980
cgaatggtta tcccctctga ataccaaacg ccataatttg aaatggatcc tccgcgatat  5040
taatttcgaa gtcgctccgg gcgaggctgt cggtattatc ggtatcaacg gtgcaggcaa  5100
gagtaccctg cttaaactca taaccgggac gtccaggccg acgactggag aaattgaaat  5160
ctccggacgt gtcgctgcat tactcgaatt ggggatgggg tttcattctg atttcactgg  5220
tcggcagaat gtttatatgt ctgggcaact gttggggtta tcgtcagaga aaataactga  5280
actgatgccg caaattgaag agtttgctga gattggggac tatatcgatc aacctgtgcg  5340
cgtctactcc agtgggatgc aagttcgatt agcttttagt gtagcgacgg ctatccgtcc  5400
tgatgtgcta attatcgatg aggcattatc tgttggggat gcatatttcc agcataaaag  5460
ctttgagcgt attcgaaaat ttcgtcagga agggaccacg ctgttgctgg tatcccatga  5520
taaacaagcg atccaaagca tttgcgaccg ggccatttta ttgaataaag gccaaattga  5580
aatggaaggt gaacctgaag cagtgatgga ttattacaat gctcttctgg ccgataaaca  5640
aaatcagtcc attaaacaag ttgagcataa tggtaaaacg caaactgttt caggcactgg  5700
tgaggtgact atctctgagg ttcatcttct cgatgaacag ggcaatgtga ctgaatttgt  5760
ttcggtaggg catcgtgtca gcttgcaggt caacgttgag gtcaaggacg atattcctga  5820
gcttgttgtc ggatatatga ttaaggatcg acttgggcag ccgattttcg ggaccaatac  5880
gtaccatctc aatcagacac tcacctccct gaaaaaagga gaaaagcgtt cgttcttatt  5940
ttctttcgat gcgagattgg gggttggctc ctattctgtc gctgtcgcgt tgcatacttc  6000
cagtacgcac ctcggcaaaa actatgaatg gcgcgatctg gccgtggtat tcaacgtcgt  6060
taacacggaa caacaagagt ttgtcggcgt gtcctggttg ccgcctgaac tggagatttc  6120
ttaatgggtt cgtcgtttta tcgttcattt gaagaacgac acagaggttc ggttgaagaa  6180
atcaagcgcc gcttgagttt ttatttacct tttcttgcag gtctgaagga catttatcct  6240
gatggcgtga ttgcggatat tggttgcgga cgtggcgaat ggttggagat cctgactgaa  6300
aatggcattg cgaacatcgg cgtcgatctc gatgatggca tgctggcgcg cgccagggag  6360
gccggactga atgtgcagaa aatggattgt ctgcagtttt tgcaaagtca ggcggatcag  6420
agcctgatag cgttgaccgg ttttcatatt gctgagcatt tgccgtttga ggtcctgcag  6480
caactcgcca tgcatacccct acgggtgctg aaaccaggtg gtttgctgat cctcgaaacg  6540
ccgaacccgg agaatgtaag cgtcggcacc tgttcatttt atatggatcc aacgcataat  6600
catcctctgc caccgccact gcttgagttt ttacctattc attatggttt tacccgagca  6660
attaccgttc gtctgcagga aaaagaggtt cttcaatctc cggatgcagc cgttaatttg  6720
gtcgatgtac tcaaaggggt gagccccgac tacagcatca ttgctcagaa agcagcgcca  6780
acagatattc ttgaacgctt tgacaccctg tttacccagc agtacggtct gacgctggat  6840
gctctgagca accgttacga tgcgattttg cgccaacagt tttcgtccgt tgtctcacgg  6900
```

-continued

```
ctggagacgt tgaaccaaac ctatatgcaa cagataagcc aaatgtcaga gactattcag  6960
acgttgcaag gtgaggttga cgatctgagt catgtcatcg atcagaacca tcagcttcat  7020
cagcaaatgg cggatttaca taacagtcgt tcatggcgta ttactcaacc actacgctgg  7080
ttgtctttgc aacgtcaatt attacgtcag gaaggggcta aagtgcgagc ccgtagggct  7140
gggaaaaaaa tattgcgcaa aggatggcg ctctcgctgg tctttttcca tcgttaccct  7200
aagtctaagg tttatctgtt taaggttctg agaaaaactg gctgctatac attgctacaa  7260
cgtttgttcc aacgcgtaat gctggtgcaa tctgacacga tgatgatgca gtccagaaga  7320
tatgatgtgg gtactgaaga aatgacaagt cgcgcgatga gtatttataa cgaattaaaa  7380
aataaaaata cggagaaata acgatgcgta ttgtcataga tttacaaggc gcacagacgg  7440
aaagccgctt tcgtggcatc ggtcgttata gtatcgcaat cgccagaggc ataatcagaa  7500
ataacagccg gcatgagatt ttcatcgcgc tatccgccat gctggatgag tcgattgcaa  7560
atattaaggc gcaatttgcc gatctcctgc cggcagaaaa tatagtcgta tggcatgccg  7620
taggccctgt tcgtgcgatg gaccaaggta atgaatggcg tcgggagagc gcagaactga  7680
ttcgggaagc gtttcttgaa tcattgtgtc cagatgtcgt tttcattacg agtttgtttg  7740
aaggtcatgt cgacgatgcg gctacatcgg tacacaaatt tagtcgtcag tataaagtag  7800
ccgtactgca ccacgatctt atccccctcg tgcaggcgga aacctatctg caggacgatg  7860
tatacaaacc ctactattta cagaaagttg agtggttaaa aaacgctgac cttttgttga  7920
ctaactctgc ttataccgca caggaagcga tcgagcatct gcatttacag ggcgatcatg  7980
tgcagaatat tgcagccgca gtcgattctc agttttgtat ggcggaggtg gcagcgagcg  8040
aaaaagagac cgtccttggc cattacggta ttcagcgcga gttcatgttg tatgcgcccg  8100
gaggatttga ctcaaggaaa aactttaaac ggttgattga ggcctatgcc gggctcagtg  8160
atgccttacg tcgcagtcat caactggtca tcgtcagtaa gctttccatc ggtgatcgtc  8220
agtatctgga atcccttgcg tcaggtaatg gtttacagca gggcgaactg gtactcactg  8280
gttatgtgcc ggaagatgag ctgatccagc tctatcgcct atgtaagctg ttcatctttg  8340
cttcactaca tgaaggtttt gggttgccgg ttctggaagc aatgtcgtgc ggtgcgccgg  8400
tgattggctc aaatgtcacc agtattcctg aagtcatcgg taatcctgag gcattattcg  8460
acccgtattc tgtctcttcc atgagggata agatcgcgca atgtttgact gatgatacct  8520
tcctcgcgcg tctgaaagaa atggcgcagc agcaagcgcg taatttctct tgggataaag  8580
ctgcggtgac tgctctggaa gctttcgaaa agatcgcggt agaagacacc ggtactgcgc  8640
aggttttgcc tgaagctttg attcagaaga tccttgctat ctcacaaggg cagccagatg  8700
accgcgatct gcgcttgtgc gcaacggcca ttgattacaa tctgaaaacg gcagaacttt  8760
atcaaatcga cgataaatcg ctgaactggc gtgtggaagg cccattcgat agctcatata  8820
gtctggcgtt ggtcaaccgc gaatttgccc gggcactctc agccgatggt gtagaggttt  8880
tattgcattc cactgaagga ccaggtgatt ttgccccaga tgcctcgttt atggcacagt  8940
cggaaaatag tgatcttctg gcattttata atcaatgtca gacccgcaag agtaacgaaa  9000
agatagatat tattagcaga aatatctatc caccgcgggt taccaaaatg gatgccaaag  9060
taaaattcct tcattgttat gcttgggaag aaacgggctt tccgcaaccg tggatcaatg  9120
aatttaatcg ggaacttgac ggagtgctgt gtacttcgga acatgttcgt aaaatactga  9180
ttgataacgg actgaatgtg cccgcatttg ttgttggcaa tggctgtgac cattggctca  9240
atatcccagc cgagacgaca aaagatgtgg atcacggaac attccgtttc ctgcacgtct  9300
cttcttgttt cccacgcaaa gggatacagg caatgcttca ggcttggggg aaggcgttca  9360
ctcgtcgtga caatgttatc ttaatcatta agacttttaa caatccgcac aatgaaattg  9420
acgcatggct ggctcaggcc caggctcaat tcatagacta tcccaaagtt gaagtgatca  9480
aagaggatat gtcagccacc gagcttaaag ggctttatga aagctgtgat gttttggttg  9540
ctccaggttg cgctgaaggc tttggtttac ctattgctga agcaatgctg agtgggctac  9600
cggctatcgt caccaattgg agcgggcaac ttgattttgt taattcacaa aattcatggc  9660
tggttgacta tcagttcact cgggtaaaaa cgcactttgg tctgttttcc tcagcctggg  9720
ccagtgtgga tattgacaac ttaacagatg cattaaaagc ggcagcctca accgataaat  9780
cagtgctgcg tgacatggcc aatgctggtc gcgagcttct tctgcagcag tttacctgga  9840
aagcggtggc tgatcgttct tgccaggcgg tcaagactct gcgtgcgcat attgatattg  9900
cacagcatcg ggcgcgcatt ggctgggtga cgacctggaa cacgaaatgt gggatcgcaa  9960
cctattccca gcatctggtg gaaagcgcac ctcatggcgc ggatgttgtt tttgctcccc  10020
aggtcagcgc tggcgatctt gtgtgtgcag acgaagagtt tgtacttcgc aactggattg  10080
taggtaaaga gagcaactat ctggaaaacc tccagccaca cattgatgct ctgagactcg  10140
atgtcattgt gatccaattc aactatggat tctttaatca tcgagaactg tcggcgttta  10200
ttcgtcgcca gcatgacgcc ggtcgttcag ttgttatgac gatgcactca actgtggatc  10260
cgctggaaaa agagccgagc tggaatttcc gtcttgctga aatgaaagag gcgctggcac  10320
tttgcgaccg gttgttggtg cattcgattg ccgatatgaa ccgccttaaa gatttaggct  10380
taactgcgaa tgttgcttta ttcccgcacg gtgttatcaa ctactccgca gcgagcgtca  10440
cacgtcaaca gcagtcttta ccgctaattg cgagctatgg cttctgctta ccgcataagg  10500
gcctgatgga actagtagaa tccgtccata gactcaagca agccggtaaa ccggttcgtt  10560
tacgactggt gaacgcagag tatcctgttg gggagtcacg cgatctggtg gcagagctta  10620
aagctgctgc tcagcggtta ggtgttaccg atctgattga gatgcataat gatttcctac  10680
ctgatgcgga gagtctgcgg ttgctttcag aagccgatct tctgattttt gcttatcaga  10740
atactgggga gtctgctagc ggggcggtac gttatggtat ggcgactcaa aaacctgttg  10800
cggtaacgcc cctggcgata tttgatgatt tggacgatgc cgtctttaaa tttgatggat  10860
gcagcgtcga tgatatcagt caggggattg accggatcct gaattccatc cgtgaacaga  10920
actcttgggc aaccaggact caacaacgtg ccgatgcatg gcgggaacaa catgattatc  10980
aagctgtttc acgccgtctg gttaatatgt gtcaaggctt agctaaagct aaatatttta  11040
aataaaaata tctctcttgt attttttgcc tttgaataca agaggggtta gataatgtgt  11100
catttattat gaaaattatt tttgctactg agccaattaa atacccatta acgggcatcg  11160
gtcggtattc cctggagctg gttaagcggc tggcggtcgc ccgcgaaatt gaagaattaa  11220
agctatttca cggtgcgtcg tttatagaac agatcccttt ggtggagaat aaaagcgata  11280
ccaaagccag caatcatggt cgtctgtcgg cgtttctacg ccgacagacg ctgttgattg  11340
aggcttatcg cttgctgcat ccgcggcgcc aggcgtgggc attgcgcgac tataaggatt  11400
atatctacca tggccccaat ttttatctgc cgcataaact ggaacgcgcc gtgaccacgt  11460
ttcatgacat atccattttt acctgcccgg aatatcatcc aaaagatcgg gttcgctata  11520
tggagaagtc cctgcatgag agtctggatt cggcaaagct gatcctgacc gtttctgatt  11580
tctcgcgcag tgaaattatc cgcttgttca actatccggc ggagcggatc gtaaccacca  11640
```

-continued

```
agctagcctg cagcagtgac tatatcccac gcagcccggc agagtgtctg ccggtactgc  11700
agaaatatca gctggcgtgg caggcctacg cgctatatat cggcactatg gagccacgta  11760
aaaatatccg aggcctgctg catgcctatc agctgctacc gatggagatc cgcatgcgct  11820
atccgctaat ccttagcggc tatcgcggct gggaagacga tgtgctgtgg cagttagtcg  11880
agcgcggtac tcgggaaggc tggatccgtt acctcggata tgttccggat gaagacctgc  11940
cgtatctgta cgcagcggcc agagtctttg tttatccctc cttctacgag ggattcggtt  12000
tacctattct tgaagcgatg tcttgcggtg tgccggtagt atgctccaat gtcacctctt  12060
tgcctgaggt tgttggcgat gccggcctcg ttgccgatcc taatgatata gacgcgatta  12120
gcgcgcaaat tttgcagagc ctgcaagatg atagctggcg ggaaatcgcc accgcgcgcg  12180
gtcttgctca ggcgaaacag ttttcgtggg agaactgtgc gacacagacc attaacgcct  12240
ataaattact ctaagggtgt cagttgagag ttctacacgt ctataagact tactatcccg  12300
atacctacgg cggtattgag caggtcattt atcagctaag tcagggctgc gcccgccggg  12360
gaatcgcagc cgatgttttc acttttagcc cggacaaaga tacaggtcct gtcgcttacg  12420
aagatcatcg ggtcatttat aataaacagc tttttgaaat tgcctccacg ccgttttcgc  12480
tgaaagcgtt aaagcgtttt aagctgatta aagatgacta cgatatcatc aactaccatt  12540
ttccgtttcc ctttatggat atgctgcatc tttcggcgcg gcctgacgcc aggactgtgg  12600
tgacctatca ctctgatata gtgaaacaaa aacggttaat gaagctgtac cagccgctgc  12660
aggagcgatt tctcagcggc gtagattgca tcgttgcctc gtcgcccaat tacgtggctt  12720
ccagccagac cctgaaaaaa tatctggata aaacggtggt gatcccgttt ggtctggagc  12780
agcaggacgt gcagcacgat ccgcagaggg tcgcgcactg gcgggaaact gtcggcgata  12840
agttctttct cttcgtcggc actttccgct actacaaagg gctgcatatt ctgatggatg  12900
ccgctgagcg tagccgactg ccagtggtgg ttgtaggggg cgggccgctg gaatcggaag  12960
tgcggcgtga agcgcagcag cgcgggctga gcaatgtgat gtttaccggc atgctcaacg  13020
acgaagataa gtacattctc ttccagctct gccggggcgt ggtattcccc tcgcatctgc  13080
gctctgaggc gtttggcatt acgttattgg aaggcgcacg ctttgcaagg ccgctgatct  13140
cttgcgagat cggtacaggt acctctttca ttaaccagga caaagtgagt ggttgcgtga  13200
ttccgccgaa tgatagccag gcgctggtgg aggcgatgaa tgagctctgg aataacgagg  13260
aaacctccaa ccgctatggc gaaaactcgc gtcgtcgttt tgaagagatg tttactgccg  13320
accatatgat tgacgcctat gtcaatctct acactacatt gctggaaagc aaatcctgag  13380
cggccgcgag ctcgtcgact cgaggatccg tgtaggctgg agctgcttcg aagttcctat  13440
actttctaga gaataggaac ttcggaatag gaactaagga ggatattcat atggataaag  13500
ccgtaagcat ataagcatgg ataagctatt tatactttaa taagtacttt gtatacttat  13560
ttgcgaacat tccaggccgc gagcattcag cgcggtgatc acacctgaca ggagtatgta  13620
atgtccaagc aacagatcgg cgtagtcggt atggcagtga tgggacgcaa ccttgcgctc  13680
aacatcgaaa gccgtggtta taccgtctct attttcaacc gttcccgtga gaagacggaa  13740
gaagtgattg ccgaaaatcc aggcaagaaa ctggttcctt actatacggt gaaagagttt  13800
gtcgaatctc tggaaacgcc tcgtcgcatc ctgttaatgg tgaaagcagg tgcaggcacg  13860
gatgctgcta ttgattccct caaaccatat ctcgataaag gagacatcat cattgatggt  13920
ggtaacacct tcttccagga cactattcgt cgtaatcgtg agctttcagc agagggcttt  13980
aacttcatcg gtaccggtgt ttctggcggt gaagaggggg cgctgaaagg tccttctatt  14040
atgcctggtg gccagaaaga agcctatgaa ttggtagcac cgatcctgac caaaatcgcc  14100
gccgtagctg aagacggtga accatgcgtt acctatattg gtgccgatgg cgcaggtcac  14160
tatgtgaaga tggttcacaa cggtattgaa tacggcgata tgcagctgat tgctgaagcc  14220
tattctctgc ttaaaggtgg cctgaacctc accaacgaag aactggcgca gacctttacc  14280
gagtggaata acggtgaact gagcagttac ctgatcgaca tcaccaaaga tatcttcacc  14340
aaaaaagatg aagacggtaa ctacctggtt gatgtgatcc tggatgaagc ggctaacaaa  14400
ggtaccggta aatggaccag ccagagcgcg ctggatctcg gcgaaccgct gtcgctgatt  14460
accgagtctg tgtttgcacg ttatatctct tctctgaaag atcagcgtgt tgccgcatct  14520
aaagttctct ctggtccgca agcacagcca gcaggcgaca aggctgagtt catcgaaaaa  14580
gttcgtcgtg cgctgtatct gggcaaaatc gtttcttacg cccagggctt ctctcagctg  14640
cgtgctgcgt ctgaagagta caactgggat ctgaactacg gcgaaatcgc gaagattttc  14700
cgtgctggct gcatcatccg tgcgcagttc ctgcagaaaa tcaccgatgc ttatgccgaa  14760
aatccacaga tcgctaacct gttgctggct ccgtacttca agcaaattgc cgatgactac  14820
cagcaggcgc tgcgtgatgt cgttgcttat gcagtacaga acggtattcc ggttccgacc  14880
ttctccgcag cggttgccta ttacgacagc taccgtgctg ctgttctgcc tgcgaacctg  14940
atccaggcac agcgtgacta ttttggtgcg catacttata agcgtattga taaagaaggt  15000
gtgttccata ccgaatggct ggattaa                                     15027
```

```
SEQ ID NO: 15         moltype = DNA  length = 11283
FEATURE               Location/Qualifiers
source                1..11283
                      mol_type = other DNA
                      organism = synthetic construct
SEQUENCE: 15
atgacgaatt taaaagcagt tattcctgta gcgggtctcg ggatgcatat gttgcctgcc  60
actaaggcga tacccaaaga gatgctacca atcgtcgaca agccaatgat tcagtacatt  120
gttgacgaga ttgtggctgc agggatcaaa gaaatcctcc tggtaactca cgcgtccaag  180
aacgcggtcg aaaaccactt cgacacctct tatgagttag aatcactcct tgagcagcgc  240
gtgaagcgtc aactgctggc ggaagtacag tccatctgtc cgccgggcgt gaccattatg  300
aacgtgcgtc agggcgaacc tttaggttta ggccactcca ttttgtgtgc gcgacctgcc  360
attggtgaca acccatttgt cgtggtactg ccagacgttg tgatcgacga tgccagcgcc  420
gacccgctac gttacaacct tgctgccatg attgcacgtt tcaacgaaac gggccgcagc  480
caggtgctgg caaaacgtat gccgggtgac ctctctgaat actccgtcat ccagactaaa  540
gagccgctgg accgtgaggg taaagtcagc cgcattgttg aatttatcga aaaaccggat  600
cagccgcaga cgctggactc agacatcatg gccgtaggtc gctatgtgct ttctgccgat  660
atttggccgg aactggaacg tactcagcct ggtgcatggg gacgtattca gctgactgat  720
gctattgccg agctggcgaa aaaacaatcc gttgatgcaa tgctgatgac cggcgacagt  780
tacgactgcg gcaaaaaaat gggctatatg caggcgtttg tgaagtatgg cctacgcaac  840
ctgaaagaag ggcgaagtt ccgtaaaggt attgagaagc tgttaagcga ataatgaaaa  900
```

-continued

```
tctgaccgga tgtaacggtt gataagaaaa ttataacggc agtgaaaatt cgcagcaaaa  960
gtaatttgtt gcgaatcttc ctgccgttgt tttatataaa ccatcagaat aacaacgagt  1020
tagcagtagg gttttattca aagttttcca ggattttcct tgtttccaga gcggattggt  1080
aagacaatta gcgtttgaat ttttcgggtt tagcgcgagt gggtaacgct cgtcacatca  1140
taggcatgca tgcagtgctc tggtagctgt aaagccaggg gcggtagcgt gcattaatac  1200
ctctattaat caaactgaga gccgcttatt tcacagcatg ctctgaagta atatggaata  1260
aattaagcta gcatgagcaa aactaaacta aatgttcttt accttgcaat aagtcagggt  1320
gccaattacc tactgccatt attaattttt ccttatcttg ttagagtcat tggtgtatcg  1380
aattttggtg atctgagttt ttcattgata actatacaag tgttgttaat ggttgttgaa  1440
tatggttttg gatatagtgg gacaagagaa atagcactaa ataacgataa aaaataccat  1500
tctgaatttt tttgcggtgt ggtgcttgct cgttttatat taatgctaat tgcagctata  1560
atactcataa tactctgttt tttttatgtt tttaacgacg ttaagtcttt gttatgtgtt  1620
ggttttctgt ccgtaattgc aggtgttttc aatccaaatt ggtttttgca aggtaaggaa  1680
atgatgagtg tgatggctgt gctgtcacta ttttcacgag gcatagcagt cgttgcagtt  1740
tatctaatta taaaacccgc aacgccgatg tacatcagtg ccttattatt gagcatgcca  1800
tatattttgt attcattctg tggcgttgcc tacttactta ttatcaagga gattttttta  1860
tgtaggccac cgataaagaa aattcaagta attttaaaaa atggatttca tttttttttgt  1920
tcaacacttg cgactagtgc atacacaatg ttgacccctc ttgtattggg tggcgtatct  1980
ggaaagtttg atgtaggcat ctttaactca gctaacatga tcaaacaagg tttggctgga  2040
cttgcatcac cattagtcca agctttttat ccaagaatta acatttttgca aagagagaat  2100
ccatatattg caaacttaaa atctagaatg attcttaaat acttgcttgt tttttacatg  2160
gctttagcaa taccattttt actttttgcc aaccaattat cattattaat attcggcatg  2220
aaaggtgaag taattgcagg tgcaatgcaa ttaatgacat tgcttcctat attcataggt  2280
tttaatacag ttgtcgggtt acttgtatta gtacctaatg ggatgcaaaa acagtatttc  2340
aaatctattt tcctaggaac tattacttgt ttaagcatag tttatccagc atgtaaatat  2400
tatggagcaa cgggtgcgat tgtgagtctt attgtagctg aaattttcgt tggcatggga  2460
atgcttaaac aattcattaa agtaaataaa accgtatgta ggcctcataa attatgaata  2520
tctcggtaat aatatctgtt tggaaacgcc cagttcaatt agaattgatt ctctctgagc  2580
tcgattctca ggctaaagac aatagtctac acctagaagt aattgtttcc gatagtcata  2640
gtggtaaaga aattgatgat gtagttgctg ataatattca taaaaagaaa aatattaata  2700
ttatccatca acatactaaa aatatactct ccgctaagcg caatttcgga gcatccctag  2760
cccatgggga ttatttaata tttcttgatg atgattgtat acccgcaagt ggatatatat  2820
catcgttgct gaactattta aaaaaaatga atagtaaaag cgttttatgt ggggaagtta  2880
gattcgaaaa tgaactcatt gagaccagca attactatcg ctacaggaac tctttacacc  2940
ctaagtttag tgatagtcct gatatctcta tgaatgcctg gacttttgtc gcaatgaatt  3000
gtgttcttga tagaaaggca ttttcatcag gtatagtttc atataatgaa aattttattg  3060
gttatggttg tgaagatcat gagtttgggt ggcaacttga aaaaaatgac ttcaaaatta  3120
tttttgctga ttttaaaata ttacatcacg aatacagtgg cgatatagaa ggatatacaa  3180
aaaaaattcg tgctacagca cgtgatggta tgaatgtatt aagcaaagta aggcctgaaa  3240
tgttttctac taataaaaaa ttattcctag ttgagaaaat atttagtaaa cacaaaacgt  3300
ttagtaaaat atgccaatca atatttttca ataaatttat ttttaaaaaa ataatacaat  3360
ttttaaaaaa aacagatgca aataaaaaac tctatttccc aattctttac agatatgtgt  3420
tgatttcggc atatatacat ggtattggag agcgtggcac ctcaaaaaca gatgatttgc  3480
ttaagaactg gtatatatag atgatgctat cttcatttat taagacattt gtatggaagg  3540
taaaaaacaa tgaagtataa tgcattgatg gctttttat tattttttgt tgttttttt  3600
agattgtcgc tgataatacc tttcttatat ttggcattta ttcctgcatt ttttggtatt  3660
atgtatttag tgcgtaattt tatgattact atgggcaatg gattggtatc tatagatcgt  3720
aaaaatttgt tgctgttatc tatattcata attattttt tattttgttt ggtttttcgat  3780
ttgtttcaaa aaagccattc ttttcaaagt tattttaccg ttagattatt tatgttgttt  3840
ttattttcat ttgttcctgc gtattattta gtaaatagat tcataaaggg tgacttgaaa  3900
ttaatggagc gaatattagt gtattctctc tgggttcaaa tagttatttt ttttggtatg  3960
tatataagtc cagagttaaa aagattgtta tatactttct ttggtatgtc tgactctgtt  4020
aatctttggg aacaaaatgc taaagtaaga ggatttgggt tgtcgggtga aataaatttc  4080
atgacaccat ttttgatgat ctatatgtca tttttttatga tgaaaaggcg ttatgcttta  4140
attactttaa tttgtctgac tcaaatcgta aattctaaca tggctgtgat tgcagccatt  4200
attggtatcg gttgctctag acttaatatt aatataaaaa ttgcaacagt attgattttg  4260
ggagttttag tttatagctt aggagcggtg ttctttcctc gattttatga tgagttcgtt  4320
tctggagatg gcacaagaac tctggatatc ttattacagc aacatgtgtt tgttgtaggt  4380
aatttagatt tttttaatat tatatttgga ttacagcaaa acatatcttc atcaatcccc  4440
gatattaaac aaagttcgga tatgggctgg gttatactgt ttaattacgg tgggttaaca  4500
tttattacac tctttttatt tttaatcttt actatttcta ttgcgacatt tggaatgaca  4560
tatcaagcaa ttatatggat gttaattggg ataattttca ataccaaagg tttagtttta  4620
ggatctaacg gctatttctt tctatctttt atatatatgt ttttgaatag agtaacactt  4680
agtggacaga gttcaattac taataagtta ggtcaagtaa gtaaatagct tccagagtat  4740
atttgtcaat gatttgaggt tcggttatta tgttttcatc taaaacactg ttaattactg  4800
gtggtactgg ctctttcggg aatgctgtat taaatagatt tcttgataca gatattgcag  4860
aaatccgtat atttagtcgt gatgaaaaaa aacaagatga tatgcggaaa aaatacaata  4920
atcaaaaatt aaagttctat attggtgatg tcagagatta ccgtagtatt ttgaatgcga  4980
ctcgcggtgt tgattttata tatcatgcag cggcacttaa gcaagttcca tcatgtgaat  5040
ttcatcctat ggaagccgtt aaaactaata tccttggtac ggaaaatgtt cttgaagcag  5100
ctatagcgaa tgaagtgaag agggttgtat gcctaagtac tgataaagct gtatacccga  5160
ttaacgcaat gggtatttca aaagctatga tggaaaaggt catggtcgcg aaatcccgta  5220
atgttgatcg caataaaaca gtaatatgtg gtacccgtta tgggaatgtt atggcatctc  5280
gcggttcagt tattccatta tttgttgatc ttattagagc gggcaagcca ctcacaataa  5340
ctgatcctaa tatgacccgc tttatgatga ctcttgagga tgcggtagat ttagttcttt  5400
atgcgtttga acatggtaat aatggtgata tctttgtgca aaaagcacct gcagcaacta  5460
ttgacacatt agctattgct ttaaaggaat tactaaatgt tcctgaccat ccggtaaatg  5520
tcattggaac gcgtcatggc gagaaattat atgaagctct acttagtcgt gaggaaatga  5580
tcgctgctat agatatgggc gattattacc gtgtcccgcc agatcttcgt gaccttaatt  5640
```

-continued

```
atggcaaata tgttgagcaa ggtgatagcc gaatatctga aatagaagat tataactctc  5700
ataatactca acggttagat gttgaaggca tgaaagagct cttgctaaaa ttagccttta  5760
ttcgagcaat tcgtgctggt gaaaaatata atctggattc atgatatgaa aatattagtt  5820
actggtgcaa atggttttat tggtcgtaat ttatgtttga ggcttgagga acttggttat  5880
aaagatctta ttagaattga tcgagaatca acgaagcaag atcttgaaca aggcttacag  5940
gatgccgatt ttatttatca cttagctggt atcaatagac ctaagactga tgatgagttt  6000
atttctggaa acagtgattt aacaaagcat atagttgagt atctcctttc tattggtaag  6060
aatacaccaa ttatgctaag ttcttcgata caagctgaac ttaataatgc ttatggggtt  6120
agcaaagctg tagctgaaag ctatgtcgaa aaatatgctg ctgctagtgg ttcttcgtat  6180
tatattttca gatatccaaa cgtttttggt aaatggtgta agccaaacta taattctttt  6240
atagcaactt tttgctacaa tatttccaat gatattgaga ttactatcaa tgatgcagca  6300
gcgccagtca atctggtcta tattgatgat gtttgtactg atgctatagc tcttctctct  6360
gggacggttg aaagtggata taaagttgtt gcaccaattt attcaacaac agttggtgaa  6420
gttgcagaat taatttatag cttcaaaaat agccgttcca ccctgatcac agaggctgtc  6480
ggggcgggat ttacccgtgc attgtattct acatggctga gttatttacc agcagagaag  6540
tttgcgtaca aggtaccttt ttatggggat gcccgcggag tcttttgtga gatgttgaaa  6600
acgccttcag cggggcagtt ttcatttttt actgctcacc ctggtattac gcgtggcgga  6660
cattaccatc acagtaaaaa tgagaagttt ttggtcattc gaggtcaggc atgctttaaa  6720
tttgaacatg tgattaccgg tgagcgatat gaactgaaag tttcatcggg tgagtttaag  6780
attgttgaaa cagttcctgg ttggacacat gacattacaa atattggaac tgatgaatta  6840
atagtcatgc tctgggcaaa tgaaattttc aaccgtgatg agcccgatac tattgcgaga  6900
cctctataat gaaaaaatta aaagttatgt ctgttgttgg aacccgtcct gagattatcc  6960
gtttgtcgag ggttcttgct aagtttgatg aatactgcga gcatattatt gtccatactg  7020
gtcaaaatta tgattacgaa ttaaatgaag tgttcttcaa tgacttgggt gttcgaaaac  7080
ctgattattt tttaaatgca gcgggtaaaa atgcggcgga aaccattggt caggttatta  7140
ttaaggtaga tgaagtatta gaaatcgaaa aacctgaagc aatactggta ttgggcgata  7200
cgaattcatg tatttctgcc attccggcca aacgccgtaa agtgcctata tttcatatgg  7260
aagcaggtaa ccgttgtttc gatcaacgcg tgcctgaaga aaccaacaga cgtattgttg  7320
accatacggc tgatatcaat atgacctaca gtgatattgc tcgtgaatat ctcttggctg  7380
aaggtatccc agctgatcgg atcataaaaa ctggtagccc tatgtttgag gttctttcat  7440
attatatgcc ccaaattgat ggttcagatg tgctatcgcg tttgaatcta cagtctggtg  7500
agttttttgt agtaagtgcg catcgtgaag agaatgttga ttctccaaaa cagctcgtaa  7560
agcttgcgaa cattctaaat actgttgctg aaaaatataa tcttccagtt attgtctcca  7620
cacacccaag gacacgtaac cgaatccgtg agcaaggaat tgaatttcat tcaaatataa  7680
atctactgaa accattgggt ttccatgatt ataaccactt gcagaagaac tcacgagctg  7740
tgctttcaga tagcggtact atcactgaag agtcatccat catgaatttc ccagcggtaa  7800
acatccggga agcgcatgag cgtccggaag gctttgagga agcatccgtc atgatggtgg  7860
ggttagagtg tgaacgcgta ttacaagcgc tggatattct ggcaacacaa ccgcgaggtg  7920
aagtccgtct tttacgtcag gttagtgatt acagcatgcc aaatgtgtcg gataaagttg  7980
tcagaattgt tcactcttac acagattatg ttaagagagt cgtctggaaa gaatattgat  8040
gaaacttgct ttaatcatag atgattacct gcccaacagt actcgtgttg gtgcaaaaat  8100
gtttcatgaa cttgctcaag aatttatcca gcgtgggcac gatgttacgg taattactcc  8160
tggtacgggc atgcaagaag agatttcttt tgataccttt caggggggtaa aaacatggcg  8220
ttttaaaagc gggccgctca aggatgtaag taaaattcag cgagcggtca atgaaacgct  8280
tttgtcctat cgggcgtgga aagccatcaa aaaatgggta aaaaaagaga cctttgaggg  8340
ggtgatttat tattcacctt ccatattctg ggggccttta gttaaaaaaa ttaaagctcg  8400
ttgccaatgt cctgcttatc ttattttaag agatatgttt ccacaatggg taattgatgc  8460
aggaatgctt aatgctggtt ccccaataga acgctacttt cgtctttttg aaaaaatatc  8520
ttatcgtcag gcaaatcgta ttggacttat gtctgataag aatcttgatg tttttcggaa  8580
agataataaa ggctatccgt gcgaagtttt gcgtaattgg gcatccctaa caccaacgat  8640
catacccaag gattatatac cactacgtaa gcgacttggc ctagaggata aaaccatttt  8700
cttctatggt ggaaacatag gtcatgcaca ggacatgaca aacttgatgc gacttgtgag  8760
aaacatggca gcatatcctc aagctcattt cctatttatt ggccaggggg atgaagttga  8820
attaattaat tcattagcat ctgagtgggc attgacgaat ttcacctatt tgccctcggt  8880
taaccaagat gaatttaagt tcattttgtc ggaaatggat atcggcttgt tttctctttc  8940
cgctagacac tcttcccata attttcctgg taagttatta ggctatatgg ttcagtcgct  9000
acctatttta ggtagcgtaa atgccggaaa tgatttgctc gacattgtca atcaaaataa  9060
tgcgggatta atccatgtca atggtgagga cgataaatta tgtcaatctg cgctattaat  9120
gttgcatgat attgatgtgc gccggcaact tggttcgggg gcgaatatat tgttgaaaga  9180
acaattctcc gttgagtctg cggcacagac gatagaaatg aggttggagg catgcaatgc  9240
gattaattga taatgaccaa ctcgacgaat tatatgatca agccgggcaa tcggaacgtt  9300
tacgttccca ccttatgatg cacggctcgc atcaagaaaa ggtacagcgt ttacttattg  9360
cattagtaaa gggcagctat gttgaaccgc attatcacga acttcctcat cagtgggaaa  9420
tgttcattgt tatggagggg caacttcagg tttgtttgta tggtagaaat ggtgaggtta  9480
taaagcaatt tatagcagga gataatactg gaatgagcat tgtggagttt tctccgggcg  9540
atatacacag tgtcgaatgc ctatctccgc gtgctcttat ggtggaagtt aaggaggggc  9600
catttgaccc ttcttttgca aaatcgttcg tgtgagcggc cgcgagctcg tcgactcgag  9660
gatccgtgta ggctggagct gcttcgaagt tcctatactt tctagagaat aggaacttcg  9720
gaataggaac taaggaggat attcatatgg ataaagccgt aagcatataa gcatggataa  9780
gctatttata ctttaataag tactttgtat acttatttgc gaacattcca ggccgcgagc  9840
attcagcgcg gtgatcacac ctgacaggag tatgtaatgt ccaagcaaca gatcggcgta  9900
gtcggtatgg cagtgatggg acgcaacctt gcgctcaaca tcgaaagccg tggttatacc  9960
gtctctattt tcaaccgttc ccgtgagaag acggaagaag tgattgccga aaatccaggc  10020
aagaaactgg ttccttacta tacggtgaaa gagtttgtcg aatctctgga aacgcctcgt  10080
cgcatcctgt taatggtgaa agcaggtgca ggcacggatg ctgctattga ttccctcaaa  10140
ccatatctcg ataaaggaga catcatcatt gatggtggta acaccttctt ccaggacact  10200
attcgtcgta atcgtgagct ttcagcagag ggctttaact tcatcggtac cggtgtttct  10260
ggcggtgaag agggggcgct gaaaggtcct tctattatgc ctggtggcca gaaagaagcc  10320
tatgaattgg tagcaccgat cctgaccaaa atcgccgccg tagctgaaga cggtgaacca  10380
```

```
tgcgttacct atattggtgc cgatggcgca ggtcactatg tgaagatggt tcacaacggt  10440
attgaatacg gcgatatgca gctgattgct gaagcctatt ctctgcttaa aggtggcctg  10500
aacctcacca acgaagaact ggcgcagacc tttaccgagt ggaataacgg tgaactgagc  10560
agttacctga tcgacatcac caaagatatc ttcaccaaaa aagatgaaga cggtaactac  10620
ctggttgatg tgatcctgga tgaagcggct aacaaaggta ccggtaaatg gaccagccag  10680
agcgcgctgg atctcggcga accgctgtcg ctgattaccg agtctgtgtt tgcacgttat  10740
atctcttctc tgaaagatca gcgtgttgcc gcatctaaag ttctctctgg tccgcaagca  10800
cagccagcag gcgacaaggc tgagttcatc gaaaaagttc gtcgtgcgct gtatctgggc  10860
aaaatcgttt cttacgccca gggcttctct cagctgcgtg ctgcgtctga agagtacaac  10920
tgggatctga actacggcga aatcgcgaag attttccgtg ctggctgcat catccgtgcg  10980
cagttcctgc agaaaatcac cgatgcttat gccgaaaatc cacagatcgc taacctgttg  11040
ctggctccgt acttcaagca aattgccgat gactaccagc aggcgctgcg tgatgtcgtt  11100
gcttatgcag tacagaacgg tattccggtt ccgaccttct ccgcagcggt tgcctattac  11160
gacagctacc gtgctgctgt tctgcctgcg aacctgatcc aggcacagcg tgactatttt  11220
ggtgcgcata cttataagcg tattgataaa gaaggtgtgt tccataccga atggctggat  11280
taa                                                                11283
```

```
SEQ ID NO: 16          moltype = DNA  length = 13435
FEATURE                Location/Qualifiers
source                 1..13435
                       mol_type = other DNA
                       organism = synthetic construct
SEQUENCE: 16
atgacgaatt taaaagcagt tattcctgta gcgggtctcg ggatgcatat gttgcctgcc  60
actaaggcga tacccaaaga gatgctacca atcgtcgaca agccaatgat tcagtacatt  120
gttgacgaga ttgtggctgc agggatcaaa gaaatcctcc tggtaactca cgcgtccaag  180
aacgcggtcg aaaaccactt cgacacctct tatgagttag aatcactcct tgagcagcgc  240
gtgaagcgtc aactgctggc ggaagtacag tccatctgtc cgccgggcgt gaccattatg  300
aacgtgcgtc agggcgaacc tttaggttta ggccactcca ttttgtgtgc gcgacctgcc  360
attggtgaca acccatttgt cgtggtactg ccagacgttg tgatcgacga tgccagcgcc  420
gacccgctac gttacaacct tgctgccatg attgcacgtt tcaacgaaac gggccgcagc  480
caggtgctgg caaaacgtat gccgggtgac ctctctgaat actccgtcat ccagactaaa  540
gagccgctgg accgtgaggg taaagtcagc cgcattgttg aatttatcga aaaaccggat  600
cagccgcaga cgctggactc agacatcatg gccgtaggtc gctatgtgct ttctgccgat  660
atttggccgg aactggaacg tactcagcct ggtgcatggg gacgtattca gctgactgat  720
gctattgccg agctggcgaa aaaacaatcc gttgatgcaa tgctgatgac cggcgacagt  780
tacgactgcg gcaaaaaaat gggctatatg caggcgtttg tgaagtatgg cctacgcaac  840
ctgaaagaag ggggcgaagtt ccgtaaaggt attgagaagc tgttaagcga ataatgaaaa  900
tctgaccgga tgtaacggtt gataagaaaa ttataacggc agtgaaaatt cgcagcaaaa  960
gtaatttgtt gcgaatcttc ctgccgttgt tttatataaa ccatcagaat aacaacgagt  1020
tagcagtagg gttttattca aagttttcca ggatttcct tgtttccaga gcggattggt  1080
aagacaatta gcgtttgaat ttttcgggtt tagcgcgagt gggtaacgct cgtcacatca  1140
taggcatgca tgcagtgctc tggtagctgt aaagccaggg gcggtagcgt gcattaatac  1200
ctctattaat caaactgaga gccgcttatt tcacagcatg ctctgaagta atatggaata  1260
aattaagtga aaatacttgt tactggtggc gcaggattta ttggttcagc tgtagttcgt  1320
cacattataa ataatacgca ggatagtgtt gttaatgtcg ataaattaac gtacgccgga  1380
aaccgggaat cacttgctga tgtttctgat tctgaacgct atgtttttga acatgcggat  1440
atttgcgatg cacctgcaat ggcacggatt tttgctcagc atcagccgga tgcagtgatg  1500
cacctggctg ctgaaagcca tgttgaccgt tcaattacag gccctgcggc atttattgaa  1560
accaatattg ttggtactta tgtccttttg gaagccgctc gcaattactg gtctgctctt  1620
gatagcgaca agaaaaatag cttccgtttt catcatattt ctactgacga agtctatggt  1680
gatttgcctc atccagatga agtaaataat acagaagaat taccccttatt tactgagacg  1740
acagcttacg cgccaagcag cccttattcc gcatccaaag catccagcga tcatttagtc  1800
cgcgcgtgga aacgtacata tggtttaccg acaattgtga ctaattgctc gaacaactat  1860
ggtccttatc atttcccgga aaagcttatt ccactggtta ttcttaatgc actggaaggt  1920
aaggcattac ctatttatgg caaaggagat cagatccgcg actggttgta tgttgaagat  1980
catgcgcgtg cgttatatac cgtcgtaacc gaaggtaaag cgggtgaaac ttataacatt  2040
ggtgggcaca acgaaaagaa aaacatcgat gtagtgctca ctatttgtga tttgctggat  2100
gagattgtac cgaaagagaa atcttatcgt gagcaaatca cttatgttgc tgatcgtccg  2160
ggacacgatc gccgctatgc tattgatgct gagaagattg gtcgcgcatt gggatggaaa  2220
ccacaggaaa cgtttgagag cggattcgt aaaacggtgg aatggtacct gtccaataca  2280
aaatgggttg ataatgtgaa aagtggtgcc tatcaatcgt ggattgaaca gaactatgag  2340
ggccgccagt aatgaatatc ctcctttttg gcaaaacagg gcaggtaggt tgggaactac  2400
agcgtgctct ggcacctttg ggtaatttga ttgcttttga tgttcactct actgattatt  2460
gcggtgattt tagtaatcct gaaggtgtag ctgaaaccgt aagaagcatt cggccggata  2520
ttattgtcaa tgcagccgct cacaccgcag tagacaaagc agaatcagaa ccggagtttg  2580
cacaattaat taacgcaaca agtgtcgaag cgattgcgaa agcagcaaat gaagttggag  2640
cctgggttat ccattactcg actgattacg tcttccctgg aaatggcgat atgccatggc  2700
tggagacgga tgcaaccgca ccactaaatg tttacggtga aaccaagtta gccggagaaa  2760
aagcgttaca ggaatattgc gcgaagcatc ttattttccg gaccagctgg gtctatgcag  2820
gaaaaggaaa taacttcgcc aaaacgatgt tacgtctggc aaaagagcgt gaagaattag  2880
cggttattaa cgatcagttt ggtgcgccaa caggtgctga actgctggct gattgtacag  2940
cacatgccat tcgtgtcgca ctgaataaac cggatgtcgc aggcttgtac catttggtag  3000
ccagtggtac cacaacctgg tacgattatg ctgcgctggt ttttgaagag gcgcgcaaag  3060
caggcattcc ccttgcactc aacaagctca acgcagtacc aacaacagcc tatcctacac  3120
cagctcgtcg tccacataac tctcgcctta atacagaaaa atttcagcag aactttgcgc  3180
ttgtcttgcc tgactggcag gttggcgtga aacgaatgct caatgaatta tttacgacta  3240
cagcaattta atagttttg catcttgttc gtgatggtgg agcaagatga attaaaagga  3300
atgatgaaat gaaaatgcgt aaaggtatta ttttagcggg tggttctggt acacgtcttt  3360
```

-continued

```
atcctgtgac tatggctgtc agtaaacagc tattacctat ttatgataaa ccgatgatct  3420
attacccgct ctctacactg atgttggcgg gtattcgcga tattttgatt atcagtacac  3480
ctcaggatac tcctcgtttt caacaattgc tgggtgacgg tagccagtgg ggcctgaatc  3540
ttcagtacaa agtgcaacct agcccagatg gcctcgcgca ggcatttatc atcggtgaag  3600
agtttattgg tggtgatgat tgtgctttgg ttcttggtga taatatcttt tacggtcacg  3660
atctgccgaa gctaatggag gccgctgtta acaaagaaag tggtgcaacg gtatttgcct  3720
atcacgttaa tgatccagaa cgctatggtg tcgttgagtt tgataaaaac ggtacggcaa  3780
tcagtctgga agaaaaaccg ttagaaccaa agagtaatta cgccgttaca ggtctgtact  3840
tttatgataa cgacgtggtt cagatggcga aaaacttgaa gccgtctgca cgtggtgagt  3900
tagaaattac agatattaac cgtatttatc ttgagcaggg acgtctgtct gtcgcgatga  3960
tggggcgtgg ctacgcgtgg ctggacacgg ggactcatca gagtctgata gaagcaagta  4020
attttattgc gacaattgaa gagcgccagg gattgaaggt ttcctgtcct gaagagattg  4080
catttcgtaa aggttttatt gatgttgagc aagtaagaaa attagctgta ccactaataa  4140
agaataatta tgggcagtat ctttataaaa tgacgaagga ttcaaattaa tgaatgtgat  4200
tagaactgaa attgaagatg tgctaattct ggagccaaga gtatttggtg atgatagagg  4260
tttcttttat gagagcttta atcaatcagc atttgaacat attctaggct atccggtcag  4320
ctttgttcaa gacaatcact cacgttcatc aaaaaatgta ctcagaggcc ttcactttca  4380
acgcggcgag tacgcacaag ataaacttgt acgctgcact catggagcag tttttgatgt  4440
tgctgttgat attcgaccca attcggtatc ctttggtaaa tgggttggtg ttctgctttc  4500
agctgataat aagcagcagt tgtggatacc aaaagggttt gctcatggct ttttggttct  4560
gtctgatatc gctgaatttc aatataaaac tacaaactat tatcatcctg aaagcgattg  4620
tggaatatgt tggaatgatg aacgcattgc aattgattgg ccccaaacat cagggttaat  4680
cctttcgcca aaagatgaaa ggctctttac gttagatgag cttatcagat taaaattaat  4740
tgcatgaata cgaataaatt atctttaaga agaaacgtta tatatctggc tgtcgttcaa  4800
ggtagcaatt atcttttacc attgcttaca tttccatatc ttgtaagaac acttggtcct  4860
gaaaatttcg gtatattcgg tttttgccaa gcgactatgc tatatatgat aatgtttgtt  4920
gaatatggtt tcaatctcac agcaactcag agtattgcca aagcagcaga tagtaaagat  4980
aaagtaacgt ctattttttg ggcggtgata ttttcaaaaa tagttcttat cgtcattaca  5040
ttgattttct taacgtcgat gaccttgctt gttcctgaat ataacaagca tgccgtaatt  5100
atatggtcgt ttgttcctgc attagtcggg aatttaatct accctatctg gctgtttcag  5160
ggaaaagaaa aaatgaaatg gctgacttta agtagtattt tatcccgctt ggctattatc  5220
cctctaacat ttatttttgt gaacacaaag tcagatatag caattgccgg ttttattcag  5280
tcaagtgcaa atctggttgc tggaattatt gcactagcta tcgttgttca tgaaggttgg  5340
attggtaaag ttacgctatc attacataat gtgcgtcgat ctttagcaga cggttttcat  5400
gtttttattt ccacatctgc tattagttta tattctacgg gaatagttat tatcctggga  5460
tttatatctg gaccaacgtc cgtagggaat tttaatgcgg ccaatactat aagaaacgcg  5520
cttcaagggc tattaaatcc tatcacccaa gcaatatacc caagaatatc aagtacgctt  5580
gttcttaatc gtgtgaaggg tgtgatttta attaaaaaat cattgacctg cttgagtttg  5640
attggtggtg ctttttcatt aattctgctc ttgggtgcat ctatactagt aaaaataagt  5700
atagggccgg gatatgataa tgcagtgatt gtgctaatga ttatatcgcc tctgcctttt  5760
cttatttcat taagtaatgt ctatggcatt caagttatgc tgacccataa ttataagaaa  5820
gaattcagta agattttaat cgctgcgggt ttgttgagtt tgttgttgat tttccgcta  5880
acaactcttt ttaaagagat tggtgcagca ataacattgc ttgcaacaga gtgcttagtt  5940
acgtcactca tgctgatgtt cgtaagaaat aataaattac tggtttgctg aggattttat  6000
gtacgattat atcattgttg gttctggttt gtttggtgcc gtttgtgcga atgagttaaa  6060
aaagctaaac aaaaaagttt tagtgattga gaaaagaaat catatcggtg gaaatgcgta  6120
cacagaggac tgtgagggta tccagattca taaatatggt gcacatattt ttcataccaa  6180
tgataaatat atatgggatt acgttaatga tttagtagaa tttaatcgtt ttactaattc  6240
tccactggcg atttataaag acaaattatt caaccttcct tttaatatga atactttcca  6300
ccaaatgtgg ggagttaaag atcctcaaga agctcaaaat atcattaatg ctcagaaaaa  6360
aaagtatggt gacaaggtac ctgaaaattt ggaggagcag gcgatttcat tagttgggga  6420
ggacttatac caagcattga taaagggtta tacggagaag cagtggggaa gaagtgcaaa  6480
agaattgcct gcatttatta ttaagcgaat cccagtgaga tttacgtttg ataacaatta  6540
tttttccgat cgctatcaag gtattccggt gggaggctac actaagctta ttgaaaaaat  6600
gcttgaaggt gtggacgtaa aattaggcat tgattttttg aaagacaaag attctctagc  6660
gagtaaagcc catagaatca tctacactgg acccattgat cagtacttcg actataggtt  6720
tggagcgtta gaatatcgct ctttaaaatt tgagacggaa cgccatgaat ttccaaactt  6780
ccaagggaat gcagtaataa atttcactga tgctaatgta ccatatacca gaataattga  6840
gcataaacat tttgactatg ttgagacaaa gcatacggtt gttacaaaag aatatccatt  6900
agagtggaaa gttggcgacg aaccctacta tccagttaat gataataaaa acatggagct  6960
ttttaagaaa tatagagagt tagctagcag agaagacaag gttatatttg gcgggcgttt  7020
ggccgagtat aaatattatg atatgcatca agtgatatct gccgctcttt atcaagtgaa  7080
aaatataatg agtacggatt aatgatctat cttgtaatta gtgtctttct cattacagca  7140
tttatctgtt tatatcttaa gaaggatata ttttatccag ccgtatgcgt taatatcatc  7200
ttcgcactgg tcttattggg atatgaaata acgtcagata tatatgcttt tcagttaaat  7260
gacgctacgt tgatttttct actttgcaat gttttgacat ttaccctgtc atgtttattg  7320
acggaaagtg tattagatct aaatatcaga aaagtcaata atgctattta tagcatacca  7380
tcgaagaaag tgcataatgt aggcttgtta gttatttctt tttcgatgat atatatatgc  7440
atgaggttaa gtaactacca gttcgggact agcttactta gctatatgaa tttgataaga  7500
gatgctgatg ttgaagacac atcaagaaat ttctcagcat acatgcagcc aatcattcta  7560
actactttg ctttatttat ttggtctaaa aaatttacta atacaaaggt aagtaaaaca  7620
tttactttac ttgtttttat tgtattcatc tttgcaatta tactgaatac tggtaagcaa  7680
attgtcttta tggttatcat ctcttatgca ttcatcgtag gtgttaatag agtaaaacat  7740
tatgtttatc ttattacagc tgtaggtgtt ctattctcct tgtatatgct ctttttacgt  7800
ggactgcctg gggggatggc atattatcta tccatgtatt tggtcagccc tataatcgcg  7860
tttcaggagt tttattttca gcaagtatct aactctgcca gttctcatgt cttttggttt  7920
tttgaaaggc tgatggggct attaacaggt ggagtctcta tgtcgttgca taaagaattt  7980
gtgtgggtgg gtttgccaac aaatgtttat actgcttttt cggattatgt ttatatttcc  8040
gcggagctaa gctatttgat gatggttatt catggctgta tttcaggtgt tttatggaga  8100
```

-continued

```
ttgtctcgaa attacatatc tgtgaaaata ttttattcat attttattta tacctttttct  8160
ttcatttttt atcatgaaag cttcatgact aatattagca gttggataca aataactctt  8220
tgtatcatag tattctctca atttcttaag gcccagaaaa taaagtgaaa atgtattttt  8280
tgaatgattt aaatttctct agacgcgatg ctggatttaa agcaagaaaa gatgcactgg  8340
acattgcttc agattatgaa aacatttctg ttgttaacat tcctctatgg ggtggagtag  8400
tccagagaat tattagttct gttaagctta gtacatttct ctgcggtctt gaaaataaag  8460
atgttttaat tttcaatttc ccgatggcca aaccattttg gcatatattg tcattctttc  8520
accgccttct aaaatttaga atagtacctc tgattcatga tattgatgaa ttaagaggag  8580
gagggggtag tgattctgtg cggcttgcta cctgtgatat ggtcataagt cacaatccac  8640
aaatgacaaa gtaccttagt aaatatatgt ctcaggataa aatcaaagac ataaaaaatat  8700
ttgattacct cgtctcatct gatgtggagc atcgagatgt tacggataag caacgagggg  8760
tcatatatgc tggcaacctt tctaggcata aatgttcttt catatatact gaaggatgcg  8820
attttactct ctttggtgtc aactatgaaa ataaagataa tcctaaatat cttggaagtt  8880
ttgatgctca atctccggaa aagattaacc tcccaggcat gcaatttgga ctcatttggg  8940
atggagattc tgtcgaaacc tgtagtggtg cctttggcga ctatttaaag tttaataacc  9000
ctcataagac atctctttat ctttcaatgg aacttccagt atttatatgg gataaagccg  9060
cccttgcgga tttcattgta gataatagaa taggatatgc agtgggatca atcaaagaaa  9120
tgcaagagat tgttgactcc atgacaatag aaacttataa gcaaattagt gagaatacaa  9180
aaattatttc tcagaaaatt cgaacaggaa gttacttcag ggatgttctt gaagaggtga  9240
tcgatgatct taaaactcgc taaacgatat ggtctctgtg gttttattcg gcttgttaga  9300
gatgtcttat tgactcgtgt attttaccgg aactgtagaa ttattcgatt tccctgctat  9360
attcgcaatg atggtagcat taattttggt gaaaatttca caagtggagt cggtctcagg  9420
ctggatgcat ttggacgtgg cgtgattttt ttttccgata atgtgcaagt taacgactat  9480
gttcatatcg cctcaattga gagcgttacg ataggtcggg atacgcttat tgcaagtaaa  9540
gtatttatta ccgatcataa tcacggttcc tttaagcact ctgatccaat gagttcgcca  9600
aatatacctc cagacatgcg cacgttggaa tcttcagctg ttgtaattgg ccagagggtt  9660
tggttgggtg agaatgtgac ggttttgcct ggaacaatta ttggtaatgg agtcgtagtc  9720
ggcgccaatt ctgttgttag aggttctatt cccgaaaata ctgtcattgc gggagtacca  9780
gcaaaaatca taaagaaata caatcatgag accaaattat gggaaaaagc atagtcgttg  9840
tttctgcggt caattttacc actggcggtc catttaccat tttgaaaaaa tttttggcag  9900
caactaataa taaagaaaat gtcagtttta tcgcattagt ccattctgct aaagagttaa  9960
aagaaagtta tccatgggtt aaattcattg agtttcctga ggttaaaggg tcgtggctaa  10020
aacgtttgca ctttgaatat gtagtttgta aaaaactttc aaaagagctg aatgctacgc  10080
attggatttg tctgcatgat attacggcca atgtcgtcac taaaaaaaga tatgtgtatt  10140
gtcataaccc tgcccctttt tataaaggaa ttttattccg tgaaattctt atggagccta  10200
gctttttctt atttaaaatg ctatacgggc tgatatataa aataaacatt aaaaaaaata  10260
ctgcagtgtt tgttcaacaa ttctggatga aagaaaaatt tatcaagaaa tattctataa  10320
ataacatcat tgtcagtcgg ccagaaatta aattatctga taaaagccaa cttactgatg  10380
atgattctca atttaagaat aaccccttctg agttgacaat attttaccct gctgttccac  10440
gagtatttaa aaattacgag cttattatta gtgcagcaag gaaattgaaa gaacaatcca  10500
atattaaatt tctgcttact atcagtggta cagaaaatgc gtatgcaaaa tatattatca  10560
gtcttgcaga aggactggat aatgttcatt tcctcgggta cttggataaa gaaaaaatcg  10620
atcattgtta taatatttca gatatagttt gttttccctc taggttagaa acatggggat  10680
tgccgttgtc tgaggctaaa gagcgaggta agtgggtatt agcatcagat ttcccattta  10740
ctagagaaac tcttggtagt tatgaaaaga aagctttttt tgattctaat aacgatgaca  10800
tgttagttaa acttattatt gacttcaaaa aaggtaacct caaaaaagat atctctgatg  10860
caaatttcat ttatcgtaat gaaaatgtat tagttgggtt tgatgaacta gttaatttta  10920
ttactgaaga acattgaaat ggtatatata ataatcgttt ccccacggaca tgaagactac  10980
atcaaaaaat tactcgaaaa tcttaatgct gacgatgagc actacaagat tatcgtacgc  11040
gacaacaaag actctctatt attgaaacaa atatgccagc attatgcagg cctggactat  11100
attagtggag gtgtatacgg ctttggtcat aataataata ttgcggtggc gtatgtaaag  11160
gaaaaatata gacccgcaga tgatgattac attttgtttt tgaatcccga tatcatcatg  11220
aagcatgatg atttgctgac atatattaaa tatgtcgaaa gtaagcgtta tgcttttagt  11280
acattatgcc tgttccgaga tgaagcgaaa tctttacatg attattccgt aagaaaattt  11340
cctgtgcttt ctgattttat tgtgtcattt atgttaggga ttaataaaac aaaaattcct  11400
aaagaaagta tctattctga tacggttgtt gattggtgcg caggatcatt tatgctggta  11460
cgtttttcag attttgtgcg tgtaaatggc ttcgatcaag gttactttat gtactgtgaa  11520
gatattgacc tgtgcttgag gcttagcctg gctggtgtca gacttcatta tgttcccgct  11580
tttcatgcga tacattatgc tcatcatgac aatcgaagtt ttttttcaaa agccttcaga  11640
tggcacttaa aaagtacttt tagatattta gccagaaaac gtattttatc aaatcgcaac  11700
tttgatcgaa tttcatcagt ttttcacccg taagagctcg gtacccgggc ctagggtgta  11760
ggctggagct gcttcgaagt tcctatactt tctagagaat aggaacttcg gaataggaac  11820
taaggaggat attcatatcc gtcgacggcg gccgccctgc aggcatgcaa gcttgatcca  11880
tatggatcgc tagcttaatt aaataaagcc gtaagcatat aagcatggat aagctattta  11940
tactttaata agtactttgt atacttattt gcgaacattc caggccgcga gcattcagcg  12000
cggtgatcac acctgacagg agtatgtaat gtccaagcaa cagatcggcg tagtcggtat  12060
ggcagtgatg ggacgcaacc ttgcgctcaa catcgaaagc cgtggttata ccgtctctat  12120
tttcaaccgt tcccgtgaga agacggaaga agtgattgcc gaaaatccag gcaagaaact  12180
ggttccttac tatacggtga aagagtttgt cgaatctctg gaaacgcctc gtcgcatcct  12240
gttaatggtg aaagcaggtg caggcacgga tgctgctatt gattccctca aaccatatct  12300
cgataaagga gacatcatca ttgatggtgg taacaccttc ttccaggaca ctattcgtcg  12360
taatcgtgag ctttcagcag agggctttaa cttcatcggt acgggtgttt ctggcggtga  12420
agagggggcg ctgaaaggtc cttctattat gcctggtggc cagaaagaag cctatgaatt  12480
ggtagcaccg atcctgacca aaatcgccgc cgtagctgaa gacggtgaac catgcgttac  12540
ctatattggt gccgatggcg caggtcacta tgtgaagatg gttcacaacg gtattgaata  12600
cggcgatatg cagctgattg ctgaagccta ttctctgctt aaaggtggcc tgaacctcac  12660
caacgaagaa ctggcgcaga cctttaccga gtggaataac ggtgaactga gcagttacct  12720
gatcgacatc accaaagata tcttcaccaa aaaagatgaa gacggtaact acctggttga  12780
tgtgatcctg gatgaagcgg ctaacaaagg tacgggtaaa tggaccagcc agagcgcgct  12840
```

```
ggatctcggc gaaccgctgt cgctgattac cgagtctgtg tttgcacgtt atatctcttc  12900
tctgaaagat cagcgtgttg ccgcatctaa agttctctct ggtccgcaag cacagccagc  12960
aggcgacaag gctgagttca tcgaaaaagt tcgtcgtgcg ctgtatctgg gcaaaatcgt  13020
ttcttacgcc cagggcttct ctcagctgcg tgctgcgtct gaagagtaca actgggatct  13080
gaactacggc gaaatcgcga agattttccg tgctggctgc atcatccgtg cgcagttcct  13140
gcaaaaaatc accgatgctt atgccgaaaa tccacagatc gctaacctgt tgctggctcc  13200
gtacttcaag caaattgccg atgactacca gcaggcgctg cgtgatgtcg ttgcttatgc  13260
agtacagaac ggtattccgg ttccgacctt ctccgcagcg gttgcctatt acgacagcta  13320
ccgtgctgct gttctgcctg cgaacctgat ccaggcacag cgtgactatt ttggtgcgca  13380
tacttataag cgtattgata aagaaggtgt gttccatacc gaatggctgg attaa       13435

SEQ ID NO: 17          moltype = DNA  length = 13228
FEATURE                Location/Qualifiers
source                 1..13228
                       mol_type = other DNA
                       organism = synthetic construct
SEQUENCE: 17
atgacgaatt taaaagcagt tattcctgta gcgggtctcg ggatgcatat gttgcctgcc  60
actaaggcga tacccaaaga gatgctacca atcgtcgaca agccaatgat tcagtacatt  120
gttgacgaga ttgtggctgc agggatcaaa gaaatcctcc tggtaactca cgcgtccaag  180
aacgcggtcg aaaaccactt cgacacctct tatgagttag aatcactcct tgagcagcgc  240
gtgaagcgtc aactgctggc ggaagtacag tccatctgtc cgccgggcgt gaccattatg  300
aacgtgcgtc agggcgaacc tttaggttta ggccactcca ttttgtgtgc gcgacctgcc  360
attggtgaca acccatttgt cgtggtactg ccagacgttg tgatcgacga tgccagcgcc  420
gacccgctac gttacaacct tgctgccatg attgcacgtt tcaacgaaac gggccgcagc  480
caggtgctgg caaaacgtat gccgggtgac ctctctgaat actccgtcat ccagactaaa  540
gagccgctgg accgtgaggg taaagtcagc cgcattgttg aatttatcga aaaaccggat  600
cagccgcaga cgctggactc agacatcatg gccgtaggtc gctatgtgct ttctgccgat  660
atttggccgg aactggaacg tactcagcct ggtgcatggg gacgtattca gctgactgat  720
gctattgccg agctggcgaa aaaacaatcc gttgatgcaa tgctgatgac cggcgacagt  780
tacgactgcg gcaaaaaaat gggctatatg caggcgtttg tgaagtatgg cctacgcaac  840
ctgaaagaag ggcgaagtt  ccgtaaaggt attgagaagc tgttaagcga ataatgaaaa  900
tctgaccgga tgtaacggtt gataagaaaa ttataacggc agtgaaaatt cgcagcaaaa  960
gtaatttgtt gcgaatcttc ctgccgttgt tttatataaa ccatcagaat aacaacgagt  1020
tagcagtagg gttttattca aagttttcca ggattttcct tgtttccaga gcggattggt  1080
aagacaatta gcgtttgaat ttttcgggtt tagcgcgagt gggtaacgct cgtcacatca  1140
taggcatgca tgcagtgctc tggtagctgt aaagccaggg gcggtagcgt gcattaatac  1200
ctctattaat caaactgaga gccgcttatt tcacagcatg ctctgaagta atatggaata  1260
aattaagtga aaatacttgt tactggtggc gcaggattta ttggttcagc tgtagttcgt  1320
cacattataa ataatacgca ggatagtgtt gttaatgtcg ataaattaac gtacgccgga  1380
aaccgggaat cacttgctga tgtttctgat tctgaacgct atgtttttga acatgcggat  1440
atttgcgatg cacctgcaat ggcacggatt tttgctcagc atcagccgga tgcagtgatg  1500
cacctggctg ctgaaagcca tgttgaccgt tcaattacag gccctgcggc atttattgaa  1560
accaatattg ttggtactta tgtccttttg gaagccgctc gcaattactg gtctgctctt  1620
gatagcgaca agaaaaatag cttccgtttt catcatattt ctactgacga agtctatggt  1680
gatttgcctc atccagatga agtaaataat acagaagaat tacccttatt tactgagacg  1740
acagcttacg cgccaagcag cccttattcc gcatccaaag catccagcga tcatttagtc  1800
cgcgcgtgga aacgtacata tggtttaccg acaattgtga ctaattgctc gaacaactat  1860
ggtccttatc atttcccgga aaagcttatt ccactggtta ttcttaatgc actggaaggt  1920
aaggcattac ctatttatgg caaaggagat cagatccgcg actggttgta tgttgaagat  1980
catgcgcgtg cgttatatac cgtcgtaacc gaaggtaaag cgggtgaaac ttataacatt  2040
ggtgggcaca acgaaaagaa aaacatcgat gtagtgctca ctatttgtga tttgctggat  2100
gagattgtac cgaaagagaa atcttatcgt gagcaaatca cttatgttgc tgatcgtccg  2160
ggacacgatc gccgctatgc tattgatgct gagaagattg gtcgcgcatt gggatggaaa  2220
ccacaggaaa cgtttgagag cgggattcgt aaaacggtgg aatggtacct gtccaataca  2280
aaatgggttg ataatgtgaa aagtggtgcc tatcaatcgt ggattgaaca gaactatgag  2340
ggccgccagt aatgaatatc ctcctttttg gcaaaacagg gcaggtaggt tgggaactac  2400
agcgtgctct ggcacctttg ggtaatttga ttgcttttga tgttcactct actgattatt  2460
gcggtgattt tagtaatcct gaaggtgtag ctgaaaccgt aagaagcatt cggccggata  2520
ttattgtcaa tgcagccgct cacaccgcag tagacaaagc agaatcagaa ccggagtttg  2580
cacaattaat taacgcaaca agtgtcgaag cgattgcgaa agcagcaaat gaagttggag  2640
cctgggttat ccattactcg actgattacg tcttccctgg aaatggcgat atgccatggc  2700
tggagacgga tgcaaccgca ccactaaatg tttacggtga aaccaagtta gccggagaaa  2760
aagcgttaca ggaatattgc gcgaagcatc ttattttccg gaccagctgg gtctatgcag  2820
gaaaaggaaa taacttcgcc aaaacgatgt tacgtctggc aaaagagcgt gaagaattag  2880
cggttattaa cgatcagttt ggtgcgccaa caggtgctga actgctggct gattgtacag  2940
cacatgccat tcgtgtcgca ctgaataaac cggatgtcgc aggcttgtac catttggtag  3000
ccagtggtac cacaacctgg tacgattatg ctgcgctggt ttttgaagag gcgcgcaaag  3060
caggcattcc ccttgcactc aacaagctca acgcagtacc aacaacagcc tatcctacac  3120
cagctcgtcg tccacataac tctcgcctta atacagaaaa atttcagcag aactttgcgc  3180
ttgtcttgcc tgactggcag gttggcgtga aacgaatgct caatgaatta tttacgacta  3240
cagcaattta atagttttg  catcttgttc gtgatggtgg agcaagatga attaaaagga  3300
atgatgaaat gaaaatgcgt aaaggtatta ttttagcggg tggttctggt acacgtcttt  3360
atcctgtgac tatggctgtc agtaaacagc tattacctat ttatgataaa ccgatgatct  3420
attacccgct ctctacactg atgttggcgg gtattcgcga tattttgatt atcagtacac  3480
ctcaggatac tcctcgtttt caacaattgc tgggtgacgg tagccagtgg ggcctgaatc  3540
ttcagtacaa agtgcaacct agcccagatg gcctcgcgca ggcatttatc atcggtgaag  3600
agtttattgg tggtgatgat tgtgctttgg ttcttggtga taatatcttt tacggtcacg  3660
atctgccgaa gctaatggag gccgctgtta acaaagaaag tggtgcaacg gtatttgcct  3720
```

-continued

```
atcacgttaa tgatccagaa cgctatggtg tcgttgagtt tgataaaaac ggtacggcaa  3780
tcagtctgga agaaaaaccg ttagaaccaa agagtaatta cgccgttaca ggtctgtact  3840
tttatgataa cgacgtggtt cagatggcga aaaacttgaa gccgtctgca cgtggtgagt  3900
tagaaattac agatattaac cgtatttatc ttgagcaggg acgtctgtct gtcgcgatga  3960
tggggcgtgg ctacgcgtgg ctggacacgg ggactcatca gagtctgata gaagcaagta  4020
attttattgc gacaattgaa gagcgccagg gattgaaggt ttcctgtcct gaagagattg  4080
catttcgtaa aggttttatt gatgttgagc aagtaagaaa attagctgta ccactaataa  4140
agaataatta tgggcagtat ctttataaaa tgacgaagga ttcaaattaa tgaatgtgat  4200
tagaactgaa attgaagatg tgctaattct ggagccaaga gtatttggtg atgatagagg  4260
tttcttttat gagagcttta atcaatcagc atttgaacat attctaggct atccggtcag  4320
ctttgttcaa gacaatcact cacgttcatc aaaaaatgta ctcagaggcc ttcactttca  4380
acgcggcgag tacgcacaag ataaacttgt acgctgcact catggagcag tttttgatgt  4440
tgctgttgat attcgaccca attcggtatc ctttggtaaa tgggttggtg ttctgctttc  4500
agctgataat aagcagcagt tgtggatacc aaaagggttt gctcatggct tttggttct  4560
gtctgatatc gctgaatttc aatataaaac tacaaactat tatcatcctg aaagcgattg  4620
tggaatatgt tggaatgatg aacgcattgc aattgattgg ccccaaacat cagggttaat  4680
cctttcgcca aaagatgaaa ggctctttac gttagatgag cttatcagat taaaattaat  4740
tgcatgaggc cggccttaag gaggactagt cccggcgcgc catgagttta atcaaaaaca  4800
gtttttggaa cctttgcggg tatgtacttc cagctattgt gacactacca gctttgggta  4860
ttatggggcg aaaattaggc ccagaattat ttggtgtatt cactttggca ttagctgttg  4920
tgggttatgc aagcattttt gatgcaggcc ttactcgcgc agtgatacga gaagtcgcaa  4980
ttgaaaaaga taatgaagaa aataagttga aaattatttc ttcagcgaca gttgtaatta  5040
tttatttgag tttggccgcc tcactcttat tattttttt tagtggtcat atcgcattgc  5100
tactgaacat tagtgagact ttttttcata atgtaagtgt ctcgcttaaa attctcgcag  5160
catccatacc attattttg attactcaaa tatggttgtc aattttagaa ggtgaagaaa  5220
gatttggttt acttaatatc tacaaatcaa ttacgggagt gatattagca atctcaccgg  5280
cattatttat acttattaaa ccctctttga tgtatgcgat aataggctta gttctagcaa  5340
ggtttttatg ttttattttg gcttttataa tttgtcacga taaagtgctt aaagctaaac  5400
taacaatcga tataccaaca attaaaagat tgtttatgtt cggtggttgg attacagtaa  5460
gtaatatcat cagccctgtg ctatcatatt ttgataggtt tattgtttca aatcaacttg  5520
gggctgctaa tgttgctttt tatactgcac catcagaaat tatttctcgg cttagtataa  5580
ttccaggtgc gttttcaaga gccttatttc caagattagc taatgcaaat aattccgctg  5640
aaagatataa aacgaaaaga ttaattacaa tttcactttt aataatcatc accctattt  5700
tttgtattgg cgtgttattt tcagagaaga taatggtttt atggatgggg gcatcatttt  5760
ttggtgagcc tggtttggta ttatcaatat tactgattgg ctttattttt aatggattgg  5820
cacaagtacc atttgccagt attcaatccc gaggtcatgc taagataact gcatttgttc  5880
atctcttaga gttgtttcct tatttattac ttttatttta cctcataaaa gcacatgggg  5940
ttgttggcgc gggtattgcg tggtcagtga ggatgatagt agattatata gcattaagtc  6000
ttttggacgg taagtatatt aataaataaa attcaaaatg caagttaata actcatggct  6060
ttatttgggt aggtgacaat ttataatgat atatatatta actttaactc ttcttctagt  6120
tatagccata atgttttctc ttctcggcac aaaaaagtagg atcacatctc cattaccttt  6180
gcattttta ccatggttac taactttaat tgtcgggata agtaattacg atcaatttta  6240
cgagtttaat gaaagaagct tttactcttt gttgatttgg tttacagtta tttttatatt  6300
ttatttcata ggggaactgg ttaattataa acgtgaaaat ataaatgttt attatggtct  6360
ttcacatatt aaatatgaat gtaaaaaata ttggatcatt gtcatcccaa tttcattata  6420
taccatttc gaaatatata tggttggtat ggggggagca gatggattct ttctcaattt  6480
acgtcttgca aatacattgg agggctatac gggtaaaaaa tttatcttaa tgcctgctgt  6540
atatcctcta atgatggcta tgttcgcaat tgtttgtcta acaaaaactt ccaaattaaa  6600
taaatactcc atttatttct ggatgttttt gtattgtatt ggcacaatgg gaaaattttc  6660
aatattaacg ccaatattga catatttaat tatttatgac ttcaaacata gattaaaagt  6720
aaaaaaaaca ataaagttta cattgttgat aattatatta gctttaactt tgcattttac  6780
acgtatggct gagaatgacc actcaacatt tttatctatt ttagggctct atatttattc  6840
accaataatt gctttaggcc agttgaatga agtaaatagt agtcattttg gtgagtatac  6900
gtttagattc atatatgcta taactaataa aattggcctt attaaagaat tgccagtaaa  6960
tactattctt gactattcat acgttcctgt accaacaaat gtatatactg cacttcaacc  7020
attttaccag gattttggtt atactggcat catatttgga gcagtattat acggactaat  7080
atatgtgagt ttatacacgg ccggtgttcg tggaaataat acacaggcat tactgattta  7140
cgcattgttt tcagttagca gtgcaacggc tttcttcgct gaaacgctag taacgaattt  7200
agctggaaat gtgatgttag tattatgtac catcttacta tggcgattta cagtaatatg  7260
caaaccagta cagtaaccat tctaatggcc acctacaatg gcgaggcctt catcaaaaat  7320
cagattttgt cactacaaca acaaacattt tctaactggc ggttatttat tcaggatgat  7380
gggtctacag acaatactat atctataata aaaaacttcc aaaaatctga ctccagaatt  7440
cggctagttg atgataattt gaaaggtcaa ggtgcaggaa aaaattttt atcgctgata  7500
aagtacagcg agacagatta tacaatttat tgtgaccaag atgatatttg gttagaaaac  7560
aaaatatttg aattagtaaa gtatgcaaat gaaattaaat tgaatgtatc agatgcgcct  7620
tcgctagttt atgctgatgg ctatgcttat atggatggtg agggtacaat cgatttttct  7680
gggatatcta acaatcatgc tgatcaatta aaggatttc ttttttaa tggtggatac  7740
caaggatgtt ctattatgtt caatcgtgca atgaccaaat ttcttctgaa ttatcgagga  7800
tttgtatatc tacatgacga tatcacaaca ttagctgcat acgctcttgg taaagtttat  7860
tttctcccga aataccttat gttatataga cagcacacga atgcggtaac tggtatcaaa  7920
acattccgca atggattgac ttctaaattt aaatcaccag taaactatct tttatcacga  7980
aaacattatc aggtaaaaaa atcttttttt gaatgtaaca gctctatctt atcagagacg  8040
aataaaaaag tttttttgga ttttatttca ttttgtgaat caaataataa atttacagat  8100
ttttttaagt tatggcgagg tgggtttaga ttaaataaca gtagaactaa attattatta  8160
aaattcttaa tacggagaaa atttagcgaa tgatttcaat acttacacct actttaatc  8220
ggcaacatac tttatcaagg ctattcaatt ctcttatatt acaaactgat aaagattttg  8280
agtggataat aattgatgat ggtagtatag atgcaacagc ggtacttgta gaagatttta  8340
gaaaaaaatg tgattttgac ttgatttatt gctatcagga aaataatggt aagcccatgg  8400
ctttaaacgc tggtgttaaa gcttgtagag gcgattatat ctttattgtt gacagtgatg  8460
```

-continued

```
atgcactaac tcccgatgcc ataaaattaa ttaaagaatc aatacatgat tgcttatctg  8520
agaaggaaag tttcagcgga gtcggtttta gaaaagcata tataaaaggg gggattattg  8580
gtaatgattt aaataattct tcagaacata tatactattt aaatgcgact gagattagca  8640
atttaataaa tggtgatgtt gcatattgtt ttaaaaaaga aagtttggta aaaaatccat  8700
tcccccgtat agaagatgaa aaatttgttc cagaattata tatttggaat aaaataactg  8760
acaaggcgaa gattcgattt aacataagca aagttatata tctttgtgag tatcttgatg  8820
atggtctttc taaaaatttc cataaccagc ttaaaaaata cccaaagggg tttaagattt  8880
attacaaaga tcaaagaaaa cgagagaaaa cttatataaa aaaaacaaag atgctaatta  8940
gatatttgca atgttgttat tatgagaaaa taaaatgaaa atactatttg tcattacagg  9000
tttaggcctt ggaggtgctg agaagcaggt ttgtctttta gctgataaat taagtttaag  9060
cgggcaccat gtaaagatta tttcacttgg acatatgtct aataataaag tctttcctag  9120
cgaaaaataat gttaatgtca ttaatgtaaa tatgtcaaaa aacatttctg gagttataaa  9180
aggttgtgtc agaattagag atgttatagc taatttcaaa ccagacattg tacacagtca  9240
tatgtttcat gcaaacatta tcactagatt gtctgtaatt ggaatcaaaa acagacctgg  9300
tattatatca actgcacata ataaaaatga aggtgggtat ttcagaatgc tcacatatag  9360
aataaccgat tgtttaagtg attgttgtac aaatgttagc aaagaagcag tggatgagtt  9420
tttacggata aaagccttta atcccgctaa agcaattact atgtataatg ggatagatac  9480
caataaattt aaatttgatt tattggcaag gagggaaatt cgagacggta ttaatataaa  9540
aaatgatgat atattattac ttgctgcagg tcgtttaacg ttagctaaag attatcctaa  9600
tttattgaat gcaatgactc tgcttcctga acactttaaa cttattatta ttggtgatgg  9660
tgaattgcgt gacgaaatta atatgcttat aaaaaaattg caattatcta atagggtgtc  9720
cttgttggga gttaaaaaaa atattgctcc ctatttttct gcatgtgata tttttgttct  9780
ctcttctcgt tgggaaggat ttggattagt cgtggcagaa gctatgtcat gtgagcgaat  9840
tgttgttggc acggattcag ggggagtaag agaagttatt ggtgacgatg attttcttgt  9900
acccatatct gattcaacac aacttgcaag caaaattgaa aaattgtctt tgagccagat  9960
acgtgatcac attggtttc ggaatcgtga gcgtatttta aaaaatttct caatagatac  10020
tattattatg cagtggcaag aactctatgg aactataatt tgctcaaaac atgaaaggta  10080
gatttatatt tggaacgtgt cttttgtttg aatttaattc aatctcaatt gagatttttg  10140
tatttcaaaa ataccatcat agctaacgat gattggtatt tattttaaga tgctttctat  10200
aaatatattg acgtttttaa tgcgccgaaa cgattgggct gggaacagag aagtaaaact  10260
gttttgagaa tgaagagttt ttgagatgtt tatggatatt aaaaattgat ccagtgaatt  10320
aattatttat aataaatcaa gatttaatgt taataaatga taatcttttc tgacactcat  10380
attaattatg agtggtacgt ttggtaaacg gtaaactatt atatgacagc tagaacaact  10440
aaagttttgc acttacaatt actcccactc ttaagtggcg ttcaaagggt aacattaaac  10500
gaaattagtg cgttatatac tgattatgat tatacactag tttgctcaaa aaaaggtcca  10560
ctaacaaaag cattgctgga atatgatgtc gattgtcatt gtatccccga acttacgaga  10620
gaaattaccg taaagaatga ttttaaagca ttgttcaagc tttataagtt cataaaaaaa  10680
gaaaaatttg acattgtgca tacacattct tcaaaaacag gtattttggg gcgagttgct  10740
gccaaattag cacgtgttgg aaaggtgatc cacactgtac atggtttttc ttttccagcc  10800
gcatctagta aaaaaagtta ttacctttat tttttcatgg aatggatagc aaagttcttt  10860
acggataagt taatcgtctt gaatgtagat gatgaatata tagcaataaa caaattaaaa  10920
ttcaagcggg ataaagtttt tttaattcct aatggagtag acactgataa gttttctcct  10980
ttagaaaata aaatttatag tagcaccttg aatctagtaa tggttggtag attatccaag  11040
caaaaagatc ctgagacatt attgcttgct gttgaaaaac tgctgaatga aaatgttaat  11100
gttaagctga cacttgtagg agatggtgaa ctaaaagaac agttagaaag caggttcaaa  11160
cggcaagatg gacgtataat ttttcatgga tggtcagata acattgttaa tattttaaaa  11220
gttaatgatc tttttatatt accttctctt tgggagggta tgccattagc aatttttagaa  11280
gcattgagct gtggacttcc atgtatagtc actaatattc caggtaataa tagcttaata  11340
gaagatggct ataatggttg tttgtttgaa attagagatt gtcagttatt atctcaaaaa  11400
atcatgtcat atgttggtaa gccagaactg attgcacagc aatctaccaa tgcacgatca  11460
tttattctga aaaattatgg attagttaaa agaaataata aggtcagaca gctatatgat  11520
aattaagagc tcggtacccg ggcctagggt gtaggctgga gctgcttcga agttcctata  11580
ctttctagag aataggaact tcggaatagg aactaaggag gatattcata tccgtcgacg  11640
gcggccgccc tgcaggcatg caagcttggt ccatatggat cgctagctta attaaataaa  11700
gccgtaagca tataagcatg gataagctat ttatacttta ataagtactt tgtatactta  11760
tttgcgaaca ttccaggccg cgagcattca gcgcggtgat cacacctgac aggagtatgt  11820
aatgtccaag caacagatcg gcgtagtcgg tatggcagtg atgggacgca accttgcgct  11880
caacatcgaa agccgtggtt ataccgtctc tattttcaac cgttcccgtg agaagacgga  11940
agaagtgatt gccgaaaatc caggcaagaa actggttcct tactatacgg tgaaagagtt  12000
tgtcgaatct ctggaaacgc ctcgtcgcat cctgttaatg gtgaaagcag gtgcaggcac  12060
ggatgctgct attgattccc tcaaaccata tctcgataaa ggagacatca tcattgatgg  12120
tggtaacacc ttcttccagg acactattcg tcgtaatcgt gagctttcag cagagggctt  12180
taacttcatc ggtaccggtg tttctggcgg tgaagagggg gcgctgaaag gtccttctat  12240
tatgcctggt ggccagaaag aagcctatga attggtagca ccgatcctga ccaaaatcgc  12300
cgccgtagct gaagacggtg aaccatgcgt tacctatatt ggtgccgatg gcgcaggtca  12360
ctatgtgaag atggttcaca acggtattga atacggcgat atgcagctga ttgctgaagc  12420
ctattctctg cttaaaggtg gcctgaacct caccaacgaa gaactggcgc agacctttac  12480
cgagtggaat aacggtgaac tgagcagtta cctgatcgac atcaccaaag atatcttcac  12540
caaaaaagat gaagacggta actacctggt tgatgtgatc ctggatgaag cggctaacaa  12600
aggtacgggt aaatggacca gccagagcgc gctggatctc ggcgaaccgc tgtcgctgat  12660
taccgagtct gtgtttgcac gttatatctc ttctctgaaa gatcagcgtg ttgccgcatc  12720
taaagttctc tctggtccgc aagcacagcc agcaggcgac aaggctgagt tcatcgaaaa  12780
agttcgtcgt gcgctgtatc tgggcaaaat cgtttcttac gcccagggct tctctcagct  12840
gcgtgctgcg tctgaagagt acaactggga tctgaactac ggcgaaatcg cgaagatttt  12900
ccgtgctggc tgcatcatcc gtgcgcagtt cctgcaaaaa atcaccgatg cttatgccga  12960
aaatccacag atcgctaacc tgttgctggc tccgtacttc aagcaaattg ccgatgacta  13020
ccagcaggcg ctgcgtgatg tcgttgctta tgcagtacag aacggtattc cggttccgac  13080
cttctccgca gcggttgcct attacgacag ctaccgtgct gctgttctgc ctgcgaacct  13140
gatccaggca cagcgtgact attttggtgc gcatacttat aagcgtattg ataaagaagg  13200
```

```
tgtgttccat accgaatggc tggattaa                                  13228

SEQ ID NO: 18          moltype = DNA  length = 13554
FEATURE                Location/Qualifiers
source                 1..13554
                       mol_type = other DNA
                       organism = synthetic construct
SEQUENCE: 18
atgacgaatt taaaagcagt tattcctgta gcgggtctcg ggatgcatat gttgcctgcc  60
actaaggcga tacccaaaga gatgctacca atcgtcgaca agccaatgat tcagtacatt  120
gttgacgaga ttgtggctgc agggatcaaa gaaatcctcc tggtaactca cgcgtccaag  180
aacgcggtcg aaaaccactt cgacacctct tatgagttag aatcactcct tgagcagcgc  240
gtgaagcgtc aactgctggc ggaagtacag tccatctgtc cgccgggcgt gaccattatg  300
aacgtgcgtc agggcgaacc tttaggttta ggccactcca ttttgtgtgc gcgacctgcc  360
attggtgaca acccatttgt cgtggtactg ccagacgttg tgatcgacga tgccagcgcc  420
gacccgctac gttacaacct tgctgccatg attgcacgtt tcaacgaaac gggccgcagc  480
caggtgctgg caaaacgtat gccgggtgac ctctctgaat actccgtcat ccagactaaa  540
gagccgctgg accgtgaggg taaagtcagc cgcattgttg aatttatcga aaaaccggat  600
cagccgcaga cgctggactc agacatcatg gccgtaggtc gctatgtgct ttctgccgat  660
atttggccgg aactggaacg tactcagcct ggtgcatggg gacgtattca gctgactgat  720
gctattgccg agctggcgaa aaaacaatcc gttgatgcaa tgctgatgac cggcgacagt  780
tacgactgcg gcaaaaaaat gggctatatg caggcgtttg tgaagtatgg cctacgcaac  840
ctgaaagaag ggcgaagtt ccgtaaaggt attgagaagc tgttaagcga ataatgaaaa  900
tctgaccgga tgtaacggtt gataagaaaa ttataacggc agtgaaaatt cgcagcaaaa  960
gtaatttgtt gcgaatcttc ctgccgttgt tttatataaa ccatcagaat aacaacgagt  1020
tagcagtagg gttttattca aagttttcca ggattttcct tgtttccaga gcggattggt  1080
aagacaatta gcgtttgaat ttttcgggtt tagcgcgagt gggtaacgct cgtcacatca  1140
taggcatgca tgcagtgctc tggtagctgt aaagccaggg gcggtagcgt gcattaatac  1200
ctctattaat caaactgaga gccgcttatt tcacagcatg ctctgaagta atatggaata  1260
aattaagcta gcagtgaaga tacttgttac tggtggcgca ggatttattg gttctgctgt  1320
tgttcgtcac ataataaata atacgcaaga tagtgttgtt aatgtcgata aattaacata  1380
cgccggaaac ctggaatcac ttgcagatgt ttctgattct gaacgctatt tctttgaaca  1440
tgcggatatt tgtgatgcag ctgcaatggc acggattttt gctcagcatc agccggatgc  1500
agtgatgcac ctggcagctg aaagccatgt tgaccgttca attacaggcc ctgcggcatt  1560
tattgaaacc aatattgtgg gtacttatgt ccttttagaa gcggctcgga attattggtc  1620
tggtctggat gatgaaaaga aaaaaaactt ccgttttcat catatttcta ctgatgaggt  1680
gtatggtgac ttaccccatc cggatgaagt aaatagcaat gaaacgttgc cgctatttac  1740
ggaaacgaca gcatacgcgc caagtagtcc atattctgct tctaaagctt ccagcgatca  1800
tttggttcgc gcatggaaac gtacttatgg tttaccgacc attgtgacta attgctcgaa  1860
caactatggt ccttatcatt tcccggaaaa gcttattcca ctggttattc ttaattcact  1920
ggaaggtaag gcattaccta tttatggcaa aggagatcag atccgcgact ggttgtatgt  1980
agaggatcat gctcgagcgt tatataccgt cgtaaccgaa ggtaaagcgg gcgaaactta  2040
taacattggt ggacacaacg aaaagaaaaa catcgacgta gtgttcacta tttgtgattt  2100
gttggatgag atagtcccga aagagaaatc ttaccgcgag caaattactt atgttaccga  2160
tcgtccggga cacgatcgcc gttatgcgat tgatgctgag aagattggtc gcgaattggg  2220
atggaaacca caggaaacgt ttgagagtgg gattcgtaaa acggtggaat ggtacctgtc  2280
caatacaaaa tgggttgata atgtgaaaag tggtgcctat caatcgtgga ttgaacagaa  2340
ctatgagggc cgccagtaat gaatatcctc ctttttggca aaacagggca ggtaggttgg  2400
gaactacagc gtgctctggc acctctgggt aatttgattg ctcttgatgt tcactccact  2460
gattactgtg gtgattttag taatcctgaa ggtgtagctg aaaccgtaag aagcattcgg  2520
cctgatatta ttgtcaacgc agccgctcac accgcagtag acaaagcaga atcagaaccg  2580
aagtttgcac aattactgaa cgcgacgagt gtcgaagcga tcgcgaaagc agccaatgaa  2640
gtcggcgcct gggttattca ctactctact gactacgtat ttccggggac cggtgaaata  2700
ccatggcagg aggaggatgc aaccgcaccg ctaaatgttt acggtgaaac caagttagcg  2760
ggagaaaaag cattacaaga gcattgtgcg aagcacctta ttttccggac cagctgggtc  2820
tatgcaggta aaggaaataa cttcgccaaa acaatgttgc gtctggcaaa agagcgtgaa  2880
gaattagccg ttattaatga tcagtttggt gcgccaactg gcgcagagtt actggctgat  2940
tgtacggcac atgctattcg tgtggcactg aataaaccgg aagtcgcagg cttgtaccat  3000
ctggtagcta gtggtaccac aacgtggcac gattatgctg cgctggtttt tgaagaggcg  3060
cgcaaagcag gcattcccct tgcactcaac aagctcaacg cagtaccaac aacagcctat  3120
cctacaccag ctcgtcgtcc acataactct cgccttaata cagaaaaatt tcagcagaac  3180
tttgcgcttg tcttgcctga ctggcaggtt ggcgtgaaac gaatgcttaa cgaattattt  3240
acgactacag caatttaata gtttttgcat cttgttcgta atggtggagc aagatgtatt  3300
aaaaggaatg atgaaatgaa aacgcgtaaa ggtattattt tggcgggtgg ttctggtact  3360
cgtctttatc ctgtgacgat ggccgtcagt aaacagctgt taccgattta tgataaaccg  3420
atgatctatt acccgctctc tacactgatg ttagcgggta ttcgcgatat tctgattatc  3480
agtacaccac aggatactcc tcgttttcaa caactgctgg gtgacgggag ccagtggggc  3540
ctgaatcttc agtacaaagt gcaaccgagt ccggatggtc ttgcgcaggc gtttattatc  3600
ggtgaagagt ttattggtgg tgatgattgt gctttggtac ttggtgataa tatcttctac  3660
ggccacgacc tgccgaagtt aatggacgta gctgttaaca aagaaagtgg tgcaacggta  3720
tttgcctatc acgttaatga tcctgaacgt tatggtgtcg tggagtttga taataacggt  3780
actgcaatta gcctggaaga aaaaccgctg gaaccaaaaa gtaactatgc ggttactggg  3840
ctttatttct atgacaatga cgttgtggaa atggcgaaaa accttaagcc ttctgcccga  3900
ggtgaactgg aaattaccga tattaaccgt atttatatgg aacaaggacg tttgtctgtc  3960
gctatgatgg ggcgtggcta tgcatggctg gatacaggga cgcatcaaag tcttattgaa  4020
gcaagcaact tcattgccac cattgaagag cgccagggac taaaggtttc ctgtccggaa  4080
gaaattgctt atcgtaaagg gtttattgat gctgagcagg taaaagtatt agccgaaccg  4140
ttgaagaaaa atgcttatgg tcagtatctg ctcaaaatga ttaaaggtta ttaataagat  4200
gaacgtaatt aaaactgaaa ttcctgatgt gctgattttt gaaccaaaag tttttgggga  4260
```

-continued

```
tgaacgtggc ttctttttttg agagttttaa tcagaggatt tttgaagaag cagtaggtcg  4320
taaggttgag tttgttcagg ataaccattc taagtccagt aaaggtgttt tacgtggtct  4380
tcattatcag ttagaacctt atgctcaagg aaaactggtg cgctgtgttg ttggcgaggt  4440
ttttgatgtt gcggttgata ttcgtaaatc gtcacctaca tttgggaaat gggttggggt  4500
gaatttgtct gctgagaata agcgtcagtt gtggattcct gagggatttg cacatggttt  4560
tttggtgctg agtgatttag cagaagtttt atataaaacg aatcaatatt atgctccatc  4620
acatgaaaaa aatattatat ggaatgacct cttgcttaat attaaatggc cgagcacagc  4680
actgatcact ctgtctgata aggatgcaaa tggggaaaga tttgaactaa gtgagttttg  4740
aaatgtctct cttaaaacat agtatatgga atgttgcggg ctactttata ccaacattaa  4800
ttgcaattcc cgcctttgga ttaattgcga ggaaaattgg tgtagaacta tttggtttgt  4860
atacgttagc aatgattttt atagggtatg caagtatatt tgatgctggg ttaacaagag  4920
ctgttgtgcg tgaaatagca ttactaaaaa acagagtgga cgattgtaat acgataatag  4980
taacttctat tatcgctgtg atatttttag ggtttatcgg aggcggggga gtgtttctgc  5040
ttaaaggcga tattattgaa ctgttaaata tctcaccaat atattacgcc gattcgataa  5100
agtctctagt attattatca tctctgatac ctgtattctt agtcacgcaa atactattag  5160
cagagcttga gggtcgggaa tattttggga ttctaaatat acaaaaaagt gtagggaatt  5220
ctttaattgc agggttacct gcattatttg ttttaattaa tcaaacgctt ttttctgcaa  5280
ttattggtgt agcgattgca agagttatat gcttgtggtt aagctacatt atgagcaggg  5340
aaagaataac tatcgatatc tcattttttt caataactgt tttaaagcgg ttatttagat  5400
atggcgggtg ggtaactata agtaacataa tatctcctat attagcgagt atggatagat  5460
ttattctatc ccatatccag ggagcatcaa aaatatcatt ctatacagtc cctaatgagc  5520
tggtaactag gcttggaata gttccaggct ctcttgggaa agctgttttt ccaaaattaa  5580
gtcatgcaag gaattttaca gcgtcatatg cagagcaaaa aaaagcttat atattaatga  5640
ctgtcattgt aatgcctttg gttttatttg tatattatta cgcaaagttt attttaacat  5700
tgtggatggg ggctgagtat gcagggattt cggtcgaaat attacggatt atgcttatag  5760
ggtatatttt taactgttat tcacaaatct cttttgccaa catacaggcc tttggaaaag  5820
caaaatacac tgcatacatc catatgatgg aatttattcc ttatttgata atgttatata  5880
taatttcaaa ggaatatggg gttattggtg ttgcgtggtt atggacaatt cgagtaataa  5940
ttgatttttt gatgctttta tatatgagtt atcgttgtaa taatcttatg aaaaaagggt  6000
agcctgatga tatatattgt ggtattaaat tggaatgggg ctatagatac cattaattgt  6060
gttaaaagtt taatggattt aaatgttagc gattataaaa ttatcattgt tgataactgt  6120
tctatggata actcatatga tactataaaa gaaaatctta attcattata tattgctgat  6180
aaaagtatca ttgaggtgaa gtatgaggat agaaataaat ataaaacctt agaaaacgat  6240
aaaatcatat taatacaatc tccgcaaaat aatgggtacg caagtggtaa taatattggc  6300
atagagttcg ctcttaatca ggagaatatg aaatacgtct gggttctgaa taatgatact  6360
gaagtggata aagaggcttt aactcattta attagtaaat gtgattcaga taaaagtata  6420
gggatttgcg gttctcgttt agtctatttt gccgacagag agatgcagca aggactaggt  6480
ggggtgcata acaaatggtt atgcactaca aaaaattatg aaatgggaag attagtttcc  6540
aaaaaatatg atgatgaagt cattagtaat gatatagatt atataattgg cgcatcgatg  6600
tttttctcta gagaatgttt ggaaacagtt ggattgatga atgaagaata ttttttatac  6660
tatgaagagt tagatatttg cctcagagca aaagcaaaga actttaaatt aggtatttgc  6720
tcagaaagtt tggtttatca taaaataggt gcaagtactg atgggggaaa gagcatgatg  6780
gctgatcttt gctcaataaa aaataggctg gtcattacag aaaggtttta tccccaatat  6840
tattggacgg tatggttgtc actttttgtt gtagcattta accgtgctag aagaggtgag  6900
tttaataaga tgaaaagatg tttgaatgtt atgtttaact tcaaacgaaa caaaggtagc  6960
aaatgccatt agaatatgca cttaatcatg gtgttaataa atctatagtt tgatatgtta  7020
ttaaagggta tttaatgaaa gtggcttttt tatctgctta tgatccacta tctacatcca  7080
gttggtctgg cacaccttat tatatgctaa aggcattatc gaagagaaat atttccattg  7140
aaatattagg accggtaaat agctatatga tatacatgtt aaaagtatat aaattaatat  7200
taaggtgttt cggaaaagaa tatgattata gtcattcgaa gttgctttcc aggtattacg  7260
gtagaatatt cggtaggaaa ttaaaaaaaa ttgatggttt ggattttatt atcgcacctg  7320
caggttcctc acaaattgct tttttaaaaa caaccatacc aataatatat ctatcggata  7380
caacatatga tcaattaaaa agctattatc cgaatttaaa taaaaaaaca attataaatg  7440
atgaggatgc aagtttaatc gaacgcaagg ctattgaaaa agcaacagta gtatctttcc  7500
catctaaatg ggcaatggat ttttgcagga attattacag attagatttt gataaattag  7560
ttgaaatacc atggggggct aatttatttg atgatattca ctttgctaat aaaaatataa  7620
ttcaaaagaa tagttatact tgtcttttct tgggagttga ttgggaaaga aaaggtggga  7680
aaacagcctt gaaagcaatt gaatatgtaa ggcagttata tgggatcgat gttagactaa  7740
aaatttgtgg atgtactccg aatcaaaaga ttttacctac ttgggttgaa ttaattgata  7800
aagtagataa aaataacgtt gacgaatatc agaaattcat cgatgtgtta tctaacgctg  7860
atatacttct tttaccaacc attgctgaat gttatggaat ggtattttgt gaagctgctg  7920
cttttggatt gcctgttgtc gctacagata caggtggagt cagttctata gttatcaacg  7980
aaaggacggg gatattaatt aaagacccgt tagactataa gcactttgga aatgcaattc  8040
ataaaataat tagttccgta gagacttatc aaaactactc ccaaaacgca agaattagat  8100
ataataatat attgcattgg gacaattggg ctaaaaagat aattgagatt atgtatgagc  8160
ataagaatag aagaatcaaa tagcacaaaa agaattatat gtttatttat actttttctt  8220
gttttccctg atttttttgtt ttatacatta ggggttgata attttagcat ttcaacgata  8280
atctcaatta cattgctttt tgttttttta agagctaaaa atatttgcaa agataatttt  8340
ctaataatag tagcgttatt catattgttg tgttttaact gtttgttaag tatgctattt  8400
aatattgaac aggctttaac atttaaagtt gtactttcaa tatatagcat cttaataatg  8460
gcatacgtct cctcttgtta tgcacagacg ttgtggttat gttctgaaga aatacttaag  8520
agatccgtct tttatttgtt cgcatttctt tgccttattg gcattataag tattctttta  8580
cagaagactg agattataca tgataaaagt atgattcttt ttcctgaacc atcagcattt  8640
gcattggttt ttatacctat cttttcattt tgtttatact atacaagagg ggggggggcta  8700
ctattgctct atatattatc tttgggtatt gcgttaggta tccagaattt aacaatgttg  8760
gtaggcattg tgattagtgt ttttgtgatg aaaaaaataa ctataaggca aactattgtt  8820
atacttttgg gggcatggat tttttccatg atattaagtg atttagacat ttcttactat  8880
acatcgcggc ttgattttaa aaatactacg aacctatcag tgcttgtata tctttcagga  8940
attgaaagag ctttcttgaa ttttattaca agttatggtc ttggtattgg ttttcaacaa  9000
```

```
atgggagtga atggggagat aggaatatat caacaaattt tagctgaact tgatgcccct  9060
atgttaaata tatacgatgg ctcatttatt tcttctaagt taatatctga gtttggggtt  9120
attggtgcat taatgtgtat tttctatttt ttttattttt cccgatttta tctgcgtttc  9180
aaaaaaagta agagatattc accgcagtat attttagcat atagcttcta catgtgtttc  9240
ttcatccctc tttttatacg tggtgctggt tatataaacc cctatgtgtt tatgttattt  9300
tcatcaatat ttttgtgcaa atatcacgct aaaaatatct tgatgaaatc taatgtccag  9360
atagctatat aatagtagat tatattatca ttatcacgta aattacatat taatagcata  9420
tatgataact aggacataaa taatgtgcat taaaaaaaaa cttaagttaa ttaaacgata  9480
tggcctttat ggtggtctta ggcttcttaa agatatattc ttaacaaaat ttttattttg  9540
ttcaaatgtt aggattatta gatttccatg ttatattaga aaagatggaa gtgttagttt  9600
tggaaaaggt tttacatcag gtgtaggatt acgagttgat gcatttatgg atgccgtagt  9660
ttccattgga gaaaatgttc aaattaatga ctatgttcac atcgcggcta ttaataatgt  9720
cattattggt agagatacat taatagcaag taaagtattt attagtgatc ataatcatgg  9780
tattttttct aaatccgata tccatagttc accaactatt attccttcgt ctaggcccct  9840
tgaatctgca cctgtgtata ttggagagcg tgtgtggatt ggcgaaaatg tgacaatatt  9900
accaggtgcg tgtataggta atggtgtagt tattggcgca aacagtgttg ttcgtggtga  9960
gattcctaat aatgtgatca ttgctggtgt tccagctaaa attgttaaaa aatataacta  10020
tgagcgtatg caatgggaaa gaatatagtt gtaatatcgg ctgttaattt tacaaccgga  10080
ggccccttta ccgtactaaa aaatgtgctt acagcaacta aagatagagc cgaatgtaaa  10140
tttattgcac tggttcatag ctctgctgaa ctaatggaat tatttccgtg ggttgaattt  10200
atagagtatc cagaagtcaa gtcttcgtgg gttaaaagat tatatttcga atatataact  10260
tgcaatagat tatctaaggt gattaaggca actcattggg tatgcttaca tgatattaca  10320
gcaaatgtta gtgtaccta tagatttgtt tattgccaca atcctgcacc gttctataaa  10380
tatttaagct atcgagatat tataggagaa cctaaatttt atcttttta tctttttat  10440
gggcttttat acaatatcaa tataaaaaag aacacagcag tttttgttca gcagcagtgg  10500
ctaaaaaaag aattcgaaaa aaaatataag ttaaagaatg ttgttgttag tcgccctgaa  10560
gatatttgcc cttttgaaag tgatggtttg gtaagaaata ataataaaaa ggatgtgagg  10620
atattttacc cagcagtgcc ccgtatattt aaaaacttg aagttatcat acgtgctgca  10680
caaatattac aagataaaaa tattcatttt tatcttactt ttgatggtac tgaaaataag  10740
tatgcaaaaa gaatatataa attagcttcc gaactgaaaa atgtacattt cctcggttac  10800
cttaatgcaa ccgagatggt taacttttat caagattcag atattatttg tttcccatcg  10860
aaactagaaa cgtggggatt accattatca gaagctaaaa catacaaaaa atggatattt  10920
gcggcagact taccttatgc tcatgaagtt ttatataact attcaaaaac tagatatttt  10980
ccatttgacg atgagaaaat acttgttcgc tacatattag agtacacaag taaaaatatg  11040
catgaagata taaaaaatag tagggtgaat tttaataatg atgcattgac tggttttgaa  11100
cagtttattg aatatatcct caaggggaac tgacgtggtt tatattataa tcgtttcaca  11160
tggccatgat gactatatag aaaatctttt attaaattta aagttgccct ctggaagatt  11220
taaaataata gttcgtgata acaaaagttc aatggtttta aaaaaaacat gcgaaaaaaa  11280
ttgcgtaacc tatttgcatg gagggcaata tggatttgga cataataata acatagcagt  11340
gtcatatata attataact tcatgattat gaataatgat tattttctct ttcttaaccc  11400
cgatgtattc ataaccagtg aaagtttgat taattatgtt gattatataa ttagtaatga  11460
ttataagttt agcacattat gtctttatcg agattttact aaaagcaaac atgattattc  11520
aatacggagt tttccaactt tatatgattt tctttgttct tttttattgg gggtgaataa  11580
aagtaaaatt aagaaggaaa atatactttc tgatactgta gttgattggt gtgctggctc  11640
atttatgctt attcatgctt taagtttctt aaatgtgaat ggttttgatc aaaaatattt  11700
tatgtattgt gaagatattg acctttgtat gcgtttaaaa ttaagtggag tagatcttta  11760
ctatactccc cattttgatg ctattcatta tgcgcagcat gaaaatagaa gaatatttac  11820
taaagcattt cgatggcata taaggagtat tacgcgctac atattacgga aaccaattct  11880
ttcttataaa aactatagaa aaattacatc cgaactggta aagtgattaa ggatccgtgt  11940
aggctggagc tgcttcgaag ttcctatact ttctagagaa taggaacttc ggaataggaa  12000
ctaaggagga tattcatatg gataaagccg taagcatata agcatggata agctatttat  12060
actttaataa gtactttgta tacttatttg cgaacattcc aggccgcgag cattcagcgc  12120
ggtgatcaca cctgacagga gtatgtaatg tccaagcaac agatcggcgt agtcggtatg  12180
gcagtgatgg gacgcaacct tgcgctcaac atcgaaagcc gtggttatac cgtctctatt  12240
ttcaaccgtt cccgtgagaa gacggaagaa gtgattgccg aaaatccagg caagaaactg  12300
gttccttact atacggtgaa agagtttgtc gaatctctgg aaacgcctcg tcgcatcctg  12360
ttaatggtga aagcaggtgc aggcacggat gctgctattg attccctcaa accatatctc  12420
gataaaggag acatcatcat tgatggtggt aacaccttct tccaggacac tattcgtcgt  12480
aatcgtgagc tttcagcaga gggctttaac ttcatcggta ccggtgtttc tggcggtgaa  12540
gagggggcgc tgaaaggtcc ttctattatg cctggtggcc agaaagaagc ctatgaattg  12600
gtagcaccga tcctgaccaa aatcgccgcc gtagctgaag acggtgaacc atgcgttacc  12660
tatattggtg ccgatggcgc aggtcactat gtgaagatgg ttcacaacgg tattgaatac  12720
ggcgatatgc agctgattgc tgaagcctat tctctgctta aaggtggcct gaacctcacc  12780
aacgaagaac tggcgcagac ctttaccgag tggaataacg gtgaactgag cagttacctg  12840
atcgacatca ccaaagatat cttcaccaaa aaagatgaag acggtaacta cctggttgat  12900
gtgatcctgg atgaagcggc taacaaaggt accggtaaat ggaccagcca gagcgcgctg  12960
gatctcggcg aaccgctgtc gctgattacc gagtctgtgt ttgcacgtta tatctcttct  13020
ctgaaagatc agcgtgttgc cgcatctaaa gttctctctg gtccgcaagc acagccagca  13080
ggcgacaagg ctgagttcat cgaaaaagtt cgtcgtgcgc tgtatctggg caaaatcgtt  13140
tcttacgccc agggcttctc tcagctgcgt gctgcgtctg aagagtacaa ctgggatctg  13200
aactacggcg aaatcgcgaa gattttccgt gctggctgca tcatccgtgc gcagttcctg  13260
cagaaaatca ccgatgctta tgccgaaaat ccacagatcg ctaacctgtt gctggctccg  13320
tacttcaagc aaattgccga tgactaccag caggcgctgc gtgatgtcgt tgcttatgca  13380
gtacagaacg gtattccggt tccgaccttc tccgcagcgg ttgcctatta cgacagctac  13440
cgtgctgctg ttctgcctgc gaacctgatc caggcacagc gtgactattt tggtgcgcat  13500
acttataagc gtattgataa agaaggtgtg ttccataccg aatggctgga ttaa        13554
```

SEQ ID NO: 19 moltype = DNA length = 15197
FEATURE Location/Qualifiers

```
source                  1..15197
                        mol_type = other DNA
                        organism = synthetic construct
SEQUENCE: 19
atgacgaatt taaaagcagt tattcctgta gcgggtctcg ggatgcatat gttgcctgcc  60
actaaggcga tacccaaaga gatgctacca atcgtcgaca agccaatgat tcagtacatt  120
gttgacgaga ttgtggctgc agggatcaaa gaaatcctcc tggtaactca cgcgtccaag  180
aacgcggtcg aaaaccactt cgacacctct tatgagttag aatcactcct tgagcagcgc  240
gtgaagcgtc aactgctggc ggaagtacag tccatctgtc cgccgggcgt gaccattatg  300
aacgtgcgtc agggcgaacc tttaggttta ggccactcca ttttgtgtgc gcgacctgcc  360
attggtgaca acccatttgt cgtggtactg ccagacgttg tgatcgacga tgccagcgcc  420
gacccgctac gttacaacct tgctgccatg attgcacgtt tcaacgaaac gggccgcagc  480
caggtgctgg caaaacgtat gccgggtgac ctctctgaat actccgtcat ccagactaaa  540
gagccgctgg accgtgaggg taaagtcagc cgcattgttg aatttatcga aaaaccggat  600
cagccgcaga cgctggactc agacatcatg gccgtaggtc gctatgtgct ttctgccgat  660
atttggccgg aactggaacg tactcagcct ggtgcatggg gacgtattca gctgactgat  720
gctattgccg agctggcgaa aaaacaatcc gttgatgcaa tgctgatgac cggcgacagt  780
tacgactgcg gcaaaaaaat gggctatatg caggcgtttg tgaagtatgg cctacgcaac  840
ctgaaagaag gggcgaagtt ccgtaaaggt attgagaagc tgttaagcga ataatgaaaa  900
tctgaccgga tgtaacggtt gataagaaaa ttataacggc agtgaaaatt cgcagcaaaa  960
gtaatttgtt gcgaatcttc ctgccgttgt tttatataaa ccatcagaat aacaacgagt  1020
tagcagtagg gttttattca aagttttcca ggattttcct tgtttccaga gcggattggt  1080
aagacaatta gcgtttgaat ttttcgggtt tagcgcgagt gggtaacgct cgtcacatca  1140
taggcatgca tgcagtgctc tggtagctgt aaagccaggg gcggtagcgt gcattaatac  1200
ctctattaat caaactgaga gccgcttatt tcacagcatg ctctgaagta atatggaata  1260
aattaagcta gcagtgaaga tacttgttac tggtggcgca ggatttattg gttctgctgt  1320
tgttcgtcac ataataaata atacgcaaga tagtgttgtt aatgtcgata aattaacata  1380
cgccggaaac ctggaatcgc tcgctgaaat ttctgattct gaacgttatt catttgagca  1440
tgcagatatc tgcgatgccg aagcgatggc tcgtattttc gcacagcacc agccagacgc  1500
ggtgatgcac ctggcagcag agagccacgt tgaccgctca ataactggcc ctgcggcatt  1560
tattgaaacc aatattgtgg gtacttatgt tcttttagaa gcggcgcgca attattggtc  1620
tggtctggat gatgaaaaga aaaaaaactt ccgctttcat catatttcta ctgatgaggt  1680
gtatggtgac ttaccccatc cggatgaagt aaatagcaat gaaacgttgc cgctatttac  1740
ggaaatgaca gcatacgcgc caagtagtcc atattctgct tctaaagctt ccagcgatca  1800
tttggttcgc gcatggaaac gtacttatgg tttaccgacc attgtgacta attgctcgaa  1860
caactatggt ccttatcatt tcccggaaaa gcttattcca ctggttattc ttaatgcact  1920
ggaaggtaag gcattaccta tttatggcaa aggagatcag atccgcgact ggttgtatgt  1980
agaggatcat gctcgagcgt tatataccgt cgtaaccgaa ggtaaagcgg gcgaaactta  2040
taacattggt ggacacaacg aaaagaaaaa catcgacgta gtgttcacta tttgtgattt  2100
gttggatgag atagtcccga aagagaaatc ttatcgtgag caaattacct atgttgctga  2160
tcgcccaggg catgatcgcc gttatgcaat tgatgccgat aaaattagcc gcgaattggg  2220
ctggaaacca caggaaacgt ttgagagcgg gattcgtaaa actgtggaat ggtatctgtc  2280
caatacaaaa tgggttgata atgtgaaaag tggtgcctat caatcgtgga ttgaacagaa  2340
ctatgggggc cgccactaat gaatatcctc ctttttggca aaacagggca ggttggttgg  2400
gaactacagc gtgctctggc acctctgggt aatttgattg ctcttgatgt tcactccact  2460
gattactgtg gtgattttag taaccctgaa ggtgtggctg aaaccgttag aagcattcgg  2520
cctgatatta ttgtcaacgc agccgctcac accgcagtag acaaagcaga atcagaaccg  2580
gagtttgcac aattactgaa cgcgacgagt gtcgaagcga tcgcgaaagc agccaatgaa  2640
gtcggcgctt gggttattca ctactctact gactacgtat ttccggggac cggtgaaata  2700
ccatggcagg aggaggatgc aaccgcaccg ctaaatgttt acggtgaaac caagttagca  2760
ggagaaaaag cattacaaga gcattgtgcg aagcacctta ttttccggac cagctgggtc  2820
tatgcaggta aaggaaataa cttcgccaaa acgatgttgc gtctggcaaa agagcgtgaa  2880
gaattagccg ttattaatga tcagtttggt gcgccaactg gcgcagagtt gctggctgat  2940
tgtacggcac atgccattcg tgtggcactg aataaaccgg aagtcgcagg tttgtaccat  3000
ctggtagcca gtggtaccac aacctggcac gattatgctg cgctggtttt tgaagaggcg  3060
cgcaaagcag gcattcccct tgcactcaac aagctcaacg cagtaccaac aacagtctat  3120
cctacaccag ctcgtcgtcc acataactct cgccttaata cagaaaaatt tcagcagaac  3180
tttgcgcttg tcttgcctga ctggcaggtt ggtgtgaaac gcatgctcaa cgaattattt  3240
acgactacag caatttaata gtttttgcat cttgttcgtg atggtggaac aagatgaatt  3300
aaaaggaatg atggaatgaa tacgcgtaaa ggtattattt tagcgggtgg ttctggtaca  3360
cgtctttatc ctgtgactat ggctgtcagt aaacagctgt taccgattta tgataaaccg  3420
atgatctatt acccgctctc tacactgatg ttggcgggta ttcgcgatat tttgattatc  3480
agcacgccac aggatactcc tcgttttcaa caactgctgg gtgatgggag ccagtggggg  3540
ctaaatcttc actacaaagt gcaaccgagt ccggatggtc ttgcgcaggc atttatcatc  3600
ggtgaagagt ttatcggtgg tgatgattgt gctttggtac ttggtgataa tatcttctac  3660
ggtcacgacc tgcctaagtt aatggatgcc gctgttaaca aagaaagtgg tgcaacggta  3720
tttgcctatc acgttaatga tcctgaacgc tatggtgtcg ttgagtttga taaaaacggt  3780
actgcaatca gcctggaaga aaaaccgtta caaccaaaaa gtaattatgc ggtaaccggg  3840
ctttatttct atgataacta cgttgtggaa atggcgaaaa atcttaagcc ttctgcccgc  3900
ggtgaactgg aaattaccga tattaaccgt atctatatgg aacaggggca tttatctgtt  3960
gccatgatgg gacgtggata tgcctggctg gacacgggga cacatcaaag tcttattgaa  4020
gcaagcaact tcattgccac cattgaagag cgccagggct tgaaagtttc ctgcccggaa  4080
gaaattgctt accgtaaagg gtttattgat gctgagcagg tgaaagtatt agctaaaccg  4140
ctgaaaaaaa atgcttatgg tcagtatctg ctaaaaatga ttaaaggtta ttaataaaat  4200
gaatgttatt aaaacagaaa ttccagatgt actgattttt gaaccgaaag tttttggtga  4260
tgagcgtggt ttctttatgg aaagctttaa tcagaaagtt ttcgaagagg ctgtagggcg  4320
gaaggttgaa tttgttcagg ataatcattc taaatcgtgt aaaggtgtac ttagaggttt  4380
acactttcag cttcctccct ttgagcaggc aaaattagta aggtgtatag ttggcgaggt  4440
atttgatgtt gcagtagaca ttagacctaa ttctgaaaca tttggttcat gggttggagt  4500
```

-continued

```
aactctttcg tcagaaaata aaaggcagct atggattcca gaaggattcg cccatggttt 4560
tttaacttta agtgatattg cagagtttgt ttataaaact aacaactatt attctttaaa 4620
tcatgaaagg ggagtcattt ggaacgatga ggaaattaac attgcctggc cctctcaatc 4680
agagaagatt ctgtcacaga aagatattaa tttaccatca tttagatttg ttcaaatgtt 4740
tagcaagtag tgttatcttt acactgcaca tagtcatcat tttttatgct ttaagtaaat 4800
tatattgcac atctataaca caaagcgcaa taatatttcg acctgatgaa ggtttgtggt 4860
tatttatctt tctaggcgtt ttttatgact aaaatagttg tggtttctac agctccaata 4920
ttcccgacaa ataatgggta caaaagttct gtattaggaa gaattgatga gttattaaat 4980
gaggataatg aggtcgtttt gattgaaata aaccttgaaa atgttacgga aaagaaagat 5040
gaattaatac caacaagatt taataatatt caaagatatg aagtaaaaaa aatatctaga 5100
tcatttattg ccgagttaca aatattattt gatatcagaa ctcggtatga acaattattt 5160
tcttctgctg acattagaga taacataaaa aagataattg atttagaaaa accttctatt 5220
attattgctg agtctatatg ggcgttgcaa gcattgccta ttgaaattag tgcgagaata 5280
cactgtgtta ttcatgatgt ggcaactgat ttctttaaag aaatgtttgt atctcataat 5340
gaggttgtac gaaaaatttt gtttttttaat gattacctaa agttgaaaat tactgaagaa 5400
aatattatca aacgtttgag agttgagcaa tttatctttc tgacagaaga agataaatgt 5460
tggtataaaa caagatacaa tattgatgag ggttgttgtt ccttagcgag caatcatctt 5520
tatgtagaaa agattaagag aactatcaat ttccaaaccc ctttcctgct tattcccggt 5580
agcattgaat tttcacaaaa tttttacggc ttaaattggt ttataaaaaa tatatatcct 5640
ggattaaata ggaaaataag aatagttgta acaggaaagg catcagataa aaaaataaag 5700
atgttaaact gtggagagga aattaccttt acgggagagc ttgacttttc cacatataat 5760
aaacttagct caacatgctt gtgtgttatt gcaccgatta caacgggcac tggaattaaa 5820
ataaaaatat tagaagctgt acaaaaaggt attcctgtac ttacaacaaa atttgcttca 5880
aaaggaatat gttccgattt atgtttttat tgcgaggagg atactgacac aaactttgtc 5940
aatttaatta acagttttct tgaaacgaca ttaagagtcc aagaatgaat ttattgcttt 6000
tttcagtcct tgcgtttggt ttaatattgg ctttggccca taataataaa agtggagata 6060
ttaacgcata cttaatgttt tttctcgtgg tcctaatggt attaatatca gggctgcgta 6120
tgaatgatag tgattatatc gaatacagga aaatgtataa tgaagtgcct attttatgtg 6180
actttagtct cgcatctata agagatatac atggggaggt aggctatcta ttcttatcat 6240
caatctttaa aactttatgc ttgccatttc aattatttct ttttttttatt gctttttttat 6300
cactcctgct tacatatttt tcattcagaa aaataagttt aataccgata ctatcgttag 6360
tttttttattt aagccatgct tttatagtta gagatttgat tcaaattagg gcaggattag 6420
ctgttagcat atcattatat tcaataatta aatttaaagg aaataaaagt ataattacag 6480
gagttttatt tgcttctttg attcattctg gggcgcttat tattgctctt tgttatcctt 6540
ttttcaaaaa aaaatacata acattaaaaa tgatgttgtt tttatttttta gtgtcaatta 6600
ttttttctta tttgaatggg cttaatttat cgatacaact cttatctcaa tatagtttgc 6660
ttccaactgc aatttcgaat tatgttggtt gggaagaata tgattatcgg gtgagtatat 6720
ttactaatcc ggttttttatt aaaggtgttt ttttaattgt cttaatgcac aaatatgtac 6780
tttcagatat taaaaatgag aaaattatag tgctttataa cttatatgtt ttaggtgtat 6840
tagctatggt tgcattgagt gggatggcta ttctttcagg ccgtctttca tcctttctga 6900
cactaggtga aagcatttta attgtatatg ctctgttcta caaaagaaat acacctctgg 6960
cgtttctaat tttttctttt ttaacaattg tgcaattagg atatgatcta tttatttcta 7020
atgtgcatcc tgagcttact ctgattatat ttgggtgaat ctaagtgaaa aataataaaa 7080
taggcatact tatctctaaa atacaaaatc ttggacctgt gaatgtagta cgaggattga 7140
taaaagaaaa taaaaaatat gcttttactg tttttttgttt aacaaatagc gtagataaaa 7200
atatatatga tgagttatgc tgtttaggag ccaaggttat attaatacca gatggtactt 7260
ggttcagcaa aattttattt gtgagaagtt ttttaaagga acatccacat aatatcttac 7320
attcacatgg gatcacggcc gatatgtttt cttactttct gaatggcgtg aaaatatcta 7380
ctattcacaa tagactagat gaggattata tcccattatt tggcgcggtt aaagggaatg 7440
ctatatatta tcttcatcgt tttatattac gaagatttaa tcatatcgtt gcttgctcag 7500
cagcggtcca atcaaaactg aaacaatcga aagtaaaaac taaaataacc accatccaga 7560
atgggattga tataactagg tttaagacac ttgagtctga taaaaaaaaa ttattgaggg 7620
aaaaacacgg atttgatagt gaaaaaagaa tatttatata ttgtggctcg ttatcattaa 7680
ggaaaaatat tgcttacctc ttggaacact tagccatcga agaaaatgat atattttttaa 7740
ttctaggtga tggtgaactt tttagatatt gtaaggataa atattctaaa gatttacggt 7800
atatatttat ggggaaagtt gaatgccctc ttgaatatta tcaattatca gatatttttg 7860
tttccgcttc tttatcggaa gggctcccct tggcactatt agaagctgcc tctactgggt 7920
gctatttata tgttagcgat atagagcccc atagagaaat tgcatctcta ttaggagagg 7980
aaaatatttc tatgtttaaa attaaggatg gatcatataa ttatttgcaa cctaaaataa 8040
aaaaagctga ctataacgct ctttctgacg ataaacttta caatatatcc gataaaaaaa 8100
tgtcaaatct ttatgacaaa ctttttgttt ctttattaga gcagaggcac taatataatg 8160
atttatgttt cggtaatttc tcatggtcat ttcaaaactc ttaaggaatt aggagcagta 8220
tcaaaattaa ataatcacag cagaattaaa gttatcatca aagataattt aggagagagc 8280
gagcttttgg atttttgtca ggaaaacaaa ataacttatt taaggtctaa agagaaaaaa 8340
ggatttggag agaataataa tgaagttttt tcctctatat cctccttaat tactaaggaa 8400
gatttttttg tggttatgaa tcctgatata tatattgagt gctctgatct attagatgtc 8460
gtagatgagt gtggttcagc gaatgttaat ctagcaacga taaatttata cagggatttt 8520
gataaaaaaa catatgataa ctcagtaagg aaatttccct cggcaattga ttttttttatg 8580
tcattttttat ttaagaaaaa tgactgtgta gtaaataaga acaaaataac gaaaccaaca 8640
tatgttgatt gggctgcagg ttctttttcta atatttaatg ccttctttta ttcaaaactc 8700
aacggattca acgaaaagta ttttatgtat tgcgaagata ttgatatatg ttggcgagct 8760
aaaaaacact tcaatacttc agttttatac tatccatgct atgcagcaat tcatttggca 8820
caatttaaca atcgtaggat ttttagtaga catttcattt ggcatataaa aagtattatc 8880
cttttttttat tatataaaaa tggtatgctg cgttctagta agttgcttta atgctaatat 8940
tcttttaaga ggtgagaatg atacctgtta ttttggctgg tggttcggga agtcgcttgt 9000
ggccactttc acgagaaaag ttccccaagc agtttttaaa gttgactggc agtttgacaa 9060
tgttgcagtc aacattgtca cgtcttaata atttaaatgc tgatgattca atagttatat 9120
gcaacgaaga gcatagattt attgttgcag aacaattaag agagttaggc aaactttcaa 9180
ataacattat tcttgaaccc aaaggtcgta atacagcccc tgctataaca ctcgcagcat 9240
```

-continued

```
tagcagcaaa aagaaaattc gctgatgaag atccattgat tcttatttta gctgcagatc  9300
acaacatcca agacgaacat gttttctgtg aggcaattaa taaggcgtca tctttagcta  9360
gttatggaaa actagtgact tttggtatcg ttccattcaa acctgaaact gggtatggct  9420
atattcgtcg cggtgatgaa gtgcctgtag atgagcagca tgcggtggcc tttgaagtgg  9480
cgcagtttgt cgaaaaaccg aatctggaaa ccgcgcaggc ctatgtggca agcggcgaat  9540
attactggaa cagcggtatg ttcctgttcc gtgccggacg ctatctcgaa gaactgaaaa  9600
agtatcgtcc ggatattctc gatgcctgtg aaaaagcgat gagcgccgtc gatccggatc  9660
tcgattttat tcgtgtggat gaagaggcgt ttctcgcttg tccggaagag tcggtggatt  9720
acgcggtcat ggaatgcacg gcagatgccg ttgtggtgcc gatggatgcg ggctggagcg  9780
atgtcggttc ctggtcttca ttatgggaga tcagcgccca caccgccgag ggcaacgttt  9840
gccacggcga tgtgattaat cacaaaactg aaaacagcta tgtgtacgcc gaatctggcc  9900
tggtcaccac cgtcggggtg aaagatttgg tggtagtgca gaccaaagat gcagtgctga  9960
ttgccgaccg taatgcggtg caggatgtga agaaagtggt cgagcagatc aaagctgatg  10020
gtcgccatga gcatcgggtg catcgcgaag tgtatcgtcc gtggggcaaa tatgactcta  10080
tcgacgcggg cgaccgctac caggtgaaac gcatcaccgt gaaaccgggc gaaggtttgt  10140
cggtacagat gcattatcat cgcgcggaac actgggtggt tgtcgcggga acggcaaaag  10200
tcactatcaa cggtgatatc aaactgcttg gtgaaaacga gtccatttat attccgctgg  10260
gggcgatgca ctgcctggaa aacccgggga aaatagattt agaattaatt gaagttcgct  10320
ctggtgcata tcttgaagaa gatgatgtta ttagatgtta tgatcgctat ggacgaaagt  10380
aatatataat aattatttca gaattagaaa tgataattat aagttttcgt ctggataaac  10440
aatagatagt atgggttgga aaatatgagt tctttaactt gttttaaagc ttacgacatt  10500
cgcgggaaat taggtgaaga actgaatgaa gatatcgcct ggcgcattgg tcgcgcctat  10560
ggcgaatttc tcaaaccgaa aaccattgtg ttaggcggtg atgtccgtct caccagcgaa  10620
accttaaaac tggcgctggc aaaaggttta caggatgcgg gcgtcgatgt gctggatatt  10680
ggcatgtccg gcaccgaaga gatttatttc gccacgttcc atctcggcgt ggatggcggc  10740
attgaagtta ccgccagcca taatccgatg gattacaacg gcatgaagct ggtgcgcgaa  10800
ggggctcgcc cgatcagcgg tgataccgga ctgcgcgacg tccagcgtct ggcagaagct  10860
aacgactttc ctcccgtcga tgaaaccaaa cgcggtcgct atcagcaaat caatctgcgt  10920
gacgcttacg ttgatcacct gttcggttat atcaatgtca aaaaccttac gccgctcaag  10980
ctggtgatca actccgggaa tggcgcagcg ggtccggtgg tggacgctat cgaagcccgc  11040
tttaaagccc tcggcgcacc ggtggagtta atcaaagtgc ataacacgcc ggacggcaat  11100
ttccccaacg gtattcctaa cccgttgctg ccggaatgtc gcgacgacac ccgcaatgcg  11160
gtcatcaaac acggcgcgga tatgggcatt gcctttgatg gcgattttga ccgctgtttc  11220
ctgtttgacg aaaaagggca gtttattgag ggctactaca ttgtcggcct gctggcagaa  11280
gcgttcctcg aaaaaaatcc cggcgcgaag atcatccacg atccacgtct ctcctggaac  11340
accattgatg tggtgacggc cgcgggcggc acgccggtga tgtcgaaaac aggacacgcc  11400
tttattaaag aacgtatgcg caaggaagac gccatctacg gtggcgaaat gagcgctcac  11460
cattacttcc gcgatttcgc ttactgtgac agcggcatga tcccgtggct gctggtcgcc  11520
gaactggtgt gcctgaaagg aaaaacgctg ggcgaactgg tgcgcgaccg gatggcggcg  11580
tttccggcaa gcggtgagat caacagaaaa ctggcgcacc ctgttgaggc gattaaccgc  11640
gtggaacagc attttagccg tgaggtgctg gcggtggatc gcaccgatgg catcagcatg  11700
acctttgccg actggcgctt taacctgcgc tcttccaaca ccgaaccggt ggtgcgcctg  11760
aatgtggaat ctcgcggtga tgttcaggtt atggtaatcc atactcaaga aatattatca  11820
attttgacgt cataaagaat aagccctgac aagttagggc ttaattaata tatattttt  11880
ttgaattggg gatttgtggt aagattttta atatgttatt taatgtggtt gaattaatgt  11940
tgactggaaa ataataatga gaacgaaaaa agcattacac aactttaaag ttgatttatt  12000
aattactttt ttattggttt tgctagggtt ttatattcga actgtttttg tttcaaaaat  12060
gggaagtgat attactggag tgatgttact attcacacag ttgacagcat atctcaattt  12120
ggcagaatta ggtattggaa ttgcagctgc cagcgtatta tataaaccgc tcagcgagaa  12180
tgaatacaat aaaataactt acataatatc tttgctctca gtcatataca aatatatatt  12240
tgtgtttgtt ttgattcttg gcgttgttat aggtatctgt atttattact ttattgattc  12300
tgtaaaggtt gtaaatggcg ttttttttata ttgggctttg ttcgttttta atacatcgtt  12360
gacatatagt tatgctaaat actccacatt attaactgct aatcagcggt actcagcagt  12420
aagaaaaatt caaggtggcg gaaaagttat aataattgta tttcagatat taattttgtg  12480
ctttacgcaa agtttcatac tttatttgtt agttgagact ttaggtattt tttctcaata  12540
tttgattttt aaaaaaataa ttgggaacgg aaatcaatat ctcagtaatg aggttttact  12600
tattgaaagc gataaacttt tgataaaaaa agaattaaaa ataagaataa aaaatatgtt  12660
cttccataaa ataggtgctg tgcttgtcct taatacagac tacctgcttg tatcaaagtt  12720
tctgacatta agttatgtga caatttttgg cagctatatg atggtatttc agatagtaac  12780
tgttttgatg tcaagttttg ttaatgctat tactgcagga atgggtaatt acttaattaa  12840
taaaagtaat ttagaaatta aggaaattac acgtcaattt tatgtgatat ttatcgcctt  12900
tgcaacattc atatcactaa atatgttttt tcttgttaat gattttatcg caaaatggat  12960
aggtgttaat tatacattaa gtaacaccct agttgcatta atgattgtta acgtattcat  13020
tagtgttgtc agggtacctt ctgatatatt aaaaaacgca agtggacatt ttggtgatat  13080
ttattatcca ttatttagaag gtgtgctgaa tattacgata tccatcattt tggctatcat  13140
tattggatta cctggcatta ttatagggac aatagtatct aacttaatag taataatgct  13200
tgcgaaacca ttatatcttt actctaagtt atttaatctt agaaatccga cgagggttta  13260
ttttgaattt atttctcggc ctatgttata ttcattatgt gtgattgggg tgagctattt  13320
attgcgcgat gaaatatatt catttaaagt aagtacatgg ttggatttta ttaacaagct  13380
actcttagtc tctactccta gcatattggt aatatgtgct attttctcta cggatagtga  13440
ctttagatta tttttcagaa aaattatata tgtgattatg aagaaataaa aatttcgaaa  13500
atgtattaat cgaaattatg caacgagctt tatttttata aatgatatgt gatcttttcg  13560
cgaataggag taaggatccg tgtaggctgg agctgcttcg aagttcctat actttctaga  13620
gaataggaac ttcggaatag gaactaagga ggatattcat atggataaag ccgtaagcat  13680
ataagcatgg ataagctatt tatactttaa taagtacttt gtatacttat ttgcgaacat  13740
tccaggccgc gagcattcag cgcggtgatc acacctgaca ggagtatgta atgtccaagc  13800
aacagatcgg cgtagtcggt atggcagtga tgggacgcaa ccttgcgctc aacatcgaaa  13860
gccgtggtta taccgtctct attttcaacc gttcccgtga gaagacggaa gaagtgattg  13920
ccgaaaatcc aggcaagaaa ctggttcctt actatacggt gaaagagttt gtcgaatctc  13980
```

-continued

```
tggaaacgcc tcgtcgcatc ctgttaatgg tgaaagcagg tgcaggcacg gatgctgcta  14040
ttgattccct caaaccatat ctcgataaag gagacatcat cattgatggt ggtaacacct  14100
tcttccagga cactattcgt cgtaatcgtg agctttcagc agagggcttt aacttcatcg  14160
gtaccggtgt ttctggcggt gaagaggggg cgctgaaagg tccttctatt atgcctggtg  14220
gccagaaaga agcctatgaa ttggtagcac cgatcctgac caaaatcgcc gccgtagctg  14280
aagacggtga accatgcgtt acctatattg gtgccgatgg cgcaggtcac tatgtgaaga  14340
tggttcacaa cggtattgaa tacggcgata tgcagctgat tgctgaagcc tattctctgc  14400
ttaaaggtgg cctgaacctc accaacgaag aactggcgca gacctttacc gagtggaata  14460
acggtgaact gagcagttac ctgatcgaca tcaccaaaga tatcttcacc aaaaaagatg  14520
aagacggtaa ctacctggtt gatgtgatcc tggatgaagc ggctaacaaa ggtaccggta  14580
aatggaccag ccagagcgcg ctggatctcg gcgaaccgct gtcgctgatt accgagtctg  14640
tgtttgcacg ttatatctct tctctgaaag atcagcgtgt tgccgcatct aaagttctct  14700
ctggtccgca agcacagcca gcaggcgaca aggctgagtt catcgaaaaa gttcgtcgtg  14760
cgctgtatct gggcaaaatc gtttcttacg cccagggctt ctctcagctg cgtgctgcgt  14820
ctgaagagta caactgggat ctgaactacg gcgaaatcgc gaagatttc cgtgctggct  14880
gcatcatccg tgcgcagttc ctgcagaaaa tcaccgatgc ttatgccgaa aatccacaga  14940
tcgctaacct gttgctggct ccgtacttca agcaaattgc cgatgactac cagcaggcgc  15000
tgcgtgatgt cgttgcttat gcagtacaga acggtattcc ggttccgacc ttctccgcag  15060
cggttgccta ttacgacagc taccgtgctg ctgttctgcc tgcgaacctg atccaggcac  15120
agcgtgacta ttttggtgcg catacttata agcgtattga taaagaaggt gtgttccata  15180
ccgaatggct ggattaa                                                 15197
```